US009072798B2

(12) United States Patent
Ritter et al.

(10) Patent No.: US 9,072,798 B2
(45) Date of Patent: Jul. 7, 2015

(54) SPECIFIC BINDING PROTEINS AND USES THEREOF

(75) Inventors: Gerd Ritter, New York, NY (US); Anne Murray, New York, NY (US); George Mark, New York, NY (US); Christoph Renner, Homburg/Saar (DE)

(73) Assignee: Ludwig Institute for Cancer Research LTD. (CH)

( * ) Notice: Subject to any disclaimer, the term of this patent is extended or adjusted under 35 U.S.C. 154(b) by 993 days.

(21) Appl. No.: 13/201,061

(22) PCT Filed: Feb. 17, 2010

(86) PCT No.: PCT/US2010/024407
§ 371 (c)(1),
(2), (4) Date: Apr. 4, 2012

(87) PCT Pub. No.: WO2010/096434
PCT Pub. Date: Aug. 26, 2010

(65) Prior Publication Data
US 2012/0183471 A1    Jul. 19, 2012

Related U.S. Application Data

(63) Continuation-in-part of application No. 12/388,504, filed on Feb. 18, 2009, now abandoned.

(51) Int. Cl.
| | |
|---|---|
| *C07K 16/28* | (2006.01) |
| *A61K 51/10* | (2006.01) |
| *A61K 39/395* | (2006.01) |
| *C07K 16/30* | (2006.01) |
| *C07K 16/42* | (2006.01) |
| *A61K 39/00* | (2006.01) |

(52) U.S. Cl.
CPC ....... *A61K 51/1078* (2013.01); *A61K 39/39541* (2013.01); *A61K 51/103* (2013.01); *A61K 51/1045* (2013.01); *A61K 2039/505* (2013.01); *C07K 16/2863* (2013.01); *C07K 16/30* (2013.01); *C07K 16/4258* (2013.01); *C07K 2317/24* (2013.01); *C07K 2317/73* (2013.01); *C07K 2317/732* (2013.01); *C07K 2317/734* (2013.01); *C07K 2317/77* (2013.01); *C07K 2317/34* (2013.01)

(58) Field of Classification Search
CPC .... C07K 16/00; C07K 16/28; C07K 2317/00; A61K 39/00; A61K 2039/505; A61K 2130/00; C07H 21/00; C12N 5/00; C12N 15/63; C12N 2015/63; C12N 2800/00
USPC ............ 530/350, 387.1, 387.3, 387.7, 388.2, 530/391.3, 391.7, 388.22; 536/23.5; 435/325
See application file for complete search history.

(56) References Cited

U.S. PATENT DOCUMENTS

| | | |
|---|---|---|
| 4,137,230 A | 1/1979 | Hashimoto |
| 4,151,042 A | 4/1979 | Higashide |
| 4,169,888 A | 10/1979 | Hanka |
| 4,190,580 A | 2/1980 | Hashimoto |
| 4,225,494 A | 9/1980 | Higashide |
| 4,248,870 A | 2/1981 | Miyashita |
| 4,256,746 A | 3/1981 | Miyashita |
| 4,260,608 A | 4/1981 | Miyashita |
| 4,263,294 A | 4/1981 | Miyashita |
| 4,264,596 A | 4/1981 | Miyashita |
| 4,265,814 A | 5/1981 | Hashimoto |
| 4,294,757 A | 10/1981 | Asai |
| 4,307,016 A | 12/1981 | Asai |
| 4,308,268 A | 12/1981 | Miyashita |
| 4,308,269 A | 12/1981 | Miyashita |
| 4,309,428 A | 1/1982 | Miyashita |
| 4,313,946 A | 2/1982 | Powell |
| 4,317,821 A | 3/1982 | Miyashita |
| 4,322,348 A | 3/1982 | Asai |
| 4,331,598 A | 5/1982 | Hasegawa |
| 4,342,566 A | 8/1982 | Theofilopoulos |
| 4,360,462 A | 11/1982 | Higashide |
| 4,361,650 A | 11/1982 | Asai |
| 4,362,663 A | 12/1982 | Kida |
| 4,364,866 A | 12/1982 | Asai |

(Continued)

FOREIGN PATENT DOCUMENTS

| | | |
|---|---|---|
| EP | 0120694 A2 | 10/1984 |
| EP | 0125023 A1 | 11/1984 |

(Continued)

OTHER PUBLICATIONS

U.S. Appl. No. 60/290,410, filed May 11, 2001.
U.S. Appl. No. 60/326,019, filed Sep. 28, 2001.
U.S. Appl. No. 60/342,258, filed Dec. 21, 2001.
Abbruzzese et al., "Phase II study of anti-epidermal growth factor receptor (EGFR) antibody cetuximab (IMC-C225) in combination with gemcitabine in patients with advanced pancreatic cancer (Abstract 518)" *Proceedings of the American Society of Clinical Oncology* (2001) 130a, 20.

(Continued)

*Primary Examiner* — Stephen Rawlings
(74) *Attorney, Agent, or Firm* — McCarter & English, LLP; Cristin H. Cowles; Kevin A. Fiala

(57) ABSTRACT

The present invention relates to specific binding members, particularly antibodies and fragments thereof, which bind to amplified epidermal growth factor receptor (EGFR) and to the de2-7 EGFR truncation of the EGFR. In particular, the epitope recognized by the specific binding members, particularly antibodies and fragments thereof, is enhanced or evident upon aberrant post-translational modification. These specific binding members are useful in the diagnosis and treatment of cancer. The binding members of the present invention may also be used in therapy in combination with chemotherapeutics or anti-cancer agents and/or with other antibodies or fragments thereof.

25 Claims, 154 Drawing Sheets

(56) References Cited

U.S. PATENT DOCUMENTS

| | | |
|---|---|---|
| 4,371,533 A | 2/1983 | Akimoto |
| 4,413,132 A | 11/1983 | Wierenga |
| 4,418,064 A | 11/1983 | Powell |
| 4,671,958 A | 6/1987 | Rodwell |
| 4,762,707 A | 8/1988 | Jansen |
| 4,816,567 A | 3/1989 | Cabilly |
| 4,867,973 A | 9/1989 | Goers |
| 4,933,294 A | 6/1990 | Waterfield |
| 4,937,183 A | 6/1990 | Ultee |
| 4,943,533 A | 7/1990 | Mendelsohn |
| 4,952,394 A | 8/1990 | Senter |
| 4,997,913 A | 3/1991 | Hellstrom |
| 5,013,547 A | 5/1991 | Sweet |
| 5,028,697 A | 7/1991 | Johnson |
| 5,034,223 A | 7/1991 | Abrams |
| 5,047,324 A | 9/1991 | Fredrickson |
| 5,087,616 A | 2/1992 | Myers |
| 5,106,951 A | 4/1992 | Morgan |
| 5,122,368 A | 6/1992 | Greenfield |
| 5,130,116 A | 7/1992 | Woo |
| 5,141,736 A | 8/1992 | Iwasa |
| 5,164,311 A | 11/1992 | Gupta |
| 5,171,563 A | 12/1992 | Abrams |
| 5,208,020 A | 5/1993 | Chari |
| 5,212,290 A | 5/1993 | Vogelstein |
| 5,217,713 A | 6/1993 | Iwasa |
| 5,225,539 A | 7/1993 | Winter |
| 5,306,809 A | 4/1994 | Boon |
| 5,332,837 A | 7/1994 | Kelly |
| 5,401,828 A | 3/1995 | Vogelstein |
| 5,416,064 A | 5/1995 | Chari |
| 5,457,105 A | 10/1995 | Barker |
| 5,459,061 A | 10/1995 | Sato |
| 5,475,092 A | 12/1995 | Chari |
| 5,541,339 A | 7/1996 | Kelly |
| 5,556,623 A | 9/1996 | Barton |
| 5,558,864 A | 9/1996 | Bendig |
| 5,563,250 A | 10/1996 | Hylarides |
| 5,585,499 A | 12/1996 | Chari |
| 5,606,017 A | 2/1997 | Willner |
| 5,612,474 A | 3/1997 | Patel |
| 5,622,929 A | 4/1997 | Willner |
| 5,635,483 A | 6/1997 | Pettit |
| 5,635,603 A | 6/1997 | Hansen |
| 5,639,641 A | 6/1997 | Pedersen |
| 5,643,573 A | 7/1997 | Barton |
| 5,665,358 A | 9/1997 | Barton |
| 5,674,977 A | 10/1997 | Gariepy |
| 5,677,171 A | 10/1997 | Hudziak |
| 5,708,146 A | 1/1998 | Willner |
| 5,708,156 A | 1/1998 | Ilekis |
| 5,720,954 A | 2/1998 | Hudziak |
| 5,739,350 A | 4/1998 | Kelly |
| 5,760,041 A | 6/1998 | Wissner |
| 5,770,195 A | 6/1998 | Hudziak |
| 5,780,588 A | 7/1998 | Pettit |
| 5,795,965 A | 8/1998 | Tsuchiya |
| 5,807,715 A | 9/1998 | Morrison |
| 5,814,317 A | 9/1998 | Vogelstein |
| 5,824,805 A | 10/1998 | King |
| 5,844,093 A | 12/1998 | Kettleborough |
| 5,846,545 A | 12/1998 | Chari |
| 5,851,526 A | 12/1998 | Welt |
| 5,869,045 A | 2/1999 | Hellstrom |
| 5,869,619 A | 2/1999 | Studnicka |
| 5,880,270 A | 3/1999 | Berninger |
| 5,891,996 A | 4/1999 | De Acosta del Rio |
| 5,911,995 A | 6/1999 | Uckun |
| 5,942,602 A | 8/1999 | Wels |
| 5,980,896 A | 11/1999 | Hellstrom |
| 6,010,902 A | 1/2000 | Ledbetter |
| 6,060,608 A | 5/2000 | Boger |
| 6,214,345 B1 | 4/2001 | Firestone |
| 6,217,866 B1 | 4/2001 | Schlessinger |
| 6,224,868 B1 | 5/2001 | Wong |
| 6,235,883 B1 | 5/2001 | Jakobovits |
| 6,281,354 B1 | 8/2001 | Boger |
| 6,306,393 B1 | 10/2001 | Goldenberg |
| 6,331,175 B1 | 12/2001 | Goldenberg |
| 6,331,415 B1 | 12/2001 | Cabilly |
| 6,333,410 B1 | 12/2001 | Chari |
| 6,340,701 B1 | 1/2002 | Chari |
| 6,355,683 B1 | 3/2002 | Baell et al. |
| 6,372,738 B2 | 4/2002 | Chari |
| 6,395,272 B1 | 5/2002 | Deo |
| 6,436,931 B1 | 8/2002 | Chari |
| 6,441,163 B1 | 8/2002 | Chari |
| 6,506,883 B2 | 1/2003 | De Acosta del Rio |
| 6,512,101 B1 | 1/2003 | King |
| RE38,008 E | 2/2003 | Abrams |
| 6,534,660 B1 | 3/2003 | Yongxin |
| 6,548,530 B1 | 4/2003 | Boger |
| 6,570,024 B2 | 5/2003 | Eldridge |
| 6,586,618 B1 | 7/2003 | Zhao |
| 6,596,757 B1 | 7/2003 | Chari |
| 6,630,579 B2 | 10/2003 | Chari |
| 6,660,742 B2 | 12/2003 | Lee |
| 6,675,105 B2 | 1/2004 | Hogarth et al. |
| 6,699,715 B1 | 3/2004 | Ledbetter |
| 6,706,708 B2 | 3/2004 | Chari |
| 6,716,821 B2 | 4/2004 | Zhao |
| 6,756,397 B2 | 6/2004 | Zhao |
| 6,759,509 B1 | 7/2004 | King |
| 6,790,954 B2 | 9/2004 | Chung |
| 6,797,492 B2 | 9/2004 | Daugherty |
| 6,835,753 B2 | 12/2004 | Baell et al. |
| 6,849,625 B2 | 2/2005 | Lambert et al. |
| 6,884,869 B2 | 4/2005 | Senter |
| 6,884,874 B2 | 4/2005 | Eldridge |
| 6,913,748 B2 | 7/2005 | Widdison |
| 6,933,368 B2 | 8/2005 | Co et al. |
| 6,941,229 B1 | 9/2005 | Elleman et al. |
| 6,946,543 B2 | 9/2005 | Ward |
| 6,989,452 B2 | 1/2006 | Ng |
| 7,008,942 B2 | 3/2006 | Chari |
| 7,049,316 B2 | 5/2006 | Zhao |
| 7,060,808 B1 | 6/2006 | Goldstein |
| 7,091,186 B2 | 8/2006 | Senter |
| 7,097,840 B2 | 8/2006 | Erickson |
| 7,098,308 B2 | 8/2006 | Senter |
| 7,129,261 B2 | 10/2006 | Ng |
| 7,129,332 B2 | 10/2006 | Pastan |
| 7,132,511 B2 | 11/2006 | Carr |
| 7,132,554 B2 | 11/2006 | Rose |
| 7,192,750 B2 | 3/2007 | Chung |
| 7,214,685 B2 | 5/2007 | Tietze |
| 7,217,819 B2 | 5/2007 | Chari |
| 7,223,837 B2 | 5/2007 | De Groot |
| 7,226,592 B2 | 6/2007 | Kreysch |
| 7,247,301 B2 | 7/2007 | Van de Winkel |
| 7,256,257 B2 | 8/2007 | Doronina |
| 7,264,806 B2 * | 9/2007 | Carr et al. .................. 424/144.1 |
| 7,276,497 B2 | 10/2007 | Chari |
| 7,276,499 B2 | 10/2007 | Chari |
| 7,276,585 B2 | 10/2007 | Lazar |
| 7,301,019 B2 | 11/2007 | Widdison |
| 7,303,749 B1 | 12/2007 | Chari |
| 7,329,760 B2 | 2/2008 | Zhao |
| 7,368,565 B2 | 5/2008 | Chari |
| 7,374,762 B2 | 5/2008 | Amphlett |
| 7,375,078 B2 | 5/2008 | Feng |
| 7,388,026 B2 | 6/2008 | Zhao |
| 7,390,898 B2 | 6/2008 | Baloglu |
| 7,396,810 B1 | 7/2008 | Clinton |
| 7,411,063 B2 | 8/2008 | Widdison |
| 7,414,073 B2 | 8/2008 | Baloglu |
| 7,423,116 B2 | 9/2008 | Doronina |
| 7,432,088 B2 | 10/2008 | Kuo |
| 7,449,559 B2 | 11/2008 | Ward |
| 7,473,796 B2 | 1/2009 | Chari |
| 7,476,669 B2 | 1/2009 | Chari |
| 7,476,724 B2 * | 1/2009 | Dennis et al. ............... 530/388.8 |
| 7,494,649 B2 | 2/2009 | Amphlett |
| 7,495,114 B2 | 2/2009 | Baloglu |

(56) References Cited

U.S. PATENT DOCUMENTS

| | | |
|---|---|---|
| 7,498,298 B2 | 3/2009 | Doronina |
| 7,498,302 B2 | 3/2009 | Ng |
| 7,501,120 B2 | 3/2009 | Amphlett |
| 7,514,080 B2 | 4/2009 | Amphlett |
| 7,517,903 B2 | 4/2009 | Chen |
| 7,521,541 B2 | 4/2009 | Eigenbrot |
| 7,528,130 B2 | 5/2009 | Chari |
| 7,550,609 B2 | 6/2009 | Chari |
| 7,553,809 B2 | 6/2009 | Baell et al. |
| 7,553,816 B2 | 6/2009 | Senter |
| 7,575,748 B1 | 8/2009 | Erickson |
| 7,585,857 B2 | 9/2009 | Chari |
| 7,589,180 B2 | 9/2009 | Old |
| 7,595,378 B2 | 9/2009 | Van de Winkel |
| 7,598,290 B2 | 10/2009 | Miller |
| 7,598,375 B2 | 10/2009 | Ho |
| 7,601,354 B2 | 10/2009 | Chari |
| 7,625,558 B2 | 12/2009 | Greene et al. |
| 7,628,986 B2 | 12/2009 | Weber |
| 7,635,570 B2 | 12/2009 | Siena |
| 7,651,687 B2 | 1/2010 | Buck |
| 7,655,660 B2 | 2/2010 | Zhao |
| 7,655,661 B2 | 2/2010 | Zhao |
| 7,659,241 B2 | 2/2010 | Senter |
| 7,667,054 B2 | 2/2010 | Miller |
| 7,691,962 B2 | 4/2010 | Boyd |
| 7,723,484 B2 | 5/2010 | Beidler |
| 7,736,644 B2 | 6/2010 | Weber |
| 7,745,394 B2 | 6/2010 | Doronina |
| 7,750,116 B1 | 7/2010 | Doronina |
| 7,754,681 B2 | 7/2010 | Feng |
| 7,767,792 B2 | 8/2010 | Johns |
| 7,790,164 B2 | 9/2010 | Cao |
| 7,807,798 B2 | 10/2010 | Jakobovits |
| 2001/0005747 A1 | 6/2001 | Ball |
| 2001/0036923 A1 | 11/2001 | Chari |
| 2001/0046686 A1 | 11/2001 | Wong |
| 2001/0048922 A1 | 12/2001 | Romet-Lemonne |
| 2001/0055595 A1 | 12/2001 | Goldenberg |
| 2002/0001587 A1 | 1/2002 | Erickson |
| 2002/0004587 A1 | 1/2002 | Miller |
| 2002/0006379 A1 | 1/2002 | Hansen |
| 2002/0012663 A1 | 1/2002 | Waksal |
| 2002/0013485 A1 | 1/2002 | Chari |
| 2002/0049335 A1 | 4/2002 | Boger |
| 2002/0062009 A1 | 5/2002 | Taylor |
| 2002/0064785 A1 | 5/2002 | Mass |
| 2002/0082424 A1 | 6/2002 | Boger |
| 2002/0156274 A1 | 10/2002 | Terfloth |
| 2002/0173629 A1 | 11/2002 | Jakobovits |
| 2003/0009152 A1 | 1/2003 | O'Hara et al. |
| 2003/0050331 A1 | 3/2003 | Ng |
| 2003/0055226 A1 | 3/2003 | Chari |
| 2003/0073731 A1 | 4/2003 | Lee |
| 2003/0073852 A1 | 4/2003 | Ng |
| 2003/0083263 A1 | 5/2003 | Doronina |
| 2003/0091561 A1 | 5/2003 | Van de Winkel |
| 2003/0096743 A1 | 5/2003 | Senter |
| 2003/0109682 A1 | 6/2003 | Santi |
| 2003/0130189 A1 | 7/2003 | Senter |
| 2003/0190363 A1 | 10/2003 | O'Connor et al. |
| 2003/0194403 A1 | 10/2003 | Van de Winkel |
| 2003/0195365 A1 | 10/2003 | Zhao |
| 2003/0199519 A1 | 10/2003 | Zhao |
| 2003/0211097 A1 | 11/2003 | Pastan |
| 2003/0211112 A1 | 11/2003 | Debinski |
| 2003/0215387 A1 | 11/2003 | Harrison |
| 2003/0224001 A1 | 12/2003 | Goldstein |
| 2004/0006212 A1 | 1/2004 | Goldstein |
| 2004/0033543 A1 | 2/2004 | Schwab |
| 2004/0086943 A1 | 5/2004 | Andres |
| 2004/0109867 A1 | 6/2004 | Yongxin |
| 2004/0131611 A1 | 7/2004 | Oliver |
| 2004/0144948 A1 | 7/2004 | Akhavan-Tafti et al. |
| 2004/0147428 A1 | 7/2004 | Pluenneke |
| 2004/0157782 A1 | 8/2004 | Doronina |
| 2004/0202666 A1 | 10/2004 | Griffiths |
| 2004/0235074 A1 | 11/2004 | Siegall |
| 2004/0235840 A1 | 11/2004 | Chari |
| 2004/0248196 A1 | 12/2004 | Adams |
| 2004/0253645 A1 | 12/2004 | Daugherty |
| 2005/0009751 A1 | 1/2005 | Senter |
| 2005/0014700 A1 | 1/2005 | Boger |
| 2005/0026987 A1 | 2/2005 | Boger |
| 2005/0031627 A1 | 2/2005 | Mazzola |
| 2005/0032860 A1 | 2/2005 | Boger |
| 2005/0053608 A1 | 3/2005 | Weber |
| 2005/0059087 A1 | 3/2005 | Weber |
| 2005/0064492 A1 | 3/2005 | DeSauvage |
| 2005/0100546 A1 | 5/2005 | Jakobovits |
| 2005/0106644 A1 | 5/2005 | Cairns |
| 2005/0107595 A1 | 5/2005 | Cairns |
| 2005/0113308 A1 | 5/2005 | Senter |
| 2005/0113571 A1 | 5/2005 | Terfloth |
| 2005/0142133 A1 | 6/2005 | Lazar |
| 2005/0152913 A1 | 7/2005 | Eldridge |
| 2005/0169933 A1 | 8/2005 | Steeves |
| 2005/0214310 A1 | 9/2005 | Toki |
| 2005/0227324 A1 | 10/2005 | Huang |
| 2005/0238640 A1 | 10/2005 | Sliwkowski |
| 2005/0238649 A1 | 10/2005 | Doronina |
| 2005/0255555 A1 | 11/2005 | Johns |
| 2005/0256030 A1 | 11/2005 | Feng |
| 2005/0271671 A1 | 12/2005 | Griffiths |
| 2005/0272083 A1 | 12/2005 | Seshagiri |
| 2005/0272798 A1 | 12/2005 | Ng |
| 2005/0276812 A1 | 12/2005 | Ebens |
| 2006/0004081 A1 | 1/2006 | Chen |
| 2006/0009462 A1 | 1/2006 | Yongxin |
| 2006/0024317 A1 | 2/2006 | Boyd |
| 2006/0029574 A1 | 2/2006 | Albitar et al. |
| 2006/0074008 A1 | 4/2006 | Senter |
| 2006/0084141 A1 | 4/2006 | Floss |
| 2006/0088523 A1 | 4/2006 | Andya |
| 2006/0116422 A1 | 6/2006 | DeGroot |
| 2006/0121044 A1 | 6/2006 | Amler |
| 2006/0147959 A1 | 7/2006 | Bell |
| 2006/0154334 A1 | 7/2006 | Tarnowski |
| 2006/0165685 A1 | 7/2006 | Kreysch |
| 2006/0182750 A1 | 8/2006 | Chari |
| 2006/0183887 A1 | 8/2006 | Jakobovits |
| 2006/0229253 A1 | 10/2006 | Doronina |
| 2006/0234343 A1 | 10/2006 | Ward |
| 2006/0247295 A1 | 11/2006 | Gangwar |
| 2007/0031402 A1 | 2/2007 | Zhang |
| 2007/0037972 A1 | 2/2007 | Ho |
| 2007/0048314 A1 | 3/2007 | Dai |
| 2007/0071675 A1 | 3/2007 | Wu |
| 2007/0092940 A1 | 4/2007 | Eigenbrot |
| 2007/0112188 A1 | 5/2007 | Widdison |
| 2007/0116707 A1 | 5/2007 | Goldstein |
| 2007/0134243 A1 | 6/2007 | Gazzard |
| 2007/0135346 A1 | 6/2007 | Zhao |
| 2007/0202101 A1 | 8/2007 | Rosen |
| 2007/0264266 A1 | 11/2007 | Chari |
| 2007/0269447 A1 | 11/2007 | Chari |
| 2007/0270585 A1 | 11/2007 | Chari |
| 2008/0008704 A1 | 1/2008 | Rubin |
| 2008/0025983 A1 | 1/2008 | Adams |
| 2008/0114153 A1 | 5/2008 | Steeves |
| 2008/0145374 A1 | 6/2008 | Steeves |
| 2008/0171040 A1 | 7/2008 | Ebens |
| 2008/0171856 A1 | 7/2008 | Steeves |
| 2008/0171865 A1 | 7/2008 | Steeves |
| 2008/0226657 A1 | 9/2008 | Doronina |
| 2008/0226659 A1 | 9/2008 | Erickson |
| 2008/0241128 A1 | 10/2008 | Jeffrey |
| 2008/0248051 A1 | 10/2008 | Doronina |
| 2008/0248053 A1 | 10/2008 | Doronina |
| 2008/0249085 A1 | 10/2008 | Cassady |
| 2008/0260685 A1 | 10/2008 | Zhao |
| 2008/0267960 A1 | 10/2008 | Drachman |
| 2008/0279868 A1 | 11/2008 | Boyd |
| 2008/0281102 A1 | 11/2008 | Gangwar |

(56) References Cited

U.S. PATENT DOCUMENTS

| | | |
|---|---|---|
| 2008/0293800 A1 | 11/2008 | Gangwar |
| 2008/0300192 A1 | 12/2008 | Doronina |
| 2008/0305044 A1 | 12/2008 | McDonagh |
| 2008/0311136 A1 | 12/2008 | Beusker |
| 2009/0010945 A1 | 1/2009 | Alley |
| 2009/0018086 A1 | 1/2009 | Doronina |
| 2009/0028821 A1 | 1/2009 | Zhao |
| 2009/0041791 A1 | 2/2009 | Feng |
| 2009/0047296 A1 | 2/2009 | Doronina |
| 2009/0053240 A1 | 2/2009 | Lazar |
| 2009/0111756 A1 | 4/2009 | Doronina |
| 2009/0117134 A1 | 5/2009 | Ward et al. |
| 2009/0137782 A1 | 5/2009 | Old |
| 2009/0142361 A1 | 6/2009 | Amphlett |
| 2009/0155282 A1 | 6/2009 | Weber |
| 2009/0156790 A1 | 6/2009 | Weber |
| 2009/0175865 A1 | 7/2009 | Eigenbrot |
| 2009/0175887 A1 | 7/2009 | Weber |
| 2009/0175888 A1 | 7/2009 | Ng |
| 2009/0202536 A1 | 8/2009 | Ebens |
| 2009/0214541 A1 | 8/2009 | Gillies |
| 2009/0220510 A1 | 9/2009 | Old |
| 2009/0240038 A1 | 9/2009 | Weber |
| 2009/0269343 A1 | 10/2009 | Bigner |
| 2009/0274713 A1 | 11/2009 | Chari |
| 2009/0280503 A1 | 11/2009 | Fiore |
| 2009/0281158 A1 | 11/2009 | Zhao |
| 2009/0297509 A1 | 12/2009 | Waksal et al. |
| 2009/0304693 A1 | 12/2009 | Ghayur |
| 2009/0306101 A1 | 12/2009 | Solca |
| 2009/0318668 A1 | 12/2009 | Beusker |
| 2009/0324621 A1 | 12/2009 | Senter |
| 2010/0008929 A1 | 1/2010 | Van De Winkel |
| 2010/0056762 A1 | 3/2010 | Old |
| 2010/0092475 A1 | 4/2010 | Johns |
| 2010/0166744 A1 | 7/2010 | Wong |
| 2010/0196265 A1 | 8/2010 | Adams |
| 2010/0203007 A1 | 8/2010 | Li |
| 2010/0322937 A1 | 12/2010 | Johns |
| 2011/0008766 A1 | 1/2011 | Ghayur |
| 2011/0076232 A1 | 3/2011 | Old |
| 2011/0150759 A1 | 6/2011 | Johns |
| 2011/0313230 A1* | 12/2011 | Johns et al. ............... 600/1 |
| 2012/0183471 A1 | 7/2012 | Old et al. |
| 2013/0095112 A1 | 4/2013 | Overgaard |
| 2013/0266573 A1 | 10/2013 | Old et al. |

FOREIGN PATENT DOCUMENTS

| | | |
|---|---|---|
| EP | 0519596 A1 | 12/1992 |
| EP | 0586002 A2 | 3/1994 |
| EP | 0699755 A2 | 3/1996 |
| EP | 1510221 A1 | 3/2005 |
| EP | 1392359 B1 | 10/2009 |
| EP | 2163256 A1 | 3/2010 |
| EP | 1392359 B1 | 7/2010 |
| WO | WO 85/03357 A1 | 8/1985 |
| WO | WO 91/03489 A1 | 3/1991 |
| WO | WO 91/16350 A1 | 10/1991 |
| WO | WO 92/15683 A1 | 9/1992 |
| WO | WO 93/011161 A1 | 6/1993 |
| WO | WO 94/13804 A1 | 6/1994 |
| WO | WO-95/20045 A1 | 7/1995 |
| WO | WO 95/25167 A1 | 9/1995 |
| WO | WO 96/16988 A1 | 6/1996 |
| WO | WO 96/40210 A1 | 12/1996 |
| WO | WO 99/44645 A1 | 9/1999 |
| WO | WO 02/11677 A2 | 2/2002 |
| WO | WO 02/092771 | 11/2002 |
| WO | WO-03/014149 A2 | 2/2003 |
| WO | WO-03/014159 A1 | 2/2003 |
| WO | WO 03/014159 A1 | 2/2003 |
| WO | 2003/072727 | 9/2003 |
| WO | WO 02/092771 A1 | 11/2003 |
| WO | WO 2004/003019 A2 | 1/2004 |
| WO | WO 2004/056847 A2 | 7/2004 |
| WO | WO 2004/085474 A2 | 10/2004 |
| WO | 2005/090407 | 9/2005 |
| WO | WO 2005/081854 A2 | 9/2005 |
| WO | WO 2005/094357 A2 | 10/2005 |
| WO | WO 2005/081854 A1 | 8/2006 |
| WO | WO-2007/080392 A2 | 7/2007 |
| WO | WO-2008/152537 A2 | 7/2007 |
| WO | WO 2007/089149 A2 | 8/2007 |
| WO | WO 2007/103288 A2 | 9/2007 |
| WO | WO 2008/033495 A2 | 3/2008 |
| WO | WO 2008/091701 A2 | 7/2008 |
| WO | WO 2008/091701 A1 | 8/2008 |
| WO | WO 2008/115404 A1 | 9/2008 |
| WO | WO 2008/154927 A1 | 12/2008 |
| WO | WO 2009/017394 A1 | 2/2009 |
| WO | WO 2009/023265 A1 | 2/2009 |
| WO | WO 2008/033495 A1 | 3/2009 |
| WO | WO 2008/115404 A1 | 9/2009 |
| WO | WO 2009/023265 A1 | 2/2010 |
| WO | WO 2010/096434 | 4/2010 |
| WO | WO 2010/096434 A2 | 8/2010 |
| WO | WO 2011/035465 A1 | 3/2011 |
| WO | WO 2011/041319 A2 | 4/2011 |
| WO | WO 2010/096434 A1 | 8/2011 |
| WO | WO-2012/135360 A1 | 10/2012 |

OTHER PUBLICATIONS

Aboud-Pirak et al., "Efficacy of antibodies to epidermal growth factor receptor against KB carcinoma in vitro and in nude mice" *Chemical Abstracts* (1989) 69068k, 110(9).

Aboud-Pirak et al., "Inhibition of human tumor growth in nude mice by a conjugate of doxorubicin with monoclonal antibodies to epidermal growth factor receptor." *Proceedings of the National Academy of Sciences of the United States of America* (1989) 3778-3781, 86(10).

Aboud-Pirak et al., "Efficacy of antibodies to epidermal growth factor receptor against KB carcinoma in vitro and in nude mice." *J. Natl. Cancer Inst.* (1988) 1605-1611, 80(20).

Adams et al., "Monoclonal antibody therapy of cancer." *Nat. Biotechnol.* (2005) 1147-1157, 23(9).

Aden et al., "Cell Surface Antigens Coded for by the Human Chromosome 7" *Immunogenetics* (1976) 209-221, 3.

Aghajanian et al., "A phase II study of cetuximab/paclitaxel/carboplatin for the initial treatment of advanced stage ovarian, primary peritoneal, and fallopian tube cancer" *Journal of Clinical Oncology, 2005 ASCO Annual Meeting Proceedings* (2005) Abstract 5047, 23(16S; Part I of II: Jun. 1 Supplement).

Agosti et al., "Expression of the epidermal growth factor receptor in astrocytic tumours is specifically associated with glioblastoma multiforme." *Virchows Archiv. A, Pathological Anatomy and Histopathology* (1992) 321-325, 420(4).

Agulnik et al., "Predictive and pharmacodynamic biomarker studies in tumor and skin tissue samples of patients with recurrent or metastatic squamous cell carcinoma of the head and neck treated with erlotinib." *Journal of Clinical Oncology* (2007) 2184-2190, 25(16).

Agus et al., "Phase I clinical study of pertuzumab, a novel HER dimerization inhibitor, in patients with advanced cancer." *J. Clin. Oncol.* (2005) 2534-2543, 23(11).

Agus et al., "Targeting ligand-activated ErbB2 signaling inhibits breast and prostate tumor growth." *Cancer Cell* (2002) 127-137, 2(2).

Akiyama et al., "Genistein, a specific inhibitor of tyrosine-specific protein kinases." *JBC* (1987) 5592-5595, 262(12).

Albanell et al., "Activated extracellular signal-regulated kinases: association with epidermal growth factor receptor/transforming growth factor alpha expression in head and neck squamous carcinoma and inhibition by anti-epidermal growth factor receptor treatments." *Cancer Res.* (2001) 6500-6510, 61(17).

Albanell et al., "Pharmacodynamic studies of the epidermal growth factor receptor inhibitor ZD1839 in skin from cancer patients: histopathologic and molecular consequences of receptor inhibition." *J. Clin. Oncol.* (2002) 110-124, 20(1).

(56) References Cited

OTHER PUBLICATIONS

Albanell et al., "Pharmacodynamic studies with the epidermal growth factor receptor tyrosine kinase inhibitor ZD1839" *Seminars in Oncology* (2001) 56-66, 28.
Aldape et al., "Immunohistochemical detection of EGFRvIII in high malignancy grade astrocytomas and evaluation of prognostic significance." *Journal of neuropathology and experimental neurology* (2004) 700-707, 63(7).
Alimirah et al., "DU-145 and PC-3 human prostate cancer cell lines express androgen receptor: implications for the androgen receptor functions and regulation." *FEBS letters* (2006) 2294-2300, 580(9).
Alroy et al., "The ErbB signaling network in embryogenesis and oncogenesis: signal diversification through combinatorial ligand-receptor interactions." *FEBS letters* (1997) 83-86, 410(1).
Anderson et al., "ZD1839 (Iressa), a novel epidermal growth factor receptor (EGFR) tyrosine kinase inhibitor, potently inhibits the growth of EGFR-positive cancer cell lines with or without erbB2 overexpression." *Int. J. Cancer* (2001) 774-782, 94(6).
Andrews et al., "Cellular pharmacology of cisplatin: perspectives on mechanisms of acquired resistance." *Cancer cells* (1990) 35-43, 2(2).
Ang et al., "Epidermal growth factor receptor and response of head-and-neck carcinoma to therapy." *Int. J. Radiat. Oncol. Biol. Phys.* (2004) 959-965, 58(3).
Ang et al., "Impact of epidermal growth factor receptor expression on survival and pattern of relapse in patients with advanced head and neck carcinoma." *Cancer Res.* (2002) 7350-7356, 62(24).
Anido et al., "ZD1839, a specific epidermal growth factor receptor (EGFR) tyrosine kinase inhibitor, induces the formation of inactive EGFR/HER2 and EGFR/HER3 heterodimers and prevents heregulin signaling in HER2-overexpressing breast cancer cells." *Clin. Cancer Res.* (2003) 1274-1283, 9(4).
Archer et al., "Regional treatment of epidermal growth factor receptor vIII-expressing neoplastic meningitis with a single-chain immunotoxin, MR-1." *Clin. Cancer Res.* (1999) 2646-2652, 5(9).
Arteaga et al., "Antibodies Against p185HER2 Enhance Etoposide-Induced Cytotoxicity Against Human Breast Carcinoma Cells." *Proceedings of the American Society of Clinical Oncology* (1993) 75 (Abstract 101), 12.
Arteaga et al., "Tyrosine kinase inhibitors-ZD1839 (Iressa)." *Current opinion in oncology* (2001) 491-498, 13(6).
Arteaga, "The epidermal growth factor receptor: from mutant oncogene in nonhuman cancers to therapeutic target in human neoplasia." *J. Clin. Oncol.* (2001) 32S-40S, 19(18; Supplement).
Arteaga et al., "Unliganded epidermal growth factor receptor dimerization induced by direct interaction of quinazolines with the ATP binding site." *JBC* (1997) 23247-23254, 272(37).
Arteaga et al., "Tyrosine kinase inhibitors: why does the current process of clinical development not apply to them?" *Cancer Cell* (2004) 525-531, 5(6).
Arteaga, "ErbB-targeted therapeutic approaches in human cancer." *Exp. Cell Res.* (2003) 122-130, 284(1).
Arteaga, "Overview of epidermal growth factor receptor biology and its role as a therapeutic target in human neoplasia." *Semin. Oncol.* (2002) 3-9, 29(5 Suppl 14).
Arteaga et al., "Overview of rationale and clinical trials with signal transduction inhibitors in lung cancer." *Semin. Oncol.* (2002) 15-26, 29(1; Suppl. 4).
Arteaga, "Epidermal growth factor receptor dependence in human tumors: more than just expression?" *Oncologist* (2002) 31-39, 7(Suppl. 4).
Ashley et al., "Monoclonal antibodies to growth factors and growth factor receptors: their diagnostic and therapeutic potential in brain tumors." *Journal of neuro-oncology* (1997) 259-273, 35(3).
Atlas et al., "Growth regulation of human renal carcinoma cells: role of transforming growth factor alpha." *Cancer Res.* (1992) 3335-3339, 52(12).
Aujame et al., "High affinity human antibodies by phage display." *Human antibodies* (1997) 155-168, 8(4).
Austin et al., "Endocytosis and sorting of ErbB2 and the site of action of cancer therapeutics trastuzumab and geldanamycin." *Mol. Biol. Cell* (2004) 5268-5282, 15(12).
Avital et al., "Radioimmunoguided surgery for recurrent colorectal cancer manifested by isolated CEA elevation." *Cancer* (2000) 1692-1698, 89(8).
Azzazy et al., "Phage display technology: clinical applications and recent innovations." *Clinical biochemistry* (2002) 425-445, 35(6).
Baerga-Ortiz et al., "Epitope mapping of a monoclonal antibody against human thrombin by H/D-exchange mass spectrometry reveals selection of a diverse sequence in a highly conserved protein." *Protein science* (2002) 1300-1308, 11(6).
Bailey et al., "Evaluation of epidermal growth factor receptor (EGFR) as a predictive marker in patients with non-small-cell lung cancer (NSCLC) receiving first-line gefitinib combined with platinum-based chemotherapy" *Journal of Clinical Oncology, 2004 ASCO Annual Meeting Proceedings (Post-Meeting Edition)* (2004) Abstract 7013, 22(14S; Jul. 15 Supplement).
Balaban et al., "The effect of ionizing radiation on signal transduction: antibodies to EGF receptor sensitize A431 cells to radiation." *Biochimica et biophysica acta* (1996) 147-156, 1314(1-2).
Baly et al., "Development and characterization of a rhuMAb HER2 antibody ADCC assay for clinical evaluation of cytotoxic potency." *Proceedings of the American Association for Cancer Research* (1997) 27-28 (Abstract 181), 38.
Bandyopadhyay et al., "Physical interaction between epidermal growth factor receptor and DNA-dependent protein kinase in mammalian cells." *JBC* (1998) 1568-1573, 273(3).
Barendswaard et al., "Rapid and specific targeting of monoclonal antibody A33 to a colon cancer xenograft in nude mice." *Int. J. Oncol.* (1998) 45-53, 12(1).
Barnette et al., "Association of the anti-inflammatory activity of phosphodiesterase 4 (PDE4) inhibitors with either inhibition of PDE4 catalytic activity or competition for [3H]rolipram binding." *Biochemical pharmacology* (1996) 949-956, 51(7).
Baselga et al., "Phase I study of AEE788, a novel multitargeted inhibitor of ErbB and VEGF receptor family tyrosine kinases (A pharmacokinetic (PK)-pharmacodynamic (PD) study to identify the optimal therapeutic dose regimen)." *J. Clinical Oncology* (2005) Abstract 3028, 23.
Baselga et al., "Cetuximab (C225) plus cisplatin/carboplatin is active in patients (pts) with recurrent/metastatic squamous cell carcinoma of the head and neck (SCCHN) progressing on a same dose and schedule platinum-based regimen" *Proceedings of the American Society of Clinical Oncology* (2002) Abstract 900, 21.
Baselga et al., "Antitumor activity of paclitaxel in combination with anti-growth factor receptor monoclonal antibodies in breast cancer xenografts." *Proceedings of the American Association for Cancer Research* (1994) 380 (Abstract 2262), 35.
Baselga, "Combining the Anti-EGFR Agent Gefitinib With Chemotherapy in Non-Small-Cell Lung Cancer: How Do We Go From Intact to Impact?" *Journal of Clinical Oncology* (2004) 759-761, 22(5).
Baselga et al., "Phase I safety, pharmacokinetic, and pharmacodynamic trial of ZD1839, a selective oral epidermal growth factor receptor tyrosine kinase inhibitor, in patients with five selected solid tumor types." *J. Clin. Oncol.* (2002) 4292-4302, 20(21).
Baselga et al., "Mechanism of action of trastuzumab and scientific update." *Semin. Oncol.* (2001) 4-11, 28(5; Suppl. 16).
Baselga, "Targeting the epidermal growth factor receptor: a clinical reality." *J. Clin. Oncol.* (2001) 41S-44S, 19(18; Supplement).
Baselga, "The EGFR as a target for anticancer therapy—focus on cetuximab." *Eur. J. Cancer* (2001) S16-22, 37 Suppl 4.
Baselga, "Clinical trials of Herceptin(R) (trastuzumab)." *Eur. J. Cancer* (2001) 18-24, 37 Suppl 1.
Baselga, "Herceptin alone or in combination with chemotherapy in the treatment of HER2-positive metastatic breast cancer: pivotal trials." *Oncology* (2001) 14-21, 61(Suppl. 2).
Baselga et al., "Mechanism of action of anti-HER2 monoclonal antibodies." *Ann Oncol.* (2001) S35-41, 12(Suppl. 1).
Baselga et al., "Phase I studies of anti-epidermal growth factor receptor chimeric antibody C225 alone and in combination with cisplatin." *J. Clin. Oncol.* (2000) 904-914, 18(4).

(56) References Cited

OTHER PUBLICATIONS

Baselga et al., "Continuous Administration of ZD1839 (Iressa), a Novel Oral Epidermal Growth Factor Receptor Tyrosine Kinase Inhibitor (EGFR-TKI), in Patients with Five Selected Tumor Types: Evidence of Activity and Good Tolerability (Abstract 686)" *Proceedings of the American Society of Clinical Oncology* (2000) 177a, 19.
Baselga et al., "ZD1839 ('Iressa') as an anticancer agent." *Drugs* (2000) 33-40; discussion 41-2, 60(Suppl. 1).
Baselga et al., "Recombinant humanized anti-HER2 antibody (Herceptin) enhances the antitumor activity of paclitaxel and doxorubicin against HER2/neu overexpressing human breast cancer xenografts." *Cancer Res.* (1998) 2825-2831, 58(13).
Baselga et al., "Phase II study of weekly intravenous recombinant humanized anti-p185HER2 monoclonal antibody in patients with HER2/neu-overexpressing metastatic breast cancer." *J. Clin. Oncol.* (1996) 737-744, 14(3).
Baselga et al., "Receptor blockade with monoclonal antibodies as anti-cancer therapy." *Pharmacology & Therapeutics* (1994) 127-154, 64(1).
Baselga et al., "Antitumor effects of doxorubicin in combination with anti-epidermal growth factor receptor monoclonal antibodies." *J. Natl. Cancer Inst.* (1993) 1327-1333, 85(16).
Baselga, "Targeting tyrosine kinases in cancer: the second wave." *Science* (2006) 1175-1178, 312(5777).
Baselga et al., "Phase II multicenter study of the antiepidermal growth factor receptor monoclonal antibody cetuximab in combination with platinum-based chemotherapy in patients with platinum-refractory metastatic and/or recurrent squamous cell carcinoma of the head and neck." *J. Clin. Oncol.* (2005) 5568-5577, 23(24).
Baselga et al., "Phase II and tumor pharmacodynamic study of gefitinib in patients with advanced breast cancer." *J. Clin. Oncol.* (2005) 5323-5333, 23(23).
Baselga et al., "Critical update and emerging trends in epidermal growth factor receptor targeting in cancer." *J. Clin. Oncol.* (2005) 2445-2459, 23(11).
Baselga et al., "Phase II study of efficacy, safety, and pharmacokinetics of trastuzumab monotherapy administered on a 3-weekly schedule." *J. Clin. Oncol.* (2005) 2162-2171; 23(10).
Baselga, "Why the epidermal growth factor receptor? The rationale for cancer therapy." *Oncologist* (2002) 2-8, 7(Suppl. 4).
Batra et al., "Epidermal growth factor ligand-independent, unregulated, cell-transforming potential of a naturally occurring human mutant EGFRvIII gene." *Cell growth & differentiation: the molecular biology journal of the American Association for Cancer Research* (1995) 1251-1259, 6(10).
Beckmann et al., "Expression analyses of epidermal growth factor receptor and HER-2/neu: no advantage of prediction of recurrence or survival in breast cancer patients." *Oncology* (1996) 441-447, 53(6).
Beers et al., "Immunotoxins with increased activity against epidermal growth factor receptor vIII-expressing cells produced by antibody phage display." *Clin. Cancer Res.* (2000) 2835-2843, 6(7).
Behr et al., "Radioimmunotherapy of small volume disease of colorectal cancer metastatic to the liver: preclinical evaluation in comparison to standard chemotherapy and initial results of a phase I clinical study." *Clin. Cancer Res.* (1999) 3232s-3242s, 5(10; Supplement).
Behr et al., "Radioimmunotherapy of small-vol. disease of metastatic colorectal cancer." *Cancer* (2002) 1373-1381, 94(4 Suppl).
Bell et al., "Inherited susceptibility to lung cancer may be associated with the T790M drug resistance mutation in EGFR." *Nature genetics* (2005) 1315-1316, 37(12).
Bell et al., "Epidermal growth factor receptor mutations and gene amplification in non-small-cell lung cancer: molecular analysis of the IDEAL/INTACT gefitinib trials." *J. Clin. Oncol.* (2005) 8081-8092, 23(31).
Bender et al., "Immunotherapy of human glioma xenografts with unlabeled, 131I-, or 125I-labeled monoclonal antibody 425 to epidermal growth factor receptor." *Cancer Res.* (1992) 121-126, 52(1).
Benichou et al., "Random fragment libraries using yeast expression plasmid." *Methods Mol. Biol.* (1996) 241-255, 66.

Bequinot et al., "Down-regulation of the epidermal growth factor receptor in KB cells is due to receptor internalization and subsequent degradation in lysosomes" *Chemical Abstract* (1984) 1592k, p. 141, 101.
Berkers et al., "The effects of receptor density and cell shape on epidermal growth factor binding." *Journal of Receptor Research* (1992) 71-100, 12(1).
Bernier, "Cetuximab in the treatment of head and neck cancer." *Expert review of anticancer therapy* (2006) 1539-1552, 6(11).
Bertics et al., "Alteration of epidermal growth factor receptor activity by mutation of its primary carboxyl-terminal site of tyrosine self-phosphorylation." *JBC* (1988) 3610-3617, 263(8).
Bertics et al., "Self-phosphorylation enhances the protein-tyrosine kinase activity of the epidermal growth factor receptor." *JBC* (1985) 14642-14647, 260(27).
Bhattacharya-Chatterjee et al., "The anti-idiotype vaccines for immunotherapy." *Current opinion in molecular therapeutics* (2001) 63-69, 3(1).
Bianco et al., "Antitumor activity of combined treatment of human cancer cells with ionizing radiation and anti-epidermal growth factor receptor monoclonal antibody C225 plus type I protein kinase A antisense oligonucleotide." *Clin. Cancer Res.* (2000) 4343-4350, 6(11).
Bianco et al., "Loss of PTEN/MMAC1/TEP in EGF receptor-expressing tumor cells counteracts the antitumor action of EGFR tyrosine kinase inhibitors." *Oncogene* (2003) 2812-2822, 22(18).
Bier et al., "Clinical trial with escalating doses of the antiepidermal growth factor receptor humanized monoclonal antibody EMD 72 000 in patients with advanced squamous cell carcinoma of the larynx and hypopharynx." *Cancer chemotherapy and pharmacology* (2001) 519-524, 47(6).
Bier et al., "Anti-(epidermal growth factor) receptor monoclonal antibodies for the induction of antibody-dependent cell-mediated cytotoxicity against squamous cell carcinoma lines of the head and neck." *Cancer Immunol. Immunother.* (1998) 167-173, 46(3).
Bier et al., "Dose-dependent access of murine anti-epidermal growth factor receptor monoclonal antibody to tumor cells in patients with advanced laryngeal and hypopharyngeal carcinoma." *European archives of oto-rhino-laryngology: official journal of the European Federation of Oto-Rhino-Laryngological Societies (EUFOS): affiliated with the German Society for Oto-Rhino-Laryngology—Head and Neck Surgery* (1995) 433-439, 252(7).
Biernat et al., "Predominant expression of mutant EGFR (EGFRvIII) is rare in primary glioblastomas." *Brain Pathology (Zurich, Switzerland)* (2004) 131-136, 14(2).
Bigner et al., "Characterization of the epidermal growth factor receptor in human glioma cell lines and xenografts." *Cancer Res.* (1990) 8017-8022, 50(24).
Bindon et al., "Importance of antigen specificity for complement-mediated lysis by monoclonal antibodies." *European Journal of Immunology* (1988) 1507-1514, 18(10).
Bird et al., "Single-chain antigen-binding proteins." *Science* (1988) 423-426, 242(4877).
Biscardi et al., "c-Src, receptor tyrosine kinases, and human cancer." *Advances in Cancer Research* (1999) 61-119, 76.
Bishop, "The molecular genetics of cancer." *Science* (1987) 305-311, 235(4786).
Bishop et al., "Differential sensitivity of cancer cells to inhibitors of the epidermal growth factor receptor family." *Oncogene* (2002) 119-127, 21(1).
Blagosklonny et al., "Why Iressa failed: toward novel use of kinase inhibitors (outlook)." *Cancer biology & Therapy* (2003) 137-140, 2(2).
Bleeker et al., "Dual mode of action of a human anti-epidermal growth factor receptor monoclonal antibody for cancer therapy." *Journal of immunology (Baltimore, Md : 1950)* (2004) 4699-4707, 173(7).
Blume-Jensen et al., "Oncogenic kinase signalling." *Nature* (2001) 355-365, 411(6835).
Boder et al., "Phage Display and Its Applications" *Methods Enzymol.* Chapter 25: "Yeast Surface Display for Directed Evolution of Protein Expression, Affinity and Stability" (2000) 430-444, 328.

(56) References Cited

OTHER PUBLICATIONS

Boder et al., "Directed evolution of antibody fragments with monovalent femtomolar antigen-binding affinity." *Proceedings of the National Academy of Sciences of the United States of America* (2000) 10701-10705, 97(20).

Boder et al., "Yeast surface display for screening combinatorial polypeptide libraries." *Nat. Biotechnol.* (1997) 553-557, 15(6).

Bogan et al., "Anatomy of hot spots in protein interfaces." *J. Mol. Biol.* (1998) 1-9, 280(1).

Boger, "Design, synthesis, and evaluation of DNA minor groove binding agents: the duocarmycins" *Pure & Appl. Chem.* (1994) 837-844, 66(4).

Boghaert et al., "Antibody-targeted chemotherapy with the calicheamicin conjugate hu3S193-N-acetyl gamma calicheamicin dimethyl hydrazide targets Lewisy and eliminates Lewisy-positive human carcinoma cells and xenografts." *Clin. Cancer Res.* (2004) 4538-4549, 10(13).

Bonner et al., "Cetuximab improves locoregional control and survival of locoregionally advanced head and neck cancer: independent review of mature data with a median follow-up of 45 months" *Presented at the Annual AACR-NCI-EORTC International Conference on Molecular Targets and Cancer Therapeutics: Discovery, Biology, and Clinical Applications; Nov. 14-18, 2005. Philadelphia, Pa.* (2011) Abstract B106.

Bonner et al., "Cetuximab prolongs survival in patients with locoregionally advanced squamous cell carcinoma of head and neck (a phase III study of high dose radiation therapy with or without cetuximab)" *Journal of Clinical Oncology, 2004 ASCO Annual Meeting Proceedings (Post-Meeting Edition)* (2004) Abstract 5507, 22(14S; Jul. 15 Supplement).

Bonner et al., "Continued response following treatment with IMC-C225, an EGFr MoAb combined with RT in advanced head and neck malignancies" *Proceedings of the Annual Meeting of the American Society of Clinical Oncology* (2000) 4a (Abstract 5F), 10.

Bonner et al., "Enhanced apoptosis with combination C225/radiation treatment serves as the impetus for clinical investigation in head and neck cancers." *J. Clin. Oncol.* (2000) 47S-53S, 18(21; Supplement).

Bonner et al., "Radiotherapy plus cetuximab for squamous-cell carcinoma of the head and neck." *N. Engl. J. Med.* (2006) 567-578, 354(6).

De Bono et al., "The ErbB receptor family: a therapeutic target for cancer." *Trends in molecular medicine* (2002) S19-26, 8(4; Supplement).

Boonstra et al., "The epidermal growth factor." *Cell biology international* (1995) 413-430, 19(5).

Bos et al., "Phase I studies of anti-epidermal growth factor receptor chimeric monoclonal antibody C225 in patients with EGFR overexpressing tumors" *American Society of Clinical Oncology* (1966) 443 (Abstract 1381), 15.

Bos et al., "PD153035, a tyrosine kinase inhibitor, prevents epidermal growth factor receptor activation and inhibits growth of cancer cells in a receptor number-dependent manner." *Clin. Cancer Res.* (1997) 2099-2106, 3(11).

Boschelli, "Small molecule inhibitors of receptor tyrosine kinases" *Drugs of the Future* (1999) 515-537, 24(5).

Bouyain et al., "The extracellular region of ErbB4 adopts a tethered conformation in the absence of ligand." *Proceedings of the National Academy of Sciences of the United States of America* (2005) 15024-15029, 102(42).

Boyer et al., "Relative cytotoxic activity of immunotoxins reactive with different epitopes on the extracellular domain of the c-erbB-2 (HER-2/neu) gene product p185." *Int. J. Cancer* (1999) 525-531, 82(4).

Brady et al., "Malignant astrocytomas treated with iodine-125 labeled monoclonal antibody 425 against epidermal growth factor receptor: a phase II trial." *Int. J. Radiat. Oncol. Biol. Phys.* (1992) 225-230, 22(1).

Brock et al., "Current perspectives in gliomas." *Medical oncology (Northwood, London, England)* (1997) 103-120, 14(2).

Brown et al., "Antibodies vol. 1: A practical approach" *Murine Monoclonal Antibodies. Antibodies* vol. 1. *A Practical Approach. D. Catty. Oxford England, IRL Press* (1988) 81-104.

Brown et al., "Antiepidermal growth factor receptor antibodies augment cytotoxicity of chemotherapeutic agents on squamous cell carcinoma cell lines." *Otolaryngology—Head and Neck Surgery: Official Journal of American Academy of Otolaryngology-Head and Neck Surgery* (2000) 75-83, 122(1).

Brüggemann et al., "The immunogenicity of chimeric antibodies." *The Journal of Experimental Medicine* (1989) 2153-2157, 170(6).

Bruns et al., "Blockade of the epidermal growth factor receptor signaling by a novel tyrosine kinase inhibitor leads to apoptosis of endothelial cells and therapy of human pancreatic carcinoma." *Cancer Res.* (2000) 2926-2935, 60(11).

Bruns et al., "Epidermal growth factor receptor blockade with C225 plus gemcitabine results in regression of human pancreatic carcinoma growing orthotopically in nude mice by antiangiogenic mechanisms." *Clin. Cancer Res.* (2000) 1936-1948, 6(5).

Bucci et al., "EGF-R expression in ductal breast cancer: proliferation and prognostic implications." *Anticancer research* (1997) 769-774, 17(1B).

Bucholtz, "Radiolabeled antibody therapy." *Seminars in oncology nursing* (1987) 67-73, 3(1).

Buchsbaum et al., "Experimental radioimmunotherapy." *Medical physics* (1993) 551-567, 20(2; Part 2).

Budillon et al., "ZD1839, An Epidermal Growth Factor Receptor Tyrosine Kinase Inhibitor, Upgregulates P27KIP1 Inducing G1 Arrest and Enhancing the Antitumor Effect of Interferon" *Proceedings of the Annual Meeting of the American Association for Cancer Research* (2000) 773 (Abstract 4910), 41.

Burgess et al., "Murine epidermal growth factor: heterogeneity on high resolution ion-exchange chromatography." *EMBO J.* (1983) 2065-2069, 2(11).

Burgess, "EGFR family: structure physiology signalling and therapeutic targets." *Growth Factors* (2008) 263-274, 26(5).

Burgess et al., "An open-and-shut case? Recent insights into the activation of EGF/ErbB receptors." *Mol. Cell* (2003) 541-552, 12(3).

Burris et al., "Phase I safety, pharmacokinetics, and clinical activity study of lapatinib (GW572016), a reversible dual inhibitor of epidermal growth factor receptor tyrosine kinases, in heavily pretreated patients with metastatic carcinomas." *J. Clin. Oncol.* (2005) 5305-5313, 23(23).

Burstein et al., "A phase II, open-label, multicenter study of lapatinib in two cohorts of patients with advanced or metastatic breast cancer who have progressed while receiving Trastuzumab-containing regimens." *Annals of Oncology* (2004) 27 (Abstract 1040), 15(Suppl. 3).

Burstein et al., "Trastuzumab and vinorelbine as first-line therapy for HER2-overexpressing metastatic breast cancer: multicenter phase II trial with clinical outcomes, analysis of serum tumor markers as predictive factors, and cardiac surveillance algorithm." *J. Clin. Oncol.* (2003) 2889-2895, 21(15).

Burtness et al., "Phase III trial comparing cisplatin (C) + placebo to C + anti-epidermal growth factor antibody (EGF-R) C225 in patients (pts) with metastatic/recurrent head & neck cancer (HNC) (Abstract 901)" *Proceedings of the American Society of Clinical Oncology* (2002) 226a, 21.

Burtness et al., "Phase III randomized trial of cisplatin plus placebo compared with cisplatin plus cetuximab in metastatic/recurrent head and neck cancer: an Eastern Cooperative Oncology Group study." *J. Clin. Oncol.* (2005) 8646-8654, 23(34).

Busam et al., "Cutaneous side-effects in cancer patients treated with the antiepidermal growth factor receptor antibody C225." *The British journal of dermatology* (2001) 1169-1176, 144(6).

Buss et al., "Altered epidermal growth factor (EGF)-stimulated protein kinase activity in variant A431 cells with altered growth responses to EGF." *Proceedings of the National Academy of Sciences of the United States of America* (1982) 2574-2578, 79(8).

Cadena et al., "Receptor protein tyrosine kinases." *In: Protein Phosphorylation (Chapter 9) (Editor: Marks; Publisher: VCH Publishers, Inc., New York, NY).* (1996) 265-284.

Cadena et al., "The intracellular tyrosine kinase domain of the epidermal growth factor receptor undergoes a conformational change upon autophosphorylation." *JBC* (1994) 260-265, 269(1).

(56) References Cited

OTHER PUBLICATIONS

Cai et al., "Quantitative PET of EGFR expression in xenograft-bearing mice using 64Culabeled cetuximab, a chimeric anti-EGFR monoclonal antibody." *European Journal of Nuclear Medicine and Molecular Imaging* (2007) 850-858, 34(6).
Caldas et al., "Humanization of the anti-CD18 antibody 6.7: an unexpected effect of a framework residue in binding to antigen." *Mol. Immunol.* (2003) 941-952, 39(15).
Callaghan et al., "A complete description of the EGF-receptor exon structure: implication in oncogenic activation and domain evolution." *Oncogene* (1993) 2939-2948, 8(11).
Campos-González et al., "Immunodetection of the ligand-activated receptor for epidermal growth factor." *Growth Factors* (1991) 305-316, 4(4).
Cappuzzo et al., "Increased HER2 gene copy number is associated with response to gefitinib therapy in epidermal growth factor receptor-positive non-small-cell lung cancer patients." *J. Clin. Oncol.* (2005) 5007-5018, 23(22).
Cappuzzo et al., "Epidermal growth factor receptor gene and protein and gefitinib sensitivity in non-small-cell lung cancer." *J. Natl. Cancer Inst.* (2005) 643-655, 97(9).
Carlin et al., "S6 is the human receptor for epidermal growth factor (EGF)" *Cell Genet.* (1982) 256, 32.
Carlin et al., "Identity of human epidermal growth factor (GFf) receptor with glycoprotein SA-7: evidence for differential phosphorylation of the two components of the EGF receptor from A431 cells." *Proceedings of the National Academy of Sciences of the United States of America* (1982) 5026-5030, 79(16).
Carpenter, "Receptors forepidermal growth factor and other polypeptide mitogens." *Annual Review of Biochemistry* (1987) 881-914, 56.
Carpenter, "Properties of the receptor for epidermal growth factor." *Cell* (1984) 357-358, 37(2).
Carteni et al., "Panitumumab a novel drug in cancer treatment." *Ann Oncol.* (2007) vi16-21, 18 Suppl 6.
Carter, "Identification and validation of cell surface antigens for antibody targeting in oncology" *Endocrine-Related Cancer* (2004) 659-687, 11(4).
Carter, "Improving the efficacy of antibody-based cancer therapies." *Nature Rev Cancer* (2001) 118-129, 1(2).
Carter et al., "Humanization of an anti-p185HER2 antibody for human cancer therapy." *Proceedings of the National Academy of Sciences of the United States of America* (1992) 4285-4289, 89(10).
Carter et al., "Tissue-specific transformation by oncogenic mutants of epidermal growth factor receptor." *Critical reviews in oncogenesis* (1994) 389-428, 5(4).
Cartron et al., "Therapeutic activity of humanized anti-CD20 monoclonal antibody and polymorphism in IgG Fc receptor FcγRIIIa gene." *Blood* (2002) 754-758, 99(3).
Casado et al., "A phase I/IIA pharmacokinetic (PK) and serial skin and tumor pharmacodynamic (PD) study of the EGFR irreversible tyrosine kinase inhibitor EKB-569 in combination with 5-fluorouracil (5FU), leucovorin (LV) and irinotecan (CPT-11) (FOLFIRI regimen) in patients (pts) with advanced colorectal cancer (ACC). " *Journal of Clinical Oncology* (2004) 255s (Abstract 3543), 22.
Casset et al., "A peptide mimetic of an anti-CD4 monoclonal antibody by rational design." *Biochem. Biophys. Res. Commun.* (2003) 198-205, 307(1).
Catimel et al., "Purification and characterization of a novel restricted antigen expressed by normal and transformed human colonic epithelium." *JBC* (1996) 25664-25670, 271(41).
Chaffanet et al., "EGF receptor amplification and expression in human brain tumours." *Eur. J. Cancer* (1992) 11-17, 28(1).
Chakravarti et al., "Insulin-like growth factor receptor I mediates resistance to anti-epidermal growth factor receptor therapy in primary human glioblastoma cells through continued activation of phosphoinositide 3-kinase signaling." *Cancer Res.* (2002) 200-207, 62(1).

Chan et al., "EGFR Tyrosine Kinase Inhibition Decreases Epithelial Proliferation in DCIS of the Breast, Whereas C-ERBB2 Blockade Does Not" *Proceedings of the Annual Meeting of the American Association for Cancer Research* (2000) 482 (Abstract 3074), 41.
Chang et al., "Ligand-induced internalization of the epidermal growth factor receptor is mediated by multiple endocytic codes analogous to the tyrosine motif found in constitutively internalized receptors." *JBC* (1993) 19312-19320, 268(26).
Chantry, "The kinase domain and membrane localization determine intracellular interactions between epidermal growth factor receptors." *JBC* (1995) 3068-3073, 270(7).
Chao, "Characterizing and engineering antibodies against the epidermal growth factor receptor (PhD Thesis)" *Submission to the Department of Chemical Engineering in partial fulfillment of the requirements for the degree of Doctor of Philosophy in Chemical Engineering at the Massachusetts Institute of Technology* (2008) 53, 54 and 78.
Chao et al., "Fine epitope mapping of anti-epidermal growth factor receptor antibodies through random mutagenesis and yeast surface display." *J. Mol. Biol.* (2004) 539-550, 342(2).
Chau et al., "The association between EGFR variant III, HPV, p16, c-MET, EGFR gene copy number and response to EGFR inhibitors in patients with recurrent or metastatic squamous cell carcinoma of the head and neck." *Head & neck oncology* (2011) 11, 3.
Chen et al., "Mice mutant for Egfr and Shp2 have defective cardiac semilunar valvulogenesis." *Nature Genetics* (2000) 296-299, 24(3).
Cherk et al., "Lack of correlation of hypoxic cell fraction and angiogenesis with glucose metabolic rate in non-small cell lung cancer assessed by 18F-Fluoromisonidazole and 18F-FDG PET." *J. Nucl. Med.* (2006) 1921-1926, 47(12).
Chien et al., "Significant structural and functional change of an antigen-binding site by a distant amino acid substitution: proposal of a structural mechanism." *Proceedings of the National Academy of Sciences of the United States of America* (1989) 5532-5536, 86(14).
Ching et al., "Expression of mRNA for epidermal growth factor, transforming growth factor-alpha and their receptor in human prostate tissue and cell lines." *Molecular and cellular biochemistry* (1993) 151-158, 126(2).
Chinkers et al., "Rapid induction of morphological changes in human carcinoma cells A-431 by epidermal growth factors." *The Journal of Cell Biology* (1979) 260-265, 83(1).
Cho et al., "Structure of the extracellular region of HER2 alone and in complex with the Herceptin Fab." *Nature* (2003) 756-760, 421(6924).
Cho et al., "Structure of the extracellular region of HER3 reveals an interdomain tether." *Science* (2002) 1330-1333, 297(5585).
Chong et al., "Phase I trial of 131I-huA33 in patients with advanced colorectal carcinoma." *Clin. Cancer Res.* (2005) 4818-4826, 11(13).
Chopra, "111In-Labeled CHX-A"-DTPA conjugated monoclonal antibody (mAb) 806 targeting the epidermal growth factor receptor deletion variant de2-7 (EGFRvIII)." *Molecular Imaging and Contrast Agent Database (MICAD) [Internet]. Bethesda(MD): National Center for Biotechnology Information (US)* (2010) 1-5.
Chopra, "125I-Labeled monoclonal antibody (mAb) 806 targeting the epidermal growth factor receptor deletion variant de2-7 (EGFRvIII)." *Molecular Imaging and Contrast Agent Database (MICAD) [Internet]. Bethesda(MD): National Center for Biotechnology Information (US)* (2010) 1-4.
Chopra, "111In-Labeled chimeric monoclonal antibody, ch806, targeting the epidermal growth factor receptor deletion variant de2-7 (EGFRvIII)." *Molecular Imaging and Contrast Agent Database (MICAD) [Internet]. Bethesda(MD): National Center for Biotechnology Information (US)* (2010) 1-5.
Chopra, "124I-Labeled residulizing ligand IMP-R4 conjugated chimeric monoclonal antibody ch806 targeting the epidermal growth factor receptor deletion variant de2-7(EGFRvIII)." *Molecular Imaging and Contrast Agent Database (MICAD) [Internet]. Bethesda(MD): National Center for Biotechnology Information (US)* (2010) 1-5.
Christensen et al., "High levels of HER-2 expression alter the ability of epidermal growth factor receptor (EGFR) family tyrosine kinase inhibitors to inhibit EGFR phosphorylation in vivo." *Clin. Cancer Res.* (2001) 4230-4238, 7(12).

(56) References Cited

OTHER PUBLICATIONS

Christensen et al., "Immunohistochemical detection of epidermal growth factor receptor in laryngeal squamous cell carcinomas." *Acta Otolaryngologica* (1992) 734-738, 112(4).

Christmann et al., "Epitope mapping and affinity purification of monospecific antibodies by *Escherichia coli* cell surface display of gene-derived random peptide libraries." *J. Immunol. Methods* (2001) 163-173, 257(1-2).

Chu et al., "Receptor dimerization is not a factor in the signalling activity of a transforming variant epidermal growth factor receptor (EGFRvIII)." *Biochem. J.* (1997) 855-861, 324 ( Pt 3).

Chung et al., "Increased epidermal growth factor receptor gene copy number is associated with poor prognosis in head and neck squamous cell carcinomas." *Journal of Clinical Oncology* (2006) 4170-4176, 24(25).

Chung et al., "Cetuximab shows activity in colorectal cancer patients with tumors that do not express the epidermal growth factor receptor by immunohistochemistry." *J. Clin. Oncol.* (2005) 1803-1810, 23(9).

Ciardiello et al., "Potentiation of cytotoxic drugs activity in human cancer cells by ZD-1839 (IRESSA), and EGFR-selective tyrosine kinase inhibitor." *Proceedings of the American Association for Cancer Research* (2000) 482 (Abstract 3075), 41.

Ciardiello et al., "Epidermal growth factor receptor (EGFR) as a target in cancer therapy: understanding the role of receptor expression and other molecular determinants that could influence the response to anti-EGFR drugs." *Eur. J. Cancer* (2003) 1348- 1354, 39(10).

Ciardiello et al., "A novel approach in the treatment of cancer: targeting the epidermal growth factor receptor." *Clin. Cancer Res.* (2001) 2958-2970, 7(10).

Ciardiello et al., "Inhibition of growth factor production and angiogenesis in human cancer cells by ZD1839 (IRESSA), a selective epidermal growth factor receptor tyrosine kinase inhibitor." *Clin. Cancer Res.* (2001) 1459-1465, 7(5).

Ciardiello et al., "Antiangiogenic and antitumor activity of anti-epidermal growth factor receptor C225 monoclonal antibody in combination with vascular endothelial growth factor antisense oligonucleotide in human GEO colon cancer cells." *Clin. Cancer Res.* (2000) 3739-3747, 6(9).

Ciardiello et al., "Antitumor effect and potentiation of cytotoxic drugs activity in human cancer cells by ZD-1839 (IRESSA), an epidermal growth factor receptor-selective tyrosine kinase inhibitor." *Clin. Cancer Res.* (2000) 2053-2063, 6(5).

Ciardiello, "Epidermal growth factor receptor tyrosine kinase inhibitors as anticancer agents." *Drugs* (2000) 25-32; discussion 41-2, 60(Suppl. 1).

Ciardiello et al., "Antitumor activity of sequential treatment with topotecan and anti-epidermal growth factor receptor monoclonal antibody C225." *Clin. Cancer Res.* (1999) 909-916, 5(4).

Ciardiello et al., "Cooperative inhibition of renal cancer growth by anti-epidermal growth factor receptor antibody and protein kinase A antisense oligonucleotide." *J. Natl. Cancer Inst.* (1998) 1087-1094, 90(14).

Ciardiello et al., "Antitumor activity of combined blockade of epidermal growth factor receptor and protein kinase A." *J. Natl. Cancer Inst.* (1996) 1770-1776, 88(23).

Ciardiello et al., "Cooperative antiproliferative effects of 8-chloro-cyclic AMP and 528 anti-epidermal growth factor receptor monoclonal antibody on human cancer cells." *Clin. Cancer Res.* (1995) 161-167, 1(2).

Ciesielski et al., "Oncogenic epidermal growth factor receptor mutants with tandem duplication: gene structure and effects on receptor function." *Oncogene* (2000) 810-820, 19(6).

Clark, "Antibody humanization: a case of the 'Emperors new clothes'?" *Immunology today* (2000) 397-402, 21(8).

Clarke et al., "Therapeutic efficacy of anti-Lewis (y) humanized 3S 193 radioimmunotherapy in a breast cancer model: enhanced activity when combined with Taxol chemotherapy" *Clin. Cancer Res.* (2000) 3621-3628, 6.

Clarke et al., "Mutant epidermal growth factor receptor enhances induction of vascular endothelial growth factor by hypoxia and insulin-like growth factor-1 via a PI3 kinase dependent pathway." *British Journal of Cancer* (2001) 1322-1329, 84(10).

Clarke et al., "In vivo biodistribution of a humanized anti-Lewis Y monoclonal antibody (hu3S193) in MCF-7 xenografted BALB/c nude mice." *Cancer Res.* (2000) 4804-4811, 60(17).

Clayton et al., "Unligated epidermal growth factor receptor forms higher order oligomers within microclusters on A431 cells that are sensitive to tyrosine kinase inhibitor binding." *Biochemistry* (2007) 4589-4597, 46(15).

Clayton et al., "Ligand-induced dimer-tetramer transition during the activation of the cell surface epidermal growth factor receptor-A multidimensional microscopy analysis." *JBC* (2005) 30392-30399, 280(34).

Clynes et al., "Inhibitory Fc receptors modulate in vivo cytotoxicity against tumor targets." *Nature Med.* (2000) 443-446, 6(4).

Co et al., "Humanized antibodies for therapy." *Nature* (1991) 501-502, 351(6326).

Cobleigh et al., "Multinational study of the efficacy and safety of humanized anti-HER2 monoclonal antibody in women who have HER2-overexpressing metastatic breast cancer that has progressed after chemotherapy for metastatic disease." *J. Clin. Oncol.*(1999) 2639-2648, 17(9).

Cochran et al., "Domain-level antibody epitope mapping through yeast surface display of epidermal growth factor receptor fragments." *J. Immunol. Methods* (2004) 147-158, 287(1-2).

Cohen et al., "Phase II study of ZD1839 (lressa) in recurrent or metastatic squamous cell carcinoma of the head and neck (SCCHN)." *Proceedings of the American Society of Clinical Oncology* (2002) 225a (Abstract 899), 21.

Cohen et al., "Safety profile of the monoclonal antibody (MoAb) IMC-C255, an anti-epidermal growth factor receptor (EGFR) used in the treatment of EGFR-positive tumors." *Proceedings of the American Society of Clinical Oncology* (2000) 474a (Abstract 1862), 19.

Cohen et al., "United States Food and Drug Administration Drug Approval summary: Gefitinib (ZD1839; Iressa) tablets." *Clin. Cancer Res.* (2004) 1212-1218, 10(4).

Cohen et al., "Epidermal growth factor-receptor-protein kinase interactions. Co-purification of receptor and epidermal growth factor-enhanced phosphorylation activity." *Journal of Biological Chemistry* (1980) 4834-4842, 255(10).

Cokgor et al., "Phase I trial results of iodine-131-labeled antitenascin monoclonal antibody 81C6 treatment of patients with newly diagnosed malignant gliomas." *J. Clin. Oncol.* (2000) 3862-3872, 18(22).

Colapinto et al., "Comparative localization of murine monoclonal antibody Me1-14 F(ab')2 fragment and whole IgG2a in human glioma xenografts." *Cancer Res.* (1988) 5701-5707, 48(20).

Collins, "Gene amplification in human gliomas." *Glia* (1995) 289-296, 15(3).

Collins, "Amplified genes in human gliomas." *Seminars in cancer biology* (1993) 27-32, 4(1).

Cortez et al., "Influence of size, surface, cell line, and kinetic properties on the specific binding of A33 antigen-targeted multilayered particles and capsules to colorectal cancer cells." *ACS nano* (2007) 93-102, 1(2).

Cortez et al., "Targeting and Uptake of Multilayered Particles to Colorectal Cancer Cells" *Advanced Materials* (2006) 1998-2003, 18.

Corti et al., "Idiotope determining regions of a mouse monoclonal antibody and its humanized versions. Identification of framework residues that affect idiotype expression." *J. Mol. Biol.* (1994) 53-60, 235(1).

Cowley et al., "Increased EGF receptors on human squamous carcinoma cell lines." *British Journal of Cancer* (1986) 223-229, 53(2).

Cragg et al., "Signaling antibodies in cancer therapy." *Curr. Opin. Immunol.* (1999) 541-547, 11(5).

Crawford et al., "ABX-EGF in combination with paclitaxel and carboplatin for advanced non-small cell lung cancer (NSCLC)" *Journal of Clinical Oncology, 2004 ASCO Annual Meeting Proceedings (Post-Meeting Edition)* (2004) 7083, 22(14S).

(56) References Cited

OTHER PUBLICATIONS

Crombet et al., "Use of the anti-EGFR antibody h-R3 in combination with radiotherapy in the treatment of advanced head and neck cancer (Abstract 53)" *Proceedings of the American Society of Clinical Oncology* (2002) 14a, 21.

Crombet et al., "Phase I clinical evaluation of a neutralizing monoclonal antibody against epidermal growth factor receptor in advanced brain tumor patients: preliminary study." *Hybridoma* (2001) 131-136, 20(2).

Crombet et al., "Use of the humanized anti-epidermal growth factor receptor monoclonal antibody h-R3 in combination with radiotherapy in the treatment of locally advanced head and neck cancer patients." *J. Clin. Oncol.* (2004) 1646-1654, 22(9).

Cunningham et al., "High-resolution epitope mapping of hGH-receptor interactions by alanine-scanning mutagenesis." *Science* (1989) 1081-1085, 244(4908).

Cunningham et al., "Cetuximab monotherapy and cetuximab plus irinotecan in irinotecan-refractory metastatic colorectal cancer." *N. Engl. J. Med.* (2004) 337-345, 351(4).

Cvrljevic et al., "Activation of Src induces mitochondrial localisation of de2-7EGFR (EGFRvIII) in glioma cells: implications for glucose metabolism." *Journal of cell science* (2011) 2938-2950, 124(Part 17).

Dadparvar et al., "Indium-111-labeled anti-EGFr-425 scintigraphy in the detection of malignant gliomas." *Cancer* (1994) 884-889, 73(3; Supplement).

Daley et al., "Transformation of an interleukin 3-dependent hematopoietic cell line by the chronic myelogenous leukemia-specific P210bcr/abl protein." *Proceedings of the National Academy of Sciences of the United States of America* (1988) 9312-9316, 85(23).

Damjanov et al., "Immunohistochemical localization of the epidermal growth factor receptor in normal human tissues." *Laboratory investigation; a journal of technical methods and pathology* (1986) 588-592, 55(5).

Damle, "Antibody-drug conjugates ace the tolerability test." *Nat. Biotechnol.* (2008) 884-885, 26(8).

Damstrup et al., "In vitro invasion of small-cell lung cancer cell lines correlates with expression of epidermal growth factor receptor." *British Journal of Cancer* (1998) 631-640, 78(5).

Damstrup et al., "Epidermal growth factor receptor mutation type III transfected into a small cell lung cancer cell line is predominantly localized at the cell surface and enhances the malignant phenotype." *Int. J. Cancer* (2002) 7-14, 97(1).

Daugherty et al., "Polymerase chain reaction facilitates the cloning, CDR-grafting, and rapid expression of a murine monoclonal antibody directed against the CD18 component of leukocyte integrins." *Nucleic acids research* (1991) 2471-2476, 19(9).

Davies et al., "Affinity improvement of single antibody VH domains: residues in all three hypervariable regions affect antigen binding." *Immunotechnology : an international journal of immunological engineering* (1996) 169-179, 2(3).

Davies et al., "Genetic analysis of epidermal growth factor action: assignment of human epidermal growth factor receptor gene to chromosome 7." *Proceedings of the National Academy of Sciences of the United States of America* (1980) 4188-4192, 77(7).

Davies et al., "Specificity and mechanism of action of some commonly used protein kinase inhibitors." *Biochem. J.* (2000) 95-105, 351(Part 1).

Davis et al., "Transgenic mice as a source of fully human antibodies for the treatment of cancer." *Cancer Metastasis Rev.* (1999) 421-425, 18(4).

Dawson et al., "A phase II trial of gefitinib (Iressa, ZD1839) in stage IV and recurrent renal cell carcinoma." *Clin. Cancer Res.* (2004) 7812-7819, 10(23).

Dazzi et al., "Expression of epidermal growth factor receptor (EGF-R) in non-small cell lung cancer. Use of archival tissue and correlation of EGF-R with histology, tumour size, node status and survival." *British Journal of Cancer* (1989) 746-749, 59(5).

Dechant et al., "Effect of combinations of EGF-R antibodies on complement-dependent tumor cell lysis" *Journal of Clinical Oncology* (2008) 14005, 26 (15S).

Decker, "Transmembrane signaling by epidermal growth factor receptors lacking autophosphorylation sites." *Journal of Biological Chemistry* (1993) 9176-9179, 268(13).

Decker, "Aspects of the metabolism of the epidermal growth factor receptor in A431 human epidermoid carcinoma cells." *Mol. Cell Biol.* (1984) 571-575, 4(4).

Deen et al., "Brain Tumor Working Group Report on the 9th International Conference on Brain Tumor Research and Therapy. Organ System Program, National Cancer Institute." *Journal of neuro-oncology* (1993) 243-272, 16(3).

Dehm et al., "SRC gene expression in human cancer: the role of transcriptional activation." *Biochemistry and cell biology* (2004) 263-274, 82(2).

Denardo et al., "Strategies for developing effective radioimmunotherapy for solid tumors." *Clin. Cancer Res.* (1999) 3219s-3223s, 5(10; Supplement).

Denardo et al., "A new era for radiolabeled antibodies in cancer?" *Curr. Opin. Immunol.* (1999) 563-569, 11(5).

Dewitt et al., "Quantitative analysis of the EGF receptor autocrine system reveals cryptic regulation of cell response by ligand capture." *Journal of cell science* (2001) 2301-2313, 114(Part 12).

Dicosimo et al., "Schedule-dependent effects of the epidermal growth factor receptor (EGFR) tyrosine kinase inhibitor gefitinib in combination with the mammalian target of rapamycin (mTOR) inhibitor everolimus (RAD001)." *Proceedings of the American Society of Clinical Oncology* (2004) 213s (Abstract 3074).

Diedrich et al., "Distribution of epidermal growth factor receptor gene amplification in brain tumours and correlation to prognosis." *Journal of Neurology* (1995) 683-688, 242(10).

Van Dijk et al., "Human antibodies as next generation therapeutics." *Current opinion in chemical biology* (2001) 368-374, 5(4).

Discafani et al., "Irreversible inhibition of epidermal growth factor receptor tyrosine kinase with in vivo activity by N-[4-[(3-bromophenyl)amino]-6-quinazolinyl]-2-butynamide (CL-387,785)." *Biochemical pharmacology* (1999) 917-925, 57(8).

Dittadi et al., "Epidermal growth factor receptor in lung malignancies. Comparison between cancer and normal tissue." *British Journal of Cancer* (1991) 741-744, 64(4).

Divgi et al., "Phase I and imaging trial of indium 111-labeled anti-epidermal growth factor receptor monoclonal antibody 225 in patients with squamous cell lung carcinoma." *J. Natl. Cancer Inst.* (1991) 97-104, 83(2).

Domagala et al., "Stoichiometry, kinetic and binding analysis of the interaction between epidermal growth factor (EGF) and the extracellular domain of the EGF receptor." *Growth Factors* (2000) 11-29, 18(1).

Van Doorn et al., "Follicular and epidermal alterations in patients treated with ZD1839 (Iressa), an inhibitor of the epidermal growth factor receptor." *The British journal of dermatology* (2002) 598-601, 147(3).

Doronina et al., "Enhanced Activity of Monomethylauristatin F through Monoclonal Antibody Delivery: Effects of Linker Technology on Efficacy and Toxicity" *Bioconiugate chemistry* (2006) 114-124, 17(1).

Downward et al., "Close similarity of epidermal growth factor receptor and v-erb-B oncogene protein sequences." *Nature* (1984) 521-527, 307(5951).

Eberhard et al., "Mutations in the epidermal growth factor receptor and in KRAS are predictive and prognostic indicators in patients with non-small-cell lung cancer treated with chemotherapy alone and in combination with erlotinib." *J. Clin. Oncol.* (2005) 5900-5909, 23(25).

Egloff et al., "Targeting epidermal growth factor receptor and SRC pathways in head and neck cancer." *Semin. Oncol.* (2008) 286-297, 35(3).

Ekstrand et al., "Altered subcellular location of an activated and tumour-associated epidermal growth factor receptor." *Oncogene* (1995) 1455-1460, 10(7).

Ekstrand et al., "Functional characterization of an EGF receptor with a truncated extracellular domain expressed in glioblastomas with EGFR gene amplification." *Oncogene* (1994) 2313-2320, 9(8).

Ekstrand et al., "Amplified and rearranged epidermal growth factor receptor genes in human glioblastomas reveal deletions of sequences

(56) References Cited

OTHER PUBLICATIONS encoding portions of the N- and/or C-terminal tails." *Proceedings of the National Academy of Sciences of the United States of America* (1992) 4309-4313, 89(10).
Ekstrand et al., "Genes for epidermal growth factor receptor, transforming growth factor alpha, and epidermal growth factor and their expression in human gliomas in vivo." *Cancer Res.* (1991) 2164-2172, 51(8).
Elleman et al., "Identification of a determinant of epidermal growth factor receptor ligand-binding specificity using a truncated, high-affinity form of the ectodomain." *Biochemistry* (2001) 8930-8939, 40(30).
Eller et al., "Activity of anti-epidermal growth factor receptor monoclonal antibody C225 against glioblastoma multiforme." *Neurosurgery* (2002) 1005-13; discussion 1013-4, 51(4).
Ellgaard et al., "Quality control in the endoplasmic reticulum." *Nat. Rev. Mol. Cell Biol.* (2003) 181-191, 4(3).
Ellis et al., "Preclinical analysis of the analinoquinazoline AG1478, a specific small molecule inhibitor of EGF receptor tyrosine kinase." *Biochemical pharmacology* (2006) 1422-1434, 71(10).
Emsley et al., "Coot: model-building tools for molecular graphics." *Acta Crystallogr. D. Biol. Crystallogr.* (2004) 2126-2132, 60(Pt 12 Pt 1).
Ennis, "Monoclonal Anti-EGF Receptor Antibodies Inhibit the Growth of Malignant and Nonmalignant Human Mammary Epithelial Cells." *J. Cell Biochem.* (1989) 104 (Abstract E207)(Suppl. 13B).
Ennis et al., "The EGF receptor system as a target for antitumor therapy." *Cancer investigation* (1991) 553-562, 9(5).
Ennis et al., "Anti-epidermal growth factor receptor antibodies inhibit the autocrine-stimulated growth of MDA-468 human breast cancer cells." *Molecular endocrinology (Baltimore, Md.)* (1989) 1830-1838, 3(11).
Epenetos et al., "Long term survival of patients with advanced ovarian cancer treated with intraperitoneal radioimmunotherapy." *International journal of gynecological cancer: official journal of the International Gynecological Cancer Society* (2000) 44-46, 10(Suppl. 1).
Epenetos et al., "Antibody guided irradiation of brain glioma by arterial infusion of radioactive monoclonal antibody against epidermal growth factor receptor and blood group A antigen." *British medical journal (Clinical research ed.)* (1985) 1463-1466, 290(6480).
Erickson, "Antibody-Maytansinoid Conjugates Are Activated in Targeted Cancer Cells by Lysosomal Degradation and Linker-Dependent Intracellular Processing" *Cancer Research* (2006) 4426-4433, 66(8).
Eriksen et al., "The EGFRvIII variant in squamous cell carcinomas of the head and neck: Expression and correlation with clinico-pathological parameters in 675 patients from the randomised DAHANCA 6/7 study." *ECCO 15—34th ESMO Multidisciplinary Congress (Berlin)* (2009) 472 (Abstract P-8507).
Ezekiel et al., "Phase I trial of chimerized anti-epidermal growth factor receptor (Anti-EGFr) antibody in combination with either once-daily or twice-daily irradiation for locally advanced head and neck malignancies." *Proceedings of the American Society of Clinical Oncology* (1999) 388a (Abstract 1501), 18.
Faillot et al., "A phase I study of an anti-epidermal growth factor receptor monoclonal antibody for the treatment of malignant gliomas." *Neurosurgery* (1996) 478-483, 39(3).
Fairlie et al., "A fusion protein system for the recombinant production of short disulfide-containing peptides." *Protein Expr. Purif.* (2002) 171-178, 26(1).
Fan et al., "Blockade of epidermal growth factor receptor by anti-EGFR monoclonal antibody 225 causes GI arrest of A431 cells with induction of p27KIPI" *Proceedings of the American Association for Cancer Research* (1996) 10 (Abstract #69), 37.
Fan et al., "Therapeutic application of anti-growth factor receptor antibodies." *Current opinion in oncology* (1998) 67-73, 10(1).
Fan et al., "Antibody-induced epidermal growth factor receptor dimerization mediates inhibition of autocrine proliferation of A431 squamous carcinoma cells." *Journal of Biological Chemistry* (1994) 27595-27602, 269(44).
Fan et al., "Antitumor effect of anti-epidermal growth factor receptor monoclonal antibodies plus cis-diamminedichloroplatinum on well established A431 cell xenografts." *Cancer Res.* (1993) 4637-4642, 53(19).
Fan et al., "Blockade of epidermal growth factor receptor function by bivalent and monovalent fragments of 225 anti-epidermal growth factor receptor monoclonal antibodies." *Cancer Res.* (1993) 4322-4328, 53(18).
Fantl et al., "Signalling by receptor tyrosine kinases." *Annual review of biochemistry* (1993) 453-481, 62.
Farrugia et al., "A possible role for metallic ions in the carbohydrate cluster recognition displayed by a Lewis Y specific antibody." *PLoS ONE* (2009) e7777, 4(11).
Feldhaus et al., "Flow-cytometric isolation of human antibodies from a nonimmune *Saccharomyces cerevisiae* surface display library." *Nat. Biotechnol.* (2003) 163-170, 21(2).
Feldkamp et al., "Expression of activated epidermal growth factor receptors, Ras-guanosine triphosphate, and mitogen-activated protein kinase in human glioblastoma multiforme specimens." *Neurosurgery* (1999) 1442-1453, 45(6).
Fendly et al., "Characterization of murine monoclonal antibodies reactive to either the human epidermal growth factor receptor or HER2/neu gene product." *Cancer Res* (1990) 1550-1558, 50(5).
Fenstermaker et al., "Deletion and tandem duplication of exons 2-7 in the epidermal growth factor receptor gene of a human malignant glioma." *Oncogene* (2000) 4542-4548, 19(39).
Ferguson, "Structure-based view of epidermal growth factor receptor regulation." *Annual review of biophysics* (2008) 353-373, 37.
Ferguson et al., "EGF activates its receptor by removing interactions that autoinhibit ectodomain dimerization." *Mol. Cell* (2003) 507-517, 11(2).
Fernandes et al., "Glycosylation-induced conformational modification positively regulates receptor-receptor association: a study with an aberrant epidermal growth factor receptor (EGFRvIII/DeltaEGFR) expressed in cancer cells." *JBC* (2001) 5375-5383, 276(7).
Ferrara et al., "Discovery and development of bevacizumab, an anti-VEGF antibody for treating cancer." *Nature reviews. Drug discovery* (2004) 391-400, 3(5).
Ferry et al., "Intermittent Oral ZD1839 (Iressa), a Novel Epidermal Growth Factor Receptor Tyrosine Kinase Inhibitor (EGFR-TKI), Show Evidence of Good Tolerability and Activity: Final Results from a Phase I Study (Abstract 5E)" *Proceedings of the American Society of Clinical Oncology* (2000) 3a, 19.
Figlin et al., "ABX-EGF, a fully human anti-epidermal growth factor receptor (EGFR) monoclonal antibody (mAb) in patients with advanced cancer: phase 1 clinical results (Abstract 35)" *Proceedings of the American Society of Clinical Oncology* (2002) 10a, 21.
Filmus et al., "Epidermal growth factor receptor gene-amplified MDA-468 breast cancer cell line and its nonamplified variants." *Mol. Cell Biol.* (1987) 251-257, 7(1).
Filmus et al., "Amplified, overexpressed and rearranged epidermal growth factor receptor gene in a human astrocytoma cell line." *Biochem. Biophys. Res. Commun.* (1985) 207-215, 131(1).
Filmus et al., "MDA-468, a human breast cancer cell line with a high number of epidermal growth factor (EGF) receptors, has an amplified EGF receptor gene and is growth inhibited by EGF." *Biochem. Biophys. Res. Commun.* (1985) 898-905, 128(2).
Finkler et al., "Phase 2 Evaluation of OSI-774, a Potent Oral Antagonist of the EGFR-TK in Patients with Advanced Ovarian Carcinoma." *Proceedings of the American Society of Clinical Oncology* (2001) 208a (Abstract 831), 20.
Di Fiore et al., "Overexpression of the human EGF receptor confers an EGF-dependent transformed phenotype to NIH 3T3 cells." *Cell* (1987) 1063-1070, 51(6).
Fischer-Colbrie et al., "EGFR and steroid receptors in ovarian carcinoma: comparison with prognostic parameters and outcome of patients." *Anticancer research* (1997) 613-619, 17(1B).

(56) References Cited

OTHER PUBLICATIONS

Fisher et al., "Induction and apoptotic regression of lung adenocarcinomas by regulation of a K-Ras transgene in the presence and absence of tumor suppressor genes." *Genes Dev.* (2001) 3249-3262, 15(24).

Flynn et al., "Campath-1H monoclonal antibody therapy." *Current opinion in oncology* (2000) 574-581, 12(6).

Fong et al., "Epidermal growth factor receptor monoclonal antibody inhibits constitutive receptor phosphorylation, reduces autonomous growth, and sensitizes androgen-independent prostatic carcinoma cells to tumor necrosis factor alpha." *Cancer Res.* (1992) 5887-5892, 52(21).

Foo et al., "Functional imaging of intratumoral hypoxia." *Molecular imaging and biology: MIB: the official publication of the Academy of Molecular Imaging* (2004) 291-305, 6(5).

Forastiere et al., "Head and neck cancer." *N. Engl. J. Med.* (2001) 1890-1900, 345(26).

Ford et al., "Pharmacogenomic approaches for identifying markers predictive of tumor response to Cetuximab (Erbitux)" *Proc. Amer. Assoc. Cancer Res.* (2004) Abstract 2032, 45.

Ford et al., "Targeting epidermal growth factor receptor in head and neck cancer." *Head & neck* (2003) 67-73, 25(1).

Fornier et al., "Trastuzumab in combination with chemotherapy for the treatment of metastatic breast cancer." *Semin. Oncol.* (2000) 38-45; discussion 92-100, 27(6; Suppl. 11).

Foulon et al., "Positively charged templates for labeling internalizing antibodies: comparison of N-succinimidyl 5-iodo-3-pyridinecarboxylate and the D-amino acid peptide KRYRR." *Nucl. Med. Biol.* (2001) 769-777, 28(7).

Foulon et al., "Radioiodination via D-amino acid peptide enhances cellular retention and tumor xenograft targeting of an internalizing anti-epidermal growth factor receptor variant III monoclonal antibody." *Cancer Res.* (2000) 4453-4460, 60(16).

Fowler et al., "A mutation in the epidermal growth factor receptor in waved-2 mice has a profound effect on receptor biochemistry that results in impaired lactation." *Proceedings of the National Academy of Sciences of the United States of America* (1995) 1465-1469, 92(5).

Fox et al., "Tumour angiogenesis." *The Journal of pathology* (1996) 232-237, 179(3).

Fraker et al., "Protein and cell membrane iodinations with a sparingly soluble chloroamide, 1,3,4,6-tetrachloro-3a,6a-diphrenylglycoluril." *Biochem. Biophvs. Res. Commun.* (1978) 849-857, 80(4).

Frame, "Newest findings on the oldest oncogene; how activated src does it." *Journal of cell science* (2004) 989-998, 117(Part 7).

Francisco, "cAC10-vcMMAE, an anti-CD30-monomethyl auristatin E conjugate with potent and selective antitumor activity" *Blood* (2003) 1458-1465, 102(4).

Frank et al., "SPOT synthesis. Epitope analysis with arrays of synthetic peptides prepared on cellulose membranes." *Methods Mol. Biol.* (1996) 149-169, 66.

Franklin et al., "Association between activation of ErbB pathway genes and survival following gefitinib treatment in advanced BAC (SWOG 0126)." *Proceedings of the Annual Meeting of the American Society of Clinical Oncology* (2004) 620s (Abstract 7015), 22.

Frederick et al., "Analysis of genomic rearrangements associated with EGRFvIII expression suggests involvement of Alu repeat elements." *Neuro-oncology* (2000) 159-163, 2(3).

Frederick et al., "Diversity and frequency of epidermal growth factor receptor mutations in human glioblastomas." *Cancer Res.* (2000) 1383-1387, 60(5).

Friedman et al., "Temozolomide and treatment of malignant glioma." *Clin. Cancer Res.* (2000) 2585-2597, 6(7).

Friedman et al., "Glioblastoma multiforme and the epidermal growth factor receptor." *N. Engl. J. Med.* (2005) 1997-1999, 353(19).

Friedman et al., "Synergistic down-regulation of receptor tyrosine kinases by combinations of mAbs: implications for cancer immunotherapy." *Proceedings of the National Academy of Sciences of the United States of America* (2005) 1915-1920, 102(6).

Friess et al., "Combination treatment with erlotinib and pertuzumab against human tumor xenografts is superior to monotherapy." *Clin. Cancer Res.* (2005) 5300-5309, 11(14).

Fry, "Site-directed irreversible inhibitors of the erbB family of receptor tyrosine kinases as novel chemotherapeutic agents for cancer." *Anti-cancer drug design* (2000) 3-16, 15(1).

Fry, "Inhibition of the epidermal growth factor receptor family of tyrosine kinases as an approach to cancer chemotherapy: progression from reversible to irreversible inhibitors." *Pharmacology & therapeutics* (1999) 207-218, 82(2-3).

Fry et al., "Specific, irreversible inactivation of the epidermal growth factor receptor and erbB2, by a new class of tyrosine kinase inhibitor." *Proceedings of the National Academy of Sciences of the United States of America* (1998) 12022-12027, 95(20).

Fry et al., "Biochemical and antiproliferative properties of 4-[ar(alk)ylamino]pyridopyrimidines, a new chemical class of potent and specific epidermal growth factor receptor tyrosine kinase inhibitor." *Biochemical pharmacology* (1997) 877-887, 54(8).

Fry et al., "A specific inhibitor of the epidermal growth factor receptor tyrosine kinase." *Science* (1994) 1093-1095, 265(5175).

Fujino et al., "A comparison of epidermal growth factor receptor levels and other prognostic parameters in non-small cell lung cancer." *Eur. J. Cancer* (1996) 2070-2074, 32A(12).

Fukai et al., "Antitumor activity of cetuximab against malignant glioma cells overexpressing EGFR deletion mutant variant III." *Cancer science* (2008) 2062-2069, 99(10).

Fukuoka et al., "Final results from a phase II trial of ZD1839 ('Iressa') for patients with advanced non-small cell lung carcinoma (IDEAL 1)." *Proceedings of the American Society of Clinical Oncology* (2002) 298a (Abstract 1188), 21.

Fukuoka et al., "Multi-institutional randomized phase II trial of gefitinib for previously treated patients with advanced non-small-cell lung cancer." *J. Clin. Oncol.* (2003) 2237- 2246, 21(12).

Gadella et al., "Oligomerization of epidermal growth factor receptors on A431 cells studied by time-resolved fluorescence imaging microscopy. A stereochemical model for tyrosine kinase receptor activation." *The Journal of cell biology* (1995) 1543-1558, 129(6).

Gamou et al., "Glycosylation of the epidermal growth factor receptor and its relationship to membrane transport and ligand binding." *Journal of biochemistry* (1988) 388-396, 104(3).

Gan et al., "Targeting a unique EGFR epitope with monoclonal antibody 806 activates NF-kappaB and initiates tumour vascular normalization." *Journal of cellular and molecular medicine* (2009) 3993-4001, 13(9B).

Gan et al., "The EGFRvIII variant in glioblastoma multiforme." *Journal of clinical neuroscience: official journal of the Neurosurgical Society of Australasia* (2009) 748-754, 16(6).

Gan et al., "The epidermal growth factor receptor (EGFR) tyrosine kinase inhibitor AG1478 increases the formation of inactive untethered EGFR dimers. Implications for combination therapy with monoclonal antibody 806." *JBC* (2007) 2840-2850, 282(5).

Garcia De Palazzo et al., "Expression of mutated epidermal growth factor receptor by non-small cell lung carcinomas." *Cancer Res.* (1993) 3217-3220, 53(14).

Garinchesa et al., "Organ-specific expression of the colon cancer antigen A33, a cell surface target for antibody-based therapy." *Int. J. Oncol.* (1996) 465-471, 9(3).

Garrett et al., "Antibodies specifically targeting a locally misfolded region of tumor associated EGFR." *Proceedings of the National Academy of Sciences of the United States of America* (2009) 5082-5087, 106(13).

Garrett et al., "The crystal structure of a truncated ErbB2 ectodomain reveals an active conformation, poised to interact with other ErbB receptors." *Mol. Cell* (2003) 495-505, 11(2).

Garrett et al., "Crystal structure of a truncated epidermal growth factor receptor extracellular domain bound to transforming growth factor alpha." *Cell* (2002) 763-773, 110(6).

Ge et al., "Evidence of high incidence of EGFRvIII expression and coexpression with EGFR in human invasive breast cancer by laser capture microdissection and immunohistochemical analysis." *Int. J. Cancer* (2002) 357-361, 98(3).

(56) References Cited

OTHER PUBLICATIONS

George et al., "Differential effects of anti-beta2-glycoprotein I antibodies on endothelial cells and on the manifestations of experimental antiphospholipid syndrome." (1998) 900-906, 97(9).

Giaccone et al., "Combination therapy with ZD1839 (Iressa), an orally active, selective, epidermal growth factor receptor tyrosine kinase inhibitor (EGFR-TKI), gemcitabine and cisplatin, in patients with advanced solid tumors: promising preliminary results on tolerability, efficacy, and pharmacokinetics." *Clinical Cancer Research* (2001) 3765s.(Abstract 553), 7.

Gibson et al., "Randomized phase III trial results of panitumumab, a fully human anti-epidermal growth factor receptor monoclonal antibody, in metastatic colorectal cancer." *Clin. Colorectal Cancer* (2006) 29-31, 6(1).

Gill et al., "Relationship between production of epidermal growth factor receptors, gene amplification, and chromosome 7 translocation in variant A431 cells." *Somatic cell and molecular genetics* (1985) 309-318, 11(4).

Gill et al., "Monoclonal anti-epidermal growth factor receptor antibodies which are inhibitors of epidermal growth factor binding and antagonists of epidermal growth factor binding and antagonists of epidermal growth factor-stimulated tyrosine protein kinase activity." *JBC* (1984) 7755-7760, 259(12).

Gill et al., "New targeted therapies in gastrointestinal cancers." *Current treatment options in oncology* (2003) 393-403, 4(5).

Giusti et al., "Somatic diversification of S107 from an antiphosphocholine to an anti-DNA autoantibody is due to a single base change in its heavy chain variable region." *Proceedings of the National Academy of Sciences of the United States of America* (1987) 2926-2930, 84(9).

Glennie et al., "Clinical trials of antibody therapy." *Immunology today* (2000) 403-410, 21(8).

Glennie et al., "Renaissance of cancer therapeutic antibodies." *Drug discovery today* (2003) 503-510, 8(11).

Gold et al., "Localization of pancreatic cancer with radiolabeled monoclonal antibody PAM4." *Crit. Rev. Oncol. Hematol.* (2001) 147-154, 39(1-2).

Goldberg, "Cetuximab." *Nature reviews. Drug discovery* (2005) S10-1(Suppl. 10).

Goldenberg et al., "Imaging of human tumor xenografts with an indium-111-labeled anti-epidermal growth factor receptor monoclonal antibody." *J. Natl. Cancer Inst.* (1989) 1616-1625, 81(21).

Goldenberg, "The role of radiolabeled antibodies in the treatment of non-Hodgkin's lymphoma: the coming of age of radioimmunotherapy." *Crit. Rev. Oncol. Hematol.* (2001) 195-201, 39(1-2).

Goldenberg, "Advancing role of radiolabeled antibodies in the therapy of cancer." *Cancer Immunol. Immunother.* (2003) 281-296, 52(5).

Goldenberg, "Targeted therapy of cancer with radiolabeled antibodies." *J. Nucl. Med.* (2002) 693-713, 43(5).

Goldman et al., "Epidermal growth factor stimulates vascular endothelial growth factor production by human malignant glioma cells: a model of glioblastoma multiforme pathophysiology." *Mol. Biol. Cell* (1993) 121-133, 4(1).

Goldman et al., "Heterodimerization of the erbB-1 and erbB-2 receptors in human breast carcinoma cells: a mechanism for receptor transregulation." *Biochemistry* (1990) 11024-11028, 29(50).

Goldstein et al., "Biological efficacy of a chimeric antibody to the epidermal growth factor receptor in a human tumor xenograft model." *Clin. Cancer Res.* (1995) 1311-1318, 1(11).

Gonzalez, "Epidermal growth factor-based cancer vaccine for non-small-cell lung cancer therapy" *Annals of Oncology* (2003) 461-466, 14(3).

Gorgoulis et al., "Molecular and immunohistochemical evaluation of epidermal growth factor receptor and c-erb-B-2 gene product in transitional cell carcinomas of the urinary bladder: a study in Greek patients." *Modern pathology : an official journal of the United States and Canadian Academy of Pathology, Inc* (1995) 758-764, 8(7).

Gorre et al., "Clinical resistance to STI-571 cancer therapy caused by BCR-ABL gene mutation or amplification." *Science* (2001) 876-880, 293(5531).

Goss et al., "Final results of the dose escalation phase of a phase I pharmacokinetics (PK), pharmacodynamic (PD), and biological activity study of ZD1839." *Proceedings of the American Society of Clinical Oncology* (2001) 85a (Abstract 335), 20.

Graeven et al., "Phase I study of the humanised anti-EGFR monoclonal antibody matuzumab (EMD 72000) combined with gemcitabine in advanced pancreatic cancer." *British Journal of Cancer* (2006) 1293-1299, 94(9).

Grandal et al., "EGFRvIII escapes down-regulation due to impaired internalization and sorting to lysosomes." *Carcinogenesis* (2007) 1408-1417, 28(7).

Grandis et al., "Elevated levels of transforming growth factor alpha and epidermal growth factor receptor messenger RNA are early markers of carcinogenesis in head and neck cancer." *Cancer Res.* (1993) 3579-3584, 53(15).

Grandis et al., "Levels of TGF-alpha and EGFR protein in head and neck squamous cell carcinoma and patient survival." *J. Natl. Cancer Inst.* (1998) 824-832, 90(11).

Graness et al., "Protein-tyrosine-phosphatase-mediated epidermal growth factor (EGF) receptor transinactivation and EGF receptor-independent stimulation of mitogen-activated protein kinase by bradykinin in A431 cells." *Biochem. J.* (2000) 441-447, 347(Part 2).

Graus-Porta et al., "Single-chain antibody-mediated intracellular retention of ErbB-2 impairs Neu differentiation factor and epidermal growth factor signaling." *Mol. Cell Biol.* (1995) 1182-1191, 15(3).

Green et al., "Monoclonal antibody therapy for solid tumors." *Cancer Treat Rev.* (2000) 269-286, 26(4).

Greenspan et al., "Defining epitopes: It's not as easy as it seems." *Nat. Biotechnol.* (1999) 936-937, 17(10).

Groner et al., "Therapeutic antibodies." *Current molecular medicine* (2004) 539-547, 4(5).

Grunwald et al., "Development of the epidermal growth factor receptor inhibitor OSI-774" *Seminars in Oncology* (2003) 23-31, 30(3; Suppl. 6).

Gschwind et al., "The discovery of receptor tyrosine kinases: targets for cancer therapy." *Nature Rev. Cancer* (2004) 361-370, 4(5).

Gullick, "Type I growth factor receptors: current status and future work." *Biochemical Society symposium* (1998) 193-198, 63.

Gullick, "A new model for the interaction of EGF-like ligands with their receptors: the new one-two." *Eur. J. Cancer* (1994) 2186, 30A(14).

Gullick, "Growth factors, growth factor receptors and neoplasia." *Human & experimental toxicology* (1991) 398-400, 10(6).

Gullick, "Prevalence of aberrant expression of the epidermal growth factor receptor in human cancers." *British medical bulletin* (1991) 87-98, 47(1).

Gulliford et al., "Intensification of growth factor receptor signalling by phorbol treatment of ligand-primed cells implies a dimer-stabilizing effect of protein kinase C-dependent juxtamembrane domain phosphorylation." *Cellular signalling* (1999) 245-252, 11(4).

Gunnett et al., "Phase II study of antiepidermal growth factor receptor (EGFR) antibody C225 alone in patients (pts) with metastatic renal carcinoma (RCC)." *Annual Meeting of the American Society of Clinical Oncology* (1999) 340a (Abstract 1309), 18.

Günther et al., "The secreted form of the epidermal growth factor receptor. Characterization and crystallization of the receptor-ligand complex." *JBC* (1990) 22082-22085, 265(36).

Gupta et al., "Development of an EGFRvIII specific recombinant antibody." *BMC biotechnology* (2010) 72, 10.

Güssow et al., "Humanization of monoclonal antibodies." *Methods in Enzymology* (1991) 99-121, 203.

Haas-Kogan et al., "Epidermal growth factor receptor, protein kinase B/Akt, and glioma response to erlotinib." *J. Natl. Cancer Inst.* (2005) 880-887, 97(12).

Haber et al., "Molecular targeted therapy of lung cancer: EGFR mutations and response to EGFR inhibitors." *Cold Spring Harbor symposia on quantitative biology* (2005) 419-426, 70.

Hackel et al., "Epidermal growth factor receptors: critical mediators of multiple receptor pathways." *Current opinion in cell biology* (1999) 184-189, 11(2).

(56) References Cited

OTHER PUBLICATIONS

Haigler et al., "Visualization by fluorescence of the binding and internalization of epidermal growth factor in human carcinoma cells A-431." *Proceedings of the National Academy of Sciences of the United States of America* (1978) 3317-3321, 75(7).
Halatsch et al., "Marked inhibition of glioblastoma target cell tumorigenicity in vitro by retrovirus-mediated transfer of a hairpin ribozyme against deletion-mutant epidermal growth factor receptor messenger RNA." *J. Neurosurq.* (2000) 297-305, 92(2).
Halatsch et al., "Epidermal growth factor receptor inhibition for the treatment of glioblastoma multiforme and other malignant brain tumours." *Cancer Treat Rev.* (2006) 74-89, 32(2).
Halatsch et al., "Inverse correlation of epidermal growth factor receptor messenger RNA induction and suppression of anchorage-independent growth by OSI-774, an epidermal growth factor receptor tyrosine kinase inhibitor, in glioblastoma multiforme cell lines." *J. Neurosurg.* (2004) 523-533, 100(3).
Haley et al., "The human EGF receptor gene: structure of the 110 kb locus and identification of sequences regulating its transcription." *Oncogene research* (1987) 375-396, 1(4).
Haley, "Regulation of epidermal growth factor receptor expression and activation: a brief review." *Symposia of the Society for Experimental Biology* (1990) 21-37, 44.
Hambek et al., "Tumor Necrosis Factor a Sensitizes Low Epidermal Growth Factor Receptor (EGFR)-expressing Carcinomas for Anti-EGFR Therapy" *Cancer Res.* (2001) 1045-1049, 61.
Hamblett et al., "Effects of drug loading on the antitumor activity of a monoclonal antibody drug conjugate." *Clin. Cancer Res.* (2004) 7063-7070, 10(20).
Han et al., "Predictive and prognostic impact of epidermal growth factor receptor mutation in non-small-cell lung cancer patients treated with gefitinib." *J. Clin. Oncol.* (2005) 2493-2501, 23(11).
Han et al., "Tyrphostin AG 1478 preferentially inhibits human glioma cells expressing truncated rather than wild-type epidermal growth factor receptors." *Cancer Res.* (1996) 3859-3861, 56(17).
Hanahan et al., "The hallmarks of cancer." *Cell* (2000) 57-70, 100(1).
Hanks et al., "The protein kinase family: conserved features and deduced phylogeny of the catalytic domains." *Science* (1988) 42-52, 241(4861).
Hanna et al., "Phase II trial of cetuximab in patients with previously treated non-small-cell lung cancer." *Journal of Clinical Oncology* (2006) 5253-5258, 24(33).
Harari et al., "Combining radiation with molecular blockade of the EGF receptor in cancer therapy." *Proceedings of the American Association for Cancer Research* (1999) 3747s (Abstract 88), 5.
Harari et al., "Molecular mechanisms underlying ErbB2/HER2 action in breast cancer." *Oncogene* (2000) 6102-6114, 19(53).
Harari, "Epidermal growth factor receptor inhibition strategies in oncology." *Endocrine-related cancer* (2004) 689-708, 11(4).
Harari et al., "Head and neck cancer as a clinical model for molecular targeting of therapy: combining EGFR blockade with radiation." *Int. J. Radiat. Oncol. Biol. Phys.* (2001) 427-433, 49(2).
Harries et al., "The development and clinical use of trastuzumab (Herceptin)." *Endocrine-related cancer* (2002) 75-85, 9(2).
Harris et al., "The Role of ERBB2 Extracellular Domain in Predicting Response to Chemotherapy in Breast Cancer Patients." *Proceedings of the Annual Meeting of the American Society of Clinical Oncology* (1996) 108 (Abstract 96), 15.
Harris et al., "Epidermal Growth Factor Receptor: A Marker of Early Relapse in Breast Cancer and Tumor Stage Progression in Bladder Cancer; Interactions with neu." *In: The Molecular Diagnostics of Human Cancer (Editors: Furth and Greaves; Publisher: Cold Spring Harbor, NY: Cold Spring Harbor Laboratory)*. (1989) 353-357.
Harris et al., "Therapeutic antibodies—the coming of age." *Trends in biotechnology* (1993) 42-44, 11(2).
Hatanpaa et al., "Epidermal growth factor receptor in glioma: signal transduction, neuropathology, imaging, and radioresistance." *Neoplasia* (2010) 675-684, 12(9).

Hayman et al., "Cell transformation by the epidermal growth factor receptor and v-erbB." *Cancer cells (Cold Spring Harbor, N.Y.: 1989)* (1991) 302-307, 3(8).
He et al., "Inhibition of human squamous cell carcinoma growth in vivo by epidermal growth factor receptor antisense RNA transcribed from the U6 promoter." *J. Natl. Cancer Inst.* (1998) 1080-1087, 90(14).
Heath et al., "The human A33 antigen is a transmembrane glycoprotein and a novel member of the immunoglobulin superfamily." *Proceedings of the National Academy of Sciences of the United States of America* (1997) 469-474, 94(2).
Hecht et al., "ABX-EGF monotherapy in patients (pts) with metastatic colorectal cancer (mCRC) (An updated analysis)." *Proceedings of the American Society of Clinical Oncology* (2004) 247s (Abstract 3511), 23.
Heimberger et al., "The natural history of EGFR and EGFRvIII in glioblastoma patients." *Journal of translational medicine* (2005) 38, 3.
Heimberger et al., "Prognostic effect of epidermal growth factor receptor and EGFRvIII in glioblastoma multiforme patients." *Clin. Cancer Res.* (2005) 1462-1466, 11(4).
Heimberger et al., "Epidermal growth factor receptor VIII peptide vaccination is efficacious against established intracerebral tumors." *Clin. Cancer Res.* (2003) 4247-4254, 9(11).
Heimberger et al., "Brain tumors in mice are susceptible to blockade of epidermal growth factor receptor (EGFR) with the oral, specific, EGFR-tyrosine kinase inhibitor ZD1839 (iressa)." *Clin. Cancer Res.* (2002) 3496-3502, 8(11).
Helin et al., "Internalization and down-regulation of the human epidermal growth factor receptor are regulated by the carboxyl-terminal tyrosines." *Journal of Biological Chemistry* (1991) 8363-8368, 266(13).
Helin et al., "The biological activity of the human epidermal growth factor receptor is positively regulated by its C-terminal tyrosines." *Oncogene* (1991) 825-832, 6(5).
Hendler et al., "Human squamous cell lung cancers express increased epidermal growth factor receptors." *J. Clin. Invest.* (1984) 647-651, 74(2).
Henn et al., "Polysomy of chromosome 7 is correlated with overexpression of the erbB oncogene in human glioblastoma cell lines." *Human genetics* (1986) 104-106, 74(1).
Henry et al., "A prostate-specific membrane antigen-targeted monoclonal antibody-chemotherapeutic conjugate designed for the treatment of prostate cancer." *Cancer Res.* (2004) 7995-8001, 64(21).
Hens et al., "Anti-EGFRvIII monoclonal antibody armed with 177Lu: in vivo comparison of macrocyclic and acyclic ligands." *Nucl. Med. Biol.* (2010) 741-750, 37(7).
Hens et al., "Labeling internalizing anti-epidermal growth factor receptor variant III monoclonal antibody with (177)Lu: in vitro comparison of acyclic and macrocyclic ligands." *Nucl. Med. Biol.* (2009) 117-128, 36(2).
Herbertson et al., "Phase I biodistribution and pharmacokinetic study of Lewis Y-targeting immunoconjugate CMD-193 in patients with advanced epithelial cancers." *Clin. Cancer Res.* (2009) 6709-6715, 15(21).
Herbst et al., "Regulation of postendocytic trafficking of the epidermal growth factor receptor through endosomal retention." *Journal of Biological Chemistry* (1994) 12865-12873, 269(17).
Herbst, "Dose-comparative monotherapy trials of ZD1839 in previously treated non-small cell lung cancer patients" *Seminars in Oncology* (2003) 30-38, 30(1).
Herbst et al., "IMC-C225, an anti-epidermal growth factor receptor monoclonal antibody, for treatment of head and neck cancer." *Expert opinion on biological therapy* (2001) 719-732, 1(4).
Herbst et al., "Phase II multicenter study of the epidermal growth factor receptor antibody cetuximab and cisplatin for recurrent and refractory squamous cell carcinoma of the head and neck." *J. Clin. Oncol.* (2005) 5578-5587, 23(24).
Herbst et al., "Phase I/II trial evaluating the anti-vascular endothelial growth factor monoclonal antibody bevacizumab in combination with the HER-1/epidermal growth factor receptor tyrosine kinase inhibitor erlotinib for patients with recurrent non-small-cell lung cancer." *J. Clin. Oncol.* (2005) 2544-2555, 23(11).

(56) References Cited

OTHER PUBLICATIONS

Herbst, "Erlotinib (Tarceva): An update on the clinical trial program" *Seminars in Oncology* (2003) 34-46, 30(3H).

Herbst et al., "IMC-C225, an anti-epidermal growth factor receptor monoclonal antibody for treatment of head and neck cancer." *Semin. Oncol.* (2002) 18-30, 29(5; Suppl. 14).

Herbst et al., "Selective oral epidermal growth factor receptor tyrosine kinase inhibitor ZD1839 is generally well-tolerated and has activity in non-small-cell lung cancer and other solid tumors: results of a phase I trial." *J. Clin. Oncol.* (2002) 3815-3825, 20(18).

Herbst, "Targeted therapy in non-small-cell lung cancer." *Oncology (Williston Park, N.Y.)* (2002) 19-24, 16(9; Suppl. 9).

Herbst et al., "Monoclonal antibodies to target epidermal growth factor receptor-positive tumors: a new paradigm for cancer therapy." *Cancer* (2002) 1593-1611, 94(5).

Herbst et al., "Epidermal growth factor receptors as a target for cancer treatment: the emerging role of IMC-C225 in the treatment of lung and head and neck cancers." *Semin. Oncol.* (2002) 27-36, 29(1 Suppl 4).

Hertler et al., "Immunotoxins: a clinical review of their use in the treatment of malignancies." *J. Clin. Oncol.* (1989) 1932-1942, 7(12).

Van Der Heyden et al., "Identification of an intracellular domain of the EGF receptor required for high-affinity binding of EGF." *FEBS letters* (1997) 265-268, 410(2-3).

Hidalgo et al., "Phase 1 trial of EKB-569, an irreversible inhibitor of the epidermal growth factor receptor (EGFR), in patients with advanced solid tumors." *Proceedings of the American Society of Clinical Oncology* (2002) 17a (Abstract 65), 21.

Hidalgo et al., "Phase I and pharmacologic study of OSI-774, an epidermal growth factor receptor tyrosine kinase inhibitor, in patients with advanced solid malignancies." *J. Clin. Oncol.* (2001) 3267-3279, 19(13).

Hills et al., "Specific targeting of a mutant, activated FGF receptor found in glioblastoma using a monoclonal antibody." *Int. J. Cancer* (1995) 537-543, 63(4).

Hirata et al., "ZD1839 (Iressa) induces antiangiogenic effects through inhibition of epidermal growth factor receptor tyrosine kinase." *Cancer Res.* (2002) 2554-2560, 62(9).

Hird et al., "Immunotherapy with Monoclonal Antibodies." *In: Genes and Cancer (Chapter 17) (Editor: Carry; Publisher: John Wiley & Sons, Ltd).* (1990) 183-189.

Hirsch et al., "Increased epidermal growth factor receptor gene copy number detected by fluorescence in situ hybridization associates with increased sensitivity to gefitinib in patients with bronchioloalveolar carcinoma subtypes: a Southwest Oncology Group Study." *J. Clin. Oncol.* (2005) 6838-6845, 23(28).

Hirsch et al., "Epidermal growth factor receptor in non-small-cell lung carcinomas: correlation between gene copy number and protein expression and impact on prognosis." *J. Clin. Oncol.* (2003) 3798-3807, 21(20).

Hoffman et al., "Phase I Trials of CDR-Grafted Humanized Monoclonal Antibody Hu3S193 in Patients with Lewis-Y Expressing Solid Tumors." *Proc. Am. Soc. Clin. Oncol.* (2001) Abstract 2634, 20.

Hoffmann et al., "Antitumor activity of anti-epidermal growth factor receptor monoclonal antibodies and cisplatin in ten human head and neck squamous cell carcinoma lines." *Anticancer research* (1997) 4419-4425, 17(6D).

Hogg, "Disulfide bonds as switches for protein function." *Trends Biochem. Sci.* (2003) 210-214, 28(4).

Holbro et al., "ErbB receptors: directing key signaling networks throughout life." *Annual review of pharmacology and toxicology* (2004) 195-217, 44.

Holbro et al., "The ErbB receptors and their role in cancer progression." *Exp. Cell Res.* (2003) 99-110, 284(1).

Holbrook et al., "Thermodynamic mixing of molecular states of the epidermal growth factor receptor modulates macroscopic ligand binding affinity." *Biochem. J.* (2000) 99-108, 352(Part 1).

Holland, "Glioblastoma multiforme: the terminator." *Proceedings of the National Academy of Sciences of the United States of America* (2000) 6242-6244, 97(12).

Holland et al., "A constitutively active epidermal growth factor receptor cooperates with disruption of G1 cell-cycle arrest pathways to induce glioma-like lesions in mice." *Genes Dev.* (1998) 3675-3685, 12(23).

Holliger et al., "Diabodies': small bivalent and bispecific antibody fragments." *Proceedings of the National Academy of Sciences of the United States of America* (1993) 6444-6448, 90(14).

Hollstein et al., "Amplification of epidermal growth factor receptor gene but no evidence of ras mutations in primary human esophageal cancers." *Cancer Res.* (1988) 5119-5123, 48(18).

Holm et al., "Functional mapping and single chain construction of the anti-cytokeratin 8 monoclonal antibody TS1." *Mol. Immunol.* (2007) 1075-1084, 44(6).

Holmes et al., "Structural consequences of humanizing an antibody." *Journal of immunology* (1997) 2192-2201, 158(5).

Holt et al., "Domain antibodies: proteins for therapy." *Trends in biotechnology* (2003) 484-490, 21(11).

Honegger et al., "Biological activities of EGF-receptor mutants with individually altered autophosphorylation sites." *EMBO J.* (1988) 3045-3052, 7(10).

Hong et al., "Efficacy and Safety of the Anti-Epidermal Growth Factor Antibody (EGFR) IMC-225, in Combination with Cisplatin in Patients with Recurrent Squamous Cell Carcinoma of the Head and Neck (SCCHN) Refractory to Cisplatin Containing Chemotherapy." *Proceedings of the American Society of Clinical Oncology* (2001) 224a (Abstract 895), 20.

Hooft et al., "Errors in protein structures." *Nature* (1996) 272, 381(6580).

Hortobagyi, "Overview of Treatment Results With Trastuzumab (Herceptin) in Metastatic Breast Cancer." *Seminars in Oncology* (2001) 43-47, 28(6; Suppl. 18).

Hosoi et al., "Exogenous ATP and other nucleoside phosphates modulate epidermal growth factor receptors of A-431 epidermoid carcinoma cells." *Proceedings of the National Academy of Sciences of the United States of America* (1989) 4510-4514, 86(12).

Huang et al., "The enhanced tumorigenic activity of a mutant epidermal growth factor receptor common in human cancers is mediated by threshold levels of constitutive tyrosine phosphorylation and unattenuated signaling." *JBC* (1997) 2927-2935, 272(5).

Huang et al., "Phosphotyrosine signaling analysis of site-specific mutations on EGFRvIII identifies determinants governing glioblastoma cell growth." *Molecular bioSystems* (2010) 1227-1237, 6(7).

Huang et al., "Uncovering therapeutic targets for glioblastoma: a systems biology approach." *Cell cycle (Georgetown, Tex.)* (2007) 2750-2754, 6(22).

Huang et al., "Quantitative analysis of EGFRvIII cellular signaling networks reveals a combinatorial therapeutic strategy for glioblastoma." *Proceedings of the National Academy of Sciences of the United States of America* (2007) 12867-12872, 104(31).

Huang et al., "Modulation of radiation response after epidermal growth factor receptor blockade in squamous cell carcinomas: inhibition of damage repair, cell cycle kinetics, and tumor angiogenesis." *Clin. Cancer Res.* (2000) 2166-2174, 6(6).

Huang et al., "Epidermal growth factor receptor blockade with C225 modulates proliferation, apoptosis, and radiosensitivity in squamous cell carcinomas of the head and neck." *Cancer Res.* (1999) 1935-1940, 59(8).

Huang et al., "Epidermal growth factor receptor inhibition in cancer therapy: biology, rationale and preliminary clinical results." *Investigational new drugs* (1999) 259-269, 17(3).

Huang et al., "Modulation of radiation response and tumor-induced angiogenesis after epidermal growth factor receptor inhibition by ZD1839 (Iressa)." *Cancer Res.* (2002) 4300-4306, 62(15).

Huang et al., "Dual-agent molecular targeting of the epidermal growth factor receptor (EGFR): combining anti-EGFR antibody with tyrosine kinase inhibitor." *Cancer Res.* (2004) 5355-5362, 64(15).

Hubbard et al., "Protein tyrosine kinase structure and function." *Annual review of biochemistry* (2000) 373-398, 69.

(56) References Cited

OTHER PUBLICATIONS

Hubbard, "EGF receptor inhibition: attacks on multiple fronts." *Cancer Cell* (2005) 287-288, 7(4).
Huber et al., "Trimodal cancer treatment: beneficial effects of combined antiangiogenesis, radiation, and chemotherapy." *Cancer Res.* (2005) 3643-3655, 65(9).
Hudson et al., "Engineered antibodies." *Nature Med.* (2003) 129-134, 9(1).
Humphrey et al., "Deletion-mutant epidermal growth factor receptor in human gliomas: effects of type II mutation on receptor function." *Biochem. Biophys. Res. Commun.* (1991) 1413-1420, 178(3).
Humphrey et al., "Anti-synthetic peptide antibody reacting at the fusion junction of deletion-mutant epidermal growth factor receptors in human glioblastoma." *Proceedings of the National Academy of Sciences of the United States of America* (1990) 4207-4211, 87(11).
Humphrey et al., "Amplification and expression of the epidermal growth factor receptor gene in human glioma xenografts." *Cancer Res.* (1988) 2231-2238, 48(8).
Humphreys et al., "Therapeutic antibody production production technologies: molecules, applications, expression and purification." *Current opinion in drug discovery & development* (2001) 172-185, 4(2).
Hunts et al., "Hyperproduction and gene amplification of the epidermal growth factor receptor in squamous cell carcinomas." *Japanese journal of cancer research: Gann* (1985) 663-666, 76(8).
Hurtt et al., "Amplification of epidermal growth factor receptor gene in gliomas: histopathology and prognosis." *Journal of neuropathology and experimental neurology* (1992) 84-90, 51(1).
Hurwitz et al., "Bevacizumab plus irinotecan, fluorouracil, and leucovorin for metastatic colorectal cancer." *N. Engl. J. Med.* (2004) 2335-2342, 350(23).
Huston et al., "Protein engineering of antibody binding sites: recovery of specific activity in an anti-digoxin single-chain Fv analogue produced in *Escherichia coli*." *Proceedings of the National Academy of Sciences of the United States of America* (1988) 5879-5883, 85(16).
Hynes et al., "ERBB receptors and cancer: the complexity of targeted inhibitors." *Nature Rev. Cancer* (2005) 341-354, 5(5).
Illidge et al., "Antibody therapy of lymphoma." *Expert opinion on pharmacotherapy* (2001) 953-961, 2(6).
Inoue et al., "Paclitaxel enhances the effects of the anti-epidermal growth factor receptor monoclonal antibody ImClone C225 in mice with metastatic human bladder transitional cell carcinoma." *Clin. Cancer Res.* (2000) 4874-4884, 6(12).
Ishida et al., "[the expression technology of chimeric and humanized antibodies]." *Nippon rinsho. Japanese journal of clinical medicine* (2002) 439-444, 60(3). **English abstract of Japanese document.
Ishitoya et al., "Gene amplification and overexpression of EGF receptor in squamous cell carcinomas of the head and neck." *British Journal of Cancer* (1989) 559-562, 59(4).
Ishizawar et al., "c-Src and cooperating partners in human cancer." *Cancer Cell* (2004) 209-214, 6(3).
Italiano, "Targeting the epidermal growth factor receptor in colorectal cancer: advances and controversies." *Oncology* (2006) 161-167, 70(3).
Iznaga-Escobar et al., "Technetium-99m-antiepidermal growth factor-receptor antibody in patients with tumors of epithelial origin: part II. Pharmacokinetics and clearances." *J. Nucl. Med.* (1998) 1918-1927, 39(11).
Jamnongjit et al., "Epidermal growth factor receptor signaling is required for normal ovarian steroidogenesis and oocyte maturation." *Proceedings of the National Academy of Sciences of the United States of America* (2005) 16257-16262, 102(45).
Janmaat et al., "Response to epidermal growth factor receptor inhibitors in non-small cell lung cancer cells: limited antiproliferative effects and absence of apoptosis associated with persistent activity of extracellular signal-regulated kinase or Akt kinase pathways." *Clin. Cancer Res.* (2003) 2316-2326, 9(6).

Jänne et al., "Epidermal growth factor receptor mutations in non-small-cell lung cancer: implications for treatment and tumor biology." *J. Clin. Oncol.* (2005) 3227-3234, 23(14).
Jaros et al., "Prognostic implications of p53 protein, epidermal growth factor receptor, and Ki-67 labelling in brain tumours." *British Journal of Cancer* (1992) 373-385, 66(2).
Jay et al., "Chemical synthesis of a biologically active gene for human immune interferon-gamma. Prospect for site-specific mutagenesis and structure-function studies." *Journal of Biological Chemistry* (1984) 6311-6317, 259(10).
Ji et al., "EGFR targeted therapy: view from biological standpoint." *Cell cycle (Georgetown, Tex.)* (2006) 2072-2076, 5(18).
Ji et al., "The impact of human EGFR kinase domain mutations on lung tumorigenesis and in vivo sensitivity to EGFR-targeted therapies." *Cancer Cell* (2006) 485-495, 9(6).
Ji et al., "Epidermal growth factor receptor variant III mutations in lung tumorigenesis and sensitivity to tyrosine kinase inhibitors." *Proceedings of the National Academy of Sciences of the United States of America* (2006) 7817-7822, 103(20).
Jiang et al., "A novel peptide isolated from a phage display peptide library with trastuzumab can mimic antigen epitope of HER-2." *JBC* (2005) 4656-4662, 280(6).
Jiang et al., "Growth suppression of human hepatocellular carcinoma xenografts by a monoclonal antibody CH12 directed to epidermal growth factor receptor variant III." (2011) 5913-5920, 286(7).
Johns, "Targeting the Transition State" *Science's STKE* (2004) tw259, 2004(242).
Johns et al., "A Novel Antibody Directed to the Epidermal Growth Factor Receptor (EGFR) Displays Additive and Synergistic Anti-tumour Activity when used in Combination with Standard EGFR Therapeutics." *The Proceedings of the 15th Annual Lorne Cancer Conference, Lorne, Victoria, Australia.* (2003) Abstract P212.
Johns et al., "A Novel Antibody Directed to the Epidermal Growth Factor Receptor (EGFR) Displays Additive and Synergistic Anti-Tumor Activity When Used in Combination with Standard EGFR Therapeutics." *Proceedings of the International Symposium sponsored by the Cancer Research Institute, New York, U.S.A.* (2002) Abstract P-08.
Johns et al., "Biological Properties of the Glioma Associated Delta 2-7 Epidermal Growth Factor Receptor." *The 11th International Conference on Second Messengers and Phosphoproteins, Melbourne, Australia* (2001) Abstract P183.
Johns et al., "Annual Branch Report 1998 ("Pre-clinical evaluation of antibodies directed to the de2-7 epidermal growth factor receptors")" *Ludwig Institute for Cancer Research* (2000) 118-119.
Johns et al., "A Novel Antibody Directed to the Epidermal Growth Factor Receptor (EGFR) Displays Additive and Synergistic Anti-tumor Activity when Used in Combination with Standard EGFR therapeutics (Abstract 2877)" *Proceedings of the American Association of Cancer Research* (2002) 580, 43.
Johns et al., "The antitumor monoclonal antibody 806 recognizes a high-mannose form of the EGF receptor that reaches the cell surface when cells over-express the receptor" *FASEB J.* (2005) 1-18, 19(3).
Johns et al., "MAb 806 enhances the efficacy of ionizing radiation in glioma xenografts expressing the de2-7 epidermal growth factor receptor." *Int. J. Radiat. Oncol. Biol. Phys.* (2010) 572-578, 78(2).
Johns et al., "The efficacy of epidermal growth factor receptor-specific antibodies against glioma xenografts is influenced by receptor levels, activation status, and heterodimerization." *Clin. Cancer Res.* (2007) 1911-1925, 13(6).
Johns et al., "The antitumor monoclonal antibody 806 recognizes a high-mannose form of the EGF receptor that reaches the cell surface when cells over-express the receptor." *FASEB J.* (2005) 780-782, 19(7).
Johns et al., "Identification of the epitope for the epidermal growth factor receptor-specific monoclonal antibody 806 reveals that it preferentially recognizes an untethered form of the receptor." *JBC* (2004) 30375-30384, 279(29).
Johns et al., "Antitumor efficacy of cytotoxic drugs and the monoclonal antibody 806 is enhanced by the EGF receptor inhibitor AG1478." *Proceedings of the National Academy of Sciences of the United States of America* (2003) 15871-15876, 100(26).

(56) References Cited

OTHER PUBLICATIONS

Johns et al., "Novel monoclonal antibody specific for the de2-7 epidermal growth factor receptor (EGFR) that also recognizes the EGFR expressed in cells containing amplification of the EGFR gene." *Int. J. Cancer* (2002) 398-408, 98(3).
Jones et al., "A quantitative protein interaction network for the ErbB receptors using protein microarrays." *Nature* (2006) 168-174, 439(7073).
De Jong et al., "Expression of growth factors, growth-inhibiting factors, and their receptors in invasive breast cancer. II: Correlations with proliferation and angiogenesis." *The Journal of pathology* (1998) 53-57, 184(1).
Jorgensen et al., "Immunoconjugates: A Therapy Whose Time Has Come?" *Preclinica* (2004) 1-4, 2.
Jorissen et al., "Characterization of a comparative model of the extracellular domain of the epidermal growth factor receptor." *Protein science* (2000) 310-324, 9(2).
Jorissen et al., "Epidermal growth factor receptor: mechanisms of activation and signalling." *Exp. Cell Res.* (2003) 31-53, 284(1).
Jost et al., "The EGF receptor—an essential regulator of multiple epidermal functions." *European journal of dermatology: EJD* (2000) 505-510, 10(7).
Jung et al., "Local immunotherapy of glioma patients with a combination of 2 bispecific antibody fragments and resting autologous lymphocytes: evidence for in situ t-cell activation and therapeutic efficacy." *Int. J. Cancer* (2001) 225-230, 91(2).
Jungbluth et al., "A monoclonal antibody recognizing human cancers with amplification/overexpression of the human epidermal growth factor receptor." *Proceedings of the National Academy of Sciences of the United States of America* (2003) 639-644, 100(2).
Jutten et al., "Binding of cetuximab to the EGFRvIII deletion mutant and its biological consequences in malignant glioma cells." *Radiotherapy and oncology* (2009) 393-398, 92(3).
Kalofonos et al., "Antibody guided diagnosis and therapy of brain gliomas using radiolabeled monoclonal antibodies against epidermal growth factor receptor and placental alkaline phosphatase." *J. Nucl. Med.* (1989) 1636-1645, 30(10).
Kamat et al., "Enhanced EGFR inhibition and distinct epitope recognition by EGFR antagonistic mAbs C225 and 425." *Cancer biology & therapy* (2008) 726-733, 7(5).
Kamb et al., "A cell cycle regulator potentially involved in genesis of many tumor types." *Science* (1994) 436-440, 264(5157).
Kaminski et al., "Iodine-131-anti-B1 radioimmunotherapy for B-cell lymphoma." *J. Clin. Oncol.* (1996) 1974-1981, 14(7).
Karnes et al., "Inhibition of epidermal growth factor receptor kinase induces protease-dependent apoptosis in human colon cancer cells." *Gastroenterology* (1998) 930-939, 114(5).
Karnes et al., "Autonomous proliferation of colon cancer cells that coexpress transforming growth factor alpha and its receptor. Variable effects of receptor-blocking antibody." *Gastroenterology* (1992) 474-485, 102(2).
Karpel-Massler et al., "Therapeutic inhibition of the epidermal growth factor receptor in high-grade gliomas: where do we stand?" *Molecular cancer research: MCR* (2009) 1000-1012, 7(7).
Kashmiri et al., "Development of a minimally immunogenic variant of humanized anti-carcinoma monoclonal antibody CC49." *Crit. Rev. Oncol. Hematol.* (2001) 3-16, 38(1).
Kasprzyk et al., "Therapy of an animal model of human gastric cancer using a combination of anti-erbB-2 monoclonal antibodies." *Cancer Res.* (1992) 2771-2776, 52(10).
Katzel et al., "Recent advances of novel targeted therapy in non-small cell lung cancer." *Journal of hematology & oncology* (2009) 2, 2.
Kawagoe et al., "Immunohistochemical demonstration of epidermal growth factor (EGF) receptors in normal human placental villi." *Placenta* (1990) 7-15, 11(1).
Kawamoto et al., "Relation of epidermal growth factor receptor concentration to growth of human epidermoid carcinoma A431 cells." *Journal of Biological Chemistry* (1984) 7761-7766, 259(12).
Kawamoto et al., "Growth stimulation of A431 cells by epidermal growth factor: identification of high-affinity receptors for epidermal growth factor by an anti-receptor monoclonal antibody." *Proceedings of the National Academy of Sciences of the United States of America* (1983) 1337-1341, 80(5).
Ke et al., "Differential expression of epidermal growth factor receptor in human head and neck cancers." *Head & neck* (1998) 320-327, 20(4).
Kelly et al., "ZD1839 ('Iressa'), an oral EGFR-TKI (epidermal growth factor receptor tyrosine kinase inhibitor): Pharmacokinetic results of a phase I study in patients with advanced cancer." *Proceedings of the Annual Meeting of the American Association for Cancer Research* (2000) 612-613 (Abstract 3896), 41.
Kelly et al., "Therapeutic efficacy of 177Lu-CHX-A"-DTPA-hu3S193 radioimmunotherapy in prostate cancer is enhanced by EGFR inhibition or docetaxel chemotherapy." *The Prostate* (2009) 92-104, 69(1).
Khazaeli et al., "Low Immunogenicity of a Chimeric Monoclonal Antibody (MoAb), IMC-C225, Used to Treat Epidermal Growth Factor Receptor-Positive Tumors." *Proceedings of the American Society of Clinical Oncology* (2000) 207a (Abstract 808), 19.
Khazaeli et al., "Human immune response to monoclonal antibodies." *Journal of immunotherapy with emphasis on tumor immunology: official journal of the Society for Biological Therapy* (1994) 42-52, 15(1).
Khazaeli et al., "Pharmacokinetics and immune response of 131I-chimeric mouse/human B72.3 (human gamma 4) monoclonal antibody in humans." *Cancer Res.* (1991) 5461-5466, 51(20).
Khazaie et al., "EGF receptor in neoplasia and metastasis." *Cancer Metastasis Rev.* (1993) 255-274, 12(3-4).
Kies et al., "Final report of the efficacy and safety of the anti-epidermal growth factor antibody Erbitux (IMC-C225), in combination with cisplatin in patients with recurrent squamous cell carcinoma of the head and neck (SCCHN) refractory to cisplatin containing chemotherapy." *Proceedings of the American Society of Clinical Oncology* (2002) 232a (Abstract 925), 21.
Kikkawa et al., "[Immunohistochemical and histopathological study of expression of epidermal growth factor receptors in gastric cancer]." *Nippon Geka Gakkai zasshi* (1993) 1231-1238, 94(12).**Abstract in English of Japanese Document.
Kil et al., "A leucine-based determinant in the epidermal growth factor receptor juxtamembrane domain is required for the efficient transport of ligand-receptor complexes to lysosomes." *JBC* (1999) 3141-3150, 274(5).
Kim et al., "A phase II study of Erbitux (IMC-225), an epidermal growth factor receptor (EGFR) blocking antibody, in combination with docetaxel in chemotherapy refractory/resistant patients with advanced non-small cell lung cancer (NSCLC) (Abstract 1168)" *Proceedings of the American Society of Clinical Oncology* (2011) 293a, 21.
Kim et al., "Epidermal growth factor receptor biology (IMC-C225)." *Current opinion in oncology* (2001) 506-513, 13(6).
Kim et al., "Regulation of epidermal growth factor receptor internalization by G protein-coupled receptors." *Biochemistry* (2003) 2887-2894, 42(10).
Kim et al., "Enhancement of colorectal tumor targeting using a novel biparatopic monoclonal antibody against carcinoembryonic antigen in experimental radioimmunoguided surgery." *Int. J. Cancer* (2002) 542-547, 97(4).
King et al., "Preparation and preclinical evaluation of humanised A33 immunoconjugates for radioimmunotherapy." *British Journal of Cancer* (1995) 1364- 1372, 72(6).
Kiyota et al., "Expression of a truncated epidermal growth factor receptor in oral squamous cell carcinomas." *Cancer Letters* (2000) 9-15, 161(1).
Kiyota et al., "Anti-epidermal growth factor receptor monoclonal antibody 225 upregulates p27(KIP1) and p15(INK4B) and induces G1 arrest in oral squamous carcinoma cell lines." *Oncology* (2002) 92-98, 63(1).
Klapper et al., "Tumor-inhibitory antibodies to HER-2/ErbB-2 may act by recruiting c-Cbl and enhancing ubiquitination of HER-2." *Cancer Res.* (2000) 3384-3388, 60(13).
Klapper et al., "Biochemical and clinical implications of the ErbB/HER signaling network of growth factor receptors." *Advances in cancer research* (2000) 25-79, 77.

(56) References Cited

OTHER PUBLICATIONS

Klijn et al., "The prognostic value of epidermal growth factor receptor (EGF-R) in primary breast cancer: results of a 10 year follow-up study." *Breast cancer research and treatment* (1994) 73-83, 29(1).

Klijn et al., "The clinical significance of epidermal growth factor receptor (EGF-R) in human breast cancer: a review on 5232 patients." *Endocrine reviews* (1992) 3-17, 13(1).

Klingbeil et al., "Analysis of substrate recognition determinants in a synthetic peptide containing the Tyr 1173 autophosphorylation site of the epidermal growth factor receptor." *Archives of biochemistry and biophysics* (1995) 745-750, 316(2).

Klingler-Hoffmann et al., "Inhibition of phosphatidylinositol 3-kinase signaling negates the growth advantage imparted by a mutant epidermal growth factor receptor on human glioblastoma cells." *Int. J. Cancer* (2003) 331-339, 105(3).

Klohs et al., "Inhibitors of tyrosine kinase." *Current opinion in oncology* (1997) 562-568, 9(6).

Knecht et al., "Carcinomas unresponsive to either cisplatinum or anti-EGFR therapy can be growth inhibited by combination therapy of both agents." *Anticancer research* (2003) 2577-2583, 23(3B).

Knutson et al., "Rapid, reversible internalization of cell surface insulin receptors. Correlation with insulin-induced down-regulation." *JBC* (1983) 12139-12142, 258(20).

Kobayashi et al., "An alternative inhibitor overcomes resistance caused by a mutation of the epidermal growth factor receptor." *Cancer Res.* (2005) 7096-7101, 65(16).

Kobayashi et al., "EGFR mutation and resistance of non-small-cell lung cancer to gefitinib." *N. Engl. J. Med.* (2005) 786-792, 352(8).

Kondo et al., "Mapping of the human gene for epidermal growth factor receptor (EGFR) on the p13 I q22 region of chromosome 7." *Cytogenet. Cell Genet.* (1983) 9-14, 35(1).

Kopetz, "Synergistic effects of combination therapy with anti-EGFR and anti-Src therapy in vitro in colon cancer" *Gastrointestinal Cancers Symposium* (2007) Abstract.

Koprivica et al., "EGFR activation mediates inhibition of axon regeneration by myelin and chondroitin sulfate proteoglycans." *Science* (2005) 106-110, 310(5745).

Korshunov et al., "Prognostic value of tumour associated antigen immunoreactivity and apoptosis in cerebral glioblastomas: an analysis of 168 cases." *Journal of clinical pathology* (1999) 574-580, 52(8).

Kosaka et al., "Mutations of the epidermal growth factor receptor gene in lung cancer: biological and clinical implications." *Cancer Res.* (2004) 8919-8923, 64(24).

Kramer et al., "Regulation of daily locomotor activity and sleep by hypothalamic EGF receptor signaling." *Science* (2001) 2511-2515, 294(5551).

Kris et al., "A phase II trial of ZD1839 ('Iressa') in advanced non-small cell lung cancer (NSCLC) patients who had failed platinum- and docetaxel-based regimens (IDEAL 2)." *Proceedings of the American Society of Clinical Oncology* (2002) 292a (Abstract 1166), 21.

Kris et al., "Objective regressions in non-small-cell lung cancer patients treated in phase I trials of oral ZD1839 (Iressa), a selective tyrosine kinase inhibitor that blocks the epidermal growth factor receptor (EGFR) (Abstract 233)" *Lung Cancer* (2000) 72, 29.

Krug et al., "Targeting Lewis Y (Le(y)) in small cell lung cancer with a humanized monoclonal antibody, hu3S193: a pilot trial testing two dose levels." *Journal of thoracic oncology: official publication of the International Association for the Study of Lung Cancer* (2007) 947-952, 2(10).

Kuan et al., "EGF mutant receptor vIII as a molecular target in cancer therapy." *Endocrine-related cancer* (2001) 83-96, 8(2).

Kuan et al., "Increased binding affinity enhances targeting of glioma xenografts by EGFRvIII-specific scFv." *Int. J. Cancer* (2000) 962-969, 88(6).

Kuan et al., "EGFRvIII as a promising target for antibody-based brain tumor therapy." *Brain tumor pathology* (2000) 71-78, 17(2).

Kuan et al., "125I-labeled anti-epidermal growth factor receptor-vIII single-chain Fv exhibits specific and high-level targeting of glioma xenografts." *Clin. Cancer Res.* (1999) 1539-1549, 5(6).

Kubo et al., "Three-dimensional magnetic resonance microscopy of pulmonary solitary tumors in transgenic mice." *Magnetic resonance in medicine: official journal of the Society of Magnetic Resonance in Medicine/Society of Magnetic Resonance in Medicine* (2006) 698-703, 56(3).

Kumar et al., "Regulation of phosphorylation of the c-erbB-2/HER2 gene product by a monoclonal antibody and serum growth factor(s) in human mammary carcinoma cells." *Mol. Cell Biol.* (1991) 979-986, 11(2).

Kunkel et al., "Inhibition of the epidermal growth factor receptor tyrosine kinase by PD153035 in human A431 tumors in athymic nude mice." *Investigational new drugs* (1996) 295-302, 13(4).

Kurpad et al., "Tumor antigens in astrocytic gliomas." *Glia* (1995) 244-256, 15(3).

Kwak et al., "Irreversible inhibitors of the EGF receptor may circumvent acquired resistance to gefitinib." *Proceedings of the National Academy of Sciences of the United States of America* (2005) 7665-7670, 102(21).

Kwok et al., "Cell cycle dependence of epidermal growth factor induced radiosensitization." *Int. J. Radiat. Oncol. Biol. Phys.* (1992) 525-527, 22(3).

Kwok et al., "Differences in EGF related radiosensitisation of human squamous carcinoma cells with high and low numbers of EGF receptors." *British Journal of Cancer* (1991) 251-254, 64(2).

Lackmann et al., "Eph, a protein family coming of age: more confusion, insight, or complexity?" *Science signaling* (2008) re2, 1(15).

Lacouture, "Mechanisms of cutaneous toxicities to EGFR inhibitors." *Nature Rev. Cancer* (2006) 803-812, 6(10).

Laderoute et al., "Epidermal growth factor modifies cell cycle control in A431 human squamous carcinoma cells damaged by ionizing radiation." *Cancer Res.* (1994) 1407-1411, 54(6).

Lakowicz, "Principles of Fluorescence Spectroscopy" *Principles of fluorescence spectroscopy. 2nd edit, Kluwer Academic/Plenum, New York* (1999). Table of Contents.

Lal et al., "Mutant epidermal growth factor receptor up-regulates molecular effectors of tumor invasion." *Cancer Res.* (2002) 3335-3339, 62(12).

Lammering et al., "Radiosensitization of malignant glioma cells through overexpression of dominant-negative epidermal growth factor receptor." *Clin. Cancer Res.* (2001) 682-690, 7(3).

Lammering et al., "Inhibition of the type III epidermal growth factor receptor variant mutant receptor by dominant-negative EGFR-CD533 enhances malignant glioma cell radiosensitivity." *Clin. Cancer Res.* (2004) 6732-6743, 10(19).

Lammering et al., "EGFRvIII-mediated radioresistance through a strong cytoprotective response." *Oncogene* (2003) 5545-5553, 22(36).

Lammerts Van Bueren et al., "The antibody zalutumumab inhibits epidermal growth factor receptor signaling by limiting intra- and intermolecular flexibility." *Proceedings of the National Academy of Sciences of the United States of America* (2008) 6109-6114, 105(16).

Lammerts Van Bueren et al., "Effect of target dynamics on pharmacokinetics of a novel therapeutic antibody against the epidermal growth factor receptor: implications for the mechanisms of action." *Cancer Res.* (2006) 7630-7638, 66(15).

Landry et al., "Antibody recognition of a conformational epitope in a peptide antigen: Fv-peptide complex of an antibody fragment specific for the mutant EGF receptor, EGFRvIII." *J. Mol. Biol.* (2001) 883-893, 308(5).

Langedijk et al., "Antigenic structure of the central conserved region of protein G of bovine respiratory syncytial virus." *Journal of virology* (1997) 4055-4061, 71(5).

Lango et al., "Targeting growth factor receptors: integration of novel therapeutics in the management of head and neck cancer." *Current opinion in oncology* (2001) 168-175, 13(3).

Lanzetti et al., "The Eps8 protein coordinates EGF receptor signalling through Rac and trafficking through Rab5." *Nature* (2000) 374-377, 408(6810).

Lapthorn et al., "Cystine nooses and protein specificity." *Nature structural biology* (1995) 266-268, 2(4).

(56) References Cited

OTHER PUBLICATIONS

De Larco et al., "Sarcoma growth factor from mouse sarcoma virus-transformed cells. Purification by binding and elution from epidermal growth factor receptor-rich cells." *JBC* (1980) 3685-3690, 255(8).

De Larco et al., "Epithelioid and fibroblastic rat kidney cell clones: epidermal growth factor (EGF) receptors and the effect of mouse sarcoma virus transformation." *Journal of cellular physiology* (1978) 335-342, 94(3).

Larysz et al., "Epidermal growth factor receptor gene expression in high grade gliomas?" *Folia neuropathologica/Association of Polish Neuropathologists and Medical.Research Centre, Polish Academy of Sciences* (2011) 28-38, 49(1).

Laskowski et al., "Procheck: a program to check the stereochemical quality of protein structures" *J. Appl. Cryst.* (1993) 283-291, 26.

Lassman et al., "Response of glioblastomas to EGFR kinase inhibitors." *N. Engl. J.Med.* (2006) 525-6; author reply 525-6, 354(5).

Lautrette et al., "Angiotensin II and EGF receptor cross-talk in chronic kidney diseases: a new therapeutic approach." *Nature Med.* (2005) 867-874, 11(8).

Lawrentschuk et al., "Assessing regional hypoxia in human renal tumours using 18F-fluoromisonidazole positron emission tomography." *BJU international* (2005) 540-546, 96(4).

Lax et al., "Epidermal growth factor (EGF) induces oligomerization of soluble, extracellular, ligand-binding domain of EGF receptor. A low resolution projection structure of the ligand-binding domain." *JBC* (1991) 13828-13833, 266(21).

Lax et al., "Noncontiguous regions in the extracellular domain of EGF receptor define ligand-binding specificity." *Cell regulation* (1991) 337-345, 2(5).

Lax et al., "Functional analysis of the ligand binding site of EGF-receptor utilizing chimeric chicken/human receptor molecules." *EMBO J.* (1989) 421-427, 8(2).

Leahy et al., "A mammalian expression vector for expression and purification of secreted proteins for structural studies." *Protein Expr. Purif.* (2000) 500-506, 20(3).

Learn et al., "Resistance to tyrosine kinase inhibition by mutant epidermal growth factor receptor variant III contributes to the neoplastic phenotype of glioblastoma multiforme." *Clin. Cancer Res.* (2004) 3216-3224, 10(9).

Lee et al., "ImmunoPET detection of xenografts expressing de2-7 EGFR using Iodine-124 labelled ch806 via residualising ligand IMPR4" *J. Nucl. Med.* (2006) 429P, 47(5, Suppl. 1).

Lee et al., "Immuno-PET of human colon xenograft- bearing BALB/c nude mice using 124I-CDR-grafted humanized A33 monoclonal antibody." *J. Nucl. Med.* (2001) 764-769, 42(5).

Lee et al., "Immuno-PET quantitation of de2-7 epidermal growth factor receptor expression in glioma using 124I-Imp-R4-labeled antibody ch806." *J. Nucl. Med.* (2010) 967-972, 51(6).

Lee et al., "Enhanced efficacy of radioimmunotherapy with 90Y-CHX-A"-DTPA-hu3S193 by inhibition of epidermal growth factor receptor (EGFR) signaling with EGFR tyrosine kinase inhibitor AG1478." *Clin. Cancer Res.* (2005) 7080s-7086s, 11.

Lee et al., "Immuno-PET for tumor targeting." *J. Nucl. Med.* (2003) 1282-1283, 44(8).

Lee et al., "Therapeutic efficacy of antiglioma mesenchymal extracellular matrix 131I-radiolabeled murine monoclonal antibody in a human glioma xenograft model." *Cancer Res.* (1988) 559-566, 48(3).

Legge, "Computational Design of Humanized Antibodies against the Epidermal Growth Factor Receptor (PhD Thesis)" *Submitted in total fulfillment of the requirements of the degree of Doctor of Philosophy. University of Melbourne.* (2003) 1-278.

Lei et al., "Enhancement of chemosensitivity and programmed cell death by tyrosine kinase inhibitors correlates with EGFR expression in non-small cell lung cancer cells." *Anticancer research* (1999) 221-228, 19.

Lenferink et al., "Blockade of the epidermal growth factor receptor tyrosine kinase suppresses tumorigenesis in MMTV/Neu + MMTV/TGF-alpha bigenic mice." *Proceedings of the National Academy of Sciences of the United States of America* (2000) 9609-9614, 97(17).

Lenz et al., "Consistent Response to Treatment with Cetuximab Monotherapy in Patients with Metastatic Colorectal Cancer." *Journal of Clinical Oncology, 2005 ASCO Annual Meeting Proceedings* (2005) Abstract 3536, 23(16S; Part I of II: Jun. 1 Supplement).

Lenz et al., "Multicenter phase II and translational study of cetuximab in metastatic colorectal carcinoma refractory to irinotecan, oxaliplatin, and fluoropyrimidines." *Journal of Clinical Oncology* (2006) 4914-4921, 24(30).

Leon et al., "Genetic aberrations in human brain tumors." *Neurosurgery* (1994) 708-722, 34(4).

Leu et al., "Functional implication of the interaction between EGF receptor and c-Src." *Frontiers in bioscience: a journal and virtual library* (2003) s28-38, 8.

Levitzki et al., "Tyrosine kinase inhibition: an approach to drug development." *Science* (1995) 1782-1788, 267(5205).

Lewis Phillips et al., "Targeting HER2-Positive Breast Cancer with Trastuzumab-DM1, an Antibody-Cytotoxic Drug Conjugate" *Cancer Research* (2008) 9280-9290, 68(22).

Li et al., "Mutant epidermal growth factor receptor displays increased signaling through the phosphatidylinositol-3 kinase/AKT pathway and promotes radioresistance in cells of astrocytic origin." *Oncogene* (2004) 4594-4602, 23(26).

Li et al., "Resistance to small molecule inhibitors of epidermal growth factor receptor in malignant gliomas." *Cancer Res.* (2003) 7443-7450, 63(21).

Li et al., "Therapeutic anti-EGFR antibody 806 generates responses in murine de novo EGFR mutant-dependent lung carcinomas." *J. Clin. Invest.* (2007) 346-352, 117(2).

Li et al., "EGF receptor variant III as a target antigen for tumor immunotherapy." *Expert Review of Vaccines* (2008) 977-985, 7(7).

Li et al., "Structural basis for EGF receptor inhibition by the therapeutic antibody IMC-11F8." *Structure* (2008) 216-227, 16(2).

Li et al., "Structural basis for inhibition of the epidermal growth factor receptor by cetuximab." *Cancer Cell* (2005) 301-311, 7(4).

Libermann et al., "Amplification, enhanced expression and possible rearrangement of EGF receptor gene in primary human brain tumours of glial origin." *Nature* (1985) 144-147, 313(5998).

Libermann et al., "Expression of epidermal growth factor receptors in human brain tumors." *Cancer Res.* (1984) 753-760, 44(2).

Lichtner et al., "Signaling-inactive epidermal growth factor receptor/ligand complexes in intact carcinoma cells by quinazoline tyrosine kinase inhibitors." *Cancer Res.* (2001) 5790-5795, 61(15).

Lin et al., "Expression cloning of human EGF receptor complementary DNA: gene amplification and three related messenger RNA products in A431 cells." *Science* (1984) 843-848, 224(4651).

Lindmo et al., "Determination of the immunoreactive fraction of radiolabeled monoclonal antibodies by linear extrapolation to binding at infinite antigen excess." *J. Immunol. Methods* (1984) 77-89, 72(1).

Lipton et al., "Elevated Serum HER-2/neu Level Predicts Decreased Response to Hormone Therapy in Metastatic Breast Cancer." *Proceedings of the American Society of Clinical Oncology* (2000) 71a (Abstract 274), 19.

Little et al., "Of mice and men: hybridoma and recombinant antibodies." *Immunology Today* (2000) 364-370, 21(8).

Liu et al., "Epidermal growth factor receptor activation: an upstream signal for transition of quiescent astrocytes into reactive astrocytes after neural injury." *The Journal of neuroscience: the official journal of the Society for Neuroscience* (2006) 7532-7540, 26(28).

Liu et al., "Clinical significance of EGFR amplification and the aberrant EGFRvIII transcript in conventionally treated astrocytic gliomas." *Journal of Molecular Medicine (Berlin, Germany)* (2005) 917-926, 83(11).

Liu et al., "The effect of epidermal growth factor receptor variant III on glioma cell migration by stimulating ERK phosphorylation through the focal adhesion kinase signaling pathway." *Archives of Biochemistry and Biophysics* (2010) 89-95, 502(2).

Liu et al., "Engineering therapeutic monoclonal antibodies." *Immunological Reviews* (2008) 9-27, 222.

Liu et al., "Generation of anti-idiotype antibodies for application in clinical immunotherapy laboratory analyses." *Hybridoma and Hybridomics* (2003) 219-228, 22(4).

(56) References Cited

OTHER PUBLICATIONS

Livneh et al., "Reconstitution of human epidermal growth factor receptors and its deletion mutants in cultured hamster cells." *Journal of Biological Chemistry* (1986) 12490-12497, 261(27).
Lo, "EGFR-targeted therapy in malignant glioma: novel aspects and mechanisms of drug resistance." *Current Molecular Pharmacology* (2010) 37-52, 3(1).
Lobuglio et al., "Mouse/human chimeric monoclonal antibody in man: kinetics and immune response." *Proceedings of the National Academy of Sciences of the United States of America* (1989) 4220-4224, 86(11).
Loew et al., "The epidermal growth factor receptor as a therapeutic target in glioblastoma multiforme and other malignant neoplasms." *Anti-Cancer Agents in Medicinal Chemistry* (2009) 703-715, 9(6).
Lofts et al., "c-erbB2 amplification and overexpression in human tumors." *In: Genes, Oncogenes, and Hormones: Advances in Cellular and Molecular Biology of Breast Cancer (Editors: Dickson and Lippman; Publisher: Kluwer Academic, Boston, MA)*. (1992) 161-179.
Van De Loosdrecht et al., "A tetrazolium-based colorimetric MTT assay to quantitate human monocyte mediated cytotoxicity against leukemic cells from cell lines and patients with acute myeloid leukemia." *J. Immunol. Methods* (1994) 311-320, 174(1- 2).
Di Lorenzo et al., "Expression of epidermal growth factor receptor correlates with disease relapse and progression to androgen-independence in human prostate cancer." *Clin. Cancer Res.* (2002) 3438-3444, 8(11).
Lorimer et al., "Activation of extracellular-regulated kinases by normal and mutant EGF receptors." *Biochimica et biophysica acta* (2001) 1-9, 1538(1).
Lorimer et al., "Recombinant immunotoxins specific for a mutant epidermal growth factor receptor: targeting with a single chain antibody variable domain isolated by phage display." *Proceedings of the National Academy of Sciences of the United States of America* (1996) 14815-14820, 93(25).
Lorimer et al., "Immunotoxins that target an oncogenic mutant epidermal growth factor receptor expressed in human tumors." *Clin. Cancer Res.* (1995) 859-864, 1(8).
Lorimer, "Mutant epidermal growth factor receptors as targets for cancer therapy." *Current Cancer Drug Targets* (2002) 91-102, 2(2).
Lorusso et al., "Improvements in quality of life and disease-related symptoms in phase I trials of the selective oral epidermal growth factor receptor tyrosine kinase inhibitor ZD1839 in non-small cell lung cancer and other solid tumors." *Clin. Cancer Res.* (2003) 2040-2048, 9(6).
Lu et al., "Fyn and SRC are effectors of oncogenic epidermal growth factor receptor signaling in glioblastoma patients." *Cancer Res.* (2009) 6889-6898, 69(17).
Ludwig Institute for Cancer Research, "Annual Branch Report 2005" *Ludwig Institute for Cancer Research* (2010) 1-7.
Ludwig Institute for Cancer Research, "Annual Research Report 2002-2003" *Ludwig Institute for Cancer Research* (2003) 1-7.
Ludwig Institute for Cancer Research, "Clinical Trial Confirms Novel EGFR Antibody Targets Tumours But Not Normal Tissues" *Ludwig Institute for Cancer Research* (2007).
Ludwig Institute for Cancer Research, "Annual Research Highlights Report 2006" *Ludwig Institute for Cancer Research* (2006) 1-56.
Ludwig Institute for Cancer Research, "Annual Research Highlights Report 2005" *Ludwig Institute for Cancer Research* (2005) 3.
Ludwig Institute for Cancer Research, "Annual Research Report 2004" *Ludwig Institute for Cancer Research* (2004) 7, 12, 79, 83-84, 98, 204 and 240.
Ludwig Institute for Cancer Research, "Annual Research Report 2002" *Ludwig Institute for Cancer Research* (2003) 8, 84-86 and 99-100.
Ludwig Institute for Cancer Research, "Annual Research Report 2003" *Ludwig Institute for Cancer Research* (2003) 81-83, 93 and 152.
Ludwig Institute for Cancer Research, "Annual Report 1999-2000" *Ludwig Institute for Cancer Research* (2000) 1-13.

Lui et al., "EGFR-mediated cell cycle regulation." *Anticancer research* (2002) 1-11, 22(1A).
Lund et al., "Phosphorylation of the epidermal growth factor receptor at threonine 654 inhibits ligand-induced internalization and down-regulation." *JBC* (1990) 20517-20523, 265(33).
Luwor et al., "A Soluble Form of the Epidermal Growth Factor Receptor (EGFR) Specific Tyrosine Kinase Inhibitor AG1478 Enhances the Efficacy of Chemotherapy." *Proceedings of the American Association for Cancer Research* (2002) 784 (Abstract 3885), 43.
Luwor et al., "The 806 Antibody Inhibits the Growth of Tumor Xenografts Expressing either the de2-7 or Amplified Epidermal Growth Factor Receptor (EGFR) but not Wild-Type EGFR." *Austin and Repatriation Medical Centre Research Week* (2001) Abstract 46.
Luwor et al., "The 806 Antibody Inhibits the Growth of Tumor Xenografts Expressing either the de2-7 or Amplified Epidermal Growth Factor Receptor (EGFR) but not Wild-Type EGFR." *Proceedings of the 13th Annual Lorne Cancer Conference, Lorne, Victoria, Australia* (2001) Abstract 208.
Luwor et al., "Monoclonal Antibody 806 Inhibits the Growth of Tumor Xenografts Expressing either the de2-7 or Amplified Epidermal Growth Factor Receptor (EGFR) but not Wild-Type EGFR." *Austin and Repatriation Medical Centre Research Week* (2000) Poster Presentation (Abstract 88).
Luwor et al., "Monoclonal Antibody 806 Inhibits the Growth of Tumor Xenografts Expressing either the de2-7 or Amplified Epidermal Growth Factor Receptor (EGFR) but not Wild-Type EGFR." *Austin and Repatriation Medical Centre Research Week* (2000) Abstract 88.
Luwor et al., "Monoclonal antibody 806 inhibits the growth of tumor xenografts expressing either the de2-7 or amplified epidermal growth factor receptor (EGFR) but not wild-type EGFR." *Cancer Res.* (2001) 5355-5361, 61(14).
Luwor, "The Monoclonal Antibody 806 and tyrosine Kinase inhibitor AG1478: Novel epidermal growth factor receptor therapeutics (PhD Thesis)" *Submitted in Total Fulfilment of the Requirements for the Degree of Doctor of Philosophy, University of Melbourne.* (2003) 1-331.
Luwor et al., "The tumor-specific de2-7 epidermal growth factor receptor (EGFR) promotes cells survival and heterodimerizes with the wild-type EGFR." *Oncogene* (2004) 6095-6104, 23(36).
Lyall et al., "EGF induces receptor down-regulation with no receptor recycling in KB Cells" *Chemical Abstracts* (1985) 56832q, 102(7).
Lydon et al., "A potent protein-tyrosine kinase inhibitor which selectively blocks proliferation of epidermal growth factor receptor-expressing tumor cells in vitro and in vivo." *Int. J. Cancer* (1998) 154-163, 76(1).
Lynch et al., "A phase II trial of cetuximab as therapy for recurrent non-small cell lung cancer (NSCLC)." *Proceedings of the American Society of Clinical Oncology* (2004) 637s (Abstract 7084), 23.
Lynch et al., "Therapeutic potential of ABX-EGF: a fully human anti-epidermal growth factor receptor monoclonal antibody for cancer treatment." *Semin. Oncol.* (2002) 47-50, 29(1 Suppl 4).
Lynch et al., "Activating mutations in the epidermal growth factor receptor underlying responsiveness of non-small-cell lung cancer to gefitinib." *N. Engl. J. Med.* (2004) 2129-2139, 350(21).
Maccallum et al., "Antibody-antigen interactions: contact analysis and binding site topography." *J. Mol. Biol.* (1996) 732-745, 262(5).
Macdiarmid et al., "Sequential treatment of drug-resistant tumors with targeted minicells containing siRNA or a cytotoxic drug." *Nat. Biotechnol.* (2009) 643-651, 27(7).
Macdonald et al., "Production and response of a human prostatic cancer line to transforming growth factor-like molecules." *British Journal of Cancer* (1990) 579-584, 62(4).
Mach, "Monoclonal Antibodies." *In: Oxford Textbook of Oncology (Chapter 1.8) (Editors: Peckham et al.; Publisher: Oxford Univ. Press, Oxford).* (1995) 81-103, 1.
Machiels et al., "Zalutumumab plus best supportive care versus best supportive care alone in patients with recurrent or metastatic squamous-cell carcinoma of the head and neck after failure of platinum-based chemotherapy: an open-label, randomised phase 3 trial" *The Lancet Oncology* (2011) 333-343, 12(4).
Maciag, "The human epidermal growth factor receptor-kinase complex" *Trends in Biochemical Sciences* (1982) 197-198, 7.

(56) References Cited

OTHER PUBLICATIONS

Maeda et al., "pH-dependent receptor/ligand dissociation as a determining factor for intracellular sorting of ligands for epidermal growth factor receptors in rat hepatocytes." *Journal of controlled release: official journal of the Controlled Release Society* (2002) 71-82, 82(1).

Magne et al., "Influence of epidermal growth factor receptor (EGFR), p53 and intrinsic Map kinase pathway status of tumour cells on the antiproliferative effect of ZD1839 ('Iressa')." *British Journal of Cancer* (2002) 1518-1523, 86(9).

Malden et al., "Selective amplification of the cytoplasmic domain of the epidermal growth factor receptor gene in glioblastoma multiforme." *Cancer Res.* (1988) 2711-2714, 48(10).

Malik et al., "Safety and efficacy of panitumumab monotherapy in patients with metastatic colorectal cancer (mCRC)" *Journal of Clinical Oncology, 2005 ASCO Annual Meeting Proceedings* (2005) Abstract 3520, 23(16S; Part I of II: Jun. 1 Supplement).

Malik et al., "Pharmacodynamic evaluation of the epidermal growth factor receptor inhibitor OSI-774 in human epidermis of cancer patients." *Clin. Cancer Res.* (2003) 2478-2486, 9(7).

Maloney et al., "IDEC-C2B8 (Rituximab) anti-CD20 monoclonal antibody therapy in patients with relapsed low-grade non-Hodgkin's lymphoma." *Blood* (1997) 2188-2195, 90(6).

Mamot et al., "Epidermal growth factor receptor-targeted immunoliposomes significantly enhance the efficacy of multiple anticancer drugs in vivo." *Cancer Res.* (2005) 11631-11638, 65(24).

Mamot et al., "Epidermal growth factor receptor (EGFR)-targeted immunoliposomes mediate specific and efficient drug delivery to EGFR- and EGFRvIII-overexpressing tumor cells." *Cancer Res.* (2003) 3154-3161, 63(12).

Mano et al., "Phase I trial of zalutumumab and irinotecan in metastatic colorectal cancer patients who have failed irinotecan-and cetuximab-based therapy" *ASCO Meeting* (2009).

Margolis et al., "All autophosphorylation sites of epidermal growth factor (EGF) receptor and HER2/neu are located in their carboxyl-terminal tails. Identification of a novel site in EGF receptor." *JBC* (1989) 10667-10671, 264(18).

Marie et al., "EGFR tyrosine kinase domain mutations in human gliomas." *Neurology* (2005) 1444-1445, 64(8).

Mariuzza et al., "The structural basis of antigen-antibody recognition." *Annual review of biophysics and biophysical chemistry* (1987) 139-159, 16.

Markowitz et al., "Growth stimulation by coexpression of transforming growth factor-alpha and epidermal growth factor-receptor in normal and adenomatous human colon epithelium." *J. Clin. Invest.* (1990) 356-362, 86(1).

Marks et al., "By-passing immunization: building high affinity human antibodies by chain shuffling." *Bio/technology (Nature Publishing Company)* (1992) 779-783, 10(7).

Martinazzi et al., "Epidermal growth factor receptor immunohistochemistry in different histological types of infiltrating breast carcinoma." *Journal of Clinical Pathology* (1993) 1009-1010, 46(11).

Maruo et al., "Immunohistochemical demonstration of elevated expression of epidermal growth factor receptor in the neoplastic changes of cervical squamous epithelium." *Cancer* (1992) 1182-1187, 69(5).

Masui et al., "Treatment with anti-EGF receptor monoclonal antibody causes regression of DiFi human colorectal carcinoma xenografts." *Proceedings of the American Association for Cancer Research* (1991) 394 (Abstract 2340), 32.

Masui et al., "Enhanced tumorigenesis of NR6 cells which express non-down-regulating epidermal growth factor receptors." *Cancer Res.* (1991) 6170-6175, 51(22).

Masui et al., "Cytotoxicity against human tumor cells mediated by the conjugate of anti-epidermal growth factor receptor monoclonal antibody to recombinant ricin A chain." *Cancer Res.* (1989) 3482-3488, 49(13).

Masui et al., "Mechanism of antitumor activity in mice for anti-epidermal growth factor receptor monoclonal antibodies with different isotypes." *Cancer Res.* (1986) 5592-5598, 46(11).

Masui et al., "Growth inhibition of human tumor cells in athymic mice by anti-epidermal growth factor receptor monoclonal antibodies." *Cancer Res.* (1984) 1002-1007, 44(3).

Matar et al., "Combined epidermal growth factor receptor targeting with the tyrosine kinase inhibitor gefitinib (ZD1839) and the monoclonal antibody cetuximab (IMC-C225): superiority over single-agent receptor targeting." *Clin. Cancer Res.* (2004) 6487-6501, 10(19).

Mateo et al., "Humanization of a mouse monoclonal antibody that blocks the epidermal growth factor receptor: recovery of antagonistic activity." *Immunotechnology: an International Journal of Immunological Engineering* (1997) 71-81, 3(1).

Matsumoto et al., "Blockade of EGF-R signaling with anti-EGFR monoclonal antibody (Mab) C225 inhibits matrix metalloproteinase-9 (MMP-9) expression and invasion of human transitional cell carcinoma (TCC) in vitro and in vivo." *Proceedings of the American Association for Cancer Research* (1998) 3 (Abstract 565), 39.

Matsuo et al., "ZD1839, a selective epidermal growth factor receptor tyrosine kinase inhibitor, shows antimetastatic activity using a hepatocellular carcinoma model." *Molecular Cancer Therapeutics* (2003) 557-561, 2(6).

Mattoon et al., "The tethered configuration of the EGF receptor extracellular domain exerts only a limited control of receptor function." *Proceedings of the National Academy of Sciences of the United States of America* (2004) 923-928, 101(4).

Maurizi et al., "Prognostic significance of epidermal growth factor receptor in laryngeal squamous cell carcinoma." *British Journal of Cancer* (1996) 1253-1257, 74(8).

Mayes et al., "Biosynthesis of the epidermal growth factor receptor in A431 cells." *EMBO J.* (1984) 531-537, 3(3).

McCafferty et al., "Phage antibodies: filamentous phage displaying antibody variable domains." *Nature* (1990) 552-554, 348(6301).

McIntosh et al., "The intraoperative detection of ovarian adenocarcinoma using radiolabeled CC49 monoclonal antibody and a hand-held gamma-detecting probe." *Cancer biotherapy & radiopharmaceuticals* (1997) 287-294, 12(4).

McLeod et al., "In vivo pharmacology and anti-tumour evaluation of the tyrphostin tyrosine kinase inhibitor RG13022." *British Journal of Cancer* (1996) 1714-1718, 74(11).

Mehra et al., "Efficient mapping of protein antigenic determinants." *Proceedings of the National Academy of Sciences of the United States of America* (1986) 7013-7017, 83(18).

Meikrantz et al., "Apoptosis and the cell cycle." *J. Cell Biochem.* (1995) 160-174, 58(2).

Meilhoc et al., "High efficiency transformation of intact yeast cells by electric field pulses." *Bio/technology (Nature Publishing Company)* (1990) 223-227, 8(3).

Mellinghoff et al., "PTEN-mediated resistance to epidermal growth factor receptor kinase inhibitors." *Clin. Cancer Res.* (2007) 378-381, 13(2 Pt 1).

Mellinghoff et al., "Molecular determinants of the response of glioblastomas to EGFR kinase inhibitors." *N. Engl. J. Med.* (2005) 2012-2024, 353(19).

Mellstedt, "Monoclonal antibodies in human cancer." *Drugs of Today (Barcelona, Spain: 1998)* (2003) 1-16, 39(Suppl. C).

Mendelsohn et al., "A phase I study of chimerized anti-epidermal growth factor receptor (EGFR) monoclonal antibody, C225, in combination with cisplatin (CDDP) in patients (pts) with recurrent head and neck squamous cell carcinoma (SCC)." *Annual Meeting of the American Society of Clinical Oncology* (1999) 389a (Abstract 1502), 18.

Mendelsohn et al., "Antibodies to growth factors and receptors." *In: Biologic Therapy of Cancer (Section 21.6) (Editors: DeVita, et al.; Publisher: JB Lippincott Co.)* (1995) 607-623.

Mendelsohn et al., "Principles of molecular cell biology of cancer: growth factors." *In: Cancer: Principles and Practice of Oncology (Chapter 7) (Editors: DeVita, et al.; Publisher: J.B. Lippincott, Philadelphia).* (1993) 114-133.

Mendelsohn et al., "The Willet F. Whitmore, Jr., Lectureship: blockade of epidermal growth factor receptors as anticancer therapy." *The Journal of Urology* (2001) 1152-1157, 165(4).

(56) References Cited

OTHER PUBLICATIONS

Mendelsohn, "The epidermal growth factor receptor as a target for cancer therapy." *Endocrine-Related Cancer* (2001) 3-9, 8(1).
Mendelsohn et al., "The EGF receptor family as targets for cancer therapy." *Oncogene* (2000) 6550-6565, 19(56).
Mendelsohn, "Blockade of receptors for growth factors: an anticancer therapy—the fourth annual Joseph H Burchenal American Association of Cancer Research Clinical Research Award Lecture." *Clin. Cancer Res.* (2000) 747-753, 6(3).
Mendelsohn, "Epidermal growth factor receptor inhibition by a monoclonal antibody as anticancer therapy." *Clin. Cancer Res.* (1997) 2703-2707, 3(12 Pt 2).
Mendelsohn et al., "Epidermal growth factor receptor family and chemosensitization." *J. Natl. Cancer Inst.* (1997) 341-343, 89(5).
Mendelsohn et al., *In Cellular and Molecular Bio. of Tumors and Preventative Clinical Applications* (New York: Alan R. Liss, Inc.) (1988) 307-312 (Reference not available).
Mendelsohn et al., "Anti-epidermal growth factor receptor monoclonal antibodies may inhibit A431 tumor cell proliferation by blocking an autocrine pathway." *Transactions of the Association of American Physicians* (1987) 173-178, 100.
Mendelsohn et al., "Epidermal growth factor receptor targeting in cancer." *Semin. Oncol.* (2006) 369-385, 33(4).
Mendelsohn et al., "Status of epidermal growth factor receptor antagonists in the biology and treatment of cancer." *J. Clin. Oncol.* (2003) 2787-2799, 21(14).
Mendelsohn, "Targeting the epidermal growth factor receptor for cancer therapy." *J. Clin. Oncol.* (2002) 1S-13S, 20(18 Suppl).
Merlino et al., "Structure and localization of genes encoding aberrant and normal epidermal growth factor receptor RNAs from A431 human carcinoma cells." *Mol. Cell Biol.* (1985) 1722-1734, 5(7).
Messa et al., "EGF, TGF-alpha, and EGF-R in human colorectal adenocarcinoma." *Acta oncoloqica (Stockholm, Sweden)* (1998) 285-289, 37(3).
Messing et al., "Epidermal growth factor—interactions with normal and malignant urothelium: in vivo and in situ studies." *The Journal of Urology* (1987) 1329-1335, 138(5).
Mickey et al., "Heterotransplantation of a human prostatic adenocarcinoma cell line in nude mice." *Cancer Res.* (1977) 4049-4058, 37(11).
Milano et al., "EGFR-targeting drugs in combination with cytotoxic agents: from bench to bedside, a contrasted reality." *British Journal of Cancer* (2008) 1-5, 99(1).
Milas et al., "In vivo enhancement of tumor radioresponse by C225 antiepidermal growth factor receptor antibody." *Clin. Cancer Res.* (2000) 701-708, 6(2).
Miller et al., "A Pilot Trial Demonstrates the Safety of ZD1839 (Iressa), an Oral Epidermal Growth Factor Receptor Tyrosine Kinase Inhibitor (EGFR-TKI), in Combination with Carboplatin (C) and Paclitaxel (P) in Previously Untreated Advanced Non-Small Cell Lung Cancer (NSCLC)." *Proc. Am. Soc. Clin. Oncol.* (2001) Abstract 1301, 20.
Mills et al., "Fully human antibodies to MCAM/MUC18 inhibit tumor growth and metastasis of human melanoma." *Cancer Res.* (2002) 5106-5114, 62(17).
Mined et al., "Regulated migration of epidermal growth factor receptor from caveolae." *JBC* (1999) 30636-30643, 274(43).
Mischel et al., "Targeted molecular therapy of GBM." *Brain Pathology (Zurich, Switzerland)* (2003) 52-61, 13(1).
Mishima et al., "Expression of a tumor-specific mutant epidermal growth factor receptor mediates glioma cell invasion in vivo" *Proc. Am. Assoc. Cancer Res.* (1999) 519, 40.
Mishima et al., "Growth suppression of intracranial xenografted glioblastomas overexpressing mutant epidermal growth factor receptors by systemic administration of monoclonal antibody (mAb) 806, a novel monoclonal antibody directed to the receptor." *Cancer Res.* (2001) 5349-5354, 61(14).
Mishima et al., "A peptide derived from the non-receptor-binding region of urokinase plasminogen activator inhibits glioblastoma growth and angiogenesis in vivo in combination with cisplatin." *Proceedings of the National Academy of Sciences of the United States of America* (2000) 8484-8489, 97(15).
Mitra et al., "Passive antibody-mediated immunotherapy for the treatment of malignant gliomas." *Neurosurgery Clinics of North America* (2010) 67-76, 21(1).
Moasser et al., "The tyrosine kinase inhibitor ZD1839 ('Iressa') inhibits HER2-driven signaling and suppresses the growth of HER2-overexpressing tumor cells." *Cancer Res.* (2001) 7184-7188, 61(19).
Modjtahedi et al., "EGFR blockade by tyrosine kinase inhibitor or monoclonal antibody inhibits growth, directs terminal differentiation and induces apoptosis in the human squamous cell carcinoma HN5." *Int. J. Oncol.* (1998) 335-342, 13(2).
Modjtahedi et al., "Phase I trial and tumour localisation of the anti-EGFR monoclonal antibody ICR62 in head and neck or lung cancer." *British Journal of Cancer* (1996) 228-235, 73(2).
Modjtahedi et al., "Differentiation or immune destruction: two pathways for therapy of squamous cell carcinomas with antibodies to the epidermal growth factor receptor." *Cancer Res.* (1994) 1695-1701, 54(7).
Modjtahedi et al., "The receptor for EGF and its ligands—expression, prognostic value and target for therapy in cancer (review)." *Int. J. Oncol.* (1994) 277-296, 4(2).
Modjtahedi et al., "Immunotherapy of human tumour xenografts overexpressing the EGF receptor with rat antibodies that block growth factor-receptor interaction." *British Journal of Cancer* (1993) 254-261, 67(2).
Modjtahedi et al., "The human EGF receptor as a target for cancer therapy: six new rat mAbs against the receptor on the breast carcinoma MDA-MB 468." *British Journal of Cancer* (1993) 247-253, 67(2).
Modjtahedi et al., "Antitumor activity of combinations of antibodies directed against different epitopes on the extracellular domain of the human EGF receptor." *Cell biophysics* (1993) 129-146, 22(1-3).
Modjtahedi et al., "Targeting of cells expressing wild-type EGFR and type-III mutant EGFR (EGFRvIII) by anti-EGFR MAb ICR62: a two-pronged attack for tumour therapy." *Int. J. Cancer* (2003) 273-280, 105(2).
Moghal et al., "Multiple positive and negative regulators of signaling by the EGF-receptor." *Current Opinion in Cell Biology* (1999) 190-196, 11(2).
Montgomery et al., "Expression of oncogenic epidermal growth factor receptor family kinases induces paclitaxel resistance and alters beta-tubulin isotype expression." *JBC* (2000) 17358-17363, 275(23).
Morales et al., "Humanized versus murine anti-human epidermal growth factor receptor monoclonal antibodies for immunoscintigraphic studies." *Nucl. Med. Biol.* (2000) 199-206, 27(2).
Morea et al., "Antibody structure, prediction and redesign." *Biophysical Chemistry* (1997) 9-16, 68(1-3).
Moriki et al., "Activation of preformed EGF receptor dimers by ligand-induced rotation of the transmembrane domain." *J. Mol. Biol.* (2001) 1011-1026, 311(5).
Moroni et al., "Gene copy number for epidermal growth factor receptor (EGFR) and clinical response to antiEGFR treatment in colorectal cancer: a cohort study." *The Lancet Oncology* (2005) 279-286, 6(5).
Morrison et al., "Recombinant chimeric monoclonal antibodies." *Important Advances in Oncology* (1990) 3-18.
Moscatello et al., "Constitutive activation of phosphatidylinositol 3-kinase by a naturally occurring mutant epidermal growth factor receptor." *Journal of Biological Chemistry* (1998) 200-206, 273(1).
Moscatello et al., "A naturally occurring mutant human epidermal growth factor receptor as a target for peptide vaccine immunotherapy of tumors." *Cancer Res.* (1997) 1419-1424, 57(8).
Moscatello et al., "Transformational and altered signal transduction by a naturally occurring mutant EGF receptor." *Oncogene* (1996) 85-96, 13(1).
Moscatello et al., "Frequent expression of a mutant epidermal growth factor receptor in multiple human tumors." *Cancer Res.* (1995) 5536-5539, 55(23).
Motoyama et al., "The efficacy of ErbB receptor-targeted anticancer therapeutics is influenced by the availability of epidermal growth factor-related peptides." *Cancer Res.* (2002) 3151-3158, 62(11).

(56) References Cited

OTHER PUBLICATIONS

Moulder et al., "Epidermal growth factor receptor (HER1) tyrosine kinase inhibitor ZD1839 (Iressa) inhibits HER2/neu (erbB2)-overexpressing breast cancer cells in vitro and in vivo." *Cancer Res.* (2001) 8887-8895, 61(24).
Moyer et al., "Induction of apoptosis and cell cycle arrest by CP-358,774, an inhibitor of epidermal growth factor receptor tyrosine kinase." *Cancer Res.* (1997) 4838-4848, 57(21).
Murshudov et al., "Refinement of macromolecular structures by the maximum-likelihood method." *Acta Crystallogr. D. Biol. Crystallogr.* (1997) 240-255, 53(Pt 3).
Murthy et al., "Binding of an antagonistic monoclonal antibody to an intact and fragmented EGF-receptor polypeptide." *Archives of biochemistry and biophysics* (1987) 549-560, 252(2).
Muthuswamy et al., "Controlled dimerization of ErbB receptors provides evidence for differential signaling by homo- and heterodimers." *Mol. Cell Biol.* (1999) 6845-6857, 19(10).
Nagane et al., "Human glioblastoma xenografts overexpressing a tumor-specific mutant epidermal growth factor receptor sensitized to cisplatin by the AG1478 tyrosine kinase inhibitor." *J. Neurosurg.* (2001) 472-479, 95(3).
Nagane et al., "Aberrant receptor signaling in human malignant gliomas: mechanisms and therapeutic implications." *Cancer Letters* (2001) S17-S21, 162 Suppl.
Nagane et al., "Drug resistance of human glioblastoma cells conferred by a tumor-specific mutant epidermal growth factor receptor through modulation of Bcl-XL and caspase-3-like proteases." *Proceedings of the National Academy of Sciences of the United States of America* (1998) 5724-5729, 95(10).
Nagane et al., "A common mutant epidermal growth factor receptor confers enhanced tumorigenicity on human glioblastoma cells by increasing proliferation and reducing apoptosis." *Cancer Res.* (1996) 5079-5086, 56(21).
Nair et al., "Crystal structure of an antibody bound to an immunodominant peptide epitope: novel features in peptide-antibody recognition." *Journal of immunology (Bethesda, MD 1950)* (2000) 6949-6955, 165(12).
Nakagawa et al., "A Phase I Intermittent Dose-Escalation Trial of ZD1939 (Iressa) in Japanese Patients with Solid malignant tumours." *Proceedings of the American Society of Clinical Oncology* (2000) 183 (Abstract 711), 19.
Naramura et al., "Therapeutic potential of chimeric and murine anti-(epidermal growth factor receptor) antibodies in a metastasis model for human melanoma." *Cancer Immunol. Immunother.* (1993) 343-349, 37(5).
Narita et al., "Mutant epidermal growth factor receptor signaling down-regulates p27 through activation of the phosphatidylinositol 3-kinase/Akt pathway in glioblastomas." *Cancer Res.* (2002) 6764-6769, 62(22).
Natale et al., "ZD1839 (Iressa): what's in it for the patient?" *Oncologist* (2002) 25-30, 7(Suppl. 4).
Neal et al., "The epidermal growth factor receptor and the prognosis of bladder cancer." *Cancer* (1990) 1619-1625, 65(7).
Neal et al., "Epidermal-growth-factor receptors in human bladder cancer: comparison of invasive and superficial tumours." *Lancet* (1985) 366-368, 1(8425).
Negri et al., "In vitro and in vivo stability and anti-tumour efficacy of an anti-EGFR/anti-CD3 F(ab')2 bispecific monoclonal antibody." *British Journal of Cancer* (1995) 928-933, 72(4).
Neidhardt et al., "Culture medium for enterobacteria." *Journal of bacteriology* (1974) 736-747, 119(3).
Nice et al., "Instrumental biosensors: new perspectives for the analysis of biomolecular interactions." *BioEssays: news and reviews in molecular, cellular and developmental biology* (1999) 339-352, 21(4).
Nicholson et al., "EGFR and cancer prognosis." *Eur. J. Cancer* (2001) S9-15, 37 Suppl 4.
Niikura et al., "Expression of epidermal growth factor-related proteins and epidermal growth factor receptor in common epithelial ovarian tumors." *International journal of gynecological pathology: official journal of the International Society of Gynecological Pathologists* (1997) 60-68, 16(1).
Nishikawa et al., "A mutant epidermal growth factor receptor common in human glioma confers enhanced tumorigenicity." *Proceedings of the National Academy of Sciences of the United States of America* (1994) 7727-7731, 91(16).
Nishikawa et al., "Immunohistochemical analysis of the mutant epidermal growth factor, ΔEGFR, in glioblastoma." *Brain tumor pathology* (2004) 53-56, 21(2).
Noonberg et al., "Tyrosine kinase inhibitors targeted to the epidermal growth factor receptor subfamily: role as anticancer agents." *Drugs* (2000) 753-767, 59(4).
Normanno et al., "Cooperative inhibitory effect of ZD1839 (Iressa) in combination with trastuzumab (Herceptin) on human breast cancer cell growth." *Ann. Oncol.* (2002) 65-72, 13(1).
Normanno et al., "Growth inhibition of human colon carcinoma cells by combinations of anti-epidermal growth factor-related growth factor antisense oligonucleotides." *Clin. Cancer Res.* (1996) 601-609, 2(3).
Normanno et al., "Epidermal growth factor receptor (EGFR) signaling in cancer." *Gene* (2006) 2-16, 366(1).
Norton et al., "Overall survival (OS) advantage to simultaneous chemotherapy (CRx) plus the humanized anti-HER2 monoclonal antibody Herceptin (H) in HER2-overexpressing (HER2+) metastatic breast cancer (MBC)." *Proceedings of the American Society of Clinical Oncology* (1999) 127a (Abstract 483), 18.
O-Charoenrat et al., "Overexpression of epidermal growth factor receptor in human head and neck squamous carcinoma cell lines correlates with matrix metalloproteinase-9 expression and in vitro invasion." *Int. J. Cancer* (2000) 307-317, 86(3).
O-Charoenrat et al., "Vascular endothelial growth factor family members are differentially regulated by c-erbB signaling in head and neck squamous carcinoma cells." *Clinical & experimental metastasis* (2000) 155-161, 18(2).
O-Charoenrat et al., "The role of c-erbB receptors and ligands in head and neck squamous cell carcinoma." *Oral oncology* (2002) 627-640, 38(7).
Ochiai et al., "EGFRvIII-targeted immunotoxin induces antitumor immunity that is inhibited in the absence of CD4+ and CD8+ T cells." *Cancer Immunol. Immunother.* (2008) 115-121, 57(1).
Oflazoglu et al., "Potent Anticarcinoma Activity of the Humanized Anti-CD70 Antibody h1F6 Conjugated to the Tubulin Inhibitor Auristatin via an Uncleavable Linker" *Clinical Cancer Research* (2008) 6171-6180, 14(19).
Ogiso et al., "Crystal structure of the complex of human epidermal growth factor and receptor extracellular domains." *Cell* (2002) 775-787, 110(6).
Ohman et al., "A new antibody recognizing the vlll mutation of human epidermal growth factor receptor." *Tumour biology: the journal of the International Society for.Oncodevelopmental Biology and Medicine* (2002) 61-69, 23(2).
Okamoto et al., "Expression of constitutively activated EGFRvIII in non-small cell lung cancer." *Cancer Science* (2003) 50-56, 94(1).
Okamoto et al., "Monoclonal antibody against the fusion junction of a deletion-mutant epidermal growth factor receptor." *British Journal of Cancer* (1996) 1366-1372, 73(11).
Olapade-Olaopa et al., "Evidence for the differential expression of a variant EGF receptor protein in human prostate cancer." *British Journal of Cancer* (2000) 186-194, 82(1).
Olayioye et al., "The ErbB signaling network: receptor heterodimerization in development and cancer." *EMBO J.* (2000) 3159-3167, 19(13).
Olayioye et al., "ErbB-1 and ErbB-2 acquire distinct signaling properties dependent upon their dimerization partner." *Mol. Cell Biol.* (1998) 5042-5051, 18(9).
Old, "Immunotherapy for cancer." *Sci. Am.* (1996) 136-143, 275(3).
Olson et al., "Transmodulation of epidermal growth factor binding by platelet-derived growth factor and 12-O-tetradecanoylphorbol-13-acetate is not sodium-dependent in Balb/c/3T3 cells." *JBC* (1990) 1847-1851, 265(4).

(56) References Cited

OTHER PUBLICATIONS

Omidfar et al., "Production of a novel camel single-domain antibody specific for the type III mutant EGFR." *Tumor biology: the journal of the International Society for Oncodevelopmental Biology and Medicine* (2004) 296-305, 25(5-6).

Omidfar et al., "Production and characterization of a new antibody specific for the mutant EGF receptor, EGFRvIII, in *Camelus bactrianus*." *Tumour biology: the journal of the International Society for Oncodevelopmental Biology and Medicine* (2004) 179-187, 25(4).

Opresko et al., "Endocytosis and lysosomal targeting of epidermal growth factor receptors are mediated by distinct sequences independent of the tyrosine kinase domain." *Journal of Biological Chemistry* (1995) 4325-4333, 270(9).

Orntoft et al., "Clinical aspects of altered glycosylation of glycoproteins in cancer." *Electrophoresis* (1999) 362-371, 20(2).

Osband et al., "Problems in the investigational study and clinical use of cancer immunotherapy." *Immunology Today* (1990) 193-195, 11(6).

Ostermann et al., "Effective Immunoconjugate Therapy in Cancer Models Targeting a Serine Protease of Tumor Fibroblasts" *Clinical Cancer Research* (2008) 4584-4592, 14(14).

Otwinowski et al., "Processing of X-ray diffraction data collected in oscillation mode" *Methods in Enzymology* (1997) 307-326, 276.

Overdijk et al., "Role of ADCC in the in vivo antitumor effects of zalutumumab, a human anti-EGF receptor antibody" *ASCO Meeting* (2010).

Overholser et al., "Epidermal growth factor receptor blockade by antibody IMC-C225 inhibits growth of a human pancreatic carcinoma xenograft in nude mice." *Cancer* (2000) 74-82, 89(1).

Owens et al., "The genetic engineering of monoclonal antibodies." *J. Immunol. Methods* (1994) 149-165, 168(2).

Ozanne et al., "Over-expression of the EGF receptor is a hallmark of squamous cell carcinomas." *The Journal of Pathology* (1986) 9-14, 149(1).

Ozawa et al., "Prognostic significance of epidermal growth factor receptor in esophageal squamous cell carcinomas." *Cancer* (1989) 2169-2173, 63(11).

Padlan et al., "Identification of specificity-determining residues in antibodies." *FASEB J.* (1995) 133-139, 9(1).

Padlan, "Anatomy of the antibody molecule." *Mol. Immunol.* (1994) 169-217, 31(3).

Padlan, "A possible procedure for reducing the immunogenicity of antibody variable domains while preserving their ligand-binding properties." *Mol. Immunol.* (1991) 489-498, 28(4-5).

Padlan, "On the nature of antibody combining sites: unusual structural features that may confer on these sites an enhanced capacity for binding ligands." *Proteins* (1990) 112-124, 7(2).

Paez et al., "EGFR mutations in lung cancer: correlation with clinical response to gefitinib therapy." *Science* (2004) 1497-1500, 304.

Paganelli et al., "Antibody-guided three-step therapy for high grade glioma with yttrium-90 biotin." *European Journal of Nuclear Medicine* (1999) 348-357, 26(4).

Pai et al., "The use of immunotoxins for cancer therapy." *Eur. J. Cancer* (1993) 1606-1609, 29A(11).

Pai et al., "Prostaglandin E2 transactivates EGF receptor: a novel mechanism for promoting colon cancer growth and gastrointestinal hypertrophy." *Nature Med.* (2002) 289-293, 8(3).

Palacios et al., "Interleukin-3 supports growth of mouse pre-B-cell clones in vitro." *Nature* (1984) 126-131, 309(5964).

Panousis et al., "Engineering and characterisation of chimeric monoclonal antibody 806 (ch806) for targeted immunotherapy of tumours expressing de2-7 EGFR or amplified EGFR." *British Journal of Cancer* (2005) 1069-1077, 92(6).

Pao et al., "Epidermal growth factor receptor mutations, small-molecule kinase inhibitors, and non-small-cell lung cancer: current knowledge and future directions." *J. Clin. Oncol.* (2005) 2556-2568, 23(11).

Pao et al., "Acquired resistance of lung adenocarcinomas to gefitinib or erlotinib is associated with a second mutation in the EGFR kinase domain." *PLoS Medicine* (2005) e73, 2(3).

Pao et al., "KRAS mutations and primary resistance of lung adenocarcinomas to gefitinib or erlotinib." *PLoS Medicine* (2005) e17, 2(1).

Pao et al., "EGF receptor gene mutations are common in lung cancers from 'never smokers' and are associated with sensitivity of tumors to gefitinib and erlotinib." *Proceedings of the National Academy of Sciences of the United States of America* (2004) 13306-13311, 101(36).

Park et al., "A review of the benefit-risk profile of gefitinib in Asian patients with advanced non-small-cell lung cancer." *Current Medical Research and Opinion* (2006) 561-573, 22(3).

Parker et al., "Preferential activation of the epidermal growth factor receptor in human colon carcinoma liver metastases in nude mice." *The Journal of Histochemistry and Cytochemistry: Official Journal of the Histochemistry Society* (1998) 595-602, 46(5).

De Pascalis et al., "Grafting of 'abbreviated' complementarity-determining regions containing specificity-determining residues essential for ligand contact to engineer a less immunogenic humanized monoclonal antibody." *Journal of immunology (Baltimore, Md: 1950)* (2002) 3076-3084, 169(6).

Pastan, "Targeted therapy of cancer with recombinant immunotoxins." *Biochimica et Biophysica Acta* (1997) C1-6, 1333(2).

Patel et al., "Monoclonal antibody cetuximab binds to and down-regulates constitutively activated epidermal growth factor receptor vlll on the cell surface." *Anticancer research* (2007) 3355-3366, 27.

Pavelic et al., "Evidence for a role of EGF receptor in the progression of human lung carcinoma." *Anticancer Research* (1993) 1133-1137, 13(4).

Pawson et al., "SH2 and SH3 domains." *Current Biology* (1994) 434-442, 3(7).

Pawson, "Protein modules and signalling networks." *Nature* (1995) 573-580, 373.

Pedersen et al., "The type III epidermal growth factor receptor mutation. Biological significance and potential target for anti-cancer therapy." *Ann Oncol.* (2001) 745-760, 12(6).

Pedersen et al., "Analysis of the epidermal growth factor receptor specific transcriptome: effect of receptor expression level and an activating mutation." *J. Cell Biochem.* (2005) 412-427, 96(2).

Pedersen et al., "[Mutations in the epidermal growth factor receptor: structure and biological function in human tumors]." *Ugeskrift for laeger* (2006) 2354-2361, 168(24).

Pegram et al., "Antibody dependent cell-mediated cytotoxicity in breast cancer patients in Phase III clinical trials of a humanized anti-HER2 antibody." *Proceedings of the Annual Meeting of the American Association for Cancer Research* (1997) 602 (Abstract 4044), 39.

Pegram et al., "Inhibitory effects of combinations of HER-2/neu antibody and chemotherapeutic agents used for treatment of human breast cancers." *Oncogene* (1999) 2241-2251, 18(13).

Pegram et al., "Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment." *J. Clin. Oncol.* (1998) 2659-2671, 16(8).

Pegram et al., "The effect of HER-2/neu overexpression on chemotherapeutic drug sensitivity in human breast and ovarian cancer cells." *Oncogene* (1997) 537-547, 15(5).

Pegram et al., "Rational combinations of trastuzumab with chemotherapeutic drugs used in the treatment of breast cancer." *J. Natl. Cancer Inst.* (2004) 739-749, 96(10).

Pelloski et al., "Epidermal growth factor receptor variant III status defines clinically distinct subtypes of glioblastoma." *Journal of Clinical Oncology* (2007) 2288-2294, 25(16).

Peng et al., "Anti-epidermal growth factor receptor monoclonal antibody 225 up-regulates p27KIP1 and induces G1 arrest in prostatic cancer cell line DU145." *Cancer Res.* (1996) 3666-3669, 56(16).

(56) References Cited

OTHER PUBLICATIONS

Perera et al., "Internalisation and Trafficking of the Monoclonal Antibody 806 Reactive Epidermal Growth Factor Receptor." *Austin Health Research Week, Austin Hospital, Melbourne, Australia* (2003) Abstract 112.
Perera et al., "The Influence of Epidermal Growth Factor Receptor (EGFR) Number and Activation on the Efficacy of Antibodies Directed to the Receptor." *Proceedings of the 14th Annual Lorne Cancer Conference, Lorne, Victoria, Australia* (2002) Abstract 216.
Perera et al., "Requirement for the von Hippel-Lindau tumor suppressor gene for functional epidermal growth factor receptor blockade by monoclonal antibody C225 in renal cell carcinoma." *Clin. Cancer Res.* (2000) 1518-1523, 6(4).
Perera, "Therapeutic Efficacy and Intracellular Trafficking of Anti-Epidermal Growth Factor Receptor Antibodies (PhD Thesis)" *Submitted in Total Fulfillment of the Requirements for the Degree of Doctor of Philosophy, University of Melbourne.* (2004) 1-239.
Perera et al., "Internalization, intracellular trafficking, and biodistribution of monoclonal antibody 806: a novel anti-epidermal growth factor receptor antibody." *Neoplasia* (2007) 1099-1110, 9(12).
Perera et al., "Treatment of human tumor xenografts with monoclonal antibody 806 in combination with a prototypical epidermal growth factor receptor-specific antibody generates enhanced antitumor activity." *Clin. Cancer Res.* (2005) 6390-6399, 11(17).
Perez-Soler et al., "A phase II trial of the epidermal growth factor receptor (EGFR) tyrosine kinase inhibitor OSI-774, following platinum-based chemotherapy in patients (pts) with advanced EGFR-expressing, non-small cell lung cancer (NSCLC)." *Proceedings of the American Society of Clinical Oncology* (2001) 310a (Abstract 1235), 20.
Perez-Soler et al., "Tumor Studies in Patients With Head & Neck Cancer Treated With Humanized Anti-Epidermal Growth Factor (EGFR) Monoclonal Antibody C225 in Combination With Cisplatin." *Proceedings of the American Society of Clinical Oncology* (1998) 393a (Abstract 1514), 17.
Perez-Soler et al., "Tumor epidermal growth factor receptor studies in patients with non-small-cell lung cancer or head and neck cancer treated with monoclonal antibody RG 83852." *J. Clin. Oncol.* (1994) 730-739, 12(4).
Pérez-Soler, "HER1/EGFR targeting: refining the strategy." *Oncologist* (2004) 58-67, 9(1).
Perl et al., "Conditional gene expression in the respiratory epithelium of the mouse." *Transgenic research* (2002) 21-29, 11(1).
Perrotte et al., "Anti-epidermal growth factor receptor antibody C225 inhibits angiogenesis in human transitional cell carcinoma growing orthotopically in nude mice." *Clin. Cancer Res.* (1999) 257-265, 5(2).
Petit et al., "Neutralizing antibodies against epidermal growth factor and ErbB-2/neu receptor tyrosine kinases down-regulate vascular endothelial growth factor production by tumor cells in vitro and in vivo: angiogenic implications for signal transduction therapy of solid tumors." *The American Journal of Pathology* (1997) 1523-1530, 151(6).
Petrides et al., "Modulation of pro-epidermal growth factor, pro-transforming growth factor alpha and epidermal growth factor receptor gene expression in human renal carcinomas." *Cancer Res.* (1990) 3934-3939, 50(13).
Pfister et al., "A phase I trial of the epidermal growth factor receptor (EGFR)-directed bispecific antibody (BsAB) MDX-447 in patients with solid tumors." *Proceedings of the American Society of Clinical Oncology* (1999) 433a (Abstract 1667), 18.
Pfosser et al., "Role of target antigen in bispecific-antibody-mediated killing of human glioblastoma cells: a pre-clinical study." *Int. J. Cancer* (1999) 612-616, 80(4).
Pfreundschuh et al., "Serological analysis of cell surface antigens of malignant human brain tumors." *Proceedings of the National Academy of Sciences of the United States of America* (1978) 5122-5126, 75(10).

Pietras et al., "Monoclonal antibody to HER-2/neureceptor modulates repair of radiation-induced DNA damage and enhances radiosensitivity of human breast cancer cells overexpressing this oncogene." *Cancer Res.* (1999) 1347-1355, 59(6).
Pietras et al., "Remission of human breast cancer xenografts on therapy with humanized monoclonal antibody to HER-2 receptor and DNA-reactive drugs." *Oncogene* (1998) 2235-2249, 17(17).
Pillay et al., "The plasticity of oncogene addiction: implications for targeted therapies directed to receptor tyrosine kinases." *Neoplasia* (2009) 448-458, 11(5).
Politi et al., "Lung adenocarcinomas induced in mice by mutant EGF receptors found in human lung cancers respond to a tyrosine kinase inhibitor or to down-regulation of the receptors." *Genes Dev.* (2006) 1496-1510, 20(11).
Pontén et al., "Long term culture of normal and neoplastic human glia." *Acta pathologica et microbiologica Scandinavica* (1968) 465-486, 74(4).
Power et al., "Construction, expression and characterisation of a single-chain diabody derived from a humanised anti-Lewis Y cancer targeting antibody using a heat-inducible bacterial secretion vector." *Cancer Immunol. Immunother.* (2001) 241-250, 50(5).
Power et al., "Synthesis of high avidity antibody fragments (scFv multimers) for cancer imaging." *J. Immunol. Methods* (2000) 193-204, 242(1-2).
Power et al., "Noncovalent scFv multimers of tumor-targeting anti-Lewis(y) hu3S193 humanized antibody." *Protein Science Publication of the Protein Society* (2003) 734-747, 12(4).
Prados et al., "Biology and treatment of malignant glioma." *Semin. Oncol.* (2000) 1-10, 27(3; Suppl. 6).
Prenzel et al., "The epidermal growth factor receptor family as a central element for cellular signal transduction and diversification." *Endocrine-Related Cancer* (2001) 11-31, 8(1).
Press et al., "Inhibition of catabolism of radiolabeled antibodies by tumor cells using lysosomotropic amines and carboxylic ionophores." *Cancer Res.* (1990) 1243-1250, 50(4).
Press et al., "Ricin A-chain containing immunotoxins directed against different epitopes on the CD2 molecule differ in their ability to kill normal and malignant T cells." *Journal of immunology (Baltimore, Md: 1950)* (1988) 4410-4417, 141(12).
Presta et al., "Humanization of an anti-vascular endothelial growth factor monoclonal antibody for the therapy of solid tumors and other disorders." *Cancer Res.* (1997) 4593-4599, 57(20).
Presta et al., "Humanization of an antibody directed against IgE." *Journal of Immunology (1950)* (1993) 2623-2632, 151(5).
Presta, "Molecular engineering and design of therapeutic antibodies." *Curr. Opin. Immunol.* (2008) 460-470, 20(4).
Presta, "Engineering of therapeutic antibodies to minimize immunogenicity and optimize function." *Advanced drug delivery reviews* (2006) 640-656, 58(5-6).
Prewett et al., "Mouse-human chimeric anti-epidermal growth factor receptor antibody C225 inhibits the growth of human renal cell carcinoma xenografts in nude mice." *Clin. Cancer Res.* (1998) 2957-2966, 4(12).
Prewett et al., "The biologic effects of C225, a chimeric monoclonal antibody to the EGFR, on human prostate carcinoma." *Journal of Immunotherapy with Emphasis on Tumor Immunology: Official Journal of the Society for Biological Therapy* (1996) 419-427, 19(6).
Prewett et al., "Anti-tumor and cell cycle responses in KB cells treated with a chimeric anti-EGFR monoclonal antibody in combination with cisplatin." *Int. J. Oncol.* (1996) 217-224, 9(2).
Prewett et al., "Enhanced antitumor activity of anti-epidermal growth factor receptor monoclonal antibody IMC-C225 in combination with irinotecan (CPT-11) against human colorectal tumor xenografts." *Clin. Cancer Res.* (2002) 994-1003, 8(5).
Prigent et al., "Enhanced tumorigenic behavior of glioblastoma cells expressing a truncated epidermal growth factor receptor is mediated through the Ras-Shc-Grb2 pathway." *Journal of Biological Chemistry* (1996) 25639-25645, 271(41).
Prigent et al., "The type 1 (EGFR-related) family of growth factor receptors and their ligands." *Progress in Growth Factor Research* (1992) 1-24, 4(1).
Privalsky et al., "The membrane glycoprotein encoded by the retroviral oncogene v-erb-B is structurally related to tyrosine-spe-

(56) References Cited

OTHER PUBLICATIONS cific protein kinases." *Proceedings of the National Academy of Sciences of the United States of America* (1984) 704-707, 81(3).
Pruss et al., "Variants of 3T3 cells lacking mitogenic response to epidermal growth factor." *Proceedings of the National Academy of Sciences of the United States of America* (1977) 3918-3921, 74(9).
Pütz et al., "Functional fine-mapping and molecular modeling of a conserved loop epitope of the measles virus hemagglutinin protein." *Eur. J. Biochem.* (2003) 1515-1527, 270(7).
Raben et al., "C225 anti-EGFR antibody potentiates radiation (RT) and chemotherapy (CT) cytotoxicity in human non-small cell lung cancer (NSCLC) cells in vitro and in vivo." *Proceedings of the American Society of Clinical Oncology* (2001) 257a (Abstract 1026), 20.
Raben et al., "Treatment of human intracranial gliomas with chimeric monoclonal antibody against the epidermal growth factor receptor increases survival of nude mice when treated concurrently with irradiation." *Proceedings of the American Association for Cancer Research* (1999) 184 (Abstract 1224), 40.
Raben et al., "ZD1839, a selective epidermal growth factor receptor tyrosine kinase inhibitor, alone and in combination with radiation and chemotherapy as a new therapeutic strategy in non-small cell lung cancer." *Semin. Oncol.* (2002) 37-46, 29(1; Suppl. 4).
Radinsky et al., "Level and function of epidermal growth factor receptor predict the metastatic potential of human colon carcinoma cells." *Clin. Cancer Res.* (1995) 19-31, 1(1).
Raizer, "HER1/EGFR tyrosine kinase inhibitors for the treatment of glioblastoma multiforme." *Journal of Neuro-Oncology* (2005) 77-86, 74(1).
Rakowicz-Szulczynska et al., "Epidermal growth factor (EGF) and monoclonal antibody to cell surface EGF receptor bind to the same chromatin receptor." *Archives of Biochemistry and Biophysics* (1989) 456-464, 268(2).
Ramnarain et al., "Differential gene expression analysis reveals generation of an autocrine loop by a mutant epidermal growth factor receptor in glioma cells." *Cancer Res.* (2006) 867-874, 66(2).
Ramos et al., "Treatment of high-grade glioma patients with the humanized anti-epidermal growth factor receptor. (EGFR) antibody h-R3: report from a phase I/II trial." *Cancer biology & therapy* (2006) 375-379, 5(4).
Ramos-Suzarte et al., "99mTc-labeled antihuman epidermal growth factor antibody in patients with tumors of epithelial origin: Part III. Clinical trials safety and diagnostic efficacy." *J. Nucl. Med.* (1999) 768-775, 40(5).
Ramsland et al., "Structural convergence of antibody binding of carbohydrate determinants in Lewis Y tumor antigens." *J. Mol. Biol.* (2004) 809-818, 340(4).
Ranson, "ZD1839 (Iressa): for more than just non-small cell lung cancer." *Oncologist* (2002) 16-24, 7(Suppl. 4).
Rao et al., "Radiosensitization of human breast cancer cells by a novel ErbB family receptor tyrosine kinase inhibitor." *Int. J. Radiat. Oncol. Biol. Phys.* (2000) 1519-1528, 48(5).
Raymond et al., "General method for plasmid construction using homologous recombination." *BioTechniques* (1999) 134-8, 140-1, 26(1).
Rayzman et al., "Monoclonal antibodies for cancer therapy." *Cancer Forum* (2002) 104-108, 26(2).
Reardon et al., "Recent advances in the treatment of malignant astrocytoma." *Journal of Clinical Oncology* (2006) 1253-1265, 24(8).
Reed, "Dysregulation of apoptosis in cancer." *J. Clin. Oncol.* (1999) 2941-2953, 17(9).
Reese et al., "Effects of the 4D5 antibody on HER2/neu heterodimerization with other class I receptors in human breast cancer cells." *Proceedings of the Annual Meeting of the American Association for Cancer Research* (1996) 51 (Abstract 353), 37.
Van Regenmortel et al., "Comparative immunological methods." *Methods in Enzymology* (1993) 130-140, 224.

Reilly et al., "A comparison of EGF and MAb 528 labeled with 111In for imaging human breast cancer." *J. Nucl. Med.* (2000) 903-911, 41(5).
Reiss et al., "Activation of the autocrine transforming growth factor alpha pathway in human squamous carcinoma cells." *Cancer Res.* (1991) 6254-6262, 51(23; Part 1).
Reist et al., "Astatine-211 labeling of internalizing anti-EGFRvIII monoclonal antibody using N-succinimidyl 5-[211At]astato-3-pyridinecarboxylate." *Nucl. Med. Biol.* (1999) 405-411, 26(4).
Reist et al., "In vitro and in vivo behavior of radiolabeled chimeric anti-EGFRvIII monoclonal antibody: comparison with its murine parent." *Nucl. Med. Biol.* (1997) 639-647, 24(7).
Reist et al., "Improved targeting of an anti-epidermal growth factor receptor variant III monoclonal antibody in tumor xenografts after labeling using N-succinimidyl 5-iodo-3-pyridinecarboxylate." *Cancer Res.* (1997) 1510-1515, 57(8).
Reist et al., "Radioiodination of internalizing monoclonal antibodies using N-succinimidyl 5-iodo-3-pyridinecarboxylate." *Cancer Res.* (1996) 4970-4977, 56(21).
Reist et al., "Tumor-specific anti-epidermal growth factor receptor variant III monoclonal antibodies: use of the tyramine-cellobiose radioiodination method enhances cellular retention and uptake in tumor xenografts." *Cancer Res.* (1995) 4375-4382, 55(19).
Reiter et al., "Comparative genomic sequence analysis and isolation of human and mouse alternative EGFR transcripts encoding truncated receptor isoforms." *Genomics* (2001) 1-20, 71(1).
Rettig et al., "Immunogenetics of human cell surface differentiation." *Annual review of immunology* (1989) 481-511, 7.
Reynolds et al., "Human transforming growth factors induce tyrosine phosphorylation of EGF receptors." *Nature* (1981) 259-262, 292(5820).
Ribas et al., "Systemic delivery of siRNA via targeted nanoparticles in patients with cancer: Results from a first-in-class phase I clinical trial" *J. Clin. Oncol.* (2010) Abstract 3022, 28(15S).
Riemer et al., "Mimotope vaccines: epitope mimics induce anti-cancer antibodies." *Immunology letters* (2007) 1-5, 113(1).
Riemer et al., "Vaccination with cetuximab mimotopes and biological properties of induced anti-epidermal growth factor receptor antibodies." *J. Natl. Cancer Inst.* (2005) 1663-1670, 97(22).
Riemer et al., "Matching of trastuzumab (Herceptin) epitope mimics onto the surface of HER-2/neu—a new method of epitope definition." *Mol. Immunol.* (2005) 1121-1124, 42(9).
Riese et al., "Specificity within the EGF family/ErbB receptor family signaling network." *BioEssays: news and reviews in molecular, cellular and developmental biology* (1998) 41-48, 20(1).
Rieske et al., "A comparative study of epidermal growth factor receptor (EGFR) and MDM2 gene amplification and protein immunoreactivity in human glioblastomas." *Polish Journal of Pathology: Official Journal of the Polish Society of Pathologists* (1998) 145-149, 49(3).
Rinehart et al., "A phase 1 clinical and pharmacokinetic study of oral CI-1033, a pan-erbB tyrosine kinase inhibitor in patients with advanced solid tumors." *Proceedings of the American Society of Clinical Oncology* (2002) 11a (Abstract 41), 21.
Ringerike et al., "High-affinity binding of epidermal growth factor (EGF) to EGF receptor is disrupted by overexpression of mutant dynamin (K44A)." *JBC* (1998) 16639-16642, 273(27).
Ritter et al., "Serological analysis of human anti-human antibody responses in colon cancer patients treated with repeated doses of humanized monoclonal antibody A33." *Cancer Res.* (2001) 6851-6859, 61(18).
Riva et al., "Role of nuclear medicine in the treatment of malignant gliomas: the locoregional radioimmunotherapy approach." *European Journal of Nuclear Medicine* (2000) 601-609, 27(5).
Rivera et al., "Current situation of Panitumumab, Matuzumab, Nimotuzumab and Zalutumumab." *Acta oncologica (Stockholm, Sweden)* (2008) 9-19, 47(1).
Ro et al., "Amplified and overexpressed epidermal growth factor receptor gene in uncultured primary human breast carcinoma." *Cancer Res.* (1988) 161-164, 48(1).

(56) References Cited

OTHER PUBLICATIONS

Robert et al., "Phase I study of anti—epidermal growth factor receptor antibody cetuximab in combination with radiation therapy in patients with advanced head and neck cancer." *J. Clin. Oncol.* (2001) 3234-3243, 19(13).
Rocha-Lima et al., "EGFR targeting of solid tumors." *Cancer control: journal of the Moffitt Cancer Center* (2007) 295-304, 14(3).
Rodeck et al., "Monoclonal antibody 425 inhibits growth stimulation of carcinoma cells by exogenous EGF and tumor-derived EGF/TGF-alpha." *J. Cell Biochem.* (1990) 69-79, 44(2).
Rodeck et al., "Interactions between growth factor receptors and corresponding monoclonal antibodies in human tumors." *J. Cell Biochem.* (1987) 315-320, 35(4).
Rodeck et al., "Tumor growth modulation by a monoclonal antibody to the epidermal growth factor receptor: immunologically mediated and effector cell-independent effects." *Cancer Res.* (1987) 3692-3696, 47(14).
Roepstorff et al., "Sequestration of epidermal growth factor receptors in noncaveolar lipid rafts inhibits ligand binding." *JBC* (2002) 18954-18960, 277(21).
Roguska et al., "A comparison of two murine monoclonal antibodies humanized by CDR-grafting and variable domain resurfacing." *Protein Engineering* (1996) 895-904, 9(10).
Roguska et al., "Humanization of murine monoclonal antibodies through variable domain resurfacing." *Proceedings of the National Academy of Sciences of the United States of America* (1994) 969-973, 91(3).
Rosell et al., "Randomized phase II study of cetuximab in combination with cisplatin (C) and vinorelbine (V) vs. CV alone in the first-line treatment of patients (pts) with epidermal growth factor receptor (EGFR)-expressing advanced non- small-cell lung cancer (NSCLC)" *Journal of Clinical Oncology, 2004 ASCO Annual Meeting Proceedings (Post-Meeting Edition)* (2004) Abstract 7012, 22(14S; Jul. 15 Supplement).
Rosell et al., "Randomized phase II study of cetuximab in combination with cisplatin (C) and vinorelbine (V) vs. CV alone in the first-line treatment of patients (pts) with epidermal growth factor receptor (EGFR)-expressing advanced non-small-cell lung cancer (NSCLC)." *Proceedings of the American Society of Clinical Oncology* (2004) 620s (Abstract 7012), 23.
Rosenberg et al., "Erbitux (IMC-225) plus weekly irinotecan (CPT-11), fluorouricil (5FU) and leucovorin (LV) in colorectal cancer (CRC) that expresses the epidermal growth factor receptor (EGFR)." *Proceedings of the American Society of Clinical Oncology* (2002) 135a (Abstract 536), 21.
Ross et al., "Anticancer antibodies." *American journal of clinical pathology* (2003) 472-485, 119(4).
Rothacker, "Ligand binding induces a conformational change in the untethered epidermal growth factor receptor" *Ludwig Institute for Cancer Research* (2010).
Rougier et al., "Cetuximab + FOLFIRI as first-line treatment for metastatic colorectal CA." *Proceedings of the Annual Meeting of the American Society of Clinical Oncology* (2004) 248s (Abstract 3513), 22.
Rowinsky et al., "Safety, pharmacokinetics, and activity of ABX-EGF, a fully human anti-epidermal growth factor receptor monoclonal antibody in patients with metastatic renal cell cancer." *J. Clin. Oncol.* (2004) 3003-3015, 22(15).
Rubin et al., "Monoclonal Antibody (MoAb) IMC-C225, an Anti-Epidermal Growth Factor Receptor (EGFr), for Patients (Pts) with EGFr-Positive Tumors Refractory to or in Relapse from Previous Therapeutic Regimens" *Proc. Am. Soc. Clin. Oncol.* (2000) Abstract 1860, 19.
Rubin et al., "Monoclonal antibody (MoAb) IMC-C225, an anti-epidermal growth factor receptor (EGFR), for patients with EGFR-positive tumors refractory to or in relapse from previous therapeutic regimens." *Proceedings of the American Society of Clinical Oncology* (2000) 474a (Abstract 1860), 193.
Rubin Grandis et al., "Inhibition of epidermal growth factor receptor gene expression and function decreases proliferation of head and neck squamous carcinoma but not normal mucosal epithelial cells." *Oncogene* (1997) 409-416, 15(4).
Rubin Grandis et al., "Quantitative immunohistochemical analysis of transforming growth factor-alpha and epidermal growth factor receptor in patients with squamous cell carcinoma of the head and neck." *Cancer* (1996) 1284-1292, 78(6).
Rubio et al., "Cetuximab in combination with oxaliplatin/5-fluorouracil (5-FU)/folinic acid (FA) (FOLFOX-4) in the first-line treatment of patients with epidermal growth factor receptor (EGFR)-expressing metastatic colorectal cancer: An international phase II study." *Journal of Clinical Oncology, 2005 ASCO Annual Meeting Proceedings* (2005) Abstract 3535, 23(16S; Part I of II: Jun. 1 Supplement).
Rusch et al., "Overexpression of the epidermal growth factor receptor and its ligand transforming growth factor alpha is frequent in resectable non-small cell lung cancer but does not predict tumor progression." *Clin. Cancer Res.* (1997) 515-522, 3(4).
Rusnak et al., "The effects of the novel EGFR/ErbB-2 tyrosine kinase inhibitor, GW2016, on the growth of human normal and transformed cell lines." *Proceedings of the American Association for Cancer Research* (2001) 803 (Abstract 4309), 42.
Rusnak et al., "The effects of the novel, reversible epidermal growth factor receptor/ErbB-2 tyrosine kinase inhibitor, GW2016, on the growth of human normal and tumor-derived cell lines in vitro and in vivo." *Molecular cancer therapeutics* (2001) 85-94, 1(2).
Safa et al., "Adjuvant immunotherapy for melanoma and colorectal cancers." *Semin. Oncol.* (2001) 68-92, 28(1).
Saikali et al., "Expression of nine tumour antigens in a series of human glioblastoma multiforme: interest of EGFRvIII, IL-13Ralpha2, gp100 and TRP-2 for immunotherapy." *Journal of Neuro-Oncology* (2007) 139-148, 81(2).
Sainsbury et al., "Epidermal-growth-factor receptor status as predictor of early recurrence of and death from breast cancer." *Lancet* (1987) 1398-1402, 1(8547).
Sainsbury et al., "Presence of epidermal growth factor receptor as an indicator of poor prognosis in patients with breast cancer." *Journal of Clinical Pathology* (1985) 1225-1228, 38(11).
Sako et al., "Single-molecule imaging of EGFR signalling on the surface of living cells." *Nature Cell Biology* (2000) 168-172, 2(3).
Sakurada et al., "Epidermal growth factor receptor tyrosine kinase inhibitors in lung cancer: impact of primary or secondary mutations." *Clinical Lung Cancer* (2006) S138-44, 7(Suppl. 4).
Salazar et al., "Dose-dependent inhibition of the EGFR and signalling pathways with the anti-EGFR monoclonal antibody (MAb) EMD 72000 administered every three weeks (q3w). A phase I pharmacokinetic/pharmacodynamic (PK/PD) study to define the optimal biological dose (OBD)." *Proceedings of the American Society of Clinical Oncology* (2004) 127s (Abstract 2002), 22.
Saleh et al., "Combined modality therapy of A431 human epidermoid cancer using anti-EGFr antibody C225 and radiation." *Cancer Biotherapy & Radiopharmaceuticals* (1999) 451-463, 14(6).
Salomon et al., "Epidermal growth factor-related peptides and their receptors in human malignancies." *Crit. Rev. Oncol. Hematol.* (1995) 183-232, 19(3).
Saltz et al., "Interim Report of Randomized Phase III Trial of Cetuximab/Bevacizumab/Irinotecan (CBI) versus Cetuximab/Bevacizumab (CB) in Irinotecan-Refractory Colorectal Cancer" *Proceedings of the American Society of Clinical Oncology* (2006) Abstract 169b.
Saltz et al., "The presence and intensity of the cetuximab-induced acne-like rash predicts increased survival in studies across multiple malignancies" *Proc. Am. Soc. Clin. Oncol.* (2003) Abstract 817, 22.
Saltz et al., "Single agent IMC-C225 (Erbitux[TM]) has activity in CPT-11 refractory colorectal cancer that expresses the epidermal growth factor receptor (EGFR)." *Proceedings of the American Society of Clinical Oncology* (2002) 127a (Abstract 504), 21.
Saltz et al., "Cetuximab (IMC-225) plus irinotecan (CPT-11) is active in CPT-11- refractory colorectal cancer (CRC) that expresses epidermal growth factor receptor (EGFR)." *Proceedings of the American Society of Clinical Oncology* (2001) 3a (Abstract 7), 20.
Saltz et al., "Phase II trial of cetuximab in patients with refractory colorectal cancer that expresses the epidermal growth factor receptor." *J. Clin. Oncol.* (2004) 1201-1208, 22(7).

(56) References Cited

OTHER PUBLICATIONS

Sampson et al., "An EGFRvIII specific peptide vaccine generates antitumor immunity through a humoral pathway." *Neuro-oncology* (1999) S103 (Abstract 135).

Sampson et al., "Unarmed, tumor-specific monoclonal antibody effectively treats brain tumors." *Proceedings of the National Academy of Sciences of the United States of America* (2000) 7503-7508, 97(13).

Sampson et al., "Tumor-specific immunotherapy targeting the EGFRvIII mutation in patients with malignant glioma." *Seminars in immunology* (2008) 267-275, 20(5).

Sanderson et al., "In vivo drug-linker stability of an anti-CD30 dipeptide-linked auristatin immunoconjugate." *Clin. Cancer Res.* (2005) 843-852, 11(2; Part 1).

Sandler, "Nondermatologic adverse events associated with anti-EGFR therapy." *Oncology (Williston Park, N.Y.)* (2006) 35-40, 20(5 Suppl 2).

De Santes et al., "Radiolabeled antibody targeting of the HER-2/neu oncoprotein." *Cancer Res.* (1992) 1916-1923, 52(7).

Santon et al., "Effects of epidermal growth factor receptor concentration on tumorigenicity of A431 cells in nude mice." *Cancer Res.* (1986) 4701-4705, 46(9).

Sartor, "Biological modifiers as potential radiosensitizers: targeting the epidermal growth factor receptor family." *Semin. Oncol.* (2000) 15-20; discussion 92-100, 27(6; Suppl. 11).

Sartor, "Mechanisms of disease: Radiosensitization by epidermal growth factor receptor inhibitors." *Nature Clinical Practice. Oncology* (2004) 80-87, 1(2).

Sarup et al., "Characterization of an anti-p185HER2 monoclonal antibody that stimulates receptor function and inhibits tumor cell growth." *Growth regulation* (1991) 72-82, 1(2).

Sato et al., "Derivation and assay of biological effects of monoclonal antibodies to epidermal growth factor receptors." *Methods in Enzymology* (1987) 63-81, 146.

Sato et al., "Biological effects in vitro of monoclonal antibodies to human epidermal growth factor receptors." *Molecular biology & medicine* (1983) 511-529, 1(5).

Sauter et al., "Patterns of epidermal growth factor receptor amplification in malignant gliomas." *The American Journal of Pathology* (1996) 1047-1053, 148(4).

Scher et al., "Changing pattern of expression of the epidermal growth factor receptor and transforming growth factor alpha in the progression of prostatic neoplasms." *Clin. Cancer Res.* (1995) 545-550, 1(5).

Schlegel et al., "Amplification of the epidermal-growth-factor-receptor gene correlates with different growth behaviour in human glioblastoma." *Int. J. Cancer* (1994) 72-77, 56(1).

Schlessinger, "Cell signaling by receptor tyrosine kinases." *Cell* (2000) 211-225, 103(2).

Schlessinger, "Common and distinct elements in cellular signaling via EGF and FGF receptors." *Science* (2004) 1506-1507, 306(5701).

Schlessinger, "Ligand-induced, receptor-mediated dimerization and activation of EGF receptor." *Cell* (2002) 669-672, 110(6).

Schmidt et al., "Suppression of metastasis formation by a recombinant single chain antibody-toxin targeted to full-length and oncogenic variant EGF receptors." *Oncogene* (1999) 1711-1721, 18(9).

Schmidt et al., "Expression of an oncogenic mutant EGF receptor markedly increases the sensitivity of cells to an EGF-receptor-specific antibody-toxin." *Int. J. Cancer* (1998) 878-884, 75(6).

Schmidt et al., "Epidermal growth factor receptor signaling intensity determines intracellular protein interactions, ubiquitination, and internalization." *Proceedings of the National Academy of Sciences of the United States of America* (2003) 6505-6510, 100(11).

Schmidt-Ullrich et al., "Radiation-induced proliferation of the human A431 squamous carcinoma cells is dependent on EGFR tyrosine phosphorylation." *Oncogene* (1997) 1191-1197, 15(10).

Schmiedel et al., "Matuzumab binding to EGFR prevents the conformational rearrangement required for dimerization." *Cancer Cell* (2008) 365-373, 13(4).

Schmitz et al., "Interaction of antibodies with ErbB receptor extracellular regions" *Experimental Cell Research* (2009) 659-670, 315(4).

Schneebaum et al., "Immunoguided lymph node dissection in colorectal cancer: a new challenge?" *World journal of surgery* (2001) 1495-1498, 25(12).

Schnürch et al., "Growth inhibition of xenotransplanted human carcinomas by a monoclonal antibody directed against the epidermal growth factor receptor." *Eur. J. Cancer* (1994) 491-496, 30A(4).

Schwechheimer et al., "EGFR gene amplification—rearrangement in human glioblastomas." *Int. J. Cancer* (1995) 145-148, 62(2).

Scott, "Structural Biology and Molecular Imaging in Cancer Therapeutics" *Bosch Institute Annual Scientific Meeting (Sydney, Australia)* (2010).

Scott, "Pathway Specific Therapeutics: from Cancer Biology to Targeted Therapy" *Garvan Signalling Symposium (Melbourne, Australia)* (2010).

Scott, "Targeting a Novel EGFR Epitope on Cancer Cells" *Ludwig Institute for Cancer Research* (2010) Abstract 014.

Scott, "Antibody Therapeutics" *Ludwig Institute Colon Cancer Initiative Symposium (Baltimore, MD, United States)* (2010).

Scott, "Development of a humanised antibody against a novel epitope of the EGFR" *2010 Australasian Vaccines & Immunotherapy Development [AVID] Meeting (Melbourne, Australia)* (2010).

Scott, "Development of a novel anti-EGFR humanised antibody—the complex path from Academia to Industry" *Lowy Symposium (Sydney, Australia)* (2010).

Scott, "Novel Antibodies that bind to a conformational epitope of EGFR" *IBC 20th Annual Antibody Engineering Conference (San Diego, CA, United States)* (2009).

Scott, "Targeting a Novel EGFR Epitope on Cancer Cells" *LICR Translational Oncology Conference (Melbourne, Australia)* (2009).

Scott, "Cell Surface Targets for Therapy" *LICR Brain Cancer Initiative Meeting (Rockville, MD, United States)* (2009).

Scott, "Targeting a Novel EGFR Epitope on Cancer Cells" *Keystone Symposia: Antibodies as Drugs: Targeted Cancer Therapies (Whistler British Columbia, Canada)* (2009).

Scott, "Therapy of EGFR Expressing Cancers with a Novel Tumour Specific Antibody" *AHMRC Congress (Brisbane, Qld, Australia)* (2008).

Scott, "Understanding the Biology of Targeted Therapies in Cancer" *University of Melbourne/Royal Melbourne Hospital/Western Hospital Consortium Seminar (Melbourne, Australia)* (2008).

Scott, "The biology of EGFR in normal and diseased tissues" *Australian Lung Cancer Conference (Surfers Paradise, Qld, Australia)* (2008).

Scott, "Recombinant Antibody Therapy of Cancer—the LICR Antibody Program" *A\*Star Agency for Science, Technology and Research, ICMB (Singapore)* (2008).

Scott, "Epidermal Growth Factor Receptor Targeting for Cancer Therapy" *3rd Barossa Meeting—Signalling Systems (Barossa Valley, South Australia)* (2007).

Scott, "Cell Surface and Intracellular targets for antibody directed cancer therapeutics" *City of Hope Cancer Center (Los Angeles, CA, United States)* (2007).

Scott, "Of Mice and Man—The Role of Growth Factor Receptors in Cancer" *Austin Hospital Division of Medicine Grand Round (Melbourne, Australia)* (2007).

Scott, "Targeting the Epidermal Growth Factor Receptor for Antibody Therapy of Solid Tumours" *Third International AntibOZ Conference (Heron Island, Queensland, Australia)* (2007).

Scott, "Targeting a Tumour Specific Epitope of the Epidermal Growth Factor Receptor" *2007 Keystone Symposium: Antibodies as Drugs: From Basic Biology to the Clinic (Alberta, Canada)* (2007).

Scott, "Targeting the Epidermal Growth Factor Receptor for Antibody Therapy of Solid Tumours" *17th Annual IBC Antibody Engineering Conference (San Diego, CA, United States)* (2006).

Scott, "EGFR Targeted Therapeutics" *ComBio 2006 (Brisbane, Australia)* (2006).

Scott, "Implications of Antibody:Receptor Binding Structure and Signalling on Tumour Growth" *Discovery Science & Biotechnology Conference (Melbourne, Australia)* (2006).

(56) References Cited

OTHER PUBLICATIONS

Scott, "Targeting the Epidermal Growth Factor Receptor for Antibody Therapy of Solid Tumours" *EGFR Cascade Meeting (San Diego, CA, United States)* (2006).
Scott, "Implications of Antibody:Receptor Binding Structure and Signalling on Tumour Growth" *Monash University—Department of Biochemistry & Molecular Biology (Melbourne, Australia)* (2005).
Scott, "Receptor Based Targets for Antibody Therapy of Solid Tumours" *The Second China International Symposium on Antibody Engineering: Current Status and Future Perspective of Antibody Therapeutics (Beijing, China)* (2005).
Scott, "Novel Antibody that Inhibits EGFR Activation" *Fifth International Congress on Monoclonal Antibodies in Cancer (Quebec City, Canada)* (2005).
Scott, "Growth Factors and their implications in head and neck cancer" *Garnett Passe Scientific Meeting: Frontiers in Othorhinolaryngology 2004 (Noosa, Queensland, Australia)* (2004).
Scott, "Recombinant Antibodies for Immune and Cell Signalling Based Therapeutics" *AntibOZ 2 Conference (Heron Island, Queensland, Australia)* (2004).
Scott, "Targeted Cancer Therapeutics—the Role of Signalling and Immune Effector Mechanisms" *Royal North Shore Hospital Scientific Forum (Sydney, NSW, Australia)* (2003).
Scott, "Targeted Therapeutics—the Role of Signalling and Immune Effector Mechanism" *Centre for Immunology and Cancer Research, University of Queensland (Brisbane, Queensland, Australia)* (2003).
Scott, "Targeted Therapeutics—the Role of Signalling and Immune Effector Mechanisms" *Peter MacCallum Cancer Immunology Program Seminar (Melbourne, Australia)* (2003).
Scott, "Comparison of Phase I Trials of Anti-Epidermal Growth Factor Receptor (EGFR) Monoclonal Antibodies (Mabs) 528 and 225 Labelled With 1-131 and In-111" *J. Nucl. Med.* (1993) 213P, 34(5).
Scott, "Molecular Targets for Cancer Therapeutics" *Baker Institute Seminar (Melbourne, Australia)* (2002).
Scott, "Molecular Targets for Cancer Therapeutics" *Cambridge University Seminar (United Kingdom)* (2002).
Scott, "Molecular Targets for Cancer Therapeutics" *Monash University Seminar (Melbourne, Australia)* (2002).
Scott et al., "Specific targeting, biodistribution, and lack of immunogenicity of chimeric anti-GD3 monoclonal antibody KM871 in patients with metastatic melanoma: results of a phase I trial." *J. Clin. Oncol.* (2001) 3976-3987, 19(19).
Scott et al., "Construction, production, and characterization of humanized anti-Lewis Y monoclonal antibody 3S193 for targeted immunotherapy of solid tumors." *Cancer Res.* (2000) 3254-3261, 60(12).
Scott et al., "Antibody-based immunological therapies." *Curr. Opin. Immunol.* (1997) 717-722, 9(5).
Scott et al., "Clinical promise of tumour immunology." *Lancet* (1997) SII19-22, 349(Suppl. 2).
Scott et al., "Tumor imaging and therapy." *Radiologic clinics of North America* (1993) 859-879, 31(4).
Scott et al., "A Phase I single dose escalation trial of ch806 in patients with advanced tumors expressing the 806 antigen." *Journal of Clinical Oncology, 2006 ASCO Annual Meeting Proceedings Part I.* (2006) 13028, 24(18S (Jun. 20 Supplement)).
Scott et al., "A phase I biodistribution and pharmacokinetic trial of humanized monoclonal antibody Hu3s193 in patients with advanced epithelial cancers that express the Lewis-Y antigen." *Clin. Cancer Res.* (2007) 3286-3292, 13(11).
Scott et al., "A phase I clinical trial with monoclonat antibody ch806 targeting transitional state and mutant epidermal growth factor receptors." *Proceedings of the National Academy of Sciences of the United States of America* (2007) 4071-4076, 104(10).
Scott et al., "A phase I trial of humanized monoclonal antibody A33 in patients with colorectal carcinoma: biodistribution, pharmacokinetics, and quantitative tumor uptake." *Clin. Cancer Res.* (2005) 4810-4817, 11(13).
Scott et al., "Immunological effects of chimeric anti-GD3 monoclonal antibody KM871 in patients with metastatic melanoma." *Cancer immunity : a journal of the Academy of Cancer Immunology* (2005) 3, 5.
Scott et al., "A Phase I dose-escalation study of sibrotuzumab in patients with advanced or metastatic fibroblast activation protein-positive cancer." *Clin. Cancer Res.* (2003) 1639-1647, 9(5).
Sellers et al., "Apoptosis and cancer drug targeting." *J. Clin. Invest.* (1999) 1655-1661, 104(12).
Senter, "Potent antibody drug conjugates for cancer therapy" *Current Opinion in Chemical Biology* (2009) 235-244, 13(3).
Senzer et al., "Phase 2 Evaluation of OSI-774, a Potent Oral Antagonist of the EGFR-TK in Patients with Advanced Squamous Cell Carcinoma of the Head and Neck." *Proceedings of the American Society of Clinical Oncology* (2001) 2a (Abstract 6), 20.
Sepp-Lorenzino et al., "Farnesyl:protein transferase inhibitors (FTIs) block tyrosine kinase signal transduction and act in concert with an anti-EGR receptor antibody to inhibit cancer cell growth." *Proceedings of the Annual Meeting of the American Association for Cancer Research* (1996) 421-422 (Abstract 2877), 37.
Seymour, "Novel anti-cancer agents in development: exciting prospects and new challenges." *Cancer Treat Rev.* (1999) 301-312, 25(5).
Sharafinski et al., "Epidermal growth factor receptor targeted therapy of squamous cell carcinoma of the head and neck." *Head & Neck* (2010) 1412-1421, 32(10).
She et al., "The BAD protein integrates survival signaling by EGFR/MAPK and PI3K/Akt kinase pathways in PTEN-deficient tumor cells." *Cancer Cell* (2005) 287-297, 8(4).
Shepherd et al., "Unraveling the mystery of prognostic and predictive factors in epidermal growth factor receptor therapy." *Journal of Clinical Oncology* (2006) 1219-20; author reply 1220-1, 24(7).
Sherrill et al., "Activation of epidermal growth factor receptor by epidermal growth factor." *Biochemistry* (1996) 5705-5718, 35(18).
Shibata et al., "Enhancing effects of epidermal growth factor on human squamous cell carcinoma motility and matrix degradation but not growth." *Tumour Biology : The Journal of the International Society for Oncodevelopmental Biology and Medicine* (1996) 168-175, 17(3).
Shigematsu et al., "Somatic mutations of epidermal growth factor receptor signaling pathway in lung cancers." *Int. J. Cancer* (2006) 257-262, 118(2).
Shigematsu et al., "Clinical and biological features associated with epidermal growth factor receptor gene mutations in lung cancers." *J. Natl. Cancer Inst.* (2005) 339-346, 97(5).
Shimizu et al., "Detection of epidermal growth factor receptor gene amplification in human squamous cell carcinomas using fluorescence in situ hybridization." *Japanese Journal of Cancer Research: Gann* (1994) 567-571, 85(6).
Shimizu et al., "Genetics of cell surface receptors for bioactive polypeptides: binding of epidermal growth factor is associated with the presence of human chromosome 7 in human-mouse cell hybrids." *Proceedings of the National Academy of Sciences of the United States of America* (1980) 3600-3604, 77(6).
Shin et al., "Epidermal growth factor receptor-targeted therapy with C225 and cisplatin in patients with head and neck cancer." *Clin. Cancer Res.* (2001) 1204-1213, 7(5).
Shin et al., "Dysregulation of epidermal growth factor receptor expression in premalignant lesions during head and neck tumorigenesis." *Cancer Res.* (1994) 3153-3159, 54(12).
Shinkawa et al., "The absence of fucose but not the presence of galactose or bisecting N-acetylglucosamine of human IgG1 complex-type oligosaccharides shows the critical role of enhancing antibody-dependent cellular cytotoxicity." *JBC* (2003) 3466-3473, 278(5).
Shinojima et al., "Prognostic value of epidermal growth factor receptor in patients with glioblastoma multiforme." *Cancer Res.* (2003) 6962-6970, 63(20).
Shintani, "Gefitinib ('Iressa', ZD1839), an epidermal growth factor receptor tyrosine kinase inhibitor, up-regulates p27KIP1 and induces G1 arrest in oral squamous cell carcinoma cell lines" *Oral oncology* (2004) 43-51, 40(1).

(56) References Cited

OTHER PUBLICATIONS

Shintani et al., "Intragenic mutation analysis of the human epidermal growth factor receptor (EGFR) gene in malignant human oral keratinocytes." *Cancer Res.* (1999) 4142-4147, 59(16).
Shusta et al., "Directed evolution of a stable scaffold for T-cell receptor engineering." *Nat. Biotechnol.* (2000) 754-759, 18(7).
Shusta et al., "Yeast polypeptide fusion surface display levels predict thermal stability and soluble secretion efficiency." *J. Mol. Biol.* (1999) 949-956, 292(5).
Sibilia et al., "The EGF receptor provides an essential survival signal for SOS-dependent skin tumor development." *Cell* (2000) 211-220, 102(2).
Siegel-Lakhai et al., "Current knowledge and future directions of the selective epidermal growth factor receptor inhibitors erlotinib (Tarceva) and gefitinib (Iressa)." *Oncologist* (2005) 579-589, 10(8).
Silver et al., "Erbb is linked to the alpha-globin locus on mouse chromosome 11." *Mol. Cell Biol.* (1985) 1784-1786, 5(7).
Sirotnak et al., "Potentiation of cytotoxic agents against human tumors in mice by ZD1839 (Iressa), an inhibitor of EGFR tyrosine kinase, does not require high levels of expression of EGFR." *Proceedings of the Annual Meeting of the American Association For Cancer Research* (2000) 482 (Abstract 3076), 41.
Sirotnak et al., "Efficacy of cytotoxic agents against human tumor xenografts is markedly enhanced by coadministration of ZD1839 (Iressa), an inhibitor of EGFR tyrosine kinase." *Clin. Cancer Res.* (2000) 4885-4892, 6(12).
Sivasubramanian et al., "Structural model of the mAb 806-EGFR complex using computational docking followed by computational and experimental mutagenesis." *Structure* (2006) 401-414, 14(3).
Sizeland et al., "Anti-sense transforming growth factor alpha oligonucleotides inhibit autocrine stimulated proliferation of a colon carcinoma cell line." *Mol. Biol. Cell* (1992) 1235-1243, 3(11).
Sizeland et al., "The proliferative and morphologic responses of a colon carcinoma cell line (LIM 1215) require the production of two autocrine factors." *Mol. Cell Biol.* (1991) 4005-4014, 11(8).
Skov et al., "Interaction of platinum drugs with clinically relevant x-ray doses in mammalian cells: a comparison of cisplatin, carboplatin, iproplatin, and tetraplatin." *Int. J. Radiat. Oncol. Biol. Phys.* (1991) 221-225, 20(2).
Slamon, "Use of Chemotherapy Plus a Monoclonal Antibody Against HER2 for Metastatic Breast Cancer That Overexpresses HER2" *The New England Journal of Medicine* (2001) 783-792, 344(11).
Slamon et al., "Addition of Herceptin (Humanized anti-HER2 antibody) to first line chemotherapy for HER2 overexpressing metastatic breast cancer (HER2+/MBC) markedly increases anticancer activity: a randomized, multinational controlled phase III trial." *Proceedings of the Annual Meeting of the American Society of Clinical Oncology* (1998) 98a (Abstract 377), 17.
Slamon et al., "Studies of the HER-2/neu proto-oncogene in human breast and ovarian cancer." *Science* (1989) 707-712, 244(4905).
Slichenmyer et al., "Anticancer therapy targeting the erbB family of receptor tyrosine kinases." *Semin. Oncol.* (2001) 67-79, 28(5; Suppl. 16).
Slieker et al., "Synthesis of epidermal growth factor receptor in human A431 cells. Glycosylation-dependent acquisition of ligand binding activity occurs post-translationally in the endoplasmic reticulum." *JBC* (1986) 15233-15241, 261(32).
Slieker et al., "Post-translational processing of the epidermal growth factor receptor. Glycosylation-dependent acquisition of ligand-binding capacity." *JBC* (1985) 687-690, 260(2).
Sliwkowski et al., "Nonclinical studies addressing the mechanism of action of trastuzumab (Herceptin)." *Semin. Oncol.* (1999) 60-70, 26(4 Suppl 12).
Smith et al., "PTEN mutation, EGFR amplification, and outcome in patients with anaplastic astrocytoma and glioblastoma multiforme." *J. Natl. Cancer Inst.* (2001) 1246-1256, 93(16).
Snyder et al., "Overview of monoclonal antibodies and small molecules targeting the epidermal growth factor receptor pathway in colorectal cancer." *Clin. Colorectal Cancer* (2005) S71-80, 5(Suppl. 2).

Sobol et al., "Epidermal growth factor receptor expression in human lung carcinomas defined by a monoclonal antibody." *J. Natl. Cancer Inst.* (1987) 403-407, 79(3).
Soderquist et al., "Glycosylation of the epidermal growth factor receptor in A-431 cells. The contribution of carbohydrate to receptor function." *Journal of Biological Chemistry* (1984) 12586-12594, 259(20).
Sok et al., "Mutant epidermal growth factor receptor (EGFRvIII) contributes to head and neck cancer growth and resistance to EGFR targeting." *Clin. Cancer Res.* (2006) 5064-5073, 12(17).
Solbach et al., "Antitumor effect of MAb EMD 55900 depends on EGF-R expression and histopathology." *Neoslasia* (2002) 237-242, 4(3).
Solomon et al., "EGFR blockade with ZD1839 ('Iressa') potentiates the antitumor effects of single and multiple fractions of ionizing radiation in human A431 squamous cell carcinoma." *Int. J. Radiat. Oncol. Biol. Phys.* (2003) 713-723, 55(3).
Solomon et al., "Rash from EGFR inhibitors: opportunities and challenges for palliation." *Current Oncology Reports* (2008) 304-308, 10(4).
Sonabend et al., "Targeting epidermal growth factor receptor variant III: a novel strategy for the therapy of malignant glioma." *Expert Review of Anticancer Therapy* (2007) S45-50, 7(12; Supplement).
Sorensen et al., "Injury-induced innate immune response in human skin mediated by transactivation of the epidermal growth factor receptor." *J. Clin. Invest.* (2006) 1878-1885, 116(7).
Sorscher, "EGFR mutations and sensitivity to gefitinib." *N. Engl. J. Med.* (2004) 1260-1261, 351(12).
Soulieres, "Multicenter Phase II Study of Erlotinib, an Oral Epidermal Growth Factor Receptor Tyrosine Kinase Inhibitor, in Patients With Recurrent or Metastatic Squamous Cell Cancer of the Head and Neck" *Journal of Clinical Oncology* (2004) 77-85, 22(1).
Spurr et al., "Mapping of cellular oncogenes; erb B on chromosome 7" *Cytogenet. Cell. Genet.* (1984) 590, 37.
Spurr et al., "Chromosomal localisation of the human homologues to the oncogenes erbA and B." *EMBO J.* (1984) 159-163, 3(1).
Sridhar et al., "Inhibitors of epidermal-growth-factor receptors: a review of clinical research with a focus on non-small-cell lung cancer." *The Lancet Oncology* (2003) 397-406, 4(7).
Stabin et al., "OLINDA/EXM: the second-generation personal computer software for internal dose assessment in nuclear medicine." *J. Nucl. Med.* (2005) 1023-1027, 46(6).
Stamos et al., "Structure of the epidermal growth factor receptor kinase domain alone and in complex with a 4-anilinoquinazoline inhibitor." *JBC* (2002) 46265-46272, 277(48).
Stancovski et al., "Mechanistic aspects of the opposing effects of monoclonal antibodies to the ERBB2 receptor on tumor growth." *Proceedings of the National Academy of Sciences of the United States of America* (1991) 8691-8695, 88(19).
Steffens et al., "Targeting of renal cell carcinoma with iodine-131-labeled chimeric monoclonal antibody G250." *J. Clin. Oncol.* (1997) 1529-1537, 15(4).
Stein et al., "Combining radioimmunotherapy and chemotherapy for treatment of medullary thyroid carcinoma: effectiveness of dacarbazine." *Cancer* (2002) 51-61, 94(1).
Stockert et al., "Annual Research Report 1997" *Ludwig Institute for Cancer Research* (1997) 212-213.
Stockert et al., "Annual Research Report 1995" *Ludwig Institute for Cancer Research* (1995) 226-227.
Stockhausen et al., "Maintenance of EGFR and EGFRvIII expressions in an in vivo and in vitro model of human glioblastoma multiforme." *Exp. Cell Res.* (2011) 1513-1526, 317(11).
Stragliotto et al., "Multiple infusions of anti-epidermal growth factor receptor (EGFR) monoclonal antibody (EMD 55,900) in patients with recurrent malignant gliomas." *Eur. J. Cancer* (1996) 636-640, 32A(4).
Studnicka et al., "Human-engineered monoclonal antibodies retain full specific binding activity by preserving non-Cdr complementarity-modulating residues." *Protein Engineering* (1994) 805-814, 7(6).
Sturgis et al., "Effects of antiepidermal growth factor receptor antibody 528 on the proliferation and differentiation of head and neck

(56) References Cited

OTHER PUBLICATIONS cancer." *Otolaryngology—Head and Neck Surgery: Official Journal of American Academy of Otolaryngology-Head and Neck Surgery* (1994) 633-643, 111(5).

Sugawa et al., "Function of aberrant EGFR in malignant gliomas." *Brain Tumor Pathology* (1998) 53-57, 15(1).

Sugawa et al., "Identical splicing of aberrant epidermal growth factor receptor transcripts from amplified rearranged genes in human glioblastomas." *Proceedings of the National Academy of Sciences of the United States of America* (1990) 8602-8606, 87(21).

Sugimura et al., "[Immunohistochemical study on the expression of epidermal growth factor receptor (EGF-R) in invasive cervical cancer of the uterus]." *Nippon Sanka Fuiinka Gakkai zasshi* (1992) 689-694, 44(6).

Sunada et al., "Monoclonal antibody against epidermal growth factor receptor is internalized without stimulating receptor phosphorylation." *Proceedings of the National Academy of Sciences of the United States of America* (1986) 3825-3829, 83(11).

Sutherland et al., "Lysosomal trafficking and cysteine protease metabolism confer target-specific cytotoxicity by peptide-linked anti-CD30-auristatin conjugates." *Journal of Biological Chemistry* (2006) 10540-10547, 281(15).

Suwa et al., "Epidermal growth factor receptor-dependent cytotoxic effect of anti-EGFR antibody-ribonuclease conjugate on human cancer cells." *Anticancer Research* (1999) 4161-4165, 19(5B).

Swaisland et al., "Pharmacokinetics and tolerability of the orally active selective epidermal growth factor receptor tyrosine kinase inhibitor ZD1839 in healthy volunteers." *Clinical pharmacokinetics* (2001) 297-306, 40(4).

Tabernero et al., "An international phase II study of cetuximab in combination with oxaliplatin/5-fluorouracil (5-FU)/folinic acid (FA) (FOLFOX-4) in the first-line treatment of patients with metastatic colorectal cancer (CRC) expressing epidermal growth factor receptor (EGFR)." *Proceedings of the American Society of Clinical Oncology* (2004) 248s (Abstract 3512), 23.

Tabernero et al., "A phase I PK and serial tumor and skin pharmacodynamic (PD) study of weekly (q1w), every 2-week (q2w) or every 3-week (q3w) 1-hour (h) infusion EMD72000, a humanized monoclonal anti-epidermal growth factor receptor (EGFR) antibody, in patients (pt) with advanced tumors." *Proceedings of the American Society of Clinical Oncology* (2003) 192 (Abstract 770), 22.

Taetle et al., "Effects of anti-epidermal growth factor (EGF) receptor antibodies and an anti-EGF receptor recombinant-ricin a chain immunoconjugate on growth of human cell" *Chemical Abstracts* (1988) 184218a, 109(21).

Taetle et al., "Effects of anti-epidermal growth factor (EGF) receptor antibodies and an anti-EGF receptor recombinant-ricin a chain immunoconjugate on growth of human cells." *J. Natl. Cancer Inst.* (1988) 1053-1059, 80(13).

Tahtis et al., "Biodistribution properties of (111)indium-labeled C-functionalized trans-cyclohexyl diethylenetriaminepentaacetic acid humanized 3S193 diabody and F(ab')(2) constructs in a breast carcinoma xenograft model." *Clin. Cancer Res.* (2001) 1061-1072, 7(4).

Tai et al., "Co-overexpression of fibroblast growth factor 3 and epidermal growth factor receptor is correlated with the development of nonsmall cell lung carcinoma." *Cancer* (2006) 146-155, 106(1).

Takahashi et al., "Radioimmunodetection of human glioma xenografts by monoclonal antibody to epidermal growth factor receptor." *Cancer Res.* (1987) 3847-3850, 47(14).

Takasu et al., "Antibody-based therapy for brain tumor." *Nippon rinsho. Japanese journal of clinical medicine* (2005) 563-568, 63(Suppl. 9).

Takasu et al., "Radioimmunoscintigraphy of intracranial glioma xenograft with a technetium-99m-labeled mouse monoclonal antibody specifically recognizing type III mutant epidermal growth factor receptor." *Journal of neuro-oncology* (2003) 247-256, 63(3).

Tan et al., "Pharmacokinetics of cetuximab after administration of escalating single dosing and weekly fixed dosing in patients with solid tumors." *Clin. Cancer Res.* (2006) 6517-6522, 12(21).

Tang et al., "Epidermal growth factor receptor vlll enhances tumorigenicity in human breast cancer." *Cancer Res.* (2000) 3081-3087, 60(11).

Tang et al., "The autocrine loop of TGF-alpha/EGFR and brain tumors." *Journal of neuro-oncology* (1997) 303-314, 35(3).

Tang et al., "Phase II study of ispinesib in recurrent or metastatic squamous cell carcinoma of the head and neck." *Investigational new drugs* (2008) 257-264, 26(3).

Tannock, "Treatment of cancer with radiation and drugs." *J. Clin. Oncol.* (1996) 3156-3174, 14(12).

Tanswell et al., "Population pharmacokinetics of antifibroblast activation protein monoclonal antibody F19 in cancer patients." *British journal of clinical pharmacology* (2001) 177-180, 51(2).

Tateishi et al., "Prognostic influence of the co-expression of epidermal growth factor receptor and c-erbB-2 protein in human lung adenocarcinoma." *Surgical oncology* (1994) 109-113, 3(2).

Temam et al., "Epidermal growth factor receptor copy number alterations correlate with poor clinical outcome in patients with head and neck squamous cancer." *Journal of Clinical Oncology* (2007) 2164-2170, 25(16).

Temming et al., "Evaluation of RGD-targeted albumin carriers for specific delivery of auristatin E to tumor blood vessels." *Bioconjugate chemistry* (2006) 1385-1394, 17(6).

Teramoto et al., "Inhibitory effect of anti-epidermal growth factor receptor antibody on a human gastric cancer." *Cancer* (1996) 1639-1645, 77(8 Suppl).

Tewes et al., "Results of a phase I trial of the humanized anti epidermal growth factor receptor (EGFR) monoclonal antibody EMD 72000 in patients with EGFR expressing solid tumors." *Proceedings of the American Society of Clinical Oncology* (2002) 95a (Abstract 378), 21.

Thaung et al., "Novel ENU-induced eye mutations in the mouse: models for human eye disease." *Human molecular genetics* (2002) 755-767, 11(7).

Thomas et al., "Pharmacokinetic and pharmacodynamic properties of EGFR inhibitors under clinical investigation." *Cancer Treat Rev.* (2004) 255-268, 30(3).

Thompson et al., "The EGF receptor: structure, regulation and potential role in malignancy." *Cancer surveys* (1985) 767-788, 4(4).

Tice et al., "Mechanism of biological synergy between cellular Src and epidermal growth factor receptor." *Proceedings of the National Academy of Sciences of the United States of America* (1999) 1415-1420, 96(4).

Tietze et al., "Novel analogues of CC-1065 and the duocarmycins for the use in targeted tumour therapies." *Anti-cancer agents in medicinal chemistry* (2009) 304-325, 9(3).

Tochon-Danguy et al., "Imaging and quantitation of the hypoxic cell fraction of viable tumor in an animal model of intracerebral high grade glioma using [18F]fluoromisonidazole (FMISO)." *Nucl. Med. Biol.* (2002) 191-197, 29(2).

Todaro et al., "Transformation by murine and feline sarcoma viruses specifically blocks binding of epidermal growth factor to cells." *Nature* (1976) 26-31, 264(5581).

Todd et al., "Epidermal growth factor receptor (EGFR) biology and human oral cancer." *Histology and histopathology* (1999) 491-500, 14(2).

Toi et al., "Epidermal growth factor receptor expression as a prognostic indicator in breast cancer." *Eur. J. Cancer* (1991) 977-980, 27(8).

Tokuda et al., "In vitro and in vivo anti-tumour effects of a humanised monoclonal antibody against c-erbB-2 product." *British Journal of Cancer* (1996) 1362-1365, 73(11).

Tokumo et al., "The relationship between epidermal growth factor receptor mutations and clinicopathologic features in non-small cell lung cancers." *Clin. Cancer Res.* (2005) 1167-1173, 11(3).

Torres et al., "Phase I/II clinical trial of the humanized anti-EGF-r monoclonal antibody h-R3 labelled with 99mTc in patients with tumour of epithelial origin." *Nuclear medicine communications* (2005) 1049-1057, 26(12).

Toth et al., "Analysis of EGFR gene amplification, protein overexpression and tyrosine kinase domain mutation in recurrent glioblastoma." *Pathology oncology research: POR* (2009) 225-229, 15(2).

(56) References Cited

OTHER PUBLICATIONS

Toyooka et al., "EGFR mutation and response of lung cancer to gefitinib." *N. Engl. J. Med.* (2005) 2136, 352(20).
Trail et al., "Monoclonal antibody drug conjugates in the treatment of cancer." *Curr. Opin. Immunol.* (1999) 584-588, 11(5).
Tran et al., "CAML is required for efficient EGF receptor recycling." *Developmental cell* (2003) 245-256, 5(2).
Traxler et al., "AEE788: a dual family epidermal growth factor receptor/ErbB2 and vascular endothelial growth factor receptor tyrosine kinase inhibitor with antitumor and antiangiogenic activity." *Cancer Res.* (2004) 4931-4941, 64(14).
Trigo et al., "Cetuximab monotherapy is active in patients (pts) with platinum-refractory recurrent/metastatic squamous cell carcinoma of the head and neck (SCCHN) (Results of a phase II study)." *Proceedings of the American Society of Clinical Oncology* (2004) 488s (Abstract 5502), 22.
Trummell et al., "The biological effects of anti-epidermal growth factor receptor and ionizing radiation in human head and neck tumor cell lines." *Proceedings of the American Association for Cancer Research* (1999) 144 (Abstract 958), 40.
Tsao et al., "Erlotinib in lung cancer—molecular and clinical predictors of outcome." *N. Engl. J. Med.* (2005) 133-144, 353(2).
Tsuchihashi et al., "Responsiveness to cetuximab without mutations in EGFR." *N. Engl. J. Med.* (2005) 208-209, 353(2).
Tsugu et al., "Localization of aberrant messenger RNA of epidermal growth factor receptor (EGFR) in malignant glioma." *Anticancer research* (1997) 2225-2232, 17(3C).
Türkeri et al., "Impact of the expression of epidermal growth factor, transforming growth factor alpha, and epidermal growth factor receptor on the prognosis of superficial bladder cancer." *Urology* (1998) 645-649, 51(4).
Turner et al., "EGF receptor signaling enhances in vivo invasiveness of DU-145 human prostate carcinoma cells." *Clinical & experimental metastasis* (1996) 409-418, 14(4).
Tzahar et al., "Bivalence of EGF-like ligands drives the ErbB signaling network." *EMBO J.* (1997) 4938-4950, 16(16).
Uegaki et al., "Clinicopathological significance of epidermal growth factor and its receptor in human pancreatic cancer." *Anticancer research* (1997) 3841-3847, 17(5B).
Uemura et al., "Internal image anti-idiotype antibodies related to renal-cell carcinoma-associated antigen G250." *Int. J. Cancer* (1994) 609-614, 56(4).
Ullrich et al., "Signal transduction by receptors with tyrosine kinase activity." *Cell* (1990) 203-212, 61(2).
Ullrich et al., "Human epidermal growth factor receptor cDNA sequence and aberrant expression of the amplified gene in A431 epidermoid carcinoma cells." *Nature* (1984) 418-425, 309(5967).
Ushiro et al., "Identification of phosphotyrosine as a product of epidermal growth factor-activated protein kinase in A-431 cell membranes." *JBC* (1980) 8363-8365, 255(18).
Vagin et al., "MOLREP: an Automated Program for Molecular Replacement" *J. Appl. Cryst.* (1997) 1022-1025, 30.
Vagin et al., "Spherically averaged phased translation function and its application to the search for molecules and fragments in electron-density maps." *Acta Crystallogr. D. Biol. Crystallogr.* (2001) 1451-1456, 57(Pt 10).
Vaidyanathan et al., "Improved xenograft targeting of tumor-specific anti-epidermal growth factor receptor variant III antibody labeled using N-succinimidyl 4-guanidinomethyl-3-iodobenzoate." *Nucl. Med. Biol.* (2002) 1-11, 29(1).
Vajdos et al., "Comprehensive functional maps of the antigen-binding site of an anti-ErbB2 antibody obtained with shotgun scanning mutagenesis." *J. Mol. Biol.* (2002) 415-428, 320(2).
Van Den Eynde et al., "Tumor Antigens" *Tumor Antigens. In: P. J. Delves and I. M. Roitt (eds.) Encyclopedia of Immunology, Second Edition (London: Academic Press)* (1998) 2424-2431.
Vanhoefer et al., "Phase I study of the humanized antiepidermal growth factor receptor monoclonal antibody EMD72000 in patients with advanced solid tumors that express the epidermal growth factor receptor." *J. Clin. Oncol.* (2004) 175-184, 22(1).
Veale et al., "The relationship of quantitative epidermal growth factor receptor expression in non-small cell lung cancer to long term survival." *British Journal of Cancer* (1993) 162-165, 68(1).
Veale et al., "Epidermal growth factor receptors in non-small cell lung cancer." *British Journal of Cancer* (1987) 513-516, 55(5).
Velu et al., "Epidermal-growth-factor-dependent transformation by a human EGF receptor proto-oncogene." *Science* (1987) 1408-1410, 238(4832).
Venter et al., "Overexpression of the c-erbB-2 oncoprotein in human breast carcinomas: immunohistological assessment correlates with gene amplification." *Lancet* (1987) 69-72, 2(8550).
Verbeek et al., "Overexpression of EGFR and c-erbB2 causes enhanced cell migration in human breast cancer cells and NIH3T3 fibroblasts." *FEBS letters* (1998) 145-150, 425(1).
Vermorken et al., "Cetuximab (Erbitux®) in recurrent/metastatic (R&M) squamous cell carcinoma of the head and neck (SCCHN) refractory to first-line platinum-based therapies" *Journal of Clinical Oncology, 2005 ASCO Annual Meeting Proceedings* (2005) Abstract 5505, 23(16S; Part I of II: Jun. 1, Supplement).
Vermorken et al., "Platinum-based chemotherapy plus cetuximab in head and neck cancer." *N. Engl. J. Med.* (2008) 1116-1127, 359(11).
Verveer et al., "Quantitative imaging of lateral ErbB1 receptor signal propagation in the plasma membrane." *Science* (2000) 1567-1570, 290(5496).
Viana-Pereira et al., "Analysis of EGFR overexpression, EGFR gene amplification and the EGFRvIII mutation in Portuguese high-grade gliomas." *Anticancer research* (2008) 913-920, 28(2A).
Van De Vijver et al., "Ligand-induced activation of A431 cell epidermal growth factor receptors occurs primarily by an autocrine pathway that acts upon receptors on the surface rather than intracellularly." *Journal of Biological Chemistry* (1991) 7503-7508, 266(12).
Viloria-Petit et al., "Acquired resistance to the antitumor effect of epidermal growth factor receptor-blocking antibodies in vivo: a role for altered tumor angiogenesis." *Cancer Res.* (2001) 5090-5101, 61(13).
Vincent et al., "Anticancer efficacy of the irreversible EGFr tyrosine kinase inhibitor PD 0169414 against human tumor xenografts." *Cancer chemotherapy and pharmacology* (2000) 231-238, 45(3).
Vitali et al., "Monoclonal Antibody 806 Inhibits the Growth of Subcutaneous and Intracranial Tumor Xenografts Expressing either the de2.7 or Amplified Epidermal Growth Factor Receptor (EGFR) but not Wild-Type EGFR." *Proceedings of the 14th Annual Lorne Cancer Conference, Lorne, Victoria, Australia* (2002) Abstract 221.
Vitali et al., "Monoclonal Antibody 806 Inhibits the Growth of Subcutaneous and Intracranial Tumor Xenografts Expressing either the de2.7 or Amplified Epidermal Growth Factor Receptor (EGFR) but not Wild-Type EGFR." *Proceedings of the 14th Annual Lorne Cancer Conference, Lorne, Victoria, Australia* (2002) Poster Presentation (Abstract 221).
Voelzke et al., "Targeting the epidermal growth factor receptor in high-grade astrocytomas." *Current treatment options in oncology* (2008) 23-31, 9(1).
Vogel et al., "First-Line Herceptin® Monotherapy in Metastatic Breast Cancer" *Oncology* (2001) 37-42, 61(Suppl. 2).
Vogel et al., "Efficacy and safety of trastuzumab as a single agent in first-line treatment of HER2-overexpressing metastatic breast cancer." *J. Clin. Oncol.* (2002) 719-726, 20(3).
Vogt et al., "Relationships linking amplification level to gene overexpression in gliomas." *PLoS ONE* (2010) e14249, 5(12).
Voldborg et al., "Epidermal growth factor receptor (EGFR) and EGFR mutations, function and possible role in clinical trials." *Ann Oncol.* (1997) 1197-1206, 8(12).
Volm et al., "Prognostic value of ERBB-1, VEGF, cyclin A, FOS, JUN and MYC in patients with squamous cell lung carcinomas." *British Journal of Cancer* (1998) 663-669, 77(4).
Wade et al., "An automated peptide and protein thiazolidine coupling chemistry for biosensor immobilization giving a unique N-terminal orientation." *Analytical biochemistry* (2006) 315-317, 348(2).
Wakeling et al., "Specific inhibition of epidermal growth factor receptor tyrosine kinase by 4-anilinoquinazolines." *Breast cancer research and treatment* (1996) 67-73, 38(1).

(56) References Cited

OTHER PUBLICATIONS

Wakeling, "Epidermal growth factor receptor tyrosine kinase inhibitors." *Current opinion in pharmacology* (2002) 382-387, 2(4).
Wakeling et al., "Human EGFR, a candidate gene for the Silver-Russell syndrome, is biallelically expressed in a wide range of fetal tissues." *European journal of human genetics: EJHG* (1998) 158-164, 6(2).
Waksal, "Role of an anti-epidermal growth factor receptor in treating cancer." *Cancer Metastasis Rev.* (1999) 427-436, 18(4).
Waldmann, "Monoclonal antibodies in diagnosis and therapy." *Science* (1991) 1657-1662, 252(5013).
Walewski et al., "Rituximab (Mabthera, Rituxan) in patients with recurrent indolent lymphoma: evaluation of safety and efficacy in a multicenter study." *Medical oncology (Northwood, London, England)* (2001) 141-148, 18(2).
Walker et al., "Activation of the Ras/mitogen-activated protein kinase pathway by kinase-defective epidermal growth factor receptors results in cell survival but not proliferation." *Mol. Cell Biol.* (1998) 7192-7204, 18(12).
Walker et al., "Biochemical characterization of mutant EGF receptors expressed in the hemopoietic cell line BaF/3." *Growth Factors* (1998) 53-67, 16(1).
Walker et al., "Reconstitution of the high affinity epidermal growth factor receptor on cell-free membranes after transmodulation by platelet-derived growth factor." *Journal of Biological Chemistry* (1991) 2746-2752, 266(5).
Walker et al., "CR1/CR2 interactions modulate the functions of the cell surface epidermal growth factor receptor." *JBC* (2004) 22387-22398, 279(21).
Walker et al., "Expression of epidermal growth factor receptor mRNA and protein in primary breast carcinomas." *Breast cancer research and treatment* (1999) 167-176, 53(2).
Walton et al., "Analysis of deletions of the carboxyl terminus of the epidermal growth factor receptor reveals self-phosphorylation at tyrosine 992 and enhanced in vivo tyrosine phosphorylation of cell substrates." *Journal of Biological Chemistry* (1990) 1750-1754, 265(3).
Wang et al., "Immunohistochemical localization of c-erbB-2 protein and epidermal growth factor receptor in normal surface epithelium, surface inclusion cysts, and common epithelial tumours of the ovary." *Virchows Archiv. A, Pathological anatomy and histopathology* (1992) 393-400, 421(5).
Wang et al., "Epidermal growth factor receptor vIII enhances tumorigenicity and resistance to 5-fluorouracil in human hepatocellular carcinoma." *Cancer Letters* (2009) 30-38, 279(1).
Wang et al., "Epidermal growth factor receptor is a cellular receptor for human cytomegalovirus." *Nature* (2003) 456-461, 424(6947).
Wang et al., "Endocytosis deficiency of epidermal growth factor (EGF) receptor-ErbB2 heterodimers in response to EGF stimulation." *Mol. Biol. Cell* (1999) 1621-1636, 10(5).
Ward et al., "Binding activities of a repertoire of single immunoglobulin variable domains secreted from *Escherichia coli*." *Nature* (1989) 544-546, 341(6242).
Wargalla et al., "Rate of internalization of an immunotoxin correlates with cytotoxic activity against human tumor cells." *Proceedings of the National Academy of Sciences of the United States of America* (1989) 5146-5150, 86(13).
Waterfield et al., "A monoclonal antibody to the human epidermal growth factor receptor." *J. Cell Biochem.* (1982) 149-161, 20(2).
Waterman et al., "Molecular mechanisms underlying endocytosis and sorting of ErbB receptor tyrosine kinases." *FEBS letters* (2001) 142-152, 490(3).
Waterman et al., "Alternative intracellular routing of ErbB receptors may determine signaling potency." *Journal of Biological Chemistry* (1998) 13819-13827, 273(22).
Waugh et al., "Epidermal growth factor receptor activation is localized within low-buoyant density, non-caveolar membrane domains." *Biochem. J.* (1999) 591-597, 337(Part 3).
Webster et al., "Engineering antibody affinity and specificity." *International journal of cancer* (1988) 13-16, 3.

Wedegaertner et al., "Effect of carboxyl terminal truncation on the tyrosine kinase activity of the epidermal growth factor receptor." *Archives of biochemistry and biophysics* (1992) 273-280, 292(1).
Wedegaertner et al., "Activation of the purified protein tyrosine kinase domain of the epidermal growth factor receptor." *Journal of Biological Chemistry* (1989) 11346-11353, 264(19).
Weiner, "An overview of monoclonal antibody therapy of cancer." *Semin. Oncol.* (1999) 41-50, 26(4 Suppl 12).
Weiss et al., "Rapid mapping of protein functional epitopes by combinatorial alanine scanning." *Proceedings of the National Academy of Sciences of the United States of America* (2000) 8950-8954, 97(16).
Wells, "EGF receptor." *The international journal of biochemistry & cell biology* (1999) 637-643, 31(6).
Wells et al., "Ligand-induced transformation by a noninternalizing epidermal growth factor receptor." *Science* (1990) 962-964, 247(4945).
Welt et al., "Phase I study of humanized A33 (huA33) antibody in patients with advanced colorectal cancer." *Proceedings of the Annual Meeting of the American Society of Clinical Oncology* (1997) 436a (Abstract 1563), 16.
Welt et al., "Phase I/II study of iodine 125-labeled monoclonal antibody A33 in patients with advanced colon cancer." *J. Clin. Oncol.* (1996) 1787-1797, 14(6).
Welt et al., "Phase I/II study of iodine 131-labeled monoclonal antibody A33 in patients with advanced colon cancer." *J. Clin. Oncol.* (1994) 1561-1571, 12(8).
Welt et al., "Antibody targeting in metastatic colon cancer: a phase I study of monoclonal antibody F19 against a cell-surface protein of reactive tumor stromal fibroblasts." *J. Clin. Oncol.* (1994) 1193-1203, 12(6).
Welt et al., "Quantitative analysis of antibody localization in human metastatic colon cancer: a phase I study of monoclonal antibody A33." *J. Clin. Oncol.* (1990) 1894-1906, 8(11).
Welt et al., "Phase I study of anticolon cancer humanized antibody A33." *Clin. Cancer Res.* (2003) 1338-1346, 9(4).
Welt et al., "Preliminary report of a phase I study of combination chemotherapy and humanized A33 antibody immunotherapy in patients with advanced colorectal cancer." *Clin. Cancer Res.* (2003) 1347-1353, 9(4).
Wen et al., "Potentiation of antitumor activity of PG-TXL with anti-EGFR monoclonal antibody C225 in MDA-MB-468 human breast cancer xenograft." *Proceedings of the American Association for Cancer Research* (2000) 323 (Abstract 2052), 51.
Weppler et al., "Expression of EGFR variant vIII promotes both radiation resistance and hypoxia tolerance." *Radiotherapy and oncology* (2007) 333-339, 83(3).
Wersäll et al., "Intratumoral infusion of the monoclonal antibody, mAb 425, against the epidermal-growth-factor receptor in patients with advanced malignant glioma." *Cancer Immunol. Immunother.* (1997) 157-164, 44(3).
Westwood et al., "Adoptive transfer of T cells modified with a humanized chimeric receptor gene inhibits growth of Lewis-Y-expressing tumors in mice." *Proceedings of the National Academy of Sciences of the United States of America* (2005) 19051-19056, 102(52).
Wheeler et al., "Mechanisms of acquired resistance to cetuximab: role of HER (ErbB) family members." *Oncogene* (2008) 3944-3956, 27(28).
Wheeler et al., "Epidermal growth factor receptor variant III mediates head and neck cancer cell invasion via STAT3 activation." *Oncogene* (2010) 5135-5145, 29(37).
Whitson et al., "Functional effects of glycosylation at Asn-579 of the epidermal growth factor receptor." *Biochemistry* (2005) 14920-14931, 44(45).
Wikstrand et al., "Antibodies and molecular immunology: immunohistochemistry and antigens of diagnostic significance" In: *Russell and Rubinstein's Pathology of Tumors of the Nervous System* (Chapter 8) (Editors: Bigner, et al.: Publishers: Arnold and Oxford University Press, Inc., New York, NY). (1998) 251-304.
Wikstrand et al., "Monoclonal antibody therapy of human gliomas: current status and future approaches." *Cancer Metastasis Rev.* (1999) 451-464, 18(4).

(56) References Cited

OTHER PUBLICATIONS

Wikstrand et al., "The class III variant of the epidermal growth factor receptor (EGFRvIII): characterization and utilization as an immunotherapeutic target." *Journal of neurovirology* (1998) 148-158, 4(2).

Wikstrand et al., "Cell surface localization and density of the tumor-associated variant of the epidermal growth factor receptor, EGFRvIII." *Cancer Res.* (1997) 4130-4140, 57(18).

Wikstrand et al., "Monoclonal antibodies against EGFRvIII are tumor specific and react with breast and lung carcinomas and malignant gliomas." *Cancer Res.* (1995) 3140-3148, 55(14).

Wikstrand et al., "Investigation of a synthetic peptide as immunogen for a variant epidermal growth factor receptor associated with gliomas." *Journal of neuroimmunology* (1993) 165-173, 46(1-2).

Wikstrand et al., "Comparative localization of glioma-reactive monoclonal antibodies in vivo in an athymic mouse human glioma xenograft model." *Journal of neuroimmunology* (1987) 37-56, 15(1).

Wikstrand et al., "Production and characterization of two human glioma xenograft-localizing monoclonal antibodies." *Cancer Res.* (1986) 5933-5940, 46(11).

Wiley et al., "The role of tyrosine kinase activity in endocytosis, compartmentation, and down-regulation of the epidermal growth factor receptor." *Journal of Biological Chemistry* (1991) 11083-11094, 266(17).

Wiley, "Trafficking of the ErbB receptors and its influence on signaling." *Exp. Cell Res.* (2003) 78-88, 284(1).

Willett et al., "Direct evidence that the VEGF-specific antibody bevacizumab has antivascular effects in human rectal cancer" *Nature Med.* (2004) 145-147, 10(2).

Williams et al., "Combination of ZD1839 ('Iressa'), an EGFR tyrosine kinase inhibitor, and radiotherapy increases antitumour efficacy in a human colon cancer xenograft model." *Proceedings of the American Association for Cancer Research* (2001) 715 (Abstract 3840), 42.

Williams et al., "ZD1839 ('Iressa'), a specific oral epidermal growth factor receptor-tyrosine kinase inhibitor, potentiates radiotherapy in a humal colorectal cancer xenograft model." *British Journal of Cancer* (2002) 1157-1161, 86(7).

Winer et al., "New Combinations with Herceptin® in Metastatic Breast Cancer." *Oncology* (2001) 50-57, 61(Suppl. 2).

Winkler et al., "Epidermal growth factor and transforming growth factor alpha bind differently to the epidermal growth factor receptor." *Biochemistry* (1989) 6373-6378, 28(15).

Winter et al., "Man-made antibodies." *Nature* (1991) 293-299, 349(6307).

Wollman et al., "Effect of epidermal growth factor on the growth and radiation sensitivity of human breast cancer cells in vitro." *Int. J. Radiat. Oncol. Biol. Phys.* (1994) 91-98, 30(1).

Woltjer et al., "Direct identification of residues of the epidermal growth factor receptor in close proximity to the amino terminus of bound epidermal growth factor." *Proceedings of the National Academy of Sciences of the United States of America* (1992) 7801-7805, 89(16).

Wong et al., "Structural alterations of the epidermal growth factor receptor gene in human gliomas." *Proceedings of the National Academy of Sciences of the United States of America* (1992) 2965-2969, 89(7).

Wong et al., "Increased expression of the epidermal growth factor receptor gene in malignant gliomas is invariably associated with gene amplification." *Proceedings of the National Academy of Sciences of the United States of America* (1987) 6899-6903, 84(19).

Wood et al., "A unique structure for epidermal growth factor receptor bound to GW572016 (Lapatinib): relationships among protein conformation, inhibitor off-rate, and receptor activity in tumor cells." *Cancer Res.* (2004) 6652-6659, 64(18).

Woodburn et al., "ZD1839 ('Iressa') A Selective Epidermal Growth Factor Receptor Tyrosine Kinase Inhibitor (EGFR-TKI): Inhibition of CFOS MRNA, an Intermediate Marker of EGFR Activation, Corre-Lates With Tumor Growth Inhibition." *Proceedings of the Annual Meeting of the American Association for Cancer Research* (2000) 402 (Abstract 2552), 41.

Woodburn et al., "ZD1839, an epidermal growth factor tyrosine kinase inhibitor selected for clinical development." *Proceedings of the Annual Meeting of the American Association for Cancer Research* (1997) 633 (Abstract 4251), 38.

Woodburn, "The epidermal growth factor receptor and its inhibition in cancer therapy." *Pharmacology & therapeutics* (1999) 241-250, 82(2-3).

Wu et al., "Human epidermal growth factor (EGF) receptor sequence recognized by EGF competitive monoclonal antibodies. Evidence for the localization of the EGF-binding site." *Journal of Biological Chemistry* (1989) 17469-17475, 264(29).

Wu et al., "Targeted delivery of methotrexate to epidermal growth factor receptor-positive brain tumors by means of cetuximab (IMC-C225) dendrimer bioconjugates." *Molecular cancer therapeutics* (2006) 52-59, 5(1).

Wu et al., "Humanization of a murine monoclonal antibody by simultaneous optimization of framework and CDR residues." *J. Mol. Biol.* (1999) 151-162, 294(1).

Wu et al., "Apoptosis induced by an anti-epidermal growth factor receptor monoclonal antibody in a human colorectal carcinoma cell line and its delay by insulin." *J. Clin. Invest.* (1995) 1897-1905, 95(4).

Xie et al., "In vitro invasiveness of DU-145 human prostate carcinoma cells is modulated by EGF receptor-mediated signals." *Clinical & experimental metastasis* (1995) 407-419, 13(6).

Xiong et al., "Cetuximab, a monoclonal antibody targeting the epidermal growth factor receptor, in combination with gemcitabine for advanced pancreatic cancer: a multicenter phase II Trial." *J. Clin. Oncol.* (2004) 2610-2616, 22(13).

Xu et al., "Antibody-induced growth inhibition is mediated through immunochemically and functionally distinct epitopes on the extracellular domain of the c-erbB-2 (HER-2/neu) gene product p185." *Int. J. Cancer* (1993) 401-408, 53(3).

Xu et al., "Characterization of epidermal growth factor receptor gene expression in malignant and normal human cell lines." *Proceedings of the National Academy of Sciences of the United States of America* (1984) 7308-7312, 81(23).

Xu et al., "Human epidermal growth factor receptor cDNA is homologous to a variety of RNAs overproduced in A431 carcinoma cells." *Nature* (1984) 806-810, 309(5971).

Yamanaka et al., "Coexpression of epidermal growth factor receptor and ligands in human pancreatic cancer is associated with enhanced tumor aggressiveness." *Anticancer research* (1993) 565-569, 13(3).

Yamazaki et al., "Inhibition of tumor growth by ribozyme-mediated suppression of aberrant epidermal growth factor receptor gene expression." *J. Natl. Cancer Inst.* (1998) 581-587, 90(8).

Yamazaki et al., "A deletion mutation within the ligand binding domain is responsible for activation of epidermal growth factor receptor gene in human brain tumors." *Japanese journal of cancer research: Gann* (1990) 773-779, 81(8).

Yamazaki et al., "Amplification of the structurally and functionally altered epidermal growth factor receptor gene (c-erbB) in human brain tumors." *Mol. Cell Biol.* (1988) 1816-1820, 8(4).

Yang et al., "Therapeutic potential of ABX-EGF, a fully human anti-EGF receptor monoclonal antibody, for cancer treatment." *Proceedings of the American Society of Clinical Oncology* (2000) 48a (Abstract 183), 19.

Yang et al., "Modification of Gemcitabine-Induced Radiosesitization by the Nitroxide Tempol." *Proceedings of the American Society of Clinical Oncology* (1999) 457a (Abstract 1765), 18.

Yang et al., "ModificaltionGenistein, a tyrosine kinase inhibitor, reduces EGF-induced EGF receptor internalization and degradation in human hepatoma HepG2 cells." *Biochem. Biophys. Res. Commun.* (1996) 309-317, 224(2).

Yang et al., "Identification and characterization of Ch806 mimotopes." *Cancer Immunology, Immunotherapy* (2010) 1481-1487, 59(10).

Yang et al., "Molecular targeting and treatment of EGFRvIII-positive gliomas using boronated monoclonal antibody L8A4." *Clin. Cancer Res.* (2006) 3792-3802, 12(12).

(56) References Cited

OTHER PUBLICATIONS

Yang et al., "Development of a syngeneic rat brain tumor model expressing EGFRvIII and its use for molecular targeting studies with monoclonal antibody L8A4." *Clin. Cancer Res.* (2005) 341-350, 11(1).
Yang et al., "Development of ANX-EGF, a fully human anti-EGF receptor monoclonal antibody, for cancer therapy." *Crit. Rev. Oncol. Hematol.* (2001) 17-23, 38(1).
Yang et al., "Eradication of established tumors by a fully human monoclonal antibody to the epidermal growth factor receptor without concomitant chemotherapy." *Cancer Res.* (1999) 1236-1243, 59(6).
Yao et al., "Enhanced expression of c-myc and epidermal growth factor receptor (C-erbB-1) genes in primary human renal cancer." *Cancer Res.* (1988) 6753-6757, 48(23).
Yarden et al., "Untangling the ErbB signalling network." *Nat. Rev. Mol. Cell Biol.* (2001) 127-137, 2(2).
Yarden et al., "Epidermal growth factor induces rapid, reversible aggregation of the purified epidermal growth factor receptor." *Biochemistry* (1987) 1443-1451, 26(5).
Yarden et al., "Self-phosphorylation of epidermal growth factor receptor: evidence for a model of intermolecular allosteric activation." *Biochemistry* (1987) 1434-1442, 26(5).
Ye et al., "Augmentation of a humanized anti-HER2 mAb 4D5 induced growth inhibition by a human-mouse chimeric anti-EGF receptor mAb C225." *Oncogene* (1999) 731-738, 18(3).
Yeatman, "A renaissance for SRC." *Nature Rev. Cancer* (2004) 470-480, 4(6).
Yen et al., "Differential regulation of tumor angiogenesis by distinct ErbB homo- and heterodimers." *Mol. Biol. Cell* (2002) 4029-4044, 13(11).
Yip et al., "Identification of epitope regions recognized by tumor inhibitory and stimulatory anti-ErbB-2 monoclonal antibodies: implications for vaccine design." *Journal of immunology (Baltimore, Md: 1950)* (2001) 5271-5278, 166(8).
Yip et al., "Structural analysis of the ErbB-2 receptor using monoclonal antibodies: Implications for receptor signalling." *Int. J. Cancer* (2003) 303-309, 104(3).
Ymer et al., "Glioma Specific Extracellular Missense Mutations in the First Cysteine Rich Region of Epidermal Growth Factor Receptor (EGFR) Initiate Ligand Independent Activation" *Cancers* (2011) 2032-2049, 3.
Ymer et al., "Constitutive synthesis of interleukin-3 by leukaemia cell line WEHI-3B is due to retroviral insertion near the gene." *Nature* (1985) 255-258, 317(6034).
Yoshida et al., "Studies of the expression of epidermal growth factor receptor in human renal cell carcinoma: a comparison of immunohistochemical method versus ligand binding assay." *Oncology* (1997) 220-225, 54(3).
Yoshida et al., "EGF and TGF-alpha, the ligands of hyperproduced EGFR in human esophageal carcinoma cells, act as autocrine growth factors." *Int. J. Cancer* (1990) 131-135, 45(1).
Yoshimoto et al., "Development of a real-time RT-PCR assay for detecting EGFRvIII in glioblastoma samples." *Clin. Cancer Res.* (2008) 488-493, 14(2).
Yoshitake et al., "Conjugation of Glucose Oxidase from Aspergillus niger and Rabbit Antibodies Using N-Hydroxysuccinimide Ester of N-(4-Carboxycyclohexylmethyl)-Maleimide" *Eur. J. Biochem.* (1979) 395-399, 101(2).
Yu et al., "Co-expression of EGFRvIII with ErbB-2 enhances tumorigenesis: EGFRvIII mediated constitutively activated and sustained signaling pathways, whereas EGF-induced a transient effect on EGFR-mediated signaling pathways." *Cancer biology & therapy* (2008) 1818-1828, 7(11).
Yu et al., "The biosynthetic gene cluster of the maytansinoid antitumor agent ansamitocin from *Actinosynnema pretiosum*." *Proceedings of the National Academy of Sciences of the United States of America* (2002) 7968-7973, 99(12).
Yu et al., "Ligand-independent dimer formation of epidermal growth factor receptor (EGFR) is a step separable from ligand-induced EGFR signaling." *Mol. Biol. Cell* (2002) 2547-2557, 13(7).

Zalutsky, "Growth factor receptors as molecular targets for cancer diagnosis and therapy." *The quarterly journal of nuclear medicine: official publication of the Italian Association of Nuclear Medicine (AIMN) [and] the International Association of Radiopharmacology (IAR)* (1997) 71-77, 41(2).
Zarcone et al., "Epidermal growth factor receptor expression: is it the same in normal and malignant endometria?" *Clinical and experimental obstetrics & gynecology* (1995) 298-300, 22(4).
Zhang et al., "Therapeutic monoclonal antibodies for the ErbB family of receptor tyrosine kinases." *Cancer biology & therapy* (2003) S122-6, 2(4; Suppl. 1).
Zhang et al., "Novel approaches to treatment of advanced colorectal cancer with anti-EGFR monoclonal antibodies." *Annals of medicine* (2006) 545-551, 38(8).
Zhang et al., "An allosteric mechanism for activation of the kinase domain of epidermal growth factor receptor." *Cell* (2006) 1137-1149, 125(6).
Zhen et al., "Characterization of glycosylation sites of the epidermal growth factor receptor." *Biochemistry* (2003) 5478-5492, 42(18).
Zhu et al., "Epidermal growth factor receptor: association of extracellular domain negatively regulates intracellular kinase activation in the absence of ligand." *Growth Factors* (2003) 15-30, 21(1).
Zhu et al., "EGFR tyrosine kinase inhibitor AG1478 inhibits cell proliferation and arrests cell cycle in nasopharyngeal carcinoma cells." *Cancer Letters* (2001) 27-32, 169(1).
Zinner et al., "A phase I clinical and biomarker study of the novel pan-erbB tyrosine kinase inhibitor, CI-1033, in patients with solid tumors." *Clinical Cancer Research* (2001) 3767s (Abstract 566), 7.
U.S. Appl. No. 10/142,653, filed May 10, 2002, Old et al.
U.S. Appl. No. 12/371,576, filed Feb. 14, 2009, Old et al.
U.S. Appl. No. 14/226,430, filed Mar, 26, 2014, Scott et al.
Ang K.K., et al. Epidermal Growth Factor Receptor and Response of Head-and-neck carcinoma to therapy, International Journal of Radiation Oncology, Biology, Physics, 2004 58(3):959-965.
Brown G., et al., "Murine Monoclonal Antibodies" in: Antibodies: A Practical Approach, vol. 1, Catty D., ed., IRL Press, 1988, pp. 81-104.
Decker M.W., et al., ABT-089 [2-Methyl-3-(2-(S)-Pyrrolidinylmethoxy) Pyridine Dihydrochloride]: II. A Novel Cholinergic Channel Modulator with Effects on Cognitive Performance in Rats and Monkeys. The Journal of Pharmacology and Experimental Therapeutics, 1997, 283:247-258.
Hoang T., et al., PD-144 Tumor Response Augmentation with Combination Cetuximab (Erbitux(R)) and Bevacizumab (Avastin(R)). Lung Cancer, 2005, 49, S108 Abstract PD144.
International Preliminary Examination Report for Application No. PCT/US02/15185, mailed on Nov. 3, 2003, 4 pages.
International Preliminary Report on Patentability and Written Opinion for Application No. PCT/US07/19988, mailed on Mar. 17, 2009, 4 pages.
International Preliminary Report on Patentability and Written Opinion for Application No. PCT/US2010/024407, mailed on Aug. 23, 2011, 14 pages.
International Preliminary Report on Patentability for Application No. PCT/US08/03369, mailed on Sep. 15, 2009, 5 pages.
International Preliminary Report on Patentability for Application No. PCT/US2005/005155, mailed on Aug. 22, 2006, 4 pages.
International Preliminary Report on Patentability for Application No. PCT/US2008/01024, mailed on Jul. 28, 2009, 5 pages.
Invitation to Pay Additional Fees for Application No. PCT/US2010/024407 mailed on Jun. 4, 2010, 10 pages.
Ounissi H., et al., Gene Homogeneity for Aminoglycoside-Modifying Enzymes in Gram-PositiveCocc, Antimicrobial Agents and Chemoherapy, 1990, 34(11):2164-2168.
Reck M., et al., Advances in Anti-VEGF and Anti-EGFR Therapy for Advanced Non-small Cell Lung Cancer, Lung Cancer, 2009, 63:1-9.
Sugimura, K., <Japanese Review Article> Human Antibody Engineering, Bio-ventures, (2002) vol. 2(4), p. 30-33.
Surmacz E. Function of the IGF-I Receptor in Breast Cancer. Journal of Mammary Gland Biology and Neoplasia, 2000, 5(1):95-105.
Written Opinion for Application No. PCT/US2010/050559, mailed on May 10, 2011, 14 pages.
Written Opinion for Application No. PCT/US2012/030971, mailed on Jun. 1, 2012, 23 pages.

(56) References Cited

OTHER PUBLICATIONS

Written Opinion for the Application No. PCT/US2008/009771, mailed on Jan. 5, 2009, 7 pages.

Yang Z., et al., The epidermal growth factor receptor tyrosine kinase inhibitor ZD1839 (Iressa) suppresses c-Src and Pak1 pathways and invasiveness of human cancer cells, Clin Can Res. 2004, 10(2):658-667.

Zhu, et al., Inhibition of tumor growth and metastasis by targeting tumor-associated angiogenesis with antagonists to the receptors of vascular endothelial growth factor, Investigational New Drugs, 1999, 17:195-212.

Ben-Bassat, H. et al. "Inhibitors of tyrosine kinases in the treatment of psoriasis" Curr Pharm Des. 2000; Jun.; 6 (9):933-42.

Kargiotis, O. et al. "Mechanisms of angiogenesis in gliomas" J Neurooncol. 2006; Jul.;78(3):281-93.

King, L. E., Jr. et al. "Epidermal growth factor/transforming growth factor alpha receptors and psoriasis" J Invest Dermatol. 1990; Nov. ;95(5):10S-12S.

Naumov, G. N. et al "Combined vascular endothelial growth factor receptor and epidermal growth factor receptor (EGFR) blockade inhibits tumor growth in xenograft models of EGFR inhibitor resistance" Clin Cancer Res. 2009; May 15:15(10):3484-94.

Patel, D. et al. "Activity and binding mechanism of cetuximab (Erbitux (R)) to the type III EGF deletion mutant receptor" Proceedings of the American Association for Cancer Research Annual Meeting. 2006;47:293.

Sakahara et al., "Effect of DTPA conjugation on the antigen binding activity and biodisruption of monoclonal antibodies against α-fetoprotein", J. Nucl. Med., 1985; 26:750-55.

Shalavin I.A. et al. <Russian article> ["Characteristics of expression of the epidermal growth factor receptor and STAT1 protein in urothelial bladder tumors"]. [Bulletin of the Novosibirsk State University, Series: biology, clinical medicine] 2008;6:31-36.

Trivin, F et al. "Complete sustained regression of extensive psoriasis with cetuximab combination chemotherapy" Acta Oncol. 2004;43(6):592-3.

Van Cruijsen H. et al. "Epidermal growth factor receptor and angiogenesis: Opportunities for combined anticancer strategies" Int J Cancer 2006; Dec. 20;117(6):883-8.

Varani, J. et al.—"Human psoriatic skin in organ culture: comparison with normal skin exposed to exogenous growth factors and effects of an antibody to the EGF receptor" Pathobiology 1998;66(6):253-9.

Zorzou, M-P. et al. "Exacerbation of psoriasis after treatment with an EGFR tyrosine kinase inhibitor" Acta Derm Venereol. 2004;84(4):308-36.

Hermanson, G.T. et al. Chapter 10 "Antibody Modification and Conjugation", Bioconjugate Techniques (1996); p. 456.

Rudikoff, S. et al. "Single amino acid substitution altering antigen-binding specificity" Proc Natl Acad Sci U S A. Mar. 1982;79(6):1979-83.

\* cited by examiner

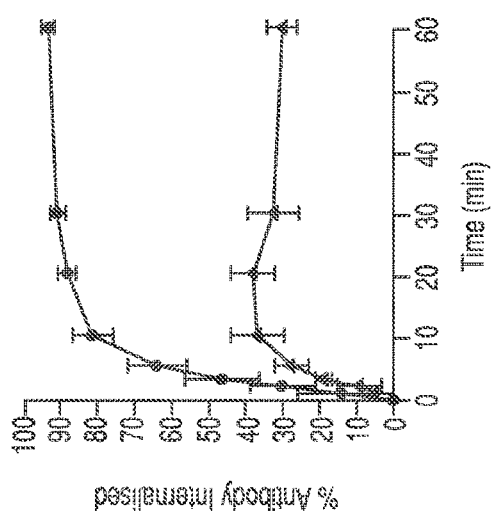

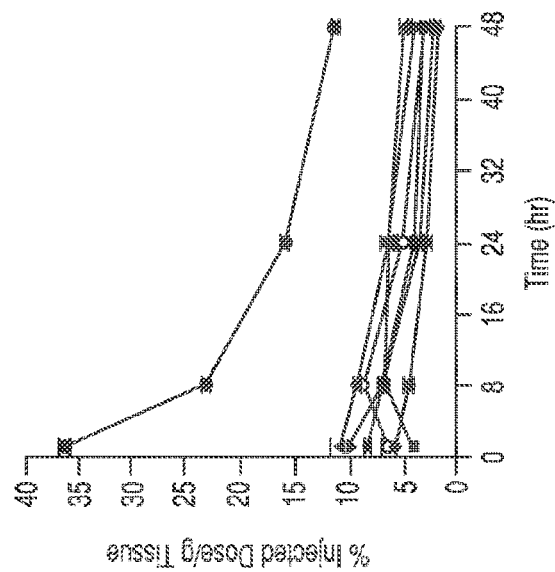
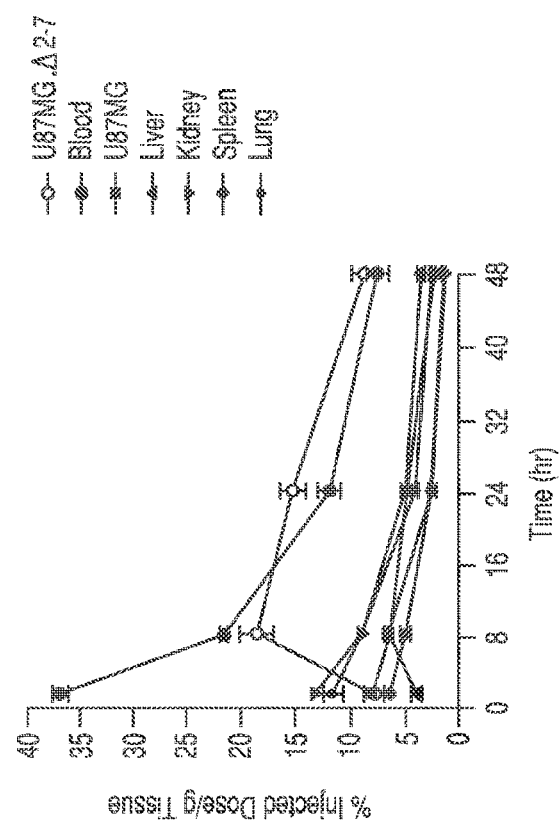
FIG. 4A
FIG. 4B

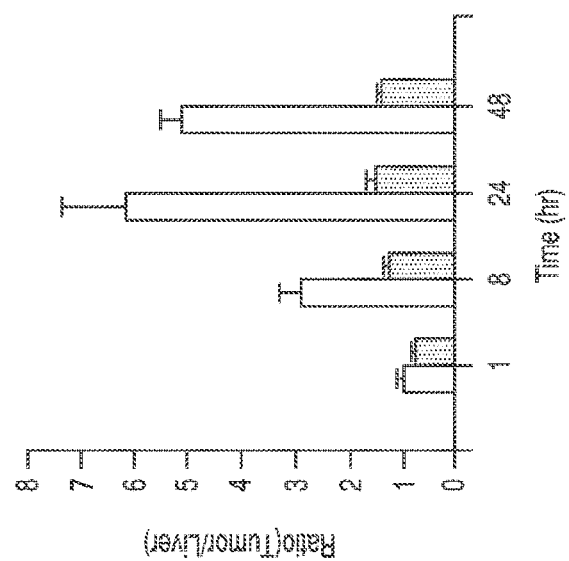
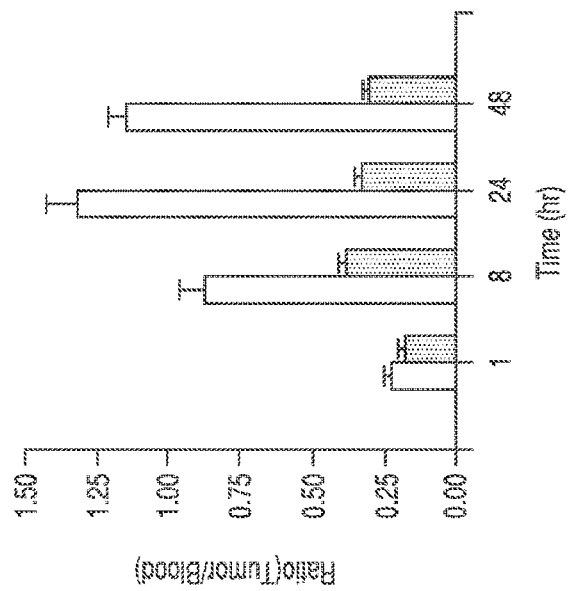
FIG. 5A
FIG. 5B

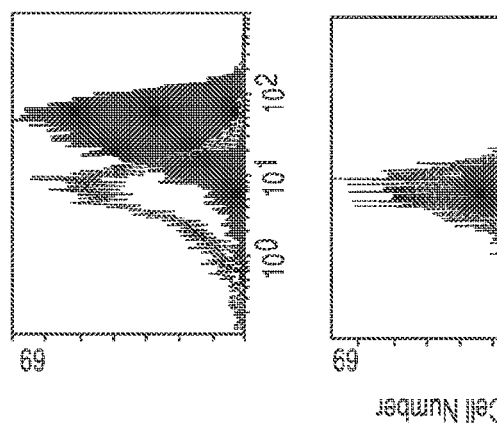
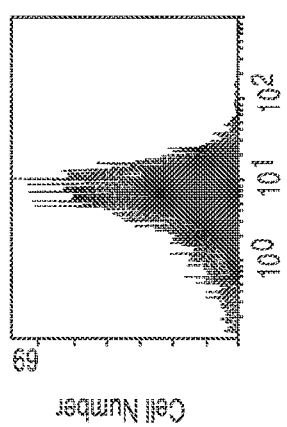
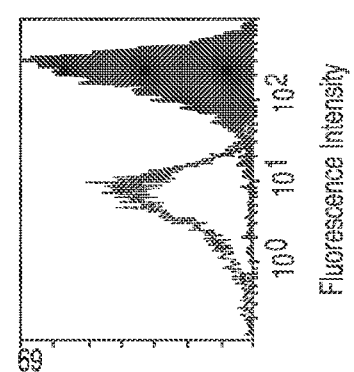
FIG. 6A
FIG. 6B
FIG. 6C

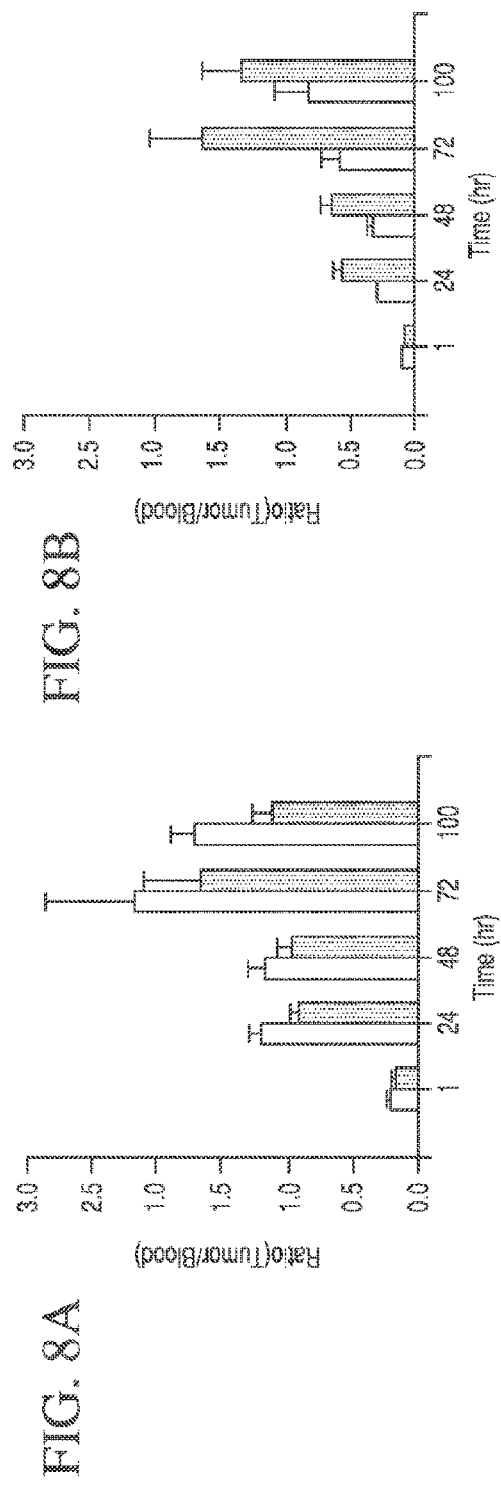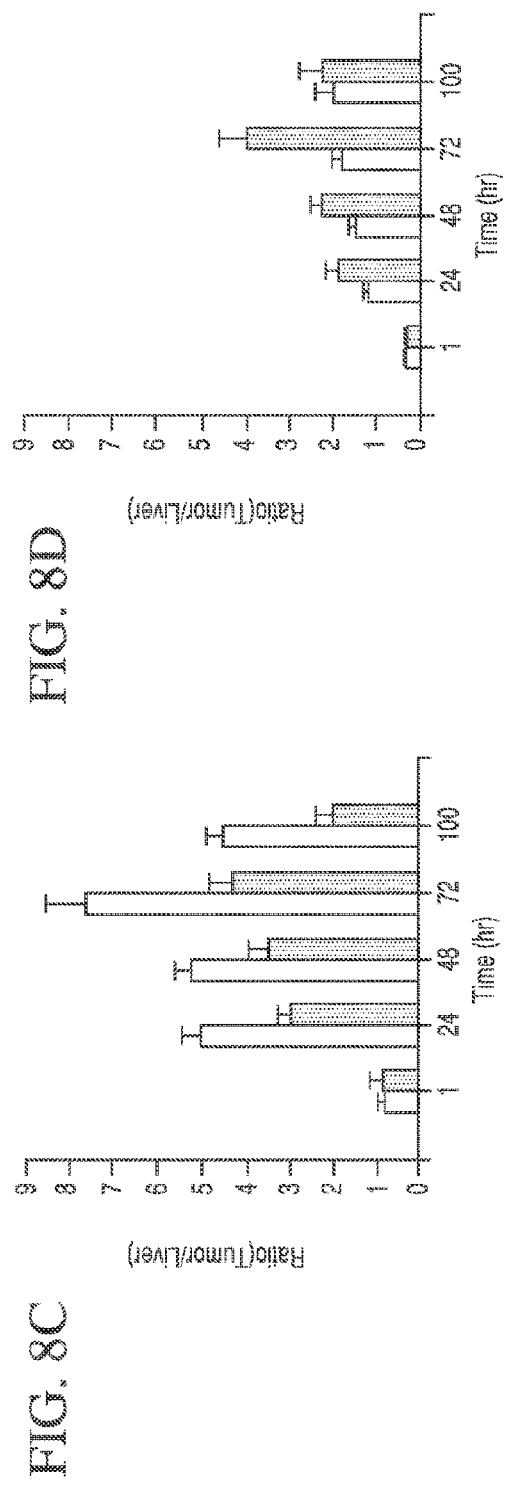

Days Post Inoculation

Days Post Inoculation

Days Post Inoculation mAb806 VH Chain (including signal peptide): Nucleic Acid and Amino Acid Sequences Nucleic Acid ATGAGAGTGCTGATTCTTTTGTGGCTGTTCACAGCCTTTCCTGGTGTCCTGTCTGATG
TGCAGCTTCAGGAGTCGGGACCTAGCCTGGTGAAACCTTCTCAGTCTCTGTCCCTCA
CCTGCACTGTCACTGGCTACTCAATCACCAGTGATTTTGCCTGGAACTGGATCCGGC
AGTTTCCAGGAAACAAGCTGGAGTGGATGGGCTACATAAGTTATAGTGGTAACACT
AGGTACAACCCATCTCTCAAAAGTCGAATCTCTATCACTCGAGACACATCCAAGAAC
CAATTCTTCCTGCAGTTGAATTCTGTGACTATTGAGGACACAGCCACATATTACTGT
GTAACGGCGGGACGCGGGTTTCCTTATTGGGGCCAAGGGACTCTGGTCACTGTCTCT
GCA (SEQ ID NO:1)

FIG.14A

Amino Acid

MRVLILLWLFTAFPGVLSDVQLQESGPSLVKPSQSLSLTCTVTGYSITSDFAWNWIRQFP
*signal peptide*

GNKLEWMGYISYSGNTRYNPSLKSRISITRDTSKNQFFLQLNSVTIEDTATYYCVTAGRG

FPYWGQGTLVTVSA (SEQ ID NO:2)

FIG.14B mAb806 VL Chain (including signal peptide): Nucleic Acid and Amino Acid Sequences Nucleic Acid Sequence ATGGTGTCCACAGCTCAGTTCCTTGCATTCTTGTTGCTTTGGTTTCCAGGTGCAAGAT
GTGACATCCTGATGACCCAATCTCCATCCTCCATGTCTGTATCTCTGGGAGACACAG
TCAGCATCACTTGCCATTCAAGTCAGGACATTAACAGTAATATAGGGTGGTTGCAGC
AGAGACCAGGGAAATCATTTAAGGGCCTGATCTATCATGGAACCAACTTGGACGAT
GAAGTTCCATCAAGGTTCAGTGGCAGTGGATCTGGAGCCGATTATTCTCTCACCATC
AGCAGCCTGGAATCTGAAGATTTTGCAGACTATTACTGTGTACAGTATGCTCAGTTT
CCGTGGACGTTCGGTGGAGGCACCAAGCTGGAAATCAAACGT (SEQ ID NO:3)

FIG.15A

Amino Acid Sequence

<u>MVSTAQFLAFLLLWFPGARC</u>DILMTQSPSSMSVSLGDTVSITCHSSQDINSNIGWLQQRP
   *Signal Peptide*
GKSFKGLIYHGTNLDDEVPSRFSGSGSGADYSLTISSLESEDFADYYCVQYAQFPWTFGG

GTKLEIKR (SEQ ID NO:4)

FIG.15B mAb8H6 H Chain (no signal peptide) Amino Acid Sequence

DVQLQESGPSLVKPSQSLSLTCTVTGYSITSDLAWNWIRQFPGNKLEWMGYISYSGNTRYNPSLKSRISITRDTSKNQFFLQLN
                                           CDR1                              CDR2
SVTTEDTATYYCVLAGIRGFSWGQGTLVTVSA (SEQ ID NO:11)
              CDR3

FIG. 16 mAb806 VL Chain (no signal peptide) Amino Acid Sequence

DILMTQSPSSMSVSLGDTVSITCHSSQDINSNIGWLQQRPGKSFKGLIYHGTNLDDEVPSRFSGSGSGADYSLTISSLESEDFAD
　　　　　　　　　　　　　　CDR1　　　　　　　　　　　　　　CDR2

YYCVQYAQFPWTFGGGTKLEIKR (SEQ ID NO: 12)
　　CDR3

FIG. 17

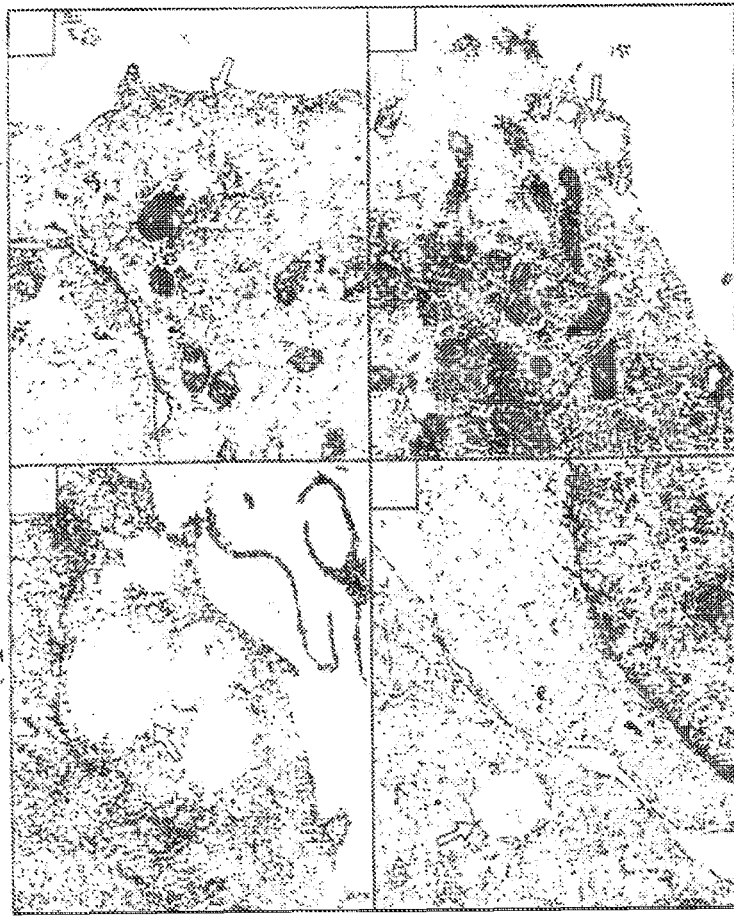

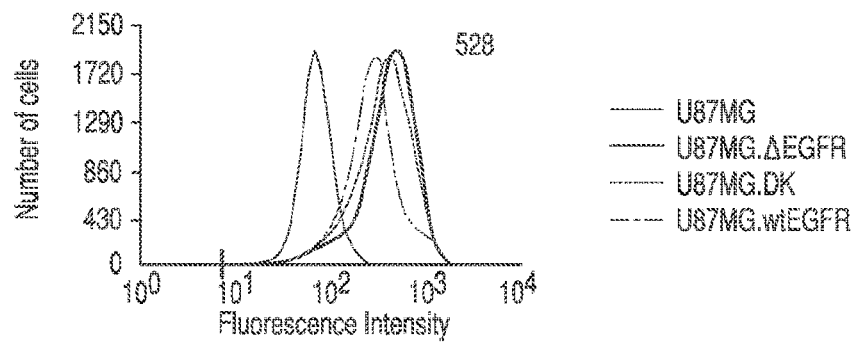
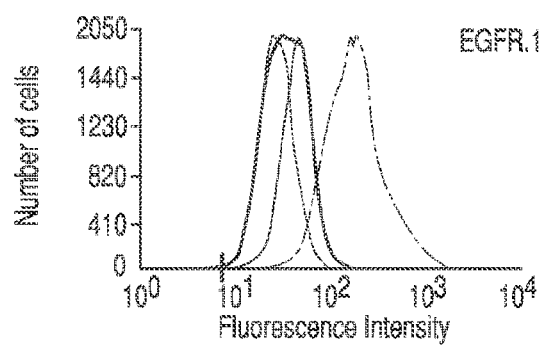
FIG. 26A
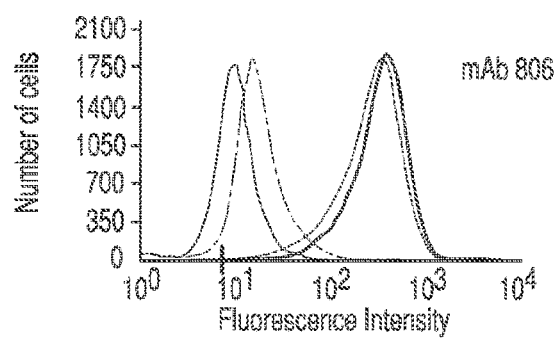
FIG. 26B

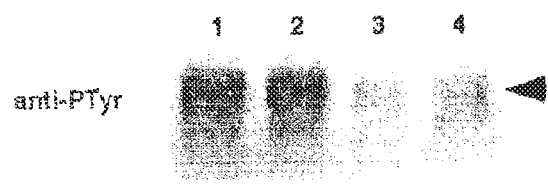
FIG.27A
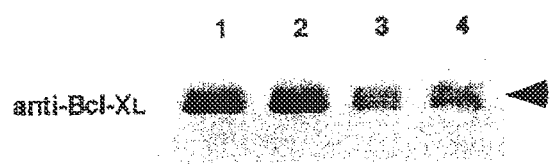
FIG.27B

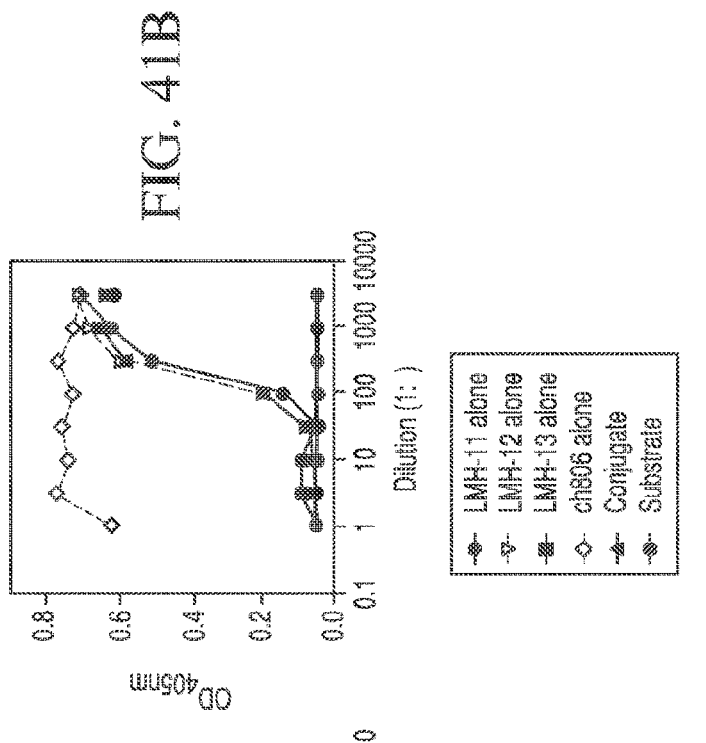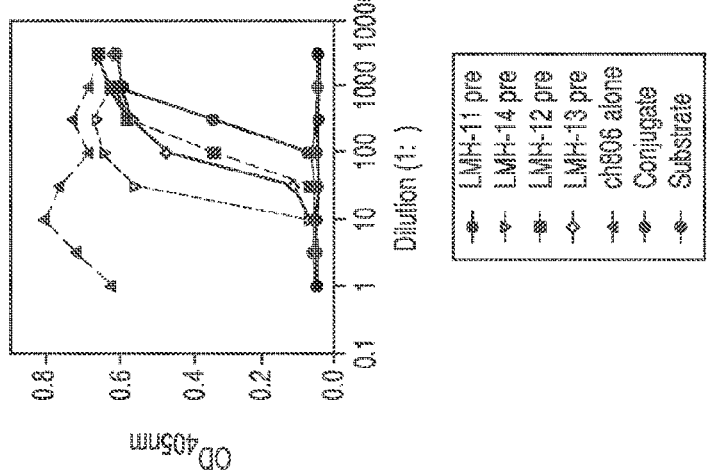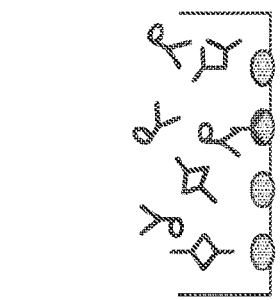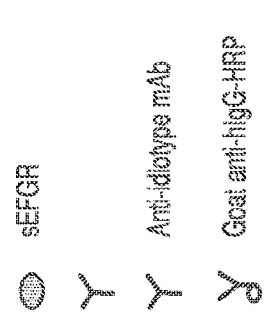
FIG. 41A  FIG. 41B  FIG. 41C

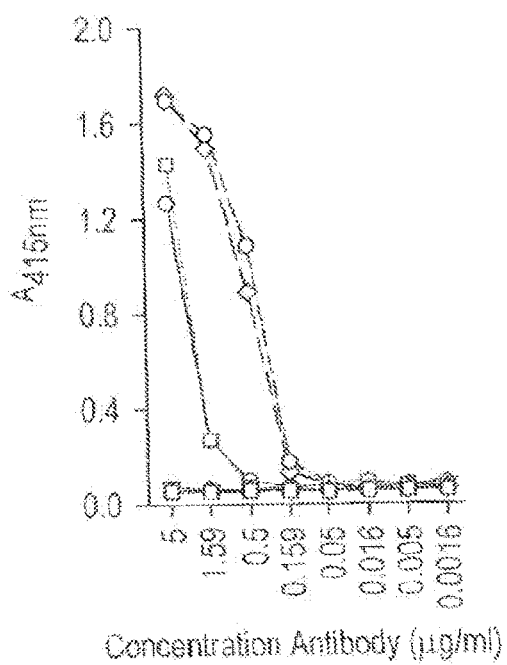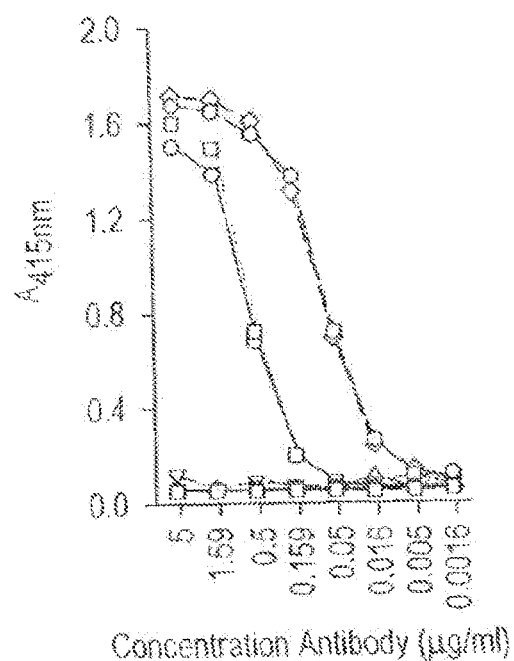

SEQ ID NO:7    pREN ch806 LC Neo Vector

```
          Xho I
   1     CTCGAGAGCGGGCAGTGAGCGCAACGCAATTAATGTGAGTTAGCTCACTC

51     ATTAGGCACCCCAGGCTTTACACTTTATGCTCCCGGCTCGTATGTTGTGT
                                      EcoRI    EF1α promoter
 101     GGAGATTGTGAGCGGATAACAATTTCACACAGAATTCGTGAGGCTCCGGT

151     GCCCGTCAGTGGGCAGAGCGCACATCGCCCACAGTCCCCGAGAAGTTGGG

201     GGGAGGGGTCGGCAATTGAACCGGTGCCTAGAGAAGGTGGCGCGGGGTAA

251     ACTGGGAAAGTGATGTCGTGTACTGGCTCCGCCTTTTTCCCGAGGGTGGG

301     GGAGAACCGTATATAAGTGCAGTAGTCGCCGTGAACGTTCTTTTTCGCAA

351     CGGGTTTGCCGCCAGAACACAGGTAAGTGCCGTGTGTGGTTCCCGCGGGC

403     CTGGCCTCTTTACGGGTTATGGCCCTTGCGTGCCTTGAATTACTTCCACG

451     CCCCTGGCTGCAGTACGTGATTCTTGATCCCGAGCTTCGGGTTGGAAGTG

501     GGTGGGAGAGTTCGAGGCCTTGCGCTTAAGGAGCCCCTTCGCCTCGTGCT

551     TGAGTTGAGGCCTGGCCTGGGCGCTGGGGCCGCCGCGTGCGAATCTGGTG

601     GCACCTTCGCGCCTGTCTCGCTGCTTTCGATAAGTCTCTAGCCATTTAAA

651     ATTTTTGATGACCTGCTGCGACGCTTTTTTTCTGGCAAGATAGTCTTGTA

701     AATGCGGGCCAAGATCTGCACACTGGTATTTCGGTTTTTGGGGCCGCGGG

751     CGGCGACGGGGCCCGTGCGTCCCAGCGCACATGTTCGGCGAGGCGGGGCC

801     TGCGAGCGCGGCCACCGAGAATCGGACGGGGGTAGTCTCAAGCTGGCCGG

851     CCTGCTCTGGTGCCTGGCCTCGCGCCGCCGTGTATCGCCCCGCCTGGGC

901     GGCAAGGCTGGCCCGGTCGGCACCAGTTGCGTGAGCGGAAAGATGGCCGC

951     TTCCCGGCCCTGCTGCAGGGAGCTCAAAATGGAGGACGCGGCGCTCGGGA

1001     GAGCGGCGGGTGAGTCACCCACACAAAGGAAAAGGGCCTTTCCGTCCTC
```

FIG. 49A

```
1051   AGCCGTCGCTTCATGTGACTCCACGGAGTACCGGGCGCCGTCCAGGCACC

1101   TCGATTAGTTCTCGAGCTTTTGGAGTACGTCGTCTTTAGGTTGGGGGGAG

1151   GGGTTTTATGCGATGGAGTTTCCCCACACTGAGTGGGTGGAGACTGAAGT

1201   TAGGCCAGCTTGGCACTTGATGTAATTCTCCTTGGAATTTGCCCTTTTTG

1251   AGTTTGGATCTTGGTTCATTCTCAAGCCTCAGACAGTGGTTCAAAGTTTT
                                 MluI        HindIII   PmeI
1301   TTTCTTCCATTTCAGGTGTACGCGTCTCGGGAAGCTTTAGTTTAAACGCC 1351   GCCACCATGGTGTCCACAGCTCAGTTCCTTGCATTCTTGTTGCTTTGGTTT
              M  V  S  T  A  Q  F  L  A  F  L  L  L  W  F 1401   CCAGGTGCAAGATGTGACATCCTGATGACCCAATCTCCATCCTCCATGTCT
        P  G  A  R  C  D  I  L  M  T  Q  S  P  S  S  M  S 1451   GTATCTCTGGGAGACACAGTCAGCATCACTTGCCATTCAAGTCAGGACATT
        V  S  L  G  D  T  V  S  I  T  C  H  S  S  Q  D  I 1501   AACAGTAATATAGGGTGGTTGCAGCAGAGACCAGGGAAATCATTTAAGGGC
        N  S  N  I  G  W  L  Q  Q  R  P  G  K  S  F  K  G 1551   CTGATCTATCATGGAACCAACTTGGACGATGAAGTTCCATCAAGGTTCAGT
        L  I  Y  H  G  T  N  L  D  D  E  V  P  S  R  F  S 1601   GGCAGTGGATCTGGAGCCGATTATTCTCTCACCATCAGCAGCCTGGAATCT
        G  S  G  S  G  A  D  Y  S  L  T  I  S  S  L  E  S 1651   GAAGATTTTGCAGACTATTACTGTGTACAGCATGCTCAGTTTCCGTGGACG
        E  D  F  A  D  Y  Y  C  V  Q  H  A  Q  F  P  W  T
                                                    BamHI
1701   TTCGGTGGAGGCACCAAGCTGGAAATCAAACGGGTGAGTGGATCCATCTGGG
        F  G  G  G  T  K  L  E  I  K  R

1751   ATAAGCATGCTGTTTTCTGTCTGTCCCTAACATGCCCTGTGATTATGCGCAAA

1801   CAACACACCCAAGGGCAGAACTTTGTTACTTAAACACCATCCTGTTTGCTTCTT

1851   TCCTCAGGAACTGTGGCTGCACCA
              T  V  A  A  P

1876   TCTGTCTTCATCTTCCCGCCATCTGATGAGCAGTTGAAATCTGGAACTGC
        S  V  F  I  F  P  P  S  D  E  Q  L  K  S  G  T  A

1926   CTCTGTTGTGTGCCTGCTGAATAACTTCTATCCCAGAGAGGCCAAAGTAC
```

FIG. 49B

```
              S   V   V   C   L   L   N   N   F   Y   P   R   E   A   K   V   Q
1976 AGTGGAAGGTGGATAACGCCCTCCAATCGGGTAACTCCCAGGAGAGTGTC
         W   K   V   D   N   A   L   Q   S   G   N   S   Q   E   S   V
2026 ACAGAGCAGGACAGCAAGGACAGCACCTACAGCCTCAGCAGCACCCTGAC
         T   E   Q   D   S   K   D   S   T   Y   S   L   S   S   T   L   T
2076 GCTGAGCAAAGCAGACTACGAGAAACACAAAGTCTACGCCTGCGAAGTCA
         L   S   K   A   D   Y   E   K   H   K   V   Y   A   C   E   V   T
2126 CCCATCAGGGCCTGAGCTCGCCCGTCACAAAGAGCTTCAACAGGGGAGAG
         H   Q   G   L   S   S   P   V   T   K   S   F   N   R   G   E
              Nhe/Xba
2176 TGTTGAGCTAGAACTAACTAACTAAGCTAGCAACGGTTTCCCTCTAGCGG
         C   *
2226 GATCAATTCCGCCCCCCCCCCTAACGTTACTGGCCGAAGCCGCTTGGAA
2276 TAAGGCCGGTCTGCGTTTGTCTATATGTTATTTTCCACCATATTGCCGTC
2326 TTTTGGCAATGTGAGGGCCCGGAAACCTGGCCCTGTCTTCTTGACGAGCA

2376 TTCCTAGGGGTCTTTCCCCTCTCGCCAAAGGAATGCAAGGTCTGTTGAAT
2426 GTCGTGAAGGAAGCAGTTCCTCTGGAAGCTTCTTGAAGACAAACAACGTC
2476 TGTAGCGACCCTTTGCAGGCAGCGGAACCCCCCACCTGGCGACAGGTGCC
2526 TCTGCGGCCAAAAGCCACGTGTATAAGATACACCTGCAAAGGCGGCACAA
2576 CCCCAGTGCCACGTTGTGAGTTGGATAGTTGTGGAAAGAGTCAAATGGCT
2626 CTCCTCAAGCGTATTCAACAAGGGCTGAAGGATGCCCAGAAGGTACCCC
2676 ATTGTATGGGATCTGATCTGGGGCCTCGGTGCACATGCTTTACGTGTGTT
2751    TAGTCGAGGTTAAAAAACGTCTAGGCCCCCCGAACCACGGGGACGTGGTT
2801    TTCCTTTGAAAAACACGATAATACCATGGTTGAACAAGATGGATTGCACG
2851    CAGGTTCTCCGGCCGCTTGGGTGGAGAGGCTATTCGGCTATGACTGGGCA
2901    CAACAGACAATCGGCTGCTCTGATGCCGCCGTGTTCCGGCTGTCAGCGCA
2951    GGGGCGCCCGGTTCTTTTTGTCAAGACCGACCTGTCCGGTGCCCTGAATG
```

FIG. 49C

```
3001  AACTGCAGGACGAGGCAGCGCGGCTATCGTGGCTGGCCACGACGGGCGTT
3051  CCTTGCGCAGCTGTGCTCGACGTTGTCACTGAAGCGGGAAGGGACTGGCT
3101  GCTATTGGGCGAAGTGCCGGGGCAGGATCTCCTGTCATCTCACCTTGCTC
3151  CTGCCGAGAAAGTATCCATCATGGCTGATGCAATGCGGCGGCTGCATACG
3201  CTTGATCCGGCTACCTGCCCATTCGACCACCAAGCGAAACATCGCATCGA
3251  GCGAGCACGTACTCGGATGGAAGCCGGTCTTGTCGATCAGGATGATCTGG
3301  ACGAAGAGCATCAGGGGCTCGCGCCAGCCGAACTGTTCGCCAGGCTCAAG
3351  GCGCGCATGCCCGACGGCGAGGATCTCGTCGTGACCCATGGCGATGCCTG
3401  CTTGCCGAATATCATGGTGGAAAATGGCCGCTTTTCTGGATTCATCGACT
3451  GTGGCCGGCTGGGTGTGGCGGACCGCTATCAGGACATAGCGTTGGCTACC
3501  CGTGATATTGCTGAAGAGCTTGGCGGCGAATGGGCTGACCGCTTCCTCGT
3551  GCTTTACGGTATCGCCGCTCCCGATTCGCAGCGCATCGCCTTCTATCGCC
                              blunt end SalI/SalI
3601  TTCTTGACGAGTTCTTCTGAGTCGATCGACCTGGCGTAATAGCGAAGAGG
3651  CCCGCACCGATCGCCCTTCCCAACAGTTGCGCAGCCTGAATGGCGAATGG
3701  GACGCGCCCTGTAGCGGCGCATTAAGCGCGGCGGGTGTGGTGGTTACGCG
3751  CAGCGTGACCGCTACACTTGCCAGCGCCCTAGCGCCCGCTCCTTTCGCTT
3801  TCTTCCCTTCCTTTCTCGCCACGTTCGCCGGCTTTCCCCGTCAAGCTCTA
3851  AATCGGGGGCTCCCTTTAGGGTTCCGATTTAGTGCTTTACGGCACCTCGA
3901  CCCCAAAAAACTTGATTAGGGTGATGGTTCACGTAGTGGGCCATCGCCCT
3951  GATAGACGGTTTTTCGCCCTTTGACGTTGGAGTCCACGTTCTTTAATAGTG
4001  GACTCTTGTTCCAAACTGGAACAACACTCAACCCTATCTCGGTCTATTTA
4051  TAAGGGATTTTGCCGATTTCGGCCTATTGGTTAAAAAATGAGCTGATTTA
4101  ACAAAATTTAACGCGAATTTTAACAAAATATTAACGCTTACAATTTAGGT
4151  GGCACTTTTCGGGGAAATGTGCGCGGAACCCCTATATTTGTTTATTTTTC
```

FIG. 49D

```
4201  TAAATACATTCAAATATGTATCCGCTCATGAGACAATAACCCTGATAAAT
4251  GCTTCAATAATATTGAAAAGGAAGAGTATGAGTATTCAACATTTCCGTG
4301  TCGCCCTTATTCCCTTTTTTGCGGCATTTTGCCTTACTGTTTTTGCTCAC
4351  CCAGAAACGCTGGTGAAAGTAAAAGATGCTGAAGATCAGTTGGGTGCACG
4401  AGTGGGTTACATCGAACTGGATCTCAACAGCGGTAAGATCCTTGAGAGTT
4451  TTCGCCCCGAAGAACGTTTTCCAATGATGAGCACTTTTAAAGTTCTGCTA
4501  TGTGGCGCGGTATTATCCCGTATTGACGCCGGGCAAGAGCAACTCGGTCG
4551  CCGCATACACTATTCTCAGAATGACTTGGTTGAGTACTCACCAGTCACAG
4601  AAAAGCATATTACGGATGGCATGACAGTAAGAGAATTATGCAGTGCTGCC
4651  ATAACCATGAGTGATAACACTGCGGCCAACTTACTTCTGACAACGATCGG
4701  AGGACCGAAGGAGCTAACCGCTTTTTTGCACAACATGGGGGATCATGTAA
4751  CTCGCCTTGATCGTTGGGAACCGGAGCTGAATGAAGCCATACCAAACGAC
4801  GAGCGTGACACCACGATGCCTGTAGCAATGGCAACAACGTTGCGCAAACT
4851  ATTAACTGGCGAACTACTTACTCTAGCTTCCCGGCAACAATTAATAGACT
4901  GGATGGAGGCGGATAAAGTTGCAGGACCACTTCTGCGCTCGGCCCTTCCG
4951  GCTGGCTGGTTTATTGCTGATAAATCTGGAGCCGGTGAGCGTGGGTCTCG
5001  CGGTATCATTGCAGCACTGGGGCCAGATGGTAAGCCCTCCCGTATCGTAG
5051  TTATCTACACGACGGGGAGTCAGGCAACTATGGATGAACGAAATAGACAG
5101  ATCGCTGAGATAGGTGCCTCACTGATTAAGCATTGGTAACTGTCAGACCA
5151  AGTTTACTCATATATACTTTAGATTGATTTAAAACTTCATTTTTAATTTA
5201  AAAGGATCTAGGTGAAGATCCTTTTTGATAATCTCATGACCAAAATCCCT
5251  TAACGTGAGTTTTCGTTCCACTGAGCGTCAGACCCCGTAGAAAAGATCAA
5301  AGGATGTTCTTGAGATCCTTTTTTTCTGCACGTAATCTGCTGCTTGCAAA
```

FIG. 49E

5351 CAAAAAACCACCGCTACCAGCGGTGGTTTGTTTGCCGGATCAAGAGCTAC

5401 CAACTCTTTTTCCGAAGGTAACTGGCTTCAGCAGAGCGCAGATACCAAAT

5451 ACTGTCCTTCTAGTGTAGCCGTAGTTAGGCCACCACTTCAAGAACTCTGT

5501 AGCACCGCCTACATACCTCGCTCTGCTAATCCTGTTACCAGTGGCTGCTG

5551 CCAGTGGCGATAAGTCGTGTCTTACCGGGTTGGACTCAAGACGATAGTTA

5601 CCGGATAAGGCGCAGCGGTCGGGCTGAACGGGGGGTTCGTGCACACAGCC

5651 CAGCTTGGAGCGAACGACCTACACCGAACTGAGATACCTACAGCGTGAGC

5701 TATGAGAAAGCGCCACGCTTCCCGAAGGGAGAAAGGCGGACAGTATCCG

5751 GTAAGCGGCAGGGTCGGAACAGGAGAGCGCACGAGGGAGCTTCCAGGGGG

5801 AAACGCCTGGTATCTTTATAGTCCTGTCGGGTTTCGCCACCTCTGACTTG

5851 AGCGTCCATTTTGTGATGCTCGTCAGGGGGCGGAGCCTATGGAAAAAC

5901 GCCAGCAACGCGGCCTTTTTACGGTTCCTGGCCTTTTGCTGGCCTTTTGC

5951 TCACATGTTCTTTCCTGCGTTATCCCCTGATTCTGTGGATAACCGTATTA

6001 CCGCCTTTGAGTGAGCTGATACCGCTCGCCGCAGCCGAACGACCGAGCGC

6051 AGCGAGTCAGTGAGCGAGGAAGCGGAAGAGCGCCCAATACGCAAACCGCC

6101 TCTCCCCGCGCGTTGGCCGATTCATTAATGCAGGTATCACGAGGCCCTTT

6151 CGTCTTCAC

FIG. 49F

SEQ ID NO:8        pREN 806 HC DHFR Vector

```
         Xho I
         CTCGAGAGCGGGCAGTGAGCGCAACGCAATTAATGTGAGTTAGCTCACTC
  2      ATTAGGCACCCCAGGCTTTACACTTTATGCTTCCGGCTCGTATGTTGTGT
                                         EcoRI   EF1α  promoter
 02      GGAGATTGTGAGCGGATAACAATTTCACACAGAATTCGTGAGGCTCCGGT
 52      GCCCGTCAGTGGGCAGAGCGCACATCGCCCACAGTCCCCGAGAAGTTGGG
 02      GGGAGGGGTCGGCAATTGAACCGGTGCCTAGAGAAGGTGGCGCGGGGTAA
 52      ACTGGGAAAGTGATGTCGTGTACTGGCTCCGCCTTTTTCCCGAGGGTGGG
 02      GGAGAACCGTATATAAGTGCAGTAGTCGCCGTGAACGTTCTTTTTCGCAA
 52      CGGGTTTGCCGCCAGAACACAGGTAAGTGCCGTGTGTGGTTCCCGCGGGC
 02      CTGGCCTCTTTACGGGTTATGGCCCTTGCGTGCCTTGAATTACTTCCACG
 52      CCCCTGGCTGCAGTACGTGATTCTTGATCCCGAGCTTCGGGTTGGAAGTG
 02      GGTGGGAGAGTTCGAGGCCTTGCGCTTAAGGAGCCCCTTCGCCTCGTGCT
 52      TGAGTTGAGGCCTGGCCTGGGCGCTGGGGCCGCCGCGTGCGAATCTGGTG
 02      GCACCTTCGCGCCTGTCTCGCTGCTTTCGATAAGTCTCTAGCCATTTAAA
 52      ATTTTTGATGACCTGCTGCGACGCTTTTTTTCTGGCAAGATAGTCTTGTA
 02      AATGCGGGCCAAGATCTGCACACTGGTATTTCGGTTTTTGGGGCCGCGGG
 52      CGGCGACGGGGCCCGTGCGTCCCAGCGCACATGTTCGGCGAGGCGGGGCC
 02      TGCGAGCGCGGCCACCGAGAATCGGACGGGGGTAGTCTCAAGCTGGCCGG
 52      CCTGCTCTGGTGCCTGGCCTCGCGCCGCCGTGTATCGCCCCGCCCTGGGC
 02      GGCAAGGCTGGCCCGGTCGGCACCAGTTGCGTGAGCGGAAAGATGGCCGC
 52      TTCCCGGCCCTGCTGCAGGGAGCTCAAAATGGAGGACGCGGCGCTCGGGA
002      GAGCGGGCGGGTGAGTCACCCACACAAAGGAAAAGGGCCTTTCCGTCCTC
```

FIG. 50A

```
1052  AGCCGTCGCTTCATGTGACTCCACGGAGTACCGGGCGCCGTCCAGGCACC

1102  TCGATTAGTTCTCGAGCTTTTGGAGTACGTCGTCTTTAGGTTGGGGGGAG

1152  GGGTTTTATGCGATGGAGTTTCCCCACACTGAGTGGGTGGAGACTGAAGT

1202  TAGGCCAGCTTGGCACTTGATGTAATTCTCCTTGGAATTTGCCCTTTTTG

1251  AGTTTGGATCTTGGTTCATTCTCAAGCCTCAGACAGTGGTTCAAAGTTTT
                          MluI        HindIII    PmeI
1302  TTTCTTCCATTTCAGGTGTACGCGTCTCGGAAGCTTTAGTTTAAACGCC 1352  GCCACCATGAGAGTGCTGATTCTTTTGTGGCTGTTCACAGCCTTTCCTGGT
              M  R  V  L  I  L  L  W  L  F  T  A  F  P  G 1401  GTCCTGTCTGATGTGCAGCTTCAGGAGTCGGGACCTAGCCTGGTGAAACCT
       V  L  S  D  V  Q  L  Q  E  S  G  P  S  L  V  K  P 1451  TCTCAGACTCTGTCCCTCACCTGCACTGTCACTGGCTACTCAATCACCAGT
       S  Q  T  L  S  L  T  C  T  V  T  G  Y  S  I  T  S 1501  GATTTTGCCTGGAACTGGATCCGGCAGTTTCCAGGAAACAAGCTGGAGTGG
       D  F  A  W  N  W  I  R  Q  F  P  G  N  K  L  E  W 1551  ATGGGCTACATAAGTTATAGTGGTAACACTAGGTACAACCCATCTCTCAAA
       M  G  Y  I  S  Y  S  G  N  T  R  Y  N  P  S  L  K 1601  AGTCGAATCTCTATCACTCGAGACACATCCAAGAACCAATTCTTCCTGCAG
       S  R  I  S  I  T  R  D  T  S  K  N  Q  F  F  L  Q 1651  TTGAATTCTGTGACTATTGAGGACACAGCCACATATTACTGTGTAACGGCG
       L  N  S  V  T  I  E  D  T  A  T  Y  Y  C  V  T  A 1701  GGACGCGGGTTTCCTTATTGGGGCCAAGGGACTCTGGTCACTGTCTCTGCA
       G  R  G  F  P  Y  W  G  Q  G  T  L  V  T  V  S  A
                                BamHI
1751  CAGTGAGTGGATCCTCTGCGCCTGGGCCCAGCTCTGTC 1801  CCACACCGCGGTCACATGGCACCACCTCTCTTGCAGCCTCCACCAAGGGC
                                                S  T  K  G
1851  CCATCGGTCTTCCCCCTGGCACCCTCCTCCAAGAGCACCTCTGGGGGCAC
      p  s  v  f  p  l  a  p  s  s  k  s  t  s  g  g  t
```

FIG. 50B

1901 AGCGGCCCTGGGCTGCCTGGTCAAGGACTACTTCCCCGAACCGGTGACGG
     A   A   L   G   C   L   V   K   D   Y   F   P   E   P   V   T   V

1951 TGTCGTGGAACTCAGGCGCCCTGACCAGCGGCGTGCACACCTTCCCGGCT
     S   W   N   S   G   A   L   T   S   G   V   H   T   F   P   A

2001 GTCCTACAGTCCTCAGGACTCTACTCCCTCAGCAGCGTGGTGACCGTGCC
     V   L   Q   S   S   G   L   Y   S   L   S   S   V   V   T   V   P

2051 CTCCAGCAGCTTGGGCACCCAGACCTACATCTGCAACGTGAATCACAAGC
     S   S   S   L   G   T   Q   T   Y   I   C   N   V   N   H   K   P

2101 CCAGCAACACCAAGGTGGACAAGAAAGTTGAGCCCAAATCTTGTGACAAA
     S   N   T   K   V   D   K   K   V   E   P   K   S   C   D   K

2151 ACTCACACATGCCCACCGTGCCCAGCACCTGAACTCCTGGGGGGACCGTC
     T   H   T   C   P   P   C   P   A   P   E   L   L   G   G   P   S

2201 AGTCTTCCTCTTCCCCCCAAAACCCAAGGACACCCTCATGATCTCCCGGA
     V   F   L   F   P   P   K   P   K   D   T   L   M   I   S   R   T

2251 CCCCTGAGGTCACATGCGTGGTGGTGGACGTGAGCCACGAAGACCCTGAG
     P   E   V   T   C   V   V   V   D   V   S   H   E   D   P   E

2301 GTCAAGTTCAACTGGTACGTGGACGGCGTGGAGGTGCATAACGCCAAGAC
     V   K   F   N   W   Y   V   D   G   V   E   V   H   N   A   K   T

2351 AAAGCCGCGGGAGGAGCAGTACAACAGCACGTACCGGGTGGTCAGCGTCC
     K   P   R   E   E   Q   Y   N   S   T   Y   R   V   V   S   V   L

2401 TCACCGTCCTGCACCAGGACTGGCTGAATGGCAAGGAGTACAAGTGCAAG
     T   V   L   H   Q   D   W   L   N   G   K   E   Y   K   C   K

2451 GTCTCCAACAAAGCCCTCCCAGCCCCCATCGAGAAAACCATCTCCAAAGC
     V   S   N   K   A   L   P   A   P   I   E   K   T   I   S   K   A

2501 CAAAGGGCAGCCCCGAGAACCACAGGTGTACACCCTGCCCCCATCCCGGG
     K   G   Q   P   R   E   P   Q   V   Y   T   L   P   P   S   R   E

2551 AGGAGATGACCAAGAACCAGGTCAGCCTGACCTGCCTGGTCAAAGGCTTC
     E   M   T   K   N   Q   V   S   L   T   C   L   V   K   G   F

2601 TATCCCAGCGACATCGCCGTGGAGTGGGAGAGCAATGGGCAGCCGGAGAA
     Y   P   S   D   I   A   V   E   W   E   S   N   G   Q   P   E   N

2651 CAACTACAAGACCACGCCTCCCGTGCTGGACTCCGACGGCTCCTTCTTCC

FIG. 50C

```
              N  Y  K  T  T  P  P  V  L  D  S  D  G  S  F  F  L
2701  TCTACAGCAAGCTCACCGTGGACAAGAGCAGGTGGCAGCAGGGGAACGTC
         Y  S  K  L  T  V  D  K  S  R  W  Q  Q  G  N  V
2751  TTCTCATGCTCCGTGATGCATGAGGCTCTGCACAACCACTACACGCAGAA
        F  S  C  S  V  M  H  E  A  L  H  N  H  Y  T  Q  K
                                                          Nhe/Xba
2801  GAGCCTCTCCCTGTCTCCGGGTAAATGAGCTAGAAACTAACTAAGCTAGC
        S  L  S  L  S  P  G  K  *
2851  AACGGTTTCCCTCTAGCGGGATCAATTCCGCCCCCCCCCCTAACGTTAC

2901  TGGCCGAAGCCGCTTGGAATAAGGCCGGTGTGCGTTTGTCTATATGTTAT

2951  TTTCCACCATATTGCCGTCTTTTGGCAATGTGAGGGCCCGGAAACCTGGC

3001  CCTGTCTTCTTGACGAGCATTCCTAGGGGTCTTTCCCTCTCGCCAAAGG

3051  AATGCAAGGTCTGTTGAATGTCGTGAAGGAAGCAGTTCCTCTGGAAGCTT

3101  CTTGAAGACAAACAACGTCTGTAGCGACCCTTTGCAGGCAGCGGAACCCC

3151  CCACCTGGCGACAGGTGCCTCTGCGGCCAAAAGCCACGTGTATAAGATAC

3201  ACCTGCAAAGGCGGCACAACCCCAGTGCCACGTTGTGAGTTGGATAGTTG

3251  TGGAAAGAGTCAAATGGCTCTCCTCAAGCGTATTCAACAAGGGGCTGAAG

3301  GATGCCCAGAAGGTACCCCATTGTATGGGATCTGATCTGGGGCCTCGGTG

3351  CACATGCTTTACGTGTGTTTAGTCGAGGTTAAAAAACGTCTAGGCCCCCC

3401  GAACCACGGGGACGTGGTTTTCCTTTGAAAAACACGATAATACCATGGTT

3451  CGACCATTGAACTGCATCGTCGCCGTGTCCCAAAATATGGGATTGGCAA

3501  GAACGGAGACCTACCCTGGCCTCCGCTCAGGAACCAGTTCAAGTACTTCC

3551  AAAGAATGACCACAACCTCTTCAGTGGAAGGTAAACAGAATCTGGTGATT

3601  ATGGGTAGGAAAACCTGGTTCTCCATTCCTGAGAAGAATCGACCTTTAAA

3651  GGACAGAATTAATGGTTCGATATAGTTCTCAGTAGAGAACTCAAAGAACC

3701  ACCACGAGGAGCTCATTTTCTTGCCAAAAGTTTGGATGATGCCTTAAGAC

3751  TTATTGAACAACCGGAATTGGCAAGTAAAGTAGACATGGTTTGGATAGTC
```

FIG. 50D

```
3801  GGAGGCAGTTCTGTTTACCAGGAAGCCATGAATCAACCAGGCCACCTCAG

3851  ACTCTTTGTGACAAGGATCATGCAGGAATTTGAAAGTGACACGTTTTTCC

3901  CAGAAATTGATTTGGGGAAATATAAACTTCTCCCAGAATACCCAGGCGTC

3951  CTCTCTGAGGTCCAGGAGGAAAAGGCATCAAGTATAAGTTTGAAGTCTA

4001  CGAGAAGAAAGACTAACAGGAAGATGCTTTCAAGTTCTCTGCTCCCTCC
                                                 Blunt end
SalI/SalI
4051  TAAAGCTATGCATTTTTATAAGACCATGGGACTTTTGCTGGTCGATCGAC

4101  CTGGCGTAATAGCGAAGAGGCCCGCACCGATCGCCCTTCCCAACAGTTGC

4151  GCAGCCTGAATGGCGAATGGGACGCGCCCTGTAGCGGCGCATTAAGCGCG

4201  GCGGGTGTGGTGGTTACGCGCAGCGTGACCGCTACACTTGCCAGCGCCCT

4251  AGCGCCCGCTCCTTTCGCTTTCTTCCCTTCCTTTCTCGCCACGTTCGCCG

4301  GCTTTCCCCGTCAAGCTCTAAATCGGGGGCTCCCTTTAGGGTTCCGATTT

4351  AGTGCTTTACGGCACCTCGACCCCAAAAAACTTGATTAGGGTGATGGTTC

4401  ACGTAGTGGGCCATCGCCCTGATAGACGGTTTTTCGCCTTTGACGTTGGA

4451  GTCCACGTTCTTTAATAGTGGACTCTTGTTCCAAACTGGAACAACACTCA

4501  ACCCTATCTCGGTCTATTTATAAGGGATTTTGCCGATTTCGGCCTATTGG

4551  TTAAAAAATGAGCTGATTTAACAAAATTTAACGCGAATTTTAACAAAATA

4601  TTAACGCTTACAATTTAGGTGGCACTTTTCGGGGAAATGTGCGCGGAACC

4651  CCTATTTGTTTATTTTTCTAAATACATTCAAATATGTATCCGCTCATG

4701  AGACAATAACCCTGATAAATGCTTCAATAATATTGAAAAAGGAAGAGTAT

4751  GAGTATTCAACATTTCCGTGTCGCCCTTATTCCCTTTTTTGCGGCATTTT

4801  GCCTTACTGTTTTTGCTCACCCAGAAACGCTGGTGAAAGTAAAAGATGCT

4851  GAAGATCAGTTGGGTGCACGAGTGGGTTACATCGAACTGGATCTCAACAG

4901  CGGTAAGATCCTTGAGAGTTTTCGCCCCGAAGAACGTTTTCCAATGATGA
```

FIG. 50E

```
4951  GCACTTTTAAAGTTCTGCTATGTGGCGCGGTATTATCCCGTATTGACGCC
5001  GGGCAAGAGCAACTCGGTCGCCGCATACACTATTCTCAGAATGACTTGGT
5051  TGAGTACTCACCAGTCACAGAAAAGCATATTACGGATGGCATGACAGTAA
5101  GAGAATTATGCAGTGCTGCCATAACCATGAGTGATAACACTGCGGCCAAC
5151  TTACTTCTGACAACGATCGGAGGACCGAAGGAGCTAACCGCTTTTTTGCA
5201  CAACATGGGGGATCATGTAACTCGCCTTGATCGTTGGGAACCGGAGCTGA
5251  ATGAAGCCATACCAAACGACGAGCGTGACACCACGATGCCTGTAGCAATG
5301  GCAACAACGTTGCGCAAACTATTAACTGGCGAACTACTTACTCTAGCTTC
5351  CCGGCAACAATTAATAGACTGGATGGAGGCGGATAAAGTTGCAGGACCAC
5401  TTCTGCGCTCGGCCCTTCCGGCTGGCTGGTTTATTGCTGATAAATCTGGA
5451  GCCGGTGAGCGTGGGTCTCGCGGTATCATTGCAGCACTGGGGCCAGATGG
5501  TAAGCCCTCCCGTATCGTAGTTATCTACACGACGGGGAGTCAGGCAACTA
5551  TGGATGAACGAAATAGACAGATCGCTGAGATAGGTGCCTCACTGATTAAG
5601  CATTGGTAACTGTCAGACCAAGTTTACTCATATATACTTTAGATTGATTT
5651  AAAACTTCATTTTTAATTTAAAAGGATCTAGGTGAAGATCCTTTTTGATA
5701  ATCTCATGACCAAAATCCCTTAACGTGAGTTTTCGTTCCACTGAGCGTCA
5751  GACCCCGTAGAAAAGATCAAAGGATGTTCTTGAGATCCTTTTTTTCTGCA
5801  CGTAATCTGCTGCTTGCAAACAAAAAACCACCGCTACCAGCGGTGGTTTG
5851  TTTGCCGGATCAAGAGCTACCAACTCTTTTTCCGAAGGTAACTGGCTTCA
5901  GCAGAGCGCAGATACCAAATACTGTCCTTCTAGTGTAGCCGTAGTTAGGC
5951  CACCACTTCAAGAACTCTGTAGCACCGCCTACATACCTCGCTCTGCTAAT
6001  CCTGTTACCAGTGGCTGCTGCCAGTGGCGATAAGTCGTGTCTTACCGGGT
6051  TGGACTCAAGACGATAGTTACCGGATAAGGCGCAGCGGTCGGGCTGAACG
```

FIG. 50F

```
6101  GGGGGTTCGTGCACACAGCCCAGCTTGGAGCGAACGACCTACACCGAACT
6151  GAGATACCTACAGCGTGAGCTATGAGAAAGCGCCACGCTTCCCGAAGGGA
6201  GAAAGGCGGACAGGTATCCGGTAAGCGGCAGGGTCGGAACAGGAGAGCGC
6251  ACGAGGGAGCTTCCAGGGGGAAACGCCTGGTATCTTTATAGTCCTGTCGG
6301  GTTTCGCCACCTCTGACTTGAGCGTCGATTTTTGTGATGCTCGTCAGGGG
6351  GGCGGAGCCTATGGAAAAACGCCAGCAACGCGGCCTTTTTACGGTTCCTG
6401  GCCTTTTGCTGGCCTTTTGCTCACATGTTCTTTCCTGCGTTATCCCCTGA
6451  TTCTGTGGATAACCGTATTACCGCCTTTGAGTGAGCTGATACCGCTCGCC
6501  GCAGCCGAACGACCGAGCGCAGCGAGTCAGTGAGCGAGGAAGCGGAAGAG
6551  CGCCCAATACGCAAACCGCCTCTCCCCGCGCGTTGGCCGATTCATTAATG
6601  CAGGTATCACGAGGCCCTTTCGTCTTCAC
```

FIG. 50G mAb124 VH Chain: Nucleic Acid and Amino Sequences

A. Nucleic Acid Sequence

GATGTGCAGCTTCAGGAGTCGGGACCTAGCCTGGTGAAACCTTCTCAGTCTCTGTCCCTCACCTGCACTGTCACTGGCT
ACTCAATCACCAGTGACTATGCCTGGAACTGGATCCGGCAGTTTCCAGGAAACAAACTGGAGTGGATGGGCTACATAA
GTTACAGTGCTAACACTAGGTACAACCCATCTCTCAAAAGTCGAATCTCTATCACTCGAGACACATCCAAGAACCAAT
TCTTCCTGCAGTTGAATTCTGTGACTACTGAGGACACAGCCACATATTACTGTGCAACGTGCGGGACGCGGGTTCCTTAC
TGGGGCCAAGGGACTCTGGTCACTGTCTCTGCA (SEQ ID NO:21)

FIG. 51A

B. Amino Acid Sequence

DVQLQESGPSLVKPSQSLSLTCTVTGYSITSDYAWNWIRQFPGNKLEWMGYISYSANTRYNPSLKSRISITRDTSKNQFFLQL
　　　　　　　　　　　　　　　　　CDR1　　　　　　　　　　　　CDR2
NSVTTEDTATYYCATAGRGFPYWGQGTLVTVSA (SEQ ID NO:22)
　　　　　　　　CDR3

FIG. 51B mAb124 VL Chain: Nucleic Acid and Amino Acid Sequences

C. Nucleic Acid Sequence

GACATCCTGATGACCCAATCTCCATGTCTCTATCTCTGGGAGACACAGTCAGTATCACTTGCCATTCAAGTCA
GGACATTAACAGTAATATAGGGTGGTTGCAGCAGAAACCAGGGAAATCATTAAGGGCCTGATCTATCATGAACCAA
CTTGGACGATGGAGTTCCATCAAGGTTCAGTGGCAGTGGATCTGGAGCCGATTATTCTCTCACCATCAGCCTGAA
TCTGAAGATTTTGTAGACTATTACTGTGTACAGTATGGTCAGTTCCGTGGAGTTCGTGGAGGCACCAAGCTGGAAA
TCAAACGG (SEQ ID NO:26)

FIG. 51C

D. Amino Acid Sequence

DILMTQSPSSMSLSLGDTVSIT<u>CHSSQDINSNIGWLQQKPGKSFKGLIY</u><u>HGTNLDD</u>GVPSRFSGSGSGADYSLTISSLESEDFVD
                                CDR1                        CDR2

YYC<u>VQYGQFPW</u>TFGGGTKLEIKR (SEQ ID NO:27)
     CDR3

FIG. 51D mAb1133 VH Chain: Nucleic Acid and Amino Acid Sequences

A. Nucleic Acid Sequence

GATGTGCAGCTTCAGGGGTGGGACCTAGCCTGGTGAAACCTTCTCAGTCTCTGTCCCTCACCTGCACTGTCACTGGCT
ACTCAATCACCAGTGATTATGCCTGGAACTGGATCCGGCAGTTTCCAGGAAACAAACTGGAGTGGATGGGCTACATAA
GCTACAGTGGTAACACTAGATACAACCCATCTCAGAAGTGAATTCTATCACTCGAGACACATCTCAAGAACCAATT
CTTCCTGCAGTTGAATTCTGTGACTACTGAGGACACAGCCACATATTACTGTGCAACGGGGGACGGGGATTTCCTTAC
TGGGGCCAAGGGACTCTGGTCACTGTCTCTGCA (SEQ ID NO:31)

FIG. 52A

B. Amino Acid Sequence

DVQLQGSGPSLVKPSQSLSLTCTVTGYSITSDYAWNWIRQFPGNKLEWMGYISYSGNTRYNPSLRSRISITRDTSKNQFFLQL
            CDR1                              CDR2

NSVITEDTAFYYCATAGRGFPYWGQGTLVTVSA (SEQ ID NO:32)
          CDR3

FIG. 52B mAb1133 VL Chain: Nucleic Acid and Amino Acid Sequences

C. Nucleic Acid Sequence

GACATCCTGATGACCCAATCTCCATCCTCCATGTCTGTGTCTCTGGGAGACACAGTCAACATCACTTGCCATTCAAGTC
AGGACATTAACAGTAATATAGGGTGGTTGCAGCAGAAACCAGGAAAATCATTTAAGGCCTGATCTATCATGGAACCA
ACTTGGAGGATGGAGTTCCATCAAGGTTCAGTGGCAGTGGATCTGGAGCCGATTATTCTCTCACCATCAGCAGCCTGGA
ATCTGAGGATTTTGCAGACTATTACTGTGTACAGTATGTCAGTTCCGTGGACGTTCGGTGGAGGCACCAAGCTGGAA
ATCAAAC (SEQ ID NO:36)

D. Amino Acid Sequence

DILMTQSPSSMSVSLGDTVNITCHSSQDINSNIGWLQQKPGKSFKGLIYHGTNLDDGVPSRFSGSGSGADYSLTISSLESEDFA
            CDR1                              CDR2
DYYCVQYGQFPWTFGGGTKLEIKR (SEQ ID NO:37)
    CDR3

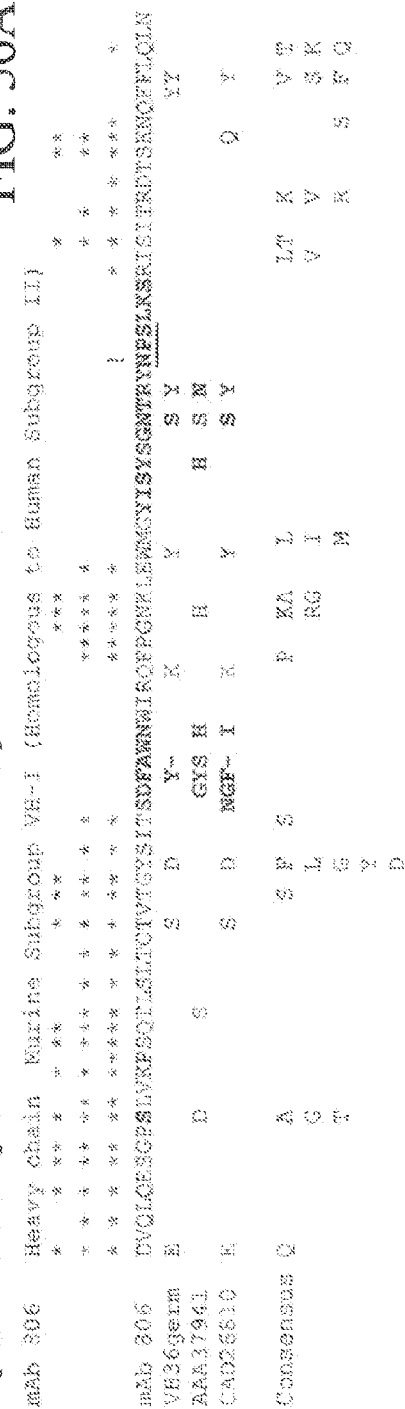

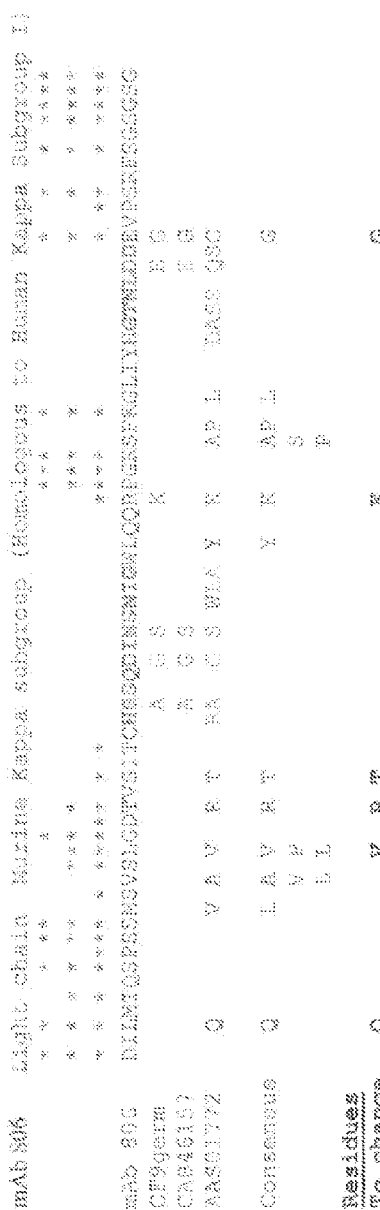
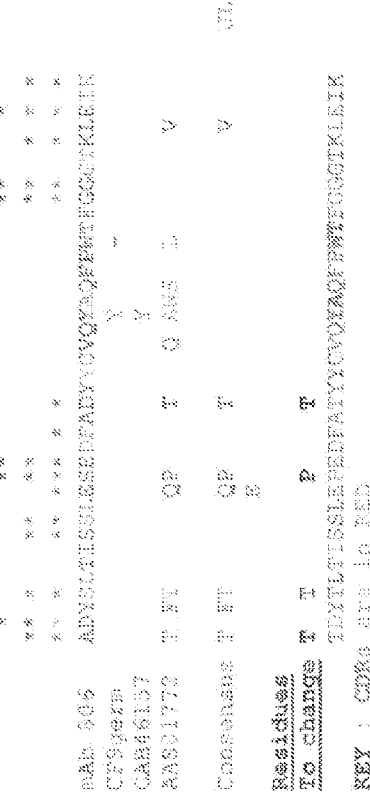

```
              DraIII  FseI          BstNI
                              ApaI                    SacII
     AAGATGGCACACCGTGGCCGGCCTCTGCGCCTGGGCCCAGCTCTGTCCCACACCGCGGTC
  1  ---------+---------+---------+---------+---------+---------+
     TTCTACCGTGTGGCACCGGCCGGAGACGCGGACCCGGGTCGAGACAGGGTGTGGCGCCAG

ApaI              BstNI
     ACATGGCACCTTTTCTCTTCCAGCCTCCACCAAGGGCCCCAGCGTGTTCCCCCTGGCCCC
 61  ---------+---------+---------+---------+---------+---------+
     TGTACCGTGGAAAAGAGAAGGTCGGAGGTGGTTCCCGGGGTCGCACAAGGGGGACCGGGG
                              A  S  T  K  G  P  S  V  F  P  L  A  P

BstNI   BstNI
     CAGCAGCAAGAGCACCAGCGGCGGTACAGCGGCCCTGGGCTGCCTGGTGAAGGACTACTT
121  ---------+---------+---------+---------+---------+---------+
     GTCGTCGTTCTCGTGGTCGCCGCCGTGTCGCCGGGACCCGACGGACCACTTCCTGATGAA
      S  S  K  S  T  S  G  G  T  A  A  L  G  C  L  V  K  D  Y  F

CCCCGAGCCCGTGACCGTGAGCTGGAACAGCGGAGCCCTGACCTCCGGCGTGCACACCTT
181  ---------+---------+---------+---------+---------+---------+
     GGGGCTCGGGCACTGGCACTCGACCTTGTCGCCTCGGGACTGGAGGCCGCACGTGTGGAA
      P  E  P  V  T  V  S  W  N  S  G  A  L  T  S  G  V  H  T  F

PstI                                BstEII
     CCCCGCCGTGCTGCAGAGCAGCGGCCTGTACAGCCTGAGCAGCGTGGTGACCGTGCCCAG
241  ---------+---------+---------+---------+---------+---------+
     GGGGCGGCACGACGTCTCGTCGCCGGACATGTCGGACTCGTCGCACCACTGGCACGGGTC
      P  A  V  L  Q  S  S  G  L  Y  S  L  S  S  V  V  T  V  P  S

BstNI
     CACCAGCCTGGGCACCCAGACCTACATCTGCAACGTGAACCACAAGCCCAGCAACACCAA
301  ---------+---------+---------+---------+---------+---------+
     GTGGTCGGACCCGTGGGTCTGGATGTAGACGTTGCACTTGGTGTTCGGGTCGTTGTGGTT
      S  S  L  G  T  Q  T  Y  I  C  N  V  N  H  K  P  S  N  T  K

BspMI
     GGTGGACAAGAAGGTGGAGCCCAAGAGCTGCGACAAGACCCACACCTGCCCCCCCTGCCC
361  ---------+---------+---------+---------+---------+---------+
     CCACCTGTTCTTCCACCTCGGGTTCTCGACGCTGTTCTGGGTGTGGACGGGGGGGACGGG
      V  D  K  K  V  E  P  K  S  C  D  K  T  H  T  C  P  P  C  P

AGCCCCAGAGCTGCTGGGCGGACCCTCCGTGTTCCTGTTCCCCCCAAAGCCCAAGGACAC
421  ---------+---------+---------+---------+---------+---------+
     TCGGGGTCTCGACGACCCGCCTGGGAGGCACAAGGACAAGGGGGGTTCGGGTTCCTGTG
      A  P  E  L  L  G  G  P  S  V  F  L  F  P  P  K  P  K  D  T

BstEII
         SciI           BspMI
     CCTGATGATCAGCAGGACCCCCGAGGTGACCTGCGTGGTGGTGGACGTGAGCCACGAGGA
481  ---------+---------+---------+---------+---------+---------+
     GGACTACTAGTCGTCCTGGGGGCTCCACTGGACGCACCACCACCTGCACTCGGTGCTCCT
      L  M  I  S  R  T  P  E  V  T  C  V  V  V  D  V  S  H  E  D
```

```
LOCUS
8C65AAG                 11891 bp    DNA     circular     27-NOV-2006
        DEFINITION  veneered 8C6 HC variable region, GeneArt human HC constant
region, veneered LC variable region, cod-opt LC constant region, combined in
large Lonza Vector.
SOURCE
  ORGANISM
COMMENT     This file is created by Vector NTI
            http://www.invitrogen.com/
COMMENT     VNTDATE|418148572
COMMENT     VNTDBDATE|428174363|
COMMENT     LSOWNER|
COMMENT     VNTNAME|8C65AAG|
COMMENT     VNTAUTHORNAME|Anne Murray|
COMMENT     VNTAUTHORTEL|646 888-2342|
COMMENT     VNTAUTHORFAX|646 422-0492|
COMMENT     VNTAUTHOREML|murraya1@mskcc.org
COMMENT     VNTAUTHORAD1|Ludwig Inst. at Memorial Sloan Kettering Cancer Center|
COMMENT     VNTAUTHORAD2|1275 York Ave.|
COMMENT     VNTAUTHORAD3|New York, NY 10021 |
COMMENT     VNTAUTHORAD4|USA|
COMMENT     VNTREPLTYPE|Plasmid
COMMENT     Vector_NTI_Display_Data_(Do_Not_Edit!)
COMMENT     (SXF
COMMENT       (CGenDoc "8C65AAG" 0 11891
COMMENT        (CDBMol 0 0 1 6558 1 0 0 1 0 "" "" 0 0 0 0 (CObList) (CObList)
(CObList)
COMMENT        (CObList) -1 "")
COMMENT        (CDocSetData 1 1 0 0 0 0 "MAIN" 1 1 1 1 0 0 1 1 1 0 10 10 40 50 0
1 0
COMMENT         (CHomObj 0 0 0 5 75) (CWordArray) (CWordArray)
COMMENT         (CStringList "BamHI" "BglII" "DraIII" "FseI" "HindIII" "MluI"
"NotI"
COMMENT          "PacI" "RsrII" "SalI") (CStringList "atg" "gtg")
COMMENT         (CStringList "taa" "tga" "tag") (CObList) 1 "{(0,1),2}" 0 0 "" 0
COMMENT        4294967295 0 1 0 0 0 0 1 "MAIN" 0 0 30 0
COMMENT         (CProteinMotifSearchObject 100 10 1 1 1 1 1 0 1 0 0 0 0))
COMMENT        (CMolPar 1 0 0 0 1 11891 0 0 0 0 0 0 0) (CStringList)
(CStringList)
COMMENT        (CObList) (COAPar 25 250 50 0 6 4 3 7) (COAPar 25 250 50 0 6 4 3
7)
COMMENT        (COAPar 25 250 50 0 6 4 3 7)
COMMENT        (CObList #0=(CRSite (CStringList) "BamHI" "ggatcc" 2 0 1 5059 0 0
"")
COMMENT        #1=(CRSite (CStringList) "BglII" "agatct" 2 0 1 8910 0 0 "")
COMMENT        #2=(CRSite (CStringList) "DraIII" "cacnnngtg" 7 0 2 128 0 543 0 0
"")
COMMENT        #3=(CRSite (CStringList) "FseI" "ggccggcc" 7 0 1 551 0 0 "")
COMMENT        #4=(CRSite (CStringList) "HindIII" "aagctt" 2 0 2 2 0 3869 0 0
"")
COMMENT        #5=(CRSite (CStringList) "MluI" "acgcgt" 2 0 1 9821 0 0 "")
COMMENT        #6=(CRSite (CStringList) "NotI" "gcggccgc" 3 0 1 1878 0 0 "")
COMMENT        #7=(CRSite (CStringList) "PacI" "ttaattaa" 6 0 1 4387 0 0 "")
COMMENT        #8=(CRSite (CStringList) "RsrII" "cggwccg" 3 0 2 3999 0 4377 0 0
"")
```

```
COMMENT         #9=(CRSite (CStringList) "SalI" "gtcgac" 2 0 1 5335 0 0 ""))
COMMENT         (CObList
COMMENT         #10=(CFSignal (CObList) "GeneArt HC C-Reg" 2 0 0 553 1643 0
COMMENT              (CStringList) (CStringList) 1 1 1 1 "")
COMMENT         #11=(CFSignal (CObList) "SV40 polyA" 25 0 0 1644 1875 0
(CStringList)
COMMENT              (CStringList) 1 1 1 1 "")
COMMENT         #12=(CFSignal (CObList) "Signal (SV40E (and SV40 ori))" 21 0 0
7356 7699
COMMENT              0 (CStringList) (CStringList) 1 1 1 1 "")
COMMENT         #13=(CFSignal (CObList) "RNA (beta-lactamase) Amp(R)" 53 0 1 6121
6981 0
COMMENT              (CStringList) (CStringList) 1 1 1 1 "")
COMMENT         #14=(CFSignal (CObList) "mRNA (GS cDNA)" 54 0 0 7707 8906 0
COMMENT              (CStringList) (CStringList) 1 1 1 1 "")
COMMENT         #15=(CFSignal (CObList) "Promoter (hCMV-MIE)" 30 0 0 9784 10926 0
COMMENT              (CStringList) (CStringList) 1 1 1 1 "")
COMMENT         #16=(CFSignal (CObList) "Intron (SV40 Intron + poly A)" 15 0 0
8909 9760
COMMENT              0 (CStringList) (CStringList) 1 1 1 1 "")
COMMENT         #17=(CFSignal (CObList) "5'UTR_1" 52 0 0 10927 11047 0
(CStringList)
COMMENT              (CStringList) 1 1 1 1 "")
COMMENT         #18=(CFSignal (CObList) "Intron_1" 15 0 0 11048 11874 0
(CStringList)
COMMENT              (CStringList) 1 1 1 1 "")
COMMENT         #19=(CFSignal (CObList) "5'UTR_2" 52 0 0 11875 11891 0
(CStringList)
COMMENT              (CStringList) 1 1 1 1 "")
COMMENT         #20=(CFSignal (CObList) "Heavy Chain 806 V-Region Insert" 45 0 0
128 542
COMMENT              0 (CStringList) (CStringList) 1 1 1 1 "")
COMMENT         #21=(CFSignal (CObList) "HtoY" 23 0 0 4315 4315 0 (CStringList)
COMMENT              (CStringList) 1 1 1 1 "")
COMMENT         #22=(CFSignal (CObList) "Light-Const. chg 2.1-3" 23 0 0 4716 4716
0
COMMENT              (CStringList) (CStringList) 1 1 1 1 "")
COMMENT         #23=(CFSignal (CObList) "Light-Chain 806 V-Region insert" 45 0 0
3999
COMMENT              4376 0 (CStringList) (CStringList) 1 1 1 1 "")
COMMENT         #24=(CFSignal (CObList) "Promoter (hCMV-MIE) (from NotI)" 30 0 0
1884
COMMENT              2902 0 (CStringList) (CStringList) 1 1 1 1 "")
COMMENT         #25=(CFSignal (CObList) "5'UTR_2" 52 0 0 3851 3867 0
(CStringList)
COMMENT              (CStringList) 1 1 1 1 "")
COMMENT         #26=(CFSignal (CObList) "Intron_1" 15 0 0 3024 3850 0
(CStringList)
COMMENT              (CStringList) 1 1 1 1 "")
COMMENT         #27=(CFSignal (CObList) "5'UTR_1" 52 0 0 2903 3023 0
(CStringList)
COMMENT              (CStringList) 1 1 1 1 "")
COMMENT         #28=(CFSignal (CObList) "SV40 poly A" 25 0 0 4827 5063 0
(CStringList)
COMMENT              (CStringList) 1 1 1 1 "")
COMMENT         #29=(CFSignal (CObList) "Codon-Optimized Kappa Constant Region" 2
```

FIG. 64B

```
0 0
COMMENT              4390 4800 0 (CStringList) (CStringList) 1 1 1 1 ""))
(CObList)
COMMENT         (CObList) (CObList) (CObList) (CObList) (CObList)
COMMENT         (CTextView 0
COMMENT         #30=(CGroupPar (CParagraph 0 (0 0) 1 2 0 0 180)
COMMENT            (CObjectList
COMMENT              #31=(CRefLinePar
COMMENT                (CLinePar (CParagraph 0 (0 0) 0 2 0 1 233) "8C65AAG"
2) 5 ""
COMMENT                   0 4)
COMMENT              #32=(CFolderPar
COMMENT                (CGroupPar (CParagraph 1 (0 0) 1 1 0 0 178)
COMMENT                   (CObjectList
COMMENT                     #33=(CLinePar (CParagraph 0 (0 0) 1 2 1 0 180)
COMMENT                        "DNA Plasmid '8C65AA6'" 1)
COMMENT                     #34=(CLinePar (CParagraph 0 (0 0) 1 2 1 0 180)
COMMENT                        "veneered 806 HC variable region, GeneArt human
HC constant region, veneered LC variable region, cod-opt LC constant region,
combined in large Lonza Vector"
COMMENT                        1)
COMMENT                     #35=(CLinePar (CParagraph 0 (0 0) 1 2 1 0 180)
COMMENT                        "Currently local object. Original author: Anne"
1)
COMMENT                     #36=(CLinePar (CParagraph 0 (0 0) 1 2 1 0 180)
COMMENT                        "Created: 08/07/06 04:22PM" 1)
COMMENT                     #37=(CLinePar (CParagraph 0 (0 0) 1 2 1 0 180)
COMMENT                        "Last Modified: 11/27/06 05:15PM" 1)
COMMENT                     #38=(CLinePar (CParagraph 0 (0 0) 1 2 1 0 180)
COMMENT                        "length: 11891 bp" 1)
COMMENT                     #39=(CLinePar (CParagraph 0 (0 0) 1 2 1 0 180)
COMMENT                        "storage type: Basic" 1)
COMMENT                     #40=(CLinePar (CParagraph 0 (0 0) 1 2 1 0 180)
COMMENT                        "form: Circular" 1)) "General Description")
COMMENT              #41=(CFolderPar
COMMENT                (CGroupPar (CParagraph 2 (0 0) 1 1 0 0 178)
(CObjectList))
COMMENT                   "Standard Fields")
COMMENT              #42=(CFolderPar
COMMENT                (CGroupPar (CParagraph 5 (0 0) 1 1 0 0 178)
COMMENT                   (CObjectList
COMMENT                     #43=(CLinePar (CParagraph 0 (0 0) 1 2 1 0 180)
"Anne" 1)))
COMMENT                   "Original Author")
COMMENT              #44=(CRefLinePar
COMMENT                (CLinePar (CParagraph 0 (0 0) 0 2 0 0 233) "Comments"
2) 1 "")
COMMENT                   0 0)
COMMENT              #45=(CFolderPar
COMMENT                (CGroupPar (CParagraph 8 (0 0) 1 2 0 0 178)
(CObjectList))
COMMENT                   "Annotations")
COMMENT              #46=(CFolderPar
COMMENT                (CGroupPar (CParagraph 12 (6 0) 1 1 0 0 178)
COMMENT                   (CObjectList
COMMENT                     #47=(CFolderPar
```

FIG. 64C

```
COMMENT                    (CGroupPar (CParagraph 2 (7 2 0) 1 1 1 0 178)
COMMENT                      (CObjectList
COMMENT                        #48=(CFolderPar
COMMENT                          (CGroupPar
COMMENT                            (CParagraph 553 (3 #10# 0) 1 2 2 0 194)
COMMENT                            (CObjectList
COMMENT                              #49=(CLinePar
COMMENT                                (CParagraph 0 (0 0) 1 2 3 0 180)
COMMENT                                "Start: 553   End: 1643" 1)
COMMENT                              #50=(CLinePar
COMMENT                                (CParagraph 0 (0 0) 1 2 3 0 180)
COMMENT                                "GeneArt Human HC C-Reg" 1)))
COMMENT                          "GeneArt HC C-Reg")
COMMENT                        #51=(CFolderPar
COMMENT                          (CGroupPar
COMMENT                            (CParagraph 4390 (3 #29# 0) 1 2 2 0
194)
COMMENT                            (CObjectList
COMMENT                              #52=(CLinePar
COMMENT                                (CParagraph 0 (0 0) 1 2 3 0 180)
COMMENT                                "Start: 4390   End: 4800" 1)))
COMMENT                          "Codon-Optimized Kappa Constant
Region")))
COMMENT                      "C-Region (2 total)")
COMMENT                    #53=(CFolderPar
COMMENT                      (CGroupPar (CParagraph 15 (7 15 0) 1 1 1 0 178)
COMMENT                        (CObjectList
COMMENT                          #54=(CFolderPar
COMMENT                            (CGroupPar
COMMENT                              (CParagraph 3024 (3 #26# 0) 1 2 2 0
194)
COMMENT                              (CObjectList
COMMENT                                #55=(CLinePar
COMMENT                                  (CParagraph 0 (0 0) 1 2 3 0 180)
COMMENT                                  "Start: 3024   End: 3850" 1)
COMMENT                                #56=(CLinePar
COMMENT                                  (CParagraph 0 (0 0) 1 2 3 0 180)
COMMENT                                  "intron" 1))) "Intron_1")
COMMENT                          #57=(CFolderPar
COMMENT                            (CGroupPar
COMMENT                              (CParagraph 8909 (3 #16# 0) 1 2 2 0
194)
COMMENT                              (CObjectList
COMMENT                                #58=(CLinePar
COMMENT                                  (CParagraph 0 (0 0) 1 2 3 0 180)
COMMENT                                  "Start: 8909   End: 9760" 1)
COMMENT                                #59=(CLinePar
COMMENT                                  (CParagraph 0 (0 0) 1 2 3 0 180)
COMMENT                                  "SV40 intron + poly A" 1)))
COMMENT                            "Intron (SV40 intron + poly A)")
COMMENT                          #60=(CFolderPar
COMMENT                            (CGroupPar
COMMENT                              (CParagraph 11048 (3 #16# 0) 1 2 2 0
194)
COMMENT                              (CObjectList
COMMENT                                #61=(CLinePar
```

FIG. 64D

```
COMMENT                                     (CParagraph 0 (0 0) 1 2 3 0 180)
COMMENT                                     "Start: 11046  End: 11874" 1)
COMMENT                                 #62=(CLinePar
COMMENT                                     (CParagraph 0 (0 0) 1 2 3 0 180)
COMMENT                                     "intron" 1)))  "Intron_1")))
COMMENT                            "Intron (3 total)")
COMMENT                       #63=(CFolderPar
COMMENT                           (CGroupPar (CParagraph 21 (7 21 0) 1 1 1 0 178)
COMMENT                            (CObjectList
COMMENT                             #64=(CFolderPar
COMMENT                                 (CGroupPar
COMMENT                                     (CParagraph 7356 (3 #12# 0) 1 2 2 0
194)
COMMENT                                     (CObjectList
COMMENT                                      #65=(CLinePar
COMMENT                                          (CParagraph 0 (0 0) 1 2 3 0 180)
COMMENT                                          "Start: 7356  End: 7699" 1)
COMMENT                                      #66=(CLinePar
COMMENT                                          (CParagraph 0 (0 0) 1 2 3 0 180)
COMMENT                                          "SV40E (and SV40 ori)" 1)))
COMMENT                                   "Signal (SV40E (and SV40 ori);")))
COMMENT                            "Misc. Feature (1 total)")
COMMENT                       #67=(CFolderPar
COMMENT                           (CGroupPar (CParagraph 23 (7 23 0) 1 1 1 0 178)
COMMENT                            (CObjectList
COMMENT                             #68=(CFolderPar
COMMENT                                 (CGroupPar
COMMENT                                     (CParagraph 4315 (3 #21# 0) 1 2 2 0
194)
COMMENT                                     (CObjectList
COMMENT                                      #69=(CLinePar
COMMENT                                          (CParagraph 0 (0 0) 1 2 3 0 180)
COMMENT                                          "Start: 4315  End: 4315" 1)
COMMENT                                      #70=(CLinePar
COMMENT                                          (CParagraph 0 (0 0) 1 2 3 0 180)
COMMENT                                          "Histidine-to-Tyrosine change in
the 806 Light-Chain variable CDR3 region"
COMMENT                                          1)))  "HtoY")
COMMENT                             #71=(CFolderPar
COMMENT                                 (CGroupPar
COMMENT                                     (CParagraph 4716 (3 #22# 0) 1 2 2 0
194)
COMMENT                                     (CObjectList
COMMENT                                      #72=(CLinePar
COMMENT                                          (CParagraph 0 (0 0) 1 2 3 0 180)
COMMENT                                          "Start: 4716  End: 4716" 1)
COMMENT                                      #73=(CLinePar
COMMENT                                          (CParagraph 0 (0 0) 1 2 3 0 180)
COMMENT                                          "Light-chain c-region change 2.1-
3" 1)))
COMMENT                                   "Light-Const. chg 2.1-3")))
COMMENT                            "Modified Base (2 total)")
COMMENT                       #74=(CFolderPar (CGroupPar (CParagraph 25 (7 25 0) 1 1 1 0 178)
COMMENT                            (CObjectList
COMMENT                             #75=(CFolderPar
```

FIG. 64E

```
COMMENT                            (CGroupPar
COMMENT                               (CParagraph 1644 (3 #11# 0) 1 2 2 0
194)
COMMENT                            (CObjectList
COMMENT                               #76=(CLinePar
COMMENT                                  (CParagraph 0 (0 0) 1 2 3 0 180)
COMMENT                                  "Start: 1644  End: 1875" 1)))
COMMENT                      "SV40 polyA")
COMMENT                   #77=(CFolderPar
COMMENT                      (CGroupPar
COMMENT                         (CParagraph 4827 (3 #28# 0) 1 2 2 0
194)
COMMENT                         (CObjectList
COMMENT                            #78=(CLinePar
COMMENT                               (CParagraph 0 (0 0) 1 2 3 0 180)
COMMENT                               "Start: 4827  End: 5063" 1)
COMMENT                            #79=(CLinePar
COMMENT                               (CParagraph 0 (0 0) 1 2 3 0 180)
COMMENT                               "SV40 poly A" 1))) "SV40 poly
A")))
COMMENT             "PolyA Signal (2 total)")
COMMENT          #80=(CFolderPar
COMMENT             (CGroupPar (CParagraph 30 (7 30 0) 1 1 1 0 178)
COMMENT                (CObjectList
COMMENT                   #81=(CFolderPar
COMMENT                      (CGroupPar
COMMENT                         (CParagraph 1884 (3 #24# 0) 1 2 2 0
194)
COMMENT                         (CObjectList
COMMENT                            #82=(CLinePar
COMMENT                               (CParagraph 0 (0 0) 1 2 3 0 180)
COMMENT                               "Start: 1884  End: 2902" 1)
COMMENT                            #83=(CLinePar
COMMENT                               (CParagraph 0 (0 0) 1 2 3 0 180)
COMMENT                               "Promoter (hCMV-MIE) (from NotI)"
1)))
COMMENT                      "Promoter (hCMV-MIE) (from NotI)")
COMMENT                   #84=(CFolderPar
COMMENT                      (CGroupPar
COMMENT                         (CParagraph 9784 (3 #15# 0) 1 2 2 0
194)
COMMENT                         (CObjectList
COMMENT                            #85=(CLinePar
COMMENT                               (CParagraph 0 (0 0) 1 2 3 0 180)
COMMENT                               "Start: 9784  End: 10926" 1)
COMMENT                            #86=(CLinePar
COMMENT                               (CParagraph 0 (0 0) 1 2 3 0 180)
COMMENT                               "hCMV-MIE promoter" 1)))
COMMENT                      "Promoter (hCMV-MIE)")))
COMMENT             "Promoter Prokaryotic (2 total)")
COMMENT          #87=(CFolderPar
COMMENT             (CGroupPar (CParagraph 45 (7 45 0) 1 1 1 0 178)
COMMENT                (CObjectList
COMMENT                   #88=(CFolderPar
COMMENT                      (CGroupPar
COMMENT                         (CParagraph 128 (3 #20# 0) 1 2 2 0 194)
```

FIG. 64F

```
COMMENT                              (CObjectList
COMMENT                                #89=(CLinePar
COMMENT                                   (CParagraph 0 (0 0) 1 2 3 0 180)
COMMENT                                   "Start: 128    End: 542 " 1)))
COMMENT                              "Heavy Chain 806 V-Region Insert")
COMMENT                           #90=(CFolderPar
COMMENT                              (CGroupPar
COMMENT                                 (CParagraph 3999 (3 #23# 0) 1 2 2 0
194)
COMMENT                                 (CObjectList
COMMENT                                   #91=(CLinePar
COMMENT                                      (CParagraph 0 (0 0) 1 2 3 0 180)
COMMENT                                      "Start: 3999   End: 4376" 1)))
COMMENT                              "Light-Chain 806 V-Region insert")))
COMMENT                           "V-Region (2 total)")
COMMENT                        #92=(CFolderPar
COMMENT                           (CGroupPar (CParagraph 52 (7 52 0) 1 1 1 0 178)
COMMENT                              (CObjectList
COMMENT                                #93=(CFolderPar
COMMENT                                   (CGroupPar
COMMENT                                      (CParagraph 2903 (3 #27# 0) 1 2 2 0
194)
COMMENT                                      (CObjectList
COMMENT                                        #94=(CLinePar
COMMENT                                           (CParagraph 0 (0 0) 1 2 3 0 180)
COMMENT                                           "Start: 2903   End: 3023" 1)
COMMENT                                        #95=(CLinePar
COMMENT                                           (CParagraph 0 (0 0) 1 2 3 0 180)
"5'UT"
COMMENT                                           1))) "5'UTR_1")
COMMENT                                #96=(CFolderPar
COMMENT                                   (CGroupPar
COMMENT                                      (CParagraph 3851 (3 #25# 0) 1 2 2 0
194)
COMMENT                                      (CObjectList
COMMENT                                        #97=(CLinePar
COMMENT                                           (CParagraph 0 (0 0) 1 2 3 0 180)
COMMENT                                           "Start: 3851   End: 3867" 1)
COMMENT                                        #98=(CLinePar
COMMENT                                           (CParagraph 0 (0 0) 1 2 3 0 180)
"5'UT"
COMMENT                                           1))) "5'UTR_2")
COMMENT                                #99=(CFolderPar
COMMENT                                   (CGroupPar
COMMENT                                      (CParagraph 10927 (3 #17# 0) 1 2 2 0
194)
COMMENT                                      (CObjectList
COMMENT                                        #100=(CLinePar
COMMENT                                           (CParagraph 0 (0 0) 1 2 3 0 180)
COMMENT                                           "Start: 10927  End: 11047" 1)
COMMENT                                        #101=(CLinePar
COMMENT                                           (CParagraph 0 (0 0) 1 2 3 0 180)
"5'UT"
COMMENT                                           1))) "5'UTR_1")
COMMENT                                #102=(CFolderPar
COMMENT                                   (CGroupPar
```

FIG. 64G

```
COMMENT                             (CParagraph 11875 (3 #19# 0) 1 2 2 0
194)
COMMENT                             (CObjectList
COMMENT                               #103=(CLinePar
COMMENT                                 (CParagraph 0 (0 0) 1 2 3 0
180)
COMMENT                                   "Start: 11875  End: 11891" 1)
COMMENT                               #104=(CLinePar
COMMENT                                 (CParagraph 0 (0 0) 1 2 3 0
180)
COMMENT                                   "5'UT" 1))) "5'UTR_2")))
COMMENT                       "5' UTR (4 total)")
COMMENT                     #105=(CFolderPar
COMMENT                       (CGroupPar (CParagraph 53 (7 53 0) 1 1 1 0
178)
COMMENT                         (CObjectList
COMMENT                           #106=(CFolderPar
COMMENT                             (CGroupPar
COMMENT                               (CParagraph 6121 (3 #13# 0) 1 2 2 0
194)
COMMENT                               (CObjectList
COMMENT                                 #107=(CLinePar
COMMENT                                   (CParagraph 0 (0 0) 1 2 3 0
180)
COMMENT                                     "Start: 6121  End: 6981
(Complementary)"
COMMENT                                       1)
COMMENT                                 #108=(CLinePar
COMMENT                                   (CParagraph 0 (0 0) 1 2 3 0
180)
COMMENT                                     "beta-lactamase" 1)))
COMMENT                             "RNA (beta-lactamase) Amp(R)")))
COMMENT                       "RNA - Misc. (1 total)")
COMMENT                     #109=(CFolderPar
COMMENT                       (CGroupPar (CParagraph 54 (7 54 0) 1 1 1 0
178)
COMMENT                         (CObjectList
COMMENT                           #110=(CFolderPar
COMMENT                             (CGroupPar
COMMENT                               (CParagraph 7707 (3 #14# 0) 1 2 2 0
194)
COMMENT                               (CObjectList
COMMENT                                 #111=(CLinePar
COMMENT                                   (CParagraph 0 (0 0) 1 2 3 0
180)
COMMENT                                     "Start: 7707  End: 8906" 1)
COMMENT                                 #112=(CLinePar
COMMENT                                   (CParagraph 0 (0 0) 1 2 3 0
180)
COMMENT                                     "GS cDNA" 1))) "mRNA (GS
cDNA)")))
COMMENT                       "mRNA (1 total)"))) "Feature Map")
COMMENT                 #113=(CFolderPar
COMMENT                   (CGroupPar (CParagraph 13 (0 0) 1 1 0 0 178)
COMMENT                     (CObjectList
COMMENT                       #114=(CRSFolderPar
```

FIG. 64H

```
COMMENT                           (CFolderPar
COMMENT                             (CGroupPar (CParagraph 37104496 (8 0) 1 1 1
0 178)
COMMENT                               (CObjectList
COMMENT                                 #115=(CGroupPar
COMMENT                                   (CParagraph 0 (10 #0# 0) 1 2 2 0
180)
COMMENT                                     (CObjectList
COMMENT                                       #116=(CLinePar
COMMENT                                         (CParagraph 0 (1 #0# 1) 1 2 2
0 191)
COMMENT                                           " N1: 5059 " 1))))) "BamHI: 1
site")
COMMENT                           1 5 "GGATCC" "CCTAGG")
COMMENT                         #117=(CRSFolderPar
COMMENT                           (CFolderPar
COMMENT                             (CGroupPar (CParagraph 37104336 (8 0) 1 1 1
0 178)
COMMENT                               (CObjectList
COMMENT                                 #118=(CGroupPar
COMMENT                                   (CParagraph 0 (10 #1# 0) 1 2 2 0
180)
COMMENT                                     (CObjectList
COMMENT                                       #119=(CLinePar
COMMENT                                         (CParagraph 0 (1 #1# 1) 1 2 2
0 191)
COMMENT                                           " N1: 8910 " 1))))) "BglII: 1
site")
COMMENT                           1 5 "AGATCT" "TCTAGA")
COMMENT                         #120=(CRSFolderPar
COMMENT                           (CFolderPar
COMMENT                             (CGroupPar (CParagraph 18147408 (8 0) 1 1 1
0 178)
COMMENT                               (CObjectList
COMMENT                                 #121=(CGroupPar
COMMENT                                   (CParagraph 0 (10 #2# 0) 1 2 2 0
180)
COMMENT                                     (CObjectList
COMMENT                                       #122=(CLinePar
COMMENT                                         (CParagraph 0 (1 #2# 1) 1 2 2
0 191)
COMMENT                                           " N1: 129 " 1)
COMMENT                                       #123=(CLinePar
COMMENT                                         (CParagraph 0 (1 #2# 2) 1 2 2
0 191)
COMMENT                                           " N2: 543 " 1))))) "DraIII: 2
sites")
COMMENT                           6 3 "CACNNNGTG" "GTGNNNCAC")
COMMENT                         #124=(CRSFolderPar
COMMENT                           (CFolderPar
COMMENT                             (CGroupPar (CParagraph 37104736 (8 0) 1 1 1
0 178)
COMMENT                               (CObjectList
COMMENT                                 #125=(CGroupPar
COMMENT                                   (CParagraph 0 (10 #3# 0) 1 2 2 0
180)
```

FIG. 64I

```
COMMENT                                    (CObjectList
COMMENT                                      #126=(CLineFar
COMMENT                                            (CParagraph 0 (1 #3# 1) 1 2 2
0 191)
COMMENT                                             " N1: 551 " 1))))) "FseI: 1
site") 6
COMMENT                                   2 "GGCCGGCC" "CCGGCCGG")
COMMENT                            #127=(CRSFolderPar
COMMENT                                    (CFolderPar
COMMENT                                     (CGroupPar (CParagraph 37104576 (8 0) 1 1 1
0 178)
COMMENT                                       (CObjectList
COMMENT                                         #128=(CGroupPar
COMMENT                                           (CParagraph 0 (10 #4# 0) 1 2 2 0
180)
COMMENT                                            (CObjectList
COMMENT                                              #129=(CLinePar
COMMENT                                                (CParagraph 0 (1 #4# 1) 1 2 2
0 191)
COMMENT                                                 " N1: 2 " 1)
COMMENT                                              #130=(CLinePar
COMMENT                                                (CParagraph 0 (1 #4# 2) 1 2 2
0 191)
COMMENT                                                 " N2: 3869 " 1))))))
COMMENT                                       "HindIII: 2 sites") 1 5 "AAGCTT" "TTCGAA")
COMMENT                            #131=(CRSFolderPar
COMMENT                                    (CFolderPar
COMMENT                                     (CGroupPar (CParagraph 27521208 (8 0) 1 1 1
0 178)
COMMENT                                       (CObjectList
COMMENT                                         #132=(CGroupPar
COMMENT                                           (CParagraph 0 (10 #5# 0) 1 2 2 0
180)
COMMENT                                            (CObjectList
COMMENT                                              #133=(CLinePar
COMMENT                                                (CParagraph 0 (1 #5# 1) 1 2 2
0 191)
COMMENT                                                 " N1: 9821 " 1))))) "MluI: 1
site")
COMMENT                                   1 5 "ACGCGT" "TGCGCA")
COMMENT                            #134=(CRSFolderPar
COMMENT                                    (CFolderPar
COMMENT                                     (CGroupPar (CParagraph 37104976 (8 0) 1 1 1
0 178)
COMMENT                                       (CObjectList
COMMENT                                         #135=(CGroupPar
COMMENT                                           (CParagraph 0 (10 #6# 0) 1 2 2 0
180)
COMMENT                                            (CObjectList
COMMENT                                              #136=(CLinePar
COMMENT                                                (CParagraph 0 (1 #6# 1) 1 2 2
0 191)
COMMENT                                                 " N1: 1878 " 1))))) "NotI: 1
site")
COMMENT                                   2 6 "GCGGCCGC" "CGCCGGCG")
COMMENT                            #137=(CRSFolderPar
```

FIG. 64J

```
COMMENT                        (CFolderPar
COMMENT                         (CGroupPar (CParagraph 37104816 (8 0) 1 1 1
0 178)
COMMENT                          (CObjectList
COMMENT                           #138=(CGroupPar
COMMENT                            (CParagraph 0 (10 #7# 0) 1 2 2 0
180)
COMMENT                             (CObjectList
COMMENT                              #139=(CLinePar
COMMENT                               (CParagraph 0 (1 #7# 1) 1 2 2
0 191)
COMMENT                                " N1: 4387 " 1))))) "PacI: 1
site")
COMMENT                   5 3 "TTAATTAA" "AATTAATT")
COMMENT                  #140=(CRSFolderPar
COMMENT                    (CFolderPar
COMMENT                     (CGroupPar (CParagraph 37104256 (8 0) 1 1 1
0 178)
COMMENT                      (CObjectList
COMMENT                       #141=(CGroupPar
COMMENT                        (CParagraph 0 (10 #8# 0) 1 2 2 0
180)
COMMENT                         (CObjectList
COMMENT                          #142=(CLinePar
COMMENT                           (CParagraph 0 (1 #8# 1) 1 2 2
0 191)
COMMENT                            " N1: 3899 " 1)
COMMENT                          #143=(CLinePar
COMMENT                           (CParagraph 0 (1 #8# 2) 1 2 2
0 191)
COMMENT                            " N2: 4377 " 1))))) "RsrII: 2
sites")
COMMENT                   2 5 "CGGWCCG" "GCCWGGC")
COMMENT                  #144=(CRSFolderPar
COMMENT                    (CFolderPar
COMMENT                     (CGroupPar (CParagraph 18147328 (8 0) 1 1 1
0 178)
COMMENT                      (CObjectList
COMMENT                       #145=(CGroupPar
COMMENT                        (CParagraph 0 (10 #9# 0) 1 2 2 0
180)
COMMENT                         (CObjectList
COMMENT                          #146=(CLinePar
COMMENT                           (CParagraph 0 (1 #9# 1) 1 2 2
0 191)
COMMENT                            " N1: 5335 " 1))))) "SalI: 1
site")
COMMENT                   1 5 "GTCGAC" "CAGCTG")))
COMMENT                "Restriction/Methylation Map")))
COMMENT         (CGraphView
COMMENT          (CWStyleSheet
COMMENT           (CObjectList
COMMENT            #147=(CWidgetStyle "RSite Label" 1 (LOGPEN 0 0 13408563) 1 0 1
COMMENT              (LOGFONT 0 0 0 0 400 0 0 0 0 3 2 1 18 "Georgia") 0.555556
0 1 5
COMMENT               "@N (@S)" 0)
```

FIG. 64K

```
COMMENT     #148=(CWidgetStyle "Signal Label" 1 (LOGPEN 0 0 0) 1 0 1
COMMENT         (LOGFONT 0 0 0 0 700 0 0 0 0 3 2 1 34 "Arial") 0.666667 0
1 1
COMMENT         "@N" 0)
COMMENT     #149=(CWidgetStyle "Molecule Label 2" 0 0 1
COMMENT         (LOGFONT 0 0 0 0 400 0 0 0 0 3 2 1 18 "Georgia") 0.555556
0 1 16
COMMENT         "@L bp" 0)
COMMENT     #150=(CWidgetStyle "Molecule Label 1" 0 0 1
COMMENT         (LOGFONT 0 0 0 0 400 0 0 0 0 3 2 1 34 "Verdana") 0.833333
0 1 1
COMMENT         "@N" 0)
COMMENT     #151=(CWidgetStyle "Shape 3" 1 (LOGPEN 0 0 3355545) 1 1
COMMENT         (LOGBRUSH 0 6724095 0) 0 0 1 (LOGSHAPE 9 1 0.8 1.8 0))
COMMENT     #152=(CWidgetStyle "Shape 1" 1 (LOGPEN 0 0 6723840) 1 1
COMMENT         (LOGBRUSH 0 10079334 0) 0 0 1 (LOGSHAPE 9 1 0.8 1.8 0))
COMMENT     #153=(CWidgetStyle "Axis" 1 (LOGPEN 0 0 10079436) 2 1
COMMENT         (LOGBRUSH 0 13434878 0) 0 0 1 (LOGSHAPE 10 1 0 0 0))
COMMENT     #154=(CWidgetStyle "Line 2" 1 (LOGPEN 0 0 6723840) 8 0 0 1
COMMENT         (LOGSHAPE 1 1.9 0 0 0))
COMMENT     #155=(CWidgetStyle "RSite" 1 (LOGPEN 0 0 10053171) 8 0 0 1
COMMENT         (LOGSHAPE 1 1.9 0 0 0))
COMMENT     #156=(CWidgetStyle "Short Signal" 1 (LOGPEN 0 0 13395507) 10 0
0 0 1
COMMENT         (LOGSHAPE 1 1.9 0 0 0))
COMMENT     #157=(CWidgetStyle "Uniq RSite Label" 1 (LOGPEN 0 0 153) 1 0 1
COMMENT         (LOGFONT 0 0 0 0 400 0 0 0 0 3 2 1 18 "Georgia") 0.555556
128 1
COMMENT         5 "@N (@S)" 0)
COMMENT     #158=(CWidgetStyle "Vanilla" 1 (LOGPEN 0 0 0) 1 1
COMMENT         (LOGBRUSH 0 16777215 0) 1
COMMENT         (LOGFONT 0 0 0 0 400 0 0 0 7 48 2 18 "Times New Roman")
0.8 0
COMMENT         1 2 "?" 0)
COMMENT     #159=(CWidgetStyle "Mark 1" 0 0 1
COMMENT         (LOGFONT 0 0 0 0 400 0 0 0 2 7 48 2 2 "Windings") 0.7 0 1
2 "?"
COMMENT         0)
COMMENT     #160=(CWidgetStyle "Motif Label" 1 (LOGPEN 0 0 16744512) 1 0 1
COMMENT         (LOGFONT 0 0 0 0 400 0 0 0 0 3 2 1 34 "Arial") 0.611111
8388608
COMMENT         1 65535 "@N (@H)" 0)
COMMENT     #161=(CWidgetStyle "Fragment Label 2" 1 (LOGPEN 0 0 0) 1 0 1
COMMENT         (LOGFONT 0 0 0 0 400 0 0 0 0 3 2 1 49 "Courier New") 1.05
0 1 48
COMMENT         "@F bp (molecule @L bp)" 0)
COMMENT     #162=(CWidgetStyle "Fragment Label 1" 1 (LOGPEN 0 0 0) 1 0 1
COMMENT         (LOGFONT 0 0 0 0 400 0 0 0 0 3 2 1 34 "Arial") 0.91 0 1 1
COMMENT         "Fragment of @N" 0)
COMMENT     #163=(CWidgetStyle "Shape 4" 1 (LOGPEN 0 0 0) 1 1
COMMENT         (LOGBRUSH 2 8388608 5) 0 0 0)
COMMENT     #164=(CWidgetStyle "Shape 2" 1 (LOGPEN 0 0 0) 1 1 (LOGBRUSH 0
128 0) 0
COMMENT         0 0)
COMMENT     #165=(CWidgetStyle "Shape 0" 1 (LOGPEN 0 0 0) 1 1 (LOGBRUSH 0 0
0) 0 0
```

FIG. 64L

```
COMMENT               0;
COMMENT               #166=(CWidgetStyle "ORF" 1 (LOGPEN 0 0 16384) 8 0 0 0 1
COMMENT                   (LOGSHAPE 7 0.2 3.41182 2.86186 0.609808))
COMMENT               #167=(CWidgetStyle "Line 4" 1 (LOGPEN 0 0 32768) 8 0 0 0 0)
COMMENT               #168=(CWidgetStyle "Line 3" 1 (LOGPEN 0 0 16711680) 8 0 0 0 0)
COMMENT               #169=(CWidgetStyle "Line 1" 1 (LOGPEN 0 0 16711680) 1 0 0 0 0)
COMMENT               #170=(CWidgetStyle "Short Promoter" 1 (LOGPEN 0 0 128) 6 0 0 0
0)
COMMENT               #171=(CWidgetStyle "Motif" 1 (LOGPEN 0 0 0) 1 0 0 0 0)
COMMENT               #172=(CWidgetStyle "Line 0" 1 (LOGPEN 0 0 0) 8 0 0 0 0)
COMMENT               #173=(CWidgetStyle "Void" 0 0 0 0 0)
COMMENT               #174=(CWidgetStyle "General Label" 1 (LOGPEN 0 0 0) 1 0 1
COMMENT                   (LOGFONT 0 0 0 0 400 0 0 0 0 3 2 1 18 "Times New Roman")
0.91 0
COMMENT               1 3 "@T @N " 0)
COMMENT               #175=(CWidgetStyle "Position" 1 (LOGPEN 0 0 0) 1 0 0 0 0)
COMMENT               #176=(CWidgetStyle "Annotation" 0 0 1
COMMENT                   (LOGFONT 0 0 0 0 400 0 0 0 0 3 2 1 18 "Times New Roman")
0.91 0
COMMENT               0 0)
COMMENT               #177=(CWidgetStyle "Position Label" 1 (LOGPEN 0 0 8388608) 1 0
1
COMMENT                   (LOGFONT 0 0 0 0 400 0 1 0 0 3 2 1 34 "Arial") 0.63
8388608 1 1
COMMENT               "@N" 0)
COMMENT               #178=(CWidgetStyle "Range" 1 (LOGPEN 0 0 0) 1 1
COMMENT                   (LOGBRUSH 0 16777215 0) 0 0 0)
COMMENT               #179=(CWidgetStyle "Range Label" 1 (LOGPEN 0 0 8388608) 1 0 1
COMMENT                   (LOGFONT 0 0 0 0 400 0 1 0 0 3 2 1 34 "Arial") 0.63
8388608 1 1
COMMENT               "@N" 0)
COMMENT               #180=(CWidgetStyle "ORF Label" 1 (LOGPEN 0 0 49216) 1 0 1
COMMENT                   (LOGFONT 0 0 0 0 400 0 0 0 0 3 2 1 18 "Times New Roman")
0.611111 0 1 65535 "@N" 0)
COMMENT               #181=(CWidgetStyle "CDS Label" 1 (LOGPEN 0 0 4227264) 1 0 1
COMMENT                   (LOGFONT 0 0 0 0 400 0 0 0 0 3 2 1 34 "Arial") 0.555556
255 1 1
COMMENT               "@N" 0)
COMMENT               #182=(CWidgetStyle "Shape 5" 1 (LOGPEN 0 0 0) 3 1
COMMENT                   (LOGBRUSH 0 16777113 0) 1
COMMENT                   (LOGFONT 0 0 0 0 400 0 0 0 7 48 2 50 "Arial") 0.9 0 0 1
COMMENT                   (LOGSHAPE 9 1 0.8 1.8 0))
COMMENT               #183=(CWidgetStyle "CDS" 1 (LOGPEN 0 0 0) 1 1 (LOGBRUSH 2 39423
3) 0 0
COMMENT               1 (LOGSHAPE 9 1 0.3 1.8 0))
COMMENT               #184=(CWidgetStyle "Label 2" 1 (LOGPEN 0 0 4227264) 1 0 1
COMMENT                   (LOGFONT 0 0 0 0 400 0 0 0 0 3 2 1 34 "Arial") 0.944444
8388608
COMMENT               1 1 "@N" 0)
COMMENT               #185=(CWidgetStyle "Label 3" 1 (LOGPEN 0 0 8421376) 1 0 1
COMMENT                   (LOGFONT 0 0 0 0 700 255 0 0 0 3 2 1 34 "Arial") 0.833333
255 1
COMMENT               5 "@N (@S)" 0)
COMMENT               #186=(CWidgetStyle "Label 4" 1 (LOGPEN 0 0 8437824) 1 0 1
COMMENT                   (LOGFONT 0 0 0 0 400 0 0 0 0 3 2 1 34 "Arial") 0.722222 0
1 5
```

FIG. 64M

```
COMMENT                 "@N (@S)" 0)
COMMENT            #187=(CWidgetStyle "Shape 6" 1 (LOGPEN 0 0 0) 1 1
COMMENT                 (LOGBRUSH 0 3394713 0) 1
COMMENT                 (LOGFONT 0 0 0 0 400 0 0 0 0 7 48 2 50 "Arial") 0.9 0 0
0)
COMMENT            #188=(CWidgetStyle "Shape 7" 1 (LOGPEN 0 0 0) 1 1
COMMENT                 (LOGBRUSH 0 3407871 0) 1
COMMENT                 (LOGFONT 0 0 0 0 400 0 0 0 0 7 48 2 50 "Arial") 0.9 0 0
0)
COMMENT            #189=(CWidgetStyle "Shape 8" 1 (LOGPEN 0 0 52275) 1 1
COMMENT                 (LOGBRUSH 0 3407871 0) 1
COMMENT                 (LOGFONT 0 0 0 0 400 0 0 0 0 7 48 2 50 "Arial") 0.9 0 0
0)
COMMENT            #190=(CWidgetStyle "Shape 9" 1 (LOGPEN 0 0 0) 1 1
COMMENT                 (LOGBRUSH 0 10040064 0) 1
COMMENT                 (LOGFONT 0 0 0 0 400 0 0 0 0 7 48 2 50 "Arial") 0.9 0 0
0))
COMMENT            0.164644 1.74233 0.164644 2.53336
COMMENT            (2 (CShapeMapEntry 0 "Shape 9" 1 "Signal Label") 45
COMMENT            (CShapeMapEntry 0 "Shape 9" 1 "Signal Label") 70
COMMENT            (CShapeMapEntry 0 "Unique RSite" 1 "Uniq RSite Label") 67
COMMENT            (CShapeMapEntry 0 "ORF" 0 "ORF Label")) 40.0378 40.0378 39 39
0.1
COMMENT            -11891) 1 0 1 1 1
COMMENT            (mapper: 26.6962 -31.9823 39 39 0.01 10 14 11891 11891 1 0 0)
COMMENT            #191=(CGroupWidget (CWidget 0 (0 0) 1 2 0 0 Nil -317 100)
COMMENT                 (CObjectList
COMMENT                 #192=(CGroupWidget (CWidget 1 (0 0) 1 2 0 0 Nil -639 100)
COMMENT                     (CObjectList
COMMENT                     #193=(CAxis
COMMENT                         (CWideLine
COMMENT                             (CWidget 0 (0 0) 1 2 0 0 #153# 37106252 0)
COMMENT                             (LOGPEN 0 0 10079436) 2 (LOGBRUSH 0 13434879
0) 1
COMMENT                             6.27471 6.27271 1 0.0214037) 0.0527557)
COMMENT                     #194=(CLabel
COMMENT                         (CWidget 1001 (0 0) 1 2 0 0 #150# 28370780
100)
COMMENT                         (LOGPEN 0 0 0) 1
COMMENT                         (LOGFONT 41 15 0 0 400 0 0 0 0 3 2 1 34
"Verdana")
COMMENT                         2.53336 0.833333 0 "8C65AAG" "@N" 1 0 0.5 0 -
6.206
COMMENT                         3.84615 1.07692 Nil)
COMMENT                     #195=(CLabel (CWidget 1002 (0 0) 1 2 0 0 #149# 0
100)
COMMENT                         (LOGPEN 0 0 0) 1
COMMENT                         (LOGFONT 27 10 0 0 400 0 0 0 0 3 2 1 18
"Georgia")
COMMENT                         2.53336 0.555556 0 "11891 bp" "@L bp" 16 0 -
0.8 0
COMMENT                         -7.47268 2.30769 0.692308 Nil))
COMMENT                     (CObjectList))
COMMENT                 #196=(CGroupWidget (CWidget 10 (6 0) 1 2 0 0 Nil 393219
100)
COMMENT                     (CObjectList
```

FIG. 64N

```
COMMENT                    #197=(CGroupWidget
COMMENT                        (CWidget 2 (7 2 0) 1 2 0 0 Nil -108 100)
COMMENT                        (CObjectList
COMMENT                        #198=(CWideArrow
COMMENT                            (CWideLine
COMMENT                                (CWidget 0 (3 #10# 0) 1 2 0 0 #190# 0
100)
COMMENT                                (LOGPEN 0 0 0) 1 (LOGBRUSH 0 10040064
0) 1
COMMENT                                5.40641 5.98197 1 0.082322) 0.8 1.8
0)
COMMENT                        #199=(CLabel
COMMENT                            (CWidget 0 (0 0) 1 2 0 0 #148#
37745700 100)
COMMENT                            (LOGPEN 0 0 0) 1
COMMENT                            (LOGFONT 32 12 0 0 700 0 0 0 0 3 2 1
34
COMMENT                            "Arial") 2.53336 0.666667 0
COMMENT                            "GeneArt HC C-Reg" "@N" 1 0 0 -15.0455
COMMENT                            9.30913 6.28205 0.846154 #198#)
COMMENT                        #200=(CWideArrow
COMMENT                            (CWideLine
COMMENT                                (CWidget 0 (3 #29# 0) 1 2 0 0 #190#
393235
COMMENT                                100) (LOGPEN 0 0 0) 1
COMMENT                                (LOGBRUSH 0 10040064 0) 1 3.74091
3.95774 1
COMMENT                                0.082322) 0.8 1.8 0)
COMMENT                        #201=(CLabel
COMMENT                            (CWidget 0 (0 0) 1 2 0 0 #148#
28396148 100)
COMMENT                            (LOGPEN 0 0 0) 1
COMMENT                            (LOGFONT 32 12 0 0 700 0 0 0 0 3 2 1
34
COMMENT                            "Arial") 2.53336 0.666667 0
COMMENT                            "Codon-Optimized Kappa Constant
Region" "@N"
COMMENT                            1 0 0 -11.1884 24.776 14.4872 0.846154
#200#))
COMMENT                        (CObjectList))
COMMENT                    #202=(CGroupWidget
COMMENT                        (CWidget 15 (7 15 0) 1 2 0 0 Nil 18088376
100)
COMMENT                        (CObjectList
COMMENT                        #203=(CLine
COMMENT                            (CWidget 0 (3 #16# 0) 1 2 0 0 #169#
18088384
COMMENT                            100) (LOGPEN 0 0 16711680) 1 0.835356
COMMENT                            1.12422 1.5737)
COMMENT                        #204=(CLabel
COMMENT                            (CWidget 0 (0 0) 1 2 0 0 #148#
18088512 100)
COMMENT                            (LOGPEN 0 0 0) 1
COMMENT                            (LOGFONT 32 12 0 0 700 0 0 0 0 3 2 1
34
COMMENT                            "Arial") 2.53336 0.666667 0
```

FIG. 64O

```
COMMENT                                      "Intron (SV40 intron + poly A)" "@N" 1
0 0
COMMENT                                      13.1146 8.30913 9.74359 0.846154
#203#)
COMMENT                              #205=(CLine
COMMENT                                      (CWidget 0 (3 #18# 0) 1 2 0 0 #169# -
1215 100)
COMMENT                                      (LOGPEN 0 0 16711680) 1 0.835356
0.00896848
COMMENT                                      0.445258)
COMMENT                              #206=(CLabel
COMMENT                                      (CWidget 0 (0 0) 1 2 0 0 #148#
27471448 100)
COMMENT                                      (LOGPEN 0 0 0) 1
COMMENT                                      (LOGFONT 32 12 0 0 700 0 0 0 3 2 1
34
COMMENT                                      "Arial") 2.53336 0.666667 0 "Intron
1" "@N"
COMMENT                                      1 0 0 14.7731 3.24241 2.74359 0.846154
#205#)
COMMENT                              #207=(CLine
COMMENT                                      (CWidget 0 (3 #26# 0) 1 2 0 0 #169#
268634520
COMMENT                                      100) (LOGPEN 0 0 16711680) 1 0.835356
COMMENT                                      4.24209 4.67838)
COMMENT                              #208=(CLabel
COMMENT                                      (CWidget 0 (0 0) 1 2 0 0 #148#
37615420 100)
COMMENT                                      (LOGPEN 0 0 0) 1
COMMENT                                      (LOGFONT 32 12 0 0 700 0 0 0 3 2 1
34
COMMENT                                      "Arial") 2.53336 0.666667 0 "Intron
1" "@N"
COMMENT                                      1 0 0 -7.95233 14.6425 2.74359
0.846154 #207#))
COMMENT                                      (CObjectList))
COMMENT                              #209=(CGroupWidget
COMMENT                                      (CWidget 21 (7 21 0) 1 2 0 0 Nil 327685 100)
COMMENT                                      (CObjectList
COMMENT                                        #210=(CWideArrow
COMMENT                                              (CWideLine
COMMENT                                               (CWidget 0 (3 #12# 0) 1 2 0 0 #152# 0
100)
COMMENT                                               (LOGPEN 0 0 6723840) 1
COMMENT                                               (LOGBRUSH 0 10079334 0) 1 2.21152
2.393 1
COMMENT                                               0.082322) 0.8 1.8 0)
COMMENT                                        #211=(CLabel
COMMENT                                              (CWidget 0 (0 0) 1 2 0 0 #148#
13088608 100)
COMMENT                                              (LOGPEN 0 0 0) 1
COMMENT                                              (LOGFONT 32 12 0 0 700 0 0 0 3 2 1
34
COMMENT                                              "Arial") 2.53335 0.666667 0
COMMENT                                              "Signal (SV40E (and SV40 ori))" "@N" 1
0 0
```

FIG. 64P

```
COMMENT                                         8.38505 12.1092 10.0513 0.846154
#210#))
COMMENT                         (CObjectList))
COMMENT                 #212=(CGroupWidget
COMMENT                         (CWidget 23 (7 23 0) 1 2 0 0 Nil 27986056
100)
COMMENT                         (CObjectList
COMMENT                         #213=(CShape
COMMENT                                 (CWidget 0 (3 #21# 0) 1 2 0 0 #172# 0
100)
COMMENT                                 (LOGPEN 0 6 0) 8 (LOGBRUSH 0 0 4)
0.835356
COMMENT                                 3.9973 0.7 2)
COMMENT                         #214=(CLabel
COMMENT                                 (CWidget 0 (0 0) 1 2 0 0 #148#
37029036 100)
COMMENT                                 (LOGPEN 0 0 0) 1
COMMENT                                 (LOGFONT 32 12 0 0 700 0 0 0 3 2 1
34
COMMENT                                 "Arial") 2.53336 0.666667 0 "HtoY"
"@N" 1 0
COMMENT                                 0 -5.40373 20.9759 1.64103 0.846154
#213#)
COMMENT                         #215=(CShape
COMMENT                                 (CWidget 0 (3 #22# 0) 1 2 0 0 #172# 0
100)
COMMENT                                 (LOGPEN 0 6 0) 8 (LOGBRUSH 0 0 4)
0.835356
COMMENT                                 3.78575 0.7 2)
COMMENT                         #216=(CLabel
COMMENT                                 (CWidget 0 (0 0) 1 2 0 0 #148#
18086616 100)
COMMENT                                 (LOGPEN 0 0 0) 1
COMMENT                                 (LOGFONT 32 12 0 0 700 0 0 0 3 2 1
34
COMMENT                                 "Arial") 2.53336 0.666667 0
COMMENT                                 "Light-Const. chg 2.1-3" "@N" 1 0 0 -
7.491
COMMENT                                 26.0426 7.64103 0.846154 #215#))
COMMENT                         (CObjectList))
COMMENT                 #217=(CGroupWidget
COMMENT                         (CWidget 25 (7 25 0) 1 2 0 0 Nil -736 100)
COMMENT                         (CObjectList
COMMENT                         #218=(CLine
COMMENT                                 (CWidget 0 (3 #11# 0) 1 2 0 0 #167#
18088376
COMMENT                                 100) (LOGPEN 0 6 32768) 8 0.835356
5.28401
COMMENT                                 5.40641)
COMMENT                         #219=(CLabel (CWidget 0 (0 0) 1 2 0 0 #148#
0 100)
COMMENT                                 (LOGPEN 0 0 0) 1
COMMENT                                 (LOGFONT 32 12 0 0 700 0 0 0 3 2 1
34
COMMENT                                 "Arial") 2.53336 0.666667 0 "SV40
polyA"
```

FIG. 64Q

```
COMMENT                             "@N" 1 0 0 -12.2962 3.57581 3.79487
0.846154
COMMENT                             #218#)
COMMENT                      #220=(CLine
COMMENT                            (CWidget 0 (3 #28# 0) 1 2 0 0 #167#
18088384
COMMENT                             100) (LOGPEN 0 6 32768) 8 0.670712
3.60216
COMMENT                             3.72719)
COMMENT                      #221=(CLabel
COMMENT                            (CWidget 0 (0 0) 1 2 0 0 #148#
37126836 100)
COMMENT                             (LOGPEN 0 0 0) 1
COMMENT                             (LOGFONT 32 12 0 0 700 0 0 0 3 2 1
34
COMMENT                             "Arial") 2.53336 0.666667 0 "SV40
poly A"
COMMENT                             "@N" 1 0 0 -5.16093 27.3093 4.02564
0.846154
COMMENT                             #220#)) (CObjectList))
COMMENT                      #222=(CGroupWidget
COMMENT                            (CWidget 30 (7 30 0) 1 2 0 0 Nil 18088376
100)
COMMENT                            (CObjectList
COMMENT                      #223=(CWideArrow
COMMENT                            (CWideLine
COMMENT                             (CWidget 0 (3 #15# 0) 1 2 0 0 #164#
28358516
COMMENT                              100) (LOGPEN 0 0 0) 1 (LOGBRUSH 0
128 0) 1
COMMENT                             0.509093 1.11209 1 0.082322) 0.8 1.8
0)
COMMENT                      #224=(CLabel
COMMENT                            (CWidget 0 (0 0) 1 2 0 0 #148#
18088512 100)
COMMENT                             (LOGPEN 0 0 0) 1
COMMENT                             (LOGFONT 32 12 0 0 700 0 0 0 3 2 1
34
COMMENT                             "Arial") 2.53336 0.666667 0
14.3466
COMMENT                             "Promoter (hCMV-MIE)" "@N" 1 0 0
COMMENT                             5.77577 7.25641 0.346154 #223#)
COMMENT                      #225=(CWideArrow
COMMENT                            (CWideLine
COMMENT                             (CWidget 0 (3 #24# 0) 1 2 0 0 #164#
196625
COMMENT                              100) (LOGPEN 0 0 0) 1 (LOGBRUSH 0
128 0) 1
COMMENT                             4.74221 5.27979 1 0.082322) 0.8 1.8
0)
COMMENT                      #226=(CLabel
COMMENT                            (CWidget 0 (0 0) 1 2 0 0 #148#
37176452 100)
COMMENT                             (LOGPEN 0 0 0) 1
COMMENT                             (LOGFONT 32 12 0 0 700 0 0 0 3 2 1
34
```

FIG. 64R

```
COMMENT                           "Arial") 2.53336 0.666667 0
COMMENT                           "Promoter (hCMV-MIE) (from NotI)" "@N"
1 0 0
COMMENT                           -14.5466 12.1092 11.1795 0.846154
#225#))
COMMENT                     (CObjectList))
COMMENT               #227=(CGroupWidget
COMMENT                     (CWidget 15 (7 49 0) 1 2 0 0 Nil -1015 100)
COMMENT                     (CObjectList
COMMENT                     #228=(CWideArrow
COMMENT                           (CWideLine
COMMENT                             (CWidget 0 (3 #20# 0) 1 2 0 0 #189#
37110564
COMMENT                             100) (LOGPEN 0 0 52275) 1
COMMENT                             (LOGBRUSH 0 3407871 0) 1 5.98725
6.20619 1
COMMENT                             0.082322) 0.8 1.8 0)
COMMENT                     #229=(CLabel (CWidget 0 (0 0) 1 2 0 0 #148#
0 100)
COMMENT                           (LOGPEN 0 0 0) 1
COMMENT                           (LOGFONT 32 12 0 0 700 0 0 0 0 3 2 1
34
COMMENT                           "Arial") 2.53336 0.666667 0
COMMENT                           "Heavy Chain 806 V-Region Insert" "@N"
1 0 0
COMMENT                           -19.2693 4.50909 11.2564 0.846154
#228#)
COMMENT                     #230=(CWideArrow
COMMENT                           (CWideLine
COMMENT                             (CWidget 0 (3 #23# 0) 1 2 0 0 #189#
37136028
COMMENT                             100) (LOGPEN 0 0 52275) 1
COMMENT                             (LOGBRUSH 0 3407871 0) 1 3.96459
4.16401 1
COMMENT                             0.082322) 0.8 1.8 0)
COMMENT                     #231=(CLabel
COMMENT                           (CWidget 0 (0 0) 1 2 0 0 #148#
18088608 100)
COMMENT                           (LOGPEN 0 0 0) 1
COMMENT                           (LOGFONT 32 12 0 0 700 0 0 0 0 3 2 1
34
COMMENT                           "Arial") 2.53336 0.666667 0
COMMENT                           "Light-Chain 806 V-Region insert" "@N"
1 0 0
COMMENT                           -10.3851 19.7092 11.0256 0.846154
#230#))
COMMENT                     (CObjectList))
COMMENT               #232=(CGroupWidget
COMMENT                     (CWidget 52 (7 52 0) 1 2 0 0 Nil 18088352
100)
COMMENT                     (CObjectList
COMMENT                     #233=(CLine
COMMENT                           (CWidget 0 (3 #17# 0) 1 2 0 0 #154#
37060946
COMMENT                             100) (LOGPEN 0 6 6723840) 8 0.835356
COMMENT                             0.445258 0.509093)
```

FIG. 64S

```
COMMENT
COMMENT
18088512 100)
COMMENT
COMMENT
34
COMMENT
"@N" 1
COMMENT
#233#)
COMMENT
COMMENT
100)
COMMENT
1.9
COMMENT
COMMENT
18088528 100)
COMMENT
COMMENT
34
COMMENT
"@N" 1
COMMENT
#235#)
COMMENT
COMMENT
100)
COMMENT
0.082322
COMMENT
COMMENT
COMMENT
18088600 100)
COMMENT
COMMENT
34
COMMENT
"@N" 1
COMMENT
#237#)
COMMENT
COMMENT
268634520
COMMENT
4.67838
COMMENT
COMMENT
COMMENT
18088564 100)
COMMENT
COMMENT
34
COMMENT
"@N" 1
```

```
#234=(CLabel
        (CWidget 0 (0 0) 1 2 0 0 #148#

(LOGPEN 0 0 0) 1
        (LOGFONT 32 12 0 0 700 0 0 0 3 2 1

"Arial") 2.53336 0.666667 0 "5'UTR 1"

0 0 13.5592 4.50909 2.61538 0.846154

#235=(CScratch
        (CWidget 0 (3 #19# 0) 1 2 0 0 #154# 0

(LOGPEN 0 6 6723840) 8 1 0.00896848

0.082322 1)
#236=(CLabel
        (CWidget 0 (0 0) 1 2 0 0 #148#

(LOGPEN 0 0 0) 1
        (LOGFONT 32 12 0 0 700 0 0 0 3 2 1

"Arial") 2.53336 0.666667 0 "5'UTR 2"

0 0 15.7121 1.97573 2.61538 0.846154

#237=(CScratch
        (CWidget 0 (3 #25# 0) 1 2 0 0 #154# 0

(LOGPEN 0 6 6723840) 8 1 4.24209 1.9

1)
#238=(CLabel
        (CWidget 0 (0 0) 1 2 0 0 #148#

(LOGPEN 0 0 0) 1
        (LOGFONT 32 12 0 0 700 0 0 0 3 2 1

"Arial") 2.53336 0.666667 0 "5'UTR 2"

0 0 -6.94704 15.9092 2.61538 0.846154

#239=(CLine
        (CWidget 0 (3 #27# 0) 1 2 0 0 #154#

100) (LOGPEN 0 6 6723840) 8 0.835356

4.74221)
#240=(CLabel
        (CWidget 0 (0 0) 1 2 0 0 #148#

(LOGPEN 0 0 0) 1
        (LOGFONT 32 12 0 0 700 0 0 0 3 2 1

"Arial") 2.53336 0.666667 0 "5'UTR 1"
```

FIG. 64T

```
COMMENT                              0 0 -3.96711 13.3758 2.61538 0.846154
#239#))
COMMENT                      (CObjectList))
COMMENT              #241=(CGroupWidget
COMMENT                      (CWidget 53 (7 53 0) 1 2 0 0 Nil 18088360
100)
COMMENT                      (CObjectList
COMMENT                      #242=(CWideArrow
COMMENT                          (CWideLine
COMMENT                              (CWidget 0 (3 #134 0) 1 2 0 0 #152# 0
100)
COMMENT                              (LOGPEN 0 0 6723840) 1
COMMENT                              (LOGBRUSH 0 10079334 0) 1 2.59031
3.04453 1
COMMENT                              0.082322) 0.8 1.8 1)
COMMENT                      #243=(CLabel
COMMENT                          (CWidget 0 (0 0) 1 2 0 0 #148#
18088592 100)
COMMENT                              (LOGPEN 0 0 0) 1
COMMENT                              (LOGFONT 32 12 0 0 700 0 0 0 0 3 2 1
34
COMMENT                              "Arial") 2.53336 0.666667 0
COMMENT                              "RNA (beta-lactamase) Amp(R)" "@N" 1 0
0
COMMENT                              6.3624 13.3758 9.74359 0.846154
#242#))
COMMENT                      (CObjectList))
COMMENT              #244=(CGroupWidget
COMMENT                      (CWidget 54 (7 54 0) 1 2 0 0 Nil 268634520
100)
COMMENT                      (CObjectList
COMMENT                      #245=(CWideArrow
COMMENT                          (CWideLine
COMMENT                              (CWidget 0 (3 #144 0) 1 2 0 0 #152# 0
100)
COMMENT                              (LOGPEN 0 0 6723840) 1
COMMENT                              (LOGBRUSH 0 10079334 0) 1 1.57476
2.20783 1
COMMENT                              0.082322) 0.8 1.8 0)
COMMENT                      #246=(CLabel
COMMENT                          (CWidget 0 (0 0) 1 2 0 0 #148#
18088520 100)
COMMENT                              (LOGPEN 0 0 0) 1
COMMENT                              (LOGFONT 32 12 0 0 700 0 0 0 0 3 2 1
34
COMMENT                              "Arial") 2.53336 0.666667 0 "mRNA (GS
cDNA)"
COMMENT                              "@N" 1 0 0 8.63373 10.8425 5.76923
0.846154
COMMENT                              #245#)) (CObjectList)) (CObjectList))
COMMENT              #247=(CGroupWidget (CWidget 11 (8 0) 1 2 0 0 Nil -1088
100)
COMMENT                      (CObjectList
COMMENT                      #248=(CGroupWidget
COMMENT                          (CWidget 1 (10 #0# 0) 1 2 0 0 Nil -1227 100)
COMMENT                          (CObjectList
```

FIG. 64U

```
COMMENT                                  #249=(CScratch
COMMENT                                      (CWidget 1 (1 #0# 1) 1 2 0 0 #155# 0
100)
COMMENT                                      (LOGPEN 0 6 10053171) 8 1 3.6048 1.9
0.082322
COMMENT                                      1)
COMMENT                                  #250=(CLabel (CWidget 0 (0 0) 1 2 0 0 #157#
0 100)
COMMENT                                      (LOGPEN 0 0 153) 1
COMMENT                                      (LOGFONT 27 10 0 0 400 0 0 0 3 2 1
18
COMMENT                                      "Georgia") 2.53336 0.555556 128
COMMENT                                      "{\\1 Bam}HI (5059)" "@N (@S)" 5 0 0 -
4.92823
COMMENT                                      28.576 4.07692 0.692308 #249#))
(CObjectList))
COMMENT                                  #251=(CGroupWidget
COMMENT                                      (CWidget 1 (10 #1# 0) 1 2 0 0 Nil 678 100)
COMMENT                                      (CObjectList
COMMENT                                      #252=(CScratch
COMMENT                                          (CWidget 1 (1 #1# 1) 1 2 0 0 #155# 0
100)
COMMENT                                          (LOGPEN 0 6 10053171) 8 1 1.57318 1.9
COMMENT                                          0.082322 1)
COMMENT                                      #253=(CLabel (CWidget 0 (0 0) 1 2 0 0 #157#
0 100)
COMMENT                                          (LOGPEN 0 0 153) 1
COMMENT                                          (LOGFONT 27 10 0 0 400 0 0 0 3 2 1
18
COMMENT                                          "Georgia") 2.53336 0.555556 128
COMMENT                                          "{\\1 Bgl}II (6910)" "@N (@S)" 5 0 0
8.917
COMMENT                                          9.57581 3.41026 0.692308 #252#))
COMMENT                                      (CObjectList))
COMMENT                                  #254=(CGroupWidget
COMMENT                                      (CWidget 1 (10 #3# 0) 1 2 0 0 Nil -320 100)
COMMENT                                      (CObjectList
COMMENT                                      #255=(CScratch
COMMENT                                          (CWidget 1 (1 #3# 1) 1 2 0 0 #155# 669
100)
COMMENT                                          (LOGPEN 0 6 10053171) 8 1 5.98303 1.9
COMMENT                                          0.082322 1)
COMMENT                                      #256=(CLabel
COMMENT                                          (CWidget 0 (0 0) 1 2 0 0 #157#
18146163 100)
COMMENT                                          (LOGPEN 0 0 153) 1
COMMENT                                          (LOGFONT 27 10 0 0 400 0 0 0 3 2 1
18
COMMENT                                          "Georgia") 2.53336 0.555556 128
COMMENT                                          "{\\1 Fse}I (551)" "@N (@S)" 5 0 0 -
14.4711
COMMENT                                          7.04245 2.64103 0.692308 #255#))
COMMENT                                      (CObjectList))
COMMENT                                  #257=(CGroupWidget
COMMENT                                      (CWidget 1 (10 #5# 0) 1 2 0 0 Nil 1368 100)
COMMENT                                      (CObjectList
```

FIG. 64V

```
COMMENT                            #258=(CScratch
COMMENT                                    (CWidget 1 (1 #5# 1) 1 2 0 0 #155#
1170 100)
COMMENT                                    (LOGPEN 0 6 10053171) 8 1 1.09287 1.9
COMMENT                              0.082322 1)
COMMENT                            #259=(CLabel
COMMENT                                    (CWidget 0 (0 0) 1 2 0 0 #157#
37574220 100)
COMMENT                                    (LOGPEN 0 0 153) 1
COMMENT                                    (LOGFONT 27 10 0 0 400 0 0 0 0 3 2 1
18
COMMENT                                    "Georgia") 2.53356 0.555556 128
COMMENT                                    "{\\1 Mid}I (9821)" "@N (@S)" 3 0 0
11.05
COMMENT                                    7.04245 3.25641 0.692308 #258#))
COMMENT                              (CObjectList))
COMMENT                            #260=(CGroupWidget
COMMENT                                    (CWidget 1 (10 #6# 0) 1 2 0 0 R11 -739 100)
COMMENT                                    (CObjectList
COMMENT                              #261=(CScratch
COMMENT                                    (CWidget 1 (1 #6# 1) 1 2 0 0 #155# 898
100)
COMMENT                                    (LOGPEN 0 6 10053171) 8 1 5.28296 1.9
COMMENT                              0.082322 1)
COMMENT                            #262=(CLabel
COMMENT                                    (CWidget 0 (0 0) 1 2 0 0 #157#
37173943 100)
COMMENT                                    (LOGPEN 0 0 153) 1
COMMENT                                    (LOGFONT 27 10 0 0 400 0 0 0 0 3 2 1
18
COMMENT                                    "Georgia") 2.53356 0.555556 128
COMMENT                                    "{\\1 Not}I (1876)" "@N (@S)" 3 0 0 -
11.7199
COMMENT                                    10.8425 3.17949 0.692308 #261#))
COMMENT                              (CObjectList))
COMMENT                            #263=(CGroupWidget
COMMENT                                    (CWidget 1 (10 #7# 0) 1 2 0 0 R11 2798729?
100)
COMMENT                                    (CObjectList
COMMENT                              #264=(CScratch
COMMENT                                    (CWidget 1 (1 #7# 1) 1 2 0 0 #155# 0
100)
COMMENT                                    (LOGPEN 0 6 10053171) 8 1 3.95932 1.9
COMMENT                              0.082322 1)
COMMENT                            #265=(CLabel
COMMENT                                    (CWidget 0 (0 0) 1 2 0 0 #157#
37188964 100)
COMMENT                                    (LOGPEN 0 0 153) 1
COMMENT                                    (LOGFONT 27 10 0 0 400 0 0 0 0 3 2 1
18
COMMENT                                    "Georgia") 1.53356 0.555556 128
COMMENT                                    "{\\1 Pac}I (1387)" "@N (@S)" 3 0 0 -
6.086
COMMENT                                    13.5093 3.33333 0.692308 #264#))
COMMENT                              (CObjectList))
COMMENT                            #266=(CGroupWidget
```

FIG. 64W

```
COMMENT                              (CWidget 1 (10 #9# 0) 1 2 0 0 Nil 18088384
100)
COMMENT                              (CObjectList
COMMENT                              #267=(CScratch
COMMENT                                   (CWidget 1 (1 #9# 1) 1 2 0 0 #155# 0
100)
COMMENT                                   (LOGPEN 0 6 10053171) 8 1 3.45919 1.9
COMMENT                                   0.082322 1)
COMMENT                              #268=(CLabel
COMMENT                                   (CWidget 0 (0 0) 1 2 0 0 #157#
18088352 100)
COMMENT                                   (LOGPEN 0 0 153) 1
COMMENT                                   (LOGFONT 27 10 0 0 400 0 0 0 0 3 2 1
18
COMMENT                                   "Georgia") 2.53336 0.555556 128
COMMENT                                   "(\\1 Sal)I (5335)" "@N (@S)" 5 0 0 -
3.73591
COMMENT                                   29.8427 2.94872 0.692308 #267#))
COMMENT                              (CObjectList))
COMMENT                         #269=(CGroupWidget
COMMENT                              (CWidget 2 (10 #2# 0) 1 2 0 0 Nil -181 100)
COMMENT                              (CObjectList
COMMENT                              #270=(CScratch
COMMENT                                   (CWidget 1 (1 #2# 1) 1 2 0 0 #155# 0
100)
COMMENT                                   (LOGPEN 0 6 10053171) 8 1 6.20619 1.9
COMMENT                                   0.082322 1)
COMMENT                              #271=(CLabel
COMMENT                                   (CWidget 0 (0 0) 1 2 0 0 #147# 393229
100)
COMMENT                                   (LOGPEN 0 0 13403563) 1
COMMENT                                   (LOGFONT 27 10 0 0 400 0 0 0 0 3 2 1
19
COMMENT                                   "Georgia") 2.53336 0.555556 0
COMMENT                                   "(\\1 Dra)III (128)" "@N (@S)" 5 0 0 -
15.8185
COMMENT                                   3.24241 3.41026 0.692308 #270#)
COMMENT                              #272=(CScratch
COMMENT                                   (CWidget 2 (1 #2# 2) 1 2 0 0 #155# 509
100)
COMMENT                                   (LOGPEN 0 6 10053171) 8 1 5.98725 1.9
COMMENT                                   0.082322 1)
COMMENT                              #273=(CLabel
COMMENT                                   (CWidget 0 (0 0) 1 2 0 0 #147# 945
100)
COMMENT                                   (LOGPEN 0 0 13403563) 1
COMMENT                                   (LOGFONT 27 10 0 0 400 0 0 0 0 3 2 1
18
COMMENT                                   "Georgia") 2.53336 0.555556 0
COMMENT                                   "(\\1 Dra)III (543)" "@N (@S)" 5 0 0 -
14.9124
COMMENT                                   5.77577 3.48718 0.692308 #272#))
COMMENT                              (CObjectList))
COMMENT                         #274=(CGroupWidget
COMMENT                              (CWidget 2 (10 #4# 0) 1 2 0 0 Nil 678 100)
COMMENT                              (CObjectList
```

FIG. 64X

```
COMMENT                          #275=(CScratch
COMMENT                                  (CWidget 1 (1 #4# 1) 1 2 0 0 #155#
1393 100)
COMMENT                                  (LOGPEN 0 6 10053171) 8 1 6.27266 1.9
COMMENT                                  0.082322 1)
COMMENT                          #276=(CLabel
COMMENT                                  (CWidget 0 (0 0) 1 2 0 0 #147#
37174492 100)
COMMENT                                  (LOGPEN 0 0 13408563) 1
COMMENT                                  (LOGFONT 27 10 0 0 400 0 0 0 3 2 1
18
COMMENT                                  "Georgia") 2.53336 0.555556 0
COMMENT                                  "{\\1 Hin}dIII (2)" "@N (@S)" 5 0 0 -
15.9515
COMMENT                                  1.97573 3.10256 0.692308 #275#)
COMMENT                          #277=(CScratch
COMMENT                                  (CWidget 2 (1 #4# 2) 1 2 0 0 #155# 0
100)
COMMENT                                  (LOGPEN 0 6 10053171) 8 1 4.23259 1.9
COMMENT                                  0.082322 1)
COMMENT                          #278=(CLabel
COMMENT                                  (CWidget 0 (0 0) 1 2 0 0 #147#
28387876 100)
COMMENT                                  (LOGPEN 0 0 13408563) 1
COMMENT                                  (LOGFONT 27 10 0 0 400 0 0 0 3 2 1
18
COMMENT                                  "Georgia") 2.53336 0.555556 0
COMMENT                                  "{\\1 Hin}dIII (3869)" "@N (@S)" 5 0 0
#277#))                                  -7.71376 17.1759 4.23077 0.692308
COMMENT                                  (CObjectList))
COMMENT                          #279=(CGroupWidget
COMMENT                                  (CWidget 2 (10 #8# 0) 1 2 0 0 Nil 1 100)
COMMENT                                  (CObjectList)
COMMENT                          #280=(CScratch
COMMENT                                  (CWidget 1 (1 #8# 1) 1 2 0 0 #155#
37028212
                                         100) (LOGPEN 0 6 10053171) 8 1
COMMENT
4.16401 1.9
COMMENT                                  0.082322 1)
COMMENT                          #281=(CLabel
COMMENT                                  (CWidget 0 (0 0) 1 2 0 0 #147#
28372436 100)
COMMENT                                  (LOGPEN 0 0 13408563) 1
COMMENT                                  (LOGFONT 27 10 0 0 400 0 0 0 3 2 1
18
COMMENT                                  "Georgia") 2.53336 0.555556 0
COMMENT                                  "{\\1 Rsr}II (3999)" "@N (@S)" 5 0 0 -
7.08453
COMMENT                                  18.4426 3.5641 0.692308 #280#)
COMMENT                          #282=(CScratch
COMMENT                                  (CWidget 2 (1 #8# 2) 1 2 0 0 #155# 0
100)
COMMENT                                  (LOGPEN 0 6 10053171) 8 1 3.96459 1.9
COMMENT                                  0.082322 1)
COMMENT                          #283=(CLabel
```

FIG. 64Y

```
COMMENT                         (CWidget 0 (0 0) 1 2 0 0 #147#
29374715 100)
COMMENT                         (LOGPEN 0 0 13408563) 1
COMMENT                         (LOGFONT 27 10 0 0 400 0 0 0 3 2 1
18
COMMENT                          "Georgia") 2.53336 0.555556 0
COMMENT                          ".\\L Rsr)II (4377)" "@N (@S)" 5 0 0 -
6.14723
COMMENT                         22.0426 3.41026 0.692308 #282#;)
COMMENT                    (CObjectList)}} (CObjectList))
COMMENT            #284=(CGroupWidget (CWidget 14 (16 0) 1 2 0 0 Nil 18088384
100)
COMMENT                    (CObjectList) (CObjectList))
COMMENT            #285=(CGroupWidget (CWidget 12 (0 0) 1 2 0 0 Nil 18088384
100)
COMMENT                    (CObjectList) (CObjectList)) (CObjectList)))
COMMENT         (CSeqView 10 10 (CObjectList) (CObList) 1 (CObList)) (CObList)
1095072823
COMMENT         (CStringList) 1145656400 2034918081 (CObList)))
FEATURES              Location/Qualifiers
     C_region         553..1643
                      /vntifkey="2"
                      /label=GeneArt\HC\C-Reg
                      /note="GeneArt human HC C-Reg"
     polyA_signal     1644..1875
                      /vntifkey="25"
                      /label=SV40\polyA
     misc_feature     7356..7699
                      /vntifkey="21"
                      /label=Signal\(SV40E\(and\SV40\ori))
                      /note="SV40E (and SV40 ori)"
     misc_RNA         complement(6121..6981)
                      /vntifkey="53"
                      /label=RNA\(beta-lactamase)\Amp(R)
                      /note="beta-lactamase"
     mRNA             7707..8906
                      /vntifkey="54"
                      /label=mRNA\(GS\cDNA)
                      /note="GS cDNA"
     promoter         9784..10926
                      /vntifkey="30"
                      /label=Promoter\(hCMV-MIE)
                      /note="hCMV-MIE promoter"
     intron           8809..9760
                      /vntifkey="15"
                      /label=Intron\(SV40\intron\+\poly\A)
                      /note="SV40 intron + poly A"
     5'UTR            10927..11047
                      /vntifkey="52"
                      /label=5'UTR_1
                      /note="5'UT"
     intron           11048..11374
                      /vntifkey="15"
                      /label=Intron_1
                      /note="intron"
     5'UTR            11875..11891
```

FIG. 64Z

```
                         /vntifkey="52"
                         /label=5'UTR_2
                         /note="5'UT"
     V_region      128..542
                         /vntifkey="45"
                         /label=Heavy\Chain\806\V-Region\Insert
     modified_base 4315..4315
                         /vntifkey="23"
                         /label=HtoY
                         /note="Histidine-to-Tyrosine change in the 806 Light-Chain
variable CDR3 region"
     modified_base 4716..4716
                         /vntifkey="23"
                         /label=Light-Const.\chg\2.1-3
                         /note="Light-chain c-region change 2.1-3"
     V_region      3899..4376
                         /vntifkey="45"
                         /label=Light-Chain\806\V-Region\insert
     promoter      1684..2902
                         /vntifkey="30"
                         /label=Promoter\(hCMV-MIE)\(from\NotI)
                         /note="Promoter (hCMV-MIE) (from NotI)"
     5'UTR         3851..3867
                         /vntifkey="52"
                         /label=5'UTR_2
                         /note="5'UT"
     intron        3024..3850
                         /vntifkey="15"
                         /label=Intron_1
                         /note="Intron"
     5'UTR         2903..3023
                         /vntifkey="52"
                         /label=5'UTR_1
                         /note="5'UT"
     polyA_signal  4827..5063
                         /vntifkey="25"
                         /label=SV40\poly\A
                         /note="SV40 poly A"
     C_region      4390..4600
                         /vntifkey="2"
                         /label=Codon-Optimized\Kappa\Constant\Region
BASE COUNT     3000 a     3039 c     2868 g     2984 t
ORIGIN
        1 aagcttgccg ccaccatgga tggacctggg ggcatccttt tcctgctagc agccgccaca
       61 gttaagggc tgccaaatcc cagtgaggag gaagggatcg aagtcaacca tcgaagcag
      121 tcaccagtg aaggggctt ccatccactc tgtgtcttc tctacaggtg tccacagca
      181 gctgcagctc caagagagtg gacctgggct tgtcaagccg agtcaaactt tgtccctaac
      241 atgtactgtg tccggatact ctatctcatc agattttgcg tggaattgca taaggcagcc
      301 accaggaaa ggtttagaat ggatgggcta catatcatac tctgggaaca ccagatatca
      361 acctctctg aaaagccgga tcacaatctc aaggacacg tcgaagaatc agttcttcct
      421 gaaactgaac tccgttacag ccgcagacac agcaacatat tactgcgtaa ccgctggcag
      481 aggttcccc tatggggac agggcccct agtgacagtg gcagcggga agatggcaca
      541 cgtggcgg cctctgcgcc tcggccagc tctgtcccac accgggtca catggcacct
      601 tctctcttcc agcctccacc aaggcccaa gcgtgttccc cctggcccc agcagcaaga
      661 gaccagcgg cggcacagcc gcctggct gctggtgaa ggactactc ccgagcccg
      721 tcacggtgag ctggaacagc ggagccctga ctccggcgt gcacacctt ccgcctgtc
```

FIG. 64AA

```
 781 tgcagagcag cggcctgtac agcctgagca gcgtggtgac cgtgcccagc agcagcctgg
 841 gcacccagac ctacatctgc aacgtgaacc acaagcccag caacaccaag gtggacaaga
 901 aggtggagcc caagagctgc gacaagaccc acacctgccc ccctgccca gcccagagc
 961 tgctgggcgg accctccgtg ttcctgttcc ccccaagcc caaggacacc ctgatgatca
1021 gcaggacccc cgaggtgacc tgcgtggtgg tggacgtgag ccacgaggac cagaggtga
1081 agttcaattg gtatgtggac ggcgtggagg tgcacaacgc caagaccaag cccagagaag
1141 agcagtacaa cagcacctac agggtggtgt ccgtgctgac cgtgctgcac caggactggc
1201 tgaacggcaa ggaatacaaa tgcaaggtct ccaacaaggc cctgccagcc cccatcgaaa
1261 agaccatcag caaggccaag ggccagccac gggagcccca ggtgtacacc ctgcccccct
1321 cccgggacga gctgaccaag aaccaggtgt ccctgacctg tctggtgaag ggcttctacc
1381 ccagcgacat cgccgtggag tgggagagca acggccagcc cgagaacaac tacaagacca
1441 cccccccagt gctggacagc gacggcagct tcttcctgta cagcaagctg accgtggaca
1501 agagcaggtg gcagcaggc aacgtgttca gctgcagcgt gatgcacgag gccctgcaca
1561 accactacac ccagaagagc ctgagcctgt cccccggcaa gtgatgacga cgcggccgtg
1621 cggacgaccg aattcattga tcataatcag ccataccaca tttgtagagg ttttacttgc
1681 tttaaaaaac ctcccacacc tccccctgaa cctgaaacat aaaatgaatg caattgttgt
1741 tgttaacttg tttattgcag cttataatgg ttacaaataa agcaatagca tcacaaattt
1801 cacaaataaa gcatttttt cactgcattc tagttgtggt ttgtccaaac tcatcaatgt
1861 atcttatcat gtctggcggc cgcgatatt tgaaaatatg gcatattgaa aatgtcgccg
1921 atgtgagttt ctgtgtaact gatatcgcca ttttccaaa agtgattttt gggcatacgc
1981 gatatctgca atagcgctta atataggtta cgggatgg cgataganga cttggtgac
2041 ttgggcgatt ctgtgtgtcg caaatatcgc agtttcgata taggtgacag acgatatgag
2101 gctatatcgc cgatagaggc gacatcaagc tggcacatgg ccaatgcata tcgatctata
2161 cattgaatca atattggcca ttagccatat tattcattgg ttatatagca taaatcaata
2221 ttggctattg gccattgcat acgttgtatc catatcataa tatgtacatt tatattggct
2281 catgtccaac attaccgcca tgttgacatt gattattgac tagttattaa tagtaatcaa
2341 ttacgggtc attagttcat agcccatata tggagttccg cgttacataa cttacggtaa
2401 atggcccgcc tggctgaccg cccaacgacc cccgcccatt gacgtcaata atgacgtatg
2461 ttcccatagt aacgccaata gggactttcc attgacgtca atgggtggag tatttacggt
2521 aaactgccca cttggcagta catcaagtgt atcatatgcc aagtacgccc cctattgacg
2581 tcaatgacgg taaatggccc gcctggcatt atgcccagta catgacctta tgggacttc
2641 ctacttggca gtacatctac gtattagtca tcgctattac catggtgatg cggttttggc
2701 agtacatcaa tgggcgtgga tagcggtttg actcacgggg atttccaagt ctccaccca
2761 ttgacgtcaa tgggagtttg ttttggcacc aaaatcaacg ggactttcca aaatgtcgta
2821 acaactccgc cccattgacg caaatgggcg gtaggcgtgt acggtgggag gtctatataa
2881 gcagagctcg tttagtgaac cgtcagatcg cctggagacg ccatccacgc tgttttgacc
2941 tccatagaag acaccgggac cgatccagcc tccgcggccg ggaacggtgc attggaacgc
3001 ggattccccg tgccaagagt gacgtaagta ccgcctatag agtctatagg cccacccct
3061 tggcttctta tgcatgctat actgtttttt gcttggatc tatacaaccc cgcttctca
3121 tgttataggt gatggtatag cttagcctat aggtgtgggt tattgaccat tattgaccac
3181 tcccctattg gtgacgatac tttccattac taatccataa catggctctt gccacaact
3241 ctcttttattg gctatatgcc aatacactgt ccttcagaga ctgacggga tctgtatt
3301 ttacaggatg gggtctcatt tattatttac aaattcacat atacaacacc acgtcccca
3361 gtgcccgcag ttttttattaa acataacgtg gatctccac gcaatctcg ggtacgtgtt
3421 ccggacatgg gctcttctcc ggtagcggcg gagcttctac atccgagccc tgctcccatg
3481 cctccagcga ctcatggtcg ctggcagct cctgctcct aacagtggag gccagactta
3541 ggcacagcac gatgccacc accaccagtg tgccgcacaa ggccgtggcg taggtgtatg
3601 tgtctgaaaa tgagctcgg gagcgggctt gacatttgga cgcatttgga agacttaagg
3661 cagggcaga agaagatgca ggcagcgag ttgttgtgtt ctgataagag tcagaggtaa
3721 ctcccgttgc ggtgctgtta acgtggagg gcagtgtagt ctgagcagta ctgttgctg
3781 ccgcgcgcg caccagacat aatagctgac agactaacag actgttcctt tccatgggtc
3841 tttctgcag tcacgtcct tgacacgaag cttgccgcca catggattg gacttggaga
3901 atactgtttc ttgtagcagc cgcaacaggt aagggctgc caaatccag tgaggaggaa
3961 gggatcgaag gtgaccatcg aagccagtca aggggcgga ccgcttccat ccactcctgt
4021 gtcttctcta caggtgttca cagtgatatt cagatgactc agagtccatc cagcatgtca
4081 gtctccgtgg gagataggt gacgataacc tgtcattcaa gccaagacat caactccaat
```

FIG. 64BB

```
4141 attggatggc tccaacagaa ggctggtaag tccttcaaag gactaatcta tcacggaaca
4201 aacttggacg acggcgtgcc atcgagattt tcagggtctg gcagcgggac cgactataca
4261 ctgaccatct ctagcttaca accagaggac ttgccacat actactgcgt ccagtcgct
4321 cagttccct ggacattcgg cgcgcaca aaactcgaaa tcaaacgtga gtagcggtcc
4381 gttaattaaa gatccttcta aactctgagg gggtcggatg acgtggccat tgttacttaa
4441 acaccatcct gtttgcttct ttcctcagga acgtgcag ctccctccgt gttcatcttc
4501 ccccatccg acgagcaact gaagtcaggc acagcctccg tgtgtgcct cctaataac
4561 ttttacccaa gagaggccaa agtccagtgg aaagtggaca acgcactaca gagcgggaac
4621 tctcaggaaa gcgtgacga gcaggactca aaagattcaa catacagcct atcttctacc
4681 ctgacactgt caaaagctga ttatgaaaag cacaaagta atgcctgtga agtaactcat
4741 cagggactca gcagccctgt cactaaaagt tttaatagag gcgaatgctg ataagcggcc
4801 gtgcggacga ccgaattcat tgatcataat cagccatacc acattgtag aggttttact
4861 tgctttaaaa aacctccac actcccct gaacctgaaa cataaaatga atgcaattgt
4921 tgtgttaac ttgttattg cagcttataa tggttacaaa taaagcaata gcatcacaaa
4981 tttcacaat aaagcatttt tttcactgca ttctagttgt ggtttgtcca aactcatcaa
5041 tgtatcttat catgtctgga tcctctaccg cggacgcatc gtggccggca tcacggggcg
5101 cacacggtgcg gttgtcgcgc cctatatcgc cgacatcacc gatggggaag atcgggtcg
5161 ccacttcggg ctcatgagcg cttgtttcgg cgtgggtatg gtggcaggcc ccgtggccgg
5221 gggactgttg ggcgccatct ccttgcatgc accattcctt gcggcggcgg tgctcaacgg
5281 cctcaaccta ctactgggct gcttcctaat gcaggagtcg cataagggag agcgtcgacc
5341 tcgggccgcg ttgctggcgt ttttccatag gctccgcccc cctgacgagc atcacaaaaa
5401 tcgacgctca agtcagaggt ggcgaaaccc gacaggacta taaagatacc aggcgtttcc
5461 ccctggaagc tccctcgtgc gctctcctgt tccgaccctg ccgcttaccg gatacctgtc
5521 cgcctttctc ccttcgggaa gcgtggcgct ttctcatagc tcacgctgta ggtatctcag
5581 ttcggtgtag gtcgttcgct ccaagctggg ctgtgtgcac gaaccccccg ttcagcccga
5641 ccgctgcgcc ttatccggta actatcgtct tgagtccaac ccggtaagac acgacttatc
5701 gccactggca gcagccactg gtaacaggat tagcagagcg aggtatgtag gcggtgctac
5761 agagttcttg aagtggtgc ctaactacgg ctactagga gaacagtat tggtatctg
5821 cgctctgctg aagccagtta ccttcggaaa aagagttggt agctcttgat ccggcaaaca
5881 aaccaccgct ggtagcggtg gtttttttgt ttgcaagcag cagattacga gcagaaaaaa
5941 aggatctcaa gaagatcctt tgatctttc tacggggtct gacgctcagt ggaacgaaaa
6001 ctcacgttaa gggattttgg tcatgagatt atcaaaaagg atcttcacct agatcctttt
6061 aaattaaaaa tgaagtttta atcaatcta agtatatat gagtaaactt ggtctgacag
6121 ttaccaatgc ttaatcagtg aggcacctat ctcagcgatc tgtctatttc gttcatccat
6181 agttgcctga ctccccgtcg tgtagataac tacgatacgg gagggcttac catctggccc
6241 cagtgctgca atgataccgc gagacccacg ctcaccggct ccagatttat cagcaataaa
6301 ccagccagcc ggaagggccg agcgcagaag tggtcctgca actttatccg cctccatcca
6361 gtctattaat tgttgccggg aagctagagt aagtagttcg ccagttaata gtttgcgcaa
6421 cgttgttgcc attgctacag gcatcgtggt gtcacgctcg tcgtttggta tggcttcatt
6481 cagctccggt tcccaacgat caaggcgagt tacatgatcc cccatgttgt gcaaaaaagc
6541 ggttagctcc ttcggtcctc cgatcgttgt cagaagtaag ttggccgcag tgttatcact
6601 catggttatg gcagcactgc ataattctct tactgtcatg ccatccgtaa gatgcttttc
6651 tgtgactggt gagtactcaa ccaagtcatt ctgagaatag tgtatgcggc gaccgagttg
6721 ctcttgcccg gcgtcaatac gggataatac cgcgccacat agcagaactt taaaagtgct
6781 catcattgga aaacgttctt cggggcgaaa actctcaagg atcttaccgc tgttgagatc
6841 cagttcgatg taacccactc gtgcacccaa ctgatcttca gcatctttta ctttcaccag
6901 cgtttctggg tgagcaaaaa caggaaggca aaatgccgca aaaaagggaa taagggcgac
6961 acggaaatgt tgaatactca tactcttcct ttttcaatat tattgaagca tttatcaggg
7021 ttattgtctc atgagcggat acatatttga atgtatttag aaaaataaac aaataggggt
7081 tccgcgcaca tttccccgaa aagtgccacc tgacgtctaa gaaaccatta ttatcatgac
7141 attaacctat aaaaataggc gtatcacgag gccctgatgg cgtttgcgg caccatcgt
7201 tcgtaatgtt ccgtggcacc gaggacaacc ctcaagagaa aatgtaatca cactggctca
7261 ccttcgggtg ggcctttctg cgtttataag agacactttt agtttaaga aggttggtaa
7321 attccttgcg gcttgcag ccagcagag tccggctgtg gaatgtgtgt cagttaggt
7381 gtggaaagtc ccaggctcc ccagcaggca gaagtatgca aagcatgcat ctcaattagt
7441 cagcaaccag gtgtggaaag tccccaggct cccagcagg caaagtatg caaagcatgc
```

FIG. 64CC

```
 7501 atctcaatta gtcagcaacc atagtccgc ccctaactcc gcccatccg ccctaactc
 7561 cgcccagttc cgcccattct ccgcccatg gctgactaat ttttttatt tatgcagagg
 7621 ccgaggccgc ctcggcctct gagctattcc agaagtagtg aggaggcttt tttggaggcc
 7681 taggcttttg caaaaagcta gcttggcc accgctcaga gcacttcca ccatggccac
 7741 ctcagcaagt tcccacttga acaaaaacat caagcaaatg tacttgtgcc tgccccaggg
 7801 tgagaaagtc caagccatgt atatctgggt tgatggtact ggagaaggac tgcgctgcaa
 7861 aacccgcacc ctggactgtg agcccaagtg tgtagaagag ttacctgagt ggaatttga
 7921 tgctctagt acctttcagt ctgagggctc caacagtgac atgtatctca gccctgttgc
 7981 catgtttcgg gaccccttcc gcagagatcc caacaagctg gtgtctgtg aagttttcaa
 8041 gtacaacggg aagcctgcag agaccaattt aaggcactcg tgtaaacgga taatggacat
 8101 ggtgagcaac cagcaccct ggtttggaat ggaacaggag tatactctga tggaacaga
 8161 tggcaccctt tttggttggc ctccaatggc ctttctggg cccaaggtc cgtattactg
 8221 tggtgtgggc gcagacaaag cctatggcag ggatatcgtg gaggctcact accgcgcctg
 8281 ctgtatgct ggggtcaaga ttacaggaac aaatgcgag gtcatgcctg cccagtggga
 8341 actccaaata ggacctctgt aaggaatccg catgggagat catctctggg tggccgttt
 8401 catcttgcat cgagtatgtg aagactttgg ggtaatagca acctttgacc ccaagcccat
 8461 tcctgggaac tggaatggtg caggctgcca taccaacttt agcaccaagg ccatgcggga
 8521 ggagaatggt ctgaagcaca tcgaggaggc catcgagaaa ctaagcaagc ggcaccggta
 8581 ccacattcga gcctacgatc ccaaggggg cctgacaat gcccgtggtc tgactgggtt
 8641 ccaagaaacg tccaacatca acgactttc tgctggtgtc gccaatcgca gtgccagcat
 8701 ccgcattccc cggactgtcg gccaggagaa gaaaggttac ttgaagacc gggcccctc
 8761 tgccaattgt gacccctttg cagtgacaga agccatcgtc cgcacatgcc ttctcaatga
 8821 gactggcgac gagcccttcc aatacaaaaa ctaattagac tttgagtgat cttgagctt
 8881 tcctagttca tcccacccccg cccagagag atctttgtga aggaacctta cttctgtggt
 8941 gtgacataat tggacaaact acctacagag atttaaagct caaggtaaa tataaaattt
 9001 ttaagtgtat aatgtgttaa actactgatt ctaattgttt gtgtattta gattccaacc
 9061 tatggaactg atgaatggga gcagtggtgg aatgcctta atgaggaaaa cctgttttgc
 9121 tcagaagaaa tgccatctag tgatgatcaa gctgtgctg acctcaaca ttctactcct
 9181 ccaaaaaaga agagaaaggt agaagaccc aaggactttc cttcagaatt gctaagtttt
 9241 ttgagtcatg ctgtgtttag taatagaact cttgcttgct ttgctattta caccacaaag
 9301 gaaaaagctg cactgctata caagaaaatt atggaaaaat attctgtaac ctttataagt
 9361 aggcataaca gttataatca taacatactg tttttcttta ctccacacag gcatagagtg
 9421 tctgctatta taactatgc tcaaaattg tgtacctta gttttaat ttgtaagggg
 9481 gttaataagg aatatttgat gtatagtgcc ttgactagag atcataatca gccataccac
 9541 atttgtagag gttttacttg ctttaaaaaa cctcccacac ctccccctga acctgaaaca
 9601 taaaatgaat gcaattgttg ttgttaactt gtttattgca gcttataatg gttacaaata
 9661 aagcaatagc atcacaaatt tcacaaataa agcatttttt tcactgcatt ctagttgtgg
 9721 tttgtccaaa ctcatcaatg tatcttatca tgtctggatc tagcttcgtg tcaaggacgg
 9781 tgactgcagt gaataataaa atgtgtgttt gtccgaaata cgcgttttga atttctgtc
 9841 gccgactaaa ttcatgtcgc gcgatagtgg tgtttatcgc cgatagagat ggcgatattg
 9901 gaaaaatcgt atttgaaaaa atggatgcgga ccgtatgtaa gtttctgtgt
 9961 aactgatatc gccattttc caaagtgat ttttggcat acgcgatatc tggcgatagc
10021 gcttatatcg tttacgggg atggcgatag acgactttgg tgacttggc gattctgtgt
10081 gtgcaaata tgcagtttc gatataggtg acagacgata tgaggctata tgccgatag
10141 aggcgacatc aagctggcac atggccaatg catatcgatc tatacattga atcaatattg
10201 gccattagcc atattattca ttggttatat agcataaatc aatattggct attggccatt
10261 gcatacgttg tatccatatc ataatatgta catttatatt ggctcatgtc aacattacc
10321 gccatgttga cattgattat tgactagtta ttaatagtaa tcaattacgg ggtcattagt
10381 tcatagccca tatatggagt tccgcgttac ataacttacg gtaaatggcc cgcctggctg
10441 accgcccaac gacccccgcc cattgacgtc aataatgacg tatgttccca tagtaacgcc
10501 aatagggact ttccattgac gtcaatgggt ggagtattta cggtaaactg cccacttggc
10561 agtacatcaa gtgtatcata tgccaagtac gccccctatt gacgtcaatg acggtaaatg
10621 gcccgcctgg cattatgccc agtacatgac cttatgggac tttcctactt ggcagtacat
10681 ctacgtatta gtcatcgcta ttaccatggt gatgcggttt tggcagtaca tcaatgggcg
10741 tggatagcgg tttgactcac ggggatttcc aagtctccac cccattgacg tcaatgggag
10801 tttgttttgg caccaaaatc aacgggactt tccaaaatgt cgtaacaact ccgccccatt
```

FIG. 64DD

```
10861 gacgcaaatg ggcggtaggc gtgtacggtg ggaggtctat ataagcagag ctgtttagt
10921 gaaccgtcag atcgcctgga gacgccatcc acgctgtttt gacctccata gaagacaccg
10981 ggaccgatcc agcctccgcg gccgggaacg gtgcattgga acgcggattc ccgtgccaa
11041 gagtcacgta agtaccgcct atagagtcta tagcccacc cccttgcctt ctatgcatg
11101 ctatactgtt ttggcttgg ggtctataca ccccgcttc ctcatgttat aggtgatggt
11161 atagcttagc ctataggtgt gggttattga ccattattga ccactccct attggtgacg
11221 atactttcca ttactaatcc ataacatggc tctttgccac aactctcttt attggctata
11281 tgccaataca ctgtccttca gagactgaca cggactctgt attttacag gatgggtct
11341 catttattat ttacaaattc acatatacaa cacacacgtc cccagtgcc gcagttttta
11401 ttaaacataa cgtgggatct ccacgcgaat ctcgggtacg tgttccggac atgggtctt
11461 ctccggtagc ggccggagctt ctacatccga gccctgctcc catgcctcca gcgactcatg
11521 gtgctcggc agctccttgc tcctaacagt ggaggccaga cttaggcaca gcacgatgcc
11591 caccaccacc agtgtgccgc acaaggccgt gcggtaggg tatgtctctg aaatgagct
11641 cgggcagcgg gctgcaccg ctgacgcatt tggaagactt aaggcagcgg cagaagaaga
11701 tgccggcagc tcagttgttg tgttctgata agagtcagag gtaactcccg ttgcggtgct
11761 gttaacggtg gagggcagtg tagtctgagc agtactcgtt gctgccgcgc gcgccaccag
11821 acataatagc tgacagacta acagactgtt cctcccatg ggtctttct gcagtcaccg
11881 tccttgacac g
//
```

FIG. 64EE

Light Chain
CDR1-806  23 RSSQDINSNIG
CDR1-175  23 HSSQDISSNIG
CDR2-806  49 YHGTNLDD
CDR2-175  49 YHGTNLED
CDR3-806  89 VQYAQFPWT
CDR3-175  89 VQYGQFPWT Heavy Chain
CDR1-806  31 SDFAWN
CDR1-175  31 SDYAWN
CDR2-806  51 YISYSGNTRYNPSLKS
CDR2-175  51 YISYSANTRYNPSLKS
CDR3-806  97 VTAGRGFPY
CDR3-175  97 ATAGRGFPY First residue number is given.
Underline indicates the residues which contact EGFR287-302

FIG. 65

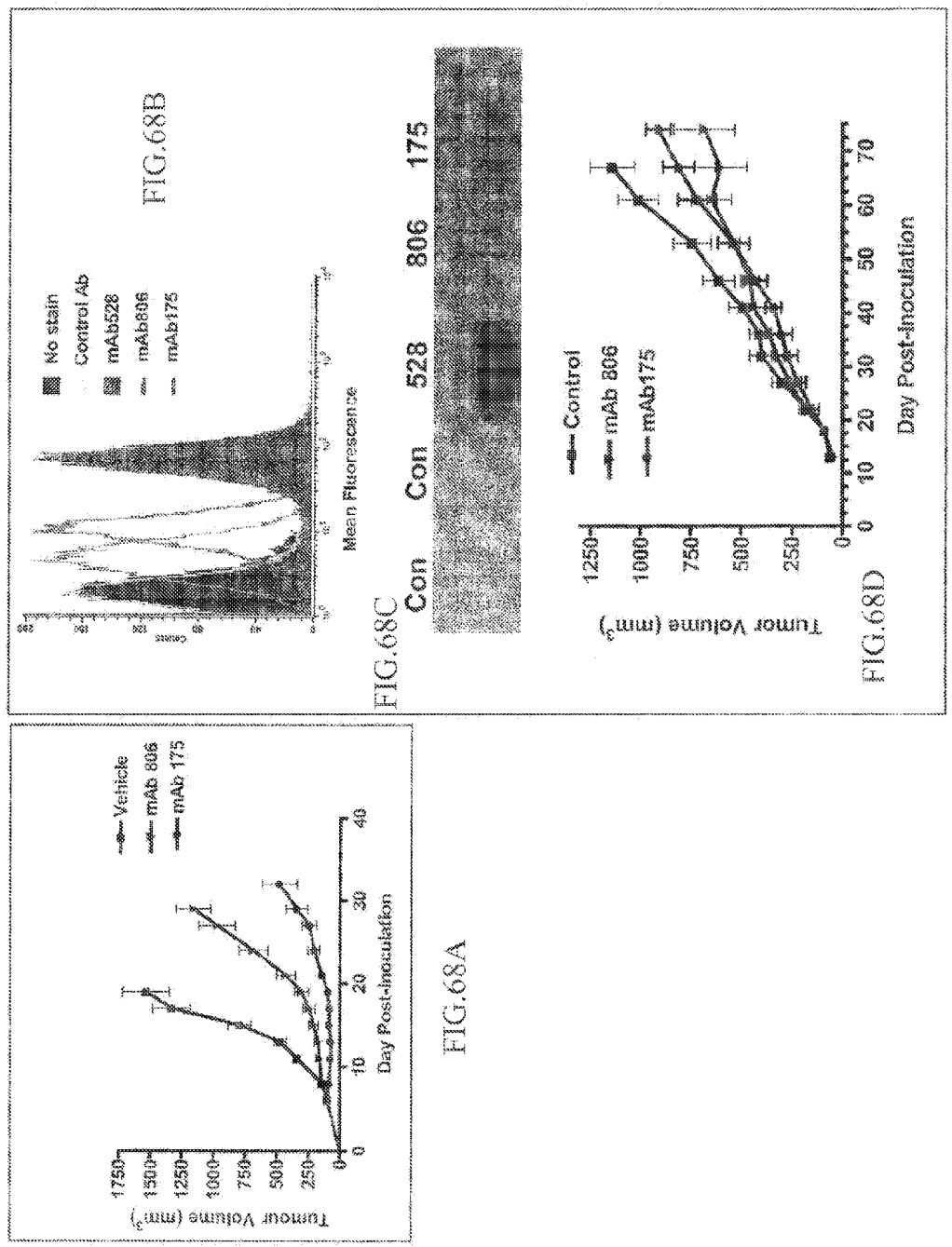

175 epitope 806 epitope

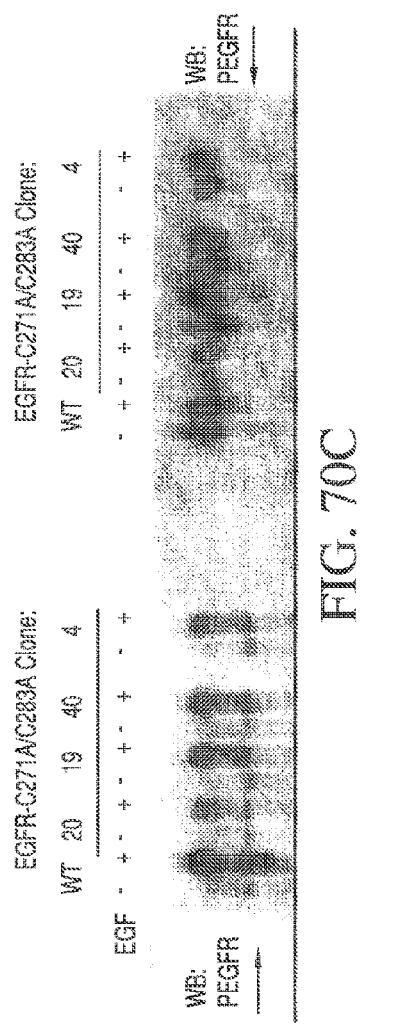
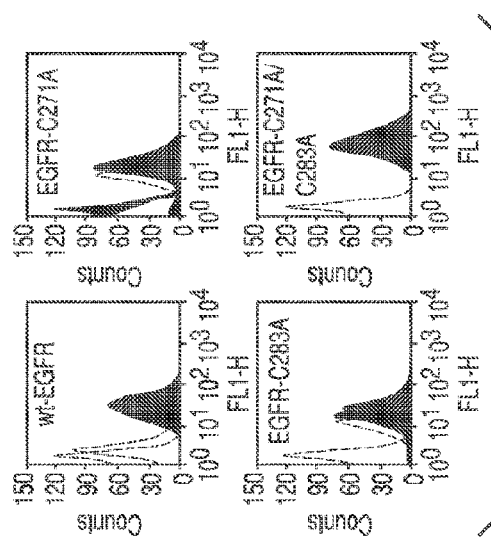
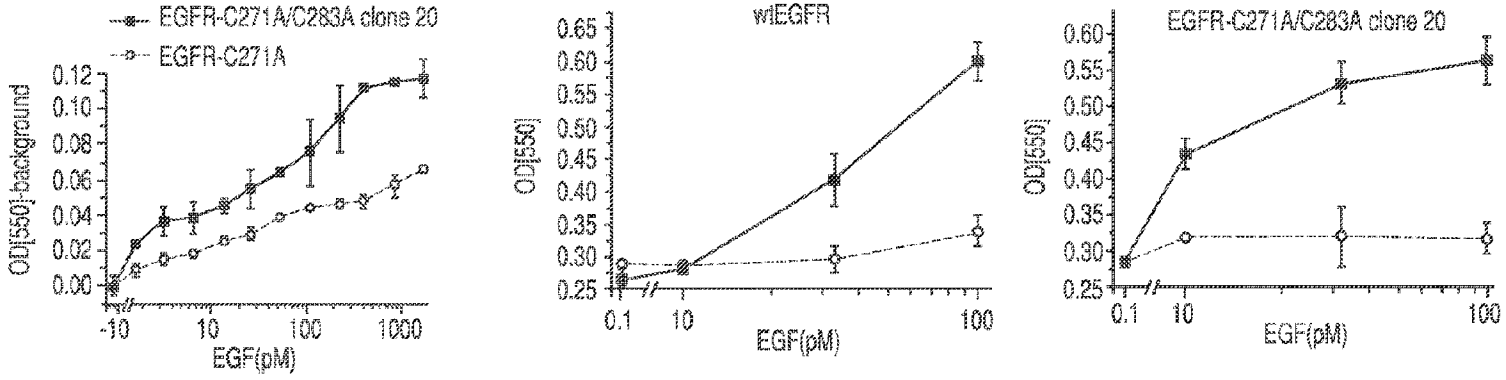
FIG. 70A
FIG. 70B
FIG. 70C
FIG. 70D

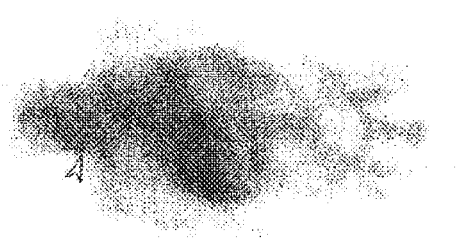
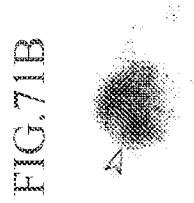
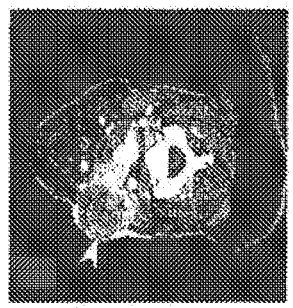
FIG. 71A
FIG. 71B
FIG. 71C mAb175 VH Chain: Nucleic Acid and Amino Sequences Nucleic Acid Sequence TTAGTCAAGCTGCAGGAGTCTGGACCTAGCTTGGTGAAACCTGGCACTGTCACTGGCTA
CTCAATCACCAGTGACTATGCCTGGAACTGGATCCGGCAGTTCCAGGAAACAAACTAAG
TTACAGTGCTAACACTAGGTACAACCCATCTCAAAAGTCGAATCTATCACTCGAGAACCAATTC
TTCCTGCAGTTGAATTCTGTGACTACTGAGGACACAGCCACATATTACTGTGCAACGGCGGGTTCCTTACT
GGGGCCAAGGGACTCTGGTCTCTGCAGCCAAAACGACACCC (SEQ ID NO:128)

FIG. 74A

Amino Acid Sequence

LVKLQESGPSLVKPSQSLSLTCTVTGYSITSDYAWNWIRQFPGNKLEWMGYISYSANTRYNPSLKSRISITRDTSKNQFFLQLN
                CDR1                                    CDR2
SVTTEDTATYYCATAGRGFPYWGQGTLVTVSA (SEQ ID NO:129)
         CDR3

FIG. 74B mAb175 VL Chain: Nucleic Acid and Amino Sequences

Nucleic Acid Sequence

GACATTGTGCTGACCCAGTCTCCATCCTCCATGTCTCTATCTCTGGGAGACACAGTCAGTATCACTTGCATTCAAGTCA
GGACATTAACAGTAATATAGGGTTGCAGCAGAAACCAGGAAAATCATTAAGGCCTGTCTATCATGAACCAA
CTTGGACGATGGAGTTCCATCAAGGTTCAGTGGCAGTGGATCTGGAGCCGATTATCTCTCACCATCAGCAGCCTGGAA
TCTGAAGATTTTGTAGACTATTACTGTGTACAGTATGGTCAGTTCCGTGGAGCTTCCGTGGAGGCACCAAGCTGGAAA
TCAAACGG (SEQ ID NO:133)

FIG. 75A

Amino Acid Sequence

DIVLTQSPSSMSLSLGDTVSITC<u>HSSQDISSNIGWL</u>QQKPGKSFKGLIYH<u>GTNLEDGVPSRFSGSGSGADYSLTISSLESEDFVD</u>
                                 CDR1                                 CDR2
YYC<u>VQYGQFPWT</u>FGGGTKLEIKR (SEQ ID NO:134)
   CDR3

FIG. 75B

Volumetric product concentration and B) viable cell concentration of GS-CHO (14D8, 15B2 and 40A10) and GS-NS0 (36) hu806 transfectants in small scale (100mL) shake flasks cultures. Product concentration was estimated by ELISA using the 806 anti-idiotype as coating antibody and ch806 Clinical Lot: J06024 as standard.

D): Purified GS-CHO hu806 15B2 transfectant product

E): Purified GS-NSO hu806 36 transfectant product

Figure 3. Size Exclusion Chromatography (Biosep SEC-S3000) Analysis of Protein-A purified hu806 antibody construct 40A10 following large scale production and protein A purification. chromatogram at A214nm is presented indicating 98.8% purity with 1.2% aggregate present.

Binding to A431 cells: Flow Cytometry analysis of Protein-A purified hu806 antibody preparations (20 μg/ml), and isotype control huA33 (20 μg/ml). Controls include secondary antibody alone (green) and ch806 (red). Hu806 constructs were produced by small scale culture.

Binding to A431 cells: Flow Cytometry analysis of purified mAb806, ch806 and hu806 40A10 antibody preparations (20 μg/ml) that bind ~ 10% of wild type EGFR on cell surface, 528 (binds both wild type and de2-7 EGFR) and irrelevant control antibody (20 μg/ml) as indicated.

Binding to U87MG.de2-7 glioma cells. Flow Cytometry analysis of purified mAb806, ch806 and hu806 40A10 antibody preparations (20 µg/ml) and 528 anti-EGFR and irrelevant control antibody (20 µg/ml).

Specific binding of $^{125}$I-radiolabelled 806 antibody constructs to: A) U87MG.de2-7 glioma cells and B) A431 carcinoma cells.

Figure 12. Scatchard Analyses: $^{125}$I-radiolabelled A) ch806 and B) hu806 antibody constructs binding to U87MG.de2-7 cells.

Figure 13. Scatchard Analyses: $^{125}$I-radiolabelled A) ch806 and B) hu806 antibody constructs binding to A431 cells.

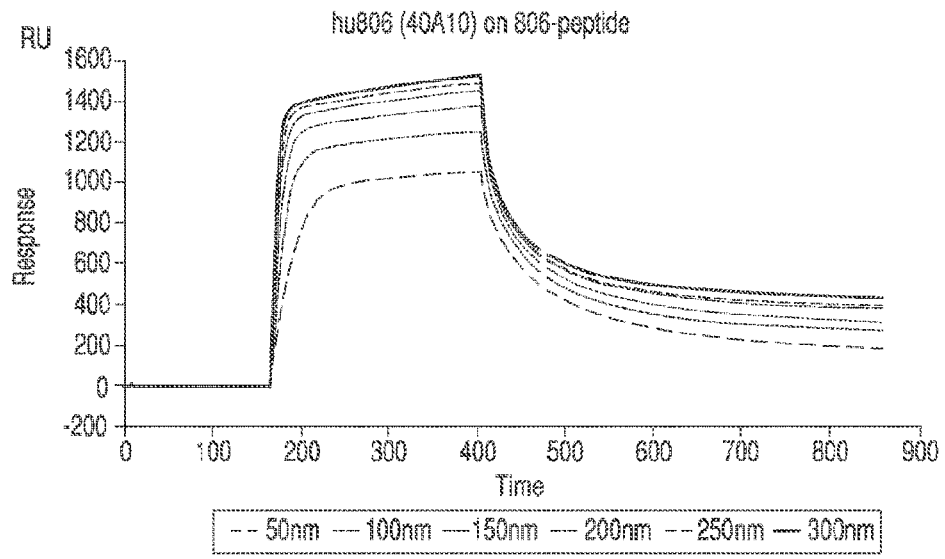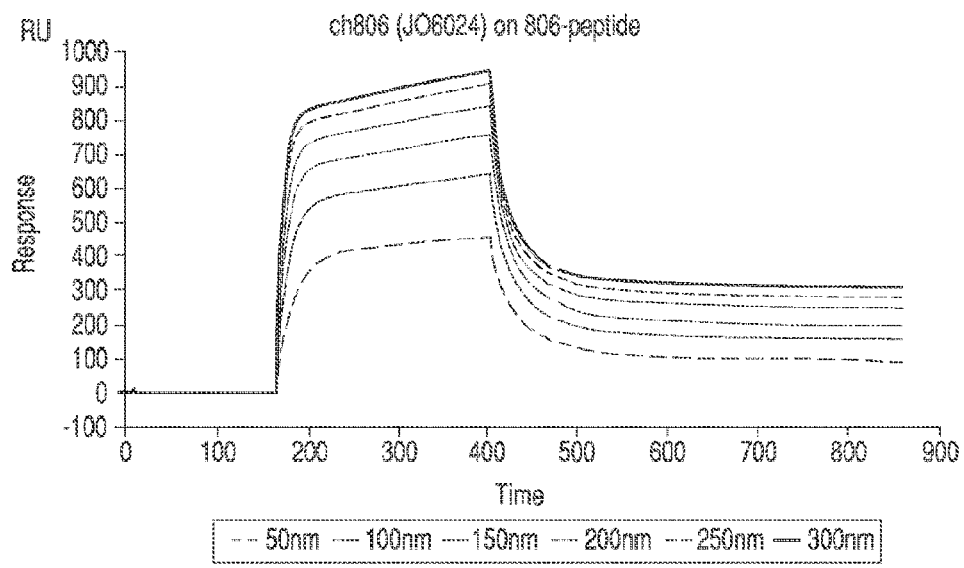
FIG. 89

Treatment of established A431 xenografts in BALB/c nude mice. Groups of 5 mice received 6 × 1 mg dose over 2 weeks antibody therapy as indicated (arrows). Mean ± SEM tumour volume is presented until study termination.

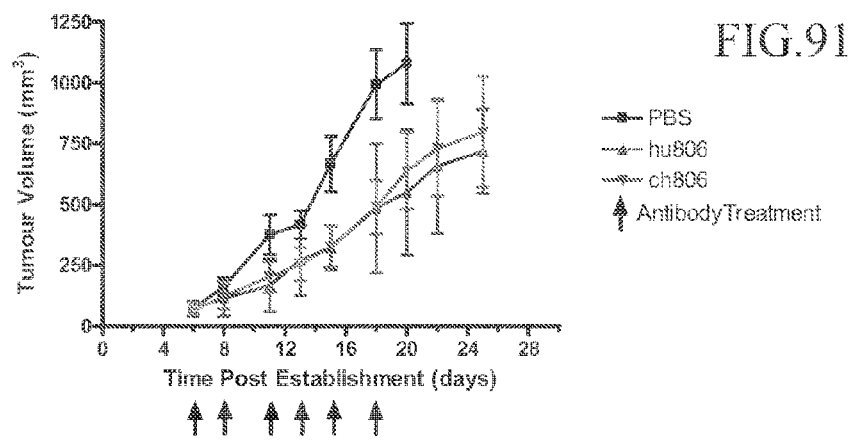

FIG.91

Figure 17. Treatment of established U87MG.de2-7 xenografts in BALB/c nude mice. Groups of 5 mice received 6 × 1 mg dose over 2 weeks antibody therapy as indicated (arrows). Mean ± SEM tumour volume is presented until study termination.

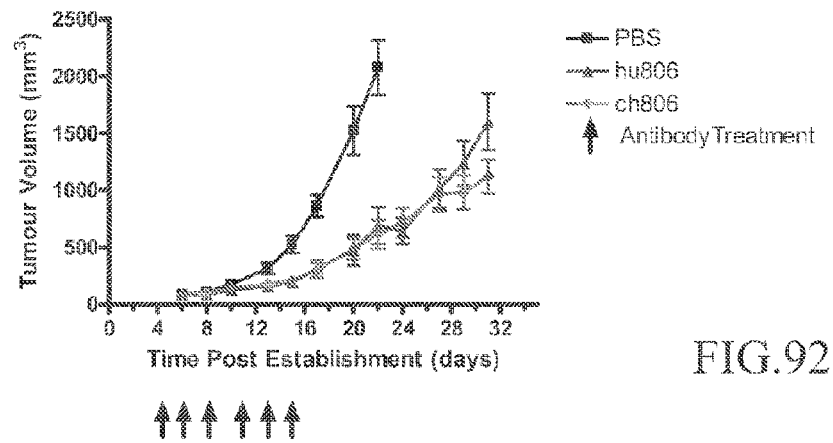

FIG.92

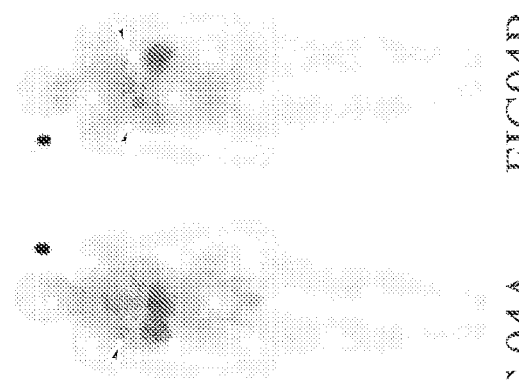
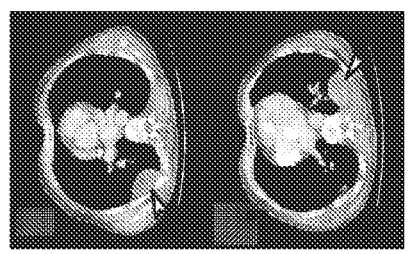
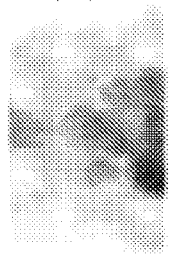 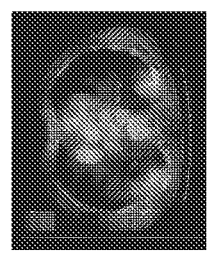
FIG. 94A  FIG. 94B  FIG. 94C  FIG. 94D  FIG. 94E  FIG. 94F

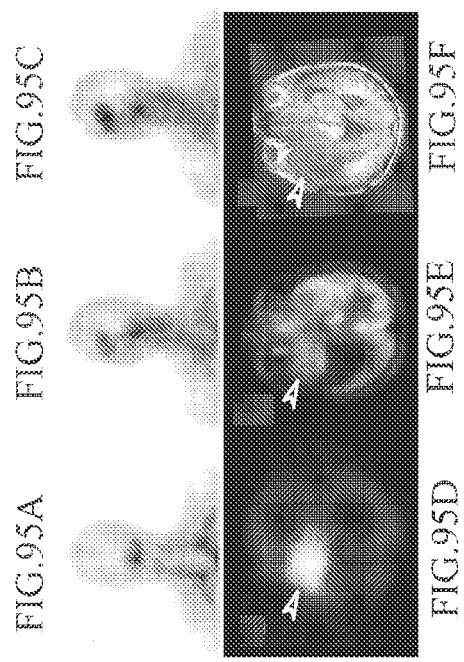

SPECIFIC BINDING PROTEINS AND USES THEREOF

RELATED APPLICATION DATA

The present is a National Stage Application under 35 U.S.C. §371 of International PCT Patent Application No. PCT/US2010/024407, filed Feb. 17, 2010, which claims priority to U.S. patent application Ser. No. 12/388,504, filed Feb. 18, 2009, now abandoned, the disclosure of which is hereby incorporated by reference in its entirety. The present application also incorporates by reference in its entirety the disclosure of each of U.S. patent application Ser. No. 10/145,598, filed May 13, 2002 (now U.S. Pat. No. 7,589,180, issued Sep. 15, 2009); U.S. Provisional Patent Application No. 60/290,410, filed May 11, 2001; U.S. Provisional Patent Application No. 60/326,019, filed Sep. 28, 2001; U.S. Provisional Patent Application No. 60/342,258, filed Dec. 21, 2001; International PCT Patent Application No. PCT/US02/15185, filed May 13, 2002 (Published as WO 02/092771 on Nov. 21, 2002); International PCT Patent Application No. PCT/US2008/009771, filed Aug. 14, 2008 (Published as WO 2009/023265 on Feb. 19, 2009); and U.S. Provisional Patent Application No. 60/964,715, filed Aug. 14, 2007.

FIELD OF THE INVENTION

The present invention relates to specific binding members, particularly antibodies and fragments thereof, which bind to amplified epidermal growth factor receptor (EGFR) and to the in-frame deletion of exons 2 to 7 of EGFR, resulting in a truncated EGFR receptor missing 267 amino acids from the extracellular domain (de2-7 EGFR). In particular, the epitope recognized by the specific binding members, particularly antibodies and fragments thereof, is enhanced or evident upon aberrant post-translational modification. These specific binding members are useful in the diagnosis and treatment of cancer. The binding members of the present invention may also be used in therapy in combination with chemotherapeutics or anti-cancer agents and/or with other antibodies or fragments thereof.

BACKGROUND OF RELATED TECHNOLOGY

The treatment of proliferative disease, particularly cancer, by chemotherapeutic means often relies upon exploiting differences in target proliferating cells and other normal cells in the human or animal body. For example, many chemical agents are designed to be taken up by rapidly replicating DNA so that the process of DNA replication and cell division is disrupted. Another approach is to identify antigens on the surface of tumor cells or other abnormal cells which are not normally expressed in developed human tissue, such as tumor antigens or embryonic antigens. Such antigens can be targeted with binding proteins such as antibodies which can block or neutralize the antigen. In addition, the binding proteins, including antibodies and fragments thereof, may deliver a toxic agent or other substance which is capable of directly or indirectly activating a toxic agent at the site of a tumor.

The EGFR is an attractive target for tumor-targeted antibody therapy because it is over-expressed in many types of epithelial tumors (Voldborg et al. (1997). Epidermal growth factor receptor (EGFR) and EGFR mutations, function and possible role in clinical trials. *Ann Oncol.* 8, 1197-206; den Eynde, B. and Scott, A. M. Tumor Antigens. In: P. J. Delves and I. M. Roitt (eds.), *Encyclopedia of Immunology*, Second Edition, pp. 2424-31. London: Academic Press (1998)). Moreover, expression of the EGFR is associated with poor prognosis in a number of tumor types including stomach, colon, urinary bladder, breast, prostate, endometrium, kidney and brain (e.g., glioma). Consequently, a number of EGFR antibodies have been reported in the literature with several undergoing clinical evaluation (Baselga et al. (2000) Phase I Studies of Anti-Epidermal Growth Factor Receptor Chimeric Antibody C225 Alone and in Combination With Cisplatin. *J. Clin. Oncol.* 18, 904; Fullot et al. (1996): A phase I study of an anti-epidermal growth factor receptor monoclonal antibody for the treatment of malignant gliomas. *Neurosurgery.* 39, 478-83; Seymour, L. (1999) Novel anti-cancer agents in development: exciting prospects and new challenges. *Cancer Treat. Rev.* 25, 301-12)).

Results from studies using EGFR mAbs in patients with head and neck cancer, squamous cell lung cancer, brain gliomas and malignant astrocytomas have been encouraging. The antitumor activity of most EGFR antibodies is enhanced by their ability to block ligand binding (Sturgis et al. (1994) Effects of antiepidermal growth factor receptor antibody 528 on the proliferation and differentiation of head and neck cancer. *Otolaryngol. Head Neck. Surg.* 111, 633-43; Goldstein et al. (1995) Biological efficacy of a chimeric antibody to the epidermal growth factor receptor in a human tumor xenograft model. *Clin. Cancer Res.* 1, 1311-8). Such antibodies may mediate their efficacy through both modulation of cellular proliferation and antibody dependent immune functions (e.g. complement activation). The use of these antibodies, however, may be limited by uptake in organs that have high endogenous levels of EGFR such as the liver and skin (Baselga et al., 2000; Fullot et al., 1996).

A significant proportion of tumors containing amplifications of the EGFR gene (i.e., multiple copies of the EGFR gene) also co-express a truncated version of the receptor (Wikstrand et al. (1998) The class III variant of the epidermal growth factor receptor (EGFR): characterization and utilization as an immunotherapeutic target. *J. Neurovirol.* 4, 148-158) known as de2-7 EGFR, ΔEGFR, or Δ2-7 (terms used interchangeably herein) (Olapade-Olaopa et al. (2000) Evidence for the differential expression of a variant EGF receptor protein in human prostate cancer. *Br. J. Cancer.* 82, 186-94). The rearrangement seen in the de2-7 EGFR results in an in-frame mature mRNA lacking 801 nucleotides spanning exons 2-7 (Wong et al. (1992) Structural alterations of the epidermal growth factor receptor gene in human gliomas. *Proc. Natl. Acad. Sci. U.S.A.* 89, 2965-9; Yamazaki et al. (1990) A deletion mutation within the ligand binding domain is responsible for activation of epidermal growth factor receptor gene in human brain tumors. *Jpn. J. Cancer Res.* 81, 773-9; Yamazaki et al. (1988) Amplification of the structurally and functionally altered epidermal growth factor receptor gene (c-erbB) in human brain tumors. *Mol. Cell. Biol.* 8, 1816-20; Sugawa et al. (1990) Identical splicing of aberrant epidermal growth factor receptor transcripts from amplified rearranged genes in human glioblastomas. *Proc. Natl. Acad. Sci. U.S.A.* 87, 8602-6). The corresponding EGFR protein has a 267 amino acid deletion comprising residues 6-273 of the extracellular domain and a novel glycine residue at the fusion junction (Sugawa et al., 1990). This deletion, together with the insertion of a glycine residue, produces a unique junctional peptide at the deletion interface (Sugawa et al., 1990).

The de2-7 EGFR has been reported in a number of tumor types including glioma, breast, lung, ovarian and prostate (Wikstrand et al. (1997) Cell surface localization and density of the tumor-associated variant of the epidermal growth factor receptor, EGFRvIII. *Cancer Res.* 57, 4130-40; Olapade- Olaopa et al. (2000) Evidence for the differential expression of a variant EGF receptor protein in human prostate cancer. *Br. J. Cancer.* 82, 186-94; Wikstrand, et al. (1995) Monoclonal antibodies against EGFRvIII in are tumor specific and react with breast and lung carcinomas and malignant gliomas. *Cancer Res.* 55, 3140-8; Garcia de Palazzo et al. (1993) Expression of mutated epidermal growth factor receptor by non-small cell lung carcinomas. *Cancer Res.* 53, 3217-20). While this truncated receptor does not bind ligand, it possesses low constitutive activity and imparts a significant growth advantage to glioma cells grown as tumor xenografts in nude mice (Nishikawa et al. (1994) A mutant epidermal growth factor receptor common in human glioma confers enhanced tumorigenicity. *Proc. Natl. Acad. Sci. U.S.A.* 91, 7727-31) and is able to transform NIH3T3 cells (Batra et al. (1995) Epidermal growth factor ligand independent, unregulated, cell-transforming potential of a naturally occurring human mutant EGFRvIII gene. *Cell Growth Differ.* 6, 1251-9) and MCF-7 cells. The cellular mechanisms utilized by the de2-7 EGFR in glioma cells are not fully defined but are reported to include a decrease in apoptosis (Nagane et al. (1996) A common mutant epidermal growth factor receptor confers enhanced tumorigenicity on human glioblastoma cells by increasing proliferation and reducing apoptosis. *Cancer Res.* 56, 5079-86) and a small enhancement of proliferation (Nagane et al., 1996).

As expression of this truncated receptor is restricted to tumor cells it represents a highly specific target for antibody therapy. Accordingly, a number of laboratories have reported the generation of both polyclonal (Humphrey et al. (1990) Anti-synthetic peptide antibody reacting at the fusion junction of deletion mutant epidermal growth factor receptors in human glioblastoma. *Proc. Natl. Acad. Sci. U.S.A.* 87, 4207-11) and monoclonal (Wikstrand et al. (1995) Monoclonal antibodies against EGFRvIII are tumor specific and react with breast and lung carcinomas and malignant gliomas; Okamoto et al. (1996) Monoclonal antibody against the fusion junction of a deletion-mutant epidermal growth factor receptor. *Br. J. Cancer.* 73, 1366-72; Hills et al. (1995) Specific targeting of a mutant, activated EGF receptor found in glioblastoma using a monoclonal antibody. *Int. J. Cancer.* 63, 537-43) antibodies specific to the unique peptide of de2-7 EGFR. A series of mouse mAbs, isolated following immunization with the unique de2-7 peptide, all showed selectivity and specificity for the truncated receptor and targeted de2-7 EGFR positive xenografts grown in nude mice (Wikstrand et al. (1995); Reist et al. (1997) Improved targeting of an anti-epidermal growth factor receptor variant III monoclonal antibody in tumor xenografts after labeling using N-succinimidyl 5-iodo-3-pyridinecarboxylate. *Cancer Res.* 57, 1510-5; Reist et al. (1995) Tumor-specific anti-epidermal growth factor receptor variant III monoclonal antibodies: use of the tyramine-cellobiose radioiodination method enhances cellular retention and uptake in tumor xenografts. *Cancer Res.* 55, 4375-82).

However, one potential shortcoming of de2-7 EGFR antibodies is that only a proportion of tumors exhibiting amplification of the EGFR gene also express the de2-7EGFR (Ekstrand et al. (1992) Amplified and rearranged epidermal growth factor receptor genes in human glioblastomas reveal deletions of sequences encoding portions of the N- and/or C-terminal tails. *Proc. Natl. Acad. Sci. U.S.A.* 89, 4309-13). The exact percentage of tumors containing the de2-7 EGFR is not completely established, because the use of different techniques (i.e. PCR versus immunohistochemistry) and various antibodies, has produced a wide range of reported values for the frequency of its presence. Published data indicates that approximately 25-30% of gliomas express de2-7 EGFR with expression being lowest in anaplastic astrocytomas and highest in glioblastoma multiforme (Wong et al. (1992); Wikstrand et al. (1998) The class III variant of the epidermal growth factor receptor (EGFR): characterization and utilization as an immunotherapeutic target. *J. Neurovirol.* 4, 148-58; Moscatello et al. (1995) Frequent expression of a mutant epidermal growth factor receptor in multiple human tumors. *Cancer Res.* 55, 5536-9). The proportion of positive cells within de2-7 EGFR expressing gliomas has been reported to range from 37-86% (Wikstrand et al. (1997)). 27% of breast carcinomas and 17% of lung cancers were found to be positive for the de2-7 EGFR (Wikstrand et al. (1997); Wikstrand et al. (1995); Wikstrand et al. (1998); and Hills et al., 1995). Thus, de2-7 EGFR specific antibodies would be expected to be useful in only a percentage of EGFR positive tumors.

Thus, while the extant evidence of activity of EGFR antibodies is encouraging, the observed limitations on range of applicability and efficacy reflected above remain. Accordingly, it would be desirable to develop antibodies and like agents that demonstrate efficacy with a broad range of tumors, and it is toward the achievement of that objective that the present invention is directed.

The citation of references herein shall not be construed as an admission that such is prior art to the present invention.

SUMMARY OF THE INVENTION

The present invention provides isolated specific binding members, particularly antibodies or fragment thereof, which recognizes an EGFR epitope which does not demonstrate any amino acid sequence alterations or substitutions from wild-type EGFR and which is found in tumorigenic, hyperproliferative or abnormal cells and is not generally detectable in normal or wild type cells (the term "wild-type cell" as used herein contemplates a cell that expresses endogenous EGFR but not the de 2-7EGFR and the term specifically excludes a cell that over-expresses the EGFR gene; the term "wild-type" refers to a genotype or phenotype or other characteristic present in a normal cell rather than in an abnormal or tumorigenic cell). In a further aspect, the present invention provides specific binding members, particularly antibodies or fragments thereof, which recognizes an EGFR epitope which is found in tumorigenic, hyperproliferative or abnormal cells and is not generally detectable in normal or wild type cells, wherein the epitope is enhanced or evident upon aberrant post translational modification or aberrant expression. In a particular non-limiting exemplification provided herein, the EGFR epitope is enhanced or evident wherein post-translational modification is not complete or full to the extent seen with normal expression of EGFR in wild type cells. In one aspect, the EGFR epitope is enhanced or evident upon initial or simple carbohydrate modification or early glycosylation, particularly high mannose modification, and is reduced or not evident in the presence of complex carbohydrate modification.

The specific binding members, which may be antibodies or fragments thereof, such as immunogenic fragments thereof, do not substantially bind to or recognize normal or wild type cells containing normal or wild type EGFR epitope in the absence of aberrant expression and in the presence of normal EGFR post-translational modification.

More particularly, the specific binding member of the invention, may be antibodies or fragments thereof, which recognizes an EGFR epitope which is present in cells over-expressing EGFR (e.g., EGFR gene is amplified) or expressing the de2-7 EGFR, particularly in the presence of aberrant post-translational modification, and that is not generally detectable in cells expressing EGFR under normal conditions, particularly in the presence of normal post-translational modification.

The present inventors have discovered novel monoclonal antibodies, exemplified herein by the antibodies designated mAb806, ch806, hu806, mAb175, mAb124, and mAb1133, which specifically recognize aberrantly expressed EGFR. In particular, the antibodies of the present invention recognize an EGFR epitope which is found in tumorigenic, hyperproliferative or abnormal cells and is not generally detectable in normal or wild type cells, wherein the epitope is enhanced or evident upon aberrant post-translational modification. The novel antibodies of the invention also recognize amplified wild type EGFR and the de2-7 EGFR, yet bind to an epitope distinct from the unique junctional peptide of the de2-7 EGFR mutation. The antibodies of the present invention specifically recognize aberrantly expressed EGFR, including amplified EGFR and mutant EGFR (exemplified herein by the de2-7 mutation), particularly upon aberrant post-translational modification. Additionally, while these antibodies do not recognize the EGFR when expressed on the cell surface of a glioma cell line expressing normal amounts of EGFR, they do bind to the extracellular domain of the EGFR (sEGFR) immobilized on the surface of ELISA plates, indicating the recognition of a conformational epitope. These antibodies bind to the surface of A431 cells, which have an amplification of the EGFR gene but do not express the de2-7 EGFR. Importantly, these antibodies did not bind significantly to normal tissues such as liver and skin, which express levels of endogenous, wild type (wt) EGFR that are higher than in most other normal tissues, but wherein EGFR is not aberrantly expressed or amplified.

The antibodies of the present invention can specifically categorize the nature of EGFR tumors or tumorigenic cells, by staining or otherwise recognizing those tumors or cells wherein aberrant EGFR expression, including EGFR amplification and/or EGFR mutation, particularly de2-7EGFR, is present. Further, the antibodies of the present invention demonstrate significant in vivo anti-tumor activity against tumors containing amplified EGFR and against de2-7 EGFR positive xenografts.

The unique specificity of these antibodies to bind to the de2-7 EGFR and amplified EGFR, but not to the normal, wild type EGFR, provides diagnostic and therapeutic uses to identify, characterize and target a number of tumor types, for example, head and neck, breast, or prostate tumors and glioma, without the problems associated with normal tissue uptake that may be seen with previously known EGFR antibodies.

Accordingly, the invention provides specific binding proteins, such as antibodies, which bind to the de2-7 EGFR at an epitope which is distinct from the junctional peptide but which do not substantially bind to EGFR on normal cells in the absence of amplification of the EGFR gene. By amplification, it is meant to include that the cell comprises multiple copies of the EGFR gene.

Preferably the epitope recognized by the inventive antibodies is located within the region comprising residues 273-501 of the mature normal or wild type EGFR sequence, and preferably comprises residues 287-302 (SEQ ID NO:14) of the mature normal or wild type EGFR sequence. Therefore, also provided are specific binding proteins, such as antibodies, which bind to the de2-7 EGFR at an epitope located within the region comprising residues 273-501 and/or 287-302 (SEQ ID NO:14) of the EGFR sequence. The epitope may be determined by any conventional epitope mapping techniques known to the person skilled in the art. Alternatively, the DNA sequence encoding residues 273-501 and/or 287-302 (SEQ ID NO:14) could be digested, and the resultant fragments expressed in a suitable host. Antibody binding could be determined as mentioned above.

In a preferred aspect, the antibodies are ones which have the characteristics of the antibodies which the inventors have identified and characterized, in particular recognizing aberrantly expressed EGFR, as found in amplified EGFR and de2-7EGFR.

In another aspect, the invention provides antibodies capable of competing with the inventive antibodies, under conditions in which at least 10% of an antibody having the VH and VL chain sequences of the inventive antibodies are blocked from binding to de2-7EGFR by competition with such an antibody in an ELISA assay. In particular, anti-idiotype antibodies are contemplated and are exemplified herein. The anti-idiotype antibodies LMH-11, LMH-12 and LMH-13 are provided herein.

The binding of an antibody to its target antigen is mediated through the complementarity-determining regions (CDRs) of its heavy and light chains, with the role of CDR3 being of particular importance. Accordingly, specific binding members based on the CDR3 regions of the heavy or light chain, and preferably both, of the inventive antibodies will be useful specific binding members for in vivo therapy.

Accordingly, specific binding proteins such as antibodies which are based on the CDRs of the inventive antibodies identified, particularly the CDR3 regions, will be useful for targeting tumors with amplified EGFR regardless of their de2-7 EGFR status. As the inventive antibodies do not bind significantly to normal, wild type receptor, there would be no significant uptake in normal tissue, a limitation of EGFR antibodies currently being developed.

In another aspect, there is provided an isolated antibody capable of binding EGFR on tumors containing amplifications of the EGFR gene, wherein cells of the tumors contain multiple copies of the EGFR gene, and on tumors that express the truncated version of the EGFR receptor de2-7, wherein the antibody does not bind to the de2-7 EGFR junctional peptide consisting of the amino acid sequence of SEQ ID NO:13, wherein the antibody binds to an epitope within the sequence of residues 287-302 (SEQ ID NO:14) of human wild-type EGFR, and wherein the antibody does not comprise a heavy chain variable region sequence having the amino acid sequence set forth in SEQ ID NO:2 and does not comprise a light chain variable region sequence having the amino acid sequence set forth in SEQ ID NO:4.

In another aspect, there is provided an isolated antibody wherein the antibody comprises a heavy chain and a light chain, the heavy chain having the amino acid sequence set forth in SEQ ID NO:42, and the light chain having the amino acid sequence set forth in SEQ ID NO:47.

In another aspect, there is provided an isolated antibody wherein the antibody comprises a heavy chain and a light chain, the heavy chain having the amino acid sequence set forth in SEQ ID NO:129, and the light chain having the amino acid sequence set forth in SEQ ID NO:134.

In another aspect, there is provided an isolated antibody, wherein the antibody comprises a heavy chain and a light chain, the heavy chain having the amino acid sequence set forth in SEQ ID NO:22, and the light chain having the amino acid sequence set forth in SEQ ID NO:27.

In another aspect, there is provided an isolated antibody, wherein the antibody comprises a heavy chain and a light chain, the heavy chain having the amino acid sequence set forth in SEQ ID NO:32, and the light chain having the amino acid sequence set forth in SEQ ID NO:37.

In another aspect, there is provided an isolated antibody, wherein the antibody comprises a heavy chain and a light chain, wherein the variable region of the heavy chain comprises polypeptide binding domain regions having amino acid sequences highly homologous to the amino acid sequences set forth in SEQ ID NOS:44, 45, and 46.

In another aspect, there is provided an isolated antibody, wherein the antibody comprises a heavy chain and a light chain, wherein the variable region of the light chain comprises polypeptide binding domain regions having amino acid sequences highly homologous to the amino acid sequences set forth in SEQ ID NOS:49, 50, and 51.

In another aspect, there is provided an isolated antibody, wherein the antibody comprises a heavy chain and a light chain, wherein the variable region of the heavy chain comprises polypeptide binding domain regions having amino acid sequences highly homologous to the amino acid sequences set forth in SEQ ID NOS:130, 131, and 132.

In another aspect, there is provided an isolated antibody, wherein the antibody comprises a heavy chain and a light chain, wherein the variable region of the light chain comprises polypeptide binding domain regions having amino acid sequences highly homologous to the amino acid sequences set forth in SEQ ID NOS:135, 136, and 137.

In another aspect, there is provided an isolated antibody, wherein the antibody comprises a heavy chain and a light chain, wherein the variable region of the heavy chain comprises polypeptide binding domain regions having amino acid sequences highly homologous to the amino acid sequences set forth in SEQ ID NOS:23, 24, and 25.

In another aspect, there is provided an isolated antibody, wherein the antibody comprises a heavy chain and a light chain, wherein the variable region of the light chain comprises polypeptide binding domain regions having amino acid sequences highly homologous to the amino acid sequences set forth in SEQ ID NOS:28, 29, and 30.

In another aspect, there is provided an isolated antibody, wherein the antibody comprises a heavy chain and a light chain, wherein the variable region of the heavy chain comprises polypeptide binding domain regions having amino acid sequences highly homologous to the amino acid sequences set forth in SEQ ID NOS:33, 34, and 35.

In another aspect, there is provided an isolated antibody, wherein the antibody comprises a heavy chain and a light chain, wherein the variable region of the light chain comprises polypeptide binding domain regions having amino acid sequences highly homologous to the amino acid sequences set forth in SEQ ID NOS:38, 39, and 40.

In another aspect, there is provided an isolated antibody, wherein the isolated antibody is the form of an antibody F(ab')2, scFv fragment, diabody, triabody or tetrabody.

In another aspect, there is provided an isolated antibody further comprising a detectable or functional label.

In another aspect, the detectable or functional label is a covalently attached drug.

In another aspect, the label is a radiolabel.

In another aspect, there is provided an isolated antibody, wherein the isolated antibody is peglyated.

In another aspect, there is provided an isolated nucleic acid which comprises a sequence encoding an isolated antibody recited herein.

In another aspect, there is provided a method of preparing an isolated antibody, comprising expressing a nucleic acid as recited above and herein under conditions to bring about expression of the antibody, and recovering the antibody.

In another aspect, there is provided a method of treatment of a tumor in a human patient which comprises administering to the patient an effective amount of an isolated antibody recited herein.

In another aspect, there is provided a kit for the diagnosis of a tumor in which EGFR is aberrantly expressed or in which EGFR is expressed in the form of a truncated protein, comprising an isolated antibody recited herein.

In another aspect, the kit further comprises reagents and/or instructions for use.

In another aspect, there is provided a pharmaceutical composition comprising an isolated antibody as recited herein.

In another aspect, the pharmaceutical composition further comprises a pharmaceutically acceptable vehicle, carrier or diluent.

In another aspect, the pharmaceutical composition further comprises an anti-cancer agent selected from the group consisting of chemotherapeutic agents, anti-EGFR antibodies, radioimmunotherapeutic agents, and combinations thereof.

In another aspect, the chemotherapeutic agents are selected from the group consisting of tyrosine kinase inhibitors, phosphorylation cascade inhibitors, post-translational modulators, cell growth or division inhibitors (e.g. anti-mitotics), signal transduction inhibitors, and combinations thereof.

In another aspect, the tyrosine kinase inhibitors are selected from the group consisting of AG1478, ZD1839, STI571, OSI-774, SU-6668, and combinations thereof.

In another aspect, the anti-EGFR antibodies are selected from the group consisting of the anti-EGFR antibodies 528, 225, SC-03, DR8.3, L8A4, Y10, ICR62, ABX-EGF, and combinations thereof.

In another aspect, there is provided a method of preventing and/or treating cancer in mammals, comprising administering to a mammal a therapeutically effective amount of a pharmaceutical composition as recited herein.

In another aspect, there is provided a method for the treatment of brain-resident cancers that produce aberrantly expressed EGFR in mammals, comprising administering to a mammal a therapeutically effective amount of a pharmaceutical composition as recited herein.

In another aspect, the brain-resident cancers are selected from the group consisting of glioblastomas, medulloblastomas, meningiomas, neoplastic astrocytomas and neoplastic arteriovenous malformations.

In another aspect, there is provided a unicellular host transformed with a recombinant DNA molecule which encodes an isolated antibody recited herein.

In another aspect, the unicellular host is selected from the group consisting of E. coli, Pseudomonas, Bacillus, Streptomyces, yeasts, CHO, YB/20, NSO, SP2/0, R1.1, B-W, L-M, COS 1, COS 7, BSC1, BSC40, and BMT10 cells, plant cells, insect cells, and human cells in tissue culture.

In another aspect, there is provided a method for detecting the presence of amplified EGFR, de2-7EGFR or EGFR with high mannose glycosylation wherein the EGFR is measured by: (a) contacting a biological sample from a mammal in which the presence of amplified EGFR, de2-7EGFR or EGFR with high mannose glycosylation is suspected with an isolated antibody of claim 1 under conditions that allow binding of the EGFR to the isolated antibody to occur; and (b) detecting whether binding has occurred between the EGFR from the sample and the isolated antibody; wherein the detection of binding indicates that presence or activity of the EGFR in the sample.

In another aspect of the method of detecting the presence of amplified EGFR, de2-7EGFR or EGFR with high mannose glycosylation, the detection of the presence of the EGFR indicates the existence of a tumor or cancer in the mammal.

In another aspect, there is provided an isolated antibody capable of binding EGFR on tumors containing amplifications of the EGFR gene, wherein cells of the tumors contain multiple copies of the EGFR gene, and on tumors that express the truncated version of the EGFR receptor de2-7, wherein the antibody comprises a heavy chain and a light chain, the heavy chain having an amino acid sequence that is substantially homologous to the amino acid sequence set forth in SEQ ID NO:42, and the light chain having an amino acid sequence that is substantially homologous to the amino acid sequence set forth in SEQ ID NO:47.

In another aspect, the heavy chain of the antibody comprises the amino acid sequence set forth in SEQ ID NO:42, and wherein the light chain of the antibody comprises the amino acid sequence set forth in SEQ ID NO:47.

In another aspect, there is provided an isolated antibody capable of binding EGFR on tumors containing amplifications of the EGFR gene, wherein cells of the tumors contain multiple copies of the EGFR gene, and on tumors that express the truncated version of the EGFR receptor de2-7, wherein the antibody comprises a heavy chain and a light chain, wherein the variable region of the heavy chain comprises polypeptide binding domain regions having amino acid sequences highly homologous to the amino acid sequences set forth in SEQ ID NOS:44, 45, and 46, and wherein the variable region of the light chain comprises polypeptide binding domain regions having amino acid sequences highly homologous to the amino acid sequences set forth in SEQ ID NOS:49, 50, and 51.

In another aspect, there is provided an isolated antibody capable of binding EGFR on tumors containing amplifications of the EGFR gene, wherein cells of the tumors contain multiple copies of the EGFR gene, and on tumors that express the truncated version of the EGFR receptor de2-7, wherein the antibody comprises a heavy chain and a light chain, the heavy chain having an amino acid sequence that is substantially homologous to the amino acid sequence set forth in SEQ ID NO:129, and the light chain having an amino acid sequence that is substantially homologous to the amino acid sequence set forth in SEQ ID NO:134.

In another aspect, the heavy chain of the antibody comprises the amino acid sequence set forth in SEQ ID NO:129, and wherein the light chain of the antibody comprises the amino acid sequence set forth in SEQ ID NO:134.

In another aspect, there is provided an isolated antibody capable of binding EGFR on tumors containing amplifications of the EGFR gene, wherein cells of the tumors contain multiple copies of the EGFR gene, and on tumors that express the truncated version of the EGFR receptor de2-7, wherein the antibody comprises a heavy chain and a light chain, wherein the variable region of the heavy chain comprises polypeptide binding domain regions having amino acid sequences highly homologous to the amino acid sequences set forth in SEQ ID NOS:130, 131, and 132, and wherein the variable region of the light chain comprises polypeptide binding domain regions having amino acid sequences highly homologous to the amino acid sequences set forth in SEQ ID NOS:135, 136, and 137.

In another aspect, there is provided an isolated antibody capable of binding EGFR on tumors containing amplifications of the EGFR gene, wherein cells of the tumors contain multiple copies of the EGFR gene, and on tumors that express the truncated version of the EGFR receptor de2-7, wherein the antibody comprises a heavy chain and a light chain, the heavy chain having an amino acid sequence that is substantially homologous to the amino acid sequence set forth in SEQ ID NO:22, and the light chain having an amino acid sequence that is substantially homologous to the amino acid sequence set forth in SEQ ID NO:27.

In another aspect, the heavy chain of the antibody comprises the amino acid sequence set forth in SEQ ID NO:22, and wherein the light chain of the antibody comprises the amino acid sequence set forth in SEQ ID NO:27.

In another aspect, there is provided an isolated antibody capable of binding EGFR on tumors containing amplifications of the EGFR gene, wherein cells of the tumors contain multiple copies of the EGFR gene, and on tumors that express the truncated version of the EGFR receptor de2-7, wherein the antibody comprises a heavy chain and a light chain, wherein the variable region of the heavy chain comprises polypeptide binding domain regions having amino acid sequences highly homologous to the amino acid sequences set forth in SEQ ID NOS:23, 24, and 25, and wherein the variable region of the light chain comprises polypeptide binding domain regions having amino acid sequences highly homologous to the amino acid sequences set forth in SEQ ID NOS:28, 29, and 30.

In another aspect, there is provided an isolated antibody capable of binding EGFR on tumors containing amplifications of the EGFR gene, wherein cells of the tumors contain multiple copies of the EGFR gene, and on tumors that express the truncated version of the EGFR receptor de2-7, wherein the antibody comprises a heavy chain and a light chain, the heavy chain having an amino acid sequence that is substantially homologous to the amino acid sequence set forth in SEQ ID NO:32, and the light chain having an amino acid sequence that is substantially homologous to the amino acid sequence set forth in SEQ ID NO:37.

In another aspect, the heavy chain of the antibody comprises the amino acid sequence set forth in SEQ ID NO:32, and wherein the light chain of the antibody comprises the amino acid sequence set forth in SEQ ID NO:37.

In another aspect, there is provided an isolated antibody capable of binding EGFR on tumors containing amplifications of the EGFR gene, wherein cells of the tumors contain multiple copies of the EGFR gene, and on tumors that express the truncated version of the EGFR receptor de2-7, wherein the antibody comprises a heavy chain and a light chain, wherein the variable region of the heavy chain comprises polypeptide binding domain regions having amino acid sequences highly homologous to the amino acid sequences set forth in SEQ ID NOS:33, 34, and 35, and wherein the variable region of the light chain comprises polypeptide binding domain regions having amino acid sequences highly homologous to the amino acid sequences set forth in SEQ ID NOS:38, 39, and 40.

In another aspect, there is provided an isolated antibody capable of binding EGFR on tumors containing amplifications of the EGFR gene, wherein cells of the tumors contain multiple copies of the EGFR gene, and on tumors that express the truncated version of the EGFR receptor de2-7, wherein the antibody does not bind to the de2-7 EGFR junctional peptide consisting of the amino acid sequence of SEQ ID NO:13, wherein the antibody binds to an epitope within the sequence of residues 287-302 of human wild-type EGFR, the antibody comprising a light chain and a heavy chain, wherein the variable region of the light chain comprises a first polypeptide binding domain region having an amino acid sequence corresponding to the amino acid sequence set forth in Formula I:

$$HSSQDIXaa_1SNIG \qquad (I),$$

wherein Xaa₁ is an amino acid residue having an uncharged polar R group (SEQ ID NO:151);

a second polypeptide binding domain region having an amino acid sequence corresponding to the amino acid sequence set forth in Formula II:

HGTNLXaa₂D        (II), wherein Xaa₂ is an amino acid residue having a charged polar R group (SEQ ID NO:152);

and a third polypeptide binding domain region having an amino acid sequence corresponding to the amino acid sequence set forth in Formula III:

VQYXaa₃QFPWT        (III), wherein Xaa₃ is selected from the group consisting of A, G, and an amino acid residue which is conservatively substituted for A or G (SEQ ID NO:153); and wherein the variable region of the heavy chain comprises a first polypeptide binding domain region having an amino acid sequence corresponding to the amino acid sequence set forth in Formula IV:

SDXaa₄AWN        (IV), wherein Xaa₄ is selected from the group consisting of F, Y, and an amino acid residue which is conservatively substituted for F or Y (SEQ ID NO:154);

a second polypeptide binding domain region having an amino acid sequence corresponding to the amino acid sequence set forth in Formula V, Formula VI, or Formula VII:

YISYSGNTRYXaa₅PSLKS        (V), wherein Xaa₅ is an amino acid residue having an uncharged polar R group (SEQ ID NO:155), YISYSXaa₆NTRYNPSLKS        (VI), wherein Xaa₆ is selected from the group consisting of G, A, and an amino acid residue which is conservatively substituted for G or A (SEQ ID NO:156), YISYSGNTRYNPSLXaa₇S        (VII), and Xaa₇ is a basic amino acid residue (SEQ ID NO:157); and a third polypeptide binding domain region having an amino acid sequence corresponding to the amino acid sequence set forth in Formula VIII:

Xaa₈TAGRGFPY        (VIII), wherein Xaa₈ is selected from the group consisting of V, A, and an amino acid residue which is conservatively substituted for V or A (SEQ ID NO:158), and wherein the antibody does not comprise a heavy chain variable region sequence having the amino acid sequence set forth in SEQ ID NO:2 and does not comprise a light chain variable region sequence having the amino acid sequence set forth in SEQ ID NO:4.

In another aspect, $X_{aa1}$ is N; $X_{aa2}$ is D; $X_{aa3}$ is A; $X_{aa4}$ is F; $X_{aa5}$ is an amino acid residue having an uncharged polar R group; $X_{aa6}$ is G; $X_{aa7}$ is K; and $X_{aa8}$ is V.

In another aspect, $X_{aa5}$ is N or Q.
In another aspect, $X_{aa1}$ is N or S.
In another aspect, $X_{aa2}$ is D or E.
In another aspect, $X_{aa3}$ is A or G.
In another aspect, $X_{aa4}$ is F or Y.
In another aspect, $X_{aa5}$ is N or Q.
In another aspect, $X_{aa6}$ is G or A, and $X_{aa7}$ is independently K or R.
In another aspect, $X_{aa8}$ is V or A.

In another aspect, there is provided an isolated antibody capable of binding EGFR on tumors containing amplifications of the EGFR gene, wherein cells of the tumors contain multiple copies of the EGFR gene, and on tumors that express the truncated version of the EGFR receptor de2-7, wherein the antibody does not bind to the de2-7 EGFR junctional peptide consisting of the amino acid sequence of SEQ ID NO:13, wherein the antibody binds to an epitope within the sequence of residues 273-501 of human wild-type EGFR, the antibody comprising a light chain and a heavy chain, wherein the variable region of the light chain comprises a first polypeptide binding domain region having the amino acid sequence HSSQDINSNIG (SEQ ID NO:18); a second polypeptide binding domain region having the amino acid sequence HGTNLDD (SEQ ID NO:19); and a third polypeptide binding domain region having the amino acid sequence VQYAQFPWT (SEQ ID NO:20), wherein the variable region of the heavy chain comprises a first polypeptide binding domain region having the amino acid sequence SDFAWN (SEQ ID NO:15); a second polypeptide binding domain region having an amino acid sequence corresponding to the amino acid sequence set forth in Formula IX:

YISYSGNTRYX_{aa9}PSLKS(IX)

wherein $X_{aa9}$ is an amino acid residue having an uncharged polar R group (SEQ ID NO:159); and a third polypeptide binding domain region having the amino acid sequence VTAGRGFPY (SEQ ID NO:17).

In another aspect, the antibody binds to an epitope within the sequence of residues 287-302 (SEQ ID NO:14) of human wild-type EGFR.

In another aspect, $X_{aa9}$ is N or Q.

In another aspect, the binding domain regions are carried by a human antibody framework.

In another aspect, the human antibody framework is a human IgG1 antibody framework.

In another aspect, there is provided an isolated antibody capable of binding EGFR on tumors containing amplifications of the EGFR gene, wherein cells of the tumors contain multiple copies of the EGFR gene, and on tumors that express the truncated version of the EGFR receptor de2-7, wherein the antibody comprises a heavy chain and a light chain, the heavy chain having an amino acid sequence that is substantially homologous to the amino acid sequence set forth in SEQ ID NO:2, and the light chain having an amino acid sequence that is substantially homologous to the amino acid sequence set forth in SEQ ID NO:4.

In another aspect, the heavy chain of the antibody comprises the amino acid sequence set forth in SEQ ID NO:2, and wherein the light chain of the antibody comprises the amino acid sequence set forth in SEQ ID NO:4.

In another aspect, there is provided, an isolated antibody capable of binding EGFR on tumors containing amplifications of the EGFR gene, wherein cells of the tumors contain multiple copies of the EGFR gene, and on tumors that express the truncated version of the EGFR receptor de2-7, wherein the antibody comprises a heavy chain and a light chain, wherein the variable region of the heavy chain comprises polypeptide binding domain regions having amino acid sequences highly homologous to the amino acid sequences set forth in SEQ ID NOS:15, 16, and 17, and wherein the variable region of the light chain comprises polypeptide binding domain regions having amino acid sequences highly homologous to the amino acid sequences set forth in SEQ ID NOS:18, 19, and 20.

Other objects and advantages will become apparent to those skilled in the art from a review of the ensuing detailed description, which proceeds with reference to the following illustrative drawings, and the attendant claims.

BRIEF DESCRIPTION OF THE DRAWINGS

FIG. 3 depicts the internalization of mAb806 and the DH8.3 antibody. U87MG.Δ2-7 cells were pre-incubated with mAb806 (▲) or DH8.3 (●) at 4° C., transferred to 37° C. and internalization determined by FACS. Data represents mean internalization at each time point±SE of 3 (DH8.3) or 4 (mAb806) separate experiments.

FIGS. 4A and 4B illustrate biodistribution (% ID/g tumor tissue) of radiolabeled (a) $^{125}$I-mAb806 and (b) $^{131}$I-DH8.3 in nude mice bearing U87MG and U87MG.Δ2-7 xenografts. Each point represents the mean of 5 mice±SE except for 1 hr where n=4.

FIGS. 5A and 5B illustrate biodistribution of radiolabeled $^{125}$I-mAb806 (open bar) and $^{131}$I-DH8.3 (filled bar) antibodies expressed as (a) tumor:blood or (b) tumor:liver ratios in nude mice bearing U87MG.Δ2-7 xenografts. Each bar represents the mean of 5 mice±SE except for 1 hr where n=4

FIGS. 6A-C illustrate flow cytometric analysis of cell lines containing amplification of the EGFR gene. A431 cells were stained with either mAb806, DH8.3 or 528 (black histograms) and compared to an irrelevant IgG2b antibody (open histogram).

FIGS. 8A-D illustrate biodistribution of radiolabeled $^{125}$I-mAb806 (open bar) and $^{131}$I-528 (filled bar) and antibodies expressed as (A, B) tumor:blood or (C, D) tumor:liver ratios in nude mice bearing (A, C) U87MG.Δ2-7 and (B, D) A431 xenografts.

FIGS. 14A and 14B illustrate the (A) nucleic acid sequence and the (B) amino acid translation thereof of the 806 VH chain gene (SEQ ID NO:1 and SEQ ID NO:2, respectively).

FIGS. 15A and 15B illustrate the (A) nucleic acid sequence and the (B) amino acid translation thereof of the 806 VL chain gene (SEQ ID NO:3 and SEQ ID NO:4, respectively).

FIG. 16 shows the VH chain sequence (SEQ ID NO:2) numbered according to Kabat, with the CDRs (SEQ ID NOS: 15, 16 and 17) underlined. Key residues of the VH chain sequence (SEQ ID NO:2) are 24, 37, 48, 67 and 78.

FIG. 17 shows the VL chain sequence (SEQ ID NO:4) numbered according to Kabat, with the CDRs (SEQ ID NOS: 18, 19 and 20) underlined. Key residues of the VL chain sequence (SEQ ID NO:4) are 36, 46, 57 and 71.

FIGS. 19A-D show analysis of internalization by electron microscopy. U87MG.Δ2-7 cells were pre-incubated with mAb806 or DH8.3 followed by gold conjugated anti-mouse IgG at 4° C., transferred to 37° C. and internalization examined at various time points by electron microscopy. (A) localization of the DH8.3 antibody to a coated pit (arrow) after 5 min; (B) internalization of mAb806 by macropinocytosis (arrow) after 2 min; (C) localization of DH8.3 to lysosomes (arrow) after 20 min; (D) localization of mAb806 to lysosomes (arrow) after 30 min. Original magnification for all images is ×30,000.

FIG. 26A shows FACS analysis of mAb806 reactivity with U87MG cell lines. U87MG, U87MG.ΔEGFR, U87MG.DK, and U87MG.wtEGFR cells were stained with anti-EGFR mAbs 528, EGFR.1, and anti-ΔEGFR antibody, mAb806. Monoclonal EGFR. 1 antibody recognized wtEGFR exclusively and monoclonal 528 antibody reacted with both wtEGFR and ΔEGFR. mAb806 reacted intensively with U87MG.ΔEGFR and U87MG.DK and weakly with U87MG.wtEGFR. Bars on the abscissa, maximum staining of cells in the absence of primary antibody. Results were reproduced in three independent experiments.

FIG. 26B shows mAb806 immunoprecipitation of EGFR forms. Mutant and wtEGFR were immunoisolated with anti-EGFR antibodies, 528, EGFR. 1, or anti-ΔEGFR antibody, mAb806, from (Lane 1) U87MG, (Lane 2) U87Δ.EGFR, (Lane 3) U87MG.DK, and (Lane 4) U87MG.wtEGFR cells, and were then detected by Western blotting with anti-pan EGFR antibody, C13.

FIGS. 27A and 27B show that systemic treatment with mAb806 decreases the phosphorylation of ΔEGFR and Bel-XL expression in U87MG.ΔEGFR brain tumors. U87MG.ΔEGFR tumors were resected at day 9 of mAb806 treatment, immediately frozen in liquid nitrogen and stored at −80° C. before tumor lysate preparation.

(A) Western blot analysis of expression and the degree of autophosphorylation of ΔEGFR. Thirty μg of tumor lysates were subjected to SDS-polyacrylamide gels, transferred to nitrocellulose membranes, and probed with anti-phosphotyrosine mAb, then were stripped and re-probed with anti-EGFR antibody, C13.

(B) Western blotting of Bcl-XL by using the same tumor lysates as in (A). Membranes were probed with anti-human Bcl-X polyclonal antibody. Lanes 1 and 2, U87MG.ΔEGFR brain tumors treated with isotype control; Lanes 3 and 4, U87MG.ΔEGFR brain tumors treated with mAb806.

Figure 28:
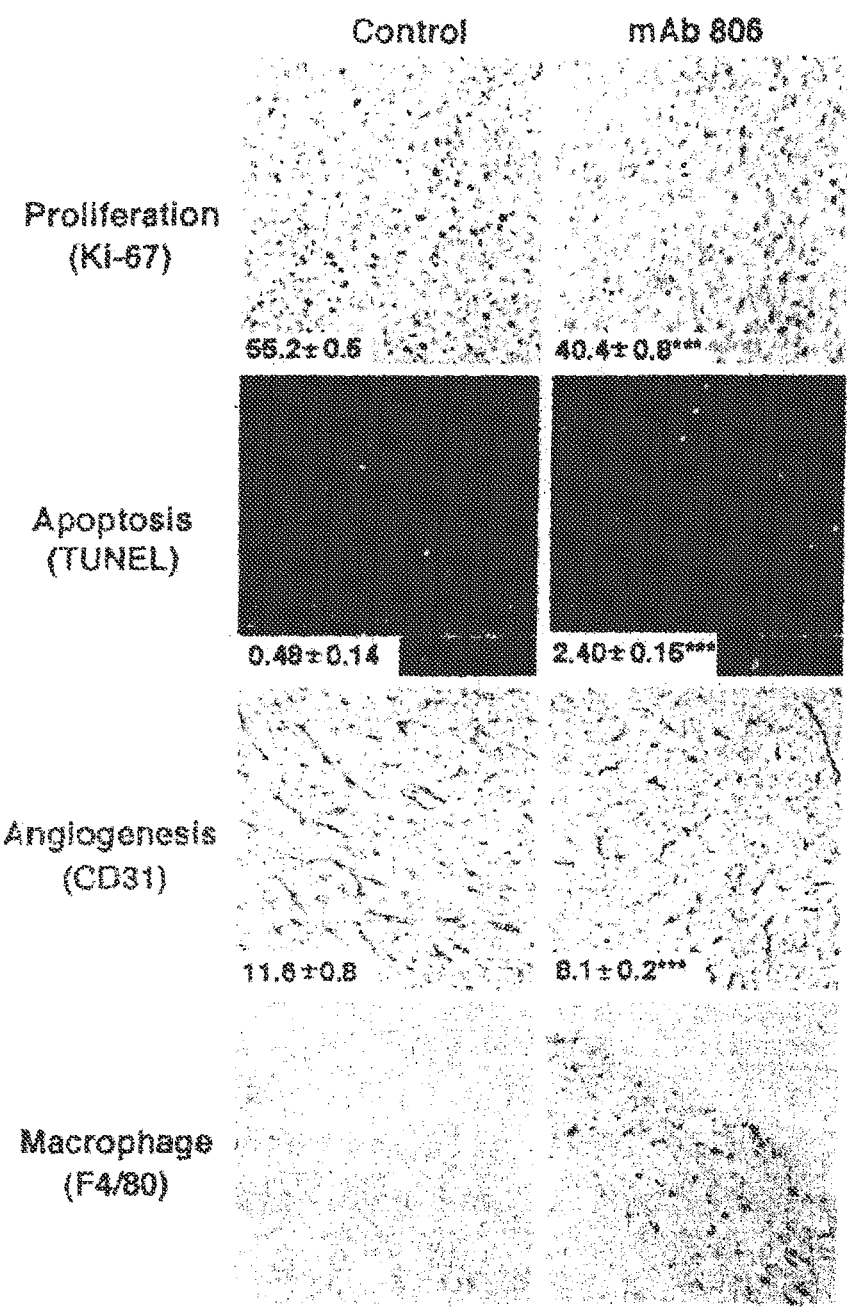

FIG. 28 shows mAb806 treatment leads to a decrease in growth and vasculogenesis and to increases in apoptosis and accumulating macrophages in U87MG.ΔEGFR tumors. Tumor sections were stained for Ki-67. Cell proliferative index was assessed by the percentage of total cells that were Ki-67 positive from four randomly selected high power fields (X400) in intracranial tumors from four mice of each group. Data are the mean±SE. Apoptotic cells were detected by TUNEL assay. Apoptotic index was assessed by the ratio of TUNEL-positive cells:total number of cells from four randomly selected high-power fields (X400) in intracranial tumors from four mice of each group. Data are the mean±SE. Tumor sections were immunostained with anti-CD31 antibody. MVAs were analyzed by computerized image analysis from four randomly selected fields (X200) from intracranial tumors from four mice of each group. Peritumoral infiltrates of macrophages in mAb806-treated U87MG.ΔEGFR tumors. Tumor sections were stained with anti-F4/80 antibody.

Figure 29:
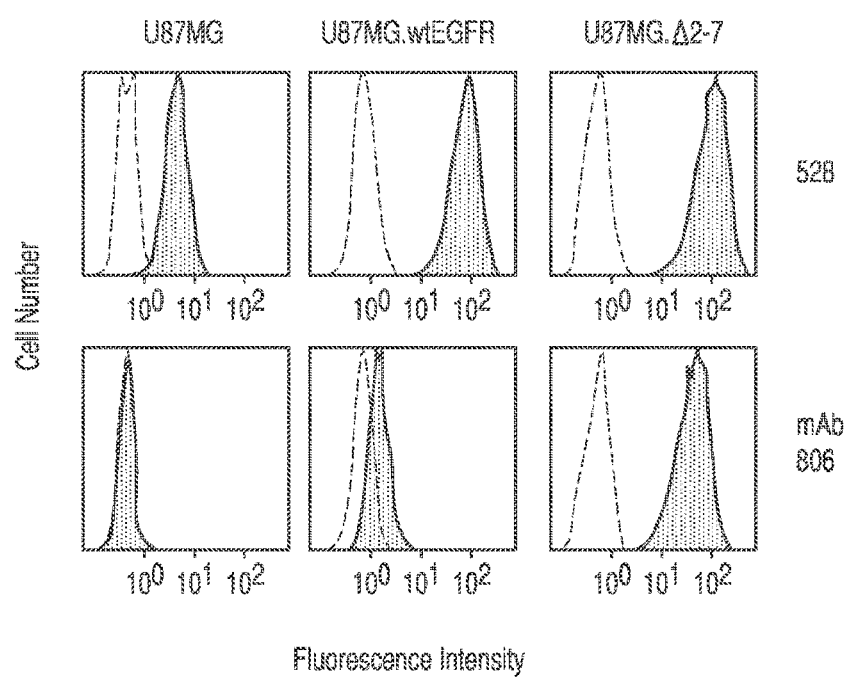

FIG. 29 shows flow cytometric analysis of parental and transfected U87MG glioma cell lines. Cells were stained with either an irrelevant IgG2b antibody (open histograms) or the 528 antibody or mAb806 (filled histograms) as indicated.

Figure 30:
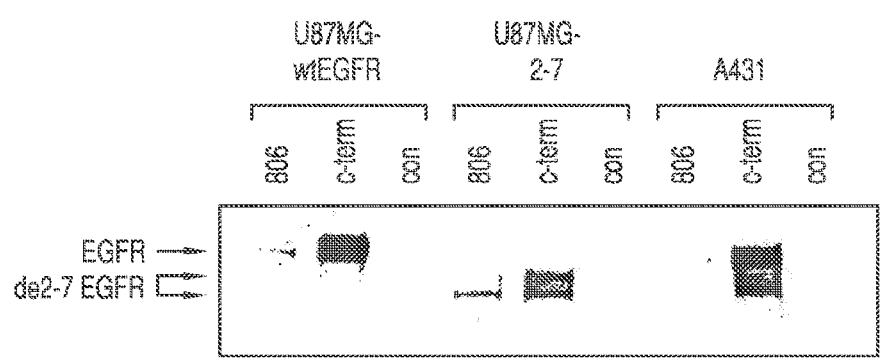

FIG. 30 shows immunoprecipitation of EGFR from cell lines. The EGFR was immunoprecipitated from $^{35}$S-labeled U87MG.wtEGFR, U87MG.Δ2-7, and A431 cells with mAb806 (806), sc-03 antibody (c-term), or a IgG2b isotype control (con). Arrows, position of the de2-7 and wt EGFR.

Figure 31:
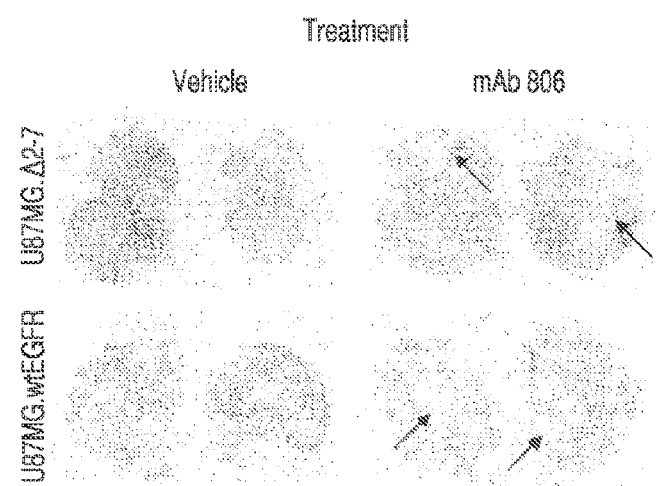

FIG. 31 shows representative H&E-stained paraffin sections of U87MG.Δ2-7 and U87MG.wtEGFR xenografts. U87MG.Δ2-7 (collected 24 days after tumor inoculation) and U87MG.wtEGFR (collected 42 days after tumor inoculation) xenografts were excised from mice treated as described in FIG. 10 above, and stained with H&E. Vehicle-treated U87MG.Δ2-7 (collected 18 days after tumor inoculation) and U87MG.wtEGFR (collected 37 days after tumor inoculation) xenografts showed very few areas of necrosis (left panel), whereas extensive necrosis (arrows) was observed in both U87MG.Δ2-7 and U87MG.wtEGFR xenografts treated with mAb806 (right panel).

Figure 32:
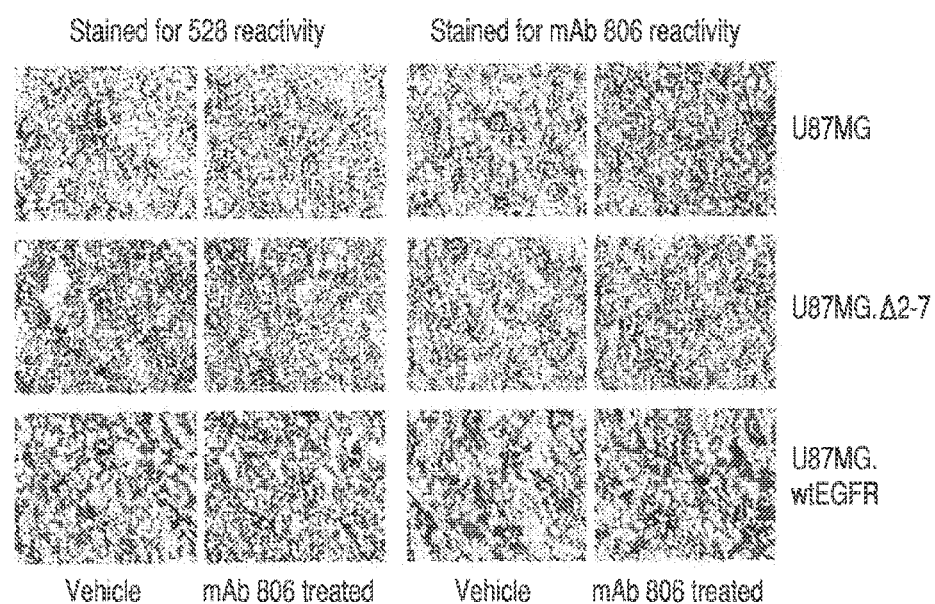

FIG. 32 shows immunohistochemical analysis of EGFR expression in frozen sections derived from U87MG, U87MG.Δ2-7, and U87MG.wtEGFR xenografts. Sections were collected at the time points described in FIG. 31 above. Xenograft sections were immunostained with the 528 antibody (left panel) and mAb806 (right panel). No decreased immunoreactivity to either wtEGFR, amplified EGFR, or de2-7 EGFR was observed in xenografts treated with mAb806. Consistent with the in vitro data, parental U87MG xenografts were positive for 528 antibody but were negative for mAb806 staining.

Figure 33:
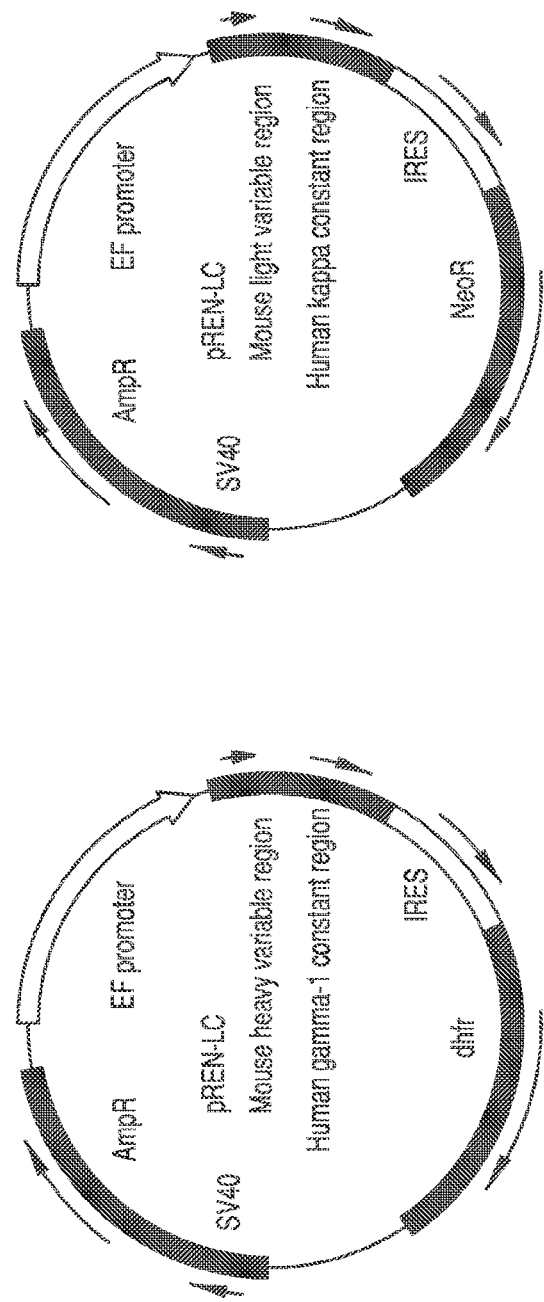

FIG. 33 shows a schematic representation of generated bicistronic expression constructs. Transcription of the chimeric antibody chains is initiated by Elongation Factor-1 promoter and terminated by a strong artificial termination sequence. IRES sequences were introduced between coding regions of light chain and NeoR and heavy chain and dhfr gene.

Figure 34B:
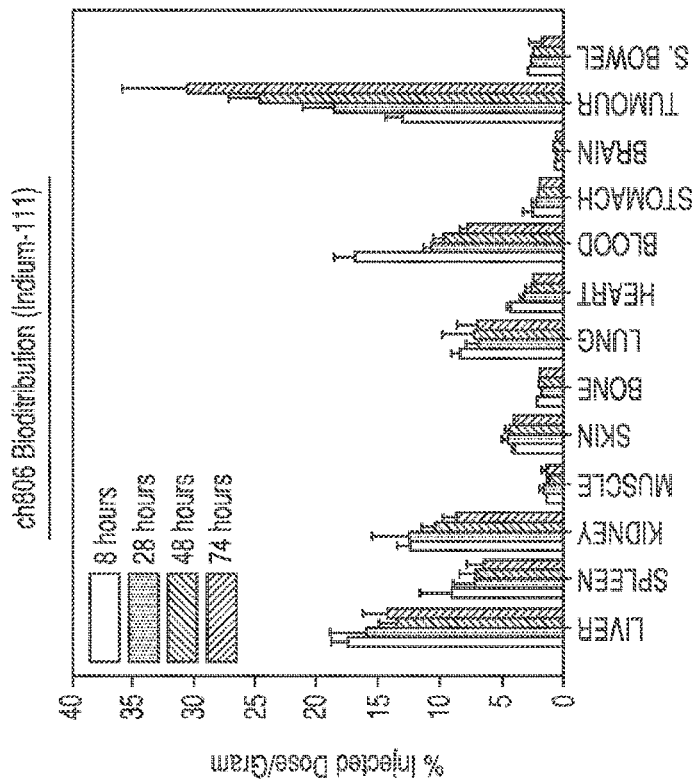
Figure 34A:
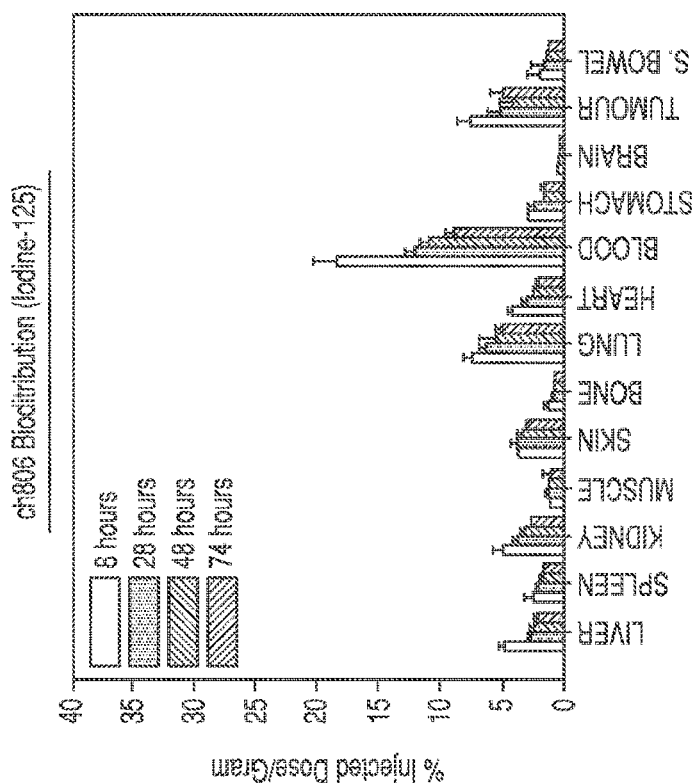

FIGS. 34A and 34B show biodistribution analysis of the ch806 radiolabeled with either (A) $^{125}$I or (B) $^{111}$In was performed in BALB/c nude mice bearing U87MG-de2-7 xenograft tumors. Mice were injected with 5 μg of radiolabeled antibody and in groups of 4 mice per time point, sacrificed at either 8, 28, 48 or 74 hours. Organs were collected, weighed and radioactivity measured in a gamma counter.

Figures 35A, 35B:
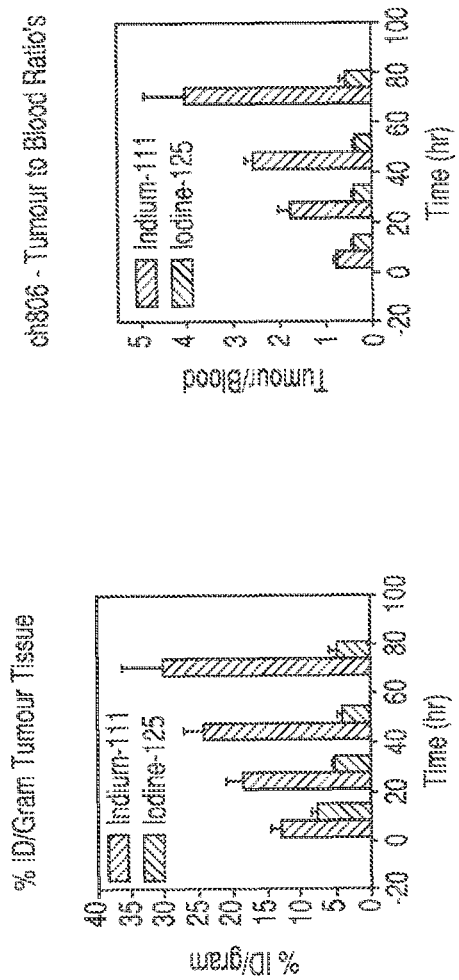

FIGS. 35A and 35B depict (A) the % ID gram tumor tissue and (B) the tumor to blood ratio. Indium-111 antibody shows approximately 30% ID/gram tissue and a tumor to blood ratio of 4.0.

Figure 36:
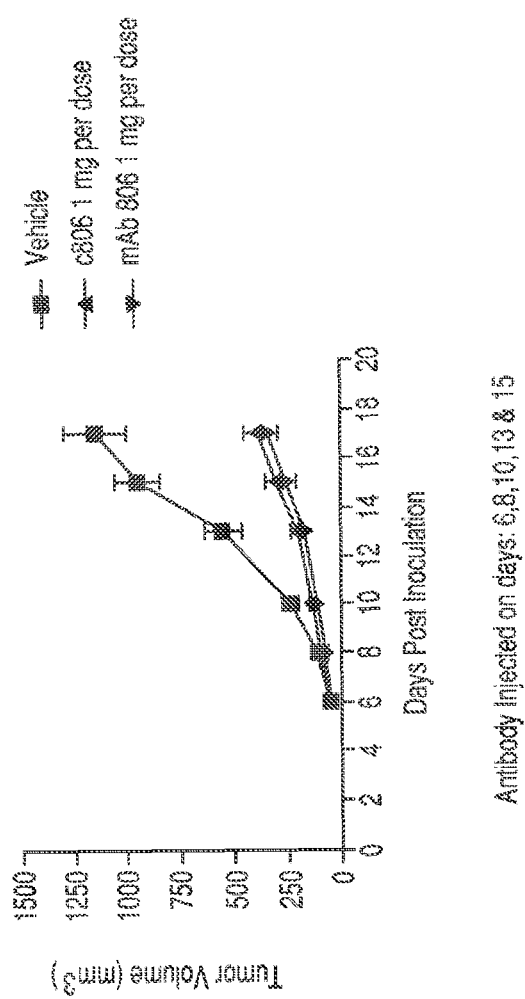

FIG. 36 depicts the therapeutic efficacy of chimeric antibody ch806 in an established tumor model. $3 \times 10^6$ U87MG.Δ2-7 cells in 100 μl of PBS were inoculated s.c. into both flanks of 4-6 week old female nude mice. mAb806 was included as a positive control. Treatment was started when tumors had reached a mean volume of 50 mm$^3$ and consisted of 1 mg of ch806 or mAb806 given i.p. for a total of 5 injections on the days indicated. Data was expressed as mean tumor volume±S.E. for each treatment group.

Figure 37:
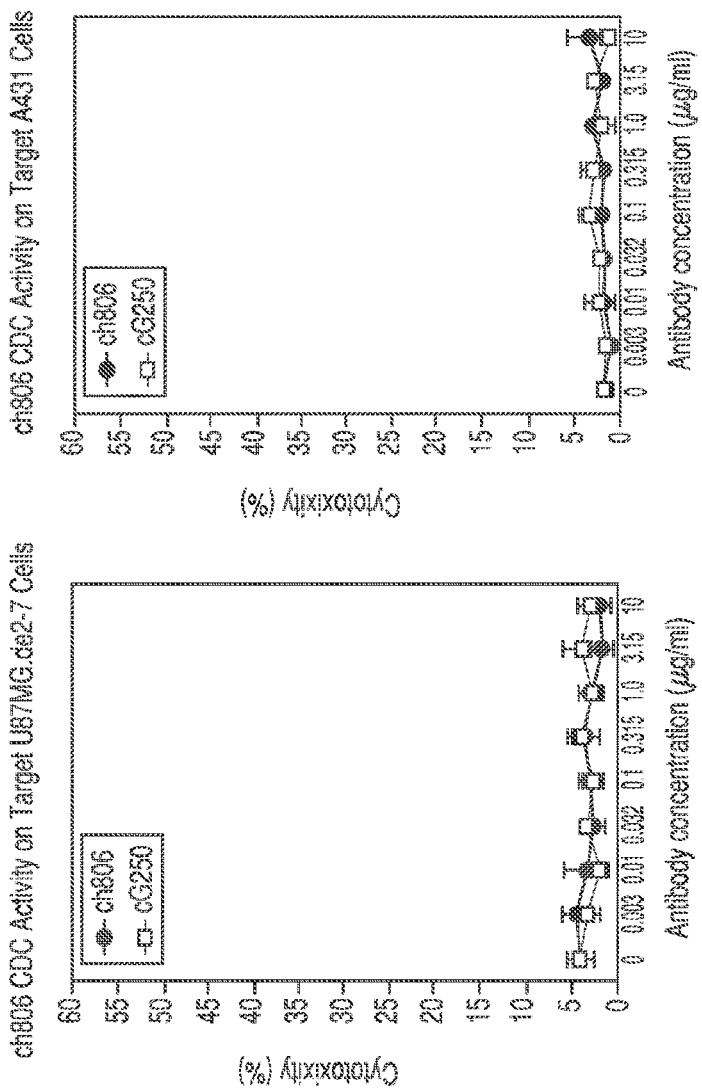

FIG. 37 shows CDC Activity on Target (A) U87MG.de2-7 and (B) A431 cells for anti-EGFR chimeric IgG1 antibodies ch806 and control cG250. Mean (bars; ±SD) percent cytotoxicity of triplicate determinations are presented.

Figure 38:
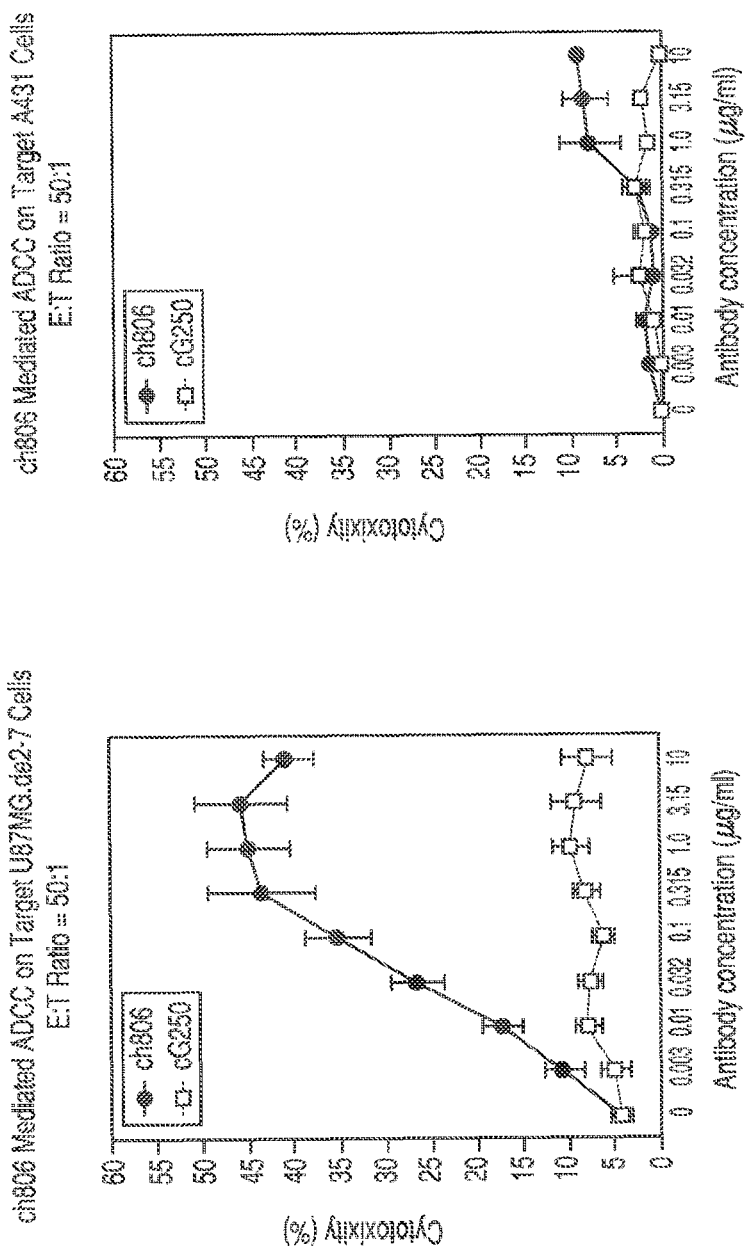

FIG. 38 shows ADCC on target (A) U87MG.de2-7 and (B) A431 cells at Effector:Target cell ratio of 50:1 mediated by ch806 and isotype control cG250 (0-10 μg/ml). Results are expressed as mean (bars; ±SD) percent cytotoxicity of triplicate determinations.

Figure 39:
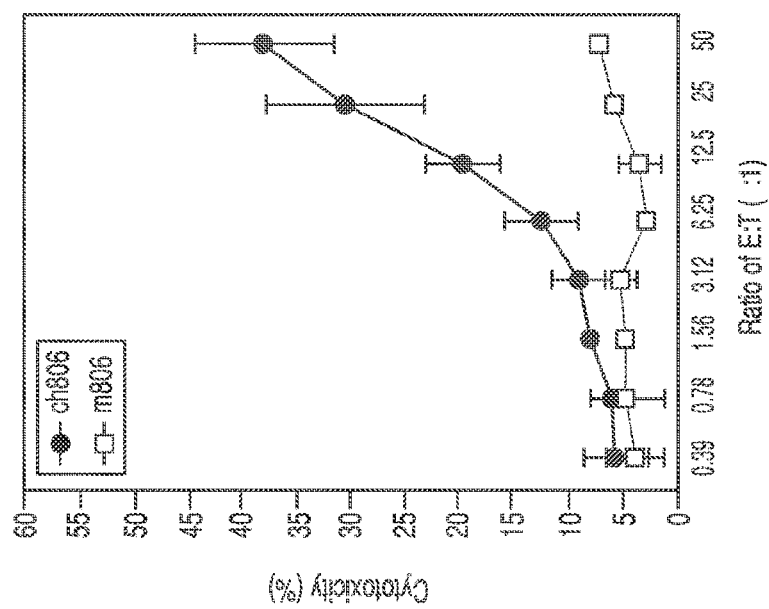

FIG. 39 shows ADCC mediated by 1 μg/ml parental mAb806 and ch806 on target U87MG.de2-7 cells over a range of Effector:Target ratios. Mean (bars; ±SD) of triplicate determinations are presented.

Figure 40:
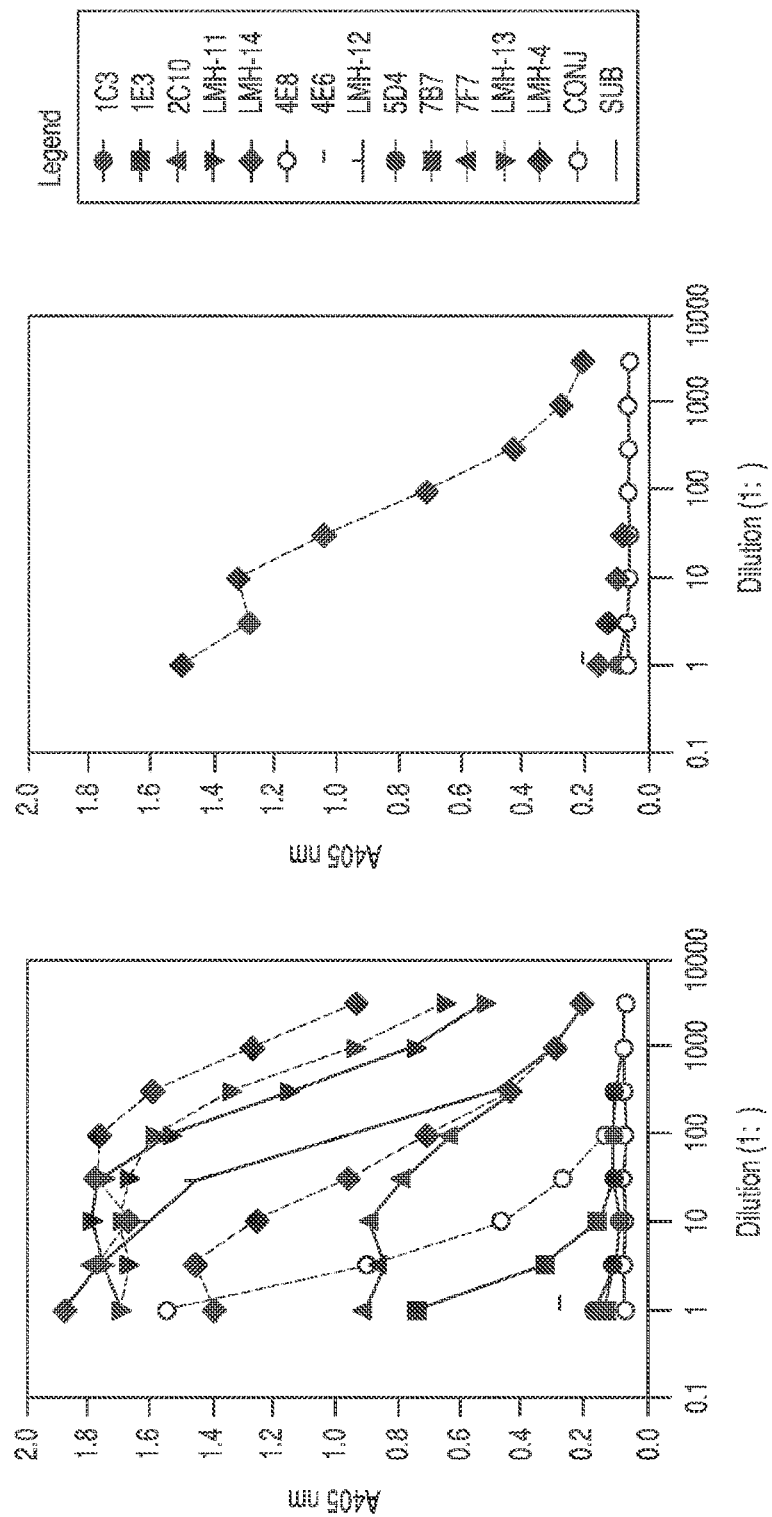

FIG. 40 shows twenty-five hybridomas producing antibodies that bound ch806 but not huIgG were initially selected. Four of these anti-ch806 hybridomas with high affinity binding (clones 3E3, 5B8, 9D6 and 4D8) were subsequently pursued for clonal expansion from single cells by limiting dilution and designated Ludwig Institute for Cancer Research Melbourne Hybridoma (LMH)-11, -12, -13 and -14, respectively. In addition, two hybridomas that produced mAbs specific for huIgG were also cloned and characterized further: clones 2C10 (LMH-15) and 2B8 (LMH-16).

FIGS. 41A, 41B, and 41C show that after clonal expansion, the hybridoma culture supernatants were examined in triplicate by ELISA for the ability to neutralize ch806 or mAb806 antigen binding activity with sEGFR621. Mean (±SD) results demonstrated the antagonist activity of anti-idiotype mAbs LMH-11, -12, -13 and -14 with the blocking in solution of both ch806 and murine mAb806 binding to plates coated with sEGFR (LMH-14 not shown).

Figure 42C:
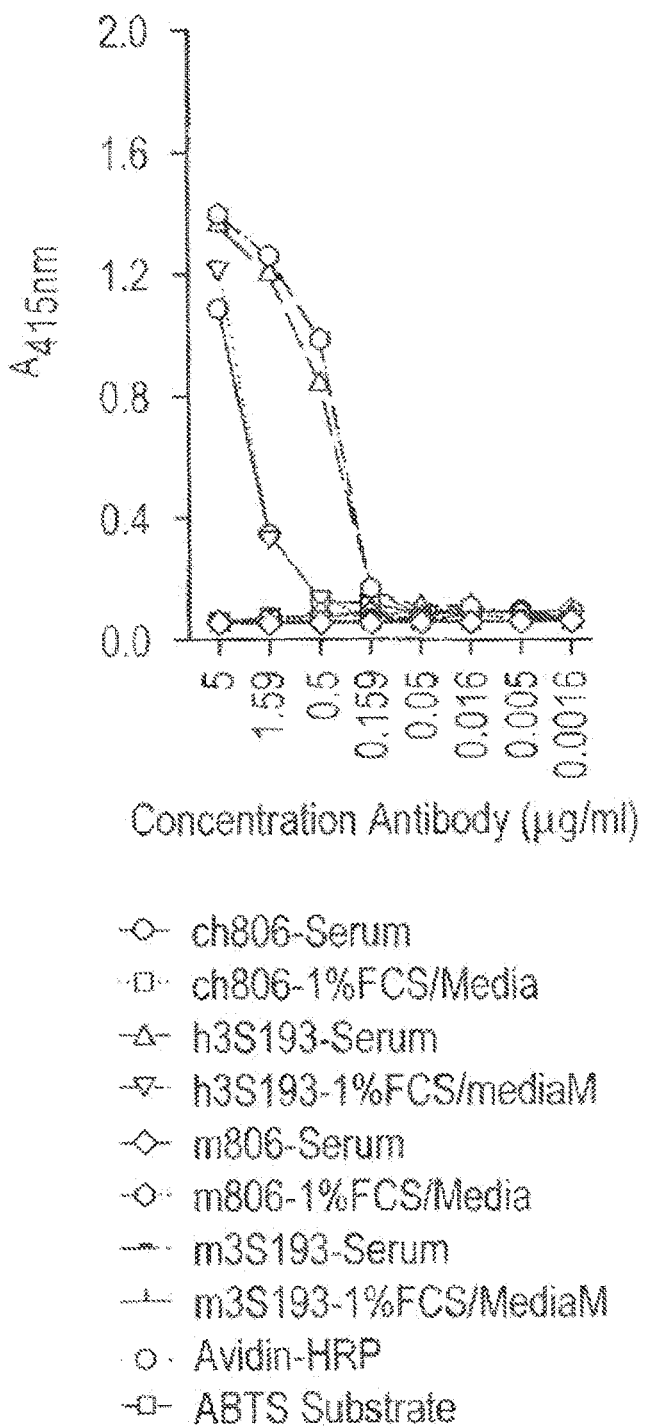

FIGS. 42A, 42B, and 42C show microtitre plates that were coated with 10 μg/ml purified (A) LMH-11, (B) LMH-12 and (C) LMH-13. The three purified clones were compared for their ability to capture ch806 or mAb806 in sera or 1% FCS/Media and then detect bound ch806 or mAb806. Isotype control antibodies hu3S193 and m3S193 in serum and 1% FCS/Media were included in addition to controls for secondary conjugate avidin-HRP and ABTS substrate. Results are presented as mean (±SD) of triplicate samples using biotinylated-LMH-12 (10 μg/ml) for detection and indicate LMH-12 used for capture and detection had the highest sensitivity for ch806 in serum (3 ng/ml) with negligible background binding.

Figure 43:
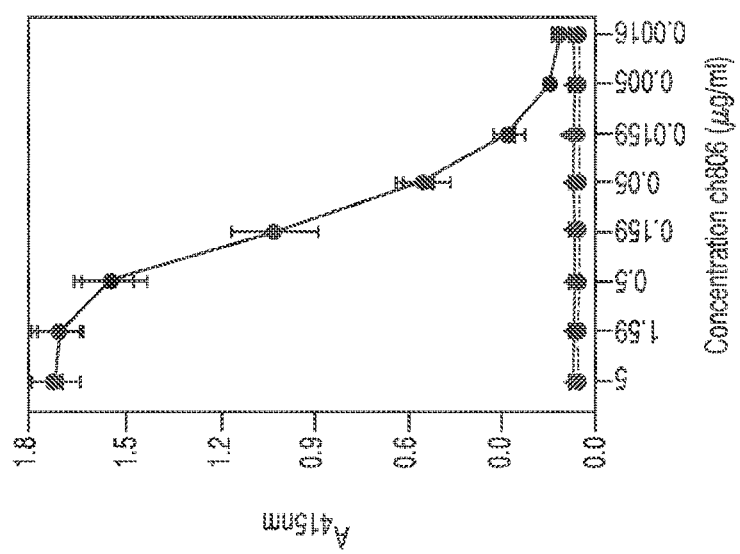

FIG. 43 shows validation of the optimal pharmacokinetic ELISA conditions using 1 μg/ml anti-idiotype LMH-12 and 1 μg/ml biotinylated LMH-12 for capture and detection, respectively. Three separate ELISAs were performed in quadruplicate to measure ch806 in donor serum (●) from three healthy donors or 1% BSA/media (■) with isotype control hu3S193 in serum (▲) or 1% BSA/media (▼). Controls for secondary conjugate avidin-HRP (♦) and ABTS substrate (hexagon) alone were also included with each ELISA. Mean (±SD) results demonstrate highly reproducible binding curves for measuring ch806 (2 μg/ml-1.6 ng/ml) in sera with a 3 ng/ml limit of detection. (n=12; 1-100 ng/ml, Coefficient of Variation<25%; 100 ng/ml-5 μg/ml, Coefficient of Variation<15%). No background binding was evident with any of the three sera tested and negligible binding was observed with isotype control hu3S193.

Figure 44:
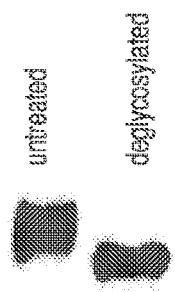

FIG. 44 depicts an immunoblot of recombinant sEGFR expressed in CHO cells, blotted with mAb806. Recombinant sEGFR was treated with PNGaseF to remove N-linked glycosylation (deglycosylated), or untreated (untreated), the protein was run on SDS-PAGE, transferred to membrane and immunoblotted with mAb806.

Figure 45:
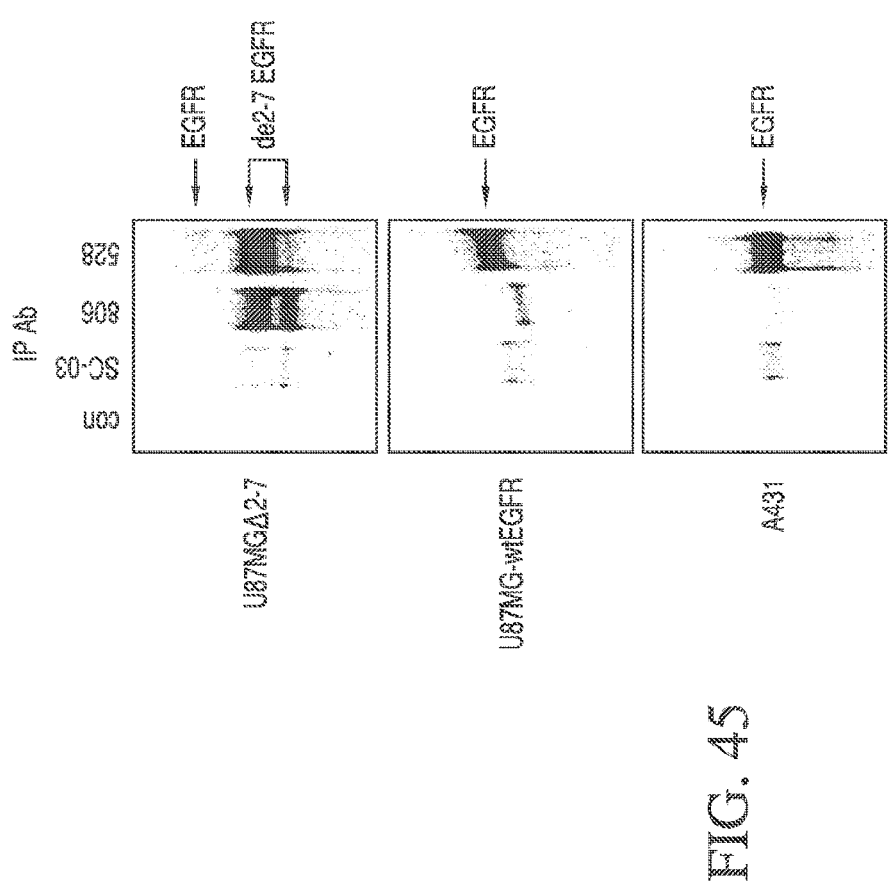

FIG. 45 depicts immunoprecipitation of EGFR from $^{35}$S-labelled cell lines (U87MG.Δ2-7, U87MG-wtEGFR, and A431) with different antibodies (SC-03, 806 and 528 antibodies).

Figure 46:
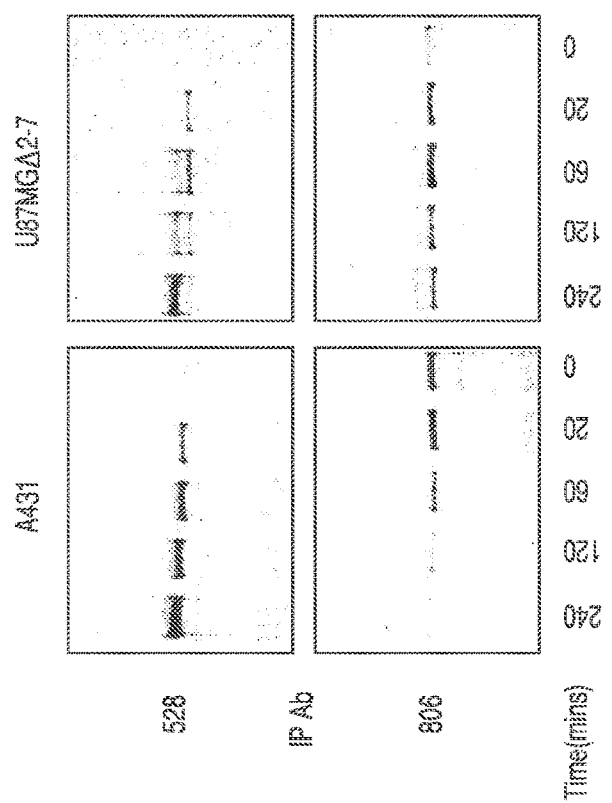

FIG. 46 depicts immunoprecipitation of EGFR from different cells (A431 and U87MG.Δ2-7) at different time points (time 0 to 240 minutes) after pulse-labeling with $^{35}$S methionine/cysteine. Antibodies 528 and 806 are used for immunoprecipitation.

Figure 47:
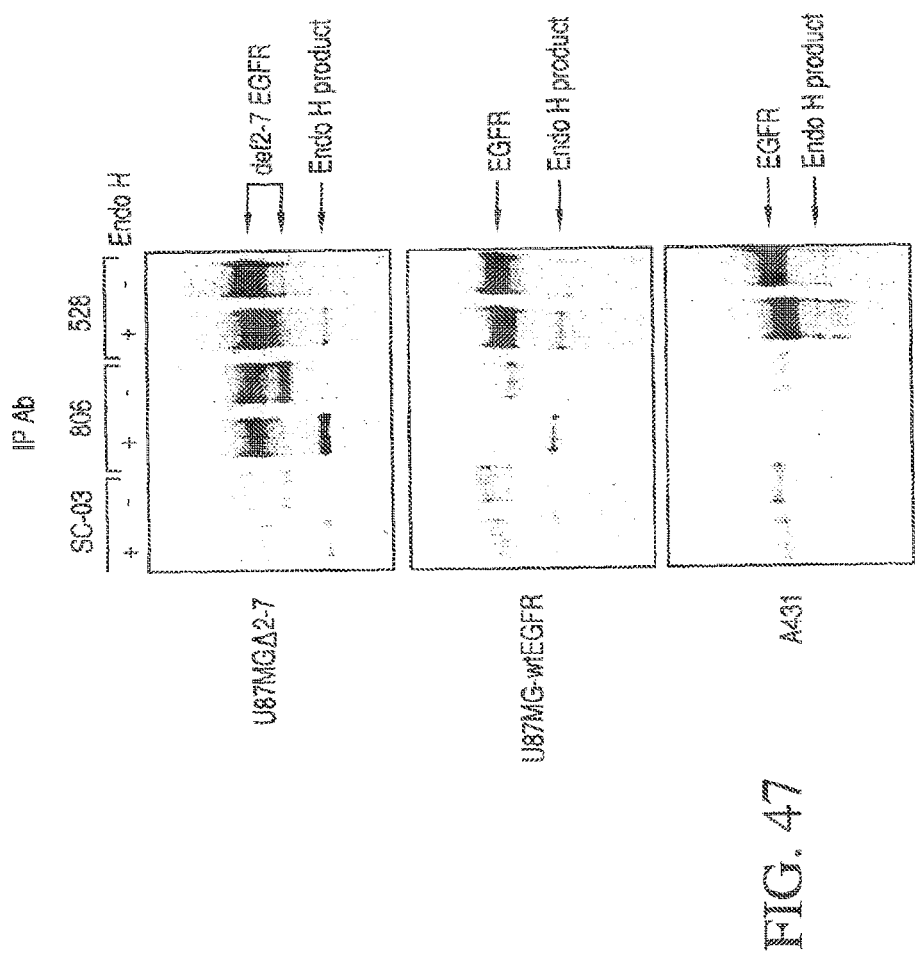

FIG. 47 depicts immunoprecipitation of EGFR from various cell lines (U87MGΔ2-7, U87MG-wtEGFR and A431) with various antibodies (SC-03, 806 and 528) in the absence of (−) and after Endo H digestion (+) to remove high mannose type carbohydrates.

Figure 48:
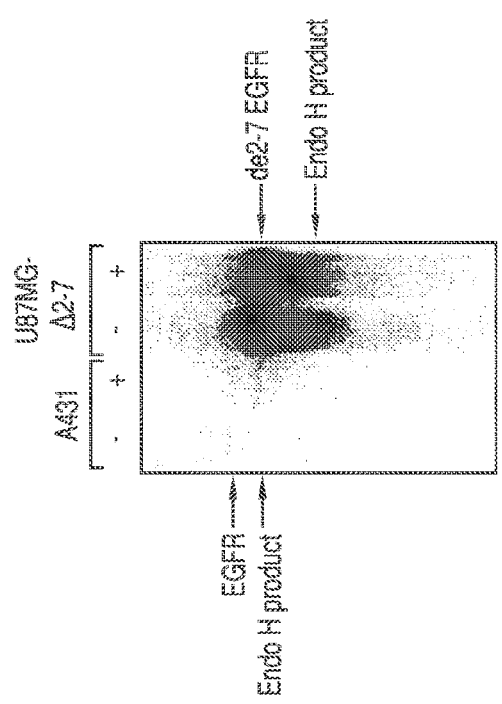

FIG. 48 depicts cell surface iodination of the A431 and U87MG.Δ2-7 cell lines followed by immunoprecipitation with the 806 antibody, and with or without Endo H digestion, confirming that the EGFR bound by mAb806 on the cell surface of A431 cells is an EndoH sensitive form.

FIGS. 49A-F show the pREN ch806 LC Neo Vector (SEQ ID NO:7).

FIGS. 50A-G show the pREN ch806 HC DHFR Vector (SEQ ID NO:8).

FIGS. 51A-D shows the mAb124 VH and VL chain nucleic acid sequences (SEQ ID NOS:21 and 26, respectively) and amino acid sequences (SEQ ID NOS:22 and 27, respectively).

FIGS. 52A-D shows the mAb1133 VH and VL chain nucleic acid sequences (SEQ ID NO:31 and 36, respectively) and amino acid sequences (SEQ ID NOS:32 and 37, respectively).

Figure 53:
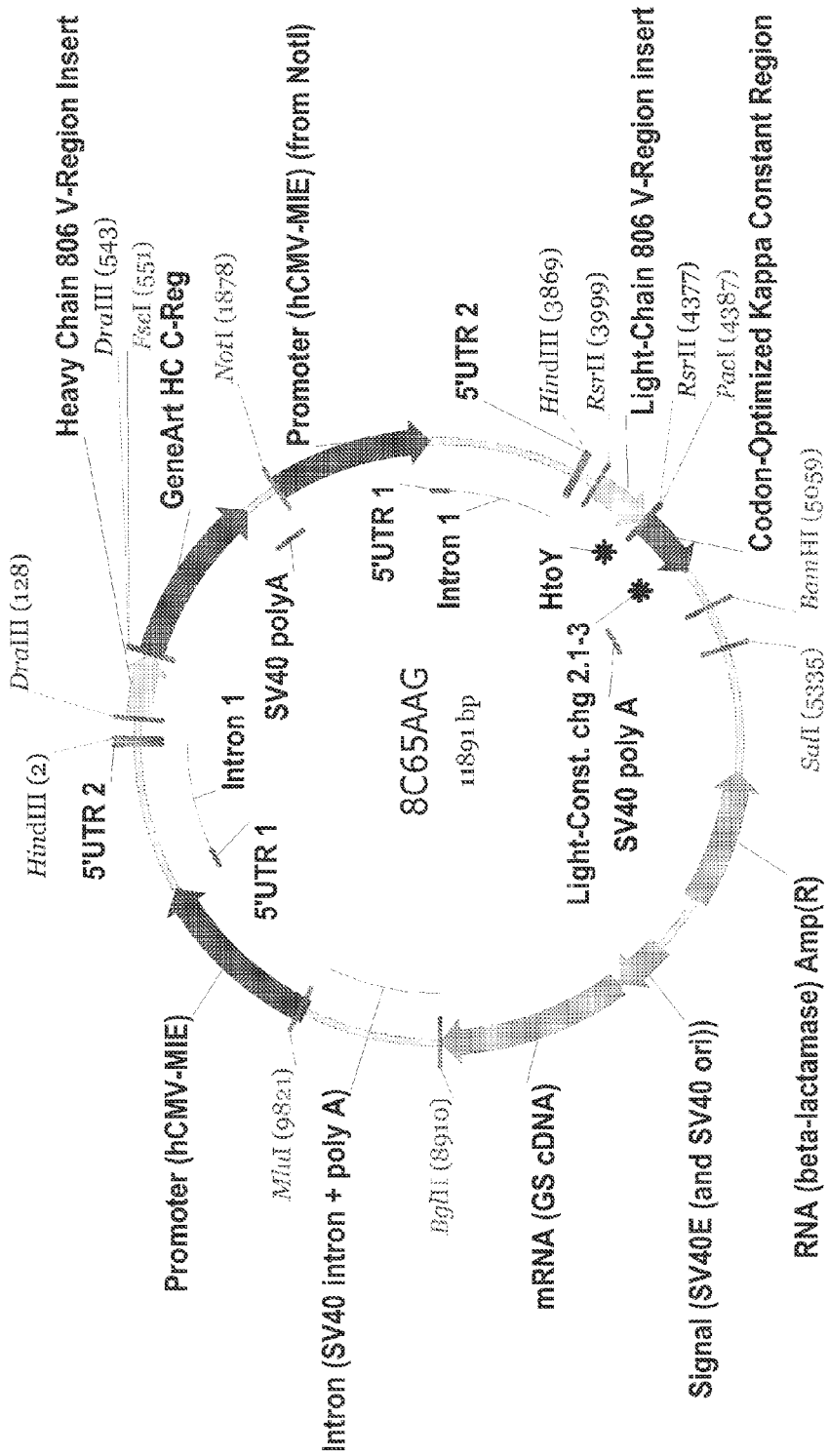
Figure 54A:
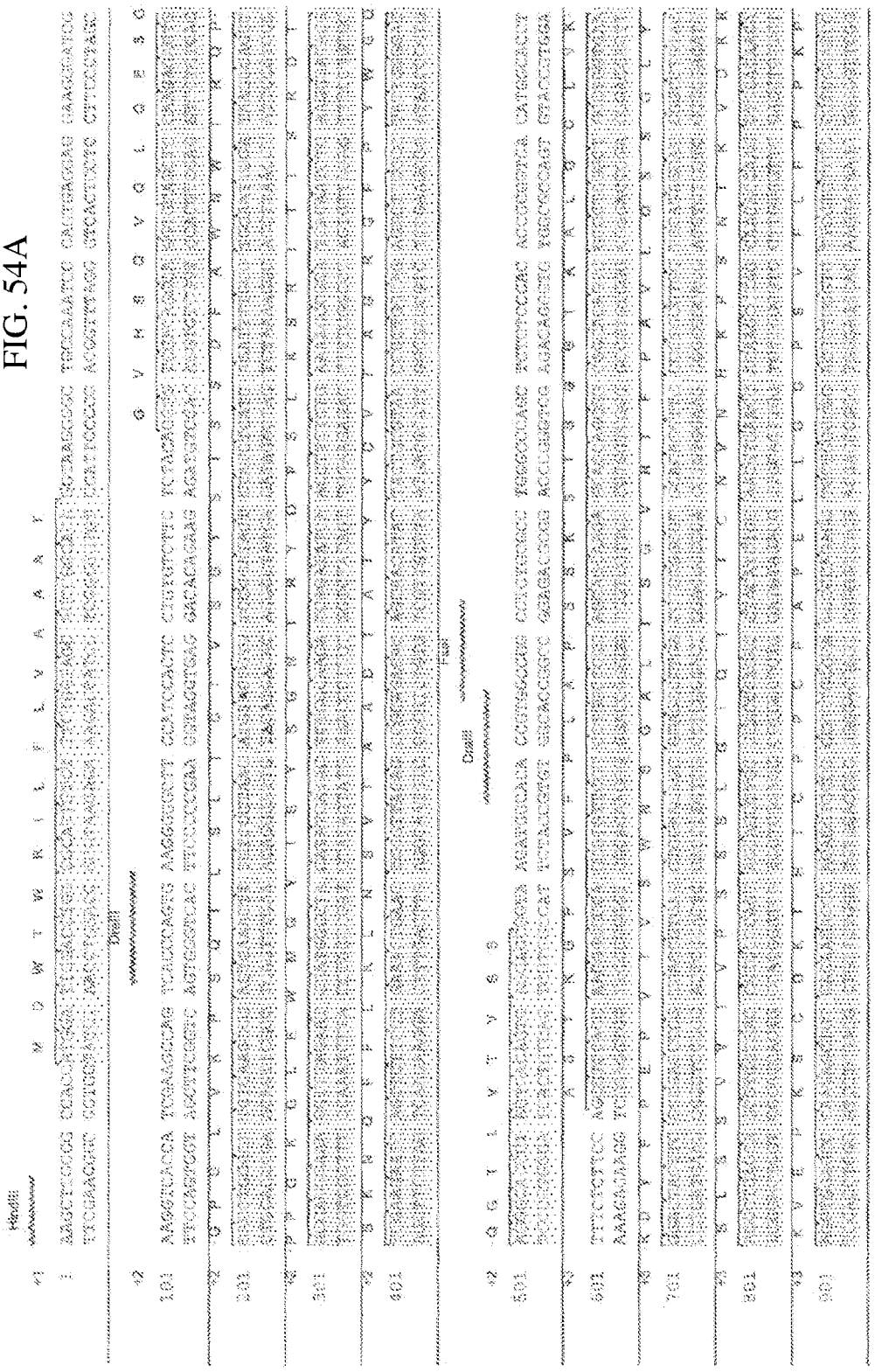
Figure 54D:
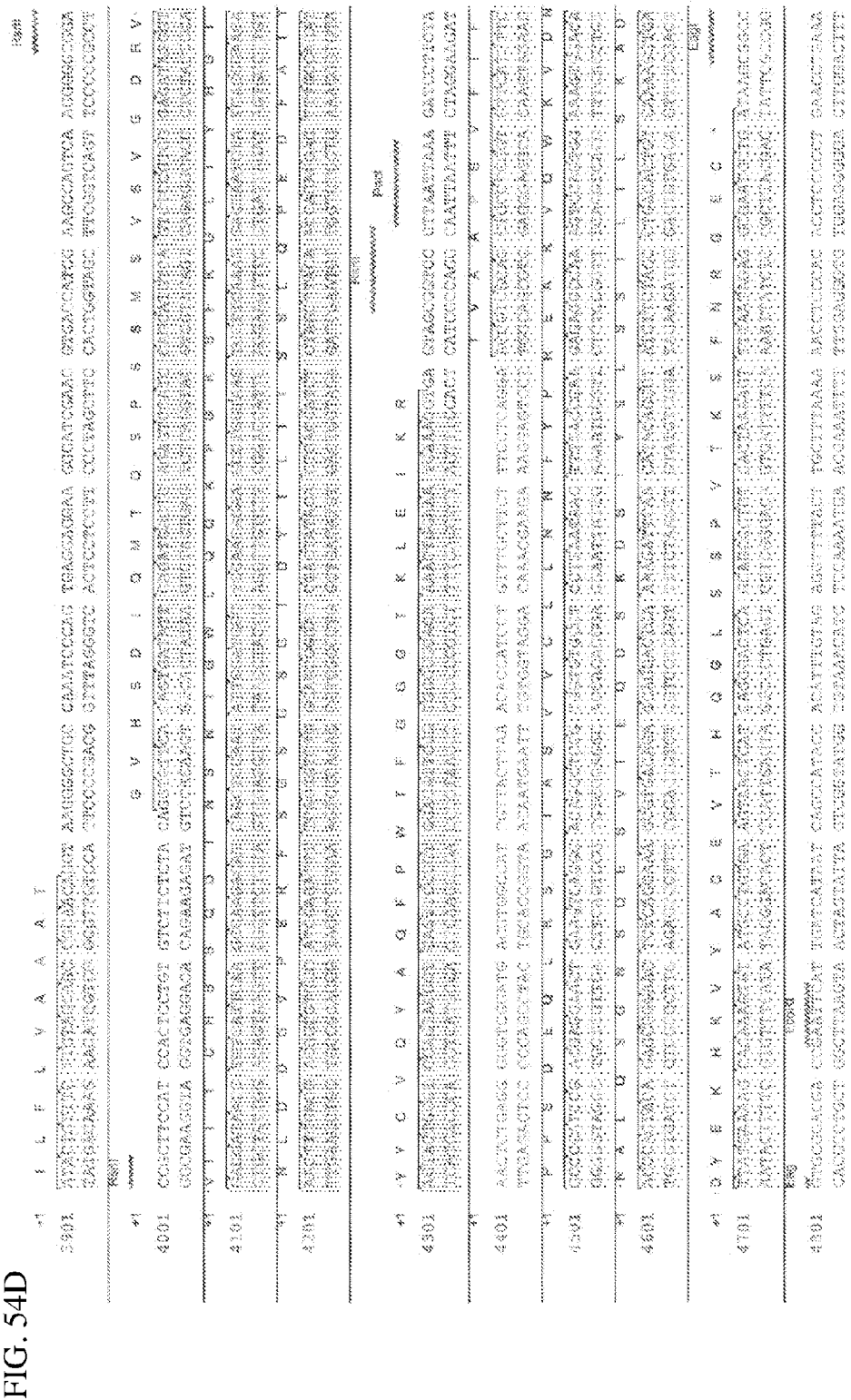

FIG. 53 shows a DNA plasmid graphic of the combined, double gene Lonza plasmid including pEE12.4 containing the hu806H (VH+CH) expression cartridge, and pEE6.4 containing the hu806L (VL+CL) expression cartridge.

Figure 54B:
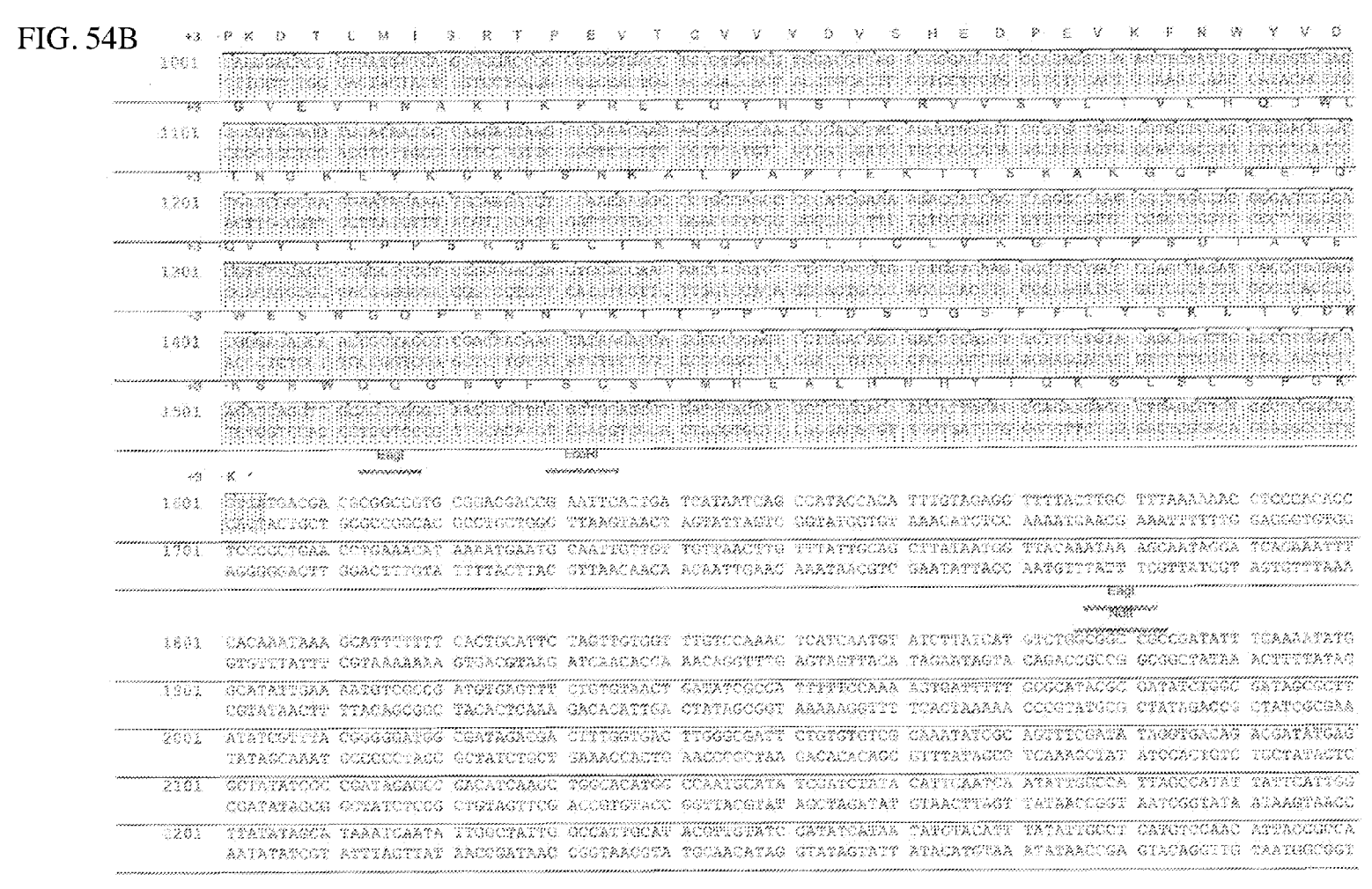
Figure 54C:
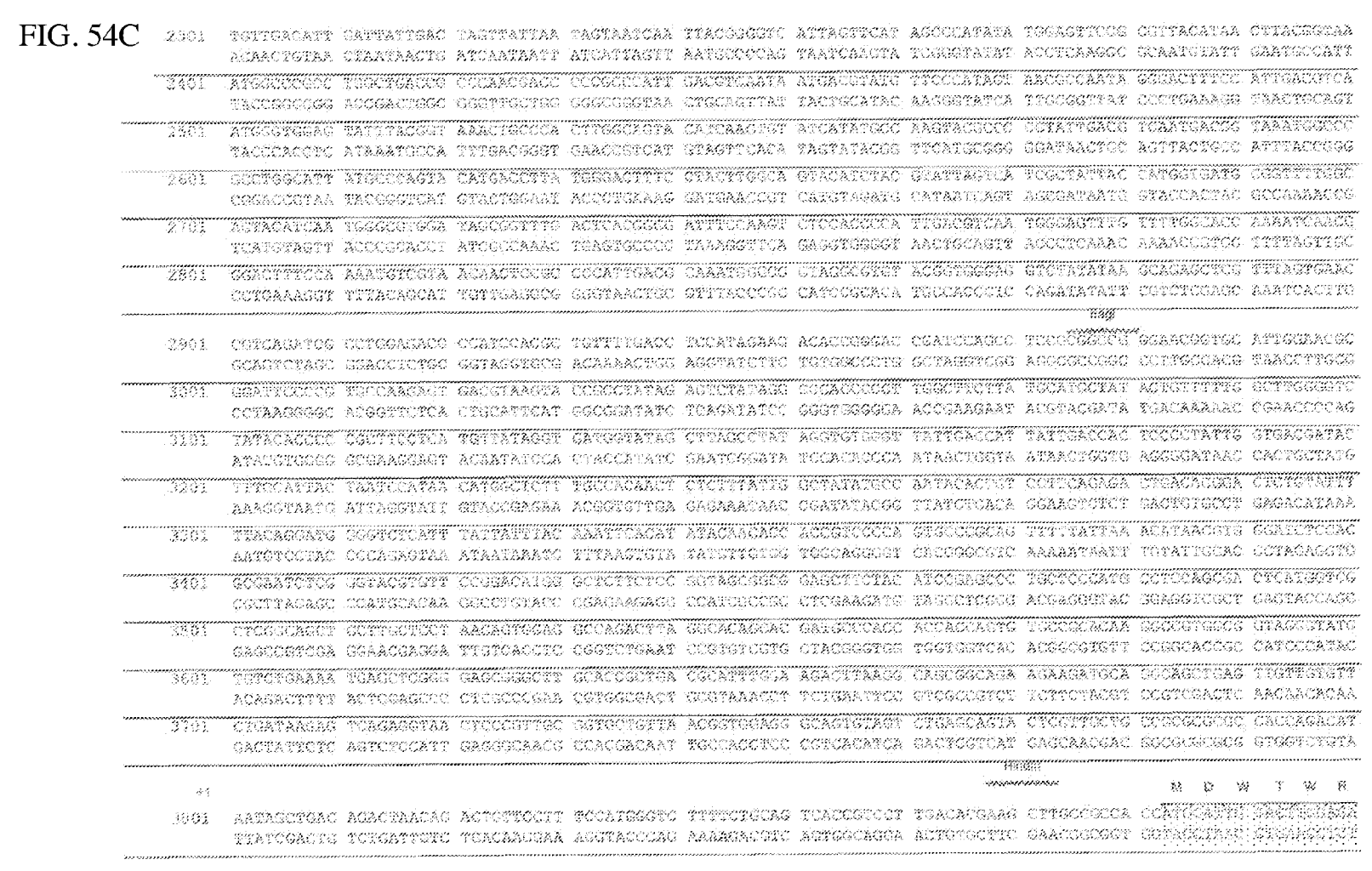
Figure 54F:
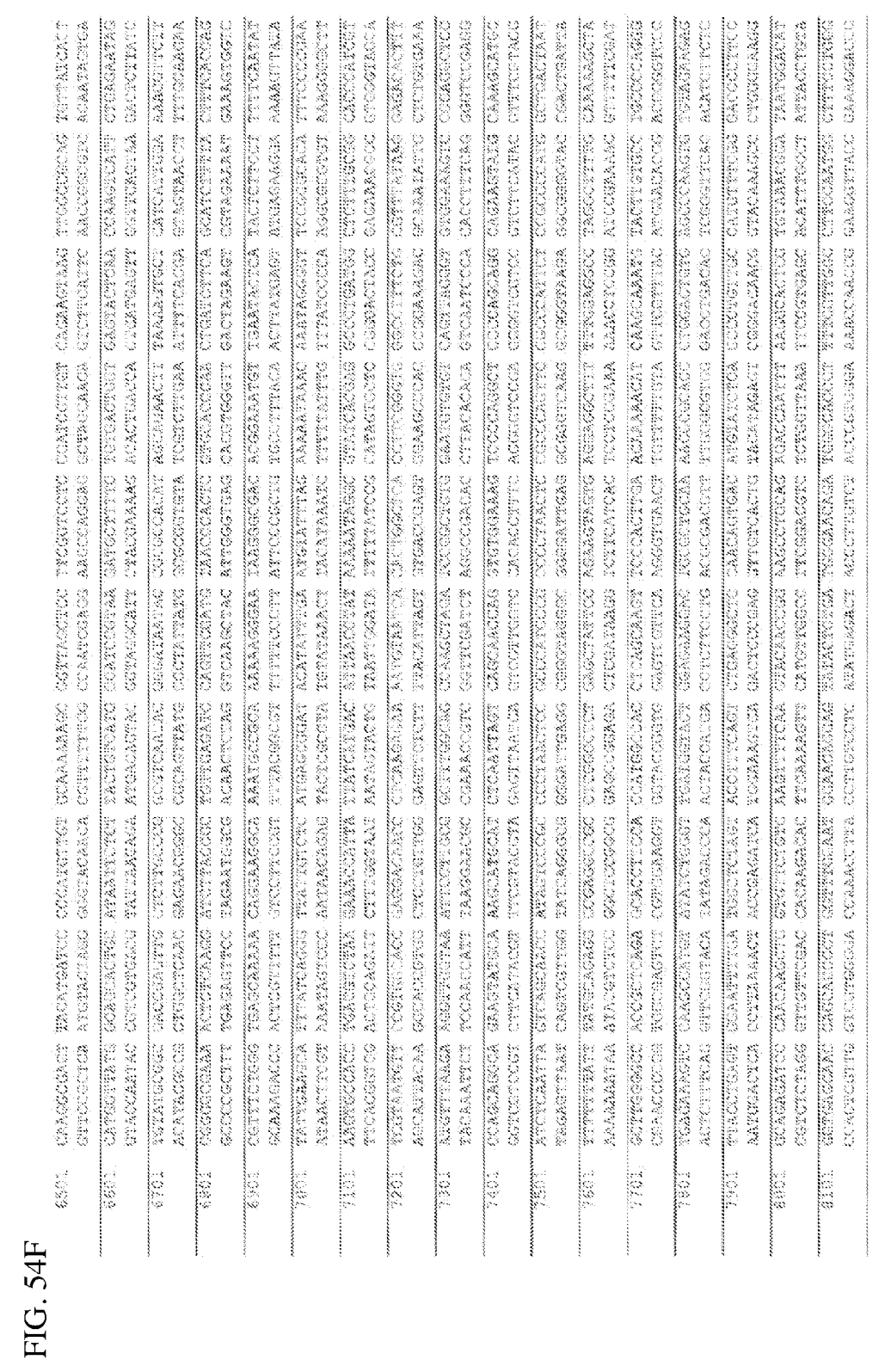
Figure 54H:
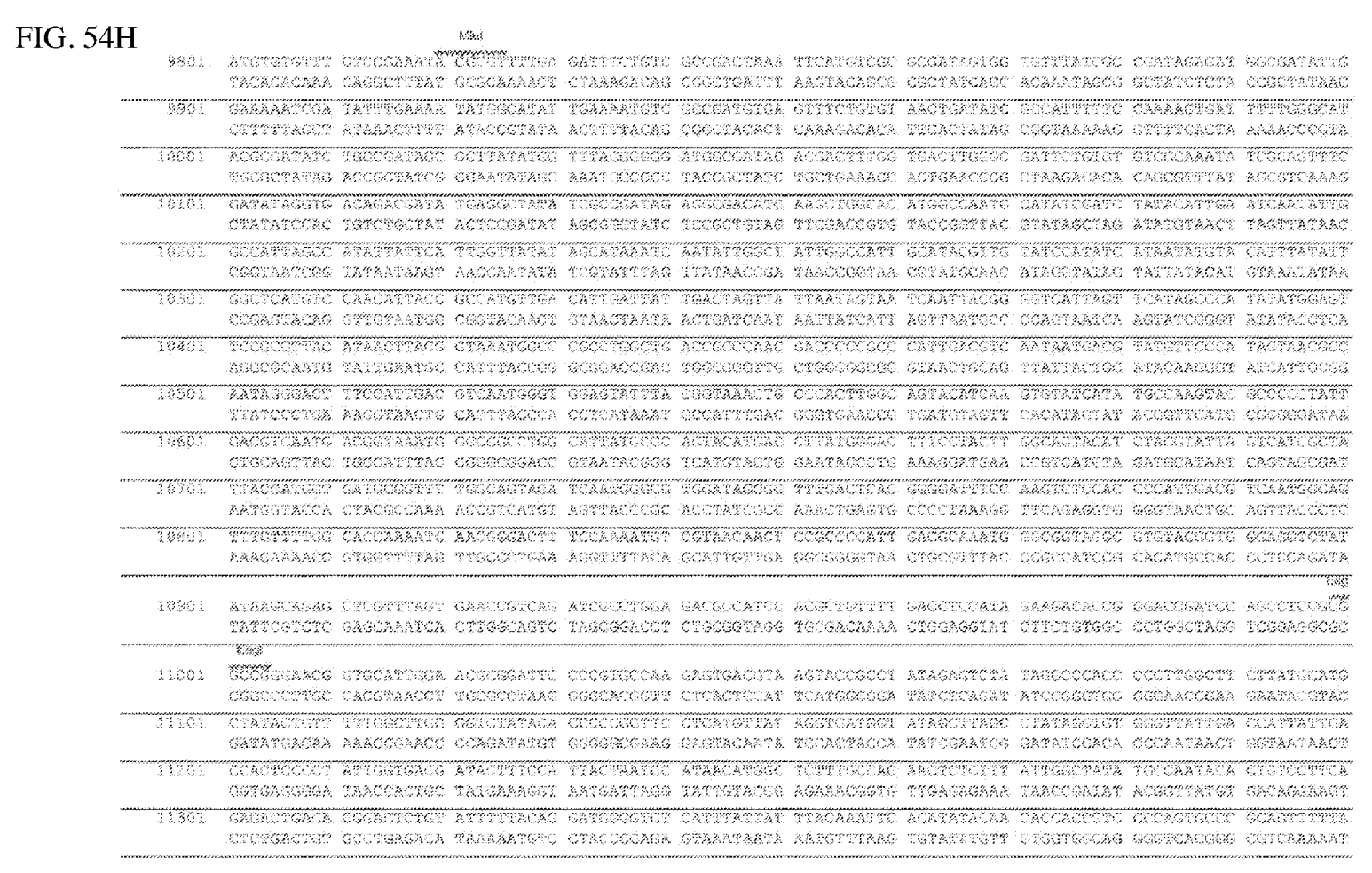
Figure 54I:
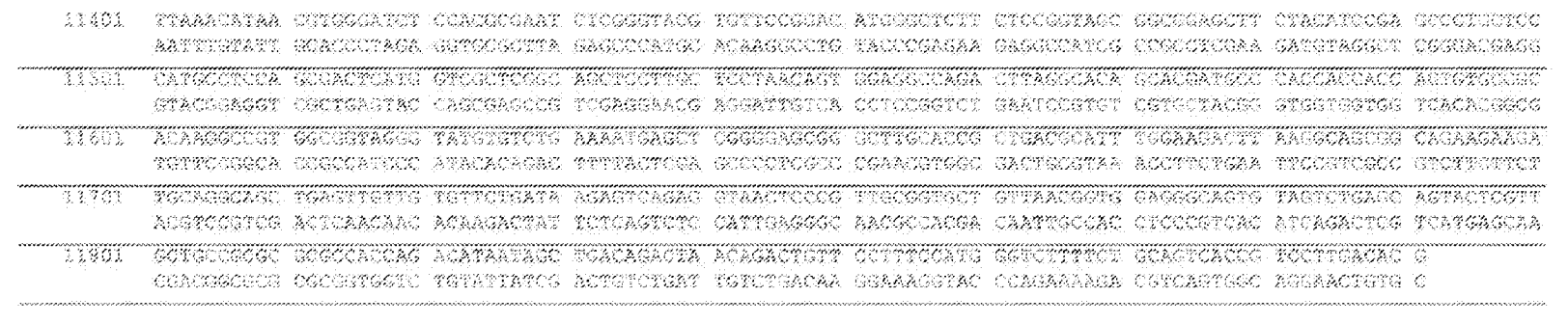

FIGS. 54A-I show the DNA sequence (SEQ ID NO:41; complement SEQ ID NO:162) of the combined Lonza plasmid described in FIG. 53. This sequence also shows all translations (SEQ ID NOS:42-51 and 163-166) relevant to the hu806 antibody. The plasmid has been sequence-verified, and the coding sequence and translation checked. Sections of the sequence have been shaded to identify regions of interest; the shaded regions correspond to actual splice junctions. The color code is as follows:

(gray): signal region, initial coding sequences found at both the heavy and light-chain variable regions;

(lavender): hu806 VH chain, veneered heavy-chain variable region;

(pink): hu806 CH chain, codon-optimized heavy-chain constant region;

(green): hu806 VL chain, veneered light-chain variable region; and (yellow): hu806 CL chain, codon-optimized light-chain constant region.

Figures 55A, 55B:
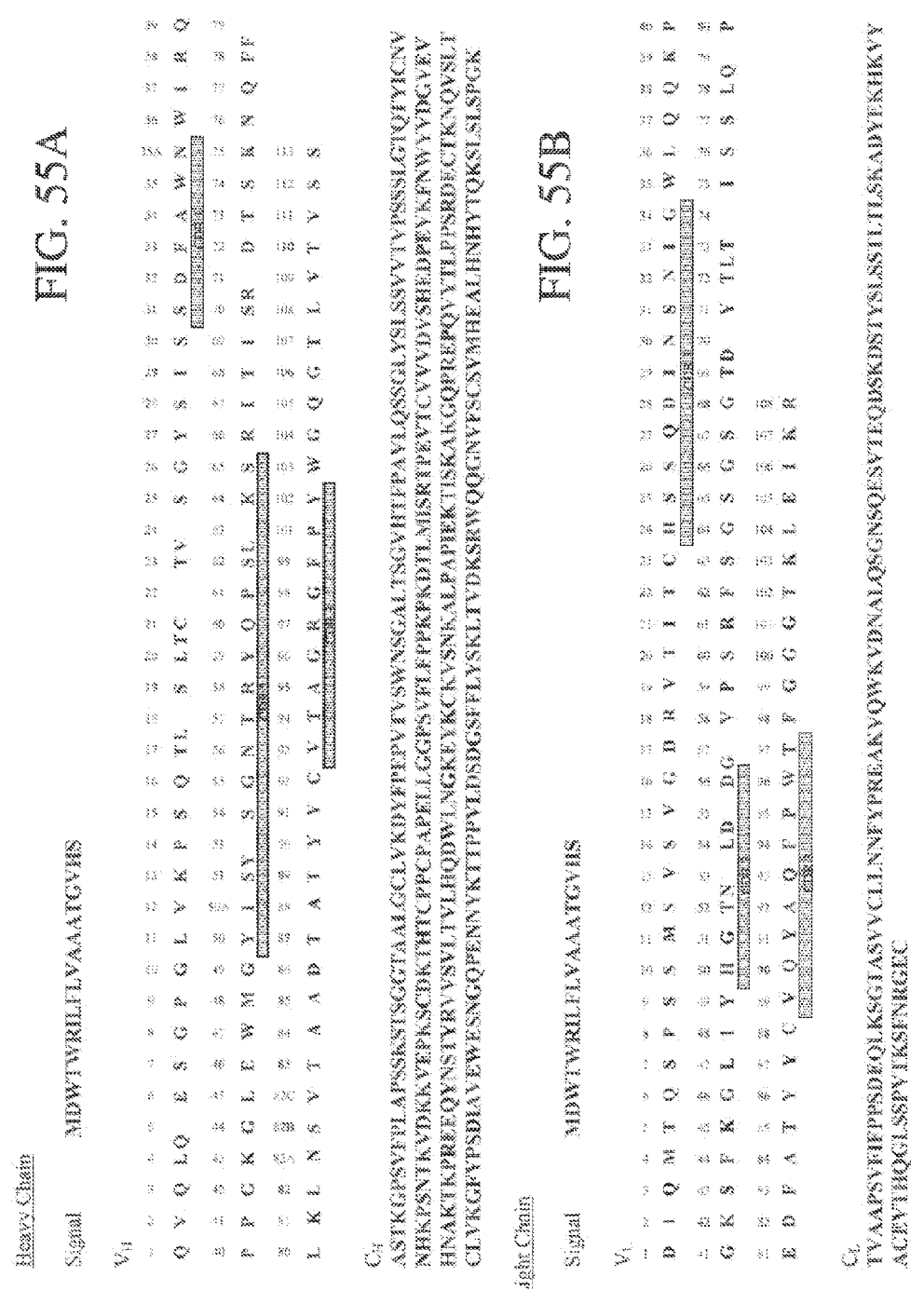

FIGS. 55A and 55B show the hu806 translated amino acid sequences (VH and VL chains of SEQ ID NOS:164 and 166 and their respective signal peptides of SEQ ID NOS:163 and 165; CH and CL chains of SEQ ID NOS:43 and 48), and give the Kabat numbers for the VH and VL chains (SEQ ID NOS: 164 and 165, respectively), with CDRs (SEQ ID NOS:44-46 and 49-51) underlined.

Figure 56C:
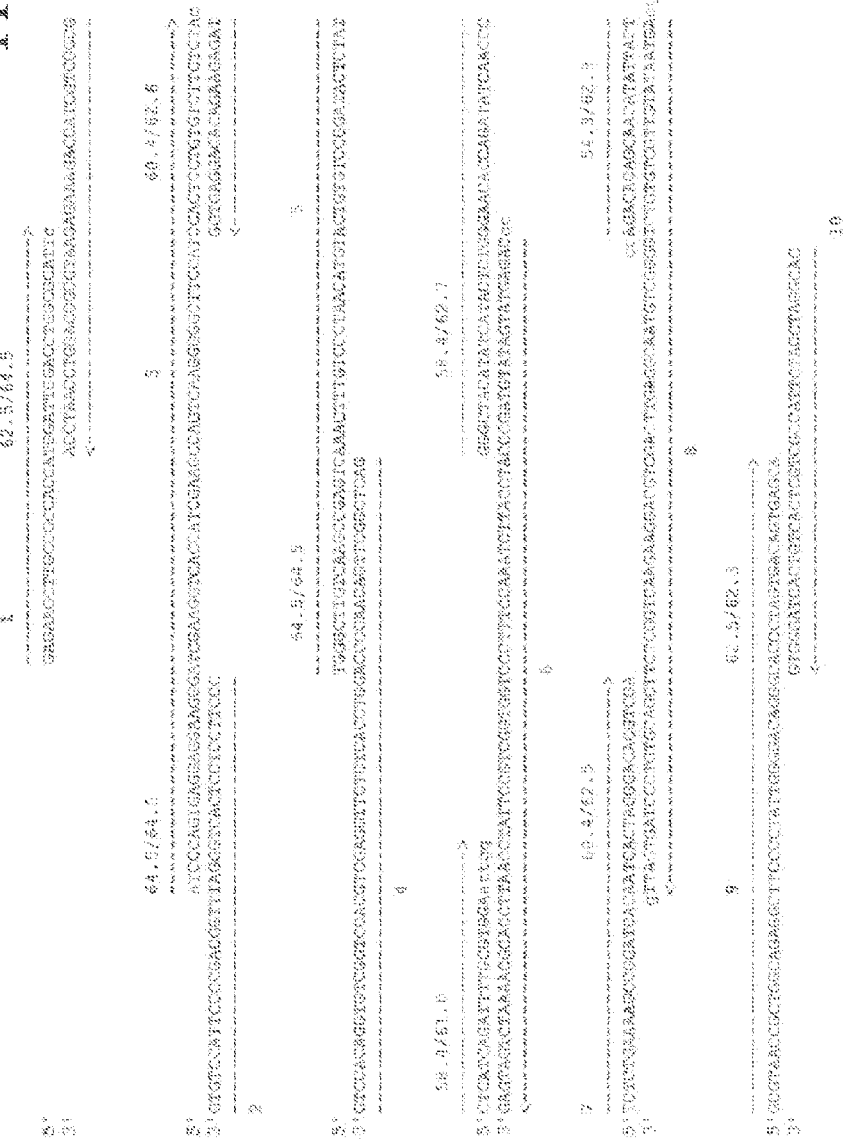
Figure 57C:
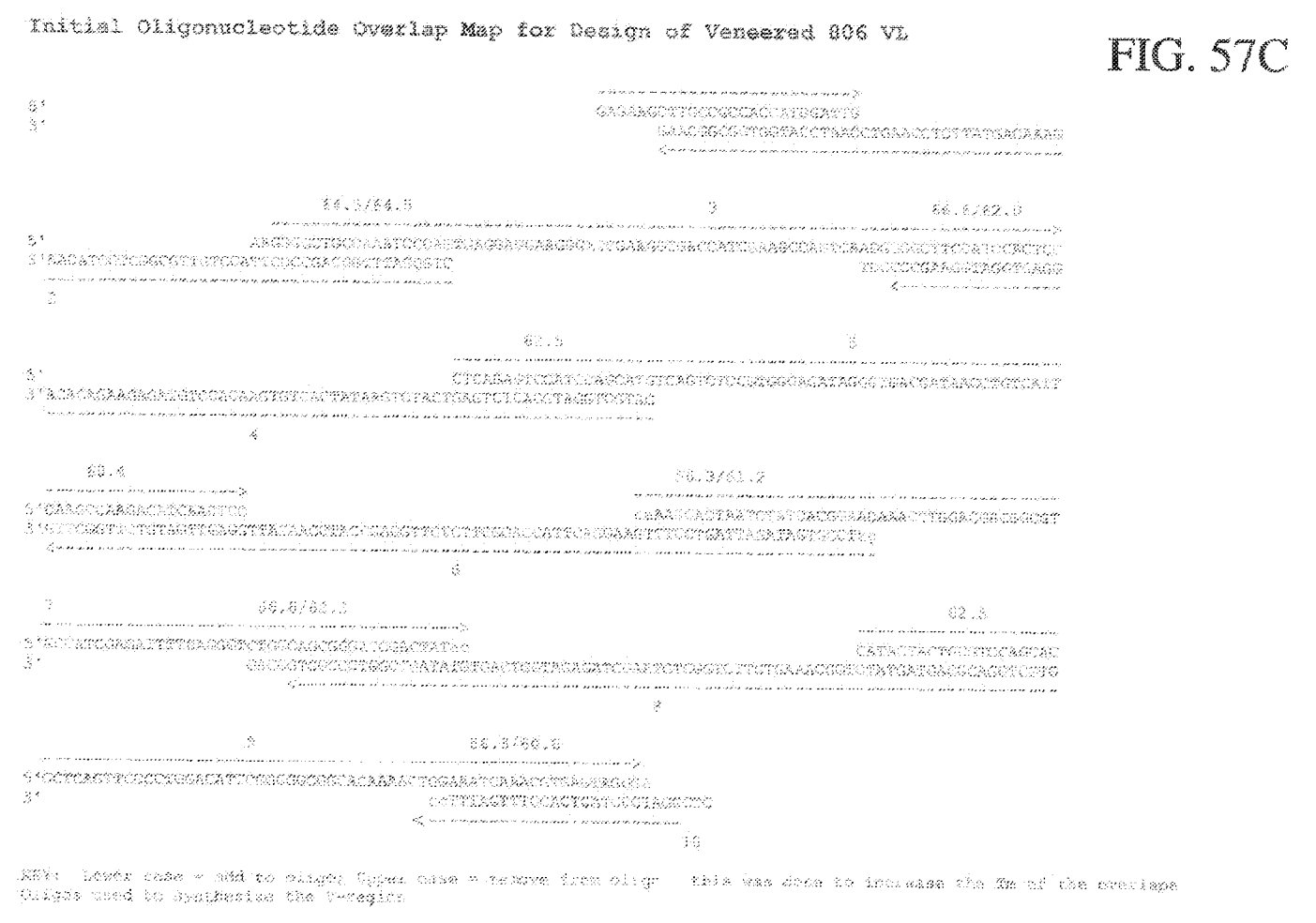

FIGS. 56A, 56B, 56C, 57A, 57B, and 57C show the initial step in veneering design, the grading of amino acid residues in the mAb806 sequence (VH chain of SEQ ID NO:167 and VL chain of SEQ ID NO:12) for surface exposure. Grades are given in the number of asterisks (*) above each residue, with the most exposed residues having three asterisks. These figures include a design indicating how the initial oligonucleotides (VH chain: FIG. 56C and SEQ ID NOS:52 and 169-177; VL chain: FIG. 57C and SEQ ID NOS: 62, 66, 68 and 181-187) overlapped to form the first veneered product (VH chain of SEQ ID NO:168 and VL chain of SEQ ID NO:180).

Figure 58B:
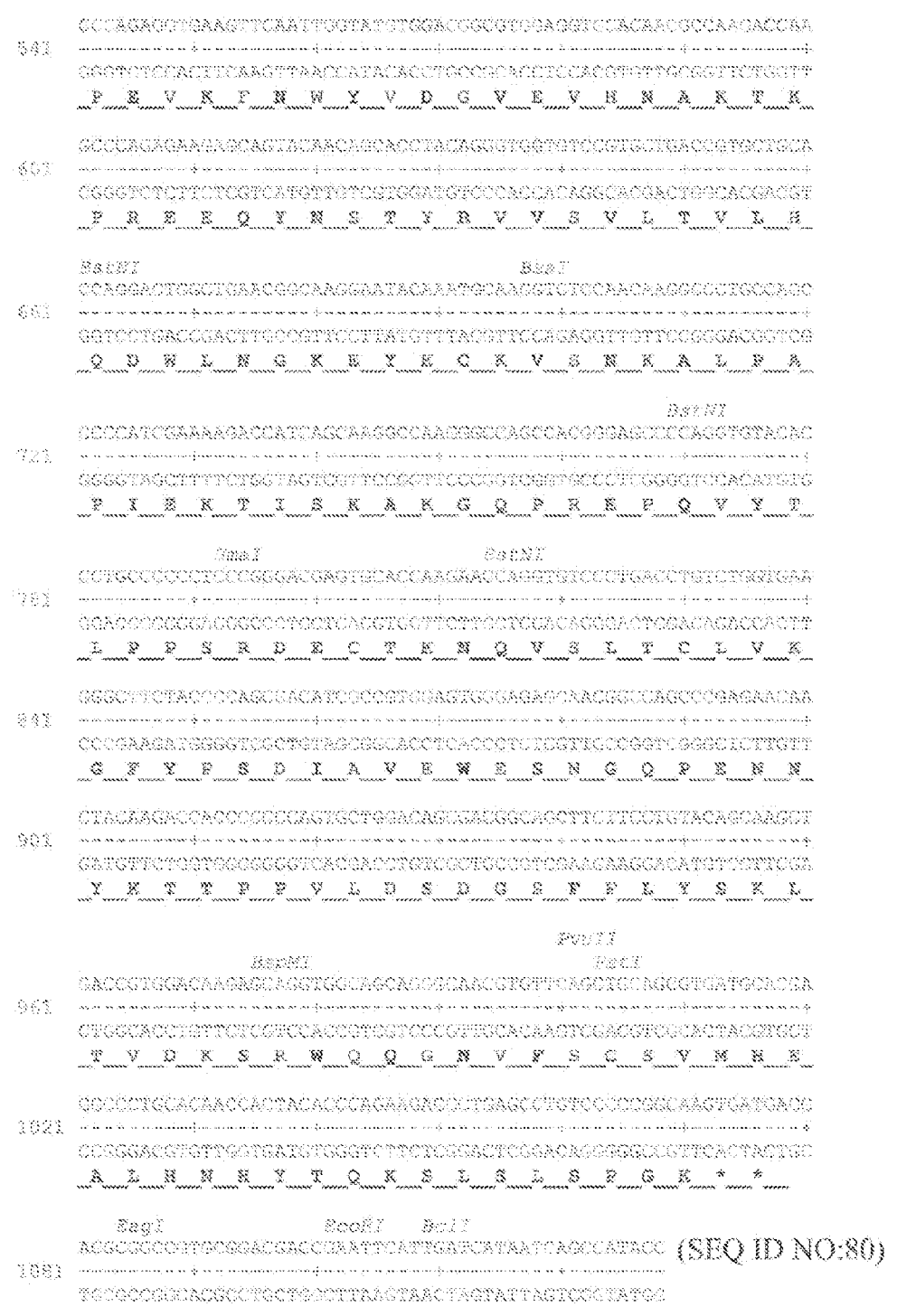

FIGS. 58A-B show a map of codon optimized huIgG1 heavy chain DNA sequence (SEQ ID NO:80; complement SEQ ID NO:178) and amino acid translation (SEQ ID NO:43).

Figure 59:
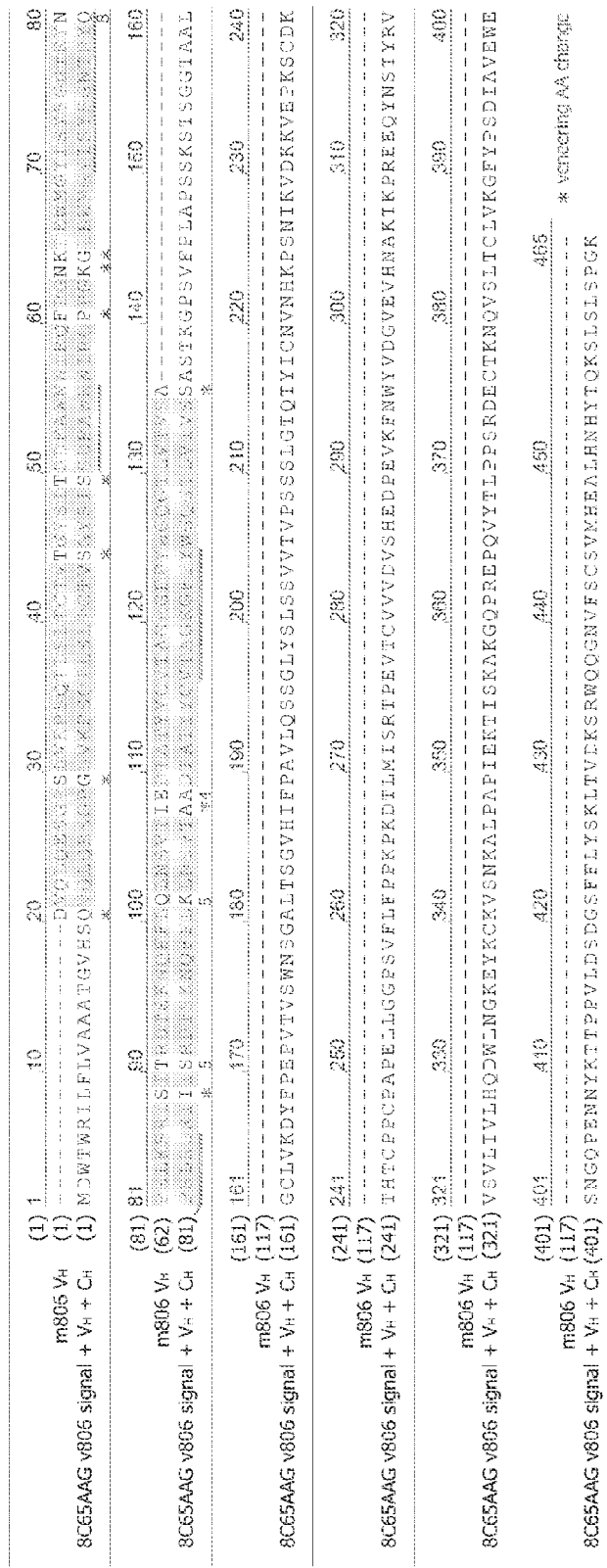

FIG. 59 shows the protein alignment comparing the hu806 VH+CH amino acid sequence (8C65AAG hu806 VH+CH; SEQ ID NO:81) to the original reference file for the mAb806 VH chain (SEQ ID NO:167). Highlighted regions indicate conserved amino acid sequences in the VH chain. The CDRs are underlined. Asterisks reflect changes that were planned and carried out in the initial veneering process. The numbered sites are references to later modifications.

Figure 60:
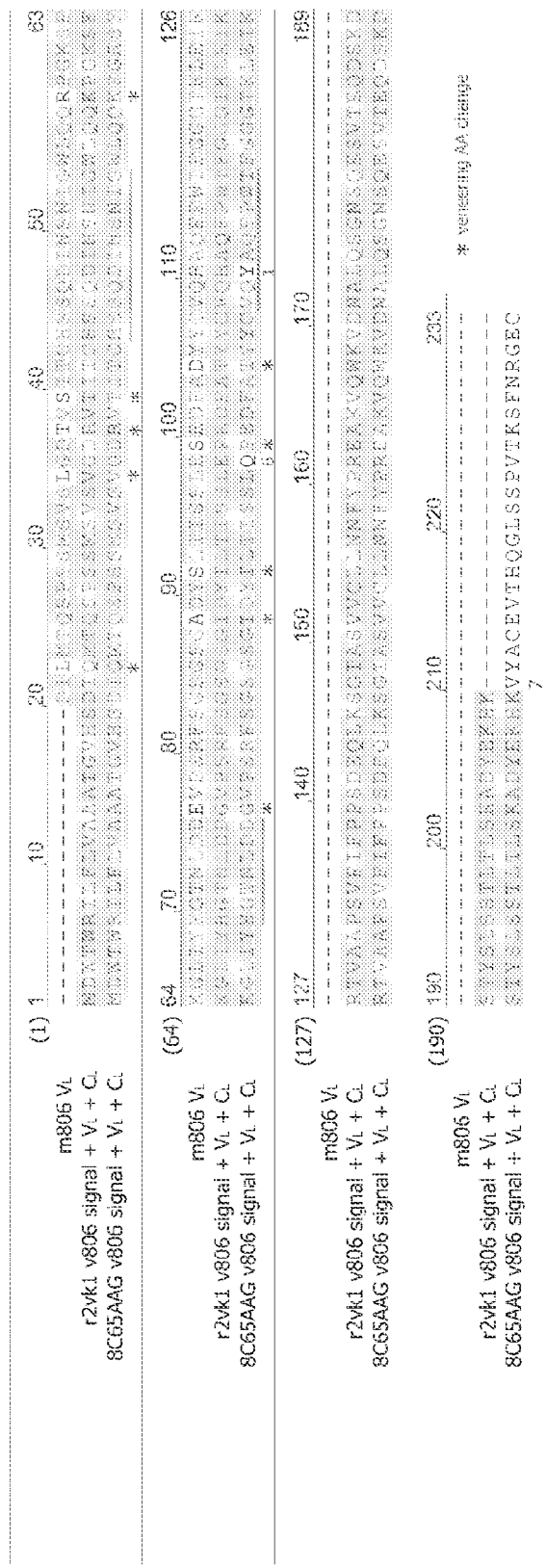

FIG. 60 shows the corresponding alignment for the hu806 VL+CL amino acid sequence (8C65AAG hu806 signal+VL+ CL; SEQ ID NO:83) to the original reference file for the mAb806 VL chain (SEQ ID NO:179). It contains an additional file (r2vkl hu806 signal+VL+CL; SEQ ID NO:82), a precursor construct, which was included to illustrate the change made at modification #7.

Figure 61:
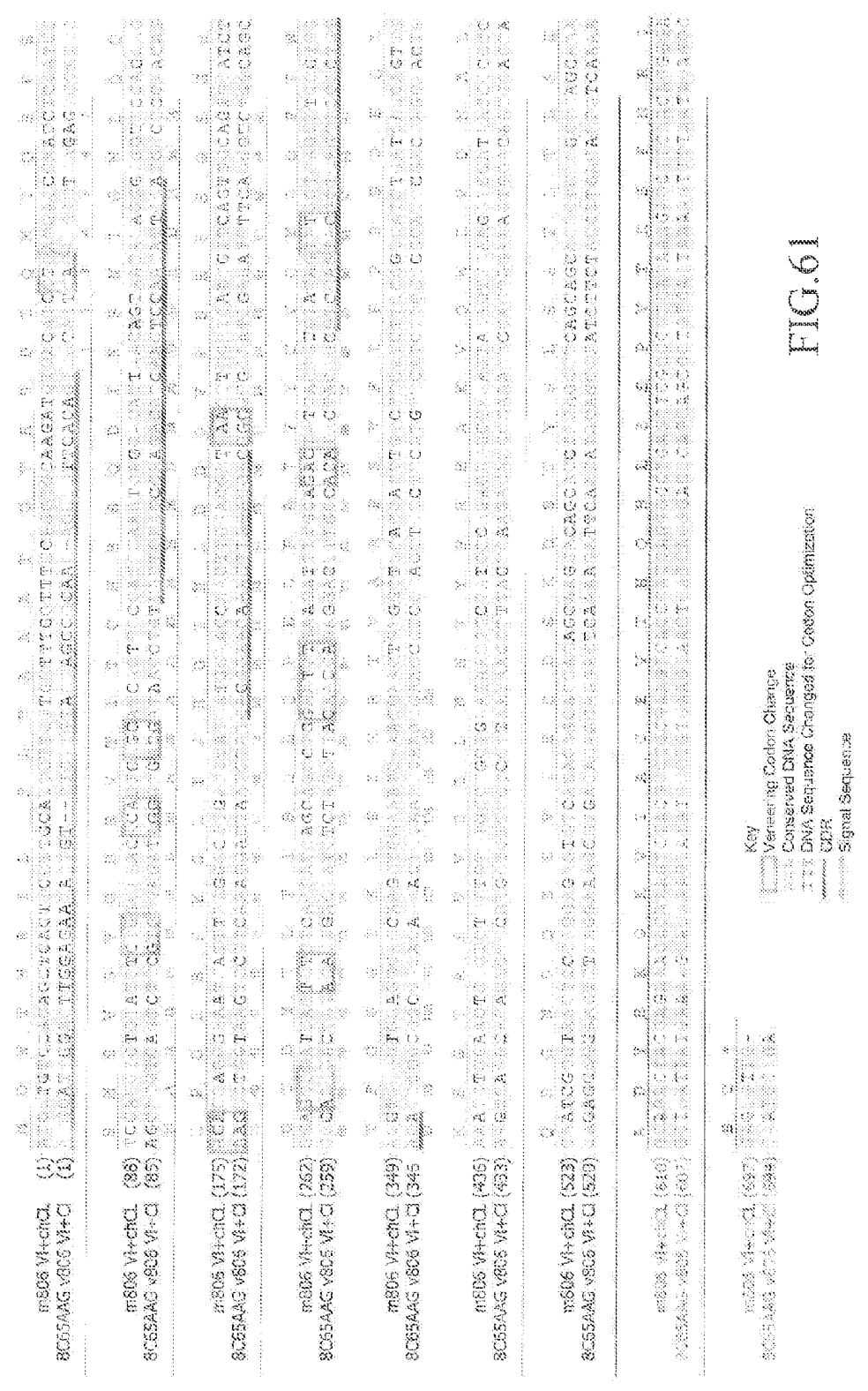

FIG. 61 shows a nucleotide and amino acid alignment of the hu806 signal+VL and CL sequences (8C65AAG hu806 Vl+Cl; SEQ ID NOS:190 and 188) with the corresponding ch806 sequences (pREN ch806 LC Neo; LICR; SEQ ID NO:189). It has been modified and annotated as described in FIG. 62.

Figure 62:

FIG. 62 shows the nucleotide alignment of the hu806 signal+VH sequence (8C65AAG hu806 VH chain; SEQ ID NO:192) with the corresponding mAb806 sequence [mAb806 VH chain before codon change (cc) and veneering (ven); SEQ ID NO:191]. The nucleotide changes behind the amino acid changes of FIGS. 59 and 60 are illustrated, as well as showing conservative nucleic acid changes that led to no change in amino acid. The intron between the signal and the VH chain in hu806 has been removed for easier viewing. The signal sequence and CDRs are underlined. The corresponding amino acid sequence (SEQ ID NO:42) has been superimposed on the alignment.

Figure 63:
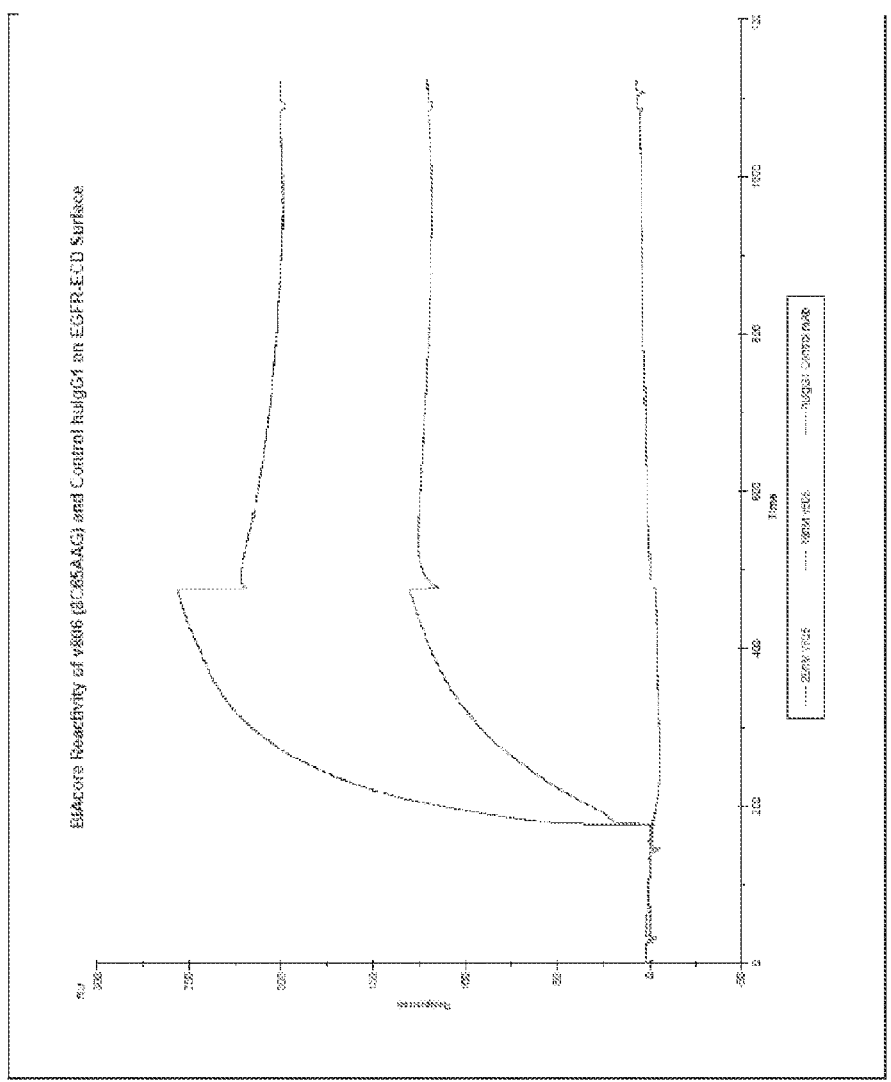

FIG. 63. shows binding of purified hu806 antibody obtained from transient transfectant 293 cells to recombinant EGFR-ECD as determined by Biacore™. No binding to the EGFR-ECD was observed with purified control human IgG1 antibody.

FIGS. 64A-EE show the GenBank formatted text document of the sequence (SEQ ID NO:41) and annotations of plasmid 8C65AAG encoding the IgG1 hu806.

FIG. 65 shows the alignment of amino acid sequences for CDRs from mAb806 (SEQ ID NOS:15-18, 20 and 193) and mAb175 (SEQ ID NOS:130-132, 135 and 194-195). Sequence differences between the two antibodies are bolded.

Figures 66A, 66B:
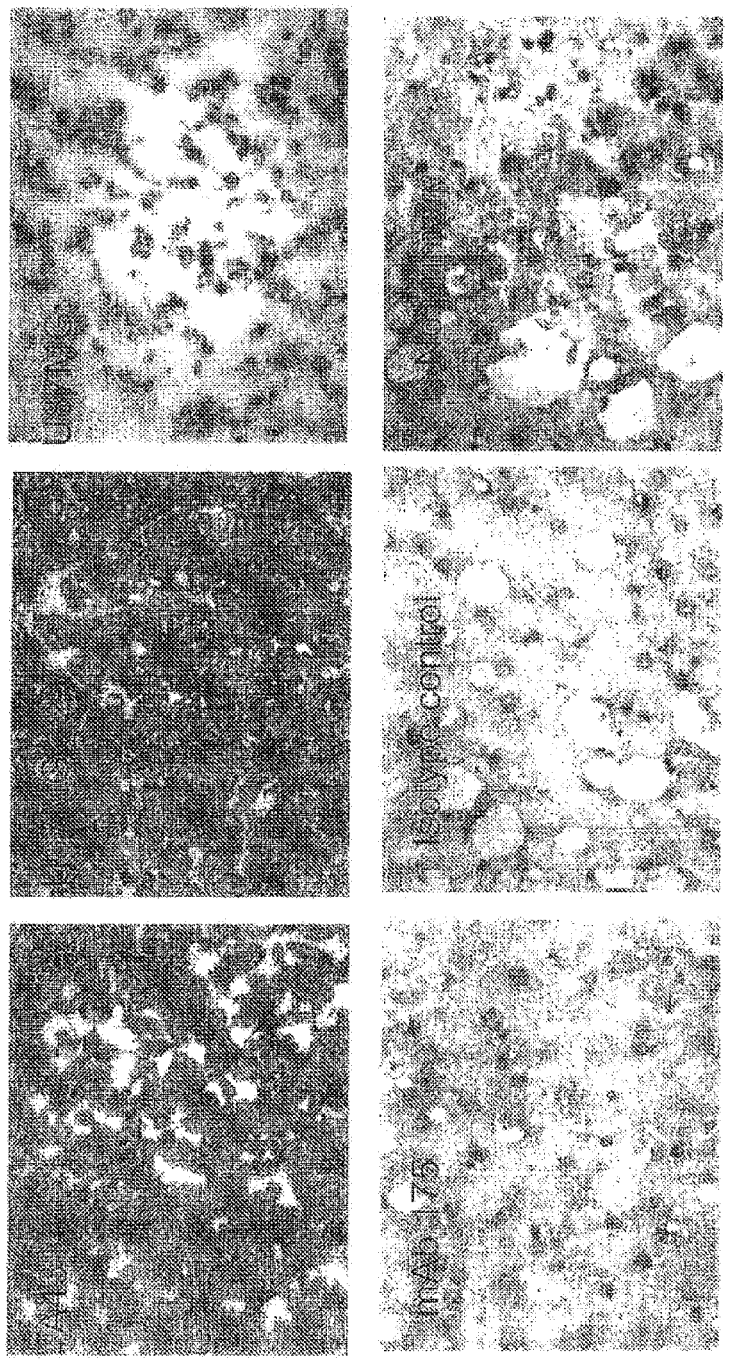

FIGS. 66A and 66B show immunohistochemical staining of cell lines and normal human liver with mAb175. (A) Biotinylated mAb175 was used to stain sections prepared from blocks containing A431 cells (over-express the wtEGFR), U87MG.Δ2-7 cells (express the Δ2-7EGFR) and U87MG cells (express the wtEGFR at modest levels). (B) Staining of normal human liver (400×) with mAb175 (left panel), isotype control (centre panel) and secondary antibody control (right panel). No specific sinusoidal or hepatocyte staining was observed.

Figure 67B:
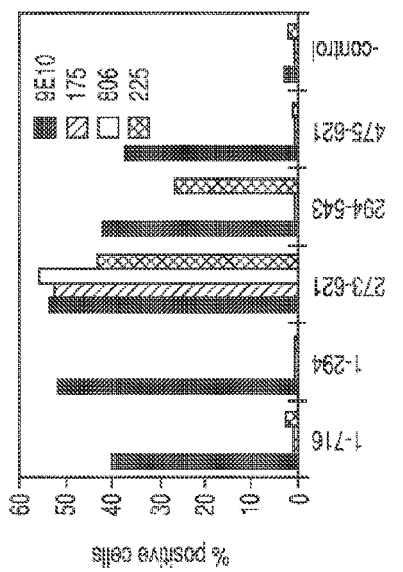
Figure 67C:
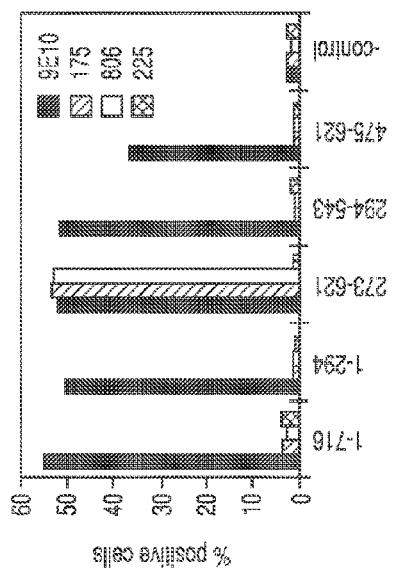
Figure 67A:
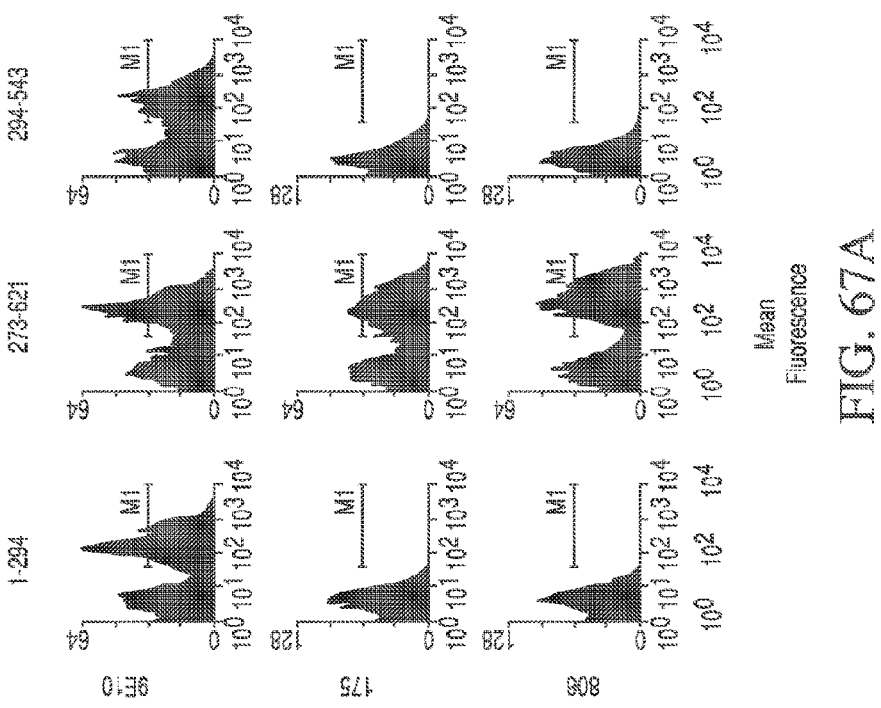

FIGS. 67A, 67B, and 67C show the reactivity of mAb806 and mAb175 with fragments of the EGFR displayed on yeast. (A) Representative flow cytometry histograms depicting the mean fluorescence signal of mAb175 and mAb806-labeling of yeast-displayed EGFR fragments. With yeast display a percentage of cells do not express protein on their surface resulting in 2 histogram peaks. The 9E10 antibody is used as a positive control as all fragments contain a linear C-terminal c-myc tag. (B) Summary of antibody binding to various EGFR fragments. (C) The EGFR fragments were denatured by heating yeast pellets to 800° C. for 30 min. The c-myc tag was still recognized by the 9E10 anti-myc antibody in all cases, demonstrating that heat treatment does not compromise the yeast surface displayed protein. The conformation sensitive EGFR antibody mAb225 was used to confirm denaturation.

FIGS. 68A, 68B, 68C, and 68D show the antitumor effects of mAb175 on brain and prostate cancer xenografts. (A) Mice (n=5) bearing U87MG.Δ2-7 xenografts were injected i.p. with PBS, 1 mg of mAb175 or mAb806 (positive control), three times weekly for two weeks on days 6, 8, 10, 13, 15 and 17 when the starting tumor volume was 100 mm$^3$ Data are expressed as mean tumor volume±SE. (B) Cells were stained with two irrelevant antibodies (blue, solid and green, hollow), mAb 528 for total EGFR (pink, solid), mAb806 (light blue, hollow) and mAb175 (orange, hollow) and then analyzed by FACS. (C) DU145 cells were lysed, subjected to IP with mAb 528, mAb806, mAb175 or two independent irrelevant antibodies and then immunoblotted for EGFR. (D) Mice (n=5) bearing DU145 xenografts were injected i.p. with PBS, 1 mg of mAb175 or mAb806, daily on days 18-22, 25-29 and 39-43 when the starting tumor volume was 85 mm$^3$ Data are expressed as mean tumor volume±SE.

FIGS. 69A, 69B, 69C, 69D, 69E, and 69F show the crystal structures of EGFR peptide 287-302 bound to the Fab fragments (A) Cartoon of Fab 806, with the light chain, red; heavy chain, blue; bound peptide, yellow; and the superposed $EGFR_{287-302}$ from EGFR, purple. (B) Cartoon of Fab 175 with the light chain, yellow; heavy chain, green; bound peptide, lilac; and $EGFR_{287-302}$ from EGFR(DI-3), purple. (C) Detail from (B) showing the similarity of $EGFR_{287-302}$ in the receptor to the peptide bound to FAb 175. Peptides backbones are shown as Ca traces and the interacting side chains as sticks. O atoms are colored red; N, blue; S, orange and C, as for the main chain. (D) Superposition of EGFR with the Fab175:peptide complex showing spacial overlap. Coloring as in (C) with the surface of EGFR187-286 colored turquoise. (E) Orthogonal view to (D) with EGFR187-286 shown in opaque blue and the surface of the light (orange) and heavy (green) chains transparent. (F) Detailed stereoview of 175 Fab complex looking into the antigen-binding site. Coloring as in (C) and side chain hydrogen bonds dotted in black. Water molecules buried upon complex formation are shown as red spheres.

FIGS. 70A, 70B, 70C, and 70D show the influence of the 271-283 cysteine bond on mAb806 binding to the EGFR. (A) Cells transfected with wtEGFR, EGFR-C271A, EGFR-C283A or the C271A/C283A mutant were stained with mAb528 (solid pink histogram), mAb806 (blue line) or only the secondary antibody (purple) and then analyzed by FACS. The gain was set up using a class-matched irrelevant antibody. (B) BaF3 cells expressing the EGFR-C271A or C271/283A EGFR were examined for their response to EGF in an MTT assay as described. $EC_{50S}$ were derived using the Bolzman fit of the data points. Data represent mean and sd of triplicate measurements. (C) BaF3 cells expressing the wild-type or the EGFR-C271A/C283A were IL-3 and serum starved, then exposed to EGF or vehicle control. Whole cell lysates were separated by SDS-PAGE and immunoblotted with anti-phosphotyrosine antibody (top panel) or anti-EGFR antibody (bottom panel). (D) BaF3 cells expressing the wild-type (left panel) or the C271A/C283A (right panel) EGFR were stimulated with increasing concentrations of EGF in the presence of no antibody (open symbols), mAb 528 (grey circles) or mAb806 (black triangles), both at 10 µg/ml. Data are expressed as mean and sd of triplicate measurements.

FIGS. 71A, 71B, and 71C show: (A) Whole body gamma camera image of the biodistribution of $^{111}$In ch806 in a patient with metastatic squamous cell carcinoma of the vocal cord, showing quantitative high uptake in tumor in the right neck (arrow). Blood pool activity, and minor catabolism of free $^{111}$In in liver, is also seen. (B) Single Photon Computed Tomography (SPECT) image of the neck of this patient, showing uptake of $^{111}$In-ch806 in viable tumor (arrow), with reduced central uptake indicating necrosis. (C) Corresponding CT scan of the neck demonstrating a large right neck tumor mass (arrow) with central necrosis.

Figure 72B:
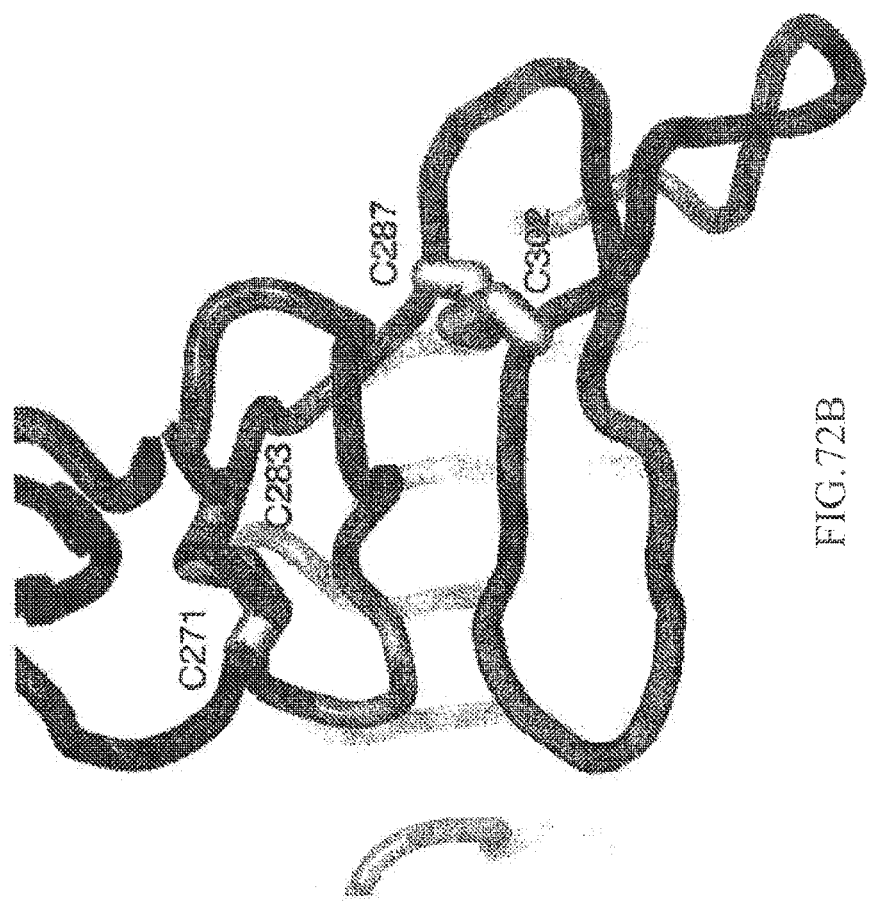
Figure 72A:
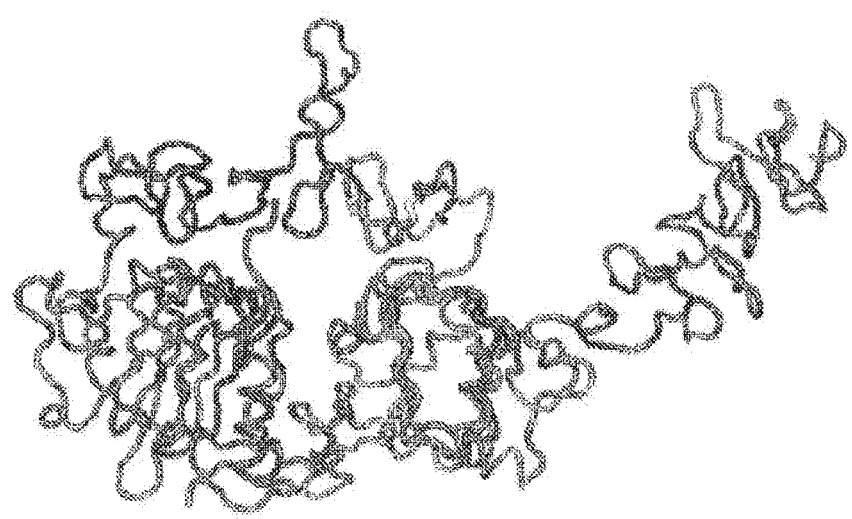

FIGS. 72A and 72B show a stereo model of the structure of the untethered EGFR1-621. The receptor backbone is traced in blue and the ligand TGF-α in red. The mAb806/175 epitope is drawn in turquoise and the disulfide bonds in yellow. The atoms of the disulfide bond which ties the epitope back into the receptor are shown in space-filling format. The model was constructed by docking the EGFR-ECD CR2 domain from the tethered conformation onto the structure of an untethered EGFR monomer in the presence of its ligand.

Figure 73:
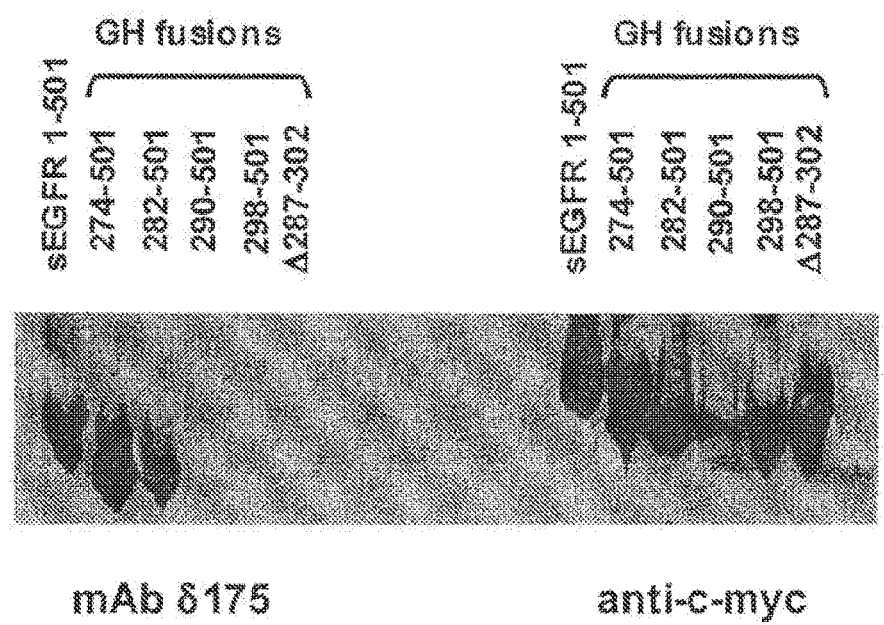

FIG. 73 shows the reactivity of mAb806 with fragments of the EGFR. Lysates from 293T cells transfected with vectors expressing the soluble 1-501 EGFR fragment or GH/EGFR fragment fusion proteins (GH-274-501, GH-282-501, GH-290-501 and GH-298-501) were resolved by SDS-PAGE, transferred to membrane and immunoblotted with mAb806 (left panel) or the anti-myc antibody 9B 11 (right panel).

FIGS. 74A and 74B show the mAb175 VH chain nucleic acid sequence (SEQ ID NO:128) and amino acid sequence (SEQ ID NO:129), respectively.

FIGS. 75A and 75B show the mAb175 VL chain nucleic acid sequence (SEQ ID NO:133) and amino acid sequence (SEQ ID NO:134), respectively.

Figure 76A:
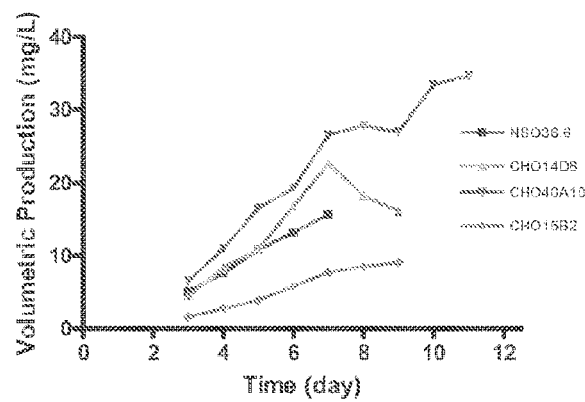
Figure 76B:
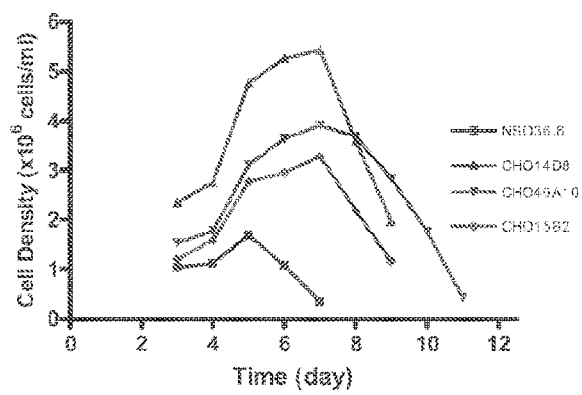
Figure 76C:
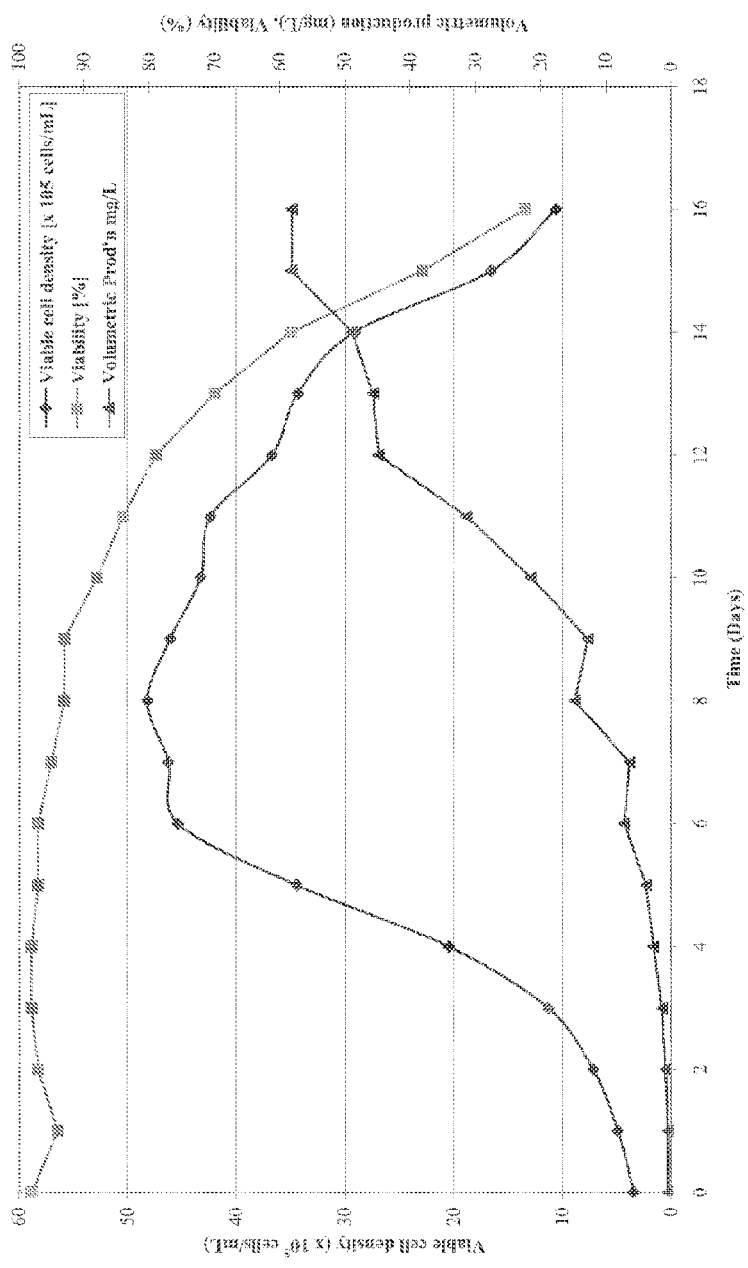
Figure 77A:
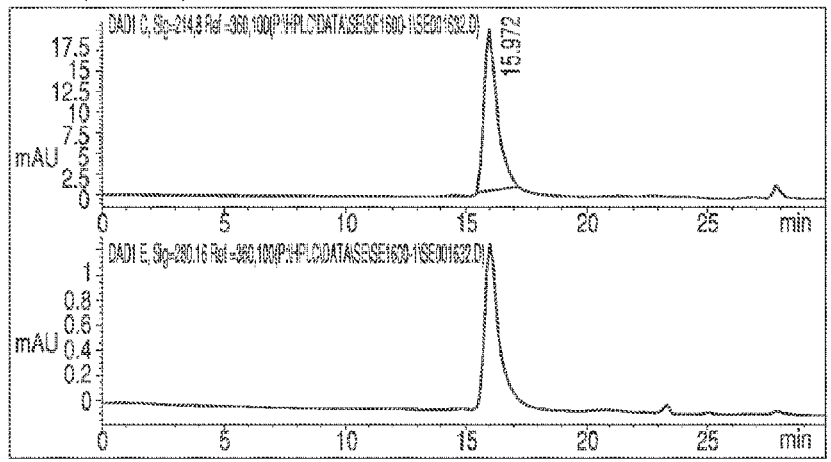
Figure 77B:
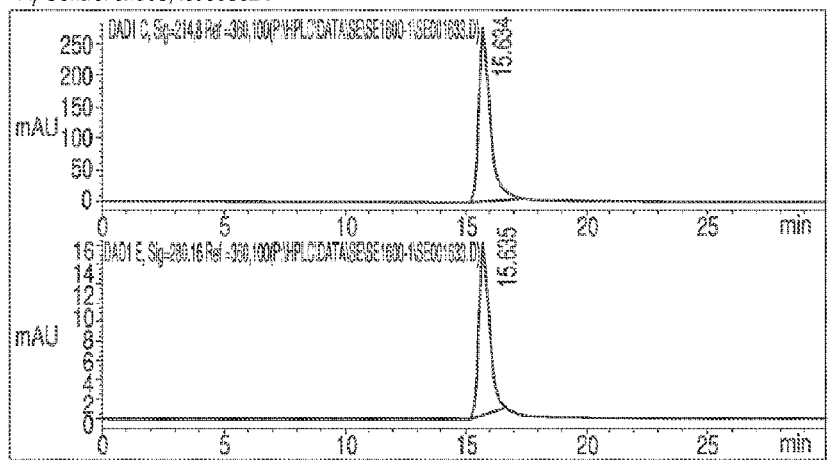
Figure 77C:
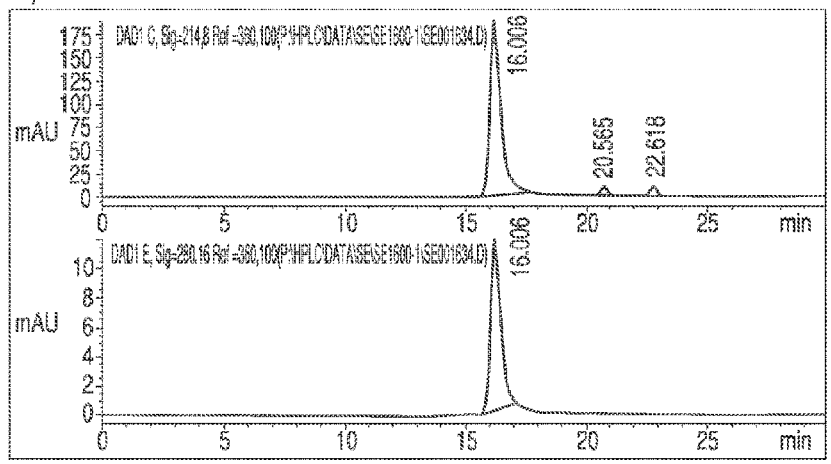
Figure 77D:
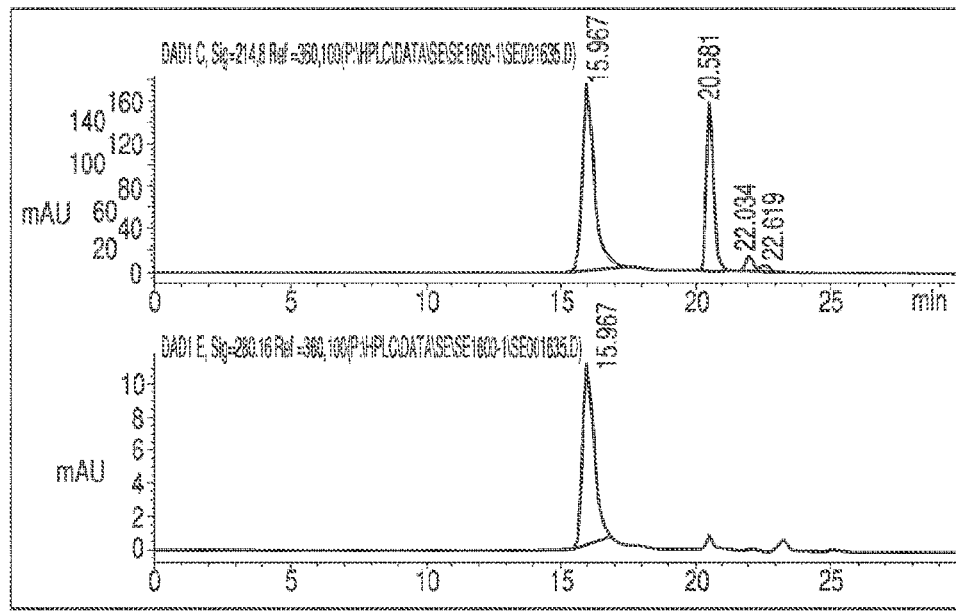
Figure 77E:
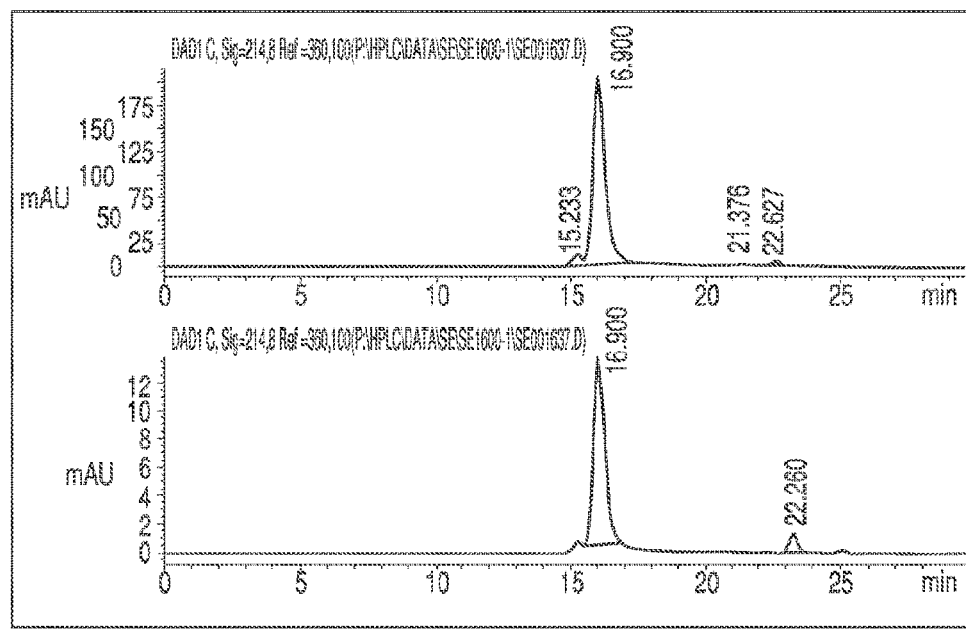

FIGS. 76A, 76B, and 76C show: (A) Volumetric product concentration and (B) viable cell concentration of GS-CHO (14D8, 15B2 and 40A10) and GS-NS0 (36) hu806 transfectants in small scale (100 mL) shake flasks cultures. Product concentration was estimated by ELISA using the 806 anti-idiotype as coating antibody and ch806 Clinical Lot: J06024 as standard; (C) GS-CHO 40A10 transfectant cell growth and volumetric production in a 15 L stirred tank bioreactor. Viable cell density (♦×$10^5$ cell/mL), cell viability (■) and production (▲mg/L).

FIGS. 77A, 77B, 77C, 77D, and 77E show Size Exclusion Chromatography (Biosep SEC-S3000) Analysis of Protein-A purified hu806 antibody constructs produced by small scale culture and control ch806 and mAb 806. Chromatograms at A214 nm are presented in the upper panels and at A280 nm in the lower panel of each Figure.

Figure 78:
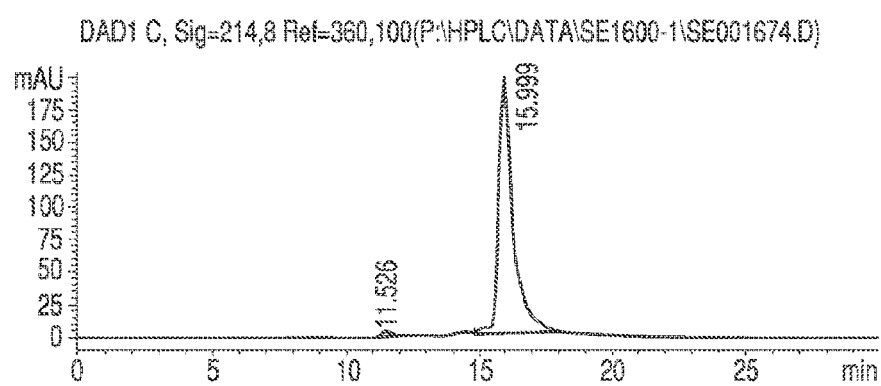

FIG. 78 shows Size Exclusion Chromatography (Biosep SEC-S3000) Analysis of Protein-A purified hu806 antibody construct 40A10 following large scale production and Protein-A purification. Chromatogram at A214 nm is presented indicating 98.8% purity with 1.2% aggregate present.

Figure 79:
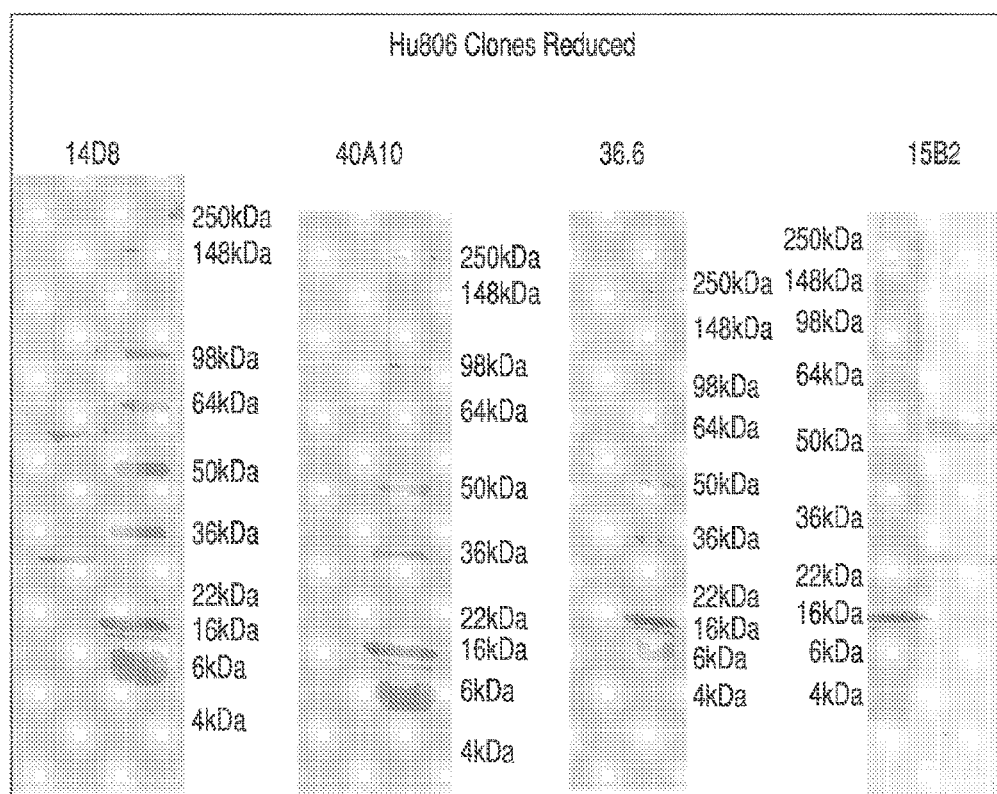

FIG. 79 shows that precast 4-20% Tris/Glycine Gels from Novex, USA were used under standard SDS-PAGE conditions to analyze purified transfectant hu806 preparations (5 µg) GS CHO (14D8, 15B2 and 40A10) and GS-NS0 (36) hu806 under reduced conditions. Proteins detected by Coomassie Blue Stain.

Figure 80:
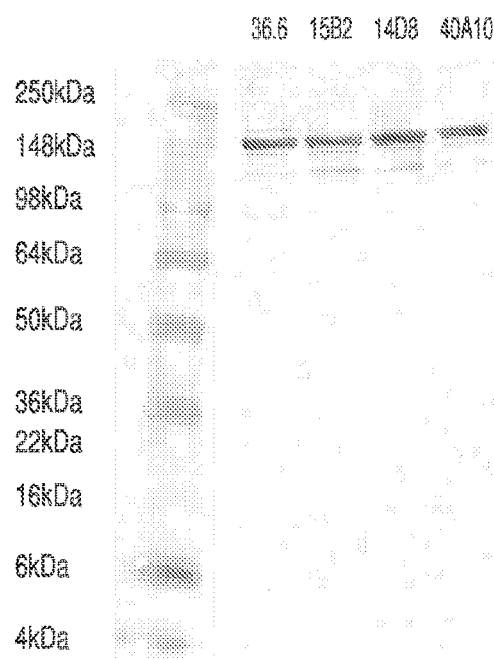

FIG. 80 shows that precast 4-20% Tris/Glycine Gels were used under standard SDS-PAGE conditions to analyze purified transfectant hu806 preparations (5 µg) GS CHO (14D8, 15B2 and 40A10) and GS-NS0 (36) under non-reduced conditions. Proteins detected by Coomassie Blue Stain.

Figure 81:
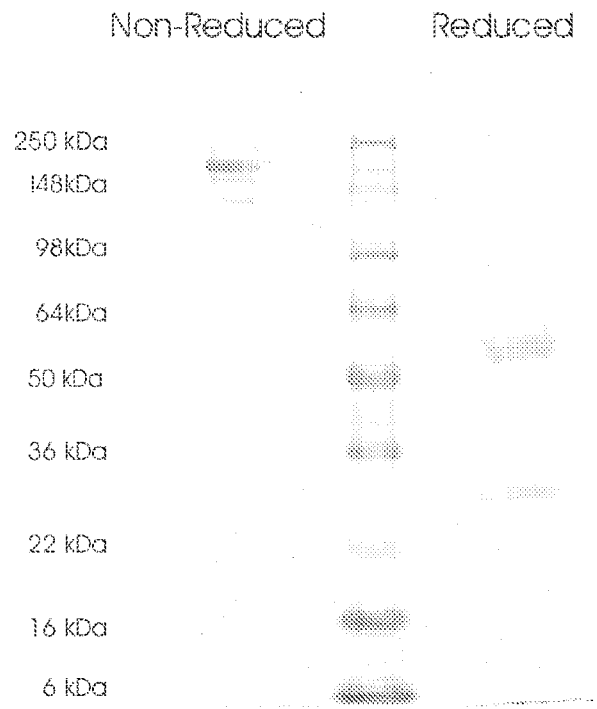

FIG. 81 shows that precast 4-20% Tris/Glycine Gels were used under standard SDS-PAGE conditions to analyze purified transfectant hu806 GS CHO 40A10 (5 µg) following large scale production. Proteins detected by Coomassie Blue Stain.

Figure 82:
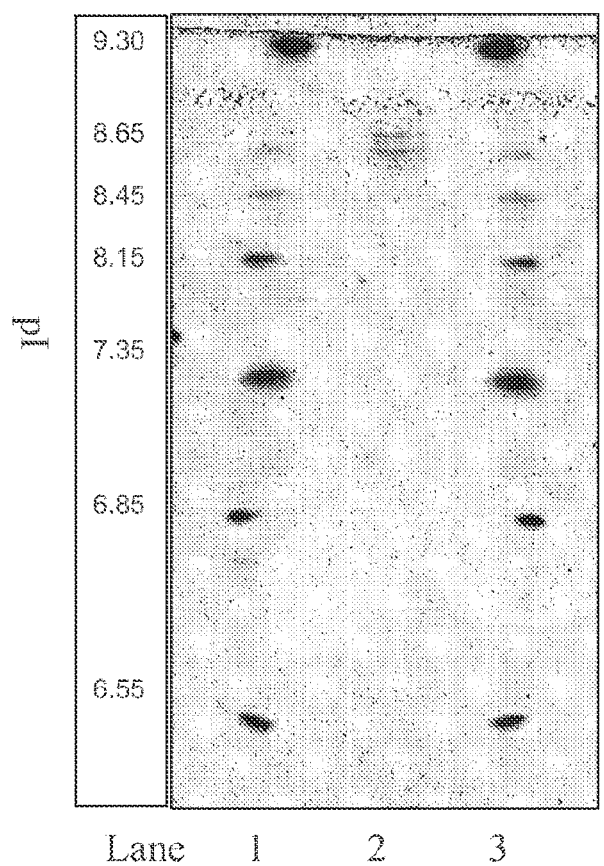

FIG. 82 shows Isoelectric Focusing gel analysis of purified transfectant hu806 GS CHO 40A10 (5 µg) following 15 L production. Proteins detected by Coomassie Blue Stain. Lane 1, pI markers; Lane 2, hu806 (three isoforms, pI 8.66 to 8.82); Lane 3, pI markers.

Figure 83:
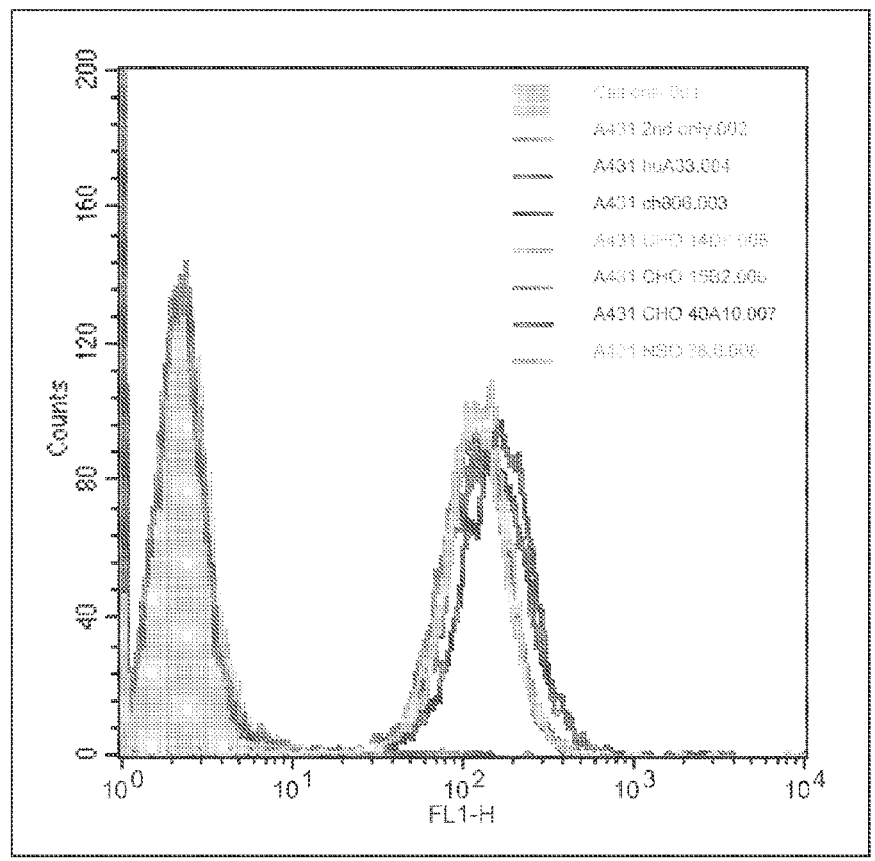

FIG. 83 shows binding to A431 cells: Flow Cytometry analysis of Protein-A purified hu806 antibody preparations (20 µg/ml), and isotype control huA33 (20 µg/ml). Controls include secondary antibody alone (green) and ch806 (red). Hu806 constructs were produced by small scale culture.

Figure 84:
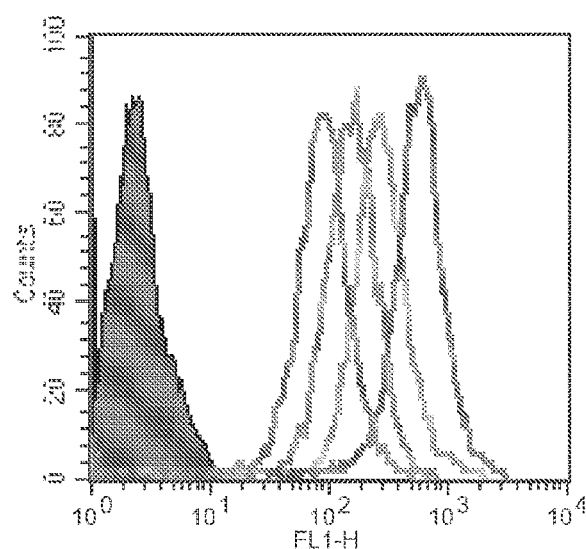

FIG. 84 shows binding to A431 cells: Flow Cytometry analysis of purified mAb806, ch806 and hu806 40A10 antibody preparations (20 µg/ml) that bind ~10% of wild type EGFR on cell surface, 528 (binds both wild type and de2-7 EGFR) and irrelevant control antibody (20 µg/ml) as indicated.

Figure 85:
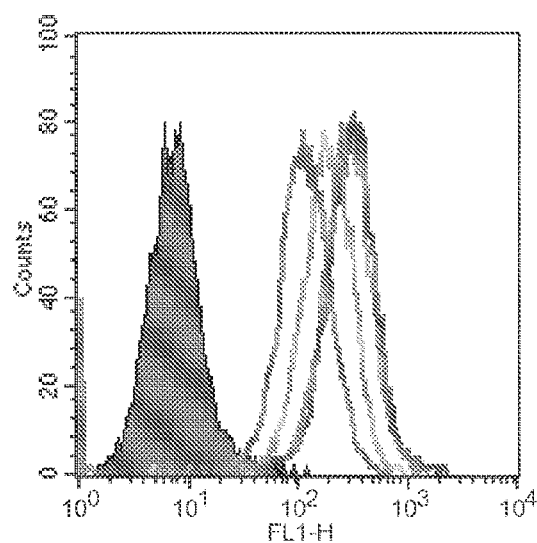

FIG. 85 shows binding to U87MG.de2-7 glioma cells. Flow Cytometry analysis of purified mAb806, ch806 and hu806 40A10 antibody preparations (20 µg/ml) and 528 anti-EGFR and irrelevant control antibody (20 µg/ml).

Figure 86:
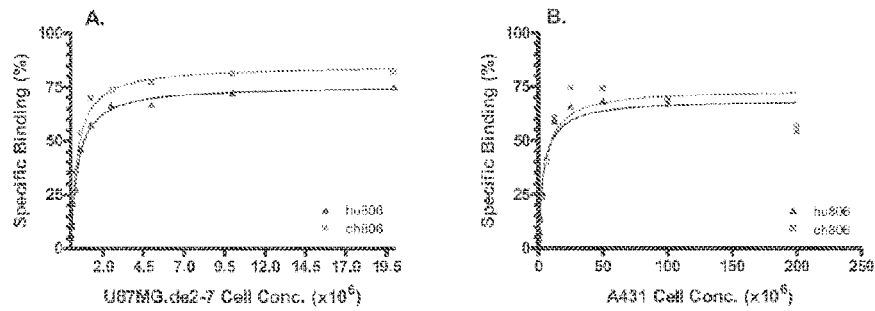

FIG. 86 shows specific binding of $^{125}$I-radiolabelled 806 antibody constructs to: (A) U87MG.de2-7 glioma cells and (B) A431 carcinoma cells.

Figure 87:
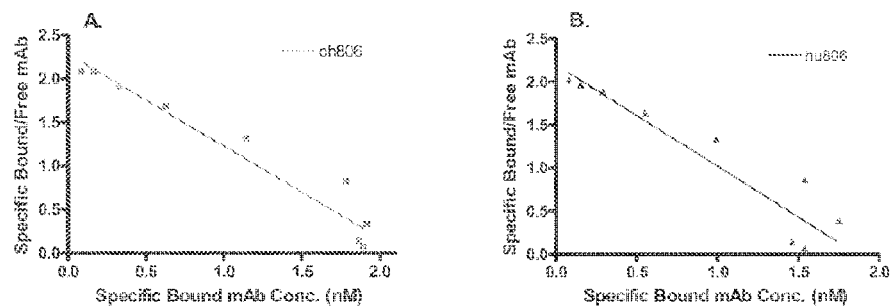

FIG. 87 shows Scatchard Analyses: $^{125}$I-radiolabelled (A) ch806 and (B) hu806 antibody constructs binding to U87MG.de2-7 cells.

Figure 88:
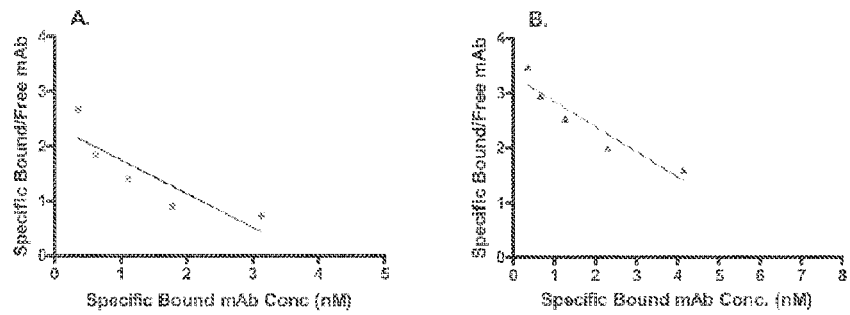

FIG. 88 shows Scatchard Analyses: $^{125}$I-radiolabelled (A) ch806 and (B) hu806 antibody constructs binding to A431 cells.

FIG. 89 shows BIAcore™ analysis of binding to 287-302 EGFR 806 peptide epitope by (A) hu806 and (B) ch806 passing over the immobilized peptide in increasing concentrations of 50 nM, 100 nM, 150 nM, 200 nM, 250 nM and 300 nM.

Figure 90:
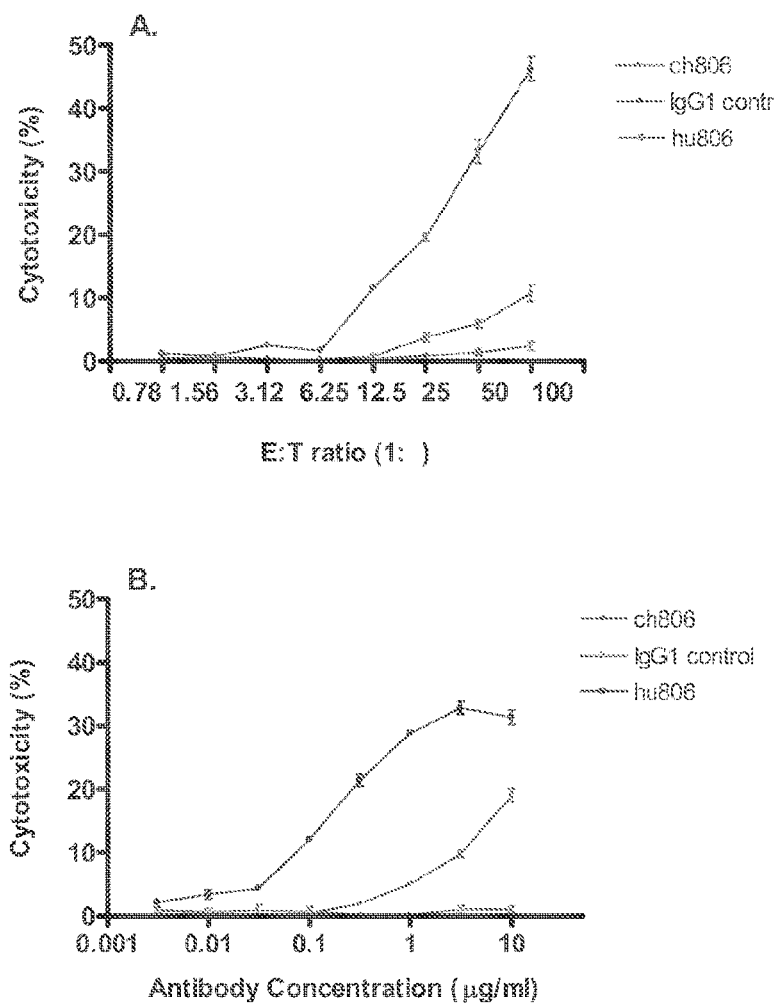

FIGS. 90A and 90B show ch806- and hu806-mediated Antibody Dependant Cellular Cytotoxicity on target A431 cells determined at (A) 1 µg/ml each antibody over a range of effector to target cell ratios (E:T=0.78:1 to 100:1); (B) at E:T=50:1 over a concentration range of each antibody (3.15 ng/ml-10 µg/ml). a on target A431.

FIG. 91 shows treatment of established A431 xenografts in BALB/c nude mice. Groups of 5 mice received 6×1 mg dose over 2 weeks antibody therapy as indicated (arrows). Mean±SEM tumor volume is presented until study termination.

FIG. 92 shows treatment of established U87MG.de2-7 xenografts in BALB/c nude mice. Groups of 5 mice received 6×1 mg dose over 2 weeks antibody therapy as indicated (arrows). Mean±SEM tumor volume is presented until study termination.

Figure 93:
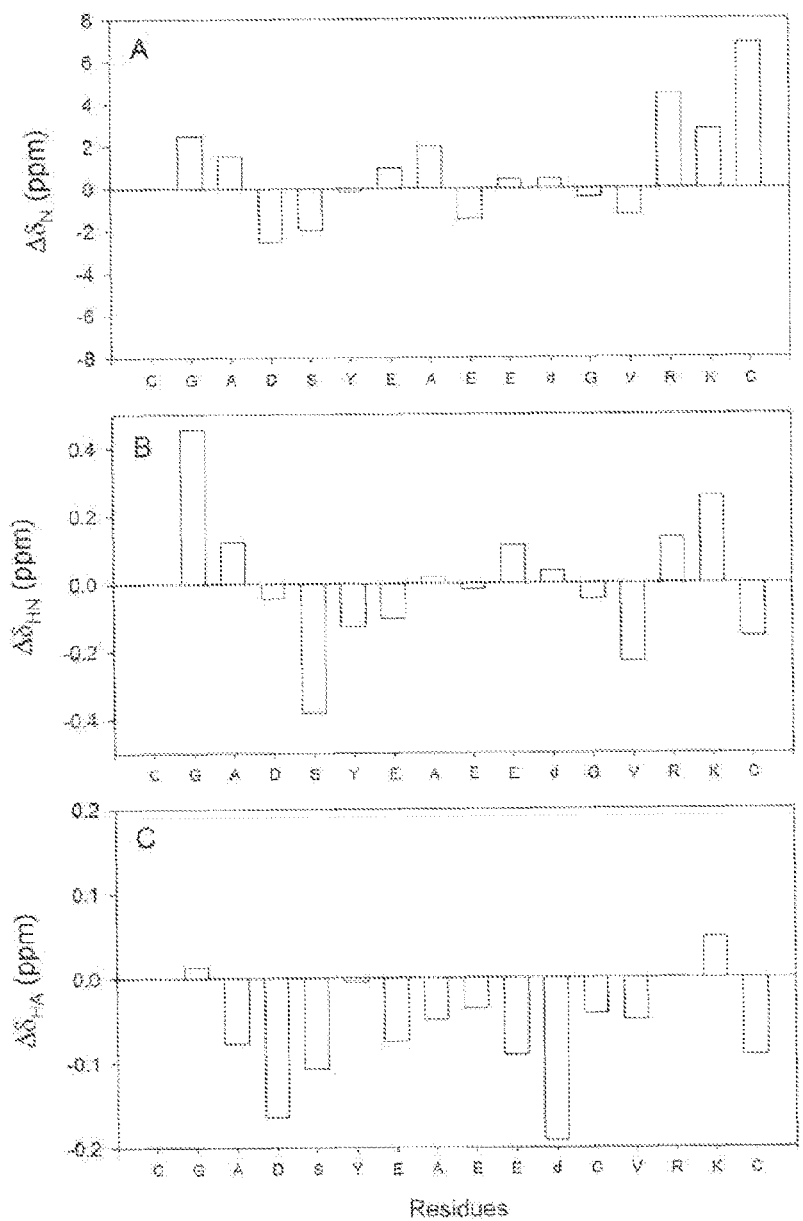
Figure 96B:
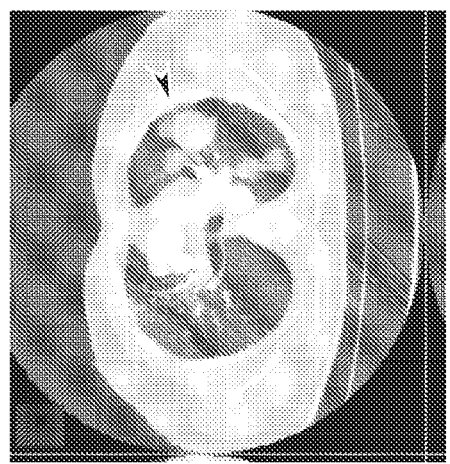
Figure 96D:
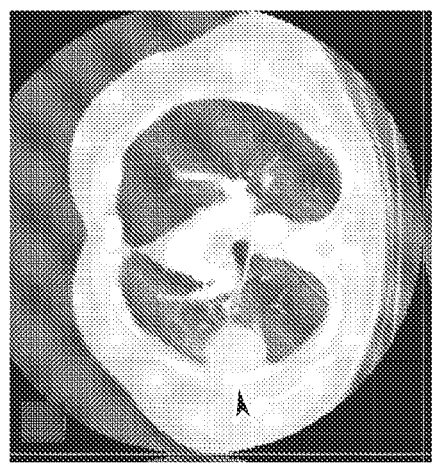
Figure 96A:
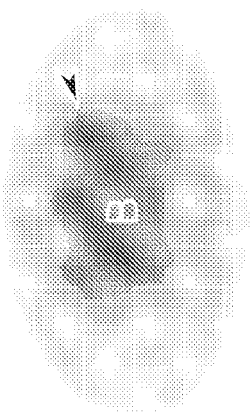
Figure 96C:
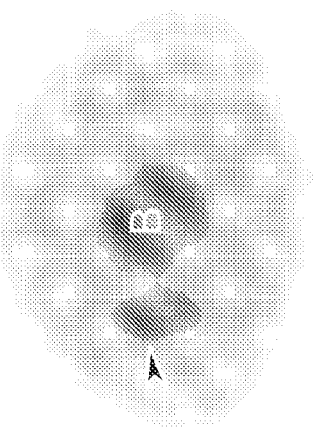

FIG. 93 shows deviations from random coil chemical shift values for the mAb806 peptide (A) N, (B) HN and (C) HA. Peptide was prepared in $H_2O$ solution containing 5% $_2H_2O$, 70 mM NaCl and 50 mM $NaPO_4$ at pH 6.8. All spectra used for sequential assignments were acquired at 298K on a Bruker Avance500.

FIGS. 94A, 94B, 94C, 94D, 94E, and 94F show whole body gamma camera images of Patient 7 A) Anterior, and B) Posterior, Day 5 post infusion of $^{111}$In-ch806. High uptake of $^{111}$In-ch806 in metastatic lesions in the lungs (arrows) is evident. C) and D) show metastatic lesions (arrows) on CT scan. E) 3D SPECT images of the chest, and F) co-registered transaxial images of SPECT and CT showing specific uptake of $^{111}$In-ch806 in metastatic lesions.

FIGS. 95A, 95B, 95C, 95D, 95E, and 95F show planar images of the head and neck of Patient 8 obtained A) Day 0, B) Day 3 and C) Day 7 post infusion of $^{111}$In-ch806. Initial blood pool activity is seen on Day 0, and uptake of $^{111}$In-ch806 in an anaplastic astrocytoma in the right frontal lobe is evident by Day 3 (arrow), and increases by Day 7. Specific uptake of $^{111}$In-ch806 is confirmed in D) SPECT image of the brain (arrow), at the site of tumor (arrow) evident in E) $^{18}$F-FDG PET, and F) MRI.

FIGS. 96A, 96B, 96C, and 96D show similar uptake of 111In-ch806 in tumor is evident in Patient 3 compared to Patient 4, despite differences in 806 antigen expression in screened tumor samples. A) $^{111}$In-ch806 localization in lung metastasis (arrow) on SPECT transaxial image in Patient 4, with cardiac blood pool activity (B) evident. B) corresponding CT scan. Archived tumor was shown to have <10% positivity for 806 expression. C) $^{111}$In-ch806 localization in lung metastasis (arrow) in Patient 3, with cardiac blood pool activity (B) evident. D) corresponding CT scan. Archived tumor was shown to have 50-75% positivity for 806 expression.

Figure 97:
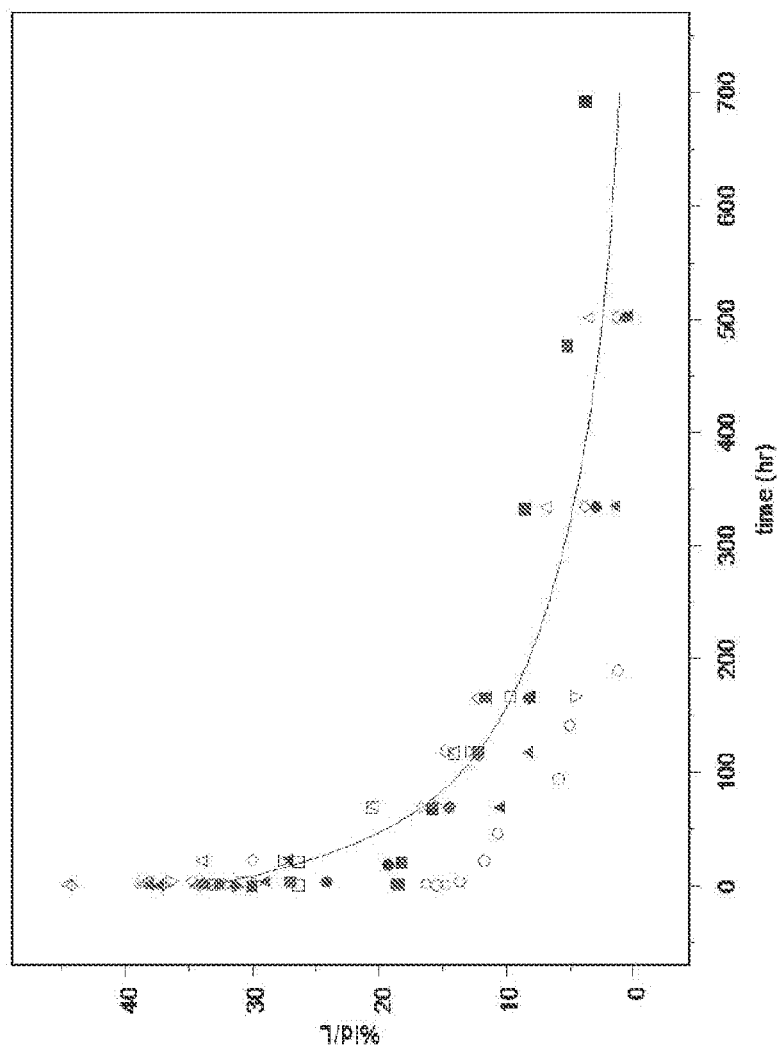

FIG. 97 shows pooled population pharmacokinetics of ch806 protein measured by ELISA. Observed and predicted ch806 (% ID/L) vs. time post infusion (hrs).

Figures 98A, 98B:
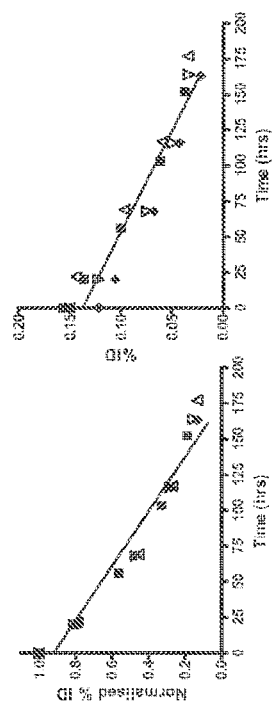

FIGS. 98A and 98B show individual patient results for A) Normalised Whole Body Clearance and B) Hepatic Clearance of $^{111}$In-ch806 at the 5 mg/m$^2$ (■), 10 mg/m$^2$ (Δ), 20 mg/m$^2$ (∇), and 40 mg/m$^2$ (♦) dose levels. Linear regression for data sets indicated in each panel [A) $r^2$=0.9595; B) $r^2$=0.9415].

DETAILED DESCRIPTION

In accordance with the present invention there may be employed conventional molecular biology, microbiology, and recombinant DNA techniques within the skill of the art. Such techniques are explained fully in the literature. See, for example, Sambrook et al., "Molecular Cloning: A Laboratory Manual" (1989); "Current Protocols in Molecular Biology" Volumes I-E [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

As used herein, the following terms are deemed to have, without limitation, the provided definitions.

The term "specific binding member" describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organization of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned with antigen-antibody type reactions.

The term "aberrant expression" in its various grammatical forms may mean and include any heightened or altered expression or overexpression of a protein in a tissue, e.g. an increase in the amount of a protein, caused by any means including enhanced expression or translation, modulation of the promoter or a regulator of the protein, amplification of a gene for a protein, or enhanced half-life or stability, such that more of the protein exists or can be detected at any one time, in contrast to a nonoverexpressed state. Aberrant expression includes and contemplates any scenario or alteration wherein the protein expression or post-translational modification machinery in a cell is taxed or otherwise disrupted due to enhanced expression or increased levels or amounts of a protein, including wherein an altered protein, as in mutated protein or variant due to sequence alteration, deletion or insertion, or altered folding is expressed.

It is important to appreciate that the term "aberrant expression" has been specifically chosen herein to encompass the state where abnormal (usually increased) quantities/levels of the protein are present, irrespective of the efficient cause of that abnormal quantity or level. Thus, abnormal quantities of protein may result from overexpression of the protein in the absence of gene amplification, which is the case e.g. in many cellular/tissue samples taken from the head and neck of subjects with cancer, while other samples exhibit abnormal protein levels attributable to gene amplification.

In this latter connection, certain of the work of the inventors that is presented herein to illustrate the invention includes the analysis of samples certain of which exhibit abnormal protein levels resulting from amplification of EFGR. This therefore accounts for the presentation herein of experimental findings where reference is made to amplification and for the use of the terms "amplification/amplified" and the like in describing abnormal levels of EFGR. However, it is the observation of abnormal quantities or levels of the protein that defines the environment or circumstance where clinical intervention as by resort to the binding members of the invention is contemplated, and for this reason, the present specification considers that the term "aberrant expression" more broadly captures the causal environment that yields the corresponding abnormality in EFGR levels.

Accordingly, while the terms "overexpression" and "amplification" in their various grammatical forms are understood to have distinct technical meanings, they are to be considered equivalent to each other, insofar as they represent the state where abnormal EFGR protein levels are present in the context of the present invention. Consequently, the term "aberrant expression" has been chosen as it is believed to subsume the terms "overexpression" and "amplification" within its scope for the purposes herein, so that all terms may be considered equivalent to each other as used herein.

The term "antibody" describes an immunoglobulin whether natural or partly or wholly synthetically produced. The term also covers any polypeptide or protein having a binding domain which is, or is homologous to, an antibody binding domain. CDR grafted antibodies are also contemplated by this term.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al. (1989) Nature 341, 544-546) which consists of a VH domain; (v) isolated CDR regions; (vi) F (ab') 2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al. (1988) Science. 242, 423-426; Huston et al. (1988) PNAS USA. 85, 5879-5883); (viii) multivalent antibody fragments (scFv dimers, trimers and/or tetramers (Power and Hudson (2000) J. Immunol. Methods 242, 193-204) (ix) bispecific single chain Fv dimers (PCT/US92/09965) and (x) "diabodies", multivalent or multispecific fragments constructed by gene fusion (WO94/13804; P. Holliger et al. (1993) Proc. Natl. Acad. Sci. USA 90, 6444-6448).

An "antibody combining site" is that structural portion of an antibody molecule comprised of light chain or heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F (ab') Z and F (v), which portions are preferred for use in the therapeutic methods described herein.

Antibodies may also be bispecific, wherein one binding domain of the antibody is a specific binding member of the invention, and the other binding domain has a different specificity, e.g. to recruit an effector function or the like. Bispecific antibodies of the present invention include wherein one binding domain of the antibody is a specific binding member of the present invention, including a fragment thereof, and the other binding domain is a distinct antibody or fragment thereof, including that of a distinct anti-EGFR antibody, for instance antibody 528 (U.S. Pat. No. 4,943,533), the chimeric and humanized 225 antibody (U.S. Pat. No. 4,943,533 and WO/9640210), an anti-de2-7 antibody such as DH8.3 (Hills, D. et al (1995) Int. J. Cancer. 63(4), 537-543), antibody L8A4 and Y10 (Reist, C J et al. (1995) Cancer Res. 55 (19):4375-4382; Foulon C F et al. (2000) Cancer Res. 60 (16):44534460), ICR62 (Modjtahedi H et al. (1993) Cell Biophys. January-June; 22 (1-3):129-46; Modjtahedi et al. (2002) P. A. A. C. R. 55 (14):3140-3148, or the antibody of Wikstrand et al (Wikstrand C. et al (1995) Cancer Res. 55 (14):3140-3148). The other binding domain may be an antibody that recognizes or targets a particular cell type, as in a neural or glial cell-specific antibody. In the bispecific antibodies of the present invention the one binding domain of the antibody of the invention may be combined with other binding domains or molecules which recognize particular cell receptors and/or modulate cells in a particular fashion, as for instance an immune modulator (e.g., interleukin (s)), a growth modulator or cytokine (e.g. tumor necrosis factor (TNF), and particularly, the TNF bispecific modality demonstrated in U.S. Ser. No. 60/355,838 filed Feb. 13, 2002, incorporated herein by its entirety) or a toxin (e.g., ricin) or antimitotic or apoptotic agent or factor.

Fab and $F(ab')_2$ portions of antibody molecules may be prepared by the proteolytic reaction of papain and pepsin, respectively, on substantially intact antibody molecules by methods that are well-known. See, for example, U.S. Pat. No. 4,342,566 to Theofilopolous et al. Fab' antibody molecule portions are also well-known and are produced from F (ab')2 portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may also contain an antibody molecule having a plurality of antibody combining sites, each immunospecific for a different antigen; e.g., a bispecific (chimeric) monoclonal antibody.

The term "antigen binding domain" describes the part of an antibody which comprises the area which specifically binds to and is complementary to part or all of an antigen. Where an antigen is large, an antibody may bind to a particular part of the antigen only, which part is termed an epitope. An antigen binding domain may be provided by one or more antibody variable domains. Preferably, an antigen binding domain comprises an antibody light chain variable region (VL) and an antibody heavy chain variable region (VH).

"Post-translational modification" may encompass any one of or combination of modification (s), including covalent modification, which a protein undergoes after translation is complete and after being released from the ribosome or on the nascent polypeptide co-translationally. Post-translational modification includes but is not limited to phosphorylation, myristylation, ubiquitination, glycosylation, coenzyme attachment, methylation and acetylation. Post-translational modification can modulate or influence the activity of a protein, its intracellular or extracellular destination, its stability or half-life, and/or its recognition by ligands, receptors or other proteins. Post-translational modification can occur in cell organelles, in the nucleus or cytoplasm or extracellularly.

The term "specific" may be used to refer to the situation in which one member of a specific binding pair will not show any significant binding to molecules other than its specific binding partner (s). The term is also applicable where e.g. an antigen binding domain is specific for a particular epitope which is carried by a number of antigens, in which case the specific binding member carrying the antigen binding domain will be able to bind to the various antigens carrying the epitope.

The term "comprise" generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention referred to above, those of skill in the art will appreciate that minor modifications to the N- or C-terminal of the peptide may however be contemplated, such as the chemical modification of the terminal to add a protecting group or the like, e.g. the amidation of the C-terminus The term "isolated" refers to the state in which specific binding members of the invention, or nucleic acid encoding such binding members will be, in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practiced in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Specific binding members may be glycosylated, either naturally or by systems of heterologous eukaryotic cells, or they may be (for example if produced by expression in a prokaryotic cell) unglycosylated.

Also, as used herein, the terms "glycosylation" and "glycosylated" includes and encompasses the post-translational modification of proteins, termed glycoproteins, by addition of oligosaccharides. Oligosaccharides are added at glycosylation sites in glycoproteins, particularly including N-linked oligosaccharides and 0-linked oligosaccharides. N-linked oligosaccharides are added to an Asn residue, particularly wherein the Asn residue is in the sequence N-X-S/T, where X cannot be Pro or Asp, and are the most common ones found in glycoproteins. In the biosynthesis of N-linked glycoproteins, a high mannose type oligosaccharide (generally comprised of dolichol, N-Acetylglucosamine, mannose and glucose is first formed in the endoplasmic reticulum (ER). The high mannose type glycoproteins are then transported from the ER to the Golgi, where further processing and modification of the oligosaccharides occurs. 0-linked oligosaccharides are added to the hydroxyl group of Ser or Thr residues. In 0-linked oligosaccharides, N-Acetylglucosamine is first transferred to the Ser or Thr residue by N-Acetylglucosaminyltransferase in the ER. The protein then moves to the Golgi where further modification and chain elongation occurs. O-linked modifications can occur with the simple addition of the OGlcNAc monosaccharide alone at those Ser or Thr sites which can also under different conditions be phosphorylated rather than glycosylated.

As used herein, "pg" means picogram, "ng" means nanogram, "ug" or "µg" mean microgram, "mg" means milligram, "ul" or "µl" mean microliter, "ml" means milliliter, "l" means liter.

The terms "806 antibody", "mAb806", "ch806", and any variants not specifically listed, may be used herein interchangeably, and as used throughout the present application and claims refer to proteinaceous material including single or multiple proteins, and extends to those proteins having the amino acid sequence data described herein and presented in SEQ ID NO:2 and SEQ ID NO:4, and the chimeric antibody ch806 which is incorporated in and forms a part of SEQ ID NOS:7 and 8, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "806 antibody", "mAb806" and "ch806" are intended to include within their scope proteins specifically recited herein as well as all substantially homologous analogs and allelic variations.

The terms "humanized 806 antibody", "hu806", and "veneered 806 antibody" and any variants not specifically listed, may be used herein interchangeably, and as used throughout the present application and claims refer to proteinaceous material including single or multiple proteins, and extends to those proteins having the amino acid sequence data described herein and presented in SEQ ID NO:42 and SEQ ID NO:47, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "humanized 806 antibody", "hu806", and "veneered 806 antibody" are intended to include within their scope proteins specifically recited herein as well as all substantially homologous analogs and allelic variations.

The terms "175 antibody" and "mAb175", and any variants not specifically listed, may be used herein interchangeably, and as used throughout the present application and claims refer to proteinaceous material including single or multiple proteins, and extends to those proteins having the amino acid sequence data described herein and presented in SEQ ID NO:129 and SEQ ID NO:134, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "175 antibody" and "mAb175" are intended to include within their scope proteins specifically recited herein as well as all substantially homologous analogs and allelic variations.

The terms "124 antibody" and "mAb124", and any variants not specifically listed, may be used herein interchangeably, and as used throughout the present application and claims refer to proteinaceous material including single or multiple proteins, and extends to those proteins having the amino acid sequence data described herein and presented in SEQ ID NO:22 and SEQ ID NO:27, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "124 antibody" and "mAb124" are intended to include within their scope proteins specifically recited herein as well as all substantially homologous analogs and allelic variations.

The terms "1133 antibody" and "mAb1133", and any variants not specifically listed, may be used herein interchangeably, and as used throughout the present application and claims refer to proteinaceous material including single or multiple proteins, and extends to those proteins having the amino acid sequence data described herein and presented in SEQ ID NO:32 and SEQ ID NO:37, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "11133 antibody" and "mAb1133" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| Table of Correspondence | | |
|---|---|---|
| Symbol | | |
| 1-Letter | 3-Letter | Amino Acid |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | aspargine |
| C | Cys | cysteine |

It should be noted that all amino-acid residue sequences are represented herein by formulae whose left and right orientation is in the conventional direction of amino terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine Dalgarno sequences in addition to the –10 and –35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding specific binding members (antibodies) of the invention which code for antibodies having the disclosed sequences but which are degenerate to such sequences. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (He or I) | AUU or AUC or AUA |
| Methionine (Met or M) | AUG |
| Valine (Valor V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in, for example, the disclosed sequences of antibodies of the present invention, such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:
Amino Acids with Nonpolar R Groups
Alanine, Valine, Leucine, Isoleucine, Proline, Phenylalanine, Tryptophan, Methionine
Amino Acids with Uncharged Polar R Groups
Glycine, Serine, Threonine, Cysteine, Tyrosine, Asparagine, Glutamine
Amino Acids with Charged Polar R Groups (Negatively Charged at pH 6.0)
Aspartic acid, Glutamic acid
Basic Amino Acids (Positively Charged at pH 6.0)
Lysine, Arginine, Histidine (at pH 6.0)
Another grouping may be those amino acids with phenyl groups:
Phenylalanine, Tryptophan, Tyrosine
Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free NH2 can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces. (3-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, preferably by at least 50 percent, preferably by at least 70 percent, preferably by at least 80 percent, preferably by at least 90%, a clinically significant change in the growth or progression or mitotic activity of a target cellular mass, group of cancer cells or tumor, or other feature of pathology. For example, the degree of EGFR activation or activity or amount or number of EGFR positive cells, particularly of antibody or binding member reactive or positive cells may be reduced.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined Tm with washes of higher stringency, if desired.

The present invention provides a novel specific binding member, particularly an antibody or fragment thereof, including immunogenic fragments, which recognizes an EGFR epitope which is found in tumorigenic, hyperproliferative or abnormal cells wherein the epitope is enhanced or evident upon aberrant post-translational modification and not detectable in normal or wild-type cells. In a particular but nonlimiting embodiment, the binding member, such as the antibody, recognizes an EGFR epitope which is enhanced or evident upon simple carbohydrate modification or early glycosylation and is reduced or not evident in the presence of complex carbohydrate modification or glycosylation. The specific binding member, such as the antibody or fragment thereof, does not bind to or recognize normal or wild-type cells containing normal or wild-type EGFR epitope in the absence of overexpression and in the presence of normal EGFR post-translational modification.

The present invention further provides novel antibodies 806, 175, 124, 1133, ch806, and hu806 and fragment thereof, including immunogenic fragments, which recognizes an EGFR epitope, particularly the EGFR peptide ($_{287}$CGADSYEMEEDGVRKC$_{302}$ (SEQ ID NO:14)), which is exposed in tumorigenic, hyperproliferative or abnormal cells wherein the epitope is enhanced,
revealed, or evident and not detectable in normal or wild-type cells. In a particular but non-limiting embodiment, the antibody recognizes an EGFR epitope which is enhanced or evident upon simple carbohydrate modification or early glycosylation and is reduced or not evident in the presence of complex carbohydrate modification or glycosylation. The antibody or fragment thereof does not bind to or recognize normal or wild-type cells containing normal or wild-type EGFR epitope in the absence of overexpression, amplification, or a tumorigenic event.

In a particular aspect of the invention and as stated above, the present inventors have discovered the novel monoclonal antibodies 806, 175, 124, 1133, ch806, and hu806 which specifically recognize amplified wild-type EGFR and the de2-7 EGFR, yet bind to an epitope distinct from the unique junctional peptide of the de2-7 EGFR mutation. Additionally, while mAb806, mAb175, mAb124, mAb1133, and hu806 do not recognize the normal, wild-type EGFR expressed on the cell surface of glioma cells, they do bind to the extracellular domain of the EGFR immobilized on the surface of ELISA plates, indicating a conformational epitope with a polypeptide aspect.

Importantly, mAb806, mAb175, mAb124, mAb1133, ch806, and hu806 do not bind significantly to normal tissues such as liver and skin, which express levels of endogenous wtEGFR that are higher than in most other normal tissues, but wherein EGFR is not overexpressed or amplified. Thus, mAb806, mAb175, mAb124, mAb1133, and hu806 demonstrate novel and useful specificity, recognizing de2-7 EGFR and amplified EGFR, while not recognizing normal, wild-type EGFR or the unique junctional peptide which is characteristic of de2-7 EGFR. In a preferred aspect mAb806, mAb175, mAb124, mAb1133, and hu806 of the present invention comprises the VH and VL chain CDR domain amino acid sequences depicted in FIGS. 14B and 15B; 74B and 75B; 51B and 51D; 52B and 52D; and 55A and 55B, respectively (SEQ ID NOS:2 and 4; 129 and 134; 22 and 27; 32 and 37; and 42 and 47, respectively; SEQ ID NO:42 including the hu806 VH chain signal peptide and VH chain sequences of SEQ ID NOS:163 and 164, respectively, and SEQ ID NO:47 including the hu806 VL chain signal peptide and VL chain sequences of SEQ ID NOS: 165 and 166, respectively).

In another aspect, the invention provides an antibody capable of competing with the 175 antibody, under conditions in which at least 10% of an antibody having the VH and VL chain sequences of the 175 antibody (SEQ ID NOS:129 and 134, respectively) is blocked from binding to de2-7EGFR by competition with such an antibody in an ELISA assay. As set forth above, anti-idiotype antibodies are contemplated herein.

The present invention relates to specific binding members, particularly antibodies or fragments thereof, which recognizes an EGFR epitope which is present in cells expressing amplified EGFR or expressing the de2-7 EGFR and not detectable in cells expressing normal or wild-type EGFR, particularly in the presence of normal posttranslational modification.

It is further noted and herein demonstrated that an additional non-limiting observation or characteristic of the antibodies of the present invention is their recognition of their epitope in the presence of high mannose groups, which is a characteristic of early glycosylation or simple carbohydrate modification. Thus, altered or aberrant glycosylation facilitates the presence and/or recognition of the antibody epitope or comprises a portion of the antibody epitope.

Glycosylation includes and encompasses the post-translational modification of proteins, termed glycoproteins, by addition of oligosaccharides. Oligosaccharides are added at glycosylation sites in glycoproteins, particularly including N-linked oligosaccharides and 0-linked oligosaccharides. N-linked oligosaccharides are added to an Asn residue, particularly wherein the Asn residue is in the sequence N-X-S/T, where X cannot be Pro or Asp, and are the most common ones found in glycoproteins. In the biosynthesis of N-linked glycoproteins, a high mannose type oligosaccharide (generally comprised of dolichol, N-Acetylglucosamine, mannose and glucose is first formed in the endoplasmic reticulum (ER). The high mannose type glycoproteins are then transported from the ER to the Golgi, where further processing and modification of the oligosaccharides normally occurs. 0-linked oligosaccharides are added to the hydroxyl group of Ser or Thr residues. In 0-linked oligosaccharides, N Acetylglucosamine is first transferred to the Ser or Thr residue by N Acetylglucosaminyltransferase in the ER. The protein then moves to the Golgi where further modification and chain elongation occurs.

In a particular aspect of the invention and as stated above, the present inventors have discovered novel monoclonal antibodies, exemplified herein by the antibodies designated mAb806 (and its chimeric ch806), mAb175, mAb124, mAb1133, and hu806 which specifically recognize amplified wild-type EGFR and the de2-7 EGFR, yet bind to an epitope distinct from the unique junctional peptide of the de2-7 EGFR mutation. The antibodies of the present invention specifically recognize overexpressed EGFR, including amplified EGFR and mutant EGFR (exemplified herein by the de2-7 mutation), particularly upon aberrant post-translational modification. Additionally, while these antibodies do not recognize the normal, wild-type EGFR expressed on the cell surface of glioma cells, they do bind to the extracellular domain of the EGFR immobilized on the surface of ELISA plates, indicating a conformational epitope with a polypeptide aspect. Importantly, these antibodies do not bind significantly to normal tissues such as liver and skin, which express levels of endogenous wtEGFR that are higher than in most other normal tissues, but wherein EGFR is not overexpressed or amplified. Thus, these antibodies demonstrate novel and useful specificity, recognizing de2-7 EGFR and amplified EGFR, while not recognizing normal, wild-type EGFR or the unique junctional peptide which is characteristic of de2-7 EGFR.

In a preferred aspect, the antibodies are ones which have the characteristics of the antibodies which the inventors have identified and characterized, in particular recognizing amplified EGFR and de2-7EGFR. In particularly preferred aspects, the antibodies are mAb806, mAb175, mAb124, mAb1133, and hu806 or active fragments thereof. In a further preferred aspect the antibody of the present invention comprises the VH and VL chain amino acid sequences depicted FIGS. 16 and 17; 74B and 75B; 51B and 51D; 52B and 52D; and 55A and 55B, respectively.

Preferably the epitope of the specific binding member or antibody is located within the region comprising residues 273-501 of the mature normal or wild-type EGFR sequence, and preferably the epitope comprises residues 287-302 of the mature normal or wild-type EGFR sequence (SEQ ID NO:14). Therefore, also provided are specific binding proteins, such as antibodies, which bind to the de2-7 EGFR at an epitope located within the region comprising residues 273-501 of the EGFR sequence, and comprising residues 287-302 of the EGFR sequence (SEQ ID NO:14). The epitope may be determined by any conventional epitope mapping techniques known to the person skilled in the art. Alternatively, the DNA sequences encoding residues 273-501 and 287-302 (SEQ ID NO:14) could be digested, and the resultant fragments expressed in a suitable host. Antibody binding could be determined as mentioned above.

In particular, the member will bind to an epitope comprising residues 273-501, and more specifically comprising residues 287-302 (SEQ ID NO:14), of the mature normal or wild-type EGFR. However other antibodies which show the same or a substantially similar pattern of reactivity also form an aspect of the invention. This may be determined by comparing such members with an antibody comprising the VH and VL chain domains shown in SEQ ID NOS:2 and 4; 129 and 134; 22 and 27; 32 and 37; and 42 and 47, respectively. The comparison will typically be made using a Western blot in which binding members are bound to duplicate blots prepared from a nuclear preparation of cells so that the pattern of binding can be directly compared.

In another aspect, the invention provides an antibody capable of competing with mAb806 under conditions in which at least 10% of an antibody having the VH and VL chain sequences of one of such antibodies is blocked from binding to de2-7EGFR by competition with such an antibody in an ELISA assay. As set forth above, anti-idiotype antibodies are contemplated and are illustrated herein.

In another aspect, the invention provides an antibody capable of competing with mAb175, mAb124, and/or mAb1133 under conditions in which at least 10% of an antibody having the VH and VL chain sequences of one of such antibodies is blocked from binding to de2-7EGFR by competition with such an antibody in an ELISA assay. As set forth above, anti-idiotype antibodies are contemplated and are illustrated herein.

In another aspect, the invention provides an antibody capable of competing with mAb806, mAb175, mAb124, mAb1133 and/or hu806, under conditions in which at least 10% of an antibody having the VH and VL chain sequences of one of such antibodies is blocked from binding to de2-7EGFR by competition with such an antibody in an ELISA assay. As set forth above, anti-idiotype antibodies are contemplated and are illustrated herein.

An isolated polypeptide consisting essentially of the epitope comprising residues 273-501 and more specifically comprising residues 287-302 (SEQ ID NO:14) of the mature wild-type EGFR forms another aspect of the present invention. The peptide of the invention is particularly useful in diagnostic assays or kits and therapeutically or prophylactically, including as an anti-tumor or anti-cancer vaccine. Thus compositions of the peptide of the present invention include pharmaceutical composition and immunogenic compositions.

Diagnostic and Therapeutic Uses

The unique specificity of the specific binding members, particularly antibodies or fragments thereof, of the present invention, whereby the binding member (s) recognize an EGFR epitope which is found in tumorigenic, hyperproliferative or abnormal cells and not detectable in normal or wild-type cells and wherein the epitope is enhanced or evident upon aberrant post-translational modification and wherein the member (s) bind to the de2-7 EGFR and amplified EGFR but not the wtEGFR, provides diagnostic and therapeutic uses to identify, characterize, target and treat, reduce or eliminate a number of tumorigenic cell types and tumor types, for example head and neck, breast, lung, bladder or prostate tumors and glioma, without the problems associated with normal tissue uptake that may be seen with previously known EGFR antibodies. Thus, cells overexpressing EGFR (e.g. by amplification or expression of a mutant or variant EGFR), particularly those demonstrating aberrant post-translational modification may be recognized, isolated, characterized, targeted and treated or eliminated utilizing the binding member (s), particularly antibody (ies) or fragments thereof of the present invention.

In a further aspect of the invention, there is provided a method of treatment of a tumor, a cancerous condition, a precancerous condition, and any condition related to or resulting from hyperproliferative cell growth comprising administration of mAb806, mAb175, mAb124, mAb1133, and/or hu806.

The antibodies of the present invention can thus specifically categorize the nature of EGFR tumors or tumorigenic cells, by staining or otherwise recognizing those tumors or cells wherein EGFR overexpression, particularly amplification and/or EGFR mutation, particularly de2-7EGFR, is present. Further, the antibodies of the present invention, as exemplified by mAb806 (and chimeric antibody ch806), mAb175, mAb124, mAb1133, and hu806, demonstrate significant in vivo anti-tumor activity against tumors containing amplified EGFR and against de2-7 EGFR positive xenografts.

As outlined above, the inventors have found that the specific binding member of the invention recognizes tumor-associated forms of the EGFR (de2-7 EGFR and amplified EGFR) but not the normal, wild-type receptor when expressed in normal cells. It is believed that antibody recognition is dependent upon an aberrant posttranslational modification (e.g., a unique glycosylation, acetylation or phosphorylation variant) of the EGFR expressed in cells exhibiting overexpression of the EGFR gene.

As described below, antibodies of the present invention have been used in therapeutic studies and shown to inhibit growth of overexpressing (e.g. amplified) EGFR xenografts and human de2-7 EGFR expressing xenografts of human tumors and to induce significant necrosis within such tumors.

Moreover, the antibodies of the present invention inhibit the growth of intracranial tumors in a preventative model. This model involves injecting glioma cells expressing de2-7 EGFR into nude mice and then injecting the antibody intracranially either on the same day or within 1 to 3 days, optionally with repeated doses. The doses of antibody are suitably about 10 µg. Mice injected with antibody are compared to controls, and it has been found that survival of the treated mice is significantly increased.

Therefore, in a further aspect of the invention, there is provided a method of treatment of a tumor, a cancerous condition, a precancerous condition, and any condition related to or resulting from hyperproliferative cell growth comprising administration of a specific binding member of the invention.

Antibodies of the present invention are designed to be used in methods of diagnosis and treatment of tumors in human or animal subjects, particularly epithelial tumors. These tumors may be primary or secondary solid tumors of any type including, but not limited to, glioma, breast, lung, prostate, head or neck tumors.

Binding Member and Antibody Generation

The general methodology for making monoclonal antibodies by hybridomas is well known Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammering et al., "Monoclonal Antibodies And T cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; and 4,493,890.

Panels of monoclonal antibodies produced against EFGR can be screened for various properties; i.e., isotype, epitope, affinity, etc. Of particular interest are monoclonal antibodies that mimic the activity of EFGR or its subunits. Such monoclonals can be readily identified in specific binding member activity assays. High affinity antibodies are also useful when immunoaffinity purification of native or recombinant specific binding member is possible.

Methods for producing polyclonal anti-EFGR antibodies are well-known in the art. See U.S. Pat. No. 4,493,795 to Nestor et al. A monoclonal antibody, typically containing Fab and/or F (ab')2 portions of useful antibody molecules, can be prepared using the hybridoma technology described in Antibodies-A Laboratory Manual, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with an appropriate EGFR.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present antibody or binding member and their ability to inhibit specified tumorigenic or hyperproliferative activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic culture medium is Dulbecco's minimal essential medium (DMEM; Dulbecco et al., Virol. 8:396 (1959)) supplemented with 4.5 gm/l glucose, 20 mm glutamine, and 20% fetal calf serum. An exemplary inbred mouse strain is the Balb/c.

Methods for producing monoclonal anti-EGFR antibodies are also well-known in the art. See Niman et al., *Proc. Natl. Acad. Sci. USA*, 80:4949-4953 (1983). Typically, the EGFR or a peptide analog is used either alone or conjugated to an immunogenic carrier, as the immunogen in the before described procedure for producing anti-EGFR monoclonal antibodies. The hybridomas are screened for the ability to produce an antibody that immunoreacts with the EGFR present in tumorigenic, abnormal or hyperproliferative cells. Other anti-EGFR antibodies include but are not limited to the HuMAX-EGFr antibody from Genmab/Medarex, the 108 antibody (ATCC HB9764) and U.S. Pat. No. 6,217,866, and antibody 14E1 from Schering A G (U.S. Pat. No. 5,942,602).

Recombinant Binding Members, Chimerics, Bispecifics and Fragments

In general, the CDR1 regions, comprising amino acid sequences substantially as set out as the CDR1 regions of SEQ ID NOS:2 and 4; 129 and 134; 22 and 27; 32 and 37; and 42 and 47, respectively, will be carried in a structure which allows for binding of the CDR1 regions to an tumor antigen. In the case of the CDR1 region of SEQ ID NO:4, for example, this is preferably carried by the VL chain region of SEQ ID NO:4 (and similarly for the other recited sequences).

In general, the CDR2 regions, comprising amino acid sequences substantially as set out as the CDR2 regions of SEQ ID NOS:2 and 4; 129 and 134; 22 and 27; 32 and 37; and 42 and 47, respectively, will be carried in a structure which allows for binding of the CDR2 regions to an tumor antigen. In the case of the CDR2 region of SEQ ID NO:4, for example, this is preferably carried by the VL chain region of SEQ ID NO:4 (and similarly for the other recited sequences).

In general, the CDR3 regions, comprising amino acid sequences substantially as set out as the CDR3 regions of SEQ ID NOS:2 and 4; 129 and 134; 22 and 27; 32 and 37; and 42 and 47, respectively, will be carried in a structure which allows for binding of the CDR3 regions to an tumor antigen. In the case of the CDR3 region of SEQ ID NO:4, for example, this is preferably carried by the VL chain region of SEQ ID NO:4 (and similarly for the other recited sequences).

By "substantially as set out" it is meant that that CDR regions, for example CDR3 regions, of the invention will be either identical or highly homologous to the specified regions of SEQ ID NOS:2 and 4; 129 and 134; 22 and 27; 32 and 37; and 42 and 47, respectively. By "highly homologous" it is contemplated that only a few substitutions, preferably from 1 to 8, preferably from 1 to 5, preferably from 1 to 4, or from 1 to 3 or 1 or 2 substitutions may be made in one or more of the CDRs. It is also contemplated that such terms include truncations to the CDRs, so long as the resulting antibody exhibits the unique properties of the class of antibodies discussed herein, as exhibited by mAb806, mAb175, mAb124, mAb1133 and hu806.

The structure for carrying the CDRs of the invention, in particular CDR3, will generally be of an antibody heavy or light chain sequence or substantial portion thereof in which the CDR regions are located at locations corresponding to the CDR region of naturally occurring VH and VL chain antibody variable domains encoded by rearranged immunoglobulin genes. The structures and locations of immunoglobulin variable domains may be determined by reference to Kabat, E. A. et al, Sequences of Proteins of Immunological Interest. 4th Edition. US Department of Health and Human Services. 1987, and updates thereof. Moreover, as is known to those of skill in the art, CDR determinations can be made in various ways. For example, Kabat, Chothia and combined domain determination analyses may be used.

Preferably, the amino acid sequences substantially as set out as the VH chain CDR residues in the inventive antibodies are in a human heavy chain variable domain or a substantial portion thereof, and the amino acid sequences substantially as set out as the VL chain CDR residues in the inventive antibodies are in a human light chain variable domain or a substantial portion thereof.

The variable domains may be derived from any germline or rearranged human variable domain, or may be a synthetic variable domain based on consensus sequences of known human variable domains. The CDR3-derived sequences of the invention, for example, as defined in the preceding paragraph, may be introduced into a repertoire of variable domains lacking CDR3 regions, using recombinant DNA technology.

For example, Marks et al (*Bio/Technology,* 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide specific binding members of the invention. The repertoire may then be displayed in a suitable host system such as the phage display system of WO92/01047 so that suitable specific binding members may be selected. A repertoire may consist of from anything from $10^4$ individual members upwards, for example from $10^6$ to $10^8$ or $10^{10}$ members.

Analogous shuffling or combinatorial techniques are also disclosed by Stemmer (*Nature,* 1994, 370:389-391), who describes the technique in relation to a p-lactamase gene but observes that the approach may be used for the generation of antibodies.

A further alternative is to generate novel VH or VL regions carrying the CDR3 derived sequences of the invention using random mutagenesis of, for example, the mAb806 VH or VL genes to generate mutations within the entire variable domain. Such a technique is described by Gram et al (1992, *Proc. Natl. Acad. Sci., USA,* 89:3576-3580), who used error-prone PCR.

Another method which may be used is to direct mutagenesis to CDR regions of VH or VL genes. Such techniques are disclosed by Barbas et al, (1994, *Proc. Natl. Acad. Sci., USA,* 91:3809-3813) and Schier et al. (1996, J. Mol. Biol. 263:551-567).

All the above described techniques are known as such in the art and in themselves do not form part of the present invention. The skilled person will be able to use such techniques to provide specific binding members of the invention using routine methodology in the art.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as discussed in more detail below.

Although in a preferred aspect of the invention specific binding members comprising a pair of binding domains based on sequences substantially set out in SEQ ID NOS:2 and 4; 129 and 134; 22 and 27; 32 and 37; and 42 and 47, respectively, are preferred, single binding domains based on these sequences form further aspects of the invention. In the case of the binding domains based on the sequence substantially set out in VH chains, such binding domains may be used as targeting agents for tumor antigens since it is known that immunoglobulin VH domains are capable of binding target antigens in a specific manner.

In the case of either of the single chain specific binding domains, these domains may be used to screen for complementary domains capable of forming a two-domain specific binding member which has in vivo properties as good as or equal to the mAb806, ch806, mAb175, mAb124, mAb1133 and hu806 antibodies disclosed herein.

This may be achieved by phage display screening methods using the so-called hierarchical dual combinatorial approach as disclosed in U.S. Pat. No. 5,969,108 in which an individual colony containing either an H or L chain clone is used to infect a complete library of clones encoding the other chain (L or H) and the resulting two-chain specific binding member is selected in accordance with phage display techniques such as those described in that reference. This technique is also disclosed in Marks et al, ibid.

Specific binding members of the present invention may further comprise antibody constant regions or parts thereof. For example, specific binding members based on VL chain sequences may be attached at their C-terminal end to antibody light chain constant domains including human Ck of Cλ chains, preferably Cλ chains. Similarly, specific binding members based on VH chain sequences may be attached at their C-terminal end to all or part of an immunoglobulin heavy chain derived from any antibody isotype, e.g. IgG, IgA, IgE, IgD and IgM and any of the isotype sub-classes, particularly IgG1, IgG2b, and IgG4. IgG1 is preferred.

The advent of monoclonal antibody (mAb) technology 25 years ago has provide an enormous repertoire of useful research reagents and created the opportunity to use antibodies as approved pharmaceutical reagents in cancer therapy, autoimmune disorders, transplant rejection, antiviral prophylaxis and as anti-thrombotics (Glennie and Johnson, 2000). The application of molecular engineering to convert murine mAbs into chimeric mAbs (mouse V-region, human C-region) and humanized reagents where only the mAb complementarity-determining regions (CDR) are of murine origin has been critical to the clinical success of mAb therapy. The engineered mAbs have markedly reduced or absent immunogenicity, increased serum half-life and the human Fc portion of the mAb increases the potential to recruit the immune effectors of complement and cytotoxic cells (Clark 2000). Investigations into the biodistribution, pharmacokinetics and any induction of an immune response to clinically administered mAbs requires the development of analyses to discriminate between the pharmaceutical and endogenous proteins.

The antibodies, or any fragments thereof, may also be conjugated or recombinantly fused to any cellular toxin, bacterial or other, e.g. pseudomonas exotoxin, ricin, or diphtheria toxin. The part of the toxin used can be the whole toxin, or any particular domain of the toxin. Such antibody-toxin molecules have successfully been used for targeting and therapy of different kinds of cancers, see e.g. Pastan, *Biochim Biophys Acta.* 1997 Oct. 24; 1333 (2):C1-6; Kreitman et al., *N Engl. J. Med.* 2001 Jul. 26; 345 (4):241-7; Schnell et al., *Leukemia.* 2000 January; 14 (1):129-35; Ghetie et al., *Mol. Biotechnol.* 2001 July; 18 (3):251-68.

Bi- and tri-specific multimers can be formed by association of different scFv molecules and have been designed as cross-linking reagents for T-cell recruitment into tumors (immunotherapy), viral retargeting (gene therapy) and as red blood cell agglutination reagents (immunodiagnostics), see e.g. Todorovska et al., *J. Immunol. Methods.* 2001 Feb. 1; 248 (1-2):47-66; Tomlinson et al., *Methods Enzymol.* 2000; 326:461-79; McCall et al., *J. Immunol.* 2001 May 15; 166 (10):6112-7.

Fully human antibodies can be prepared by immunizing transgenic mice carrying large portions of the human immunoglobulin heavy and light chains. These mice, examples of such mice are the Xenomouse™ (Abgenix, Inc.) (U.S. Pat. Nos. 6,075,181 and 6,150,584), the HuMAb-Mouse™ (Medarex, Inc./GenPharm) (U.S. Pat. Nos. 5,545,806 and 5,569,825), the TransChromo Mouse™ (Kirin) and the KM Mouse™ (Medarex/Kirin), are well known within the art.

Fully human antibodies can also be generated using phage display from human libraries. Phage display may be performed using methods well known to the skilled artisan, as in Hoogenboom et al. and Marks et al. (Hoogenboom H R and Winter G. (1992) *J. Mol. Biol.* 227 (2):381-8; Marks J D et al. (1991) *J. Mol. Biol.* 222 (3):581-97; and also U.S. Pat. Nos. 5,885,793 and 5,969,108).

Therapeutic Antibodies and Uses

The in vivo properties, particularly with regard to tumor: blood ratio and rate of clearance, of specific binding members of the invention will be at least comparable to mAb806. Following administration to a human or animal subject such a specific binding member will show a peak tumor to blood ratio of >1:1. Preferably at such a ratio the specific binding member will also have a tumor to organ ratio of greater than 1:1, preferably greater than 2:1, more preferably greater than 5:1. Preferably at such a ratio the specific binding member will also have an organ to blood ratio of <1:1 in organs away from the site of the tumor. These ratios exclude organs of catabolism and secretion of the administered specific binding member. Thus in the case of scFvs and Fabs (as shown in the accompanying examples), the binding members are secreted via the kidneys and there is greater presence here than other organs. In the case of whole IgGs, clearance will be at least in part, via the liver. The peak localization ratio of the intact antibody will normally be achieved between 10 and 200 hours following administration of the specific binding member. More particularly, the ratio may be measured in a tumor xenograft of about 0.2-1.0 g formed subcutaneously in one flank of an athymic nude mouse.

Antibodies of the invention may be labelled with a detectable or functional label. Detectable labels include, but are not limited to, radiolabels such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{121}$I, $^{124}$I, $^{125}$I, $^{131}$I, $^{111}$In, $^{211}$At, $^{198}$Au, $^{67}$CU, $^{225}$Ac, $^{213}$Bi, $^{99}$Tc and $^{186}$Re, which may be attached to antibodies of the invention using conventional chemistry known in the art of antibody imaging. Labels also include fluorescent labels and labels used conventionally in the art for MRI-CT imagine. They also include enzyme labels such as horseradish peroxidase. Labels further include chemical moieties such as biotin which may be detected via binding to a specific cognate detectable moiety, e.g. labeled avidin.

Functional labels include substances which are designed to be targeted to the site of a tumor to cause destruction of tumor tissue. Such functional labels include cytotoxic drugs such as 5-fluorouracil or ricin and enzymes such as bacterial carboxypeptidase or nitroreductase, which are capable of converting prodrugs into active drugs at the site of a tumor.

Also, antibodies including both polyclonal and monoclonal antibodies, and drugs that modulate the production or activity of the specific binding members, antibodies and/or their subunits may possess certain diagnostic applications and may for example, be utilized for the purpose of detecting and/or measuring conditions such as cancer, precancerous lesions, conditions related to or resulting from hyperproliferative cell growth or the like. For example, the specific binding members, antibodies or their subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity (ies) of the specific binding members of the invention may be discovered or synthesized, and may be used in diagnostic and/or therapeutic protocols.

The radiolabeled specific binding members, particularly antibodies and fragments thereof, are useful in in vitro diagnostics techniques and in in vivo radioimaging techniques and in radioimmunotherapy. In the instance of in vivo imaging, the specific binding members of the present invention may be conjugated to an imaging agent rather than a radioisotope (s), including but not limited to a magnetic resonance image enhancing agent, wherein for instance an antibody molecule is loaded with a large number of paramagnetic ions through chelating groups. Examples of chelating groups include EDTA, porphyrins, polyamines crown ethers and polyoximes. Examples of paramagnetic ions include gadolinium, iron, manganese, rhenium, europium, lanthanium, holmium and erbium. In a further aspect of the invention, radiolabeled specific binding members, particularly antibodies and fragments thereof, particularly radioimmunoconjugates, are useful in radioimmunotherapy, particularly as radiolabeled antibodies for cancer therapy. In a still further aspect, the radiolabelled specific binding members, particularly antibodies and fragments thereof, are useful in radioimmuno-guided surgery techniques, wherein they can identify and indicate the presence and/or location of cancer cells, precancerous cells, tumor cells, and hyperproliferative cells, prior to, during or following surgery to remove such cells.

Immunoconjugates or antibody fusion proteins of the present invention, wherein the specific binding members, particularly antibodies and fragments thereof, of the present invention are conjugated or attached to other molecules or agents further include, but are not limited to binding members conjugated to a chemical ablation agent, toxin, immunomodulator, cytokine, cytotoxic agent, chemotherapeutic agent or drug.

Radioimmunotherapy (RAIT) has entered the clinic and demonstrated efficacy using various antibody immunoconjugates. $^{131}$I labeled humanized anti-carcinoembryonic antigen (anti-CEA) antibody hMN-14 has been evaluated in colorectal cancer (Behr T M et al (2002) *Cancer* 94 (4Suppl):1373-81) and the same antibody with 90Y label has been assessed in medullary thyroid carcinoma (Stein R et al (2002) *Cancer* 94 (1):51-61). Radioimmunotherapy using monoclonal antibodies has also been assessed and reported for non-Hodgkin's lymphoma and pancreatic cancer (Goldenberg D M (2001) *Crit. Rev. Oncol. Hematol.* 39 (1-2):195-201; Gold D V et al. (2001) *Crit. Rev. Oncol. Hematol.* 39 (1-2) 147-54).

Radioimmunotherapy methods with particular antibodies are also described in U.S. Pat. Nos. 6,306,393 and 6,331,175. Radioimmunoguided surgery (RIGS) has also entered the clinic and demonstrated efficacy and usefulness, including using anti-CEA antibodies and antibodies directed against tumor-associated antigens (Kim J C et al (2002) *Jut. J. Cancer* 97(4):542-7; Schneebaum, S. et al. (2001) *World J. Surg.* 25(12):1495-8; Avital, S. et al. (2000) *Cancer* 89(8):1692-8; McIntosh D G et al (1997) *Cancer Biother. Radiopharm.* 12 (4):287-94).

Antibodies of the present invention may be administered to a patient in need of treatment via any suitable route, usually by injection into the bloodstream or CSF, or directly into the site of the tumor. The precise dose will depend upon a number of factors, including whether the antibody is for diagnosis or for treatment, the size and location of the tumor, the precise nature of the antibody (whether whole antibody, fragment, diabody, etc), and she nature of the detectable or functional label attached to the antibody. Where a radionuclia is used for therapy, a suitable maximum single dose is about 45 mCi/m$^2$, to a maximum of about 250 mCi/m$^2$. Preferable dosage is in the range of 15 to 40 mCi, with a further preferred dosage range of 20 to 30 mCi, or 10 to 30 mCi. Such therapy may require bone marrow or stem cell replacement. A typical antibody dose for either tumor imaging or tumor treatment will be in the range of from 0.5 to 40 mg, preferably from 1 to 4 mg of antibody in F(ab')2 form. Naked antibodies are preferable administered in doses of 20 to 1000 mg protein per dose, or 20 to 500 mg protein per dose, or 20 to 100 mg protein per dose. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

These formulations may include a second binding protein, such as the EGPR binding proteins described supra. In an especially preferred form, this second binding protein is a monoclonal antibody such as 528 or 225, discussed infra.

Pharmaceutical and Therapeutic Compositions

Specific binding members of the present invention will usually be administered in the form of a pharmaceutical composition, which may comprise at least one component in addition to the specific binding member.

Thus pharmaceutical compositions according to the present invention, and for use in accordance with the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

A composition may be administered alone or in combination with other treatments, therapeutics or agents, either simultaneously or sequentially dependent upon the condition to be treated. In addition, the present invention contemplates and includes compositions comprising the binding member, particularly antibody or fragment thereof, herein described and other agents or therapeutics such as anti-cancer agents or therapeutics, hormones, anti-EGFR agents or antibodies, or immune modulators. More generally these anti-cancer agents may be tyrosine kinase inhibitors or phosphorylation cascade inhibitors, post-translational modulators, cell growth or division inhibitors (e.g. anti-mitotics), or signal transduction inhibitors. Other treatments or therapeutics may include the administration of suitable doses of pain relief drugs such as non-steroidal anti-inflammatory drugs (e.g., aspirin, paracetamol, ibuprofen or ketoprofen) or opiates such as morphine, or anti-emetics. The composition can be administered in combination (either sequentially (i.e. before or after) or simultaneously) with tyrosine kinase inhibitors (including, but not limited to AG1478 and ZD1839, STI571, OSI-774, SU-6668), doxorubicin, temozolomide, cisplatin, carboplatin, nitrosoureas, procarbazine, vincristine, hydroxyurea, 5-fluoruracil, cytosine arabinoside, cyclophosphamide, epipodophyllotoxin, carmustine, lomustine, and/or other chemotherapeutic agents. Thus, these agents may be anti-EGFR specific agents, or tyrosine kinase inhibitors such as AG1478, ZD1839, STI571, OSI-774, or SU-6668 or may be more general anti-cancer and anti-neoplastic agents such as doxorubicin, cisplatin, temozolomide, nitrosoureas, procarbazine, vincristine, hydroxyurea, 5-fluoruracil, cytosine arabinoside, cyclophosphamide, epipodophyllotoxin, carmustine, or lomustine. In addition, the composition may be administered with hormones such as dexamethasone, immune modulators, such as interleukins, tumor necrosis factor (TNF) or other growth factors or cytokines which stimulate the immune response and reduction or elimination of cancer cells or tumors.

An immune modulator such as TNF may be combined together with a member of the invention in the form of a bispecific antibody recognizing the EGFR epitope recognized by the inventive antibodies, as well as binding to TNF receptors. The composition may also be administered with, or may include combinations along with other anti-EGFR antibodies, including but not limited to the anti-EGFR antibodies 528, 225, SC-03, DR8.3, L8A4, Y10, ICR62 and ABX-EGF.

Previously the use of agents such as doxorubicin and cisplatin in conjunction with anti-EGFR antibodies have produced enhanced anti-tumor activity (Fan et al, 1993; Baselga et al, 1993). The combination of doxorubicin and mAb 528 resulted in total eradication of established A431 xenografts, whereas treatment with either agent alone caused only temporary in vivo growth inhibition (Baselga et al, 1993). Likewise, the combination of cisplatin and either mAb528 or 225 also led to the eradication of well established A431 xenografts, which was not observed when treatment with either agent was used (Fan et al, 1993).

Conventional Radiotherapy

In addition, the present invention contemplates and includes therapeutic compositions for the use of the binding member in combination with conventional radiotherapy. It has been indicated that treatment with antibodies targeting EGF receptors can enhance the effects of conventional radiotherapy (Milas et al., *Clin. Cancer Res.* 2000 February: 6 (2):701, Huang et al., *Clin. Cancer Res.* 2000 June: 6 (6): 2166).

As demonstrated herein, combinations of the binding member of the present invention, particularly an antibody or fragment thereof, preferably the mAb806, ch806, mAb175, mAb124, mAb1133 or hu806 or a fragment thereof, and anti-cancer therapeutics, particularly anti-EGFR therapeutics, including other anti-EGFR antibodies, demonstrate effective therapy, and particularly synergy, against xenografted tumors. In the Examples, it is demonstrated, for example, that the combination of AG1478 and mAb806 results in significantly enhanced reduction of A431 xenograft tumor volume in comparison with treatment with either agent alone. AG1478 (4-(3-chloroanilino)-6,7-dimethoxyquinazoline) is a potent and selective inhibitor of the EGF receptor kinase and is particularly described in U.S. Pat. No. 5,457,105, incorporated by reference herein in its entirety (see also, Liu, W. et al (1999) *J. Cell Sci.* 112:2409; Eguchi, S. et al. (1998) *J. Biol. Chem.* 273:8890; Levitsky, A. and Gazit, A. (1995) *Science* 267:1782). The Specification Examples further demonstrate therapeutic synergy of antibodies of the present invention with other anti-EGFR antibodies, particularly with the 528 anti-EGFR antibody.

The present invention further contemplates therapeutic compositions useful in practicing the therapeutic methods of this invention. A subject therapeutic composition includes, in admixture, a pharmaceutically acceptable excipient (carrier) and one or more of a specific binding member, polypeptide analog thereof or fragment thereof, as described herein as an active ingredient. In a preferred embodiment, the composition comprises an antigen capable of modulating the specific binding of the present binding member/antibody with a target cell.

The preparation of therapeutic compositions which contain polypeptides, analogs or active fragments as active ingredients is well understood in the art. Typically, such compositions are prepared as injectables, either as liquid solutions or suspensions. However, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of EFGR binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

Diagnostic Assays

The present invention also relates to a variety of diagnostic applications, including methods for detecting the presence of stimuli such as aberrantly expressed EGFR, by reference to their ability to be recognized by the present specific binding member. As mentioned earlier, the EGFR can be used to produce antibodies to itself by a variety of known techniques, and such antibodies could then be isolated and utilized as in tests for the presence of particular EGFR activity in suspect target cells.

Diagnostic applications of the specific binding members of the present invention, particularly antibodies and fragments thereof, include in vitro and in vivo applications well known and standard to the skilled artisan and based on the present description. Diagnostic assays and kits for in vitro assessment and evaluation of EGFR status, particularly with regard to aberrant expression of EGFR, may be utilized to diagnose, evaluate and monitor patient samples including those known to have or suspected of having cancer, a precancerous condition, a condition related to hyperproliferative cell growth or from a tumor sample. The assessment and evaluation of EGFR status is also useful in determining the suitability of a patient for a clinical trial of a drug or for the administration of a particular chemotherapeutic agent or specific binding member, particularly an antibody, of the present invention, including combinations thereof, versus a different agent or binding member. This type of diagnostic monitoring and assessment is already in practice utilizing antibodies against the HER2 protein in breast cancer (Hercep Test, Dako Corporation), where the assay is also used to evaluate patients for antibody therapy using Herceptin. In vivo applications include imaging of tumors or assessing cancer status of individuals, including radioimaging.

As suggested previously, the diagnostic method of the present invention comprises examining a cellular sample or medium by means of an assay including an effective amount of an antagonist to an EFGR/protein, such as an anti-EFGR antibody, preferably an affinity-purified polyclonal antibody, and more preferably a mAb. In addition, it is preferable for the anti-EFGR antibody molecules used herein be in the form of Fab, Fab', F (ab')$_2$ or F (v) portions or whole antibody molecules. As previously discussed, patients capable of benefiting from this method include those suffering from cancer, a pre-cancerous lesion, a viral infection, pathologies involving or resulting from hyperproliferative cell growth or other like pathological derangement. Methods for isolating EFGR and inducing anti-EFGR antibodies and for determining and optimizing the ability of anti-EFGR antibodies to assist in the examination of the target cells are all well-known in the art.

Preferably, the anti-EFGR antibody used in the diagnostic methods of this invention is an affinity purified polyclonal antibody. More preferably, the antibody is a monoclonal antibody (mAb). In addition, the anti-EFGR antibody molecules used herein can be in the form of Fab, Fab', F (ab')$_2$ or F (v) portions of whole antibody molecules.

As described in detail above, antibody (ies) to the EGFR can be produced and isolated by standard methods including the well known hybridoma techniques. For convenience, the antibody (ies) to the EGFR will be referred to herein as $Ab_1$ and antibody (ies) raised in another species as $Ab_2$.

The presence of EGFR in cells can be ascertained by the usual in vitro or in vivo immunological procedures applicable to such determinations. A number of useful procedures are known. Three such procedures which are especially useful utilize either the EGFR labeled with a detectable label, antibody Ab, labeled with a detectable label, or antibody Ab2 labeled with a detectable label. The procedures may be summarized by the following equations wherein the asterisk indicates that the particle is labeled, and "R" stands for the EGFR:

$$R^* + Ab_1 = R^*Ab_1, \quad \text{A.}$$

$$R + Ab^* = RAb_1^* \quad \text{B.}$$

$$R + Ab_1 + Ab_2^* = RAb_1Ab_2^* \quad \text{C.}$$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody," or "DASP" procedure.

In each instance above, the EGFR forms complexes with one or more antibody (ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-EGFR antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red®, AMCA™ blue and Lucifer Yellow. A particular detecting material is anti-rabbit antibody prepared in goats and conjugated with fluorescein through an isothiocyanate.

The EGFR or its binding partner (s) such as the present specific binding member, can also be labeled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{121}$I, $^{124}$I, $^{125}$I, $^{131}$I, $^{111}$In, $^{211}$At, $^{198}$Au, $^{67}$Cu $^{225}$Ac, $^{213}$Bi, $^{99}$Tc and $^{186}$Re.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654, 090; 3,850,752; and 4,016,043 are referred to by way of example for their disclosure of alternate labeling material and methods.

A particular assay system that may be advantageously utilized in accordance with the present invention, is known as a receptor assay. In a receptor assay, the material to be assayed such as the specific binding member, is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the specific binding member may be radiolabeled and combined, for example, with antibodies or other inhibitors thereto, after which binding studies would be carried out. Solutions would then be prepared that contain various quantities of labeled and unlabeled uncombined specific binding member, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

An assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

In a further embodiment of this invention, commercial test kits suitable for use by a medical specialist may be prepared to determine the presence or absence of aberrant expression of EGFR, including but not limited to amplified EGFR and/or an EGFR mutation, in suspected target cells. In accordance with the testing techniques discussed above, one class of such kits will contain at least the labeled EGFR or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence or capability of cells for aberrant expression or post-translational modification of EGFR, comprising:

(a) a predetermined amount of at least one labeled immunochemically reactive component obtained by the direct or indirect attachment of the present specific binding member or a specific binding partner thereto, to a detectable label;

(b) other reagents; and (c) directions for use of said kit.

More specifically, the diagnostic test kit may comprise:

(a) a known amount of the specific binding member as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g., "competitive," "sandwich," "double antibody," etc.), and comprises:

(a) a labeled component which has been obtained by coupling the specific binding member to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component (s) to be determined; and (iv) a ligand capable of binding with at least one of the binding partners of at least one of the component (s) to be determined; and (c) directions for the performance of a protocol for the detection and/or determination of one or more components of an immunochemical reaction between the EFGR, the specific binding member, and a specific binding partner thereto.

In accordance with the above, an assay system for screening potential drugs effective to modulate the activity of the EFGR, the aberrant expression or post-translational modification of the EGFR, and/or the activity or binding of the specific binding member may be prepared. The receptor or the binding member may be introduced into a test system, and the prospective drug may also be introduced into the resulting cell culture, and the culture thereafter examined to observe any changes in the S-phase activity of the cells, due either to the addition of the prospective drug alone, or due to the effect of added quantities of the known agent (s).

Nucleic Acids

The present invention further provides an isolated nucleic acid encoding a specific binding member of the present invention. Nucleic acid includes DNA and RNA. In a preferred aspect, the present invention provides a nucleic acid which codes for a polypeptide of the invention as defined above, including a polypeptide as set out as the CDR residues of the VH and VL chains of the inventive antibodies.

The present invention also provides constructs in the form of plasmids, vectors, transcription or expression cassettes which comprise at least one polynucleotide as above.

The present invention also provides a recombinant host cell which comprises one or more constructs as above. A nucleic acid encoding any specific binding member as provided itself forms an aspect of the present invention, as does a method of production of the specific binding member which method comprises expression from encoding nucleic acid therefor. Expression may conveniently be achieved by culturing under appropriate conditions recombinant host cells containing the nucleic acid. Following production by expression a specific binding member may be isolated and/or purified using any suitable technique, then used as appropriate.

Specific binding members and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is *E. coli*.

The expression of antibodies and antibody fragments in prokaryotic cells such as *E. coli* is well established in the art. For a review, see for example Pluckthun, A. *Bio/Technology* 9:545-551 (1991). Expression in eukaryotic cells in culture is also available to those skilled in the art as an option for production of a specific binding member, see for recent reviews, for example Raff, M. E. (1993) *Curr. Opinion Biotech.* 4:573-576; Trill J. J. et al. (1995) *Curr. Opinion Biotech* 6:553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

The present invention also provides a method which comprises using a construct as stated above in an expression system in order to express a specific binding member or polypeptide as above.

As stated above, the present invention also relates to a recombinant DNA molecule or cloned gene, or a degenerate variant thereof, which encodes a specific binding member, particularly antibody or a fragment thereof, that possesses an amino acid sequence set forth in SEQ ID NOS:2 and 4; 129 and 134; 22 and 27; 32 and 37; and/or 42 and 47, preferably a nucleic acid molecule, in particular a recombinant DNA molecule or cloned gene, encoding the binding member or antibody has a nucleotide sequence or is complementary to a DNA sequence encoding one of such sequences.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMB9 and their derivatives, plasmids such as RP4; phage DNAs, e.g., the numerous derivatives of phage X, e.g., NM989, and other phage DNA, e.g., M13 and filamentous single stranded phage DNA; yeast plasmids such as the 2u plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage $\lambda$, the control regions of fd coat protein, the promoter for 3-phosphoglycerate kinase or other glycolytic enzymes, the promoters of acid phosphatase (e.g., Pho5), the promoters of the yeast-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, YB/20, NSO, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that specific binding member analogs may be prepared from nucleotide sequences of the protein complex/subunit derived within the scope of the present invention. Analogs, such as fragments, may be produced, for example, by pepsin digestion of specific binding member material. Other analogs, such as muteins, can be produced by standard site-directed mutagenesis of specific binding member coding sequences. Analogs exhibiting "specific binding member activity" such as small molecules, whether functioning as promoters or inhibitors, may be identified by known in vivo and/or in vitro assays.

As mentioned above, a DNA sequence encoding a specific binding member can be prepared synthetically rather than cloned. The DNA sequence can be designed with the appropriate codons for the specific binding member amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature*, 292:756 (1981); Nambair et al., *Science*, 223:1299 (1984); Jay et al., *J. Biol. Chem.*, 259:6311 (1984).

Synthetic DNA sequences allow convenient construction of genes which will express specific binding member analogs or "muteins". Alternatively, DNA encoding muteins can be made by site-directed mutagenesis of native specific binding member genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science*, 244:182-188 (April 1989). This method may be used to create analogs with unnatural amino acids.

The present invention extends to the preparation of antisense oligonucleotides and ribozymes that may be used to interfere with the expression of the EGFR at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule (See Weintraub, 1990; Marcus-Sekura, 1988.). In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only mRNAs with particular sequences are inactivated.

Investigators have identified two types of ribozymes, Tetrahymena-type and "hammerhead"-type (Hasselhoff and Gerlach, 1988). Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs for EFGRs and their ligands.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

Generation and Isolation of Antibodies

Cell Lines

For immunization and specificity analyses, several cell lines, native or transfected with either the normal, wild-type or "wtEGFR" gene or the ΔEGFR gene carrying the Δ2-7 deletion mutation were used: Murine fibroblast cell line NR6, NR6$_{\Delta EGFR}$ (transfected with ΔEGFR) and NR6$_{wtEGFR}$ (transfected with wtEGFR), human glioblastoma cell line U87MG (expressing low levels of endogenous wtEGFR), U87MG$_{wtEGFR}$ (transfected with wtEGFR), U87MG$_{\Delta EGFR}$ (transfected with ΔEGFR), and human squamous cell carcinoma cell line A431 (expressing high levels of wtEGFR).

For immunization and specificity analyses, several cell lines, native or transfected with either the normal, wild-type or "wtEGFR" gene or the ΔEGFR gene carrying the de2-7 or Δ2-7 deletion mutation were used: Murine fibroblast cell line NR6, NR6$_{\Delta EGFR}$ (transfected with ΔEGFR) and NR6$_{wtEGFR}$ (transfected with wtEGFR), human glioblastoma cell line U87MG (expressing low levels of endogenous wtEGFR), U87MG$_{wtEGFR}$ or "U87MG.wtEGFR" (transfected with wtEGFR), U87MG$_{\Delta EGFR}$ or "U87MG.Δ2-7" (transfected with ΔEGFR), and human squamous cell carcinoma cell line A431 (expressing high levels of wtEGFR). The NR6, NR6$_{\Delta EGFR}$, and NR6$_{wtEGFR}$ cell lines were previously described (Batra et al. (1995) Epidermal Growth Factor Ligand-independent, Unregulated, Cell-Transforming Potential of a Naturally Occurring Human Mutant EGFRvIII Gene. *Cell Growth Differ.* 6(10): 1251-1259). The NR6 cell line lacks normal endogenous EGFR. (Batra et al., 1995). U87MG cell lines and transfections were described previously (Nishikawa et al. (1994) A mutant epidermal growth factor receptor common in human glioma confers enhanced tumorigenicity. *Proc. Natl. Acad. Sci. U.S.A.* 91, 7727-7731).

The U87MG astrocytoma cell line (Ponten, J. and Macintyre, E. H. (1968) Long term culture of normal and neoplastic human glia. *Acta. Pathol. Microbiol. Scand.* 74, 465-86) which endogenously expresses low levels of the wtEGFR, was infected with a retrovirus containing the de2-7 EGFR to produce the U87MG.Δ2-7 cell line (Nishikawa et al., 1994). The transfected cell line U87MG.wtEGFR was produced as described in Nagane et al. (1996) *Cancer Res.* 56, 5079-5086. Whereas U87MG cells express approximately 1×10⁵ EGFR, U87MG.wtEGFR cells express approximately 1×10⁶ EGFR, and thus mimic the situation seen with gene amplification. The murine pro-B cell line BaF/3, which does not express any known EGFR related molecules, was also transfected with de2-7 EGFR. resulting in the BaF/3. Δ2-7 cell line (Luwor et al. (2004) The tumor-specific de2-7 epidermal growth factor receptor (EGFR) promotes cells survival and heterodimerizes with the wild-type EGFR, *Oncogene* 23: 6095-6104). Human squamous carcinoma A431 cells were obtained from ATCC (Rockville, Md.). The epidermoid carcinoma cell line A431 has been described previously (Sato et al. (1987) Derivation and assay of biological effects of monoclonal antibodies to epidermal growth factor receptors. *Methods Enzymol.* 146, 63-81).

All cell lines were cultured in DMEM/F-12 with GlutaMAX™ (Life Technologies, Inc., Melbourne, Australia and Grand Island, N.Y.) supplemented with 10% FCS (CSL, Melbourne, Australia); 2 mM glutamine (Sigma Chemical Co., St. Louis, Mo.), and penicillin/streptomycin (Life Technologies, Inc., Grand Island, N.Y.). In addition, the U87MG.Δ2-7 and U87MG.wtEGFR cell lines were maintained in 400 mg/ml of Geneticin® (Life Technologies, Inc., Melbourne, Victoria, Australia). Cell lines were grown at 37° C. in a unmodified atmosphere of 5% $CO_2$.

Reagents

The de2-7 EGFR unique junctional peptide has the amino acid sequence: LEEKKGNYVVTDH (SEQ ID NO:13). Biotinylated unique junctional peptides (Biotin-LEEKKGNYVVTDH (SEQ ID NO:5) and LEEKKGNYV-VTDH-Biotin (SEQ ID NO:6)) from de2-7 EGFR were synthesized by standard Fmoc chemistry and purity (>96%) determined by reverse phase HPLC and mass spectral analysis (Auspep, Melbourne, Australia).

Antibodies Used in Studies

In order to compare our findings with other reagents, additional mAbs were included in our studies. These reagents were mAb528 to the wtEGFR (Sato et al. (1983) *Mol. Biol. Med.* 1(5), 511-529) and DH8.3, which was generated against a synthetic peptide spanning the junctional sequence of the Δ2-7 EGFR deletion mutation. The DH8.3 antibody (IgG1), which is specific for the de2-7 EGFR, has been described previously (Hills et al. (1995) Specific targeting of a mutant, activated EGF receptor found in glioblastoma using a monoclonal antibody. *Int. J. Cancer.* 63, 537-43, 1995) and was obtained following immunization of mice with the unique junctional peptide found in de2-7 EGFR (Hills et al., 1995).

The 528 antibody, which recognizes both de2-7 and wild-type EGFR, has been described previously (Masui et al. (1984) Growth inhibition of human tumor cells in athymic mice by anti-epidermal growth factor receptor monoclonal antibodies. *Cancer Res.* 44, 1002-7) and was produced in the Biological Production Facility, Ludwig Institute for Cancer Research (Melbourne, Australia) using a hybridoma (ATCC HB-8509) obtained from the American Type Culture Collection (Rockville, Md.). The polyclonal antibody SC-03 is an affinity purified rabbit polyclonal antibody raised against a carboxy terminal peptide of the EGFR (Santa Cruz Biotechnology Inc.).

Antibody Generation

The murine fibroblast line $NR6_{\Delta EGFR}$ was used as immunogen. Mouse hybridomas were generated by immunizing BALB/c mice five times subcutaneously at 2- to 3-week intervals, with $5 \times 10^5$-$2 \times 10^6$ cells in adjuvant. Complete Freund's adjuvant was used for the first injection. Thereafter, incomplete Freund's adjuvant (Difco™, Voigt Global Distribution, Lawrence, Kans.) was used. Spleen cells from immunized mice were fused with mouse myeloma cell line SP2/0 (Shulman et al. (1978) Nature 276:269-270). Supernatants of newly generated clones were screened in hemadsorption assays for reactivity with cell line NR6, $NR6_{wtEGFR}$, and $NR6_{\Delta EGFR}$ and then analyzed by hemadsorption assays with human glioblastoma cell lines U87MG, $U87MG_{wtEGFR}$, and $U87_{\Delta EGFR}$. Selected hybridoma supernatants were subsequently tested by western blotting and further analyzed by immunohistochemistry. Newly generated mAbs showing the expected reactivity pattern were purified.

Five hybridomas were established and three clones, 124 (IgG2a), 806 (IgG2b), and 1133 (IgG2a) were initially selected for further characterization based on high titer (1:2500) with $NR6_{\Delta EGFR}$ and low background on NR6 and $NR6_{wtEGFR}$ cells in the rosette hemagglutination assay. A fourth clone, 175 (IgG2a) was subsequently further characterized and is discussed separately in Example 23, below. In a subsequent hemagglutination analysis, these antibodies showed no reactivity (undiluted supernatant≤10%) with the native human glioblastoma cell line U87MG and $U87MG_{wtEGFR}$, but were strongly reactive with $U87MG_{\Delta EGFR}$; less reactivity was seen with A431. By contrast, in FACS analysis, 806 was unreactive with native U87MG and intensively stained $U87MG_{\Delta EGFR}$ and to a lesser degree $U87MG_{wtEGFR}$ indicating binding of 806 to both, ΔEGFR and wtEGFR (see below).

In Western blot assays, mAb124, mAb806 and mAb1133 were then analyzed for reactivity with wtEGFR and ΔEGFR. Detergent lysates were extracted from $NR6_{\Delta EGFR}$, $U87MG_{\Delta EGFR}$ as well as from A431. All three mAbs showed a similar reactivity pattern with cell lysates staining both the wtEGFR (170 kDa) and ΔEGFR protein (140 kDa). As a reference reagent, mAbR.I. known to be reactive with the wtEGFR (Waterfield et al. (1982) *J. Cell Biochem.* 20(2), 149-161) was used instead of mAb528, which is known to be non-reactive in western blot analysis. mAbR.I. showed reactivity with wild-type and ΔEGFR. All three newly generated clones showed reactivity with ΔEGFR and less intense with wtEGFR. DH8.3 was solely positive in the lysate of $U87MG_{\Delta EGFR}$ and $NR6_{\Delta EGFR}$.

The immunohistochemical analysis of clones 124, 806, and 1133 as well as mAb528 and mAbDH8.3 on xenograft tumors U87MG, $U87MG_{\Delta EGFR}$, and A431 are shown in Table 1. All mAbs showed strong staining of xenograft $U87MG_{\Delta EGFR}$. Only mAb528 showed weak reactivity in the native U87MG xenograft. In A431 xenografts, mAb528 showed strong homogeneous reactivity. mAb124, mAb806, and mAb1133 revealed reactivity with mostly the basally located cells of the squamous cell carcinoma of A431 and did not react with the upper cell layers or the keratinizing component. DH8.3 was negative in A431 xenografts.

TABLE 1

Immunohistochemical Analysis of Antibodies 528, DH8.3, and 124, 806 and 1133

| Antibody | xenograft ΔU87MG$_{\Delta EGFR}$ | xenograft A431 | xenograft U87MG (native) |
|---|---|---|---|
| mAb528 | pos. | pos. | pos. (focal staining) |
| mAb124 | pos. | pos. (predominantly basal cells) | — |
| mAb806 | pos. | pos. (predominantly basal cells) | — |
| mAb1133 | pos. | pos. (predominantly basal cells) | — |
| DH8.3 | pos. | — | — | minor stromal staining due to detection of endogenous mouse antibodies.

Sequencing

The variable heavy (VH) and variable light (VL) chains of mAb806, mAb124 and mAb1133 were sequenced, and their complementarity determining regions (CDRs) identified, as follows:

mAb806 mAb806 VH chain: nucleic acid sequence (SEQ ID NO:1) and amino acid sequence, with signal peptide (SEQ ID NO:2) are shown in FIGS. 14A and 14B, respectively (signal peptide underlined in FIG. 14B). Complementarity determining regions CDR1, CDR2, and CDR3 (SEQ ID NOS: 15, 16, and 17, respectively) are indicated by underlining in FIG. 16. The mAb806 VH chain amino acid sequence without its signal peptide (SEQ ID NO:11) is shown in FIG. 16.

mAb806 VL chain: nucleic acid sequence (SEQ ID NO:3) and amino acid sequence, with signal peptide (SEQ ID NO:4) are shown in FIGS. 15A and 15B, respectively (signal peptide underlined in FIG. 15B). Complementarity determining regions CDR1, CDR2, and CDR3 (SEQ ID NOS: 18, 19, and 20, respectively) are indicated by underlining in FIG. 17. The mAb806 VL chain amino acid sequence without its signal peptide (SEQ ID NO:12) is shown in FIG. 17.

mAb 124 mAb124 VH chain: nucleic acid (SEQ ID NO:21) and amino acid (SEQ ID NO:22) sequences are shown in FIGS. 51A and 51B, respectively. Complementarity determining regions CDR1, CDR2, and CDR3 (SEQ ID NOS: 23, 24, and 25, respectively) are indicated by underlining.

mAb124 VL chain: nucleic acid (SEQ ID NO:26) and amino acid (SEQ ID NO:27) sequences are shown in FIGS. 51C and 51D, respectively. Complementarity determining regions CDR1, CDR2, and CDR3 (SEQ ID NOS: 28, 29, and 30, respectively) are indicated by underlining.

mAb1133 mAb1113 VH chain: nucleic acid (SEQ ID NO:31) and amino acid (SEQ ID NO:32) sequences are shown in FIGS. 52A and 52B, respectively. Complementarity determining regions CDR1, CDR2, and CDR3 (SEQ ID NOS: 33, 34, and 35, respectively) are indicated by underlining.

mAb1133 VL chain: nucleic acid (SEQ ID NO:36) and amino acid (SEQ ID NO:37) sequences are shown in FIGS. 52C and 52D, respectively. Complementarity determining regions CDR1, CDR2, and CDR3 (SEQ ID NOS: 38, 39, and 40, respectively) are indicated by underlining.

Example 2

Binding of Antibodies to Cell Lines by FACS mAb806 was initially selected for further characterization, as set forth herein and in the following Examples. mAb124 and mAb1133 were also selected for further characterization, as discussed in Example 26 below, and found to have properties corresponding to the unique properties of mAb806 discussed herein.

In order to determine the specificity of mAb806, its binding to U87MG, U87MG.Δ2-7 and U87MG.wtEGFR cells was analyzed by flow activated cell sorting (FACS). Briefly, cells were labelled with the relevant antibody (10 µg/ml) followed by fluorescein-conjugated goat anti-mouse IgG (1:100 dilution; Calbiochem San Diego, Calif., USA; Becton-Dickinson PharMingen, San Diego, Calif., US) as described previously (Nishikawa et al., 1994). FACS data was obtained on a Coulter Epics Elite ESP by observing a minimum of 5,000 events and analyzed using EXPO (version 2) for Windows. An irrelevant IgG2b was included as an isotype control for mAb806 and the 528 antibody was included as it recognizes both the de2-7 and wtEGFR.

Figure 1:
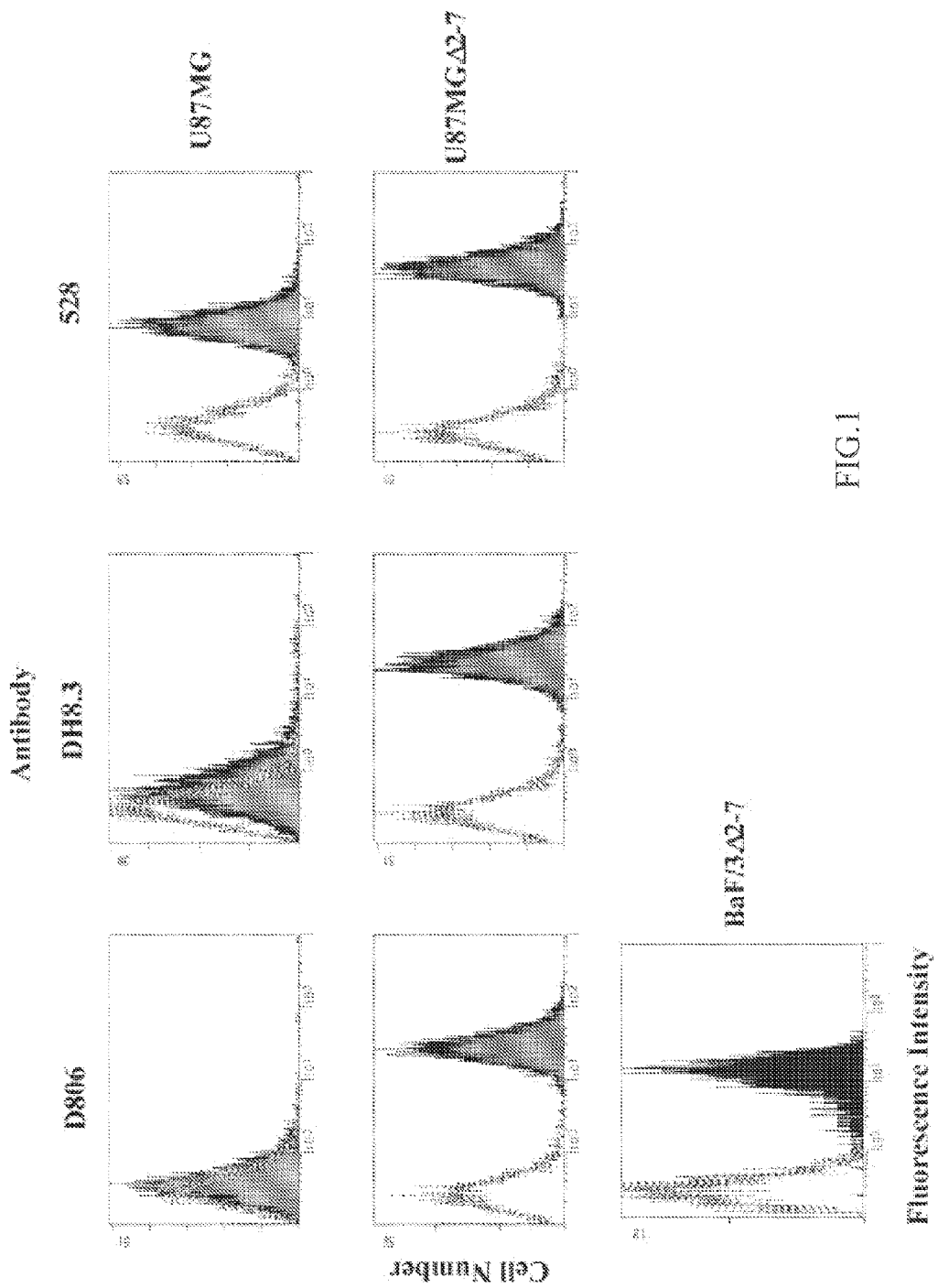
FIG. 1 presents the results of flow cytometric analysis of glioma cell lines. U87MG (light gray histograms) and U87MG.Δ2-7 (dark gray histograms) cells were stained with either an irrelevant IgG2b antibody (open histograms), DH8.3 (specific for de2-7 EGFR), mAb806 or 528 (binds both wild type and de2-7 EGFR) as indicated.

Only the 528 antibody was able to stain the parental U87MG cell line (FIG. 1) consistent with previous reports demonstrating that these cells express the wtEGFR (Nishikawa et al, 1994). mAb806 and DH8.3 had binding levels similar to the control antibody, clearly demonstrating that they are unable to bind the wild-type receptor (FIG. 1). Binding of the isotype control antibody to U87MG.Δ2-7 and U87MG.wtEGFR cells was similar as that observed for the U87MG cells.

mAb806 stained U87MG.Δ2-7 and U87MG.wtEGFR cells, indicating that mAb806 specifically recognizes the de2-7 EGFR and amplified EGFR (FIG. 1). DH8.3 antibody stained U87MG.Δ2-7 cells, confirming that DH8.3 antibody specifically recognizes the de2-7 EGFR (FIG. 1). As expected, the 528 antibody stained both the U87MG.Δ2-7 and U87MG.wtEGFR cell lines (FIG. 1). As expected, the 528 antibody stained U87MG.Δ2-7 with a higher intensity than the parental cell as it binds both the de2-7 and wild-type receptors that are co-expressed in these cells (FIG. 1). Similar results were obtained using a protein A mixed hemadsorption which detects surface bound IgG by appearance of Protein A coated with human red blood cells (group O) to target cells. Monoclonal antibody 806 was reactive with U87MG.Δ2-7 cells but showed no significant reactivity (undiluted supernatant less than 10%) with U87MG expressing wild-type EGFR. Importantly, mAb806 also bound the BaF/3.Δ2-7 cell line, demonstrating that the co-expression of wtEGFR is not a requirement for mAb806 reactivity (FIG. 1).

Example 3

Binding of Antibodies in Assays

To further characterize the specificity of mAb806 and the DH8.3 antibody, their binding was examined by ELISA. Two types of ELISA were used to determine the specificity of the antibodies. In the first assay, plates were coated with sEGFR (10 µg/ml in 0.1 M carbonate buffer pH 9.2) for 2 h and then blocked with 2% human serum albumin (HSA) in PBS. sEGFR is the recombinant extracellular domain (amino acids 1-621) of the wild-type EGFR), and was produced as previously described (Domagala et al. (2000) Stoichiometry, kinetic and binding analysis of the interaction between Epidermal Growth Factor (EGF) and the Extracellular Domain of the EGF receptor. *Growth Factors*. 18, 11-29). Antibodies were added to wells in triplicate at increasing concentration in 2% HSA in phosphate-buffered saline (PBS). Bound antibody was detected by horseradish peroxidase conjugated sheep anti-mouse IgG (Silenus, Melbourne, Australia) using ABTS (Sigma, Sydney, Australia) as a substrate and the absorbance measured at 405 nm.

Figure 2A:
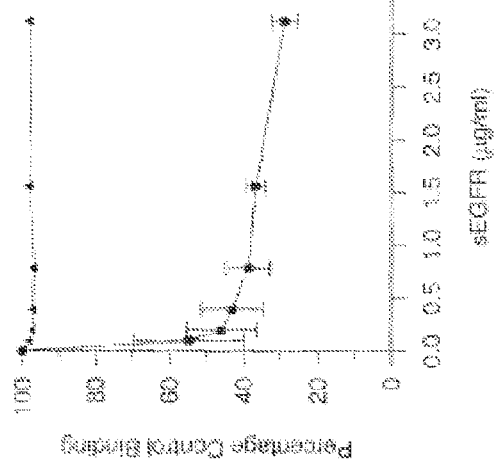
FIGS. 2A-D present the results of ELISA of mAb806, mAbDH8.3 and mAb528. (A) binding of increasing concentrations of mAb806 (▲) DH8.3 (●) or 528 (■) antibody to sEGFR coated ELISA plates. (B) inhibition of mAb806 and mAb528 binding to sEGFR coated ELISA plates by increasing concentrations of soluble EGFR (sEGFR) in solution. (C) binding of increasing concentrations of DH8.3 to the de2-7 junctional peptide illustrates binding curves for mAb806 and mAb528 to immobilized wild-type sEGFR (D).
Figure 2B:
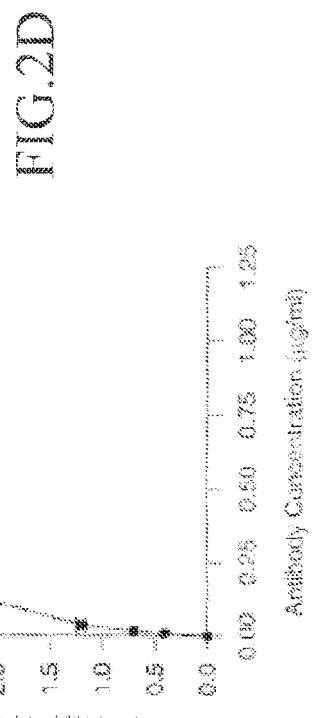
Figure 2C:
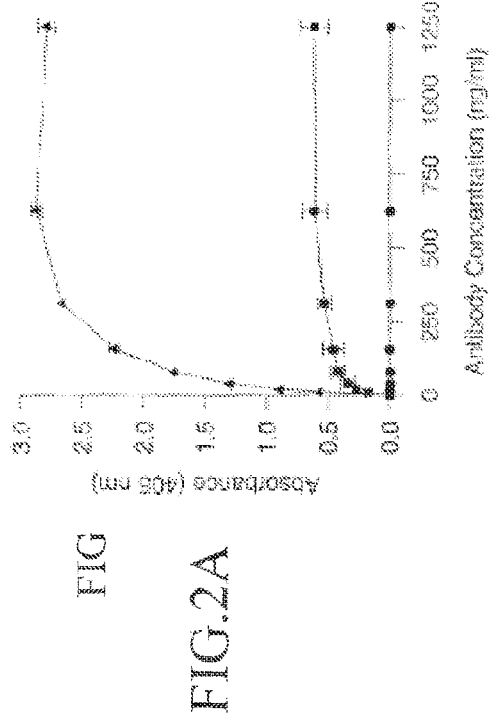

Both mAb806 and the 528 antibody displayed dose-dependent and saturating binding curves to immobilized wild-type sEGFR (FIG. 2A). As the unique junctional peptide found in the de2-7 EGFR is not contained within the sEGFR, mAb806 must be binding to an epitope located within the wild-type EGFR sequence. The binding of the 528 antibody was lower than that observed for mAb806, probably because it recognizes a conformational determinant. As expected, the DH8.3 antibody did not bind the wild-type sEGFR even at concentrations up to 10 µg/ml (FIG. 2A). Although sEGFR in solution inhibited the binding of the 528 antibody to immobilized sEGFR in a dose-dependent fashion, it was unable to inhibit the binding of mAb806 (FIG. 2B). This suggests that mAb806 can only bind wild-type EGFR once immobilized on ELISA plates, a process that may induce conformational changes. Similar results were observed using a BIAcore™ whereby mAb806 bound immobilized sEGFR but immobilized mAb806 was not able to bind sEGFR in solution (FIG. 2C).

Figure 2D:
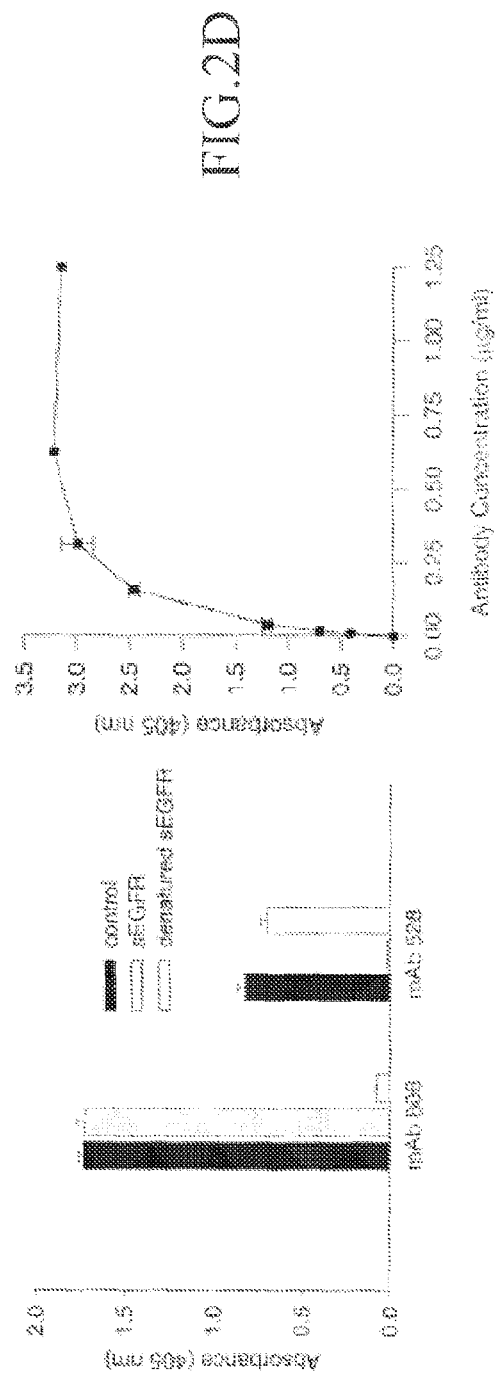

Following denaturation by heating for 10 min at 95° C., sEGFR in solution was able to inhibit the binding of mAb806 to immobilized sEGFR (FIG. 2C), confirming that mAb806 can bind the wild-type EGFR under certain conditions. Interestingly, the denatured sEGFR was unable to inhibit the binding of the 528 antibody (FIG. 2C), demonstrating that this antibody recognizes a conformational epitope. The DH8.3 antibody exhibited dose-dependent and saturable binding to the unique de2-7 EGFR peptide (FIG. 2D). Neither mAb806 or the 528 antibody bound to the peptide, even at concentrations higher than those used to obtain saturation binding of DH8.3, further indicating mAb806 does not recognize an epitope determinant within this peptide.

In the second assay, the biotinylated de2-7 specific peptide (Biotin LEEKKGNYVVTDH (SEQ ID NO:5)) was bound to ELISA plates precoated with streptavidin (Pierce, Rockford, Ill.). Antibodies were bound and detected as in the first assay. Neither mAb806 nor the 528 antibody bound to the peptide, even at concentrations higher than those used to obtain saturation binding of DH8.3, further indicating that mAb806 does not recognize an epitope determinant within this peptide.

To further demonstrate that mAb806 recognizes an epitope distinct from the junction peptide, additional experiments were performed. C-terminal biotinylated de2-7 peptide (LEEKKGNYVVTDH-Biotin (SEQ ID NO:6)) was utilized in studies with mAb806 and mAbL8A4, generated against the de2-7 peptide (Reist et al. (1995) Cancer Res. 55(19), 4375-4382; Foulon et al. (2000) Cancer Res. 60(16), 4453-4460).

Reagents Used in Peptide Studies
  Junction Peptide: LEEKKGNYVVTDH-OH (Biosource, Camarillo, Calif.);
  Peptide C: LEEKKGNYVVTDH(K-Biot)-OH (Biosource, Camarillo, Calif.);
  sEGFR: CHO-cell-derived recombinant soluble extracellular domain (amino acids 1-621) of the wild-type EGFR (LICR Melbourne);
  mAb806: mouse monoclonal antibody, IgG$_{2b}$ (LICR NYB);
  mAbL8A4: mouse monoclonal antibody, IgG$_1$ (Duke University);
  IgG$_1$ isotype control mAb;
  IgG$_{2b}$ isotype control mAb.

Figure 2E:
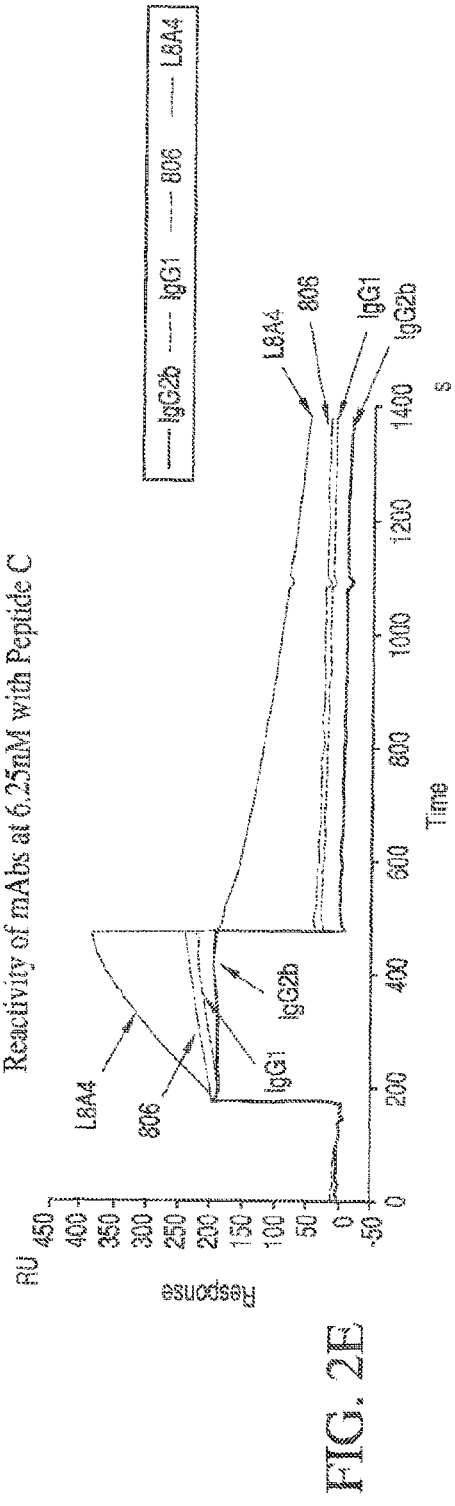
FIGS. 2E and 2F graphically present the results of BIAcore™ binding studies using C-terminal biotinylated peptide and including a monoclonal antibody of the invention, along with other known antibodies, among them the L8A4 antibody which recognizes the junction peptide of the de2-7 EGFR mutant, and controls.
Figure 2F:
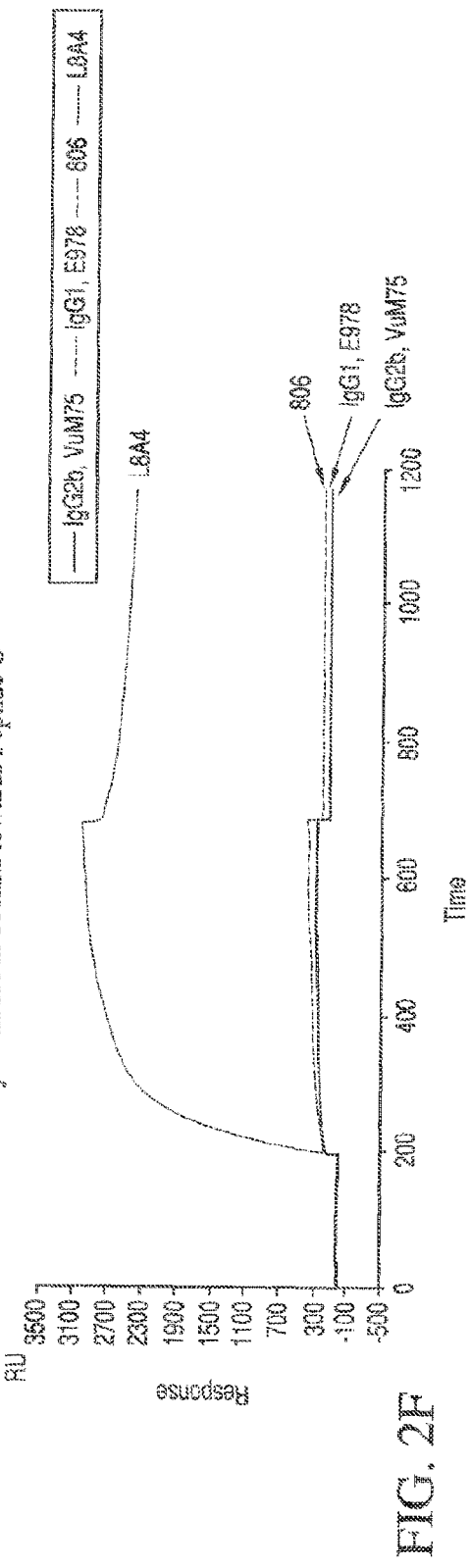

Peptide C was immobilized on a Streptavidin microsensor chip at a surface density of 350RU (+/-30RU). Serial dilutions of mAbs were tested for reactivity with the peptide. Blocking experiments using non-biotinylated peptide were performed to assess specificity.

mAbL8A4 showed strong reactivity with Peptide C even at low antibody concentrations (6.25 nM) (FIG. 2E). mAb806 did not show detectable specific reactivity with Peptide C up to antibody concentrations of 100 nM (highest concentration tested) (FIGS. 2E and 2F). It was expected that mAbL8A4 would react with Peptide C because the peptide was used as the immunogen in the generation of mAbL8A4. Addition of the Junction Peptide (non-biotinylated, 50 µg/ml) completely blocks the reactivity of mAbL8A4 with Peptide C, confirming the antibody's specificity for the junction peptide epitope.

In a second set of BIAcore™ experiments, sEGFR was immobilized on a CM microsensor chip at a surface density of ~4000RU. Serial dilutions of mAbs were tested for reactivity with sEGFR.

mAb806 was strongly reactive with denatured sEGFR while mAbL8A4 did not react with denatured sEGFR. Reactivity of mAb806 with denatured sEGFR decreases with decreasing antibody concentrations. It was expected that mAbL8A4 does not react with sEGFR because mAbL8A4 was generated using the junction peptide as the immunogen and sEGFR does not contain the junction peptide.

Dot-blot immune stain experiments were also performed. Serial dilutions of peptide were spotted in 0.5 µl onto a PVDF or nitrocellulose membranes. Membranes were blocked with 2% BSA in PBS, and then probed with 806, L8A4, DH8.3 and control antibodies. Antibodies L8A4 and DH8.3 bound to peptide on the membranes (data not shown). mAb806 did not bind peptide at concentrations where L8A4 clearly showed binding (data not shown). Control antibodies were also negative for peptide binding.

mAb806 bound to the wtEGFR in cell lysates following immunoblotting (results not shown). This is different from the results obtained with DH8.3 antibody, which reacted with de2-7 EGFR but not wtEGFR. Thus, mAb806 can recognize the wtEGFR following denaturation but not when the receptor is in its natural state on the cell surface.

Example 4

Scatchard Analysis

A Scatchard analysis using U87MG.Δ2-7 cells was performed following correction for immunoreactivity in order to determine the relative affinity of each antibody. Antibodies were labelled with $^{125}$I (Amrad, Melbourne, Australia) by the Chloramine T method and immunoreactivity determined by Lindmo assay (Lindmo et al. (1984) Determination of the immunoreactive fraction of radiolabeled monoclonal antibodies by linear extrapolation to binding at infinite antigen excess. J. Immunol. Methods. 72, 77-89).

All binding assays were performed in 1% HSA/PBS on 1-2×10$^6$ live U87MG.Δ2-7 or A431 cells for 90 min at 4° C. with gentle rotation. A set concentration of 10 ng/ml $^{125}$I-labeled antibody was used in the presence of increasing concentrations of the appropriate unlabeled antibody. Non-specific binding was determined in the presence of 10,000-fold excess of unlabeled antibody. Neither $^{125}$I-radiolabeled mAb806 or the DH8.3 antibody bound to parental U87MG cells. After the incubation was completed, cells were washed and counted for bound $^{125}$I-labeled antibody using a COBRA II gamma counter (Packard Instrument Company, Meriden, Conn., USA).

Both mAb806 and the DH8.3 antibody retained high immunoreactivity when iodinated and was typically greater than 90% for mAb806 and 45-50% for the DH8.3 antibody. mAb806 had an affinity for the de2-7 EGFR receptor of $1.1×10^9$ M$^{-1}$ whereas the affinity of DH8.3 was some 10-fold lower at $1.0×10^8$ M$^{-1}$. Neither iodinated antibody bound to U87MG parental cells. mAb806 recognized an average of $2.4×10^5$ binding sites per cell with the DH8.3 antibody binding an average of $5.2×10^5$ sites. Thus, there was not only good agreement in receptor number between the antibodies, but also with a previous report showing $2.5×10^5$ de2-7 receptors per cell as measured by a different de2-7 EGFR specific antibody on the same cell line (Reist et al. (1997) Improved targeting of an anti-epidermal growth factor receptor variant III monoclonal antibody in tumor xenografts after labeling using N-succinimidyl 5-iodo-3-pyridinecarboxylate. Cancer Res. 57, 1510-5).

Example 5

Internalization of Antibodies by U87MG.Δ2-7 Cells

The rate of antibody internalization following binding to a target cell influences both its tumor targeting properties and therapeutic options. Consequently, the inventors examined the internalization of mAb806 and the DH8.3 antibody following binding to U87MG.Δ2-7 cells by FACS. U87MG.Δ2-7 cells were incubated with either mAb806 or the DH8.3 antibody (10 µg/ml) for 1 h in DMEM at 4° C. After washing, cells were transferred to DMEM pre-warmed to 37° C. and aliquots taken at various time points following incubation at 37° C. Internalization was stopped by immediately washing aliquots in ice-cold wash buffer (1% HSA/PBS). At the completion of the time course cells were stained by FACS as described above. Percentage internalization was calculated by comparing surface antibody staining at various time points to zero time using the formula: percent antibody internalized=(mean fluorescence at $time_x$–background fluorescence)/(mean fluorescence at $time_0$–background fluorescence)×100. This method was validated in one assay using an iodinated antibody (mAb806) to measure internalization as previously described (Huang et al. (1997) The enhanced tumorigenic activity of a mutant epidermal growth factor receptor common in human cancers is mediated by threshold levels of constitutive tyrosine phosphorylation and unattenuated signaling. *J. Biol. Chem.* 272, 2927-35). Differences in internalization rate at different time points were compared using Student's t-test. Throughout this research, data were analyzed for significance by Student's t-test, except for the in vivo survival assays, which were analyzed by Wilcoxon analysis.

Both antibodies showed relatively rapid internalization reaching steady-state levels at 10 min for mAb806 and 30 min for DH8.3 (FIG. 3). Internalization of DH8.3 was significantly higher both in terms of rate (80.5% of DH8.3 internalized at 10 min compared to 36.8% for mAb806, p<0.01) and total amount internalized at 60 min (93.5% versus 30.4%, p<0.001). mAb806 showed slightly lower levels of internalization at 30 and 60 min compared to 20 min in all 4 assays performed (FIG. 3). This result was also confirmed using an internalization assay based on iodinated mAb806 (data not shown).

Example 6

Electron Microscopy Analysis of Antibody Internalization

Given the above noted difference in internalization rates between the antibodies, a detailed analysis of antibody intracellular trafficking was performed using electron microscopy.

U87MG.Δ2-7 cells were grown on gelatin coated chamber slides (Nunc, Naperville, Ill.) to 80% confluence and then washed with ice cold DMEM. Cells were then incubated with mAb806 or the DH8.3 antibody in DMEM for 45 min at 4° C. After washing, cells were incubated for a further 30 min with gold-conjugated (20 nm particles) anti-mouse IgG (BBInternational, Cardiff, UK) at 4° C. Following a further wash, pre-warmed DMEM/10% PCS was added to the cells, which were incubated at 37° C. for various times from 1-60 min. Internalization of the antibody was stopped by ice-cold media and cells fixed with 2.5% glutaraldehyde in PBS/0.1% HSA and then post-fixed in 2.5% osmium tetroxide. After dehydration through a graded series of acetone, samples were embedded in Epon/Araldite resin, cut as ultra-thin sections with a Reichert Ultracut-S microtome (Leica) and collected on nickel grids. The sections were stained with uranyl acetate and lead citrate before being viewed on a Philips CM12 transmission electron microscope at 80 kV. Statistical analysis of gold grains contained within coated pits was performed using a Chi-square test.

While the DH8.3 antibody was internalized predominantly via coated-pits, mAb806 appeared to be internalized by macropinocytosis (FIG. 19). In fact, a detailed analysis of 32 coated pits formed in cells incubated with mAb806 revealed that none of them contained antibody. In contrast, around 20% of all coated-pits from cells incubated with DH8.3 were positive for antibody, with a number containing multiple gold grains. A statistical analysis of the total number of gold grains contained within coated-pits found that the difference was highly significant (p<0.01). After 20-30 min both antibodies could be seen in structures that morphologically resemble lysosomes (FIG. 19C). The presence of cellular debris within these structures was also consistent with their lysosome nature.

Example 7

Biodistribution of Antibodies in Tumor Bearing Nude Mice

The biodistribution of mAb806 and the DH8.3 antibody was compared in nude mice containing U87MG xenografts on one side and U87MG.Δ2-7 xenografts on the other. A relatively short time period was chosen for this study as a previous report demonstrated that the DH8.3 antibody shows peak levels of tumor targeting between 4-24 h (Hills et al. (1995) Specific targeting of a mutant, activated EGF receptor found in glioblastoma using a monoclonal antibody. Int. J. Cancer. 63, 537-43).

Tumor xenografts were established in nude BALB/c mice by s.c. injection of 3×10⁶ U87MG, U87MG.Δ2-7 or A431 cells. de2-7 EGFR expression in U87MG.Δ2-7 xenografts remained stable throughout the period of biodistribution as measured by immunohistochemistry at various time points (data not shown). A431 cells retained their mAb806 reactivity when grown as tumor xenografts as determined by immunohistochemistry. U87MG or A431 cells were injected on one side 7-10 days before U87MG.Δ2-7 cells were injected on the other side because of the faster growth rate observed for de2-7 EGFR expressing xenografts. Antibodies were radiolabeled and assessed for immunoreactivity as described above and were injected into mice by the retro-orbital route when tumors were 100-200 mg in weight. Each mouse received two different antibodies (2 µg per antibody): 2 µCi of $^{125}$I-labeled mAb806 and 2 µCi of $^{131}$I labelled DH8.3 or 528. Unless indicated, groups of 5 mice were sacrificed at various time points post-injection and blood obtained by cardiac puncture. The tumors, liver, spleen, kidneys and lungs were obtained by dissection. All tissues were weighed and assayed for $^{125}$I and $^{131}$I activity using a dual-channel counting Window. Data was expressed for each antibody as % ID/g tumor determined by comparison to injected dose standards or converted into tumor to blood/liver ratios (i.e. % ID/g tumor divided by % ID/g blood or liver). Differences between groups were analyzed by Student's t-test. After injection of radiolabeled mAb806, some tumors were fixed in formalin, embedded in paraffin, cut into 5, µm sections and then exposed to X-ray film (AGFA, Mortsel, Belgium) to determine antibody localization by autoradiography.

Figure 20:
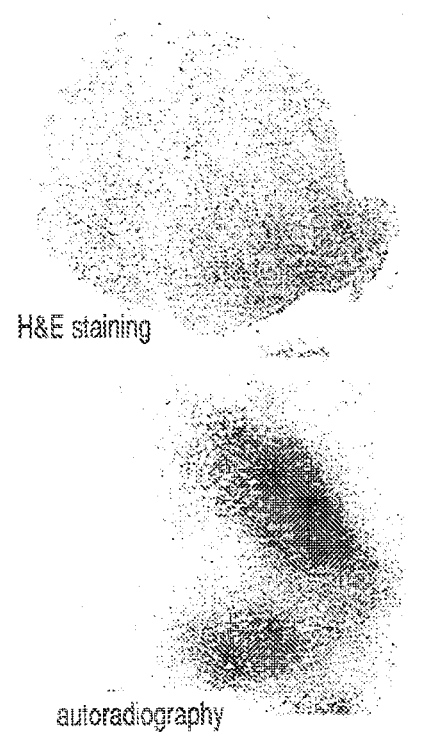
FIG. 20 shows autoradiography of a U87MG.Δ2-7 xenograft section collected 8 hr after injection of $^{125}$I-mAb806.

In terms of % ID/g tumor, mAb806 reached its peak level in U87MG.Δ2-7 xenografts of 18.6% m/g tumor at 8 h (FIG. 4A), considerably higher than any other tissue except blood. While DH8.3 also showed peak tumor levels at 8 h, the level was a statistically (p<0.001) lower 8.8% m/g tumor compared to mAb806 (FIG. 4B). Levels of both antibodies slowly declined at 24 and 48 h. Autoradiography of U87MG.Δ2-7 xenograft tissue sections collected 8 hr after injection with $^{125}$I-labeled mAb806 alone, clearly illustrates localization of antibody to viable tumor (FIG. 20). Neither antibody showed specific targeting of U87MG parental xenografts (FIGS. 4A and 4B). With regards to tumor to blood/liver ratios, mAb806 showed the highest ratio at 24 h for both blood (ratio of 1.3) and liver (ratio of 6.1) (FIGS. 5A and 5B). The DH8.3 antibody had its highest ratio in blood at 8 h (ratio of 0.38) and at 24 h in liver (ratio of 1.5) (FIGS. 5A and 5B), both of which are considerably lower than the values obtained for mAb806.

As described above, levels of mAb806 in the tumor peaked at 8 hours. While this peak is relatively early compared to many tumor-targeting antibodies, it is completely consistent with other studies using de2-7 EGFR specific antibodies which all show peaks at 4-24 hours post-injection when using a similar dose of antibody (Hills et al., 1995; Reist et al., 1997; Reist et al. (1996) Radioiodination of internalizing monoclonal antibodies using N-succinimidyl 5-iodo-3-pyridinecarboxylate. *Cancer Res.* 56, 4970-7). Indeed, unlike the earlier reports, the 8 h time point was included on the assumption that antibody targeting would peak rapidly. The % ID/g tumor seen with mAb806 was similar to that reported for other de2-7 EGFR specific antibodies when using standard iodination techniques (Hills et al., 1995; Huang et al., 1997; Reist et al. (1995) Tumor-specific anti-epidermal growth factor receptor variant III monoclonal antibodies: use of the tyramine-cellobiose radioiodination method enhances cellular retention and uptake in tumor xenografts. *Cancer Res.* 55, 4375-82).

The reason for the early peak is probably two-fold. Firstly, tumors expressing the de2-7 EGFR, including the transfected U87MG cells, grow extremely rapidly as tumor xenografts. Thus, even during the relatively short period of time used in these biodistribution studies, the tumor size increases to such an extent (5-10 fold increase in mass over 4 days) that the % ID/g tumor is reduced compared with slow growing tumors. Secondly, while internalization of mAb806 was relatively slow compared to DH8.3, it is still rapid with respect to many other tumor antibody/antigen systems. Internalized antibodies undergo rapid proteolysis with the degradation products being excreted from the cell (Press et al. (1990) Inhibition of catabolism of radiolabeled antibodies by tumor cells using lysosomotropic amines and carboxylic ionophores. *Cancer Res.* 50, 1243-50). This process of internalization, degradation and excretion reduces the amount of iodinated antibody retained within the cell. Consequently, internalizing antibodies display lower levels of targeting than their non-internalizing counterparts. The electron microscopy data reported herein demonstrates that internalized mAb806 is rapidly transported to lysosomes where rapid degradation presumably occurs. This observation is consistent with the swift expulsion of iodine from the cell.

The previously described L8A4 monoclonal antibody directed to the unique junctional peptide found in the de2-7 EGFR, behaves in a similar fashion to mAb806 (Reist et al. (1997) In vitro and in vivo behavior of radiolabeled chimeric anti-EGFRvIII monoclonal antibody: comparison with its murine parent. *Nucl. Med. Biol.* 24, 639-47). Using U87MG cells transfected with the de2-7 EGFR, this antibody had a similar internalization rate (35% at 1 hour compared to 30% at 1 hour for mAb806) and displayed comparable in vivo targeting when using 3T3 fibroblasts transfected with de2-7 EGFR (peak of 24% ID/g tumor at 24 hours compared to 18% ID/g tumor at 8 hours for mAb806) (Reist et al. (1997) Improved targeting of an anti-epidermal growth factor receptor variant III monoclonal antibody in tumor xenografts after labeling using N-succinimidyl 5-iodo-3-pyridinecarboxylate. *Cancer Res.* 57, 1510-5).

Interestingly, in vivo retention of this antibody in tumor xenografts was enhanced when labeled with N-succinimidyl 5-iodo-3-pyridine carboxylate (Reist et al., 1997). This labeled prosthetic group is positively charged at lysosmal pH and thus has enhanced cellular retention (Reist et al. (1996) Radioiodination of internalizing monoclonal antibodies using N-succinimidyl 5-iodo-3-pyridinecarboxylate. *Cancer Res.* 56, 4970-7). Enhanced retention is potentially useful when considering an antibody for radioimmunotherapy and this method could be used to improve retention of iodinated mAb806 or its fragments.

Example 8

Binding of mAb806 to Cells Containing Amplified EGFR

To examine if mAb806 could recognize the EGFR expressed in cells containing an amplified receptor gene, its binding to A431 cells was analyzed. As described previously, A431 cells are human squamous carcinoma cells and express high levels of wtEGFR. Low, but highly reproducible, binding of mAb806 to A431 cells was observed by FACS analysis (FIG. 6). The DH8.3 antibody did not bind A431 cells, indicating that the binding of mAb806 was not the result of low level de2-7 EGFR expression (FIG. 6). As expected, the anti-EGFR 528 antibody showed strong staining of A431 cells (FIG. 6). Given this result, binding of mAb806 to A431 was characterized by Scatchard analysis. While the binding of iodinated mAb806 was comparatively low, it was possible to get consistent data for Scatchard. The average of three such experiments gave a value for affinity of $9.5 \times 10^7$ $M^{-1}$ with $2.4 \times 10^5$ receptors per cell. Thus, the affinity for this receptor was some 10-fold lower than the affinity for the de2-7 EGFR. Furthermore, mAb806 appears to only recognize a small portion of EGFR found on the surface of A431 cells. The 528 antibody measured approximately $2 \times 10^6$ receptors per cell which is in agreement with numerous other studies (Santon et al. (1986) Effects of epidermal growth factor receptor concentration on tumorigenicity of A431 cells in nude mice. *Cancer Res.* 46, 4701-5).

Figure 21:
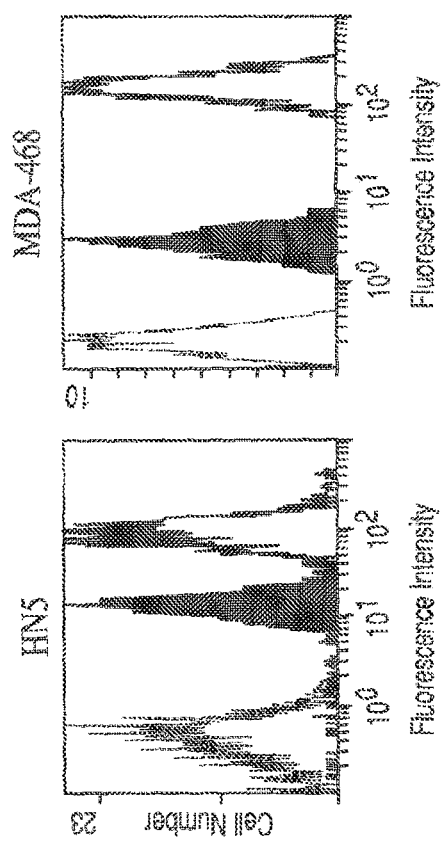
FIG. 21 shows flow cytometric analysis of cell lines containing amplification of the EGFR gene. HN5 and MDA-468 cells were stained with an irrelevant IgG2b antibody (open histogram with dashed line), mAb806 (black histogram) or 528 (open histogram with closed lines). The DH8.3 antibody was completely negative on both cell lines (data not shown).

To ensure that these results were not simply restricted to the A431 cell line, mAb806 reactivity was examined in 2 other cells lines exhibiting amplification of the EGFR gene. Both the HN5 head and neck cell line (Kwok T T and Sutherland R M (1991) Differences in EGF related radiosensitisation of human squamous carcinoma cells with high and low numbers of EGF receptors. *Br. J. Cancer.* 64, 251-4) and the MDA-468 breast cancer cell line (Filmus et al. (1985) MDA-468, a human breast cancer cell line with a high number of epidermal growth factor (EGF) receptors, has an amplified EGF receptor gene and is growth inhibited by EGF. Biochem. *Biophys. Res. Commun.* 128, 898-905) have been reported to contain multiple copies of the EGFR gene. Consistent with these reports, the 528 antibody displayed intense staining of both cell lines (FIG. 21). As with the A431 cell line, the mAb806 clearly stained both cell lines but at a lower level than that observed with the 528 antibody (FIG. 21). Thus, mAb806 binding is not simply restricted to A431 cells but appears to be a general observation for cells containing amplification of the EGFR gene.

Recognition of the wild-type sEGFR by mAb806 clearly requires some denaturation of the receptor in order to expose the epitope. The extent of denaturation required is only slight as even absorption of the wild-type sEGFR on to a plastic surface induced robust binding of mAb806 in ELISA assays. As mAb806 only bound approximately 10% of the EGFR on the surface of A431 cells, it is tempting to speculate that this subset of receptors may have an altered conformation similar to that induced by the de2-7 EGFR truncation. Indeed, the extremely high expression of the EGFR mediated by gene amplification in A431 cells may cause some receptors to be incorrectly processed leading to altered conformation. Interestingly, semi-quantitative immunoblotting of A431 cell lysates with mAb806 showed that it could recognize most of the A431 EGF receptors following SDS-PAGE and western transfer. This result further supports the argument that mAb806 is binding to a subset of receptors on the surface of A431 cells that have an altered conformation. These observations in A431 cells are consistent with the immunohistochemistry data demonstrating that mAb806 binds gliomas containing amplification of the EGFR gene. As mAb806 binding was completely negative on parental U87MG cells it would appear this phenomenon may be restricted to cells containing amplified EGFR although the level of "denatured" receptor on the surface of U87MG cells may be below the level of detection. However, this would seem unlikely as iodinated mAb806 did not bind to U87MG cell pellets containing up to $1 \times 10^7$ cells.

Example 9

In Vivo Targeting of A431 Cells by mAb806

A second biodistribution study was performed with mAb806 to determine if it could target A431 tumor xenografts. The study was conducted over a longer time course in order obtain more information regarding the targeting of U87MG.Δ2-7 xenografts by mAb806, which were included in all mice as a positive control. In addition, the anti-EGFR 528 antibody was included as a positive control for the A431 xenografts, since a previous study demonstrated low but significant targeting of this antibody to A431 cells grown in nude mice (Masui et al. (1984) Growth inhibition of human tumor cells in athymic mice by anti-epidermal growth factor receptor monoclonal antibodies. *Cancer Res.* 44, 1002-7).

Figure 7B:
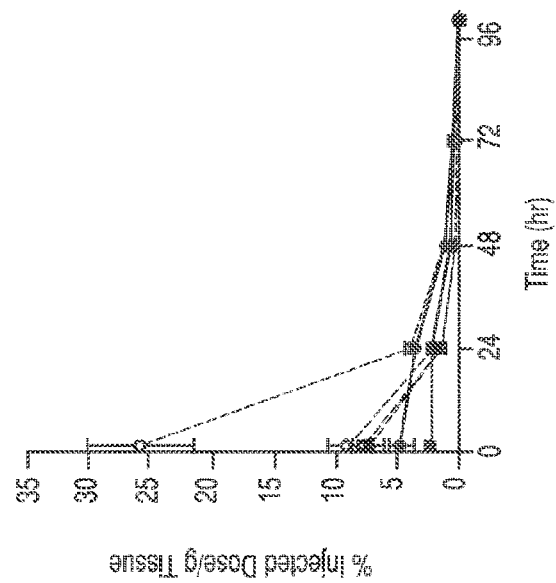
FIGS. 7A and 7B illustrate biodistribution (% ID/g tumor tissue) of radiolabeled (a) $^{125}$I-mAb806 and (b) $^{131}$I-528 in nude mice bearing U87MG.Δ2-7 and A431 xenografts.
Figure 7A:
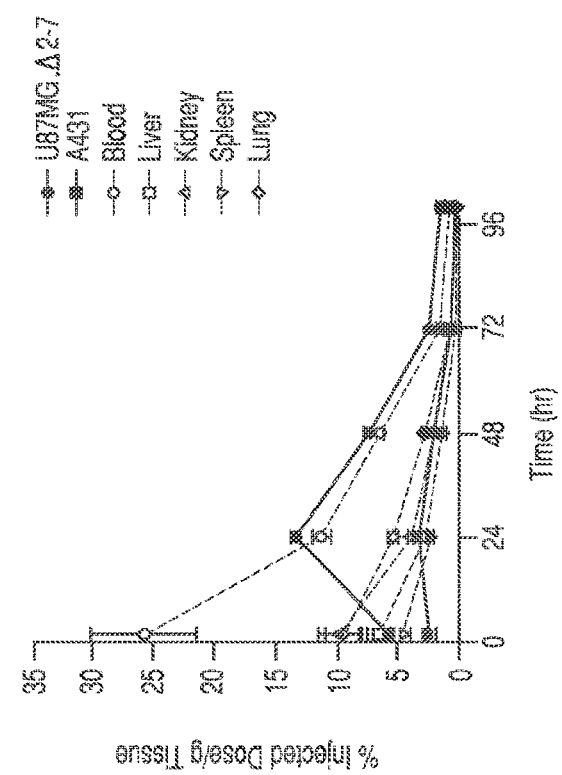
Figure 23:
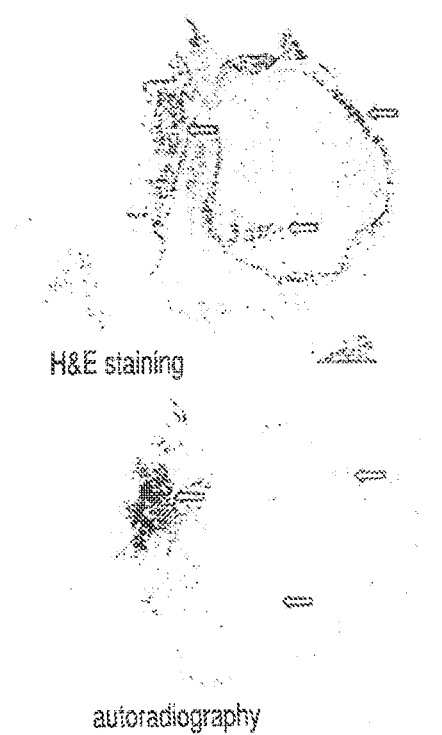
FIG. 23 shows autoradiography of an A431 xenograft section collected 24 hr after injection of $^{125}$I-mAb806, areas of localization to viable tissue are indicated (arrows).

During the first 48 h, mAb806 displayed almost identical targeting properties as those observed in the initial experiments (FIG. 7A compared with FIG. 4A). In terms of % ID/g tumor, levels of mAb806 in U87MG.Δ2-7 xenografts slowly declined after 24 h but always remained higher than levels detected in normal tissue. Uptake in the A431 xenografts was comparatively low, however there was a small increase in % ID/g tumor during the first 24 h not observed in normal tissues such as liver, spleen, kidney and lung (FIG. 7A). Uptake of the 528 antibody was very low in both xenografts when expressed as % ID/g tumor (FIG. 7B) partially due to the faster clearance of this antibody from the blood. Autoradiography of A431 xenograft tissue sections collected 24 hr after injection with $^{125}$I-labeled mAb806 alone, clearly illustrates localization of antibody to viable tumor around the periphery of the tumor and not central areas of necrosis (FIG. 23). In terms of tumor to blood ratio mAb806 peaked at 72 h for U87MG.Δ2-7 xenografts and 100 h for A431 xenografts (FIGS. 8A, B). While the tumor to blood ratio for mAb806 never surpassed 1.0 with respect to the A431 tumor, it did increase throughout the entire time course (FIG. 8B) and was higher than all other tissues examined (data not shown) indicating low levels of targeting.

The tumor to blood ratio for the 528 antibody showed a similar profile to mAb806 although higher levels were noted in the A431 xenografts (FIGS. 8A, B). mAb806 had a peak tumor to liver ratio in U87MG.Δ2-7 xenografts of 7.6 at 72 h, clearly demonstrating preferential uptake in these tumors compared to normal tissue (FIG. 8C). Other tumor to organ ratios for mAb806 were similar to those observed in the liver (data not shown). The peak tumor to liver ratio for mAb806 in A431 xenografts was 2.0 at 100 h, again indicating a slight preferential uptake in tumor compared with normal tissue (FIG. 8D).

Example 10

Therapy Studies

The effects of mAb806 were assessed in two xenograft models of disease—a preventative model and an established tumor model.

Xenograft Models

Consistent with previous reports (Nishikawa et al., *Proc. Natl. Acad. Sci. U.S.A.*, 91(16), 7727-7731), U87MG cells transfected with de2-7 EGFR grew more rapidly than parental cells and U87MG cells transfected with the wtEGFR. Therefore, it was not possible to grow both cell types in the same mice.

Tumor cells ($3 \times 10^6$) in 100 ml of PBS were inoculated subcutaneously into both flanks of 4-6 week old female nude mice (Animal Research Centre, Western Australia, Australia). Therapeutic efficacy of mAb806 was investigated in both preventative and established tumor models. In the preventative model, 5 mice with two xenografts each were treated intraperitoneally with either 1 or 0.1 mg of mAb806 or vehicle (PBS) starting the day before tumor cell inoculation. Treatment was continued for a total of 6 doses, 3 times per week for 2 weeks. In the established model, treatment was started when tumors had reached a mean volume of 65±6.42 mm$^3$ (U87MG.Δ2-7), 84±9.07 mm3 (U87MG), 73±7.5 mm$^3$ (U87MG.wtEGFR) or 201±19.09 mm$^3$ (A431 tumors). Tumor volume in mm$^3$ was determined using the formula (length×width)/2, where length was the longest axis and width the measurement at right angles to the length (Clark et al. (2000) Therapeutic efficacy of anti-Lewis (y) humanized 3S 193 radioimmunotherapy in a breast cancer model: enhanced activity when combined with Taxol chemotherapy. *Clin. Cancer Res.* 6, 3621-3628). Data was expressed as mean tumor volume±S.E. for each treatment group. Statistical analysis was performed at given time points using Student's t-test. Animals were euthanized when the xenografts reached an approximate volume of 1.5 cm$^3$ and the tumors excised for histological examination. This research project was approved by the Animal Ethics Committee of the Austin and Repatriation Medical Centre.

Histological Examination of Tumor Xenografts

Xenografts were excised and bisected. One half was fixed in 10% formalin/PBS before being embedded in paraffin. Four micron sections were then cut and stained with haematoxylin and eosin (H&E) for routine histological examination. The other half was embedded in Tissue Tek® OCT compound (Sakura Finetek, Torrance, Calif.), frozen in liquid nitrogen and stored at −80° C. Thin (5 micron) cryostat sections were cut and fixed in ice-cold acetone for 10 min followed by air drying for a further 10 min. Sections were blocked in protein blocking reagent (Lipshaw Immunon, Pittsburgh U.S.A.) for 10 min and then incubated with biotinylated primary antibody (1 mg/ml), for 30 min at room temperature (RT). All antibodies were biotinylated using the ECL™ protein biotinylation module (Amersham, Baulkham Hills, Australia), as per the manufacturer's instructions. After rinsing with PBS, sections were incubated with a streptavidin horseradish peroxidase complex for a further 30 min (Silenus, Melbourne, Australia). Following a final PBS wash the sections were exposed to 3-amino-9-ethylcarbozole (AEC) substrate (0.1 M acetic acid, 0.1 M sodium acetate, 0.02 M AEC (Sigma Chemical Co., St Louis, Mo.)) in the presence of hydrogen peroxide for 30 min. Sections were rinsed with water and counterstained with hematoxylin for 5 min and mounted.

Figure 9A:
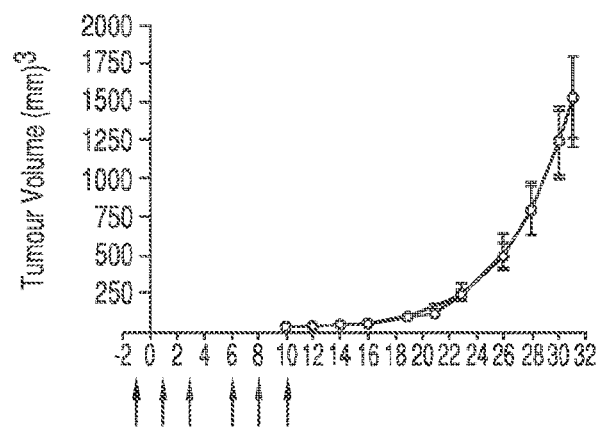
FIGS. 9A and 9B illustrate anti-tumor effect of mAb806 on (A) U87MG and (B) U87MG.Δ2-7 xenograft growth rates in a preventative model. $3\times10^6$ U87MG or U87MG.Δ2-7 cells were injected s.c. into both flanks of 4-6 week old BALB/c nude mice, (n=5) at day 0. Mice were injected i.p. with either 1 mg of mAb806 (●); 0.1 mg of mAb806 (▲); or vehicle (o) starting one day prior to tumor cell inoculation. Injections were given three times per week for two weeks as indicated by the arrows. Data are expressed as mean tumor volume±S.E.
Figure 9B:
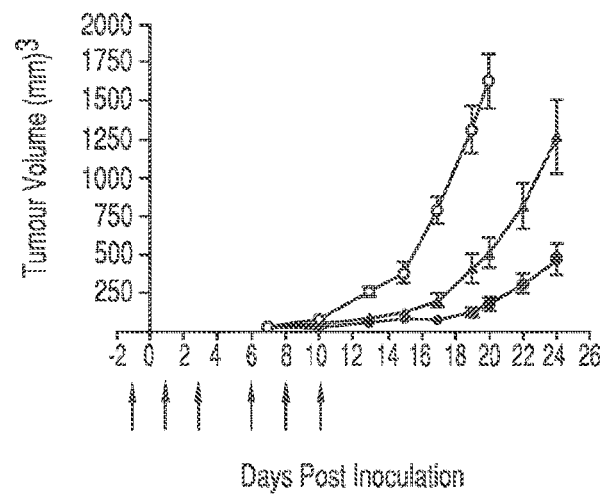

Efficacy of mAb806 in Preventative Model mAb806 was examined for efficacy against U87MG and U87MG.Δ2-7 tumors in a preventative xenograft model. Antibody or vehicle were administered i.p. the day before tumor inoculation and was given 3 times per week for 2 weeks. mAb806 had no effect on the growth of parental U87MG xenografts, which express the wtEGFR, at a dose of 1 mg per injection (FIG. 9A). In contrast, mAb806 significantly inhibited the growth of U87MG.Δ2-7 xenografts in a dose dependent manner (FIG. 9B). At day 20, when control animals were sacrificed, the mean tumor volume was $1637\pm178.98$ mm$^3$ for the control group, a statistically smaller $526\pm94.74$ mm$^3$ for the 0.1 mg per injection group ($p<0.0001$) and $197\pm42.06$ mm$^3$ for the 1 mg injection group ($p<0.0001$). Treatment groups were sacrificed at day 24 at which time the mean tumor volumes was $1287\pm243.03$ mm$^3$ for the 0.1 mg treated group and $492\pm100.8$ mm$^3$ for the 1 mg group.

Efficacy of mAb806 in Established Xenograft Model

Figure 10A:
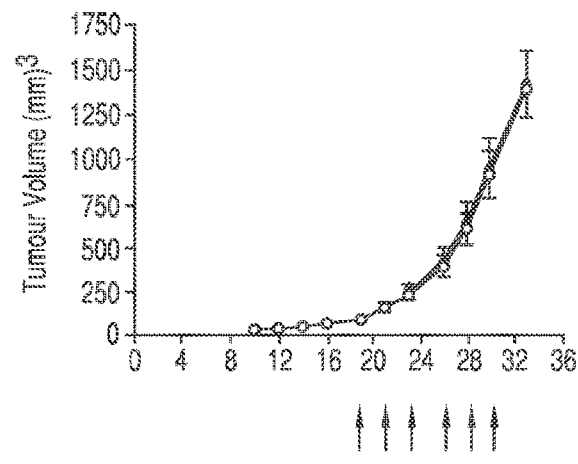
FIGS. 10A, 10B, and 10C illustrate the anti-tumor effect of mAb806 on (A) U87MG, (B) U87MG.Δ2-7 and (C) U87MG.wtEGFR xenografts in an established model. $3\times10^6$ U87MG, U87MG.Δ2-7, or U87MG.wtEGFR cells, were injected s.c. into both flanks of 4-6 week old BALB/c nude mice, (n=5). Mice were injected i.p. with either 1 mg doses of mAb806 (●); 0.1 mg doses of mAb806 (▲); or vehicle (o) starting when tumors had reached a mean tumor volume of 65-80 mm$^3$. Injections were given three times per week for two weeks as indicated by the arrows. Data are expressed as mean tumor volume±S.E.
Figure 10B:
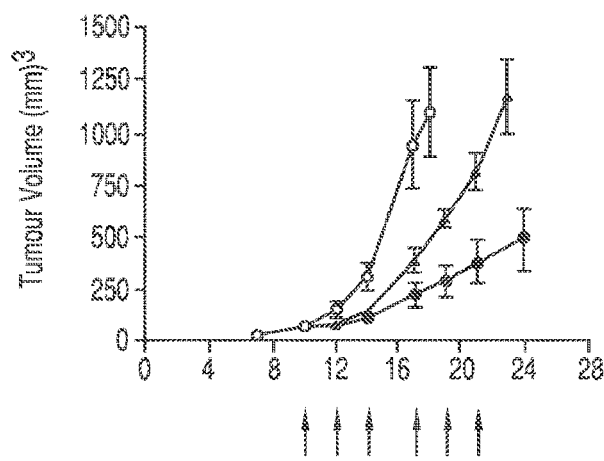

Given the efficacy of mAb806 in the preventative xenograft model, its ability to inhibit the growth of established tumor xenografts was then examined Antibody treatment was as described in the preventative model except that it commenced when tumors had reached a mean tumor volume of $65\pm6.42$ mm$^3$ for the U87MG.Δ2-7 xenografts and $84\pm9.07$ mm$^3$ for the parental U87MG xenografts. Once again, mAb806 had no effect on the growth of parental U87MG xenografts at a dose of 1 mg per injection (FIG. 10A). In contrast, mAb806 significantly inhibited the growth of U87MG.Δ2-7 xenografts in a dose dependent manner (FIG. 10B). At day 17, one day before control animals were sacrificed, the mean tumor volume was $935\pm215.04$ mm$^3$ for the control group, $386\pm57.51$ mm$^3$ for the 0.1 mg per injection group ($p<0.01$) and $217\pm58.17$ mm$^3$ for the 1 mg injection group ($p<0.002$).

Figure 10C:
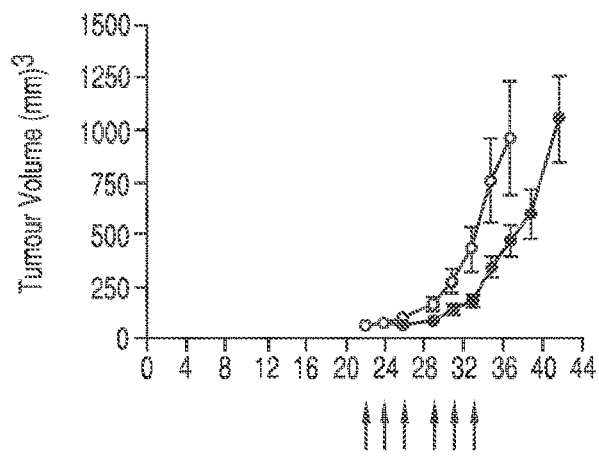

To examine whether the growth inhibition observed with mAb806 was restricted to cell expressing de2-7 EGFR, its efficacy against U87MG.wtEGFR tumor xenografts was examined in an established model. These cells serve as a model for tumors containing amplification of the EGFR gene without de2-7 EGFR expression. mAb806 treatment commenced when tumors had reached a mean tumor volume of $73\pm7.5$ mm$^3$ mAb806 significantly inhibited the growth of established U87MG.wtEGFR xenografts when compared to control tumors treated with vehicle (FIG. 10C). On the day control animals were sacrificed, the mean tumor volume was $960\pm268.9$ mm$^3$ for the control group and $468\pm78.38$ mm$^3$ for the group treated with 1 mg injections ($p<0.04$).

Histological and Immunohistochemical Analysis of Established Tumors

To evaluate potential histological differences between mAb806-treated and control U87MG.Δ2-7 and U87MG.wtEGFR xenografts (collected at days 24 and 42 respectively), formalin-fixed, paraffin embedded sections were stained with H&E. Areas of necrosis were seen in sections from both U87MG.Δ2-7 (collected 3 days after treatment finished), and U87MG.wtEGFR xenografts (collected 9 days after treatment finished) treated with mAb806. This result was consistently observed in a number of tumor xenografts (n=4). However, analysis of sections from xenografts treated with control did not display the same areas of necrosis seen with mAb806 treatment. Sections from mAb806 or control treated U87MG xenografts were also stained with H&E and revealed no differences in cell viability between the two groups, further supporting the hypothesis that mAb806 binding induces decreased cell viability/necrosis within tumor xenografts.

An immunohistochemical analysis of U87MG, U87MG.Δ2-7 and U87MG.wtEGFR xenograft sections was performed to determine the levels of de2-7 and wtEGFR expression following mAb806 treatment. Sections were collected at days 24 and 42 as above, and were immunostained with the 528 or 806 antibodies. As expected, the 528 antibody stained all xenograft sections with no obvious decrease in intensity between treated and control tumors. Staining of U87MG sections was undetectable with the mAb806, however positive staining of U87MG.Δ2-7 and U87MG.wtEGFR xenograft sections was observed. There was no difference in mAb806 staining density between control and treated U87MG.Δ2-7 and U87MG.wtEGFR xenografts suggesting that antibody treatment does not down regulate de2-7 or wtEGFR expression.

Treatment of A431 Xenografts with mAb806

Figure 11A:
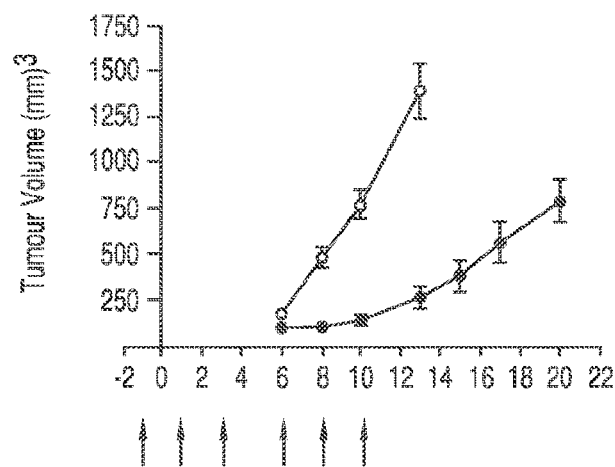
FIGS. 11A and 11B illustrate anti-tumor effect of mAb806 on A431 xenografts in (A) preventative and (B) established models. $3\times10^6$ A431 cells were injected s.c. into both flanks of 4-6 week old BALB/c nude mice (n=5). Mice were injected i.p. with either 1 mg doses of mAb806 (●); or vehicle (o), starting one day prior to tumor cell inoculation in the preventative model, or when tumors had reached a mean tumor volume of 200 mm$^3$ Injections were given three times per week for two weeks as indicated by the arrows. Data are expressed as mean tumor volume±S.E.

To demonstrate that the anti-tumor effects of mAb806 were not restricted to U87MG cells, the antibody was administered to mice with A431 xenografts. These cells contain an amplified EGFR gene and express approximately $2\times10^6$ receptors per cell. As described above, mAb806 binds about 10% of these EGFR and targets A431 xenografts. mAb806 significantly inhibited the growth of A431 xenografts when examined in the previously described preventative xenograft model (FIG. 11A). At day 13, when control animals were sacrificed, the mean tumor volume was $1385\pm147.54$ mm$^3$ in the control group and $260\pm60.33$ mm$^3$ for the 1 mg injection treatment group ($p<0.0001$).

In a separate experiment, a dose of 0.1 mg mAb also significantly inhibited the growth of A431 xenografts in a preventative model.

Figure 11B:
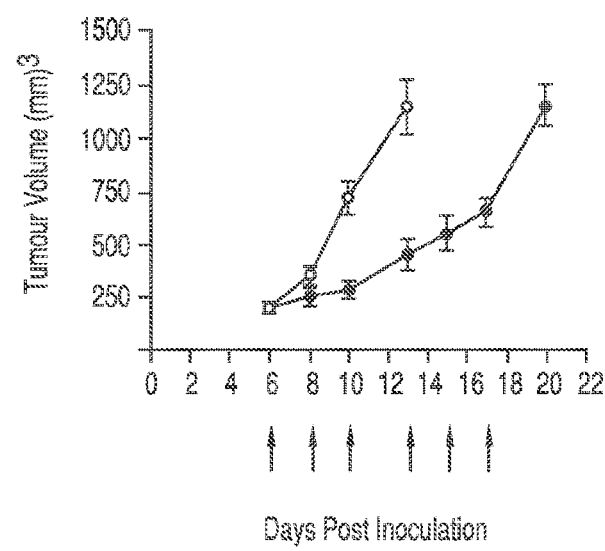

Given the efficacy of mAb806 in the preventative A431 xenograft model, its ability to inhibit the growth of established tumor xenografts was examined. Antibody treatment was as described in the preventative model except it was not started until tumors had reached a mean tumor volume of $201\pm19.09$ mm$^3$ mAb806 significantly inhibited the growth of established tumor xenografts (FIG. 11B). At day 13, when control animals were sacrificed, the mean tumor volume was $1142\pm120.06$ mm$^3$ for the control group and $451\pm65.58$ mm$^3$ for the 1 mg injection group ($p<0.0001$).

In summary, the therapy studies with mAb806 described here clearly demonstrated dose dependent inhibition of U87MG.Δ2-7 xenograft growth. In contrast, no inhibition of parental U87MG xenografts was observed despite the fact they continue to express the wtEGFR in vivo. mAb806 not only significantly reduced xenograft volume, it also induced significant necrosis within the tumor. This is the first report showing the successful therapeutic use of such an antibody in vivo against a human de2-7 EGFR expressing glioma xenografts.

Gene amplification of the EGFR has been reported in a number of different tumors and is observed in approximately 50% of gliomas (Voldberg et al., 1997). It has been proposed that the subsequent EGFR over-expression mediated by receptor gene amplification may confer a growth advantage by increasing intracellular signaling and cell growth (Filmus et al., 1987). The U87MG cell line was transfected with the wtEGFR in order to produce a glioma cell that mimics the process of EGFR gene amplification. Treatment of established U87MG.wtEGFR xenografts with mAb806 resulted in significant growth inhibition. Thus, mAb806 also mediates in vivo antitumor activity against cells containing amplification of the EGFR gene. Interestingly, mAb806 inhibition of U87MG.wtEGFR xenografts appears to be less effective than that observed with U87MG.Δ2-7 tumors. This probably reflects the fact that mAb806 has a lower affinity for the amplified EGFR and only binds a small proportion of receptors expressed on the cell surface. However, it should be noted that despite the small effect on U87MG.wtEGFR xenograft volumes, mAb806 treatment produced large areas of necrosis within these xenografts.

To rule out the possibility that mAb806 only mediates inhibition of the U87MG derived cell lines we tested its efficacy against A431 xenografts. This squamous cell carcinoma derived cell line contains significant EGFR gene amplification which is retained both in vitro and in vivo. Treatment of A431 xenografts with mAb806 produced significant growth inhibition in both a preventative and established model, indicating the anti-tumor effects of mAb806 are not restricted to transfected U87MG cell lines.

Example 11

Combination Therapy Treatment of A431 Xenografts with mAb806 and AG1478

Figure 12:
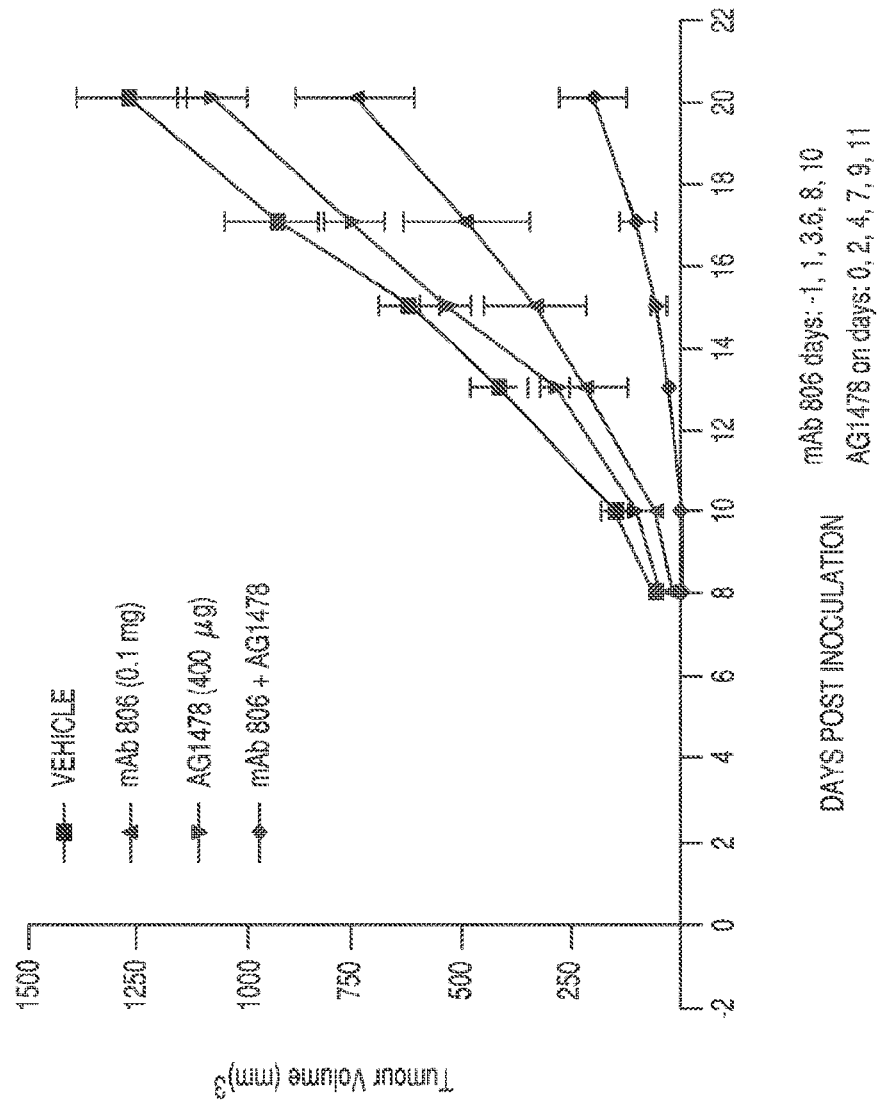
FIG. 12 illustrates the anti-tumor effect of treatment with mAb806 combined with treatment with AG1478 on A431 xenografts in a preventative model. Data are expressed as mean tumor volume±S.E.

The anti-tumor effects of mAb806 combined with AG1478 was tested in mice with A431 xenografts. AG1478 (4-(3-Chloroanilino)-6,7-dimethoxyquinazoline) is a potent and selective inhibitor of the EGFR kinase versus HER2-neu and platelet-derived growth factor receptor kinase (Calbiochem Cat. No. 658552). Three controls were included: treatment with vehicle only, vehicle+mAb806 only, and vehicle+ AG1478 only. The results are illustrated in FIG. 12. 0.1 mg mAb806 was administered at 1 day prior to xenograft and 1, 3, 6, 8 and 10 days post xenograft. 400 μg AG1478 was administered at 0, 2, 4, 7, 9, and 11 days post xenograft.

Both AG1478 and mAb806, when administered alone, produced a significant reduction of tumor volume. However, in combination, the reduction of tumor volume was greatly enhanced.

Figure 13:
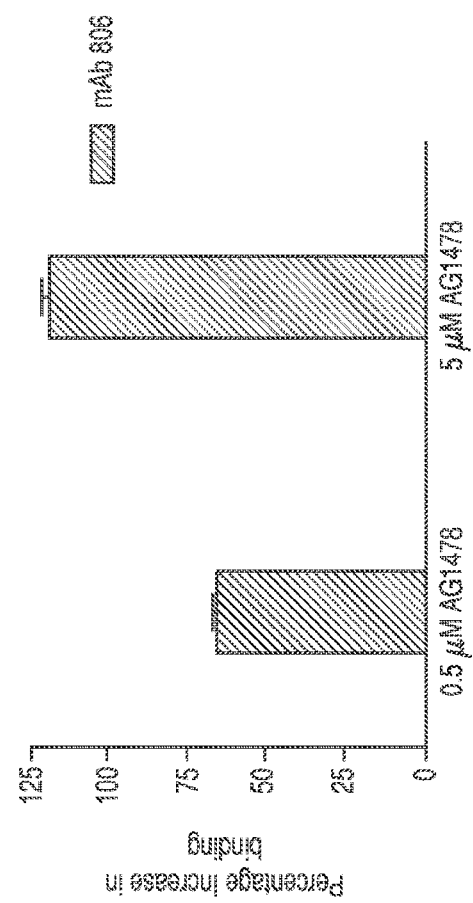
FIG. 13 depicts mAb806 binding to A431 cells in the presence of increasing concentrations of AG1478 (0.5 μM and 5 μM).

In addition, the binding of mAb806 to EGFR of A431 cells was evaluated in the absence and presence of AG1478. Cells were placed in serum free media overnight, then treated with AG1478 for 10 min at 37° C., washed twice in PBS, then lysed in 1% Triton and lysates prepared by centrifugation for 10 min at 12,000 g. Lysate was then assessed for 806 reactivity by an ELISA in a modified version of an assay described by Schooler and Wiley, Analytical Biochemistry 277, 135-142 (2000). Plates were coated with 10 μg/ml of mAb806 in PBS/EDTA overnight at room temperature and then washed twice. Plates were then blocked with 10% serum albumin/ PBS for 2 hours at 37° C. and washed twice. A 1:20 cell lysate was added in 10% serum albumin/PBS for 1 hour at 37° C., then washed four times. Anti-EGFR(SC-03; Santa Cruz Biotechnology Inc.) in 10% serum albumin/PBS was reacted 90 min at room temperature, the plate washed four times, and anti-rabbit-HRP (1:2000 if from Silenus) in 10% serum albumin/PBS was added for 90 min at room temperature, washed four times, and color developed using ABTS as a substrate. It was found that mAb806 binding is significantly increased in the presence of increasing amounts of AG1478 (FIG. 13).

Example 12

Immunoreactivity in Human Glioblastomas Pre-Typed for EGFR Status

Given the high incidence of EGFR expression, amplification and mutation in glioblastomas, a detailed immunohistochemical study was performed in order to assess the specificity of 806 in tumors other than xenografts. A panel of 16 glioblastomas was analyzed by immunohistochemistry. This panel of 16 glioblastomas was pre-typed by RT-PCR for the presence of amplified wild-type EGFR and de2-7 EGFR expression. Six of these tumors expressed only the wtEGFR transcript, 10 had wtEGFR gene amplification with 5 of these showing wild-type EGFR transcripts only, and 5 both wild-type EGFR and de2-7 gene transcript.

Immunohistochemical analysis was performed using 5 mm sections of fresh frozen tissue applied to histology slides and fixed for 10 minutes in cold acetone. Bound primary antibody was detected with biotinylated horse anti-mouse antibody followed by an avidin-biotin-complex reaction. Diaminobenzidine tetrahydrochloride (DAB) was used as chromogen. The extent of the immunohistochemical reactivity in tissues was estimated by light microscopy and graded according to the number of immunoreactive cells in 25% increments as follows:
Focal=less than 5%
+=5-25%
++=25-50%
+++=50-75%
++++=>75%

The 528 antibody showed intense reactivity in all tumors, while DH8.3 immunostaining was restricted to those tumors expressing the de2-7 EGFR (Table 2). Consistent with the previous observations in FACS and rosetting assays, mAb806 did not react with the glioblastomas expressing the wtEGFR transcript from nonamplified EGFR genes (Table 2). This pattern of reactivity for mAb806 is similar to that observed in the xenograft studies and again suggests that this antibody recognizes the de2-7 and amplified EGFR but not the wtEGFR when expressed on the cell surface.

TABLE 2

Immunoreactivity of mAbs528, DH8.3 and 806 on glioblastomas pre-typed for the presence of wild-type EGFR and mutated de2-7 EGFR and for their amplification status

| Amplification | de2-7 EGFR Expression | 528 | DH8.3 | 806 |
| --- | --- | --- | --- | --- |
|  | No | ++++ | − | − |
|  | No | ++++ | − | −* |
|  | No | ++++ | − | − |
|  | No | ++ | − | − |
|  | No | +++ | − | − |
|  | No | ++++ | − | − |
| Yes | No | ++++ | − | ++++ |
| Yes | No | ++++ | − | + |
| Yes | No | ++++ | − | +++ |
| Yes | No | ++++ | − | ++++ |
| Yes | No | ++++ | − | +−++++ |
| Yes | Yes | ++++ | ++++ | ++++ |
| Yes | Yes | ++++ | ++++ | ++++ |
| Yes | Yes | ++++ | ++++ | ++++ |
| Yes | Yes | ++++ | ++++ | ++++ |
| Yes | Yes | ++++ | ++ | ++ |

*focal staining

Example 13

EGFR Immunoreactivity in Normal Tissue

In order to determine if the de2-7 EGFR is expressed in normal tissue, an immunohistochemical study with mAb806 and DH8.3 was conducted in a panel of 25 tissues. There was no strong immunoreactivity with either mAb806 or DH8.3 in any tissue tested, suggesting that the de2-7 EGFR is absent in normal tissues (Table 3). There was some variable staining present in tonsils with mAb806 that was restricted to the basal cell layer of the epidermis and mucosal squamous cells of the epithelium. In placenta, occasional immunostaining of the trophoblast epithelium was observed. Interestingly, two tissues that express high endogenous levels of wtEGFR, the liver and skin, failed to show any significant mAb806 reactivity. No reactivity was observed with the liver samples at all, and only weak and inconsistent focal reactivity was detected occasionally (in no more than 10% of all samples studied) in basal keratinocytes in skin samples and in the squamous epithelium of the tonsil mucosa, further demonstrating that this antibody does not bind the wtEGFR expressed on the [0457] surface of cells to any significant extent (Table 3). All tissues were positive for the wtEGFR as evidenced by the universal staining seen with the 528 antibody (Table 3).

TABLE 3

Reactivity of 582, DH8.3 and 806 on normal tissues

| Tissue | 528 | DH8.3 | 806 |
|---|---|---|---|
| Esophagus | pos | – | – |
| Stomach | pos | – | – |
| Duodenum | pos | – | – |
| Small intestine/duodenum | pos | – | – |
| Colon | pos | – | – |
| Liver | pos | – | – |
| Salivary glands (parotid) | pos | – | – |
| Kidney | pos | – | – |
| Urinary Bladder | pos | – | – |
| Prostate | pos | – | – |
| Testis | pos | – | – |
| Uterus (cx/endom) | pos | –* | – |
| Fallopian tube | pos | – | – |
| Ovary | pos | – | – |
| Breast | pos | –* | – |
| Placenta | pos | – | – |
| Peripheral nerve | pos | – | – |
| Skeletal muscle | pos | – | – |
| Thyroid gland | pos | – | – |
| Lymph node | pos | – | – |
| Spleen | pos | – | – |
| Tonsil | pos | – | – occ. weak reactivity of basal layer of squamous epithelium |
| Heart | pos | – | – |
| Lung | pos | – | – |
| Skin | pos | – | – occ. weak reactivity of basal layer of squamous epithelium |

*some stromal staining in various tissue

Example 14

EGFR Immunoreactivity in Various Tumors

The extent of de2-7 EGFR in other tumor types was examined using a panel of 12 different malignancies. The 528 antibody showed often homogeneous staining in many tumors analyzed except melanoma and seminoma. When present, DH8.3 immunoreactivity was restricted to the occasional focal tumor cell indicating there is little if any de2-7 EGFR expression in tumors outside the brain using this detection system (Table 4). There was also focal staining of blood vessels and a varying diffuse staining of connective tissue with the DH8.3 antibody in some tumors (Table 4). This staining was strongly dependent on antibody concentration used and was considered nonspecific background reactivity. The mAb806 showed positive staining in 64% of head and neck tumors and 50% of lung carcinomas (Table 4). There was little mAb806 reactivity elsewhere except in urinary tumors that were positive in 30% of cases.

Since the head and neck and lung cancers were negative for the DH8.3 antibody the reactivity seen with the mAb in these tumors maybe associated with EGFR gene amplification.

TABLE 4

Monoclonal antibodies 528, DH8.3 and 806 on tumor panel

| Tumor | 528 | DH8.3 | 806 |
|---|---|---|---|
| Malignant melanoma metastases | 0/10 | 0/10 | 0/10 |
| Urinary bladder (tcc, sqcc, adeno) | 10/10 (7x++++, 2x++++, 1x+) | 0/10* | 3/10* (2x++++, 1x++) |
| Mammary gland | 6/10 (3x++++, 3x++) | 1/10 (1x+) | 1/10 (foc) |
| Head + neck cancer (sqcc) | 11/11 (1x+++-10x++++) | 0/11* | 7/11 (3x++++, 3x+++, 1x+) |
| Lung (sqcc, adeno, neuroend) | 12/12 (10x++++-1x+++) | 0/12* | 6/12 (3x++++ 3x+++) |
| Leiomyosarcoma | 5/5 (4x++++, 1x+) | 0/5 | 0/5 |
| Liposarcoma | 5/5 (2x + 3x +++) | 0/5 | 0/5* |
| Synovial sarcoma | 4/5* (4x ++++) | 0/5 | 0/5* |
| Mfh Malignant fibrous histiocytoma | 4/5* | 0/5* | 0/5* |
| Colonic carcinoma | 10/10 (9x++++, 1x+) | 0/10* | 0/10 |
| Seminoma | 1/10* | 1/10* | 0/10 |
| Ovary (serous-papillary) | 4/5 (3x++++, 1x+) | 0/5* | 0/5 |

*focal staining

Example 15

Immunoreactivity in Human Glioblastomas Unselected for EGFR Status

In order to confirm the unique specificity and to evaluate the reactivity of mAb806, it was compared to the 528 and DH8.3 antibodies in a panel of 46 glioblastomas not preselected for their EGFR status. The 528 antibody was strongly and homogeneously positive in all samples except two (Nos. 27 and 29) (44/46, 95.7%). These two cases were also negative for mAb806 and mAbDH8.3. The mAb806 was positive in 27/46 (58.7%) cases, 22 of which displayed homogeneous immunoreactivity in more than 50% of the tumor. The DH8.3 antibody was positive in 15/46 (32.6%) glioblastomas, 9 of which showed homogeneous immunoreactivity. The immunochemical staining of these unselected tumors is tabulated in Table 5.

There was concordance between mAb806 and DH8.3 in every case except one (No. 35). A molecular analysis for the presence of EGFR amplification was done in 44 cases (Table 5). Of these, 30 cases co-typed with the previously established mAb806 immunoreactivity pattern: e.g., 16 mAb806-negative cases revealed no EGFR amplification and 14 EGFR-amplified cases were also mAb806 immunopositive. However, 13 cases, which showed 806 immunoreactivity, were negative for EGFR amplification while one EGFR-amplified case was mAb806 negative. Further analysis of the mutation status of these amplification negative and 806 positive cases is described below and provides explanation for most of the 13 cases which were negative for EGFR amplification and were recognized by 806.

Subsequently, a molecular analysis of the deletion mutation by RT-PCR was performed on 41/46 cases (Table 5). Of these, 34 cases co-typed with DH8.3 specific for the deletion mutation: 12 cases were positive in both RT-PCR and immunohistochemistry and 22 cases were negative/negative. Three cases (#2, #34, and #40) were DH8.3 positive/RT-PCR negative for the deletion mutation and three cases (#12, #18, and #39) were DH8.3 negative/RT-PCR positive. As expected based on our previous specificity analysis, mAb806 immunoreactivity was seen in all DH8.3 positive tissues except in one case (#35).

Case #3 also revealed a mutation (designated A2 in Table 5), which included the sequences of the de2-7 mutation but this did not appear to be the classical de2-7 deletion with loss of the 801 bases (data not shown). This case was negative for DH8.3 reactivity but showed reactivity with 806, indicating that 806 may recognize an additional and possibly unique EGFR mutation.

TABLE 5

Immunohistochemical Analysis of 46 Unselected Glioblastomas With mAbs 528, 806, and DH8.3

| # | 528 | 806 | DH8.3 | EGFR Amp.* | 5' MUT |
|---|-----|-----|-------|------------|--------|
| 1 | ++++ | ++++ | ++ | A | 5' MUT |
| 2 | ++++ | ++++ | ++++ | N | WT |
| 3 | ++++ | ++++ (det.) | neg. | N | A2 |
| 4 | ++++ | ++++ | neg. | N | WT |
| 5 | ++++ | ++++ | ++++ | N | 5' MUT |
| 6 | ++++ | ++++ | neg. | A | WT |
| 7 | ++++ | ++++ | ++++ | N | 5' MUT |
| 8 | ++++ | ++++ | ++++ | A | 5' MUT |
| 9 | ++++ | ++++ | neg. | A | WT |
| 10 | ++++ | neg. | neg. | N | WT |
| 11 | ++ | ++ | ++ | A | 5' MUT |
| 12 | ++++ | ++ | neg. | A | 5' MUT |
| 13 | ++++ | ++++ | neg. | N | WT |
| 14 | ++ | neg. | neg. | Nd | nd |
| 15 | ++ | ++ | neg. | N | WT |
| 16 | + | neg. | neg. | N | nd |
| 17 | ++++ | neg. | neg. | N | WT |
| 18 | ++++ | ++++ | neg. | A | 5' MUT |
| 19 | ++++ | ++++ | neg. | N | WT |
| 20 | ++++ | neg. | neg. | N | WT |
| 21 | ++++ | ++++ | neg. | N | WT |
| 22 | +++ | neg. | neg. | N | WT |
| 23 | ++++ | ++++ | ++ | N | 5' MUT |
| 24 | ++++ | ++++ | neg. | A | WT |
| 25 | ++++ | neg. | neg. | N | WT |
| 26 | ++++ | ++++ | +++ | A | 5' MUT |
| 27 | neg. | neg. | neg. | N | WT |
| 28 | +++ | neg. | neg. | N | WT |
| 29 | neg. | neg. | neg. | N | WT |
| 30 | ++++ | ++++ | neg. | N | WT |
| 31 | ++++ par det | neg. | neg. | N | nd |
| 32 | ++ | +++ | ++ | N | 5' MUT |
| 33 | +++ | ++++ | ++++ | A | 5' MUT |
| 34 | ++++ | +++ | ++++ | N | WT |
| 35 | ++++ | neg. | ++++ | A | 5' MUT |
| 36 | +++ | ++ | +++ | A | 5' MUT |
| 37 | ++++ | + | + | A | 5' MUT |
| 38 | ++++ | neg. | neg. | N | WT |
| 39 | ++ | neg. | neg. | N | 5' MUT |
| 40 | ++++ | ++++ | + | A | WT |
| 41 | ++ | neg. | neg. | N | WT |
| 42 | ++++ | ++++ | neg. | A | WT |
| 43 | ++++ | neg. | neg. | nd | nd |
| 44 | ++++ | neg. | neg. | N | WT |
| 45 | ++++ | neg. | neg. | N | WT |
| 46 | ++++ | neg. | neg. | N | nd |

*N = not amplified, A-amplified,
†WT = wild-type, 5' MUT
nd = not done

The 806 antibody reactivity co-typed with amplified or de2-7 mutant EGFR in 19/27 or over 70% of the cases. It is notable that 2 of these 8 cases were also DH8.3 reactive.

Example 16

Systemic Treatment and Analysis of Intracranial Glioma Tumors

To test the efficacy of the anti-ΔEGFR monoclonal antibody, mAb806, we treated nude mice bearing intracranial ΔEGFR-overexpressing glioma xenografts with intraperitoneal injections of mAb806, the isotype control IgG or PBS.

Because primary explants of human glioblastomas rapidly lose expression of amplified, rearranged receptors in culture, no existing glioblastoma cell lines exhibit such expression. To force maintenance of expression levels comparable with those seen in human tumors, U87MG, LN-Z308, and A1207 (gift from Dr. S. Aaronson, Mount Sinai Medical Center, New York, N.Y.) cells were infected with ΔEGFR, kinase-deficient ΔEGFR (DK), or wild-type EGFR (wtEGFR) viruses, which also conferred resistance to G418 as described previously (Nishikawa et al. (1994) A mutant epidermal growth factor receptor common in human glioma confers enhanced tumorigenicity. *Proc. Natl. Acad. Sci. U.S.A.*, 91, 7727-7731).

Populations expressing similar levels of the various EGFR alleles (these expression levels correspond approximately to an amplification level of 25 gene copies; human glioblastomas typically have amplification levels from 10 to 50 gene copies of the truncated receptor) were selected by FACS as described previously (Nishikawa et al., 1994) and designated as U87MG.ΔEGFR, U87MG.DK, U87MG.wtEGFR, LN-Z308.ΔEGFR, LN-Z308.DK, LN-Z308.wtEGFR, A1207.ΔEGFR, A1207.DK, and A1207.wtEGFR, respectively. Each was maintained in medium containing G418 (U87MG cell lines, 400 μg/ml; LN-Z308 and A1207 cell lines, 800 μg/ml).

U87MG.ΔEGFR cells ($1\times10^5$) or $5\times10^5$ LN-Z308.ΔEGFR, A1207.ΔEGFR, U87MG, U87MG.DK, and U87MG.wtEGFR cells in 5 μl of PBS were implanted into the right corpus stratum of nude mice brains as described previously (Mishima et al. (2000) A peptide derived from the non-receptor binding region of urokinase plasminogen activator inhibits glioblastoma growth and angiogenesis in vivo in combination with cisplatin. *Proc. Natl. Acad. Sci. U.S.A.* 97, 8484-8489). Systemic therapy with mAb806, or the IgG2b isotype control, was accomplished by i.p. injection of 1 μg of mAbs in a volume of 100 μl every other day from post-implantation day 0 through 14. For direct therapy of intracerebral U87MG.ΔEGFR tumors, 10 μg of mAb806, or the IgG2b isotype control, in a volume of 5 μl were injected at the tumor-injection site every other day starting at day 1 for 5 days.

Figure 24A:
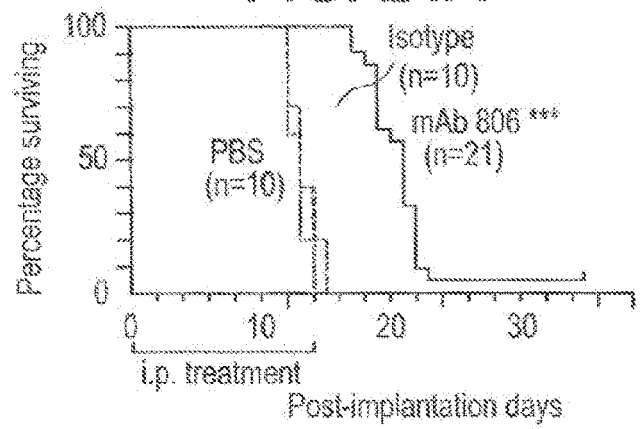
FIGS. 24A and 24B show extended survival of nude mice bearing intracranial U87MG.ΔEGFR (A) and LN-Z308.ΔEGFR (B) xenografts with systemic mAb806 treatment. U87MG.EGFR cells ($1\times10^5$) or LN-Z308.ΔEGFR cells ($5\times10^5$) were implanted into nude mice brains, and the animals were treated with either mAb806, PBS, or isotype IgG from post-implantation days 0 through 14.

Animals treated with PBS or isotype control IgG had a median survival of 13 days, whereas mice treated with mAb806 had a 61.5% increase in median survival up to 21 days (P<0.001; FIG. 24A).

Treatment of mice 3 days post-implantation, after tumor establishment, also extended the median survival of the mAb806-treated animals by 46.1% (from 13 days to 19 days; P<0.01) compared with that of the control groups (data not shown).

Figure 24B:
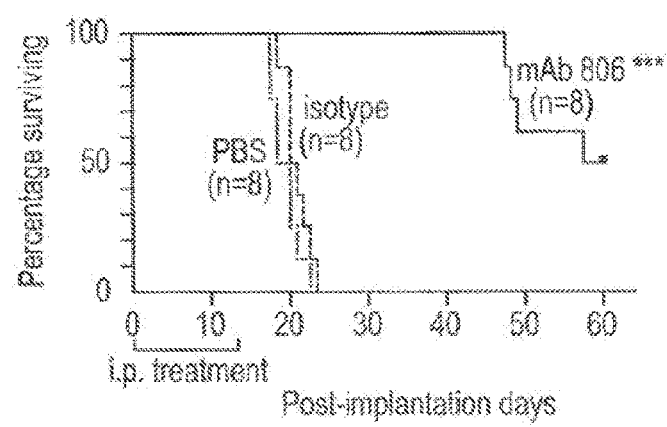

To determine whether these antitumor effects of mAb806 extended beyond U87MG.ΔEGFR xenografts, similar treatments were administered to animals bearing other glioma cell xenografts of LN-Z308.ΔEGFR and A1207.ΔEGFR. The median survival of mAb806-treated mice bearing LN-Z308.ΔEGFR xenografts was extended from 19 days for controls to 58 days (P<0.001; FIG. 24B). Remarkably, four of eight mAb806-treated animals survived beyond 60 days (FIG. 24B). The median survival of animals bearing A1207.ΔEGFR xenografts was also extended from 24 days for controls to 29 days (P<0.01; data not shown).

mAb806 Treatment Inhibits ΔEGFR-Overexpressing Brain Tumor Growth

Figure 24E:
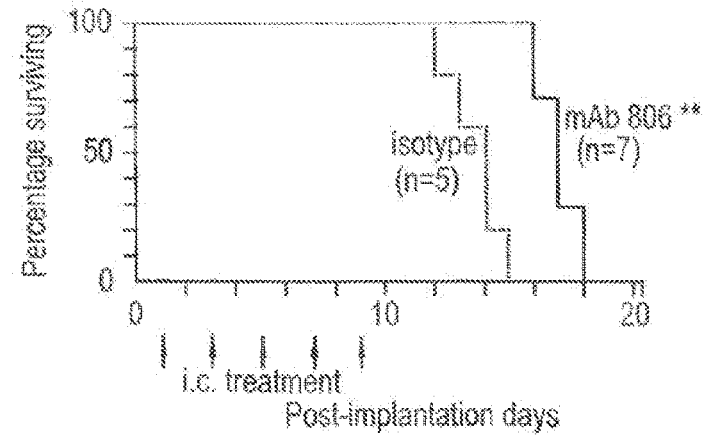
FIG. 24E shows extended survival of nude mice bearing intracranial U87MG.ΔEGFR xenografts with intratumoral mAb806 treatment. U87MG.ΔEGFR cells were implanted as described. 10 mg of mAb806 or isotype IgG control in a volume of 5 μl were injected at the tumor-injection site every other day starting at day 1 for five times.
Figure 24C:
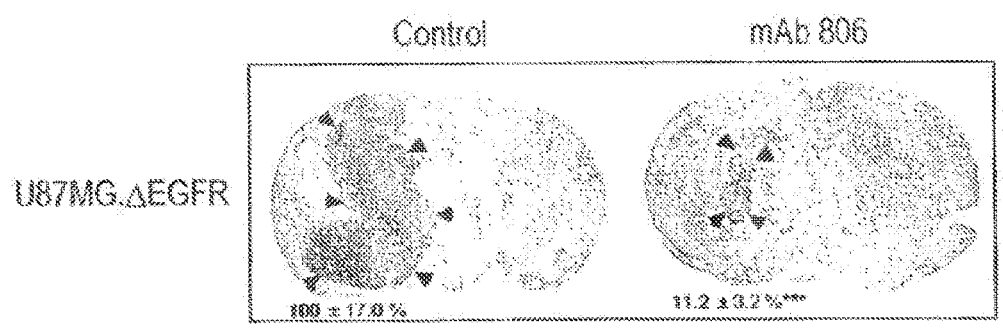
FIGS. 24C and 24D show growth inhibition of intracranial tumors by mAb806 treatment. Nude mice (five per group), treated with either mAb806 or the isotype IgG control, were euthanized on day 9 for U87MG.EGFR(C) and on day 15 for LN-Z308.ΔEGFR (D), and their brains were harvested, fixed, and sectioned. Data were calculated by taking the tumor volume of control as 100%. Values are mean±SD. ***, P<0.001; control versus mAb806. Arrowheads, tumor tissue.
Figure 24D:
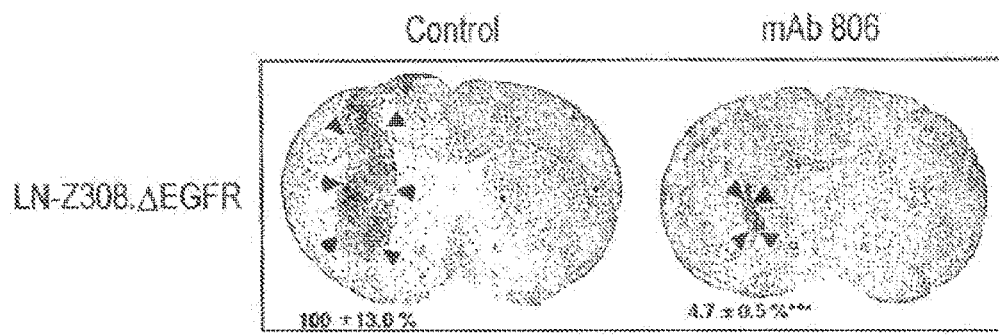

Mice bearing U87MG.ΔEGFR and LN-Z308.ΔEGFR xenografts were euthanized at day 9 and day 15, respectively. Tumor sections were histopathologically analyzed and tumor volumes were determined Consistent with the results observed for animal survival, mAb806 treatment significantly reduced the volumes by about 90% of U87MG.ΔEGFR. (P<0.001; FIG. 24C) and LN-Z308.ΔEGFR by more than 95% (P<0.001; FIG. 24D) xenografts in comparison to that of the control groups. Similar results were obtained for animals bearing A1207.ΔEGFR tumors (65% volume reduction, P<0.01; data not shown).

Figure 25A:
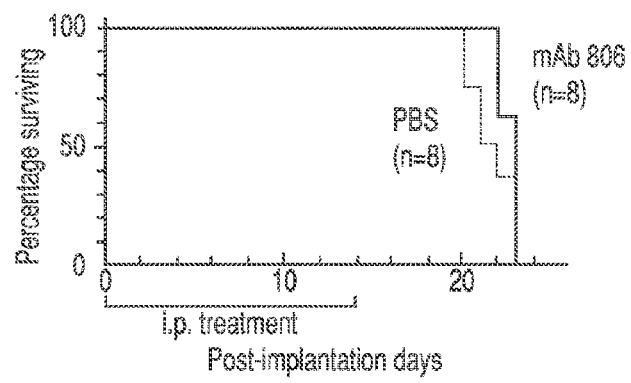
FIGS. 25A, 25B, and 25C show that mAb806 extends survival of mice with U87MG.wtEGFR brain tumors but not with U87MG.DK. or U87MG brain tumors. U87MG (A), U87MG.DK (B), or U87MG.wtEGFR(C) cells ($5\times10^5$) were implanted into nude mice brains, and the animals were treated with mAb806 from post-implantation days 0 through 14 followed by observation after discontinuation of therapy.
Figure 25B:
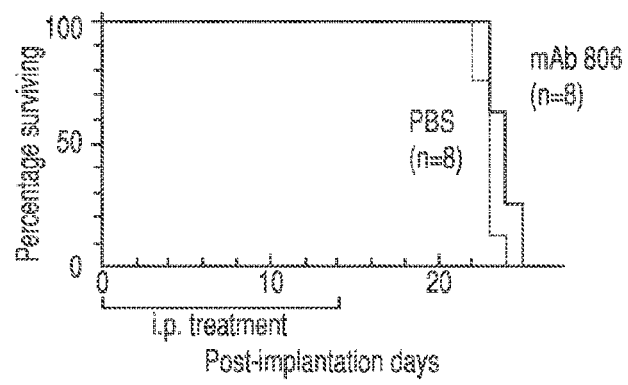
Figure 25C:
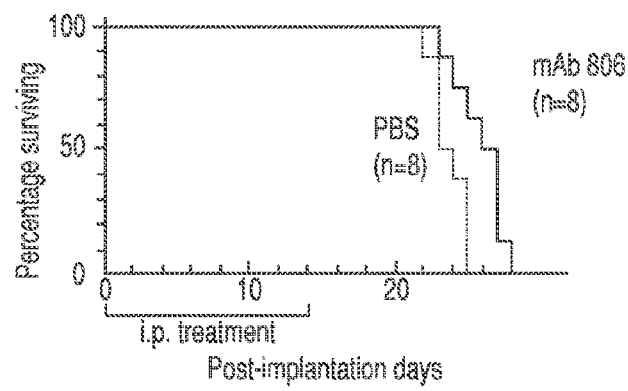

Intratumoral Treatment with mAb806 Extends Survival of Mice Bearing U87MG.ΔEGFR Brain Tumors The efficacy of direct intratumoral injection of mAb806 for the treatment of U87MG.ΔEGFR xenografts was also determined Animals were given intratumoral injections of mAb806 or isotype control IgG one day post-implantation. Control animals survived for 15 days, whereas mAb806 treated mice remained alive for 18 days (P<0.01; FIG. 24E). While the intratumoral treatment with mAb806 was somewhat effective, it entailed the difficulties of multiple intracranial injections and increased risk of infection. We therefore focused on systemic treatments for further studies.

mAb806 Treatment Slightly Extends Survival of Mice Bearing U87MG.wtEGFR but not U87MG or U87MG.DK Intracranial Xenografts To determine whether the growth inhibition by mAb806 was selective for tumors expressing ΔEGFR, we treated animals bearing U87MG, U87MG.DK (kinase deficient ΔEGFR) and U87MG.wtEGFR brain xenografts. mAb806 treatment did not extend survival of mice implanted with U87MG tumors (FIG. 25A) which expressed a low level of endogenous wild-type EGFR (wtEGFR) (Huang et al. (1997) The enhanced tumorigenic activity of a mutant epidermal growth factor receptor common in human cancers is mediated by threshold levels of constitutive tyrosine phosphorylation and unattenuated signaling. *J. Biol. Chem.*, 272, 2927-2935), or animals bearing U87MG.DK xenografts which overexpressed a kinase-deficient ΔEGFR in addition to a low level of endogenous wtEGFR (FIG. 25B). The mAb806 treatment slightly extended the survival of mice bearing U87MG.wtEGFR tumors (P<0.05, median survival 23 days versus 26 days for the control groups) which overexpressed wtEGFR (FIG. 25C).

mAb806 Reactivity Correlates with In Vivo Anti-Tumor Efficacy

To understand the differential effect of mAb806 on tumors expressing various levels or different types of EGFR, we determined mAb806 reactivity with various tumor cells by FACS analysis. Stained cells were analyzed with a FACS Calibur™ using Cell Quest™ software (Becton-Dickinson PharMingen). For the first antibody, the following mAbs were used: mAb806, anti EGFR mAb clone 528, and clone EGFR. 1. Mouse IgG2a or IgG2b was used as an isotype control.

Consistent with previous reports (Nishikawa et al. (1994) A mutant epidermal growth factor receptor common in human glioma confers enhanced tumorigenicity. *Proc. Natl. Acad. Sci. U.S.A.*, 91, 7727-7731), the anti-EGFR mAb528 recognized both ΔEGFR and wtEGFR and demonstrated stronger staining for U87MG.ΔEGFR cells compared with U87MG cells (FIG. 26A, 528).

In contrast, antibody EGFR.1 reacted with wtEGFR but not with ΔEGFR (Nishikawara et al., 1994), because U87MG.ΔEGFR cells were as weakly reactive as U87MG cells (FIG. 26A, panel EGFR.1).

This EGFR.1 antibody reacted with U87MG.wtEGFR more intensively than with U87MG cells, because U87MG.wtEGFR cells overexpressed wtEGFR (FIG. 26A, panel EGFR.1). Although mAb806 reacted intensely with U87MG.ΔEGFR and U87MG.DK cells and not with U87MG cells, it reacted weakly with U87MG.wtEGFR, which indicated that mAb806 is selective for ΔEGFR with a weak cross-activity to overexpressed wtEGFR (FIG. 26A, panel mAb806).

This level of reactivity with U87MG.wtEGFR was quantitatively and qualitatively similar to the extension of survival mediated by the antibody treatment (FIG. 25C).

We further determined mAb806 specificity by immunoprecipitation. EGFRs in various cell lines were immunoprecipitated with antibodies mAb806, anti-EGFR mAb clone 528 (Oncogene Research Products, Boston, Mass.), or clone EGFR.1 (Oncogene Research Products).

Briefly, cells were lysed with lysis buffer containing 50 mM HEPES (pH 7.5), 150 mM NaCl, 10% glycerol, 1% Triton X-100, 2 mM EDTA, 0.1% SDS, 0.5% sodium deoxycholate, 10 mM sodium PPi, 1 mM phenylmethlsulfonyl fluoride, 2 mM Na3 V0$_4$, 5 µg/ml leupeptin, and 5 µg/ml aprotinin. Antibodies were incubated with cell lysates at 4° C. for 1 h before the addition of protein-A and -G Sepharose Immunoprecipitates were washed twice with lysis buffer and once with HNTG buffer [50 mM HEPES (pH 7.5), 150 mM NaCl, 0.1% Triton X-100, and 10% glycerol], electrophoresed, and transferred to nitrocellulose membranes.

Blots of electrophoretically-separated proteins were probed with the anti-EGFR antibody, C13 (provided by Dr. G. N. Gill, University of California, San Diego, Calif.), used for detection of both wild-type and ΔEGFR on immunoblots (Huang et al., 1997), and proteins were visualized using the ECL™ chemiluminescent detection system (Amersham Pharmacia Biotech.). Antibodies to Bcl-X (rabbit poly-clonal antibody; Transduction Laboratories, Lexington, Ky.) and phosphotyrosine (4G10, Upstate Biotechnology, Lake Placid, N.Y.) were used for Western blot analysis as described previously (Nagane et al. (1998) Drug resistance of human glioblastoma cells conferred by a tumor-specific mutant epidermal growth factor receptor through modulation of Bcl-XL and caspase-3-like proteases. *Proc. Natl. Acad. Sci U.S.A.* 95, 5724-5729).

Consistent with the FACS analysis, antibody 528 recognized wtEGFR and mutant receptors (FIG. 26B-*panel* IP: 528), whereas antibody EGFR.1 reacted with wtEGFR but not with the mutant species (FIG. 26B, panel IP:EGFR.1). Moreover, the levels of mutant receptors in U87MG.ΔEGFR and U87MG.DK cells are comparable with those of wtEGFR in the U87MG.wtEGFR cells (FIG. 26B, panel IP: 528).

However, antibody mAb806 was able to precipitate only a small amount of the wtEGFR from the U87MG.wtEGFR cell lysates as compared with the larger amount of mutant receptor precipitated from U87MG.ΔEGFR and U87MG.DK cells, and an undetectable amount from the U87MG cells (FIG. 26B, panel IP:mAb806). Collectively, these data suggest that mAb806 recognizes an epitope in ΔEGFR that also exists in a small fraction of wtEGFR only when it is overexpressed on the cell surface (see further discussion of and references to the mAb806 epitope below).

mAb806 Treatment Reduces ΔEGFR Autophosphorylation and Down-Regulates Bcl.X$_L$ Expression in U87MG.ΔEGFR Brain Tumors The mechanisms underlying the growth inhibition by mAb806 were next investigated. Since the constitutively active kinase activity and autophosphorylation of the carboxyl terminus of ΔEGFR are essential for its biological functions (Nishikawa et al. (1994) A mutant epidermal growth factor receptor common in human glioma confers enhanced tumorigenicity. *Proc. Natl. Acad. Sci. U.S.A.* 91, 7727-7731; Huang et al., 1997; Nagane et al. (1996) A common mutant epidermal growth factor receptor confers enhanced tumorigenicity on human glioblastoma cells by increasing proliferation and reducing apoptosis. *Cancer Res.*, 56, 5079-5086; Nagane et al. (2001) Aberrant receptor signaling in human malignant gliomas: mechanisms and therapeutic implications. *Cancer Lett.* 162 (Suppl. 1), S17-S21) ΔEGFR phosphorylation status was determined in tumors from treated and control animals. As shown in FIG. 27A, mAb806 treatment dramatically reduced ΔEGFR autophosphorylation, although receptor levels were only slightly decreased in the mAb806-treated xenografts. We have previously shown that receptor autophosphorylation causes upregulation of the antiapoptotic gene, Bcl-X$_L$, which plays a key role in reducing apoptosis of ΔEGFR-overexpressing tumors (Nagane et al., 1996; Nagane et al., 2001). Therefore, the effect of mAb806 treatment on Bcl-X$_L$ expression was next determined ΔEGFR tumors from mAb806-treated animals did indeed show reduced levels of Bcl-X$_L$ (FIG. 27A).

mAb806 Treatment Decreases Growth and Angiogenesis, and Increases Apoptosis in U87MG.ΔEGFR Tumors In light of the in vivo suppression caused by mAb806 treatment and its biochemical effects on receptor signaling, we determined the proliferation rate of tumors from control or treated mice. The proliferative index, measured by Ki-67 staining of the mAb806-treated tumors, was significantly lower than that of the control tumors (P<0.001; FIG. 28).

Briefly, to assess angiogenesis in tumors, they were fixed in a solution containing zinc chloride, paraffin embedded, sectioned, and immunostained using a monoclonal rat anti-mouse CD31 antibody (Becton-Dickinson PharMingen; 1:200). Assessment of tumor cell proliferation was performed by Ki-67 immunohistochemistry on formalin-fixed paraffin-embedded tumor tissues. After deparaffinization and rehydration, the tissue sections were incubated with 3% hydrogen peroxide in methanol to quench endogenous peroxidase. The sections were blocked for 30 min with goat serum and incubated overnight with the primary antibody at 4° C. The sections were then washed with PBS and incubated with a biotinylated secondary antibody for 30 min. After several washes with PBS, products were visualized using streptavidin horseradish peroxidase with diaminobenzidine as chromogen and hematoxylin as the counterstain. As a measure of proliferation, the Ki-67 labeling index was determined as the ratio of labeled:total nuclei in high-power (3400) fields.

Approximately 2000 nuclei were counted in each case by systematic random sampling. For macrophage and NK cell staining, frozen sections, fixed with buffered 4% paraformaldehyde solution, were immunostained using biotinylated mAbF4/80 (Serotec, Raleigh, N.C.) and polyclonal rabbit anti-asialo GM1 antibody (Dako Chemicals, Richmond, Va.), respectively. Angiogenesis was quantitated as vessel area using computerized analysis. For this purpose, sections were immunostained using anti-CD31 and were analyzed using a computerized image analysis system without counterstain. MVAs were determined by capturing digital images of the sections at 3200 magnification using a CCD color camera as described previously (Mishima et al., 2000). Images were then analyzed using Image Pro® Plus version 4.0 software (Media Cybernetics, Silver Spring, Md.) and MVA was determined by measuring the total amount of staining in each section. Four fields were evaluated for each slide. This value was represented as a percentage of the total area in each field. Results were confirmed in each experiment by at least two observers (K. M., H-J. S. H.).

In addition, apoptotic cells in tumor tissue were detected by using the TUNEL method as described previously (Mishima et al., 2000). TUNEL-positive cells were counted at X400. The apoptotic index was calculated as a ratio of apoptotic cell number:total cell number in each field. Analysis of the apoptotic index through TUNEL staining demonstrated a significant increase in the number of apoptotic cells in mAb806 treated tumors as compared with the control tumors (P<0.001; FIG. 28).

The extent of tumor vascularization was also analyzed by immunostaining of tumors from treated and control specimens for CD31. To quantify tumor vascularization, microvascular areas (MVAs) were measured using computerized image analysis. mAb806-treated tumors showed 30% less MVA than did control tumors (P<0.001; FIG. 28).

To understand whether interaction between receptor and antibody may elicit an inflammatory response, we stained tumor sections for the macrophage marker, F4/80, and the NK cell marker, asialo GM1. Macrophages were identified throughout the tumor matrix and especially accumulated around the mAb806-treated-U87MG.ΔEGFR-tumor periphery (FIG. 28). We observed few NK cells infiltrated in and around the tumors and no significant difference between mAb806-treated and isotype-control tumors (data not shown).

Example 17

Combination Immunotherapy with mAb806 and mAb528

The experiments set forth herein describe in vivo work designed to determine the efficacy of antibodies in accordance with this invention.

Female nude mice, 4-6 weeks old, were used as the experimental animals. Mice received subcutaneous inoculations of $3 \times 10^6$ tumor cells in each of their flanks.

The animals received either U87MG.D2-7, U87MG.DK, or A431 cells, all of which are described, supra. Therapy began when tumors had grown to a sufficient size.

Mice then received injections of one of (i) phosphate buffered saline, (ii) mAb806 (0.5 mg/injection), (iii) mAb528 (0.5 mg/injection), or (iv) a combination of both mAbs. With respect to "(iv)," different groups of mice received either 0.5 mg/injection of each mAb, or 0.25 mg/injection of each mAb.

The first group of mice examined were those which had received U87MG.D2-7 injections. The treatment protocol began 9 days after inoculation, and continued 3 times per week for 2 weeks (i.e., the animals were inoculated 9, 11, 13, 16, 18 and 20 days after they were injected with the cells). At the start of the treatment protocol, the average tumor diameter was 115 mm³ Each group contained 50 mice, each with two tumors.

Figure 18A:
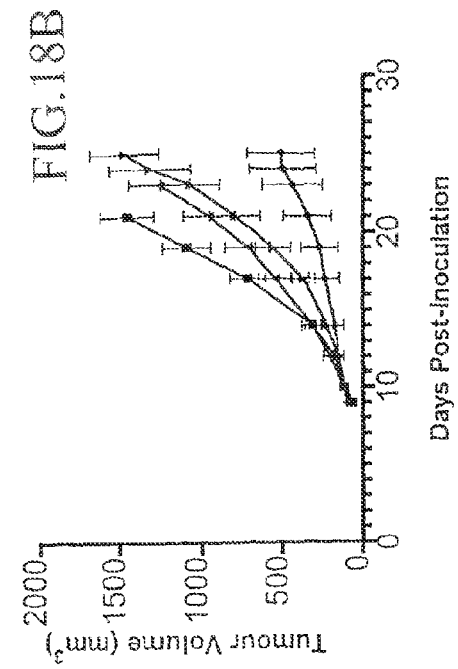
FIGS. 18A-18D show the results of in vivo studies designed to determine the therapeutic effect of combination antibody therapy, particularly mAb806 and the 528 antibody. Mice received inoculations of U87MG.D2-7 (A and B), U87MG.DK (C), or A431 (D) cells.

Within the group of mice which received the combination of antibodies (0.5 mg/injection of each), there were three complete regressions. There were no regressions in any of the other groups. FIG. 18A shows the results graphically.

Figure 18B:
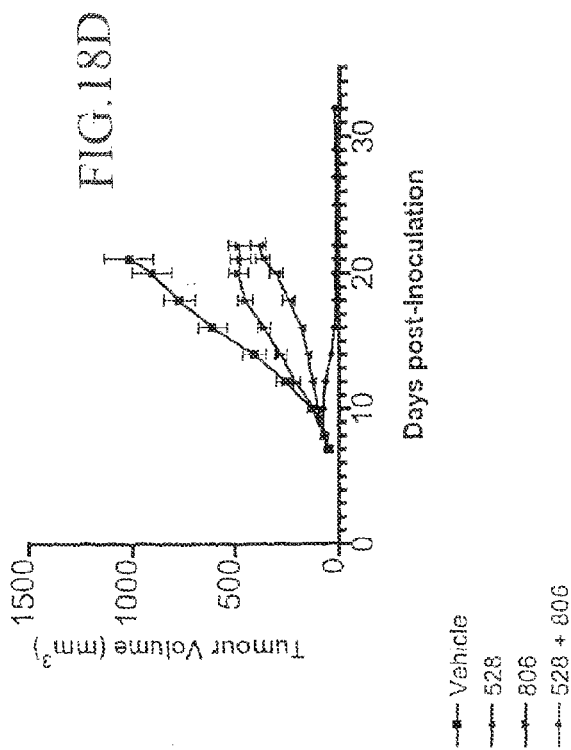

In a second group of mice, the injected materials were the same, except the combination therapy contained 0.25 mg of each antibody per injection. The injections were given 10, 12, 14, 17, 19 and 21 days after inoculation with the cells. At the start of the therapy the average tumor size was 114 mm³ Results are shown in FIG. 18B.

Figure 18C:
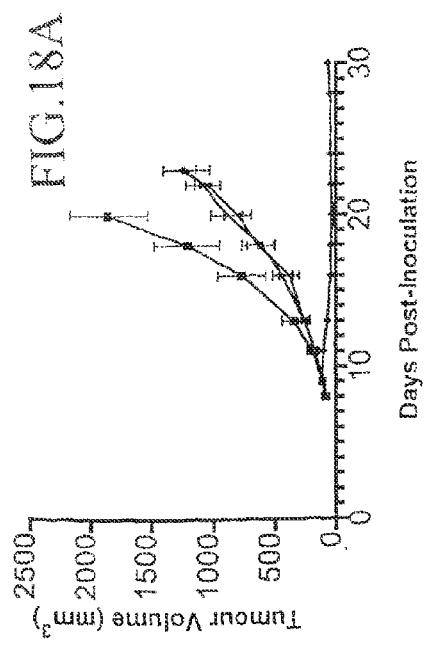

The third group of mice received inoculations of U87MG.DK. Therapeutic injections started 18 days after inoculation with the cells, and continued on days 20, 22, 25, 27 and 29. The average tumor size at the start of the treatment was 107 mm³ FIG. 18C summarizes the results. The therapeutic injections were the same as in the first group.

Finally, the fourth group of mice, which had been inoculated with A431 cells, received injections as in groups I and III, at 8, 10, 12 and 14 days after inoculation. At the start, the average tumor size was 71 mm³ Results are shown in FIG. 18D.

The results indicated that the combination antibody therapy showed a synergistic effect in reducing tumors. See FIG. 18A. A similar effect was seen at a lower dose, as per FIG. 18B, indicating that the effect is not simply due to dosing levels.

The combination therapy did not inhibit the growth of U87MG.DK (FIG. 18C), indicating that antibody immune function was not the cause for the decrease seen in FIGS. 18A and 18B.

Figure 18D:
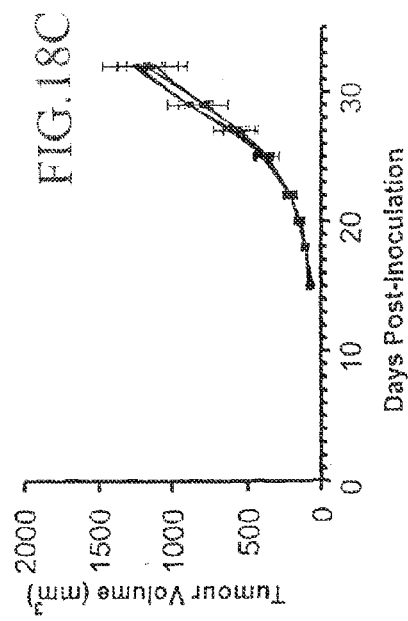

It is noted that, as shown in FIG. 18D, the combination therapy also exhibited synergistic efficacy on A431 tumors, with 4 doses leading to a 60% complete response rate. These data suggest that the EGFR molecule recognized by mAb806 is functionally different from that inhibited by 528.

Example 18 mAb806 Inhibition of Tumor Xenografts Growth

As discussed herein, and further demonstrated and discussed in this Example, mAb806 has been unexpectedly been found to inhibit the growth of tumor xenografts expressing either de2-7 or amplified EGFR, but not wild-type EGFR Cell lines and antibodies were prepared as described in Example 1. To determine the specificity of mAb806, its binding to U87MG, U87MG.D2-7, and U87MG.wtEGFR cells was analyzed by FACS. Briefly, cultured parental and transfected U87MG cell lines were analyzed for wild-type and de2-7EGFR expression using the 528, 806, and DH8.3 antibodies. Cells (1 3 10 6) were incubated with 5 μg/ml of the appropriate antibody or an isotype-matched negative control in PBS containing 1% HSA for 30 min at 4° C. After three washes with PBS/1% HSA, cells were incubated an additional 30 min at 4° C. with FTTC-coupled goat anti-mouse antibody (1:100 dilution; Calbiochem, San Diego, Calif.). After three subsequent washes, cells were analyzed on an Epics Elite ESP (Beckman Coulter, Hialeah, Fla.) by observing a minimum of 20,000 events and analyzed using EXPO (version 2) for Windows. An irrelevant IgG2b (mAb 100-310 directed to the human antigen A33) was included as an isotype control for mAb806, and the 528 antibody was included because it recognizes both the de2-7 and wtEGFR.

Only the 528 antibody was able to stain the parental U87MG cell line (FIG. 29), consistent with previous reports demonstrating that these cells express the wtEGFR (Nishikawa et al. (1994) A mutant epidermal growth factor receptor common in human glioma confers enhanced tumorigenicity. *Proc. Natl. Acad. Sci. U.S.A.* 91, 7727-7731). mAb806 had binding levels similar to the control antibody, clearly demonstrating that it is unable to bind the wtEGFR (FIG. 29). Binding of the isotype control antibody to the U87MG.D2-7 and U87MG.wtEGFR cell lines was similar to that observed for the U87MG cells. mAb806 stained U87MG.D2-7 and U87MG.wtEGFR cells, indicating that mAb806 specifically recognized the de2-7 EGFR and a subset of the overexpressed EGFR (FIG. 29). As expected, the 528 antibody stained both the U87MG.D2-7 and U87MG.wtEGFR cell lines (FIG. 29). The intensity of 528 antibody staining on U87MG.wtEGFR cells was much higher than mAb806, suggesting that mAb806 only recognizes a portion of the overexpressed EGFR. The mAb806 reactivity observed with U87MG.wtEGFR cells is similar to that obtained with A431 cells, another cell line that over expresses the wtEGFR.3

A Scatchard analysis was performed using U87MG.D2-7 and A431 cells to determine the relative affinity and binding sites for mAb806 on each cell line. mAb806 had an affinity for the de2-7EGFR receptor of $1.1 \times 10^9 M^{-1}$ and recognized an average (three separate experiments) of $2.4 \times 10^5$ binding sites/cell, as noted in Example 4. In contrast, the affinity of mAb806 for the wtEGFR on A431 cells was only $9.5 \times 10^7$ $M^{-1}$, as noted in Example 8. Interestingly, mAb806 recognized $2.3 \times 10^5$ binding sites on the surface of A431, which is some 10-fold lower than the reported number of EGFR found in these cells. To confirm the number of EGFR on the surface of our A431 cells, we performed a Scatchard analysis using $^{125}I$-labeled 528 antibody. As expected, this antibody bound to approximately $2 \times 10^6$ sites on the surface of A431 cells. Thus, it appears that mAb806 only binds a portion of the EGFR receptors on the surface of A431 cells. Importantly, $^{125}I$-labeled mAb806 did not bind to the parental U87MG cells at all, even when the number of cells was increased to $1 \times 10^7$.

mAb806 reactivity was further characterized in the various cell lines by immunoprecipitation after $^{35}S$-labeling using mAb806, sc-03 (a commercial polyclonal antibody specific for the COOH-terminal domain of the EGFR) and a IgG2b isotype control. Briefly, cells were labeled for 16 h with 100 mCi/ml of Tran $^{35}S$-Label (ICN Biomedicals, Irvine, Calif.) in DMEM without methionine/cysteine supplemented with 5% dialyzed FCS. After washing with PBS, cells were placed in lysis buffer (1% Triton X-100, 30 mM HEPES, 150 mM NaCl, 500 μM 4-(2-aminoethyl)benzenesulfonylfluoride (AEBSF), 150 nM aprotinin, 1 μM E-64 protease inhibitor, 0.5 mM EDTA, and 1 μM leupeptin, pH 7.4) for 1 h at 4° C. Lysates were clarified by centrifugation for 10 min at 12,000 g and then incubated with 5 μg of appropriate antibody for 30 min at 4° C. before the addition of Protein A-Sepharose Immunoprecipitates were washed three times with lysis buffer, mixed with SDS sample buffer, separated by gel electrophoresis using a 4-20% Tris/glycine gel that was then dried, and exposed to X-ray film.

Figure 22:
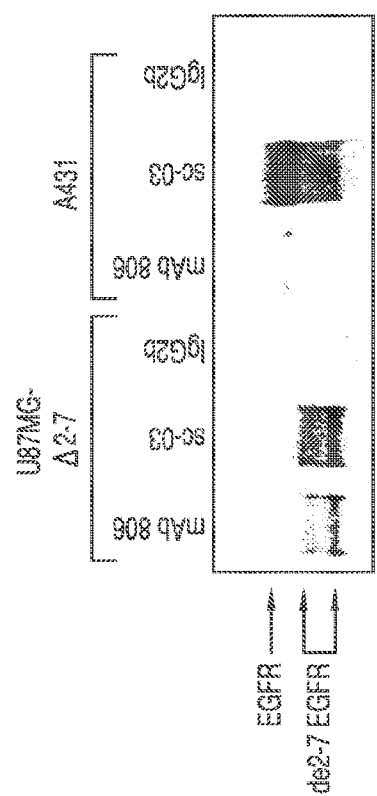
FIG. 22 shows immunoprecipitation of EGFR from cell lines. The EGFR was immunoprecipitated from $^{35}$S-labeled U87MG.Δ2-7 or A431 cells with mAb806, sc-03 antibody or a IgG2b isotype control. Arrows at the side indicate the position of the de2-7 and wt EGFR. Identical banding patterns were obtained in 3 independent experiments.

The sc-03 antibody immunoprecipitated three bands from U87MG.Δ2-7 cells; a doublet corresponding to the 2 de2-7 EGFR bands observed in these cells and a higher molecular weight band corresponding to the wtEGFR (FIGS. 22 and 30). In contrast, while mAb806 immunoprecipitated the two de2-7 EGFR bands, the wtEGFR was completely absent. The pattern seen in U87MG.wtEGFR and A431 cells was essentially identical. The sc-03 antibody immunoprecipitated a single band corresponding to the wtEGFR from A431 cells (FIGS. 22 and 30). mAb806 also immunoprecipitated a single band corresponding to the wtEGFR from both U87MG.wtEGFR and A431 cells (FIGS. 22 and 30). Consistent with the FACS and Scatchard data, the amount of EGFR immunoprecipitated by mAb806 was substantially less than the total EGFR present on the cell surface. Given that mAb806 and the sc-03 immunoprecipitated similar amounts of the de2-7 EGFR, this result supports the notion that the mAb806 antibody only recognizes a portion of the EGFR in cells overexpressing the receptor. Comparisons between mAb806 and the 528 antibody showed an identical pattern of reactivity (data not shown). An irrelevant IgG2b (an isotype control for mAb806) did not immunoprecipitate EGFR from either cell line (FIGS. 22 and 30). Using identical conditions, mAb806 did not immunoprecipitate the EGFR from the parental U87MG cells (data not shown).

mAb806 was also examined for efficacy against U87MG and U87MG.Δ2-7 tumors in a preventative xenograft model. Antibody or vehicle was administered i.p. the day before tumor inoculation and was given three times per week for 2 weeks. At a dose of 1 mg/injection, mAb806 had no effect on the growth of parental U87MG xenografts that express the wtEGFR (FIG. 9A). In contrast, mAb806 inhibited significantly the growth of U87MG.Δ2-7 xenografts in a dose-dependent manner (FIG. 9B). Twenty days after tumor inoculation, when control animals were sacrificed, the mean tumor volume was $1600 \pm 180$ mm$^3$ for the control group, a significantly smaller $500 \pm 95$ mm$^3$ for the 0.1 mg/injection group ($P<0.0001$) and $200 \pm 42$ mm$^3$ for the 1 mg/injection group ($P<0.0001$). Treatment groups were sacrificed at day 24, at which time the mean tumor volumes were $1300 \pm 240$ mm$^3$ for the 0.1 mg treated group and $500 \pm 100$ mm$^3$ for the 1 mg group ($P<0.005$).

Given the efficacy of mAb806 in the preventative xenograft model, its ability to inhibit the growth of established tumor xenografts was examined. Antibody treatment was as described in the preventative model, except that it commenced when tumors had reached a mean tumor volume of 65 mm$^3$ (10 days after implantation) for the U87MG.Δ2-7 xenografts and 84 mm$^3$ (19 days after implantation) for the parental U87MG xenografts (see Example 10). Once again, mAb806 had no effect on the growth of parental U87MG xenografts, even at a dose of 1 mg/injection (FIG. 10A). In contrast, mAb806 significantly inhibited the growth of U87MG.Δ2-7 xenografts in a dose-dependent manner (FIG. 10B). At day 17, one day before control animals were sacrificed, the mean tumor volume was $900 \pm 200$ mm$^3$ for the control group, $400 \pm 60$ mm$^3$ for the 0.1 mg/injection group ($P<0.01$), and $220 \pm 60$ mm$^3$ for the 1 mg/injection group ($P<0.002$). Treatment of U87MG.Δ2-7 xenografts with an IgG2b isotype control had no effect on tumor growth (data not shown).

To examine whether the growth inhibition observed with mAb806 was restricted to cells expressing de2-7 EGFR, its efficacy against the U87MG.wtEGFR xenografts was also examined in an established model. These cells serve as a model for tumors containing amplification of the EGFR gene without de2-7 EGFR expression. mAb806 treatment commenced when tumors had reached a mean tumor volume of 73 mm$^3$ (22 days after implantation). mAb806 significantly inhibited the growth of established U87MG.wtEGFR xenografts when compared with control tumors treated with vehicle (FIG. 10C). On the day control animals were sacrificed, the mean tumor volume was $1000 \pm 300$ mm$^3$ for the control group and $500 \pm 80$ mm$^3$ for the group treated with 1 mg/injection ($P<0.04$).

To evaluate potential histological differences between mAb806-treated and control U87MG.Δ2-7 and U87MG.wtEGFR xenografts, formalin-fixed, paraffin-embedded sections were stained with H&E (FIG. 31). Areas of necrosis were seen in sections from mAb806-treated U87MG.Δ2-7 (mAb806-treated xenografts were collected 24 days after tumor inoculation and vehicle treated xenografts at 18 days), and U87MG.wtEGFR xenografts (mAb806 xenografts were collected 42 days after tumor inoculation and vehicle treated xenografts at 37 days; FIG. 31). This result was consistently observed in a number of tumor xenografts (n=4 for each cell line). However, sections from U87MG.Δ2-7 and U87MG.wtEGFR xenografts treated with vehicle (n=5) did not display the same areas of necrosis seen after mAb806 treatment (FIG. 31). Vehicle and mAb806-treated xenografts removed at identical times also showed these differences in tumor necrosis (data not shown). Thus, the increase in necrosis observed was not caused by the longer growth periods used for the mAb806-treated xenografts. Furthermore, sections from mAb806-treated U87MG xenografts were also stained with H&E and did not reveal any areas of necrosis (data not shown), further supporting the hypothesis that mAb806 binding induces decreased cell viability, resulting in increased necrosis within tumor xenografts.

An immunohistochemical analysis of U87MG, U87MG.Δ2-7, and U87MG.wtEGFR xenograft sections was performed to determine the levels of de2-7 and wtEGFR expression after mAb806 treatment (FIG. 32). As expected, the 528 antibody stained all xenografts sections with no obvious decrease in intensity between treated and control tumors (FIG. 32). Staining of U87MG sections was undetectable with the mAb806; however, positive staining of U87MG.Δ2-7 and U87MG.wtEGFR xenograft sections was observed (FIG. 32). There was no difference in mAb806 staining intensity between control and treated U87MG.Δ2-7 and U87MG.wtEGFR xenografts, suggesting that antibody treatment does not lead to the selection of clonal variants lacking mAb806 reactivity.

To demonstrate that the antitumor effects of mAb806 were not restricted to U87MG cells, the antibody was administrated to mice containing A431 xenografts. These cells contain an amplified EGFR gene and express approximately $2 \times 10^6$ receptors/cells. We have previously shown that mAb806 binds ~10% of these EGFRs and targets A431 xenografts (Garcia et al. (1993) Expression of mutated epidermal growth factor receptor by non-small cell along carcinomas. *Cancer Res.* 53, 3217-3220). mAb806 significantly inhibited the growth of A431 xenografts when examined in the preventative xenograft model described previously (FIG. 11A). At day 13, when control animals were sacrificed, the mean tumor volume was $1400\pm150$ mm$^3$ in the vehicle-treated group and $260\pm60$ mm$^3$ for the 1 mg/injection treatment group (P<0.0001). In a separate experiment, a dose of 0.1 mg of mAb also inhibited significantly (P<0.05) the growth of A431 xenografts in a preventative model (data not shown) (see Example 10).

Given the efficacy of mAb806 in the preventative A431 xenograft model, its ability to inhibit the growth of established tumor xenografts was examined Antibody treatment was as described in the preventative model, except it was not started until tumors had reached a mean tumor volume of $200\pm20$ mm$^3$ mAb806 significantly inhibited the growth of established A431 xenografts (FIG. 11B). At day 13, the day control animals were sacrificed, the mean tumor volume was $1100\pm100$ mm$^3$ for the control group and $450\pm70$ mm$^3$ for the 1 mg/injection group (P<0.0001).

Example 19

Construction, Expression and Analysis of Chimeric 806 Antibody

Chimeric antibodies are a class of molecules in which heavy and light chain variable regions of for instance, a mouse, rat or other species are joined onto human heavy and light chain regions, Chimeric antibodies are produced recombinantly. One advantage of chimeric antibodies is that they can reduce xenoantigenic effects, the inherent immunogenicity of non-human antibodies (for instance, mouse, rat or other species). In addition, recombinantly prepared chimeric antibodies can often be produced in large quantities, particularly when utilizing high level expression vectors.

For high level production, the most widely used mammalian expression system is one which utilizes the gene amplification procedure offered by dehydrofolate reductase deficient ("dhfr-") Chinese hamster ovary cells. The system is well known to the skilled artisan. The system is based upon the dehydrofolate reductase "dhfr" gene, which encodes the DHFR enzyme, which catalyzes conversion of dehydrofolate to tetrahydrofolate. In order to achieve high production, dhfr- CHO cells are transfected with an expression vector containing a functional DHFR gene, together with a gene that encodes a desired protein. In this case, the desired protein is recombinant antibody heavy chain and/or light chain.

By increasing the amount of the competitive DHFR inhibitor methotrexate (MTX), the recombinant cells develop resistance by amplifying the dhfr gene. In standard cases, the amplification unit employed is much larger than the size of the dhfr gene, and as a result the antibody heavy chain is co-amplified.

When large scale production of the protein, such as the antibody chain, is desired, both the expression level, and the stability of the cells being employed, are critical. In long term culture, recombinant CHO cell populations lose homogeneity with respect to their specific antibody productivity during amplification, even though they derive from a single, parental clone.

Bicistronic expression vectors were prepaid for use in recombinant expression of the chimeric antibodies. These bicistronic expression vectors, employ an "internal ribosomal entry site" or "IRES." In these constructs for production of chimeric anti-EGFR, the immunoglobulin chains and selectable markers cDNAs are linked via an IRES. IRES are cis-acting elements that recruit the small ribosomal subunits to an internal initiator codon in the mRNA with the help of cellular trans-acting factors. IRES facilitate the expression of two or more proteins from a polycistronic transcription unit in eukaryotic cells. The use of bicistronic expression vectors in which the selectable marker gene is translated in a cap dependent manner, and the gene of interest in an IRES dependent manner, has been applied to a variety of experimental methods. IRES elements have been successfully incorporated into vectors for cellular transformation, production of transgenic animals, recombinant protein production, gene therapy, gene trapping, and gene targeting.

Synopsis of Chimeric Antibody 806 (ch806) Construction

The chimeric 806 antibody was generated by cloning the VH and VL chains of the 806 antibody from the parental murine hybridoma using standard molecular biology techniques. The VH and VL chains were then cloned into the pREN mammalian expression vectors, the construction of which are set forth in SEQ ID NO:7 and SEQ ID NO:8, and transfected into CHO (DHFR-/-ve) cells for amplification and expression. Briefly, following trypsinization $4 \times 10^6$ CHO cells were co-transferred with 10 μg of each of the LC and HC expression vectors using electroporation under standard conditions. Following a 10 min rest period at room temperature, the cells were added to 15 ml medium (10% fetal calf serum, hypoxanthine/thymidine supplement with additives) and transferred to 15×10 cm cell culture petri dishes. The plates were then placed into the incubator under normal conditions for 2 days.

At this point, the addition of gentamycin, 5 nM methotrexate, the replacement of fetal calf serum with dialyzed fetal calf serum and the removal of hypoxanthine/thymidine, initiated the selection for clones that were successfully transfected with both the LC and HC from the medium. At day 17 following transfection, individual clones growing under selection were picked and screened for expression of the chimeric 806 antibody. An ELISA was utilized for screening and consisted of coating an ELISA plate with denatured soluble EGF receptor (denatured EGFR is known to allow 806 binding). This assay allows for the screening of production levels by individual clones and also for the functionality of the antibody being screened. All clones were shown to be producing functional ch806 and the best producer was taken and expanded for amplification. To amplify the level of ch806 being produced, the highest producing clone was subjected to reselection under a higher methotrexate concentration (100 nM vs. 5 nM). This was undertaken using the aforementioned procedures.

Clones growing at 100 nM MTX were then passed onto the Biological Production Facility, Ludwig Institute, Melbourne, Australia for measurement of production levels, weaning off serum, cell banking. The cell line has been shown to stably produce ~10 mg/liter in roller bottles.

The nucleic acid sequence of the pREN ch806 LC neo vector is provided in SEQ ID NO:7. The nucleic acid sequence of the pREN ch806 HC DHFR vector is provided in SEQ ID NO:8.

FIG. 33 depicts the vectors pREN-HC and pREN-LC, which employ an IRES. The pREN bicistronic vector system is described and disclosed in co-pending U.S. Patent Application No. 60/355,838 filed Feb. 13, 2002, which is incorporated herein by reference in its entirety.

ch806 was assessed by FACS analysis to demonstrate that the chimeric 806 displays identical binding specificity to that of the murine parental antibody. Analysis was performed using wild-type cells (U87MG parental cells), cells overexpressing the EGF receptor (A431 cells and UA87.wtEGFR cells) and UA87.Δ2-7 cells (data not shown). Similar binding specificity of mAb806 and ch806 was obtained using cells overexpressing EGFR and cells expressing the de2-7 EGFR. No binding was observed in wild-type cells. Scatchard analysis revealed a binding affinity for radiolabeled ch806 of $6.4 \times 10^9 \text{ M}^{-1}$ using U87MGde2-7 cells (data not shown).

Biodistribution analysis of the ch806 antibody was performed in BALB/c nude mice bearing U87MG-de2-7 xenograft tumors, and the results are shown in FIG. 34. Mice were injected with 5 µg of radiolabelled antibody and were sacrificed in groups of four per time point at 8, 24, 48 and 74 hours. Organs were collected, weighed and radioactivity measured in a gamma counter. $^{125}$I-labelled ch806 displays reduced targeting to the tumor compared to $^{111}$In-labelled ch806, which has high tumor uptake and cumulative tumor retention over the 74 hour time period. At 74 hours, the $^{111}$In-labelled antibody displays approximately 30% ID/gram tissue and a tumor to blood ratio of 4.0 (FIG. 35). The $^{111}$In-labelled ch806 shows some nonspecific retention in the liver, spleen and kidneys. This is common for the use of this isotope and decreases with time, which supports that this binding is non-specific to ch806 and due to $^{111}$In binding.

Chimeric antibody ch806 was assessed for therapeutic efficacy in an established tumor model. $3 \times 10^6$ U87MG.Δ2-7 cells in 100 µl of PBS were inoculated s.c. into both flanks of 4-6 week old female nude mice (Animal Research Center, Western Australia, Australia). The mAb806 was included as a positive control. The results are depicted in FIG. 36. Treatment was started when tumors had reached a mean volume of 50 mm$^3$ and consisted of 1 mg of ch806 or mAb806 given i.p. for a total of 5 injections on the days indicated. Tumor volume in mm$^3$ was determined using the formula (length×width$^2$)/2, where length was the longest axis and width the measurement at right angles to the length. Data was expressed as mean tumor volume+/−S.E. for each treatment group. The ch806 and mAb806 displayed nearly identical anti-tumor activity against U87MG.Δ2-7 xenografts.

Analysis of Ch806 Immune Effector Function
Materials and Methods
Antibodies and Cell Lines Murine anti-de2-7 EGFR monoclonal mAb806, chimeric antibody ch806 (IgG1) and control isotype matched chimeric anti-G250 monoclonal antibody cG250 were prepared by the Biological Production Facility, Ludwig Institute for Cancer Research, Melbourne, Australia. Both complement-dependant cytotoxicity (CDC) and antibody-dependent cellular-cytotoxicity (ADCC) assays utilized U87MG.de2-7 and A431 cells as target cells. The previously described U87MG.de2-7 cell line is a human astrocytoma cell line infected with a retrovirus containing the de2-7EGFR (Nishikawa et al. (1994) *Proc. Natl. Acad. Sci. U.S.A.* 91, 7727-31). Human squamous carcinoma A431 cells were purchased from the American Type Culture Collection (Manassas, Va.). All cell lines were cultured in DMEM/F-12 with Glutamax™ (Life Technologies, Melbourne, Australia) supplemented with 10% heat-inactivated FCS(CSL, Melbourne, Australia), 100 units/ml penicillin and 100 µg/ml streptomycin. To maintain selection for retrovirally transfected U87MG.de2-7 cells, 400 µg/ml G418 was included in the media.

Preparation of Human Peripheral Blood Mononuclear Cells (PBMC) Effector Cells

PBMCs were isolated from healthy volunteer donor blood. Heparinized whole blood was fractionated by density centrifugation on Ficoll-Hypaque (ICN Biomedical Inc., Ohio, USA). PBMC fractions was collected and washed three times with RPMI$^+$ 1640 supplemented with 100 U/ml penicillin and 100 µg/ml streptomycin, 2 mM L-glutamine, containing 5% heat-inactivated FCS.

Preparation of Target Cells

CDC and ADCC assays were performed by a modification of a previously published method (Nelson, D. L. et al. (1991) In: J. E. Colignan, A. M. Kruisbeek, D. D. Margulies, E. M. Shevach, and W. Strober (eds.), Current Protocols in Immunology, pp. 7.27.1. New York: Greene Publishing Wiley Interscience). Briefly, $5 \times 10^6$ target U87MG.de2-7 and A431 cells were labeled with 50 µCi$^{51}$Cr (Geneworks, Adelaide, Australia) per $1 \times 10^6$ cells and incubated for 2 hr at 37° C. The cells were then washed three time with PBS (0.05M, pH 7.4) and a fourth wash with culture medium. Aliquots ($1 \times 10^4$ cells/50 µl) of the labeled cells were added to each well of 96-well microtitre plates (NUNC, Roskilde, Denmark).

CDC Assay

To 50 µl labeled target cells, 50 µl ch806 or isotype control antibody cG250 were added in triplicate over the concentration range 0.00315-10 µg/ml, and incubated on ice 5 min. Fifty µl of freshly prepared healthy donor complement (serum) was then added to yield a 1:3 final dilution of the serum. The microtitre plates were incubated for 4 hr at 37° C. Following centrifugation, the released $^{51}$Cr in the supernatant was counted (Cobra II automated Gamma Counter, Can berra Packard, Melbourne, Australia). Percentage specific lysis was calculated from the experimental $^{51}$Cr release, the total (50 µl target cells+100 µl 10% Tween 20) and spontaneous (50 µl target cells+100 µl medium) release.

ADCC Assay ch806-mediated ADCC effected by healthy donor PBMCs was measured by two 4-hr $^{51}$1Cr release assays. In the first assay, labelled target cells were plated with the effector cells in 96-well "U" bottom microplates (NUNC, Roskilde, Denmark) at effector/target (E:T) cell ratios of 50:1. For ADCC activity measurements, 0.00315-10 µg/ml (final concentration) test and control antibodies were added in triplicate to each well. In the second ADCC assay, the ADCC activity of ch806 was compared with the parental murine mAb806 over a range of Effector: Target cell ratios with the test antibody concentration constant at 1 µg/ml. In both assays, micotitre plates were incubated at 37° C. for 4 hours, then 50 µl supernatant was harvested from each well and released $^{51}$Cr was determined by gamma counting (Cobra II automated Gamma Counter, Can berra Packard, Melbourne, Australia). Controls included in the assays corrected for spontaneous release (medium alone) and total release (10% Tween20/PBS). Appropriate controls with the same subclass antibody were run in parallel.

The percentage cell lysis (cytotoxicity) was calculated according to the formula:

$$\text{Percentage Cytotoxicity} = \frac{\text{Sample Counts} - \text{Spontaneous Release}}{\text{Total Release} - \text{Spontaneous Release}} \times 100$$

The percent (%) cytotoxicity was plotted versus concentration of antibody (µg/ml).

Results

The results of the CDC analyses are presented in FIG. 37. Minimal CDC activity was observed in the presence of up to 10 µg/ml ch806 with CDC comparable to that observed with isotype control cG250.

ch806 mediated ADCC on target U87MG.de2-7 and A431 cells at E:T ratio of 50:1 is presented in FIG. 38. Effective ch806 specific cytotoxicity was displayed against target U87MG.de2-7 cells, but minimal ADCC was mediated by ch806 on A431 cells. The levels of cytotoxicity achieved reflect the number of ch806 binding sites on the two cell populations. Target U87MG.de2-7 cells express ~1×10$^6$ de2-7EGFR which are specifically recognized by ch806, while only a subset of the 1×10$^6$ wild-type EGFR molecules expressed on A431 cells are recognized by ch806 (see above Examples).

Further ADCC analyses were performed to compare the ADCC mediated by 1 µg/ml ch806 on target U87MG.de2-7 cells with that effected by 1 µg/ml parental murine mAb806. Results are presented in FIG. 39. Chimerization of mAb806 has effected marked improvement of the ADCC achieved by the parental murine mAb with greater than 30% cytotoxicity effected at E:T ratios 25:1 and 50:1.

The lack of parental murine mAb806 immune effector function has been markedly improved upon chimerization. ch806 mediates good ADCC, but minimal CDC activity.

Example 20

Generation of Anti-Idiotype Antibodies to Chimeric Antibody Ch806

To assist the clinical evaluation of mAb806 or ch806, laboratory assays are required to monitor the serum pharmacokinetics of the antibodies and quantitate any immune responses to the mouse-human chimeric antibody. Mouse monoclonal anti-idiotypic antibodies (anti-ids) were generated and characterized for suitability as ELISA reagents for measuring ch806 in patient sera samples and use as positive controls in human anti-chimeric antibody immune response analyses. These anti-idiotype antibodies may also be useful as therapeutic or prophylactic vaccines, generating a natural anti-EGFR antibody response in patients.

Methods for generating anti-idiotype antibodies are well known in the art (Chatterjee et al., 2001; Uemura et al., 1994; Steffens et al., 1997; Safa and Foon, 2001; Brown and Ling, 1988).

Briefly, mouse monoclonal anti-idiotypic antibodies (anti-ids) were generated as follows. Splenocytes from mice immunized with ch806 were fused with SP2/0-AG14 plasmacytoma cells and antibody producing hybridomas were selected through ELISA for specific binding to ch806 and competitive binding for antigen (FIG. 40). Twenty-five hybridomas were initially selected and four, designated LMH-11, -12, -13, and -14, secreted antibodies that demonstrated specific binding to ch806, mAb806 and were able to neutralize ch806 or mAb806 antigen binding activity (FIG. 41). The recognition of the ch806/mAb806 idiotope or CDR region was demonstrated by lack of cross-reactivity with purified polyclonal human IgG.

In the absence of readily available recombinant antigen de2-7 EGFR to assist with the determination of ch806 in serum samples, the ability of the novel anti-idiotype ch806 antibodies to concurrently bind 806 variable regions was exploited in the development of a sensitive, specific ELISA for measuring ch806 in clinical samples (FIG. 42). Using LMH-12 for capture and Biotinylated-LMH-12 for detection, the validated ELISA demonstrated highly reproducible binding curves for measuring ch806 (2 µg/ml-1.6 ng/ml) in sera with a 3 ng/ml limit of detection. (n=12; 1-100 ng/ml, Coefficient of Variation<25%; 100 ng/ml-5 µg/ml, Coefficient of Variation<15%). No background binding was evident with the three healthy donor sera tested and negligible binding was observed with isotype control hu3S193. The hybridoma produces high levels of antibody LMH-12, and larger scale production is planned to enable the measurement of ch806 and quantitation of any immune responses in clinical samples (Brown and Ling, 1988).

Results

Mice Immunization and hybridoma clone selection Immunoreactivity of pre- and post-immunization sera samples indicated the development of high titer mouse anti-ch806 and anti-huIgG mAbs. Twenty-five hybridomas producing antibodies that bound ch806, but not huIgG, were initially selected. The binding characteristics of some of these hybridomas are shown in FIGS. 42A and 42B. Four of these anti-ch806 hybridomas with high affinity binding (clones 3E3, SB8, 9D6, and 4D8) were subsequently pursued for clonal expansion from single cells by limiting dilution and designated Ludwig Institute for Cancer Research Melbourne Hybridoma (LMH)-11, -12, -13, and -14, respectively (FIG. 42).

Binding and Blocking Activities of Selected Anti-Idiotype Antibodies

The ability of anti-ch806 antibodies to concurrently bind two ch806 antibodies is a desirable feature for their use as reagents in an ELISA for determining serum ch806 levels. Clonal hybridomas, LMH-11, -12, -13, and -14 demonstrated concurrent binding (data not shown).

After clonal expansion, the hybridoma culture supernatants were examined by ELISA for the ability to neutralize ch806 or mAb806 antigen binding activity with sEGFR621. Results demonstrated the antagonist activity of anti-idiotype mAbs LMH-11, -12, -13, and -14 with the blocking in solution of both ch806 and murine mAb806 binding to plates coated with sEGFR (FIG. 41 for LMH-11, -12, -13).

Following larger scale culture in roller bottles the binding specificity's of the established clonal hybridomas, LMH-11, -12, -13, and -14 were verified by ELISA. LMH-11 through-14 antibodies were identified as isotype IgG1K by mouse monoclonal antibody isotyping kit.

ch806 in Clinical Serum Samples Pharmacokinetic ELISA Assay Development

To assist with the determination of ch806 in serum samples, the ability of the anti-idiotype ch806 antibodies to concurrently bind the 806 variable region was exploited in the development of a sensitive and specific ELISA assay for ch806 in clinical samples. The three purified clones LMH-11, -12, and -13 (FIGS. 49B and 49C, respectively were compared for their ability to capture and then detect bound ch806 in sera. Results indicated using LMH-12 (10 µg/ml) for capture and biotinylated LMH-12 for detection yielded the highest sensitivity for ch806 in serum (3 ng/ml) with negligible background binding.

Having established the optimal pharmacokinetic ELISA conditions using 1 µg/ml anti-idiotype LMH-12 and 1 µg/ml biotinylated LMH-12 for capture and detection, respectively, validation of the method was performed. Three separate ELISAs were performed in quadruplicate to measure ch806 in donor serum from three healthy donors or 1% BSA/media with isotype control hu3S193. Results of the validation are presented in FIG. 43 and demonstrate highly reproducible binding curves for measuring ch806 (2 µg/ml-1.6 ng/ml) in sera with a 3 ng/ml limit of detection. (n=12; 1-100 ng/ml, Coefficient of Variation<25%; 100 ng/ml-5 lag/ml, Coefficient of Variation<15%). No background binding was evident with any of the three sera tested and negligible binding was observed with isotype control hu3S193.

Example 21

Assessment of Carbohydrate Structures and Antibody Recognition

Experiments were undertaken to further assess the role of carbohydrate structures in the binding and recognition of the EGFR, both amplified and de2-7 EGFR, by the mAb806 antibody.

To determine if carbohydrate structures are directly involved in the mAb806 epitope, the recombinant sEGFR expressed in CHO cells was treated with PNGase F to remove N-linked glycosylation. Following treatment, the protein was run on SDS-PAGE, transferred to membrane and immunoblotted with mAb806 (FIG. 44). As expected, the deglycosylated sEGFR ran faster on SDS-PAGE, indicating that the carbohydrates had been successfully removed. The mAb806 antibody clearly bound the deglycosylated material demonstrating the antibody epitope is peptide in nature and not solely a glycosylation epitope.

Lysates, prepared from cell lines metabolically labelled with $^{35}$S, were immunoprecipitated with different antibodies directed to the EGFR (FIG. 45). As expected, the 528 antibody immunoprecipitated three bands from U87MG.Δ2-7 cells, an upper band corresponding to the wild-type (wt) EGFR and two lower bands corresponding to the de2-7 EGFR. These two de2-7 EGFR bands have been reported previously and are assumed to represent differential glycosylation (Chu et al. (1997) *Biochem. J. June* 15; 324 (Pt 3): 885-861). In contrast, mAb806 only immunoprecipitated the two de2-7 EGFR bands, with the wild-type receptor being completely absent even after over-exposure (data not shown). Interestingly, mAb806 showed increased relative reactivity with the lower de2-7 EGFR band but decreased reactivity with the upper band when compared to the 528 antibody. The SC-03 antibody, a commercial rabbit polyclonal antibody directed to C-terminal domain of the EGFR, immunoprecipitated the three EGFR bands as seen with the 528 antibody, although the total amount of receptor immunoprecipitated by this antibody was considerably less. No bands were observed when using an irrelevant IgG2b antibody as a control for mAb806 (see Example 18).

The 528 antibody immunoprecipitated a single band from U87MG.wtEGFR cells corresponding to the wild-type receptor (FIG. 45). mAb806 also immunoprecipitated a single band from these cells, however, this EGFR band clearly migrated faster than the 528 reactive receptor. The SC-03 antibody immunoprecipitated both EGFR reactive bands from U87MG.wtEGFR cells, further confirming that the mAb806 and 528 recognize different forms of the EGFR in whole cell lysates from these cells.

As observed with U87MG.wtEGFR cells, the 528 antibody immunoprecipitated a single EGFR band from A431 cells (FIG. 45). The 528 reactive EGFR band is very broad on these low percentage gels (6%) and probably reflects the diversity of receptor glycosylation. A single EGFR band was also seen following immunoprecipitation with mAb806. While this EGFR band did not migrate considerably faster than the 528 overall broad reactive band, it was located at the leading edge of the broad 528 band in a reproducible fashion. Unlike U87MG.Δ2-7 cell lysates, the total amount of EGFR immunoprecipitated by mAb806 from A431 lysates was considerably less than with the 528 antibody, a result consistent with our Scatchard data showing mAb806 only recognizes a portion of the EGFR on the surface of these cells (see Example 4). Immunoprecipitation with SC-03 resulted in a single broad EGFR band as for the 528 antibody. Similar results were obtained with HN5 cells (data not shown). Taken together, this data indicates that mAb806 preferentially reacts with faster migrating species of the EGFR, which may represent differentially glycosylated forms of the receptor.

In order to determine at what stage of receptor processing mAb806 reactivity appeared a pulse/chase experiment was conducted. A431 and U87MG.Δ2-7 cells were pulsed for 5 min with $^{35}$S methionine/cysteine, then incubated at 37° C. for various times before immunoprecipitation with mAb806 or 528 (FIG. 46). The immunoprecipitation pattern in A431 cells with the 528 antibody was typical for a conformational dependent antibody specific for the EGFR. A small amount of receptor was immunoprecipitated at 0 min (i.e. after 5 min pulse) with the amount of labelled EGFR increasing at each time point. There was also a concurrent increase in the molecular weight of the receptor with time. In contrast, the mAb806 reactive EGFR material was present at high levels at 0 min, peaked at 20 min and then reduced at each further time point. Thus, it appears that mAb806 preferentially recognizes a form of the EGFR found at an early stage of processing.

The antibody reactivity observed in pulse-labelled U87MG.Δ2-7 cells was more complicated Immunoprecipitation with the 528 antibody at 0 min revealed that a small amount of the lower de2-7 EGFR band was labelled (FIG. 46). The amount of 528 reactive de2-7 EGFR lower band increased with time, peaking at 60 min and declining slowly at 2 and 4 h. No significant amount of the labelled upper band of de2-7 EGFR was detected until 60 min, after which the level continued to increase until the end of the time course. This clearly indicates that the upper de2-7 EGFR is a more mature form of the receptor. mAb806 reactivity also varied during the time course study, however mAb806 preferentially precipitated the lower band of the de27 EGFR. Indeed, there were no significant levels of mAb806 upper band seen until 4 h after labeling.

The above experiments suggest that mAb806 preferentially reacts with a more immature glycosylation form of the de2-7 and wtEGFR. This possibility was tested by immunoprecipitating the EGFR from different cells lines labelled overnight with $^{35}$S methionine/cysteine and then subjecting the resultant precipitates to Endoglycosidase H (Endo H) digestion. This enzyme preferentially removes high mannose type carbohydrates (i.e. immature glycosylation) from proteins while leaving complex carbohydrates (i.e. mature glycosylation) intact. Immunoprecipitation and digestion with Endo H of labelled U87MG.Δ2-7 cell lysates with 528, mAb806 and SC-03 gave similar results (FIG. 47).

As predicted, the lower de2-7 EGFR band was fully sensitive to Endo H digestion, migrating faster on SDS-PAGE after Endo H digestion, demonstrating that this band represents the high mannose form of the de2-7 EGFR. The upper de2-7 EGFR band was essentially resistant to Endo H digestion, showing only a very slight difference in migration after Endo H digestion, indicating that the majority of the carbohydrate structures are of the complex type. The small but reproducible decrease in the molecular weight of the upper band following enzyme digestion suggests that while the carbohydrates on the upper de2-7 EGFR band are predominantly of the complex type, it does possess some high mannose structures. Interestingly, these cells also express low amounts of endogenous wtEGFR that is clearly visible following 528 immunoprecipitation. There was also a small but noticeable reduction in molecular weight of the wild-type receptor following Endo H digestion, indicating that it also contains high mannose structures.

The sensitivity of the immunoprecipitated wtEGFR to Endo H digestion was similar in both U87MG.wtEGFR and A431 cells (FIG. 47). The bulk of the material precipitated by the 528 antibody was resistant to the Endo H enzyme although a small amount of the material was of the high mannose form. Once again there was a small decrease in the molecular weight of the wtEGFR following Endo H digestion suggesting that it does contain some high mannose structures. The results using the SC-03 antibody were similar to the 528 antibody. In contrast, the majority of the EGFR precipitated by mAb806 was sensitive to Endo H in both U87MG.wtEGFR and A431 cells, confirming that mAb806 preferentially recognizes the high mannose form of the EGFR. Similar results were obtained with HN-5 cells, wherein the majority of the material precipitated by mAb806 was sensitive to Endo H digestion, while the majority of the material precipitated by mAb528 and SC-03 was resistant to Endo H digestion (data not shown).

Cell surface iodination of the A431 cell line, was performed with $^{125}$I followed by immunoprecipitation with the 806 antibody. The protocol for surface iodination was as follows: The cell lysis, immunoprecipitation, Endo H digestion, SDS PAGE and autoradiography are as described above herein. For labeling, cells were grown in media with 10% FCS, detached with EDTA, washed twice with PBS then resuspended in 400 µl of PBS (approx 2-3×10$^6$ cells). To this was added 15 µl of $^{125}$I (100 mCi/ml stock), 100 µl bovine lactoperoxidase (1 mg/ml) stock, 10 µl H$_2$O$_2$ (0.1% stock) and this was incubated for 5 min. A further 10 µl H$_2$O$_2$ was then added and the incubation continued for a further 3 min. Cells were then washed again 3 times with PBS and lysed in 1% Triton. Cell surface iodination of the A431 cell line with lactoperoxidase, followed by immunoprecipitation with the 806 antibody, showed that, similar to the whole cell lysates described above, the predominant form of the EGFR recognized by 806 bound on the cell surface of A431 cells was sensitive to EndoH digestion (FIG. 48). This confirms that the form of EGFR bound by 806 on the cell surface of A431 cells is an EndoH sensitive form and thus is the high mannose type.

Example 22

Humanized (Veneered) Antibody 806

A. hu806 Construction

An expression vector for a humanized 806 antibody (hu806) was constructed. The vector, termed 8C65AAG (11891 bp; SEQ ID NO:41), was designed to contain both genes for a full length hu806 in a single GS promoter-driven gene expression cassette (FIGS. 53 and 54A-I).

The heavy chain variable (VH) and constant (CH) regions (SEQ ID NOS:42 and 43, respectively) are shown in FIG. 55A, with the VH region CDR1, CDR2, and CDR3 (SEQ ID NOS:44, 45, and 46, respectively) indicated by underlining.

The light chain variable (VL) and constant (CL) regions (SEQ ID NOS:47 and 48, respectively) are shown in FIG. 55B, with the VL region CDR1, CDR2, and CDR3 (SEQ ID NOS:49, 50, and 51, respectively) indicated by underlining.

To obtain a humanized 806 antibody construct, the veneering (v) technology (Daugherty et al. (1991) Polymerase chain reaction facilitates the cloning, CDR-grafting, and rapid expression of a murine monoclonal antibody directed against the CD18 component of leukocyte integrins. *Nucleic Acids Res.* 19(9), 2471-6; U.S. Pat. No. 6,797,492 to Daugherty; Padlan, E. A. (1991) A possible procedure for reducing the immunogenicity of antibody variable domains while preserving their ligand-binding properties. *Mol. Immunol.* 28(4-5), 489-98; European Patent No. 519596 to Padlan et al.) was employed. In order to minimize the immunogenicity of 806 antibody variable domains, while preserving ligand-binding properties, replacement of the surface-exposed residues in the framework regions which differ from those usually found in human antibodies was undertaken. To achieve this, VL and VH chain of the mouse monoclonal antibody (mAb) 806 have been re-engineered by gene-synthesis and overlapping PCR primer technology. The CL (kappa) chain was assembled in the same manner. To demonstrate the preservation of intact binding sites, vVL and vVH were also expressed in a scFv format that demonstrated good binding to the synthetic peptide that comprises the 806 antigenic epitope by ELISA and to recombinant EGF Receptor (EGFR) extracellular domain (ECD) as measured by surface plasmon resonance (SPR) analysis.

The v806VL and v806VH have been engineered into a full length human IgG1 context using a codon-optimized kappa-LC and a newly designed codon- and splice-site optimized human IgG1 heavy chain constant region to achieve stable gene expression in NS0 and CHO cell systems. The expression system is based on the LONZA GS expression system using the pEE12.4 and pEE6.4 heavy and light chain expression vectors as provided by LONZA Biologics.

The hu806 antibody product (FIG. 55) obtained by transient expression of the 8C65AAG vector was reactive with recombinant EGFR-ECD by SPR, and with the synthetic EGFR 806 peptide epitope by ELISA. The 8C65AAG vector was transferred to LICR Affiliate Christoph Renner (University of Zurich) for generation of stable GS-NS0 hu806 cell lines and to LICR, Melbourne Centre, for the generation of GS-CHO hu806 cell lines.

Strategy for Construction, Amplification and Cloning of hu806 Antibody Genes

Veneering and Codon Optimization

Antibody veneering is a humanization strategy aimed at countering HAMA (human anti-mouse antibody) responses. Mouse mAbs are considered "foreign" antigens by a patient's immune system and an immune response is induced, even upon a single administration, preventing further use of the reagent in those patients. In the first step of the mAb806 veneering process, the amino acid sequences of the VL and VH chains in mAb806 were analyzed, and each amino acid residue in the mAb806 protein sequence was graded for surface exposure (FIG. 56 and FIG. 57). Only those amino acids that resided on the outside of the antibody molecule were considered for possible modification, as these were the only ones that would be exposed to antibody recognition. Using BLAST, the mAb806 protein sequence was compared to three human antibody sequences (VH36 germ, CAD26810, and AAA37941). Wherever a mAb806 surface residue did not match the consensus of the human antibody sequences, that residue was identified to be changed to the consensus sequence. Initially 12 amino acids in the VL were subjected to veneering; and 14 in the VH chain of ch806 (FIG. 56 and FIG. 57).

Codon optimization is a means of improving the heterologous expression of antibodies or other proteins based on the codon bias of the system used to express these antibodies. One of the goals in the creation of hu806 was to utilize codon optimization to improve expression levels for this antibody. The expression system is based upon the LONZA GS expression system using the pEE12.4 and pEE6.4 HC and LC expression vectors as provided by LONZA Biologics and NS0 and/or CHO cells as production cells. Thus, decisions about which codon to use for a given amino acid were made with consideration for whether or not that codon would be favored in the NS0/CHO expression systems.

Construction and Amplification of 806 DNA Sequences by PCR

The sequences for veneered, codon optimized versions of the variable heavy (VH) and variable light (VL) regions of the hu806 antibody were synthesized in the following manner: For each region (VH or VL), 8-10 oligonucleotides were designed as overlapping sense and antisense primers. These oligos would overlap each other in such a way as to cover the entire hu806 VH or VL sequence, including the signal sequence, coding sequences, introns, and include a HindIII site at the 5' terminus and a 3' BamHI site at the 3' terminus. The oligonucleotide maps are presented in FIGS. 56B and 57B, and the primer details are provided below.

Briefly, the hu806 VH or VL was assembled by PCR as follows: Initially v806hc- or v806lc-oligos 1, 2, 3, 4, oligos 5, 6, and oligos 7, 8, 9, 10 were combined in three separate reactions. Aliquots (50 pmol) of each flanking oligo, and 5 pmol of each internal oligo were added to a 50 μl PCR reaction containing 25 μl of 2×HotStar Taq® Master Mix (Qiagen) and 48 μl of nuclease free water. The thermo cycle program was as follows: 95° C.; 15", [94° C.; 30", 58° C.; 30", 72° C.; 30"]×20 cycles, 72° C.; 10", 4° C. The products of these three reactions were excised after separation by gel electrophoresis. They were then purified using a salt column (Qiagen-Qiaspin Minipreps), and combined. These products were further amplified by PCR using primers 1 and 10. The product of this second reaction included restriction enzyme sites for HindIII and BamHI, enabling insertion into expression plasmids.

| Oligonucleotides used to PCR synthesize the hu806 V-regions: | | SEQ ID NO: |
|---|---|---|
| v806 VH: | | |
| V806hc-1: | GAGAAGCTTGCCGCCACCATGGATTGGACCTGG CGCATTC | 52 |
| v806hc-2: | CCCTTCCTCCTCACTGGGATTTGGCAGCCCCTT ACCTGTGGCGGCTGCTACCAGAAAGAGAATGCG CCAGGTCCAATCC | 53 |
| v806hc-3: | CCCAGTGAGGAGGAAGGGATCGAAGGTCACCAT CGAAGCCAGTCAAGGGGGCTTCCATCCACTCCT GTGTCTTCTCTAC | 54 |
| v806hc-4: | GACTCGGCTTGACAAGCCCAGGTCCACTCTCTT GGAGCTGCACCTGGCTGTGGACACCTGTAGAGA AGACACAGGAGTGG | 55 |
| v806hc-5: | GGGCTTGTCAAGCCGAGTCAAACTTTGTCCCTA ACATGTACTGTGTCCGGATACTCTATCTCATCA GATTTTGCGTGGAATTGG | 56 |
| v806hc-6: | CCCAGAGTATGATATGTAGCCCATCCATTCTAA ACCTTTCCCTGGTGGCTGCCTTATCCAATTCCA CGCAAAATCTGATG | 57 |
| v806hc-7: | GGGCTACATATCATACTCTGGGAACACCAGATA TCAACCCTCTCTGAAAAGCCGGATCACAATCAC TAGGGACACGTCG | 58 |
| v806hc-8: | GCAGTAATATGTTGCTGTGTCTGGGGCTGTAAC GGAGTTCAGCTGCAGGAAGAACTGGCTCTTCGA CGTGTCCCTAGTGATTG | 59 |
| v806hc-9: | CCAGACACAGCAACATATTACTGCGTAACCGCT GGCAGAGGCTTCCCCTATTGGGACAGGGCACC CTAGTGACAGTGAGC | 60 |
| v806hc-10: | CACGGATCCATCTTACCGCTGCTCACTGTCACT AGGGTG | 61 |
| v806 VL: | | |
| v806lc-1: | GAGAAGCTTGCCGCCACCATGGATTG | 62 |
| v806lc-2: | CTGGGATTTGGCAGCCCCTTACCTGTTGCGGCT GCTACAAGAAACAGTATTCTCCAAGTCCAATCC ATGGTGGCGGCAAG | 63 |
| v806lc-3: | GGGGCTGCCAAATCCCAGTGAGGAGGAAGGGAT CGAAGGTGACCATCGAAGCCAGTCAAGGGGGCT TCCATCCACTCC | 64 |
| v806lc-4: | CATGCTGGATGGACTCTGAGTCATCTGAATATC ACTGTGAACACCTGTAGAGAAGACACAGGAGTG GATGGAAGCCC | 65 |
| v806lc-5: | CTCAGAGTCCATCCAGCATGTCAGTCTCCGTGG GAGATAGGGTGACGATAACCTGTCATTCAAGCC AAGACATCAACTCC | 66 |
| v806lc-6: | GTTCCGTGATAGATTAGTCCTTTGAAGGACTTA CCAGGCTTCTGTTGGAGCCATCCAATATTGGAG TTGATGTCTTGGCTTG | 67 |
| v806lc-7: | CAAAGGACTAATCTATCACGGAACAAACTTGGA CGACGGCGTGCCATCGAGATTTTCAGGGTCTGG CAGCGGGACCGACTATAC | 68 |
| v806lc-8: | GTGCTGGACGCAGTAGTATGTGGCAAAGTCTTC TGGCTCTAAGCTAGAGATGGTCAGTGTATAGTC GGTCCCGCTG | 69 |
| v806lc-9: | CATACTACTGCGTCCAGCACGCTCAGTTCCCCT GGACATTCGGCGGCGGCACAAAACTGGAAATCA AACGTGAGTAGGG | 70 |
| v806lc-10: | CTCGGATCCCTACTCACGTTTGATTTCC | 71 | hu806 CL:

A codon-optimized version of the constant kappa light chain (CL) was prepared in a manner similar to that used for the variable regions However, the initial PCR step involved the creation of only two preliminary products using oligos VKlcons-1, 2, 3, 4; and 5, 6, 7, 8. In addition, the flanking restriction sites for this product were BamHI and NotI prior to plasmid insertion.

| Oligonucleotides used to PCR synthesize the hu806 CL-regions: | | SEQ ID NO: |
|---|---|---|
| VKlcons-1: | GACGGATCCTTCTAAACTCTGAGGGGTCGG ATGACG | 72 |

-continued

| Oligonucleotides used to PCR synthesize the hu806 CL-regions: | | SEQ ID NO: |
|---|---|---|
| VK1cons-2: | GGAGCTGCGACGGTTCCTGAGGAAAGAAGCAAACAGGATGGTGTTTAAGTAACAATGGCCACGTCATCCGACCCCCTC | 73 |
| VK1cons-3: | GGAACCGTCGCAGCTCCCTCCGTGTTCATCTTCCCCCCATCCGACGAGCAACTGAAGTCAGGCACAGCCTCCGTGGTG | 74 |
| VK1cons-4: | GTGCGTTGTCCACTTTCCACTGGACTTTGGCCTCTCTTGGGTAAAAGTTATTAAGGAGGCACACCACGGAGGCTGTGC | 75 |
| VK1cons-5: | GTGGAAAGTGGACAACGCACTACAGAGCGGGAACTCTCAGGAAAGCGTGACAGAGCAGGACTCAAAAGATTCAACATACAGCC | 76 |
| VK1cons-6: | CTTCACAGGCATATACCTTGTGCTTTTCATAATCAGCTTTTGACAGTGTCAGGGTAGAAGATAGGCTGTATGTTGAATCTTTTGAGTC | 77 |
| VK1cons-7: | GCACAAGGTATATGCCTGTGAAGTAACTCATCAGGGACTCAGCAGCCCTGTCACTAAAAGTTTTAATAGAG | 78 |
| VK1cons-8: | CCTGCGGCCGCTTATCAGCATTCGCCTCTATTAAAACTTTTGGTGAGAGGG | 79 | hu806 CH:

A synthetic, humanized version of the IgG1 constant heavy chain (CH) gene (SEQ ID NO:80) was purchased from Gene-Art, Regensburg, Germany. The gene was codon optimized for expression in CHO/NS0 cells. Details of the gene sequence, restriction sites, etc, are shown in FIGS. 58A-B.

Construction of Expression Plasmids

For transient transfection and preliminary testing, hu806 VH and VL sequences prepared in the manner described above were ligated into expression vectors containing generic constant regions. These vectors, provided by LICR Affiliate Christoph Renner (University of Zurich, Switzerland), were known as pEAK8 HC (which contained a generic CH), and a33-xm-lc (which contained a generic CL). Vectors were digested using BamHI and HindIII in the presence of CIP then hu806 VH and VL were ligated into the corresponding vectors. The resulting plasmids were used to transform Top10 chemically competent E. coli (Invitrogen) according to the manufacturer's directions. Transformed E. coli were plated on LB+Ampicillin plates, and resistant clones were screened by restriction digestion and PCR. In general, eight positive clones detected in this manner would be isolated and further amplified. DNA purified from these colonies were analyzed by automated DNA sequencing.

Codon-optimized versions of the constant regions were added to these constructs by restriction enzyme-digestion and ligation using BamHI and NotI. These transformants were selected, sequenced, and analyzed as stated above. Prior to the full-length antibody chains being ligated into the Lonza GS system the BamHI site between the variable and constant region sequences was destroyed, in one case, by digestion using BamHI, fill-in using DNA Polymerase, and blunt-end ligation.

Restriction fragments containing hu806 (VH+CH) or hu806 (VL+CL) were then digested with NotI followed by HindIII. These digestions were designed to create a blunt end at the NotI site, and thus were done in series in the following manner: The plasmid was first digested with NotI. Fully digested (single-cut) plasmid was separated by electrophoresis using a 1% agarose gel. This product was then excised and purified on a salt column and filled-in using DNA Polymerase. The product of this reaction was salt-column purified and then digested with HindIII. This product (~1.3 Kb for hu806 (VH+CH), and ~0.8 Kb for hu806 (VL+CL) was then separated by gel electrophoresis, excised, and purified.

Vectors pEE12.4 and pEE6.4 (Lonza Biologics plc, Slough, UK) were each digested on HindIII and PmlI. hu806 (VH+CH) was ligated to pEE12.4 to create pEE12.4-hu806H, and hu806 (VL+CL) was ligated to pEE6.4 to create pEE6.4-hu806L.

After screening, a combined, double gene Lonza plasmid was created to contain both the hu806 heavy and light chain sequences. Briefly, the pEE12.4-hu806H and pEE6.4-hu806L vectors were digested with NotI and SalI restriction enzymes. The resultant fragments, which contained the GS transcription unit and hCMV-MIE promoter, followed by the hu806 Heavy or Light chain expression cassette, were isolated and ligated together. The resulting "combined" Lonza plasmid (Designated 8C65AAG) was used for single-plasmid transient transfections in a HEK 293 system and stable transfections in NS0 and CHO systems. A plasmid map is shown in FIG. 53.

Modifications to Constructs

The complete sequence verified amino acid sequences of the veneered hu806 Hc and hu806Lc are shown in comparison to mAb806 in FIG. 59 and FIG. 60, respectively. Flanking the hu806 sequence within the appendices are asterisks (*) indicating initial veneering changes and numbers (1-8) refer to the numbered modifications No. 1 to No. 8 described herein.

With regard to FIG. 60, the reference file (mAb806 LC) incorrectly indicates Histidine (H), not the correct Tyrosine (Y) at position 91; the subject of modification #1. The original, uncorrected file sequence is included in FIG. 60, to illustrate the necessary modification made to hu806 at position 91.

A number of modifications were made to the hu806 cDNA sequences after the initial construction and sequencing phase. The reasons for making these modifications included: introduction of 4 restriction enzyme sites for sequence modification purposes, to correct 2 amino acid errors in the sequence introduced during PCR, to correct one amino acid error arising from the initial mAb806 documentation, and to engineer 4 additional amino acid changes to effect additional veneering variants. The following 8 stages of modifications were performed:

1. hu806 VL: CDR3 H91Y

The document from which the original oligonucleotides were created incorrectly stated that there was a CAC (Histidine, H) at position 91 in the CDR3 of the mAb806 VL sequence. Site-directed mutagenesis was used to generate the correct sequence of TAC (Tyrosine, Y; Patent WO02/092771). The consequent change in the amino acid sequence at this position was from CVQHAQF (SEQ ID NO:84) to CVQYAQF (SEQ ID NO:85). The final DNA and translated protein sequence in comparison to ch806 are shown in FIG. 61.

Sense primer for the histidine to tyrosine modification of the hu806 VL region (PDV1; 40 mer)
(SEQ ID NO: 86)
5' CCACATACTACTGCGTCCAGTACGCTCAGTTCCCCTGGAC-3'

Antisense primer for the histidine to tyrosine modification of the hu806 VL region (PDV2; 20 mer)
(SEQ ID NO: 87)
5'-CTGGACGCAGTAGTATGTGG-3'

2. hu806 Heavy Chain: Addition of Restriction Sites DraIII and FseI

Restriction enzyme sites were added to the introns surrounding the hu806 VH and VL regions. These restriction sites (unique in the pREN vector system, LICR) were designed to ease the process of making modifications to the expression cassettes. The hu806 VH sequence, not including the initial signal region, could be removed or inserted by single-digestion on DraIII. In addition, FseI could be used, in concert with NotI (pREN system) or EcoRI (Lonza System) to cut out the constant region, fulfilling the function of BamHI from the original sequence.

These modifications were achieved using a two-step PCR process. The products were then digested with HindIII and BglII. They were then ligated into pREN vectors containing codon-optimized constant regions, which had been digested on HindIII and BamHI. This re-ligation process destroyed the BamHI site.

```
Sense primer for variable region upstream of first
DraIII site (806 heavy chain DraIII Up; 26 mer)
                                        (SEQ ID NO: 88)
5'-GAGAAGCTTGCCGCCACCATGGATTG-3'

Antisense primer incorporating DraIII site I
(806 heavy chain DraIII Down; 28 mer)
                                        (SEQ ID NO: 89)
5'-CACTGGGTGACTGGCTTCGATGGTGACC-3'

Sense primer for the HC variable region between
the two DraIII sites (806 heavy chain DraIII-
FseI Up; 49 mer)
                                        (SEQ ID NO: 90)
5'-GGTCACCATCGAAGCCAGTCACCCAGTGAAGGGGGCTTCCATCCA
CTCC-3'

Antisense primer incorporating the DraIII site II,
and the FseI site (806 heavy chain DraIII-FseI
Down; 44 mer)
                                        (SEQ ID NO: 91)
5'-CCAAGATCTGGCCGGCCACGGTGTGCCATCTTACCGCTGCTCAC-3'
```

3. hu806 Light Chain: Addition of Restriction Sites RsrII and PacI

For the hu806 light chain, the restriction sites added were RsrII, having the same function as DraIII in the heavy chain, and PacI, which matched the function of FseI.

```
Sense primer for variable region upstream of
first RsrII site (806 light chain RsrII Up;
22 mer)
                                        (SEQ ID NO: 92)
5'-GAGAAGCTTGCCGCCACCATGG-3'

Antisense primer incorporating RsrII site I
(806 light chain RsrII Down; 25 mer)
                                        (SEQ ID NO: 93)
5'-CGGTCCGCCCCCTTGACTGGCTTCG-3'

Sense primer for the LC variable region
between the two RsrII sites (806 light chain
RsrII-PacI Up; 45 mer)
                                        (SEQ ID NO: 94)
5'-CGAAGCCAGTCAAGGGGGCGGACCGCTTCCATCCACTCCTG
TGTC-3'

Antisense primer incorporating the RsrII
site II, and the PacI site (806 light chain
RsrII-PacI Down; 50 mer)
                                        (SEQ ID NO: 95)
5'-CCAAGATCTTTAATTAACGGACCGCTACTCACGTTTGATTT
CCAGTTTTG-3'
```

4. hu806 VH: Reveneering P85A

The protein sequence for the parental mAb806 at VH amino acids 81-87 is SVTIEDT (SEQ ID NO:96). As part of the veneering process, isoleucine and glutamic acid at positions 84 and 85 were changed to alanine-proline to read SVTAPDT (SEQ ID NO:97; FIG. 56). Upon further analysis, it was decided that alanine might have been a better choice than proline in this case. Site-directed mutagenesis was used to generate this secondary change (SVTAADT, SEQ ID NO:98) using the primers listed below. Final DNA and translated protein sequences are presented in FIG. 62.

```
Sense primer (Fx3; 49 mer)
                                        (SEQ ID NO: 99)
5'-CTGCAGCTGAACTCCGTTACAGCCGCAGACACAGCAACA
TATTACTGCG-3'

Antisense primer (Fx4; 49 mer)
                                        (SEQ ID NO: 100)
5'-CGCAGTAATATGTTGCTGTGTCTGCGGCTGTAACGGAGT
TCAGCTGCAG-3'
```

5. hu806 VH: Additional Veneering

The hu806 heavy chain variable region sequence underwent three further mutations following the initial veneering: T70S, S76N and Q81K. The change at position 76 from serine to asparagine represented a correction back to the original sequence of mAb806 molecule. The additional changes in the framework were included because they represent residues that are not found in mouse antibodies but are found in human antibodies. Accordingly, the protein sequence TRDTSKSQF-FLQ (SEQ ID NO:101) was veneered to SRDTSKNQFFLK (SEQ ID NO:102). Final DNA and translated protein sequences in comparison to mAb806 are presented in FIG. 62.

```
Sense Primer for HC variable region 5' PCR
fragment (hu806HCfx2-5p-U; 49 mer)
                                        (SEQ ID NO: 103)
5'-GGTCACCATCGAAGCCAGTCACCCAGTGAAGGGGGCTTCCATCCACT
CC-3'

Antisense Primer for 5' PCR fragment,
incorporates first two changes (hu806HCfx2-
5p-D; 45 mer)
                                        (SEQ ID NO: 104)
5'-GATTCTTCGACGTGTCCCTTGAGATTGTGATCCGGCTTTTCAGA
G-3'

Sense Primer for 3' PCR fragment, incorporates
all changes (hu806HCfx2-3p-U; 55 mer)
                                        (SEQ ID NO: 105)
5'-CAAGGGACACGTCGAAGAATCAGTTCTTCCTGAAACTGAACTCCGTT
ACAGCCGC-3'

Antisense Primer for HC variable region 3' PCR
fragment (hu806HCfx2-3p-D; 44 mer)
                                        (SEQ ID NO: 106)
5'-CCAAGATCTGGCCGGCCACGGTGTGCCATCTTACCGCTGCTCAC-3'
```

6. hu806 VL: E79Q Veneering

This was the only post-construction VL veneering modification performed. At position 79 site directed mutagenesis was employed to correct the sequence SSLEPE (SEQ ID NO:107) to SSLQPE (SEQ ID NO:108). Final DNA and translated protein sequences in comparison to ch806 are presented in FIG. 61.

```
Sense Primer for LC variable region 5' PCR
fragment (hu806LC-5p-U; 45 mer)
                                 (SEQ ID NO: 109)
5'-CGAAGCCAGTCAAGGGGGCGGACCGCTTCCATCCACTCCTGTG
TC-3'

Antisense Primer for 5' PCR fragment,
incorporates intended mutation (hu806LC-5p-D;
34 mer)
                                 (SEQ ID NO: 110)
5'-CTCTGGTTGTAAGCTAGAGATGGTCAGTGTATAG-3'

Sense Prime for LC variable region 3' PCR
fragment incorporates intended mutation
(hu806LC-3p-U; 45 mer)
                                 (SEQ ID NO: 111)
5'-CCATCTCTAGCTTACAACCAGAGGACTTTGCCACATACTACTGC
G-3'

Antisense Primer for LC variable region 3' PCR
fragment (hu806LC-3p-D; 50 mer)
                                 (SEQ ID NO: 112)
5'-CCAAGATCTTTAATTAACGGACCGCTACTCACGTTTGATTTCCA
GTTTTG-3'
```

7. hu806 Light Chain: Kappa Constant Region Splice-Junction Modification

This point mutation was required to correct an error in the splicing of the codon-optimized version of the kappa constant region. Prior to this change, the portion of the amino acid chain beginning with VYACEVTH (SEQ ID NO:113) and continuing to the end of the molecule would not have been included in the final antibody (FIG. 60).

```
Sense primer for LC constant kappa 5' PCR
fragment (F1; 21 mer)
                                 (SEQ ID NO: 114)
5'-GGCGGCACAAAACTGGAAATC-3'

Antisense primer for LC constant kappa 5' PCR
fragment, incorporates correction (F2; 59 mer)
                                 (SEQ ID NO: 115)
5'-GATGAGTTACTTCACAGGCATATACTTTGTGCTTTTCATAATC
AGCTTTTGACAGTGTC-3'

Sense primer for LC constant kappa 3' PCR
fragment, incorporates correction (F3; 26 mer)
                                 (SEQ ID NO: 116)
5'-AGTATATGCCTGTGAAGTAACTCATC-3'

Antisense primer for LC constant kappa 3' PCR
fragment. (F4; 17 mer)
                                 (SEQ ID NO: 117)
5'-GCCACGATGCGTCCGGC-3'
```

8. hu806 VH: N60Q

In addition to the veneering changes made to antibody 806 in the initial stages of construction, Asparagine at position 60 in VH CDR2 was changed to Glutamine at this time. N-Glycosylation follows the scheme: N X S/T, where X is any amino acid. The amino acid sequence from position 60 was N P S, which follows this scheme. However, it is infrequently the case that proline (as in our example) or cysteine is found at the X position for N-glycosylation. It was of concern that inconsistent glycosylation could lead to variations in the reactivity of the antibody. Thus, asparagine was removed, and replaced with its most closely related amino acid, glutamine, removing any potential for this site to be glycosylated (FIG. 59 and FIG. 62).

Binding of Veneered hu806 Antibody 8C65AAG Construct

Transient transfection of 293FT cells with the final plasmid 8C65AAG was performed to enable the preparation of small quantities of hu806 for initial antigen binding verification. Culture supernatants from several small-scale replicate transient transfections were pooled, concentrated and hu806 antibody was collected using a protein-A chromatography step. Approximately 1-2 μg of hu806 antibody was obtained as measured by a quantitative huIgG1 ELISA and the antibody was analyzed by Biacore™ for binding to recombinant EGFR-ECD (FIG. 63). Bovine immunoglobulin from the cell culture medium co-purified with hu806 and represented the major fraction of total IgG, limiting quantitative assessment of hu806 binding.

```
Sequencing Primers
RenVecUPSTREAM: Sense primer, begins sequencing
upstream of variable region in peak8, and a33xm
vectors.
                                 (SEQ ID NO: 118)
5'-GCACTTGATGTAATTCTCCTTGG-3'

RevVecDwnStrmHC: Antisense primer begins
sequencing downstream of variable region on
peak8 heavy-chain plasmid. Anneal within non-
codon-optimized HC constant region.
                                 (SEQ ID NO: 119)
5'-GAAGTAGTCCTTGACCAGG-3'

RenVecDwnstrmLC: Antisense primer, begins
sequencing downstream of variable region on
a33-xm-lc light-chain plasmid. Anneals within
non-codon-optimized LC constant region.
                                 (SEQ ID NO: 120)
5'-GAAGATGAAGACAGATGGTGCAG-3'

Upstrm Lonza: Sense primer, begins sequencing
upstream of variable region in Lonza vectors
pEE 12.4 and pEE 6.4. Cannot be used with
combined Lonza because this is a duplicate
region in the combined plasmid.
                                 (SEQ ID NO: 121)
5'-CGGTGGAGGGCAGTGTAGTC-3'

Dnstrm 6-4: Antisense primer, begins sequencing
downstream of constant region in Lonza vector
pEE 6.4
                                 (SEQ ID NO: 122)
5'-GTGATGCTATTGCTTTATTTG-3'

Dnstrm 12-4: Antisense primer, begins sequencing
downstream of constant region in Lonza vector
pEE12.4
                                 (SEQ ID NO: 123)
5'-CATACCTACCAGTTCTGCGCC-3'

Cod-Opt LC const E: Sense primer, internal to
the codon-optimized light-chain v-kappa constant
region
                                 (SEQ ID NO: 124)
5'-CCATCCTGTTTGCTTCTTTCC-3'

Cod-Opt LC const F: Antisense primer, internal
to the codon-optimized light-chain v-kappa
constant region (vk).
                                 (SEQ ID NO: 125)
5'-GACAGGGCTGCTGAGTC-3'

806HCspec: Sense primer, internal and unique to
the veneered version of the 806 HC variable
region.
                                 (SEQ ID NO: 126)
5'-GTGCAGCTCCAAGAGAGTGGAC-3'

806LCspec: Sense primer, internal and unique to
the veneered version of the 806 LC variable
region.
                                 (SEQ ID NO: 127)
5'-CAGAGTCCATCCAGCATGTC-3'
```

A GenBank formatted text document of the sequence and annotations of plasmid 8C65AAG encoding the IgG1 hu806 is set forth in FIGS. 64A-EE.

FIG. 53 was created using Vector NTI® (Invitrogen).

FIGS. 59-62 were created using Vector NTI® AlignX.

Discussion

The veneering of the 806 anti-EGF receptor antibody involved mutation of 14 amino acids in the VH (FIG. 59 and FIG. 62), and 12 changes to the VL chain (FIG. 60 and FIG. 61) with codon optimization as indicated for expression in mammalian CHO or NSO cells. The final double gene vector, designated 8C65AAG, has been sequence-verified, and the coding sequence and translation checked. Binding to recombinant EGFR extracellular domain was confirmed by Biacore™ analyses using transiently expressed hu806 product.

Stable single clones producing high levels of intact hu806 antibody have been selected in glutamine-free medium as recommended by LONZA. Stable clones have been gradually weaned off serum to obtain serum-free cultures.

B. In Vitro and In Vivo Characterization of hu806

The higher producing stable GS-CHO hu806 transfectants 14D8, 15B2 and 40A10 and GS-NS0 hu806 transfectant 36 were progressed and small scale cultures instigated to enable preliminary hu806 product purification and characterization. Results indicated similar physicochemical properties. Accordingly a larger scale (15 L) stirred tank culture was undertaken for the highest producing transfectant (GS-CHO hu806 40A10) and purified product underwent additional in vitro characterization and in vivo therapy studies in U87MG.de2-7 and A431 xenograft models.

Methodology and Results
Production and Down Stream Processing:
Small Scale

The shake flasks experiments were performed with E500 shake flasks with a 100 mL cell culture volume. FIG. 76 presents the cell viability and antibody productivity charts for the four transfectants during the culture. Product concentration was estimated by ELISA using the 806 anti-idiotype antibody LMH-12 (Liu et al. (2003) Generation of anti-idiotype antibodies for application in clinical immunotherapy laboratory analyses. *Hybrid Hybridomics.* 22(4), 219-28) as coating antibody, and ch806 Clinical Lot: J06024 as standard. Material at harvest was centrifuged and supernatant was 0.2 µm filtered then the antibodies were affinity purified by Protein-A chromatography.

Large Scale

The CHO-K1SV transfectant cell line expressing hu806 candidate clone 40A10 was cultured in a 15 L stirred tank bioreactor with glucose shot feeding for 16 days using CD-CHO (Invitrogen)/25 µM L-Methionine sulfoximine (MSX; Sigma)/GS supplements (Sigma) as the base media. FIG. 76C presents the cell growth and volumetric production in the 15 L stirred tank bioreactor. Final yield was 14.7 L at 58 mg/L by ELISA.

Material at harvest was centrifuged and supernatant was 0.2 µm filtered then concentrated to 2 L using 2×30K membranes in Pall Centrimate concentrator. Aliquots (4×500 ml) were subsequently applied to a 250 mL Protein A column and eluted with 50 mM Citrate pH 4.5 containing 200 mM NaCl. Eluted antibody from the 4 runs was then pooled, concentrated and dialyzed into PBS, pH 7.4.

The hu806 products from the small and large scale cultures were quantified by OD A280 nm. The antibody samples recovered from rProtein-A were assessed by Size Exclusion Chromatography (SEC) (small scale, FIG. 77; large scale, FIG. 78), 4-20% Tris-Glycine SDS-PAGE under reduced and non-reduced conditions (FIG. 79-81), and Isoelectric Focusing was performed with an Amersham Multiphor™ II Electrophoresis system on an Ampholine PAG plate (pH 3.5-9.5) according to the manufacturer's instructions (FIG. 82).

The Protein-A affinity purified hu806 antibodies displayed symmetrical protein peaks and identical SEC elution profiles to the ch806 clinical reference material. The SDS-PAGE gel profiles were consistent with an immunoglobulin. The IEF pattern indicated three isoforms with pI ranging from 8.66 to 8.82 which was consistent with the calculated pI of 8.4 for the protein sequence.

Binding Analyses
FACS Analysis

The estimates of antibody concentration determined for each sample by the OD A280 nm were utilised for FACS analyses with the adenocarcinoma cell line A431 cells (containing EGFR gene amplification). We have previously observed that mAb806 bound approximately 10% of the $~2\times10^6$ wtEGFR expressed on A431 tumor cells compared with the wtEGFR-specific mAb528 (Johns et al. (2002) Novel monoclonal antibody specific for the de2-7 epidermal growth factor receptor (EGFR) that also recognizes the EGFR expressed in cells containing amplification of the EGFR gene. *Int. J. Cancer.* 98(3), 398-408). Cells were stained with either one of the four hu806 samples, an irrelevant IgG2b antibody, or positive control ch806; each were assessed at a concentration of 20 µg/ml. Control for secondary antibody alone was also included [Goat anti hu-IgG (Fc specific) FITC conjugated]. Composite FACS binding curves are presented in FIG. 83 and demonstrate equivalent staining for all constructs.

The cell binding characteristics of hu806 40A10 sample produced by large scale culture was also assessed by FACS for binding A431 as well as U87MG.de2-7 glioma cells expressing the variant EGFRvIII receptor (Johns et al., 2002). Representative results of duplicate analyses are presented in FIG. 84 and FIG. 85, respectively. Controls included an irrelevant IgG2b antibody (shaded histograms), ch806 or 528 (binds both wild-type and de2-7 EGFR) as indicated.

The ch806 and the hu806 antibody demonstrated similar staining of the A431 and U87MG.de2-7 cell lines supporting our previous observations that mAb806 specifically recognized the de2-7 EGFR and a subset of the over-expressed EGFR (Luwor et al. (2001) Monoclonal antibody 806 inhibits the growth of tumor xenografts expressing either the de2-7 or amplified epidermal growth factor receptor (EGFR) but not wild-type EGFR. *Cancer Res.* 61(14), 5355-61). As expected, the 528 antibody stained both the U87MG.de2-7 and A431 cell lines (FIGS. 84 and 85).

Cell Binding Analyses

The antigen binding capabilities of the radioimmunoconjugates were assessed by cell adsorption assays (Lindmo et al. (1984) Determination of the immunoreactive fraction of radiolabeled monoclonal antibodies by linear extrapolation to binding at infinite antigen excess. *J. Immunol. Methods.* 72(1), 77-89) using the U87MG.de2-7 glioma cell line and A431 epidermoid carcinoma cells expressing the amplified EGFR gene.

Immunoreactive fractions of hu806 and ch806 radioconjugates were determined by binding to antigen expressing cells in the presence of excess antigen. Results for U87MG.de2-7 cell binding of $^{125}$I-hu806 and $^{125}$I-ch806 are presented in FIG. 86A over the cell concentration range $20\times10^6$ to $0.03\times10^6$ cells/sample. Results for A431 cell binding of $^{125}$I-hu806 and $^{125}$I-ch806 are presented in FIG. 86B over the cell concentration range $200\times10^6$ to $0.39\times10^6$ cells/sample.

Scatchard analyses were used to calculate the association constant (Ka) (Lindmo et al., 1984). The binding of low levels (20 ng) of labeled antibody alone was compared with binding in the presence of excess unlabeled antibody. The immunoreactive fraction was taken into account in calculating the amount of free, reactive antibody as previously described (Clarke et al. (2000) In vivo biodistribution of a humanized anti-Lewis Y monoclonal antibody (hu3 S193) in MCF-7 xenografted BALB/c nude mice. *Cancer Res.* 60(17), 4804-11) and specific binding (nM; total antibody×% bound) was graphed against specific binding/reactive free (FIGS. 87 and 88). The association constant was determined from the negative slope of the line.

The binding affinity for $^{125}$I-hu806 binding EGFRvIII on U87MG.de2-7 cells was determined to be $1.18 \times 10^9$ M$^{-1}$. The Ka for $^{125}$I-ch806 was $1.06 \times 10^9$ M$^{-1}$. These observations are in agreement with the reported results of Ka values for $^{111}$In- and $^{125}$I-ch806 of $1.36 \times 10^9$ M-1 and $1.90 \times 10^9$ M$^{-1}$, respectively, which is highly comparable to that of the parental murine mAb806 of $1.1 \times 10^9$ M$^{-1}$ (Panousis et al. (2005) Engineering and characterization of chimeric monoclonal antibody 806 (ch806) for targeted immunotherapy of tumours expressing de2-7 EGFR or amplified EGFR. *Br. J. Cancer.* 92(6), 1069-77).

The scatchard analysis on A431 cells demonstrated high affinity binding by both 806 constructs to a minor population of EGFR on these cells. The Ka for $^{125}$I-ch806 was $0.61 \times 10^9$ M$^{-1}$; and for $^{125}$I-hu806 the Ka=$0.28 \times 10^9$ M$^{-1}$.

Biosensor Analysis

Biosensor analyses were performed on a BIAcore™ 2000 biosensor using a carboxymethyldextran-coated sensor chip (CM5). The chip was derivatized on channel 3 with the 806 epitope peptide (EGFR amino acids 287-302; SEQ ID NO: 14; see U.S. patent application Ser. No. 11/060,646, filed Feb. 17, 2005; U.S. Provisional Patent Application No. 60/546,602, filed Feb. 20, 2004; and U.S. Provisional Patent Application No. 60/584,623, filed Jul. 1, 2004, the disclosure of each is which is hereby incorporated in its entirety), using standard amine coupling chemistry. Channel 2 was derivatized with a control antigen used for system suitability determination. Channel 1 was derivatized with ethanolamine and used as a blank control channel for correction of refractive index effects. Samples of hu806 were diluted in HBS buffer (10 mM HEPES, pH 7.4; 150 mM NaCl; 3.4 mM di-Na-EDTA; 0.005% Tween-20), and aliquots (120 µl) containing 50 nM, 100 nM, 150 nM, 200 nM, 250 nM and 300 nM were injected over the sensor chip surface at a flow rate of 30 µl/min. After the injection phase, dissociation was monitored by flowing HBS buffer over the chip surface for 600s. Bound antibody was eluted and the chip surface regenerated between samples by injection of 20 µl of 10 mM sodium hydroxide solution. Positive control, ch806, was included. The binding parameters were determined using the equilibrium binding model of the BIAevaluation™ software. FIG. 89 present the sensorgrams generated.

Dose dependant binding was observed with both hu806 and the positive control, ch806, on channel 3. System suitability was confirmed by dose dependant binding of the appropriate monoclonal antibody to control channel 2. No cross reactivity was observed between hu806 (or ch806) and the control antibody. Our analyses determined that the apparent K$_D$ (1/Ka) was 37 nM for hu806 and 94 nM for ch806.

Antibody Dependent Cellular Cytotoxicity Analyses

ADCC analyses were performed using purified hu806 antibody 40A10 preparation with target A431 adenocarcinoma cells and freshly isolated healthy donor peripheral blood mononuclear effector cells. Briefly, all analyses were performed in triplicate with 1) 1 µg/ml each antibody over a range of effector to target cell ratios (E:T=0.78:1 to 100:1) and also 2) at E:T=50:1 over a concentration range of each antibody (3.15 ng/ml-10 µg/ml). Controls for antibody isotype, spontaneous and total cytotoxicity were included in triplicate and calculations for specific cytotoxicity were as previously described (Panousis et al., 2005). Results are presented in FIG. 90.

The hu806 consistently demonstrated superior ADCC activity to the chimeric ch806 IgG1. In the representative experiment shown, hu806 at 1 µg/mL effected an ADCC of 30% cytotoxicity in contrast to ch806 5% cytoxicity.

In Vivo 806 Therapy Study

The therapeutic efficacy of hu806 was investigated using established A431 adenocarcinoma or U87MG-de2-7 glioma xenografts in BALB/c nude mice. To establish xenografts, mice were injected subcutaneously into the right and left inguinal mammary line with $1 \times 10^6$ A431 adenocarcinoma cells or $1 \times 10^6$ U87MG.de2-7 glioma cells in 100 µl of PBS. Tumor volume (TV) was calculated by the formula [(length× width)/2] where length was the longest axis and width the measurement at right angles to length. In an initial experiment, groups of five BALB/c nude mice (n=10 tumours/ group) with established A431 or U87MG.de2-7 xenografts received treatment of 1 mg hu806, or 1 mg ch806 antibody or PBS vehicle control by IP injection. Therapy was administered on days 6, 8, 11, 13, 15 and 18 for A431, and days 4, 6, 8, 11, 13 and 15 for the U87MG.de2-7 cell lines respectively. Mean±SEM tumor volumes until termination of the experiments due to ethical considerations of tumor burden are presented in FIG. 91 for the A431 xenograft until day 25, and in FIG. 92 for U87MG.de2-7 xenografts until day 31.

The in vivo therapy assessments with hu806 showed a marked reduction in A431 xenograft growth compared with PBS vehicle control. The A431 xenograft growth curve observed for hu806 was highly comparable to the ch806 treatment group. In the established U87MG.de2-7 xenografts, the PBS control group was euthanized at day 20. The hu806 therapy demonstrated significant reduction in tumor growth by day 20 compared to the PBS controls (P<0.001), and continued tumor growth retardation after day 20 similar to the ch806 group.

Discussion

The Protein-A affinity purified hu806 antibodies displayed identical SEC elution profiles to the ch806 clinical reference material, and SDS-PAGE gel profiles consistent with an immunoglobulin. The IEF pattern was consistent with the anticipated pI of 8.4.

Through Scatchard cell binding and Biosensor epitope binding analyses the hu806 antibody demonstrated highly comparable binding curves and affinity parameters to the ch806 antibody. The binding affinity of hu806 and ch806 to EGFRvIII and over expressed wild-type EGFR are similar and in the low nanomolar range. Cell binding through FACS analyses supported these observations.

Furthermore, the hu806 demonstrates markedly improved ADCC over the ch806 construct on target antigen positive A431 cells.

The in vivo therapeutic assessments with hu806 showed a marked reduction in A431 xenograft growth, which was highly comparable to the ch806 treatment group. In the established U87MG.de2-7 xenografts, hu806 therapy demonstrated significant reduction in tumor growth by day 20 compared to the PBS controls and continued tumor growth retardation after day 20 similar to the ch806 group.

Example 23

Monoclonal Antibody 175

As discussed in Example 1, clone 175 (IgG2a) was selected for further characterization.

a. Materials and Methods

Cell Lines

The Δ2-7EGFR transfected 1587MG.Δ2-7 (Huang et al. (1997) *J. Biol. Chem.*, 272, 2927-2935) and the A431 cell lines (Ullrich et al. (1984) *Nature*. 309, 418-425) have been described previously. The hormone-independent prostate cell line DU145 (Mickey et al. (1977) *Cancer Res*. 37, 4049-4058) was obtained from the ATCC (atcc.org).

All cell lines were maintained in DMEM (Life Technologies, Grand Island, N.Y.) containing 10% FCS(CSL, Melbourne), 2 mM glutamine (Sigma Chemical Co, St. Louis), and penicillin/streptomycin (Life Technologies, Grand Island). In addition, the U87MG.Δ2-7 cell line was maintained in 400 mg/ml of Geneticin® (Life Technologies, Inc, Grand Island). BaF/3 (Palacios et al. (1984) *Nature*. 309, 126-131) and BaF/3 cell lines expressing different EGF receptors (Walker et al. (2004) *J. Biol. Chem.* 2(79), 22387-22398) were maintained routinely in RPMI 1640 (GIBCO BRL) supplemented with 10% fetal calf serum (GIBCO BRL) and 10% WEHI-3B conditioned medium (Ymer et al. (1985) *Nature*. 19-25; 317, 255-258) as a source of IL-3. All cell lines were grown at 37° C. in an air/$CO_2$ (95%-5%) atmosphere.

Antibodies and Peptides mAb806 and mAb175 were generated at the Ludwig Institute for Cancer Research (LICR) New York Branch and were produced and purified in the Biological Production Facility (Ludwig Institute for Cancer Research, Melbourne). The murine fibroblast line $NR6_{\Delta EGFR}$ was used as immunogen. Mouse hybridomas were generated by immunizing BALB/c mice five times subcutaneously at 2- to 3-week intervals, with $5\times10^5$-$2\times10^6$ cells in adjuvant. Complete Freund's adjuvant was used for the first injection. Thereafter, incomplete Freund's adjuvant (Difco) was used. Spleen cells from immunized mice were fused with mouse myeloma cell line SP2/0. Supernatants of newly generated clones were screened in hemadsorption assays for reactivity with cell line NR6, $NR6_{wtEGFR}$, and $NR6_{\Delta EGFR}$ and then analyzed by hemadsorption assays with human glioblastoma cell lines U87MG, $U87MG_{wtEGFR}$, and $U87MG_{\Delta EGFR}$.

Intact mAbs (50 mg) were digested in PBS with activated papain for 2-3 hours at 37° C. at a ratio of 1:20 and the papain was inactivated with iodoacetamide. The digestion was then passed over a column of Protein-A sepharose (Amersham) in 20 mM sodium phosphate buffer pH 8.0, with the flow-through further purified by cation exchange using on a Mono-S column (Amersham). Protein was then concentrated using a 10,000 MWCO centrifugal concentrator (Millipore). For Fab-peptide complexes a molar excess of lyophilized peptide was added directly to the Fab and incubated for 2 hours at 4° C. before setting up crystallization trials.

Mapping of mAb175 Using EGFR Fragments Expressed in Mammalian Cells

The day prior to transfection with these fragments, human 293T embryonic-kidney fibroblasts were seeded at $8\times10^5$ per well in 6-well tissue culture plates containing 2 ml of media. Cells were transfected with 3-4 μg of plasmid DNA complexed with Lipofectamine™ 2000 (Invitrogen) according to the manufacturer's instructions. 24 to 48 h after transfection, cell cultures were aspirated and cell mono layers lysed in 250 μl of lysis buffer (1% Triton X-100, 10% glycerol, 150 mM NaCl, 50 mM HEPES pH 7.4, 1 mM EGTA and Complete Protease Inhibitor mix (Roche). Aliquots of cell lysate (10-15 μl) were mixed with SDS sample buffer containing 1.5% β-mercaptoethanol, denatured by heating for 5 min at 100° C. and electrophoresed on 10% NuPAGE® Bis-Tris polyacrylamide gels (Invitrogen). Samples were then electro-transferred to nitrocellulose membranes that were rinsed in TBST buffer (10 mM Tris-HCl, pH 8.0, 100 mM NaCl and 0.1% Tween-20) and blocked in TBST containing 2.5% skim milk for 30 min at room temperature. Membranes were incubated overnight at 4° C. with 0.5 μg/ml of mAb175 in blocking buffer. Parallel membranes were probed overnight with mAb 9B11 (1:5000, Cell Signaling Technology, Danvers, Massachusetts) to detect the c-myc epitope. Membranes were washed in TBST, and incubated in blocking buffer containing horseradish peroxidase-conjugated rabbit anti-mouse IgG (Biorad) at a 1:5000 dilution for 2 h at room temperature. Blots were then washed in TBST, and developed using autoradiographic film following incubation with Western Pico Chemiluminescent Substrate (Pierce, Rockford, Ill.).

Mapping of mAb175 Using EGFR Fragments Expressed in Mammalian Cells and Yeast

A series of overlapping c-myc-tagged EGFR ectodomain fragments, starting at residues 274, 282, 290 and 298 and all terminating at amino acid 501 and fused to growth hormone have been described previously (Johns et al. (2004) *J. Biol. Chem.* 279, 30375-30384). Expression of EGFR proteins on the yeast cell surface was performed as previously described (Johns et al., 2004).

Briefly, transformed colonies were grown at 30° C. in minimal media containing yeast nitrogen base, casein hydrolysate, dextrose, and phosphate buffer pH 7.4, on a shaking platform for approximately one day until an $OD_{600}$ of 5-6 was reached. Yeast cells were then induced for protein display by transferring to minimal media containing galactose, and incubated with shaking at 30° C. for 24 h. Cultures were then stored at 4° C. until analysis. Raw ascites fluid containing the c-myc monoclonal antibody 9E10 was obtained from Covance (Richmond, Calif.). $1\times10^6$ yeast cells were washed with ice-cold FACS buffer (PBS containing 1 mg/ml BSA) and incubated with either anti-c-myc ascites (1:50 dilution), or human EGFR monoclonal antibody (10 μg/ml) in a final volume of 50 μl, for 1 hr at 4° C. The cells were then washed with ice cold FACS buffer and incubated with phycoerythrin-labelled anti-mouse IgG (1:25 dilution), in a final volume of 50 μl for 1 h at 4° C., protected from light. After washing the yeast cells with ice-cold FACS buffer, fluorescence data was obtained with a Coulter Epics XL flow cytometer (Beckman-Coulter), and analyzed with WinMDI cytometry software (J. Trotter, Scripps University). For determination of linear versus conformational epitopes, yeast cells were heated at 80° C. for 30 min, then chilled on ice 20 min prior to labeling with antibodies. The series of EGFR mutants listed in Table 7 have been described previously (Johns et al., 2004).

Surface Plasmon Resonance (BIAcore™)

A BIAcore™ 3000 was used for all experiments. The peptides containing the putative mAb806 epitope were immobilized on a CM5 sensor chip using amine, thiol or Pms coupling at a flow rate of 5 μl/min (Wade et al. (2006) *Anal. Biochem.* 348, 315-317). The mAb806 and mAb175 were passed over the sensor surface at a flow rate of 5 μl/min at 25° C. The surfaces were regenerated between runs by injecting 10 mM HCl at a flow rate of 10 μl/min.

Immunoprecipitation and Western Blotting

Cells were lysed with lysis buffer (1% Triton X-100, 30 mM HEPES, 150 mM NaCl, 500 mM 4-(2-aminoethyl)benzenesulfonylfluoride, 150 nM aprotinin, 1 mM E-64 protease inhibitor, 0.5 mM EDTA, and 1 mM leupeptin, pH 7.4) for 20 minutes, clarified by centrifugation at 14,000×g for 30 minutes, immunoprecipitated with the relevant antibodies at a final concentration of 5 μg/ml for 60 minutes and captured by Sepharose-A beads overnight. Samples were then eluted with 2×NuPAGE® SDS Sample Buffer (Invitrogen), resolved on NuPAGE® gels (either 3-8% or 4-12%), electro-transferred onto Immobilon®-P transfer membrane (Millipore) then probed with the relevant antibodies before detection by chemoluminescence radiography.

Immunohistochemistry

Frozen sections were stained with 5 µg/ml mAb175 or irrelevant isotype control for 60 min at room temperature. Bound antibody was detected using the Dako EnVision™+ HRP detection system as per manufacturer's instructions. Sections were finally rinsed with water, counterstained with hematoxylin and mounted.

Xenograft Models

U87MG.Δ2-7 cells ($3\times10^6$) in 100 µL of PBS were inoculated s.c. into both flanks of 4- to 6-week-old, female Balb/c nude mice (Animal Research Centre, Perth, Australia). All studies were conducted using established tumor models as reported previously (Perera et al. (2005) *Clin. Cancer Res.* 11, 6390-6399). Treatment commenced once tumors had reached the mean volume indicated in the appropriate figure legend. Tumor volume in $mm^3$ was determined using the formula (length×width$^2$)/2, where length was the longest axis and width was the perpendicular measurement. Data are expressed as mean tumor volume±SE for each treatment group. All data was analyzed for significance by one-sided Students t test where $p<0.05$ was considered statistically significant. This research project was approved by the Animal Ethics Committee of the Austin Hospital.

Generation and Characterization of Stable Cell Lines Expressing EGFR Mutant Constructs Mutations of the wtEGFR were generated using a site-directed mutagenesis kit (Stratagene, La Jolla, Calif.). The template for each mutagenesis was the human EGFR cDNA (accession number x00588) (Ullrich et al. (1984) *Nature.* 309, 418-425). Automated nucleotide sequencing of each construct was performed to confirm the integrity of the EGFR mutations. Wild-type and mutant (C173A/C281A) EGFR were transfected into BaF/3 cells by electroporation.

Stable cell lines expressing the mutant EGFR were obtained by selection in neomycin-containing medium. After final selection, mRNA was isolated from each cell line, reverse transcribed and the EGFR sequence amplified by PCR. All mutations in the expressed EGFR were confirmed by sequencing the PCR products. The level of EGFR expression was determined by FACS analysis on a FACStar™ (Becton and Dickinson, Franklin Lakes, N.J.) using the anti-EGFR antibody mAb528 (Masui et al. (1984) *Cancer Res.* 44, 10024007; Gill et al. (1984) *J. Biol. Chem.* 259, 7755-7760) at 10 µg/ml in PBS, 5% FCS, 5 mM EDTA followed by Alexa 488-labeled anti-mouse Ig (1:400 final dilution). Background fluorescence was determined by incubating the cells with an irrelevant, class-matched primary antibody. All cells were routinely passaged in RPMI, 10% FCS, 10% WEHI3B conditioned medium and 1.5 mg/ml G418.

EGF-Dependent Activation of Mutant EGFR

Cells expressing the wtEGFR or C271A/C283 A-EGFR were washed and incubated for 3 hr in medium without serum or IL-3. Cells were collected by centrifugation and resuspended in medium containing EGF (100 ng/ml) or an equivalent volume of PBS. Cells were harvested after 15 min, pelleted and lysed directly in SDS/PAGE sample buffer containing p-mercaptoethanol. Samples were separated on NuPAGE® 4-12% gradient gels, transferred to Immobilon® PVDF membrane and probed with anti-phosphotyrosine (4G10, Upstate Biotechnologies) or anti-EGFR antibodies (mAb806, produced at the LICR). Reactive bands were detected using chemiluminescence.

Effect of EGF and Antibodies on Cell Proliferation

Cells growing in log phase were harvested and washed twice with PBS to remove residual IL-3. Cells were resuspended in RPMI 1640 plus 10% FCS and seeded into 96-well plates at $10^5$ cells/well with carrier only or with increasing concentrations of EGF. Where appropriate, a fixed concentration of mAb528 or mAb806 (2 µg/well) was also added to the cultures. Proliferation was determined using the MTT assay (van de Loosdrecht et al. (1994). *J. Immunol. Methods.* 174, 311-320).

Reactivity with Conformation-Specific Antibodies

Cells were collected by centrifugation and stained with the control or test antibodies (all at 10 µg/ml in FACS buffer for 40 min on ice, washed in FACS buffer) followed by Alexa 488-labeled anti-mouse Ig (1:400 final dilution, 20 min on ice). The cells were washed with ice-cold FACS buffer, collected by centrifugation, and analyzed on a FACScan™; peak fluorescence channel and median fluorescence were determined for each sample using the statistical tool in Cell Quest™ (Becton and Dickinson). Background (negative control) fluorescence was deducted from all measurements. The median fluorescence values were chosen as most representative of peak shape and fluorescence intensity and were used to derive the ratio of mAb806 to mAb528 binding.

Crystal Structure Determinations of Fab 175, and Fab 806, Fab-Peptide Complexes And the NMR Structure of the 806 Peptide Epitope in Solution Structures were determined by molecular replacement and refinement converged with R=0.225/Rfree=0.289 for Fab806 and R=0.226/Rfree=0.279 for Fab806:peptide; R=0.210/Rfree=0.305 for Fab806 and R=0.203/Rfree=0.257 for Fab806:peptide.

Crystals of native 806 Fab were grown by hanging drop vapor diffusion using 10 mg/ml Fab and a reservoir containing 0.1M Sodium acetate buffer pH 4.6, 6-8% PEG6000 and 15-20% Isopropanol. For data collection crystals were transferred to a cryoprotectant solution containing 0.1M Sodium acetate buffer pH 4.6, 10% PEG6000, 15-20% Isopropanol and 10% glycerol. Crystals were then mounted in a nylon loop and flash frozen directly into liquid nitrogen.

Crystals of 806 Fab-peptide complex were grown by hanging drop vapor diffusion using 10 mg/ml Fab-peptide complex and a reservoir containing 0.2M ammonium acetate 16-18% PEG 5,000 monomethylether, crystals quality was then improved through seeding techniques. For data collection crystals were transferred to a cryoprotectant solution consisting of reservoir supplemented with 25% glycerol. Crystals were then mounted in a nylon loop and flash frozen directly into liquid nitrogen.

Crystals of 175 Fab-peptide complex were initially grown by free interface diffusion using a Topaz crystallization system (Fluidigm, San Francisco). Microcrystals were grown by hanging drop vapor diffusion using 7 mg/ml Fab with similar conditions 0.1M Bis-tris propane buffer, 0.2M ammonium acetate and 18% PEG 10,000. Microcrystals were then improved by streak seeding into 0.15m Sodium formate and 15% PEG 1500 to yield small plate shaped crystals. For data collection crystals were transferred to a cryoprotectant solution consisting of reservoir supplemented with 25% glycerol. Crystals were then mounted in a nylon loop and flash frozen directly into liquid nitrogen.

Diffraction data on 806 Fab and 175 Fab complex crystals were collected in-house using a R-AXIS IV detector on a Rigaku Micromax™-007 generator fitted with AXCO optics, these data were then processed using CrystalClear™. 806 Fab-peptide complex data were collected on an ADSC quantum315 CCD detector at beamline X29, Brookhaven National Laboratory, these data were processed with HKL2000 (Otwinowski, Z. and Minor, W. (1997) *Processing of X-ray diffraction data collected in oscillation mode.* Academic Press (New York)) (data collection statistics are shown in Table 9). Native 806 Fab was solved by molecular replacement using the program MOLREP (Vagin, A. and Teplyakov, A. (1997) *J. Appl. Cryst.* 30, 1022-1025) using the coordinates of the Fab structure 2E8 refinement of the structure was performed in REFMAC5 (Murshudov et al. (1997) *Acta crystallographica* 53, 240-255) and model building in Coot (Emsley, P. and Cowtan, K. (2004) *Acta crystallographica* 60, 2126-2132).

Both 806-peptide and 175 Fab-peptide structures were solved by molecular replacement using the program MOLREP using the coordinates of the 806 Fab structure, refinement and rebuilding were again performed in REFMAC5, and COOT and O. Validation of the final structures were performed with PROCHECK (Laskowski et al. (1993) *J. Appl. Cryst.* 26, 283-291) and WHATCHECK (Hooft et al. (1996) *Nature* 381, 272).

NMR Studies

For NMR studies, $^{15}$N-labelled peptide was produced recombinantly as a fusion to the SH2 domain of SHP2 using the method previously described by Fairlie et al. (Fairlie et al. (2002) *Protein expression and purification* 26, 171-178) except that the *E. coli* were grown in Neidhardt's minimal medium supplemented with $^{15}$NH$_4$Cl (Neidhardt et al. (1974) *Journal of bacteriology* 119, 736-747). The peptide was cleaved from the fusion partner using CNBr, purified by reversed-phase HPLC and its identity confirmed by MALDI-TOF mass spectrometry and N-terminal sequencing. The methionine residue within the 806 antibody-binding sequence was mutated to leucine to enable cleavage from the fusion partner, but not within the peptide itself.

Samples used for NMR studies were prepared in H$_{2O}$ solution containing 5% $^2$H$_2$O, 70 mM NaCl and 50 mM NaPO$_4$ at pH 6.8. All spectra were acquired at 298K on a Bruker Avance500 spectrometer using a cryoprobe. Sequential assignments of the peptide in the absence of m806Fab were established using standard 2D TOCSY and NOESY as well as $^{15}$N-edited TOCSY and NOESY spectra. Interaction between the peptide and fAb806 was examined by monitoring $^{15}$N HSQC spectra of the peptide in the absence and presence of fAb806. Spectral perturbation of $^{15}$N HSQC spectra of the peptide in the presence of fAb806 clearly indicates the peptide was able to bind to the fAb806 under the presence solution conditions. Detailed conformation of the peptide in the complex form was not determined. Deviations from random coil chemical shift values for the mAb806 peptide are shown in FIG. 93.

Biodistribution of chAb806 Tumor in Patients

To demonstrate the tumor specificity of mAb806 in vivo, a chimeric version (ch806) was engineered and produced under cGMP conditions (Panousis et al. (2005) *Br. J. Cancer.* 92, 1069-1077). A Phase I first-in-man trial was conducted to evaluate the safety, biodistribution and immune response of ch806 in patients with 806 positive tumors, and the results of safety, biodistribution and pharmacokinetics have been reported previously (Scott et al. (2007) *Proc. Natl. Acad. Sci. U.S.A.* 104, 4071-4076). To define the specificity of ch806 in tumor compared to normal tissue (i.e., liver) in patients, the quantitative uptake of ch806 in tumor and liver was performed by calculation of % injected dose (ID) of $^{111}$In-ch806 from whole body gamma camera images obtained over one week following injection of 5-7mCi (200-280 MBq)$^{111}$In-ch806. Liver and tumor dosimetry calculations were performed based on regions of interest in each individual patient. $^{111}$In-ch806 infusion image dataset, corrected for background and attenuation, allowing calculation of cumulated activity. Dosimetry calculation was performed to derive the concentration of $^{111}$In-ch806 in tumor and liver over a one week period post injection.

b. Sequencing

The variable heavy (VH) and variable light (VL) chains of mAb175 were sequenced, and their complementarity determining regions (CDRs) identified, as follows:

mAb175 VH chain: nucleic acid (SEQ ID NO:128) and amino acid (SEQ ID NO:129) sequences are shown in FIGS. 74A and 74B, respectively. Complementarity determining regions CDR1, CDR2, and CDR3 (SEQ ID NOS:130, 131, and 132, respectively) are indicated by underlining in FIG. 74B.

mAb175 VL chain: nucleic acid (SEQ ID NO:133) and amino acid (SEQ ID NO:134) sequences are shown in FIGS. 75A and 75B, respectively. Complementarity determining regions CDR1, CDR2, and CDR3 (SEQ ID NOS: 135, 136, and 137, respectively) are indicated by underlining in FIG. 75B.

The sequence data for mAb175 is based on both sequence and crystal structure data, as the cell line is not clonal, and therefore multiple sequences have been obtained from the cell line. The sequences of mAb175 set forth above have been confirmed by crystal structure, and differ by a single amino acid in each of the VL chain CDR1 and CDR2 from previous sequences based on standard sequence data alone. A different isotype of mAb175 (an unusual IgG2a isotype) has also been obtained, based on the final sequence and crystal structure data.

mAb175 Specificity

Preliminary binding studies suggested that mAb175 displayed similar specificity for EGFR as mAb806. In the CDR regions of mAb806 (IgG2b) and mAb175 (IgG2a), the amino acid sequences are almost identical, with only one amino acid difference in each (FIG. 65; See Example 26, below). All these differences preserve the charge and size of the sidechains. Clearly these antibodies have arisen independently.

c. Experiments

A set of immunohistochemistry experiments were conducted to analyze the specificity of mAb175 binding. mAb175 stains sections of A431 xenografts that overexpress the EGFR (FIG. 66A) and sections of U87MG.Δ2-7 glioma xenografts that express the Δ2-7EGFR (FIG. 66A). In contrast, mAb175 does not stain U87MG xenograft sections. The U87MG cell line only expresses modest levels of the wild-type EGFR (FIG. 66A) and has no detectable EGFR autocrine loop. Most importantly, mAb175 does not bind to normal human liver sections (FIG. 66B). Thus, mAb175 appears to demonstrate the same specificity as mAb806, i.e. it detects over-expressed and truncated human EGFR, but not the wtEGFR expressed at modest levels.

Identification of the mAb175 Epitope

Since mAb175 also binds the Δ2-7EGFR, in which amino acids 6-273 are deleted, and EGFR$_{1-501}$, the mAb 175 epitope must be contained within residues 274-501. When determining the epitope of mAb806, we expressed a series of c-myc-tagged EGFR fragments fused to the carboxy terminus of human GH, all terminating at amino acid 501 (Chao et al. (2004) *J. Mol. Biol.* 342, 539-550; Johns et al. (2004) *J. Biol. Chem.* 279, 30375-30384).

The mAb175 also reacted with both the 274-501 and 282-501 EGFR fragments in Western blots, but did not detect fragments commencing at amino acid 290 or 298 (FIG. 73). The presence of all GH-EGFR fusion proteins was confirmed using the c-myc antibody, 9EI0 (FIG. 73). Therefore, a critical determinant of the mAb175 epitope is located near amino acid 290. Finally, a 274-501 EGFR fragment with the mAb806 epitope deleted (Δ287-302) was also negative for mAb175 binding (FIG. 73), suggesting that this region similarly determined most of the mAb175 binding.

A second approach was used to characterize the mAb175 epitope further. Fragments encompassing extracellular domains of the EGFR were expressed on the surface of yeast and tested for mAb175 binding by indirect immunofluorescence using flow cytometry. The mAb175 recognized the yeast fragment 273-621, which corresponds to the extracellular domain of the Δ2-7 EGFR, but not to fragments 1-176, 1-294, 294-543, or 475-621 (FIG. 67A and FIG. 67B). Thus, at least part of the mAb175 epitope must be contained within the region between amino acids 274-294, agreeing with immunoblotting data using EGFR fragments. Since mAb175 binds to the denatured fragment of the 273-621 (FIG. 67C), the epitope must be linear in nature (FIG. 73). It is clear that mAb806 and mAb 175 recognize a similar region and conformation of the EGFR.

Using surface plasmon resonance (BIAcore™) the binding of mAb175 to the EGFR peptide ($_{287}$CGADSYE-MEEDGVRKC$_{302}$; SEQ ID NO: 138)) was investigated. The EGFR$_{287\text{-}302}$ was immobilized on the biosensor surface using amine, thiol-disulfide exchange or Pms-Ser coupling chemistries. The latter method immobilizes the peptide exclusively through the N-terminal cysteine (Wade et al. (2006) *Anal. Biochem.* 348, 315-317).

mAb175 bound the EGFR$_{287\text{-}302}$ in all orientations (Table 6). The affinity of mAb175 for EGFR$_{287\text{-}302}$ ranged from 35 nM for Pms-serine coupling to 154 nM for amine coupling. In all cases the binding affinity of mAb175 for EGFR$_{287\text{-}302}$ was lower than that obtained for mAb806 (Table 6). We also determined the affinity of mAb175 to two different extracellular fragments of the EGFR. mAb175 bound the 1-501 fragment with an affinity similar to that obtained using the peptide (16 nM versus 35 nM) (Table 6). As expected, the affinity of mAb175 against the 1-621 full length extracellular domain, which can form the tethered conformation, was much lower (188 nM). Although mAb806 and mAb 175 have similar affinities for EGFR$_{287\text{-}302}$, mAb175 appears to display a higher affinity for the extra-cellular domain of the EGFR (Table 6). Clearly, the mAb 175 epitope is contained within the EGFR$_{287\text{-}302}$ and, like mAb806, the binding affinity to extra-cellular domain of the EGFR is dependent on conformation.

TABLE 6

BIAcore™ determination of antibody affinities for mAb806 and mAb175 binding to EGFR epitopes

| EGFR Fragment | K$_D$ for mAb175 (nM) | K$_D$ for mAb806 (nM) |
|---|---|---|
| 287-302 (Pms-Ser coupling) | 35 | 16 |
| 287-302 (Thiol coupling) | 143 | 84 |
| 287-302 (Amine coupling) | 154 | 85 |
| 1-501 (Unable to form tether) | 16 | 34 |
| 1-621 (Can form tether) | 188 | 389 |

The panel of mutants of the 273-621 EGFR fragment, expressed on the surface of yeast (Chao et al. (2004) *J. Mol. Biol.* 342, 539-550; Johns et al. (2004) *J. Biol. Chem.* 279, 30375-30384) was used to characterize the fine structure of the mAb175 epitope. mAb 175 and mAb806 displayed a near identical pattern of reactivity to the mutants (Table 7). Disruption of the 287-302 disulfide bond only had a moderate effect on the epitope reactivity as the antibody bound to all mutants at C287 and to some but not all mutants at C302 (Table 7) Amino acids critical for mAb175 binding include E293, G298, V299, R300 and C302 (Table 7). mAb175 appeared moderately more sensitive to mutations V299 and D297 but mAb806 also showed reduced binding to some mutations at these sites (Table 7). Again, the mAb175 epitope appears to be essentially the same as the epitope recognized by mAb806.

TABLE 7

Display of EGFR Epitope 287-302 mutations on yeast and the binding scores for mAb806 and mAb175

| EGFR Mutant | mAb806 Binding | mAb175 Binding |
|---|---|---|
| C287A | + | + |
| C287G | + | + |
| C287R | + | + |
| C287S | + | + |
| C287W | + | + |
| C287Y | + | + |
| G288A | ++ | ++ |
| A289K | ++ | ++ |
| D290A | ++ | ++ |
| S291A | ++ | ++ |
| Y292A | ++ | ++ |
| E293A | + | + |
| E293D | + | + |
| E293G | + | + |
| E293K | − | − |
| M294A | ++ | ++ |
| E295A | ++ | ++ |
| E296A | ++ | ++ |
| D297A | ++ | + in contact |
| D297Y | + | + |
| G298A | + | + |
| G298D | − | − |
| G298S | − | − |
| V299A | ++ | + in contact |
| V299D | − | − |
| V299K | ++ | + in contact |
| R300A | ++ | ++ |
| R300C | + | + |
| R300P | − | − |
| K301A | ++ | ++ |
| K301E | + | + |
| C302A | − | − |
| C302F | + | + |
| C302G | − | − |
| C302R | + | + |
| C302S | − | − |
| C302Y | + | + |

Efficacy of mAb175 Against Tumor Xenografts Stimulated by Δ2-7EGFR or an EGFR Autocrine Loop The in vivo anti-tumor activity of mAb806 and mAb175 against U87MG.Δ2-7 glioma xenografts was examined. Xenografts were allowed to establish for 6 days before antibody therapy (3 times a week for 2 weeks on days indicated) commenced. At this time, the average tumor volume was 100 mm$^3$ (FIG. 68A). mAb175 treatment resulted in a reduction in overall tumor growth rate compared to treatment with vehicle or mAb806 and was highly significant at day 19 post-inoculation (P<0.0001 versus control and P<0.002 versus mAb806), when the control group was sacrificed for ethical reasons. The average tumor volume at this time was 1530, 300 and 100 mm$^3$ for the vehicle, mAb806 and mAb175 treatment groups, respectively (FIG. 68A), confirming the antitumor activity of mAb175 activity against xenografts expressing the Δ2-7 EGFR.

Even though U87MG cells express approximately 1×10$^5$ EGFR per cell, mAb 806 is not able to recognize any of the surface EGFR, and not surprisingly, does not inhibit U87MG in vivo growth. Furthermore these cells do not co-express any EGFR ligand. A study was conducted as to whether the EGFR epitope is transiently exposed, and hence able to be recognized by mAb806 and mAb175 in cells containing an EGFR autocrine loop. The prostate cell line DU145 expresses the wtEGFR at levels similar to that observed in U87MG cells, however unlike the U87MG cells, the DU145 cells contain an amplification of the TGF-α gene and thus exhibit an EGFR/TGF-α autocrine loop. Both mAb175 and 806 bind to DU145 cells as determined by FACS analysis (FIG. 68B) and both are able to immunoprecipitate a small proportion of the EGFR extracted from these cells (FIG. 68C). Both techniques showed greater binding of mAb175, however, when compared to mAb528, which binds to the L2 domain, mAb175 and mAb806 only bind a subset of EGFR on the surface of these cells (FIG. 68B and FIG. 68C). Similar observations were seen with a second prostate cell line (LnCap); (data not shown) and a colon line (LIM1215) both of which also contain EGFR autocrine loops (Sizeland, A. M. and Burgess, A. W. (1992) *Mol Cell Biol.* 3, 1235-1243; Sizeland, A. M. and Burgess, A. W. (1991) *Mol Cell Biol.* 11, 4005-4014). Clearly, mAb806 and mAb175 can recognize only a small proportion of the EGFR on cells in the presence of an autocrine stimulation loop.

Since mAb175 and mAb806 bind more effectively to the EGFR expressed in DU145 cells than U87MG cells, a study was conducted to analyze the anti-tumor activity of these antibodies in DU145 xenografts grown in nude mice. Xenografts were allowed to establish for 18 days before therapy commenced (3 times a week for 3 weeks on days indicated). At this time the average tumor volume was 90 mm$^3$ (FIG. 68D). Both mAb175 and mAb806 inhibited the growth of DU145 xenografts. The control group was sacrificed on day 67 and had a mean tumor volume of 1145 mm$^3$ compared with 605 and 815 mm$^3$ for the mAb806 and mAb 175 groups respectively (p<0.007 and 0.02 respectively) (FIG. 68D).

3D-Structure of $EGFR_{287-302}$ in Contact with the Fab Fragments of mAb806 and mAb175

Figure 69C:
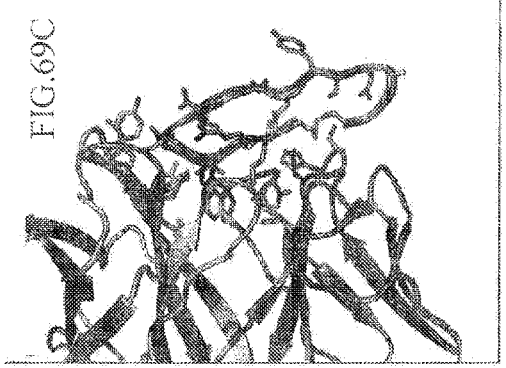
Figure 69F:
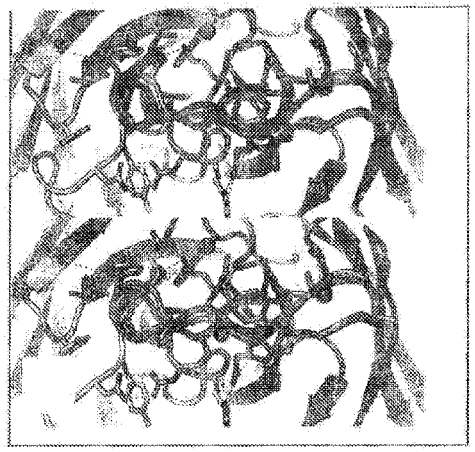
Figure 69B:
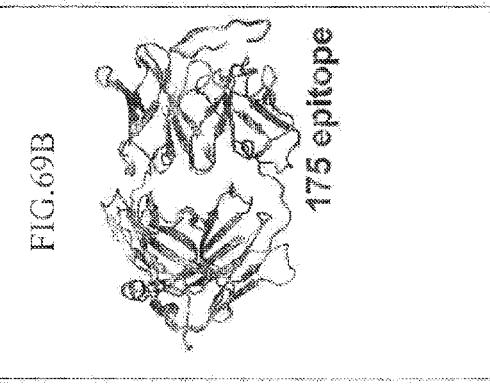
Figure 69E:
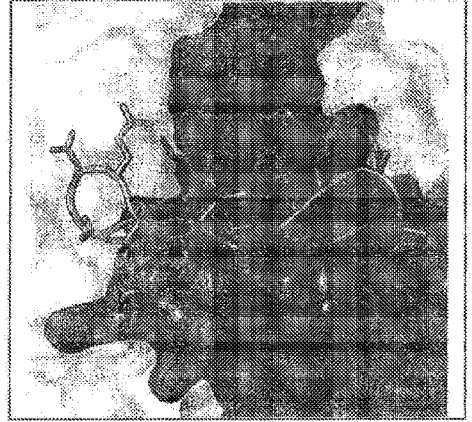
Figure 69A:
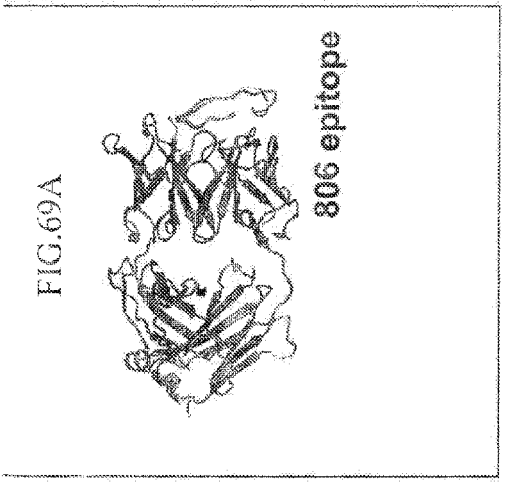
Figure 69D:
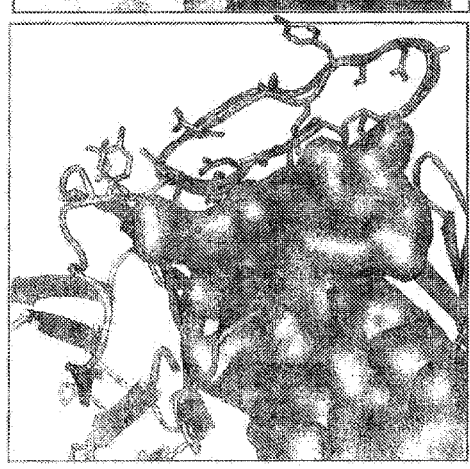

In order to understand the molecular details of how mAb806 and mAb 175 could recognize EGFR in some, but not all conformations, the crystal structures of Fab fragments for both antibodies were determined in complex with the oxidized $EGFR_{287-302}$ epitope (at 2.0 and 1.59 Å resolution respectively, FIGS. 69A & 69B) and alone (at 2.3 Å and 2.8 Å resolution, respectively). In both cases, the free and complexed Fab structures were essentially the same and the conformations of the peptide and CDR loops of the antibodies were well defined (FIG. 69). The epitope adopts a β-ribbon structure, with one edge of the ribbon pointing towards the Fab and V299 buried at the centre of the antigen-binding site (FIGS. 69C-E). Both ends of the epitope are exposed to solvent, consistent with these antibodies binding much longer polypeptides.

Of the 20 antibody residues in contact with the epitope, there are only two substitutions between mAb806 and mAb 175 (FIG. 65). mAb 175 contact residues are: light-chain S30, S31, N32, Y49, H50, Y91, F94, W96 and heavy-chain D32, Y33, A34, Y51, S53, Y54, S55, N57, R59, A99, G100, R101; the mAb806 contact residues are the same, with sequence differences for the light-chain, N30 and heavy-chain, F33. $EGFR_{287-302}$ binds to the Fab through close contacts between peptide residues 293-302, with most of the contacts being between residues 297 and 302. The only hydrogen bonds between main chain atoms of $EGFR_{287-302}$ and the Fab are for residues 300 and 302 (FIG. 69F). Recognition of the epitope sequence occurs through side-chain hydrogen bonds to residues E293 (to H50 and R101 of the Fab), D297 (to Y51 and N57), R300 (to D32) and K301 (via water molecules to Y51 and W96). Hydrophobic contacts are made at G298, V299 and C302.

The conformation of the epitope backbone between 293 and 302 was essentially identical in the Fab806 and Fab175 crystals (runs deviation=0.4 Å, for Cα atoms in these residues). Although constrained by the disulfide bond, the N-terminus of the peptide (287-292) does not make significant contact in either antibody structure and conformations in this region differ. However, this segment in the Fab806 complex appears rather disordered. More interestingly, the conformation of the $EGFR_{287-302}$ peptide in contact with the antibodies is quite closely related to the $EGFR_{287-302}$ conformation observed in the backbone of the tethered or untethered EGFR structures (Li et al., 2005; Garrett et al., 2002). For $EGFR_{287-302}$ from the Fab175 complex, the rms deviations in Cα positions are 0.66 and 0.75 Å, respectively (FIG. 69).

To gain further insight into the recognition of EGFR by mAb806 and mAb175, the conformation of $^{15}$N-labelled oxidized peptide $EGFR_{287-307}$ was studied by NMR spectroscopy in solution, free and in the presence of 806 Fab (see Materials and Methods). For the free peptide, resonances were assigned and compared to those for random coil. Essentially, the free peptide adopted a random coil structure, not the beta ribbon as seen in the native EGFR (Garrett et al. (2002) *Cell* 20; 110, 763-773).

Upon addition of the Fab, resonance shifts were observed. However, due to the weak signal arising from significant line broadening upon addition of the Fab and successful crystallization of the complexes, the solution structure of the Fab806-epitope complex was not pursued further. Clearly though, when the peptide binds to the Fab fragment of mAb806 (or mAb175) it appears that the Fab selects or induces the conformation of the peptide which matches that peptide in the native receptor.

In order to study why mAb806 and mAb175 recognize only some conformations of EGFR, the Fab fragment of mAb175 was docked onto an extra-cellular domain of EGFR (tethered and untethered monomers) by superimposing $EGFR_{287-302}$. For a Δ2-7-like fragment there were no significant steric clashes with the receptor. In the untethered form there was substantially more accessible surface area of the Fab buried (920 Å$^2$ compared with 550 $^{Å2}$ in the tethered form). Therefore, this antigen may make additional contacts with non-CDR regions of the antibody, as has been indicated by yeast expression mutants (Chao et al. (2004) *J. Mol. Biol.* 342, 539-550). Conversely, docking the whole EGFR ectodomain onto the Fab, there is substantial spatial overlap with the part of the CR1 domain preceding the epitope (residues 187-286) and running through the centre of the Fab (FIGS. 69D and 69E). Hence, as the CR1 domain has essentially the same structure in tethered or untethered conformations, mAb806 or mAb 175 will be unable to bind to either form of EGFR. Clearly, there must be a difference between the orientation of the epitope with respect to the CRI domain in either known conformations of the wtEGFR and the orientation that permits epitope binding. Inspection of the CR1 domain indicated that the disulfide bond (271-283) preceding $EGFR_{287-302}$ constrains the polypeptide which blocks access to the epitope; disruption of this disulfide, even though it is not involved in direct binding to the antibodies, would be expected to allow partial unfolding of the CR1 domain so that mAb175 or mAb806 could gain access to the epitope.

Breaking of the EGFR 271-283 Disulfide Bond Increases mAb806 Binding

Disulfide bonds in proteins provide increased structural rigidity but in some cell surface receptors, particularly those for cytokines and growth factors, transient breaking of disulfide bonds and disulfide exchange can control the receptor's function (Hogg, P. J. (2003) *Trends in biochemical sciences* 28, 210-214). As this was one mechanism by which mAb806 and mAb175 could gain access to their binding site, increasing the accessibility of the epitope was attempted by mutating either or both of the cysteine residues at positions 271 and 283 to alanine residues (C271A/C283A). The vectors capable of expressing full length C271A-, C283A- or C271A/C283A-EGFR were transfected into the IL-3 dependent Ba/F3 cell line. Stable Ba/F3 clones, which expressed the C271A- and C271A/C283A-EGFR mutant at levels equivalent to the wtEGFR were selected (FIG. 70A. Ba/F3 cells expressing high levels of mutant C283A-EGFR were not observed. As previously described, the wtEGFR reacts poorly with mAb806; however, the mutant receptors reacted equally strongly with mAb528, mAb806 and the anti-FLAG antibody, suggesting that the receptor is expressed at the cell surface, is folded correctly and that the epitope for mAb806 is completely accessible in such cases. To confirm that mAb806 recognizes the C271A/C283A mutant more efficiently than the wtEGFR, the ratio of mAb806 binding to the binding of mAb528 was determined. Since both the wild-type and C271A/C283A EGFR were N-terminally FLAG-tagged, the ratio of mAb806 and mAb528 binding to the M2 antibody was also determined. As reported previously, mAb806 only recognized a small proportion of the total wtEGFR expressed on the surface of Ba/F3 cells (the mAb806/528 binding ratio is 0.08) (Table 8). In contrast, mAb806 recognized virtually all of the C271A/C283A mutant EGFR expressed on the cell surface (an mAb806/528 binding ratio of 1.01) (FIG. 70A and Table 8).

TABLE 8 mAb806 reactivity with cells expressing the wild-type or C271A/C283A EGFR

| Cell Line | Ratios of antibody binding | | |
|---|---|---|---|
| | mAb 528/M2 | mAb806/M2 | mAb806/mAb 528 |
| wtEGFR-FLAG | 1.37 | 0.11 | 0.08 |
| wt-EGFR | — | — | 0.07 |
| C271/283* | 1.08 ± 0.10 | 1.09 ± 0.38 | 1.01 ± 0.13 |

*Average for four independent clones

Mutation of the two cysteines did not compromise EGF binding or receptor function. BaF3 cells expressing the C271A/C283A EGFR mutant proliferate in the presence of EGF (FIG. 70B). A left-shift in the dose response curve for EGF in cells expressing the C271A/C283A mutations was reproducibly observed, suggesting either higher affinity for the ligand, or enhanced signaling potential for the mutant receptor. Western blotting analysis confirmed that the C271A/C283A mutant is expressed at similar levels to the wtEGFR and is tyrosine phosphorylated in response to EGF stimulation (FIG. 70C). Consistent with previous studies in other cell lines, mAb806 has no effect on the in vitro EGF-induced proliferation of Ba/F3 cells expressing the wtEGFR, while the ligand blocking mAb528 completely inhibits the EGF-induced proliferation of these cells (FIG. 70D, left panel). In contrast, mAb806 totally ablated the EGF-induced proliferation in BaF3 cells expressing the C271A/C283A mutant (FIG. 70D, right panel). When the 271-283 cysteine loop is disrupted, not only does mAb806 bind more effectively, but once bound, mAb806 prevents ligand induced proliferation.

TABLE 9

Data Collection and Refinement Statistics

| | 806 (native) | 806 (peptide) | 175 (native) | 175 (peptide) |
|---|---|---|---|---|
| | Data Collection | | | |
| Space Group | $P2_12_12$ | $P2_1$ | $P2_12_12_1$ | $P2_12_12$ |
| Cell Dimensions (Å) | | | | |
| A | 140.37 | 35.92 | 36.37 | 83.17 |
| B | 74.62 | 83.16 | 94.80 | 69.26 |
| C | 83.87 | 72.21 β = 92.43 | 108.90 | 71.47 |
| Source | in-house | BNL X29 | in-house | in-house |
| Wavelength (Å) | 1.542 | 1.1 | 1.542 | 1.542 |
| Resolution Range (Å) | 29.7-2.2 (2.27-2.20) | 50-2.0 (2.07-2.0) | 50-2.8 (2.87-2.8) | 14.18-1.59 (1.65-1.59) |
| $R_{merge}$ (%) | 6.4 (26.7) | 6.6 (28.2) | | 8.6 (30.0) |
| I/σI | 12.2 (3.2) | 22 (3.15) | | 10.2 (2.2) |
| Completeness (%) | 98.3 (91.3) | 96.6 (79.2) | 98.4 (90.5) | 78.8 (11.8) 98.1 at 1.89 Å |
| Total Reflections | 156497 | 98374 | | 205401 |
| Unique Reflections | 44905 | 27692 | 9171 | 43879 |
| | Refinement | | | |
| Resolution range (Å) | 20-2.3 | 72.17-2.00 | 50-2.6 | 14.18-1.6 |
| Reflections | 37397 | 26284 | 9171 | 41611 |
| $R_{cryst}$ | 0.225 | 0.226 | 0.210 | 0.203 |
| $R_{free}$ | 0.289 | 0.279 | 0.305 | 0.257 |
| Protein Atoms | 6580 | 3294 | 3276 | 3390 |
| Solvent Atoms | 208 | 199 | 46 | 247 |
| r.m.s.d bond length (Å) | 0.022 | 0.007 | 0.015 | 0.014 |
| r.m.s.d bond length (°) | 1.70 | 1.12 | 1.77 | 1.48 |
| Average B-factor (Å$^2$) | 40.3 | 33.6 | 37.5 | 20.7 |
| Overall anisotrpic B-factors (Å$^2$) B11 | −1.52 | 2.42 | 0.20 | 1.13 |

Discussion

Structural studies with the $EGFR_{287-302}$ epitope show that both mAb806 and mAb175 recognized the same 3D-structural motif in the wtEGFR structures, indicating that this backbone conformation also occurs in and is exposed in the Δ2-7EGFR. Critically, however, the orientation of the epitope in these structures would prevent antibody access to the relevant amino acids. This is consistent with the experimental observation that mAb806 does not bind wtEGFR expressed on the cell surface at physiological levels.

The results with the $EGFR_{C271A/C283A}$ mutant indicate that the CR1 domain can open up to allow mAb806 and mAb175 to bind stoichiometrically to this mutant receptor. This mutant receptor can still adopt a native conformation as it is fully responsive to EGF stimulation but, unlike the wtEGFR, is fully inhibited by mAb806. If a misfolded form of the EGFR with this disulfide bond broken were to exist on the surface of cancer cells, the data clearly shows it would be capable of initiating cell signaling and should be inhibited by either mAb806 or mAb175.

Another explanation of the data is that during ligand activation the structural rearrangement of the receptor could induce local unfolding in the vicinity of the epitope, allowing the receptor to adopt a conformation which permits binding. In crystal structures, the epitope lies near the physical centre of the EGFR ectodomain and access to the epitope is blocked by both the folded CR1 domain and the quaternary structure of the EGFR ectodomain. In the tethered and the untethered conformations, the integrity of the CR1 domain is stabilized by additional interactions with either the L1:ligand:L2 domains (untethered) or the L2:CR2 domains (tethered). However, the epitope region has some of the highest thermal parameters found in the ectodomain: the mAb806/175 epitope is structurally labile. During receptor activation, when the receptor undergoes a transition between the tethered and untethered conformations, mAb806 and mAb175 can access the epitope. Thus at the molecular level, these mechanisms could contribute to the negligible binding of mAb806 and mAb175 to normal cells and the substantially higher levels of binding to tumor cells which have overexpressed and/or activated EGFR.

Example 24

Monoclonal Antibodies 124 and 1133

As discussed in Example 1 above, mAb124 and mAb1133 were generated at the same time as mAb806 and found to display similar properties, in particular specificity for the over-expressed wild-type EGFR, to the unique properties of mAb806 discussed herein.

Initial screens were conducted in New York (Jungbluth et al. (2003) A Monoclonal Antibody Recognizing Human Cancers with Amplification/Over-Expression of the Human Epidermal Growth Factor Receptor PNAS. 100, 639-644. ELISA competition assessments and Biacore™ analyses were conducted to determine whether mAb124 and/or mAb1133 recognize an epitope identical to mAb806 or an alternative EGFR determinant.

FACS Analysis

Antibody binding to U87MG.Δ2-7, A431 and HN5 cells was assessed by FACS. All antibodies displayed a similar specificity as that of mAb806 with strong binding to the de2-7 EGFR and low binding to over-expressed wild-type EGFR.

Competition ELISA

A series of competition ELISAs were conducted to determine whether the 124 and 1133 antibodies competed with the mAb806 epitope. Briefly, the denatured soluble domain of the EGFR (sEGFR) was coated on to ELISA plates. The unlabeled 124 or 1133 antibodies were then added across the plate in increasing concentrations. Following washing, biotinylated mAb806 was added to each well to determine if it could still bind the sEGFR. Detection of bound mAb806 was achieved using streptavidin-conjugated HRP. If an antibody binds the same (or overlapping) epitope as mAb806 then mAb806 binding is not expected.

Results are summarized in Table 10. A concentration dependant inhibitory binding effect was observed for mAb124 and mAb1133: mAb806 binding increased as concentration of unlabeled antibody was decreased, suggesting that the 124 and 1133 antibodies recognize an epitope identical to mAb806 or one in close proximity.

TABLE 10

Summary mAb124 and mAb1133 Competition ELISA binding to sEGFR.

| Unlabeled Blocking Antibody | Binding of biotin-labeled 806 |
| --- | --- |
| 124 | None |
| 1133 | None |
| 806 (control for inhibition) | None |
| Irrelevant IgG2b | ++++ |

FACS Analysis: Cell Binding Competition

U87MG.Δ2-7 cells were pre-incubated with unlabeled antibody 124, 1133. Positive control 806 and isotype control were included in the assay. Cells were washed, then stained with Alexa 488-conjugated mAb806 and the level of 806 binding was determined by FACS.

Results are summarized in Table 11. The 124 and 1133 antibodies blocked mAb806 binding to the cell surface indicating recognition of an epitope identical to mAb806 or one in close proximity.

TABLE 11

FACS Analysis: U87MG.Δ2-7 Cell Binding Competition

| Unlabeled Blocking Antibody | Inhibition of Alexa488-labeled 806 |
| --- | --- |
| 124 | +++ |
| 1133 | +++ |
| 806 | ++++ |
| IgG2b control | none |

BIAcore™ Analysis: Binding to the mAb806 peptide epitope

The EGFR amino acid sequence $_{287}$CGADSYE-MEEDGVRKC$_{302}$ (SEQ ID NO:14) containing the mAb806 epitope was synthesized as a peptide and immobilized onto the biosensor chip. Binding of antibodies 124, 1133 and 806 (200 nM) to this peptide was measured. Maximal binding resonance units (RU) obtained are summarized in Table 12. The 124, 1133 showed clear binding to the peptide confirming recognition of the 806 peptide epitope.

TABLE 12

BIAcore™ Analysis: Maximal binding to the mAb806 peptide epitope

| Antibody | Binding to mAb806 peptide (RU) |
| --- | --- |
| 806 | 1100 |
| 124 | 1000 |
| 1133 | 800 |

Discussion

As shown in this Example, mAb124 and mAb1133 bind to the EGFR peptide recognized by mAb806 and block binding of mAb806 to the extracellular domain of EGFR and cells expressing the de2-7 EGFR. Thus, these three antibodies recognize the same determinant on EGFR.

Example 25

Clinical Testing of ch806

A clinical study was designed to examine the in-vivo specificity of ch806 in a tumor targeting/biodistribution/pharmacokinetic analysis in patients with diverse tumor types.
1. Materials and Methods
Trial Design This first-in-man trial was an open label, dose escalation Phase I study. The primary objective was to evaluate the safety of a single infusion of ch806 in patients with advanced tumors expressing the 806 antigen. The secondary study objectives were to determine the biodistribution, pharmacokinetics and tumor uptake of $^{111}$In-ch806; determine the patient's immune response to ch806; and to assess early evidence of clinical activity of ch806. A single dose was chosen for this study in order to optimally assess the in-vivo specificity of ch806 for EGFR expressed on tumor. The protocol was approved by the Human Research and Ethics Committee of the Austin Hospital prior to study commencement. The trial was performed under the Australian Therapeutic Goods Administration Clinical Trials Exemption (CTX) scheme. All patients gave written informed consent.

Eligibility criteria included: advanced or metastatic tumors positive for 806 antigen expression based on chromogenic in-situ hybridisation or immunohistochemistry of archived tumor samples (tumors were defined as 806 positive if immunohistochemical assessment of archived tumour samples showed any cells positive for 806 expression, see below); histological or cytologically proven malignancy; measurable disease on CT scan with at least one lesion≥2 cm; expected survival of at least 3 months; Karnofsky performance scale (KPS)≥70; adequate hematologic, hepatic and renal function; age>18 yrs; and able to give informed consent. Exclusion criteria included: active central nervous system metastases (unless adequately treated and stable); chemotherapy, immunotherapy, biologic therapy, or radiation therapy within four weeks prior to study entry; prior antibody exposure [unless no evidence of human anti-chimeric antibodies (HACA)]; failure to fully recover from effects of prior cancer therapy; concurrent use of systemic corticosteroids or immunosuppressive agents; uncontrolled infection or other serious disease; pregnancy or lactation; women of childbearing potential not using medically acceptable means of contraception.

Patients received a single infusion of ch806 trace labelled with Indium-111 ($^{111}$In 200-280 MBq; 5-7 mCi) by intravenous infusion in normal saline/5% human serum albumin over 60 minutes. The planned dose escalation meant patients were enrolled into one of four dose levels: 5, 10, 20 and 40 mg/m$^2$. These doses were chosen to allow assessment of the specificity of ch806 to EGFR expressed on tumor, and to determine if any normal tissue compartment binds ch806 (and affects pharmacokinetics or biodistribution) in-vivo. Biodistribution, pharmacokinetics, and immune response were evaluated in all patients.

Whole body gamma camera imaging for assessment of biodistribution and tumour uptake was performed on Day 0, Day 1, Day 2 or 3, Day 4 or 5, and Day 6 or 7 following $^{111}$In-ch806 infusion. Blood samples for pharmacokinetics were obtained at these time-points, and additionally on Day 14 (±2 days) and Day 21 (±2 days). Blood samples for assessment of HACA levels were obtained at baseline, and weekly until Day 30. Toxicity assessment was performed at each study visit. Physical examination and routine hematology and biochemistry were performed weekly until end of study (Day 30). Restaging was performed on Day 30.
Dose Escalation Criteria The first patient at each dose level was observed for four weeks prior to enrollment of any additional patients. If no dose limiting toxicity (DLT) was observed in any of the first 2 patients within 4 weeks of the infusion of ch8063, 4 patients were then to be entered on the next highest dosage tier. If one patient in any cohort of 2 patients experienced a DLT within 4 weeks from the first dose, an additional 4 patients (maximum of 6) were entered at that dosage level. If no more than one patient out of 6 in any dose level experienced ≥Grade 3 toxicity, subsequent patients were entered at the next dose level.

DLT was defined as Grade 3 non-haematological toxicity, or Grade 4 haematological toxicity as defined by the NCI Common Terminology Criteria for Adverse Events (CTCAE v3.0). Maximum tolerated dose (MTD) was defined as the ch806 dose below that where 2 or more patients out of 6 experienced DLT.
Radiolabeling of Ch806

Clinical grade ch806 was produced in the Biological Production Facility of the Ludwig Institute for Cancer Research, Melbourne, Australia. The antibody ch806 was labelled with $^{111}$In (MDS Nordion, Kanata, Canada) via the bi-functional metal ion chelate CHX-A"-DTPA according to methods described previously (Scott et al. (2000) Cancer Res 60, 3254-3261; Scott et al. (2001) J. Clin. Oncol. 19(19), 3976-3987).
Gamma Camera Imaging Whole body images of $^{111}$In-ch806 biodistribution were obtained in all patients on Day 0 after infusion of $^{111}$In-ch806, and on at least 3 further occasions up to Day 7 following infusion. Single photon emission computed tomography (SPECT) images of a region of the body with known tumor were also obtained on at least one occasion during this period. All gamma camera images were acquired on a dual-headed gamma camera (Picker International, Cleveland, Ohio).
Pharmacokinetics Blood for pharmacokinetic analysis was collected on Day 0—pre $^{111}$In-ch806 infusion; then at 5 minutes, 60 minutes, 2 h and 4 h post $^{111}$In-ch806 infusion, Day 1, Day 2 or 3, Day 4 or 5, and Day 6 or 7. Further blood for pharmacokinetics of ch806 protein was also obtained on Day 14 (±2 days) and Day 21 (±2 days) and Day 30 (±2 days).

Serum samples were aliquoted in duplicate and counted in a gamma scintillation counter (Packard Instruments, Melbourne, Australia), along with appropriate $^{111}$In standards. The results of the serum were expressed as % injected dose per liter (% ID/L). Measurement of patient serum ch806 protein levels following each infusion was performed using a validated protocol for the immunochemical measurement of ch806 protein in human serum[40]. The limit of quantitation for ch806 in serum samples was 70 ng/mL. All samples were assayed in triplicate and were diluted by a factor of at least 1:2. Measured serum levels of ch806 were expressed as µg/mL.

Pharmacokinetic calculations were performed on serum $^{111}$In-ch806 measurements following the infusion, and ELISA determined patient sera ch806 protein levels, using a curve fitting program (WinNonlin Pro Node 5.0.1, Pharsight Co., Mountain View, Calif.). Estimates were determined for the following parameters: T½α and T½β (half lives of the initial and terminal phases of disposition); Vl, volume of central compartment; $C_{max}$ (maximum serum concentration); AUC (area under the serum concentration curve extrapolated to infinite time); and CL (total serum clearance).

Whole Body Clearance and Tumor and Organ Dosimetry of $^{111}$In-ch806

Whole body and normal organ (liver, lungs, kidney and spleen) dosimetry calculations were performed based on regions of interest in each individual patient $^{111}$In-ch806 infusion image dataset, allowing calculation of cumulated activity and analysis using OLINDA for final dosimetry results (Stabin et al. (2005) *J. Nucl. Med.* 46(6), 1023-1027). Regions of interest were also defined for suitable tumors at each time point on $^{111}$In-ch806 image datasets, corrected for background and attenuation, and dosimetry calculation was performed to derive the concentration of $^{111}$In-ch806 in tumor/gm (Scott et al. (2005) *Clin. Cancer Res.* 11(13), 4810-4817). This was converted to µg ch806/gm tumor tissue based on the injected mg ch806 protein dose.

HACA Analysis

Blood samples for HACA assessment were taken prior to ch806 infusion, then weekly until 30 days after ch806 infusion. Samples were analysed by ELISA, and by surface plasmon resonance technology using a BIAcore™2000 instrument, as described previously (Scott et al., 2005; Liu et al. (2003) *Hybrid Hybridomics* 22(4), 219-28; Ritter et al. (2001) *Cancer Res.* 61(18), 685-6859).

Immunohistochemistry Method

Formalin-fixed paraffin embedded tumor tissue from each patient on the trial was immunostained as follows: Briefly, 4 µm sections of paraffin embedded tissue were mounted onto SuperFrost® Plus slides (Menzel-Glaser, Germany), de-paraffinized and rehydrated prior to microwave antigen retrieval in Target Retrieval Solution, pH 6.0 (10 min; Dako, Glostrup, Denmark). Sections were then treated with 3% H2O2 for 10 min, to eliminate endogenous peroxidase and incubated at room temperature for 60 min with m806 antibody (4 µg/ml) or with appropriate concentration of isotype-matched negative control antibody (IgG2b; Chemicon, Temecula, Calif.). Antibody binding was detected using the PowerVision® Kit (Immuno Vision Technologies, Brisbane, Calif.). To allow visualization of the immunostaining, sections were incubated with the chromogen 3-amino-9-ethylcarbazole (0.4%, Sigma Chemical Co. MO, USA) for 10 min and counterstained with Mayer's haematoxylin. Negative controls for the immunostaining procedure were prepared by omission of the primary antibody. Results were expressed as a percentage of positive tumor cell staining.

Chromogenic In Situ Hybridization Method

Formalin fixed paraffin embedded tumor tissue from each patient on the trial was sectioned and mounted on SuperFrost® Plus slides, de-paraffinized and rehydrated prior to pre-treatment with the SpotLight® Tissue Pre-treatment Kit (Zymed Laboratories Inc. South San Francisco, Calif.). Sections were then covered with the SpotLight® EGFR DNA probe, denatured at 95° C. for 10 min and incubated overnight at 37° C. Following hybridization, slides were washed in 0.5×SSC. Detection of the probe was carried out using the SpotLight® CISH™ Polymer Detection Kit. Sections that showed clusters of signals or ≥5 individual signals in >25% of cancer cells were considered to have an amplification of the EGFR gene that correlated with m806 reactivity.

2. Results

Patients

Eight patients (1 female and 7 male; mean age of 61 years (range 44-75)] completed the trial (Table 13). Primary tumor sites, prior therapy history, and sites of disease at study entry are also shown in Table 13. All 8 patients had 806 antigen positivity in archived tumors (Table 13).

All patients fulfilled inclusion criteria and, except for Patient 8 (who had a primary brain tumor), all had metastatic disease at study entry. Sites of disease classified as target lesions included: lung (5 patients), brain (1 patient), lymph nodes (1 patient), supraglottis (1 patient). Other sites of metastatic disease (non-target lesions) included a supra-renal mass, bone and lymph nodes (Table 13). The median Karnofsky performance status was 90 (range 80-100).

TABLE 13

Patient Characteristics

| Pt. No. | Dose Level (mg/m²) | Age (yrs) | Sex | KPS (%) | Site of Primary Tumour | IHC of positive cells (%) | Prior Therapies | Disease Sites at Study Entry | Tumor response to ch806 |
|---|---|---|---|---|---|---|---|---|---|
| 1 | 5 | 71 | M | 10 | NSCLC | 50-75 | RT | Lung, Adrenal | PD |
| 8 | 5 | 44 | M | 90 | Anaplastic astrocytoma | >75* | Surgery, RT, CT | Brain | SD |
| 2 | 10 | 49 | F | 80 | SCC Anus | <10 | Chemo, RT | LN, Lung, Bone | SD |
| 3 | 10 | 75 | M | 90 | NSCLC | 50-75 | Surgery RT | Lung | SD |
| 4 | 20 | 52 | M | 100 | Colon | <10† | Surgery, CT | Lung, LN | PD |
| 5 | 20 | 65 | M | 80 | Mesothelioma | >75 | RT, CT | Lung | SD |
| 6 | 40 | 59 | M | 80 | SCC vocal cord | >75 | Surgery, RT, CT | Soft Tissue | SD |
| 7 | 40 | 71 | M | 90 | SCC skin | 50-75 | Surgery, CT | Lung, LN | PD |

Abbreviations:
F = female;
M = male;
NSCLC = non small cell lung carcinoma;
SCC = squamous cell carcinoma;
RT = radiotherapy;
CT = chemotherapy;
LN = lymph nodes;

TABLE 13-continued

Patient Characteristics

| Pt. No. | Dose Level (mg/m²) | Age (yrs) | Sex | KPS (%) | Site of Primary Tumour | IHC of positive cells (%) | Prior Therapies | Disease Sites at Study Entry | Tumor response to ch806 |
| --- | --- | --- | --- | --- | --- | --- | --- | --- | --- |

PD = progressive disease;
SD = stable disease
*positive for de2-7 EGFR expression
†positive for EGFR gene amplification Adverse Events and HACA Adverse events related to ch806 are listed in Tables 14 and 18. No infusion related adverse events were observed. There was no DLT, and hence MTD was not reached. The principle toxicities that in the investigator's opinion were possibly attributable to ch806 were: transient pruritis, mild nausea, fatigue/lethargy, and possible effects on serum ALP and GGT levels. A CTC grade 2 elevation in GGT level in Patient 5 was observed, however this was on a background of a baseline grade 1 elevation, and was transient in nature. Three serious adverse events (SAEs) were reported but none were attributed to ch806. Overall, ch806 was safe and well tolerated at all dose levels with generally predictable and manageable minor toxicities being observed. Further dose escalation was not performed due to the limited amount of cGMP ch806 available for the trial.

A positive immune response to ch806 (with concordance of both ELISA and BIAcore™ methodologies) was observed in only one of the eight patients (Patient 1).

TABLE 14

Occurrence of Adverse Events Related to ch806

| Adverse Event | Dose Level (mg/m²)* | | | | Total Number of Episodes of Each Event |
| --- | --- | --- | --- | --- | --- |
| | 5 | 10 | 20 | 40 | |
| Dizziness | 0 | 0 | 0 | 1 | 1 |
| Fatigue | 0 | 0 | 1 | 0 | 1 |
| Lethargy | 0 | 0 | 0 | 1 | 1 |
| Appetite suppressed | 0 | 0 | 0 | 1 | 1 |
| Nausea | 0 | 1 | 0 | 1 | 2 |
| Pruritis | 1 | 0 | 0 | 0 | 1 |
| ALP - elevated | 0 | 0 | 1 | 0 | 1 |
| GGT - elevated | 0 | 0 | 1 | 0 | 1 |
| Total | 1 | 1 | 3 | 4 | 9 |

*Numbers represent number of episodes of any event at each dose level

TABLE 15

Distribution of Study Agent Related Adverse Events

| Dose Level (mg/m²) | Maximum CTC Grade Toxicity* | | | |
| --- | --- | --- | --- | --- |
| | 1 = Mild | 2 = Moderate | 3 = Severe | 4 = Life-threatening |
| 5 | 1 | 0 | 0 | 0 |
| 10 | 1 | 0 | 0 | 0 |
| 20 | 2 | 1 | 0 | 0 |
| 40 | 4 | 0 | 0 | 0 |
| Overall | 8 | 1 | 0 | 0 |

*Number of patients

Radiolabeling of ch806

There were a total of 8 infusions of $^{111}$In-ch806 administered during the trial. The mean (±SD) radiochemical purity and immunoreactivity of $^{111}$In-ch806 was measured to be 99.3±0.1% and 77.4±7.0% respectively.

Biodistribution of ch806

The initial pattern of $^{111}$In-ch806 biodistribution in patients at all dose levels was consistent with blood pool activity, which cleared gradually with time. Over the one week period post injection the uptake of $^{111}$In-ch806 in liver and spleen was consistent with the normal clearance of $^{111}$In-chelate metabolites through the reticuloendothelial system. Specific localization of $^{111}$In-ch806 was observed in target lesions (≥2 cm) of all patients at all dose levels (FIG. 94), including target lesions located in the lungs (Patients 1, 3, 4, 5, and 7), the abdomen (Patients 1 and 2), and the supraglottic region in the right side of the neck (Patient 6). High uptake of $^{111}$In-ch806 in a brain tumor (Patient 8) was also demonstrated (FIG. 95). Importantly, uptake of $^{111}$In-ch806 in tumor was not dependent on a the level of 806 antigen expression. For example, Patient 4 demonstrated high uptake by both lung target lesions, despite <10% positivity by IHC for 806 reactivity in archived tumor (FIG. 96). This degree of uptake of $^{111}$In-ch806 in target lesions in Patient 4 was comparable to that seen in Patient 3, where 50-75% of tumor cells were positive for 806 antigen staining on archived sample immunohistochemistry (FIG. 96).

Pharmacokinetics

Individual patient pharmacokinetic parameters T½α and T½β, V1, $C_{max}$, AUC and CL for the single infusion of $^{111}$In-ch806 are shown in Table 16. The Kruskal-Wallis rank sum test was applied to the alpha and beta half lives, V1 and clearance. No significant difference between dose levels was observed (P>0.05).

The pharmacokinetic curve fit to the pooled population ELISA data is shown in FIG. 97. The mean±SD pharmacokinetic parameters were T½α 29.16±21.12 hrs, T½β 172.40±90.85 hrs, V1 2984.59±91.91 ml, and CL 19.44±4.05 ml/hr. Measured peak and trough ch806 serum concentrations ($C_{max}$ and $C_{min}$) data are presented in Table 17 for each patient. As expected, linear relationships were observed for $C_{max}$ and $C_{min}$ with each dose level. The mean±SD values determined for the ch806 ELISA pharmacokinetic data were in good agreement with the values obtained for the $^{111}$In-ch806 pharmacokinetic data (Table 16).

TABLE 16

Mean ± SD Pharmacokinetic Parameter Estimates for $^{111}$In-CHX-A"-DTPA-ch806 in each Dose Level and across all Dose Levels.

| Dose Level (mg/m²) | T½ α (hr) Mean | SD | T½ β (hr) Mean | SD | V1 (mL) Mean | SD | CL (mL/hr) Mean | SD | AUC (hr * mg/mL) Mean | SD |
|---|---|---|---|---|---|---|---|---|---|---|
| 5 | 10.91 | 3.4 | 183.9 | 110.2 | 2963.06 | 493.23 | 21.97 | 16.59 | 541.17 | 371.75 |
| 10 | 11.75 | 4.4 | 124.5 | 9.25 | 3060.29 | 721.70 | 28.58 | 8.60 | 566.79 | 26.39 |
| 20 | 9.34 | 8.3 | 125.3 | 73.66 | 2902.06 | 1064.77 | 30.98 | 21.65 | 1438.12 | 957.18 |
| 40 | 8.95 | 3.2 | 133.9 | 10.79 | 4742.42 | 169.10 | 37.99 | 6.47 | 2269.04 | 381.68 |
| ALL | 10.24 | 1.32 | 141.90 | 28.30 | 3416.96 | 886.04 | 29.88 | 6.61 | | |

TABLE 17

Cmax and Cmin Serum ch806 Levels Determined by ELISA Analysis.

| PT. NO. | DOSE LEVEL (MG/M²) | $C_{max}$* (µG/ML) | $C_{min}$* (µG/ML) |
|---|---|---|---|
| 1 | 5 | 1.38 ± 0.02 | 0.10 ± 0.05† |
| 8 | 5 | 1.52 ± 0.17 | 0.96 ± 0.08 |
| 2 | 10 | 5.92 ± 0.11 | 1.50 ± 0.01 |
| 3 | 10 | 6.27 ± 0.45 | 1.83 ± 0.20 |
| 4 | 20 | 12.25 ± 0.66 | 4.05 ± 0.05 |
| 5 | 20 | 11.22 ± 0.77 | 1.58 ± 0.04 |
| 6 | 40 | 27.76 ± 2.10 | 6.90 ± 0.38 |
| 7 | 40 | 32.32 ± 0.84 | 6.80 ± 0.13 |

*$C_{max}$ = 60 min post injection.;
$C_{min}$ = Day 7
†Day 8 serum level

Dosimetry of $^{111}$In-ch806

Whole body clearance was similar in all patients across all dose levels, with a $T_{1/2}$ biologic (mean±SD) of 948.6±378.6 hrs. Due to the relatively short physical half-life, calculation of biological halftime was extremely sensitive to small changes in effective halftime. There was no statistical significant difference in whole body clearance between dose levels [Kruskal-Wallis rank sum test: P-value=0.54] (FIG. 98).

The clearance of $^{111}$In-ch806 from normal organs (liver, lungs, kidney and spleen) showed no difference between dose levels, and the mean $T_{1/2}$ effective was calculated to be 78.3, 48.6, 69.7 and 66.2 hrs respectively. There was no statistically significant difference in clearance between these normal organs. In particular, liver clearance showed no difference between dose levels (FIG. 98), indicating no saturable antigen compartment in the liver for ch806.

Tumor dosimetry analysis was completed for 6 patients. Patients 1 and 2 had target lesions close to the cardiac blood pool, or motion during some image acquisitions, which prevented accurate analysis. The measured peak uptake of $^{111}$In-ch806 occurred 5-7 days post infusion, and ranged from 5.2–13.7×10$^{-3}$% injected dose/gm tumor tissue.

Assessment of Clinical Activity

At the completion of this one month study period 5 patients were found to have stable disease, and 3 patients progressive disease (Table 13). Interestingly, one patient (Patient 7, 40 mg/m² dose level) had clinical evidence of transient shrinkage of a palpable auricular lymph node (proven to be metastatic SCC on fine needle aspiration) during the study period, which suggests possible biologic activity of ch806. However, this patient had confirmed progressive disease by RECIST at study completion.

Additional Data

Eight patients [1 female and 7 male; mean age of 61 years (range 44-75)] completed this phase 1 trial as reported (Scott et al. (2007) Proc. Natl. Acad. Sci. U.S.A. 104, 4071-4076). All patients fulfilled inclusion criteria and, except for Patient 8 (who had a primary brain tumor), all had metastatic disease at study entry. Ab uptake by the tumor was seen in all patients, and $^{111}$In-ch806, the chimerized version of mAb806, demonstrated prompt and high level uptake in tumor (FIG. 71). The clearance of $^{111}$In-ch806 from normal organs (liver, lungs, kidney and spleen) showed no difference between dose levels (Scott et al., 2007). In particular, liver clearance showed no difference between dose levels, indicating no saturable antigen compartment in the liver for ch806. Total liver uptake was a maximum of 14.45±2.43% ID immediately post infusion, and declined to 8.45±1.63% ID by 72 hours, and 3.18±0.87% ID by one week post infusion. This is in marked contrast to the uptake of antibodies to wtEGFR (e.g. 225), which have been shown to reach over 30% ID in liver (for a 40 mg dose) for over 3 days post infusion (Divgi et al. (1991) J. Natl. Cancer Inst. 83, 97-104). The measured peak tumor uptake of $^{111}$In-ch806 occurred 5-7 days post infusion. Calculation of quantitative tumor uptake in Patients 1 and 3 could not be accurately performed due to proximity of target lesion to cardiac blood pool and patient movement. Peak ch806 uptake in tumor ranged from 5.21 to 13.73×10$^{-3}$% ID/gm tumor tissue. Calculation of actual ch806 concentration in tumor showed peak values of (mean±SD) 0.85±0 µg/gm (5 mg/$^{m2}$), 0.92±0 µg/gm (10 mg/$^{m2}$), 3.80±1.10 µg/gm (20 mg/m²), and 7.05±1.40 µg/gm (40 mg/m²).

Discussion

As set forth in this Example, this study represents the first reported demonstration of the biodistribution and tumor targeting of a chimeric antibody against an epitope only exposed on overexpressed, mutant or ligand activated forms of the EGFR. Ch806 showed excellent targeting of tumor sites in all patients, no evidence of normal tissue uptake, and no significant toxicity. These in vitro and in vivo characteristics of ch806 distinguish it from all other antibodies targeting EGFR.

At doses up to 40 mg/m², ch806 was well tolerated, no DLT was observed and MTD was not reached. The principle toxicities that were possibly attributable to ch806 were transient pruritis, mild nausea, fatigue/lethargy, and possible effects on serum ALP and GGT levels. The advanced nature of these patient's malignancies meant their disease could also have been contributing factors to these adverse events. Of the adverse events that were possibly related to study drug, all were mild, many were self-limiting, and none required any active treatment. Importantly, no skin rash or gastrointestinal tract disturbances were observed in any patient, even at the highest dose level. The excellent tolerability of ch806 in this single-dose study justifies the next step of testing in repetitive dose trials.

The biodistribution of ch806 in all patients showed gradual clearance of blood pool activity, and no definite normal tissue uptake of [111]In-ch806. Excellent tumor uptake of ch806 was also evident in all patients, including lung, lymph node, and adrenal metastases, and in mesothelioma and glioma. This was observed at all dose levels including 5 mg/m² (the lowest dose studied), which is one tenth to one twentieth of the dose required to visualise uptake in tumor by other antibodies to wtEGFR[33]. This difference in uptake of ch806 compared to antibodies to wtEGFR can be attributed to their substantial normal tissue (liver and skin) uptake due to wtEGFR acting as an antigen sink[33]. In addition, the localization of [111]In-ch806 was high even in patients with low expression of 806 assessed by immunohistochemistry of archived tumor samples (FIG. 96). The uptake of [111]In-ch806 in glioma was particularly impressive (FIG. 97), and comparable to any published data on antibody targeting of brain tumor following systemic or even locoregional infusion. This data supports the unique selectivity of ch806 to EGFR expressed by a broad range of tumors, and confirms the lack of normal tissue uptake of this antibody in human.

Pharmacokinetic analyses showed that ch806 has a terminal half-life of more than a week, and no dose dependence of [111]In-ch806 serum clearance. Linear relationships also were observed for AUC, Cmax and Cmin, with dose levels above 10 mg/m² achieving trough serum concentrations above 1 µg/mL. The Vl, Cl, T½α and T½β values were consistent between dose levels, and in keeping with typical IgG1 human antibodies (Scott et al., 2005; Steffens et al. (1997) *J. Clin. Oncol* 15, 1529-1537; Scott et al. (2001) *J. Clin. Oncol.* 19(19), 3976-3987). The clearance of ch806 was also determined to be slower when ELISA ch806 calculations were compared to [111]In-ch806 measurements. While this difference may be explained by the small number of patients studied, the longer sampling time points for the ch806 ELISA would support this value as being more representative of true ch806 clearance. The pharmacokinetic values for ch806 are comparable to other chimeric antibodies reported to date (Steffens et al., 1997; Scott et al., 2001), and supports a weekly dosing schedule of ch806.

The quantitative dosimetry and pharmacokinetic results indicate that there is no saturable normal tissue compartment for ch806 for the dose levels assessed in this trial. Importantly, the lack of dose dependence on pharmacokinetic and whole body and liver organ clearance is in marked contrast to all reported studies of antibodies to wtEGFR (Baselga J. and Artega C. L. (2005) *J. Clin. Oncol.* 23, 2445-2449; Divgi et al. *J. Natl. Cancer Inst.* 83(2), 97-104; Baselga J (2001) *Eur. J. Cancer* 37 Suppl. 4, S16-22; Gibson et al. (2006) *Clin. Colorectal Cancer* 6(1), 29-31; Rowinsky et al. (2004) *J. Clin. Oncol.* 22, 3003-3015; Tan et al. (2006) *Clin. Cancer Res.* 12(21), 6517-6522) supporting the tumour specificity and lack of normal tissue binding of ch806 in humans. These observations provide compelling evidence of the potential for ch806 (or humanized forms) to selectively target EGFR in tumor, avoid the normal toxicity of other EGFR antibodies and kinase inhibitors (particularly skin) (Lacouture A E (2006) *Nature Rev. Cancer* 6, 803-812; Adams G. P. and Weiner L. M. (2005) *Nat. Biotechnol.* 23(9), 1147-1157) and potentially achieve greater therapeutic effect. Moreover, the possibility of payload delivery (due to the rapid internalisation of mAb 806 in tumor cells), and combination treatment with other biologics such as EGFR antibodies and tyrosine kinase inhibitors where combined toxicity is likely be minimised, is strongly supported by the data from this trial. This study provides clear evidence of the ability to target an epitope on EGFR that is specific for tumor, and further clinical development of this unique approach to cancer therapy is ongoing.

Example 26

Sequence Comparisons

The VH chain and VL chain CDRs for each of mAb806, mAb175, mAb124, mAb1133 and hu806 are set forth and compared herein.

TABLE 18

Murine Antibody Isotype and CDR Sequence Comparisons (Kabat)[1]

| | CDR1 | CDR2 | CDR3 |
|---|---|---|---|
| A. Variable Light Chain | | | |
| 806 (IgG2b) | HSSQDINSNIG (SEQ ID NO: 18) | HGTNLDD (SEQ ID NO: 19) | VQYAQFPWT (SEQ ID NO: 20) |
| 124 (IgG2a) | HSSQDINSNIG (SEQ ID NO: 28) | HGTNLDD (SEQ ID NO: 29) | VQYGQFPWT (SEQ ID NO: 30) |
| 175 (IgG2a) | HSSQDISSNIG (SEQ ID NO: 135) | HGTNLED (SEQ ID NO: 136) | VQYGQFPWT (SEQ ID NO: 137) |
| 1133 (IgG2a) | HSSQDINSNIG (SEQ ID NO: 38) | HGTNLDD (SEQ ID NO: 39) | VQYGQFPWT (SEQ ID NO: 40) |
| B. Variable Heavy Chain | | | |
| 806 (IgG2b) | SDFAWN (SEQ ID NO: 15) | YISYSGNTRYNPSLKS (SEQ ID NO: 16) | VTAGRGFPY (SEQ ID NO: 17) |
| 124 (IgG2a) | SDYAWN (SEQ ID NO: 23) | YISYSANTRYNPSLKS (SEQ ID NO: 24) | ATAGRGFPY (SEQ ID NO: 25) |
| 175 (IgG2a) | SDYAWN (SEQ ID NO: 130) | YISYSANTRYNPSLKS (SEQ ID NO: 131) | ATAGRGFPY (SEQ ID NO: 132) |
| 1133 (IgG2a) | SDYAWN (SEQ ID NO: 33) | YISYSGNTRYNPSLRS (SEQ ID NO: 34) | ATAGRGFPY (SEQ ID NO: 35) |

[1]differences to the mAb806 CDR sequences are underlined

The CDRs given above for the respective antibody isotypes are based on a Kabat analysis. As will be apparent to those of skill in the art, the CDRs may also be defined based on other analysis, for example a composite of Kabat and Chothia definitions. For example, applying a composite Kabat and Chothia analysis to the above isotypes, the sequences of the VL chain CDRs and VH chains CDRs for the respective isotypes are as set forth in Table 19.

TABLE 19

Murine Antibody Isotype and CDR Sequence Comparisons (Composite Kabat and Chothia)[1]

| | CDR1 | CDR2 | CDR3 |
|---|---|---|---|
| A. Variable Light Chain | | | |
| 806 (IgG2b) | HSSQDINSNIG (SEQ ID NO: 18)[2] | HGTNLDD (SEQ ID NO: 139)[2] | VQYAQFPWT (SEQ ID NO: 20)[2] |
| 124 (IgG2a) | HSSQDINSNIG (SEQ ID NO: 28) | HGTNLDD (SEQ ID NO: 140) | VQYGQFPWT (SEQ ID NO: 30) |

TABLE 19-continued

Murine Antibody Isotype and CDR Sequence Comparisons (Composite Kabat and Chothia)[1]

| | CDR1 | CDR2 | CDR3 |
|---|---|---|---|
| 175 (IgG2a) | HSSQDISSNIG (SEQ ID NO: 135) | HGTNLED (SEQ ID NO: 141) | VQYGQFPWT (SEQ ID NO: 137) |
| 1133 (IgG2a) | HSSQDINSNIG (SEQ ID NO: 38) | HGTNLDD (SEQ ID NO: 142) | VQYGQFPWT (SEQ ID NO: 40) |

B. Variable Heavy Chain

| | CDR1 | CDR2 | CDR3 |
|---|---|---|---|
| 806 (IgG2b) | GYSITSDFAWN (SEQ ID NO: 143)[3] | GYISYS-GNTRYNPSLKS (SEQ ID NO: 44)[3] | VTAGRGFPY (SEQ ID NO: 17)[3] |
| 124 (IgG2a) | GYSITSDYAWN (SEQ ID NO: 145) | GYISYSANTRYNPSLKS (SEQ ID NO: 46) | ATAGRGFPY (SEQ ID NO: 25) |
| 175 (IgG2a) | GYSITSDYAWN (SEQ ID NO: 147) | GYISYSANTRYNPSLKS (SEQ ID NO: 48) | ATAGRGFPY (SEQ ID NO: 132) |
| 1133 (IgG2a) | GYSITSDYAWN (SEQ ID NO: 149) | GYISYSGNTRYNPSLRS (SEQ ID NO: 50) | ATAGRGFPY (SEQ ID NO: 35) |

[1]differences to the mAb806 CDR sequences are underlined
[2]See FIG. 17 of co-pending U.S. patent application no. 10/145,598 (U.S. Pat. No. 7,589,180)
[3]See FIG. 16 of co-pending U.S. patent application no. 10/145,598 (U.S. Pat. No. 7,589,180)

TABLE 20 mAb806 and hu806 CDR Sequence Comparisons (Kabat)[1]

| | CDR1 | CDR2 | CDR3 |
|---|---|---|---|

A. Variable Light Chain

| | CDR1 | CDR2 | CDR3 |
|---|---|---|---|
| mAb806 | HSSQDINSNIG (SEQ ID NO: 18) | HGTNLDD (SEQ ID NO: 19) | VQYAQFPWT (SEQ ID NO: 20) |
| hu806 | HSSQDINSNIG (SEQ ID NO: 49) | HGTNLDD (SEQ ID NO: 50) | VQYAQFPWT (SEQ ID NO: 51) |

B. Variable Heavy Chain

| | CDR1 | CDR2 | CDR3 |
|---|---|---|---|
| mAb806 | SDFAWN (SEQ ID NO: 15) | YISYSGNTRYNPSLKS (SEQ ID NO: 16) | VTAGRGFPY (SEQ ID NO: 17) |
| hu806 | SDFAWN (SEQ ID NO: 44) | YISYSGNTRYQPSLKS (SEQ ID NO: 45) | VTAGRGFPY (SEQ ID NO: 46) |

[1]differences to the mAb806 CDR sequences are underlined

As shown above, the CDR sequences of mAb806, mAb175, mAb124 and mAb1133 isotypes are identical except for highly conservative amino acid changes that would be expected to give rise to homologous protein folding for epitope recognition. This data, cumulatively with the binding and other data provided in the Examples above, shows that these isotypes and the hu806 are closely-related family member variants exhibiting the same unique properties discussed above for mAb806 (e.g., binding to an epitope on the EGFR that is accessible to binding only in overexpressed, mutated or ligand activated forms of the EGFR, resulting in unique specificity for tumor-expressed EGFR, but not wtEGFR in normal tissue) and demonstrating that antibodies of distinct variable region sequences, particularly of varying CDR sequences, have the same characteristics and binding capabilities.

REFERENCES

Aboud-Pirak, E., Hurwitz, E., Bellot, F., Schlessinger, J., and Sela, M. (1989) *Proc. Natl. Acad. Sci. USA.* 86, 3778-3781.

Aboud-Pirak, E., Hurwitz, E., Pirak, M. E., Bellot, F., Schlessinger, J., and Sela, M. (1988) *J. Natl. Cancer Inst.* 80, 1605-1611.

Arteaga, C. l. and Baselga, J. (2004) *Cancer Cell.* 5, 525-531.

Ashley, D. M., Batra, S. K., and Bigner, D. D. "Monoclonal antibodies to growth factors and growth factor receptors: their diagnostic and therapeutic potential in brain tumors." *J. Neurooncol.*, 35: 259-273, 1997.

Atlas, I., Mendelsohn, J., Baselga, J., Fair, W. R., Masui, H., and Kumar, R. "Growth regulation of human renal carcinoma cells: role of transforming growth factor a." *Cancer Res.*, 52: 3335-3339, 1992.

Baselga J, Pfister D, Cooper M R, et al. "Phase I studies of anti-epidermal growth factor receptor chimeric antibody C225 alone and in combination with cisplatin." *J. Clin. Oncol.* 2000; 18: 904-14.

Baselga, l. (2006) *Science.* 312, 1175-1178.

Baselga J. and Arteaga, C. L. (2005) *J. Clin. Oncol.* 23, 2445-2459.

Baselga, J. Clinical trials of Herceptin (R) (trastuzumab). *Eur. J. Cancer,* 37: 1824, 2001.

Baselga, J., Norton, L., Albanell, J., Kim, Y. M., and Mendelsohn, J. "Recombinant humanized anti-HER2 antibody (Herceptin) enhances the antitumor activity of paclitaxel and doxorubicin against HER2/neu overexpressing human breast cancer xenografts." *Cancer Res.*, 58: 2825-2831, 1998.

Baselga, J., Norton, L., Masui, H., Pandiella, A., Coplan, K., Miller, W. H., and Mendelsohn, J. "Antitumor effects of doxorubicin in combination with anti-epidermal growth factor receptor monoclonal antibodies." *J. Natl. Cancer Inst.* (Bethesda), 85: 1327-1333, 1993.

Baselga, J., Pfister, D., Cooper, M. R., Cohen, R., Burtness, B., Bos, M., D'Andrea, G., Seidman, A., Norton, L., Gunnett, K., Falcey, J., Anderson, V., Waksal, H., and Mendelsohn, J. "Phase I Studies of Anti-Epidermal Growth Factor Receptor Chimeric Antibody C225 Alone and in Combination With Cisplatin." *J. Clin. Oncol.* 18: 904, 2000.

Baselga, J., Tripathy, D., Mendelsohn, J., Baughman, S., Benz, C. C, Dantis, L., Sklarin, N. T., Seidman, A. D., Hudis, C. A., Moore, J., Rosen, P. P., Twaddell, T., Henderson, l. C., and Norton, L. "Phase II study of weekly intravenous recombinant humanized anti-p185HER2 monoclonal antibody in patients with HER2/neu-overexpressing metastatic breast cancer."*J. Clin. Oncol.,* 14: 737-744, 1996.

Batra S K, Castelino-Prabhu S, Wikstrand C J, et al. "Epidermal growth factor ligand-independent, unregulated, cell-transforming potential of a naturally occurring human mutant EGFRvIII gene." *Cell Growth Differ.* 1995; 6: 1251-9.

Bernier, J. (2006) *Expert. Rev Anticancer Ther.* 6, 1539-1552.

Bhattacharya-Chatterjee, M., S. K. Chatterjee, et al. (2001). "The anti-idiotype vaccines for immunotherapy." *Curr. Opin. Mol. Ther.* 3(1): 63-9. *Biol. Cell.* 13, 4029-4044.

Bouyain, S., Longo, P. A., L1, S., Ferguson, K. M., and Leahy, D. J. (2005) *Proc. Natl. Acad. Sci. USA.* 102, 15024-15029.

Brady, L. W., Miyamoto, C., Woo, D. V., Rackover, M., Emrich, J., Bender, H., Dadparvar, S., Steplewski, Z., Koprowski, H., Black, P., et al. "Malignant astrocytomas treated with iodine-125 labeled monoclonal antibody 425 against epidermal growth factor receptor: a Phase I trial." *Int. J. Radiat. Oncol. Biol. Phys.*, 22: 225-230, 1992.

Brown, G. and N. Ling (1988). Murine Monoclonal Antibodies. Antibodies, Volume 1. A Practical Approach. D. Catty. Oxford, England, IRL Press: 81-104.

Burgess, A. W., Cho, H. S., Eigenbrot, C., Ferguson, K. M., Garrett, T. P., Leahy, D. J., Lemmon, M. A., Sliwkowski, M. x., Ward, C. W., and Yokoyama, S. (2003) *Mol. Cell.* 12, 541-552.

Chao, G., Cochran, 1. R, and Wittrup, K. D. (2004) *J. Mol. Biol.* 342, 539-550.

Cho, H. S, and Leahy, D. J. (2002) *Science* 297, 1330-1333.

Cho, H. S., Mason, K., Ramyar, K. x., Stanley, A. M., Gabelli, S. B., DelUley, D. W., Jr., and Leahy, D. J. (2003) *Nature* 421, 756-760.

Clarke, K., et al., "In vivo biodistribution of a humanized anti-Lewis Y monoclonal antibody (hu3S193) in MCF-7 xenografted BALB/c nude mice." *Cancer Res,* 2000. 60(17): p. 4804-11.

Clarke, K., Lee, F. T., Brechbiel, M. W., Smyth, F. E., Old, L. J., and Scott, A. M. "Therapeutic efficacy of anti-Lewis (y) humanized 3S193 radioimmunotherapy in a breast cancer model: enhanced activity when combined with Taxol chemotherapy." *Clin. Cancer Res.,* 6: 3621-3628, 2000.

Clayton, A. H., Walker, F., Orchard, S. G., Henderson, C., Fuchs, D., Rothacker, J., Nice, E. C., and Burgess, A. W. (2005) *J. Biol. Chem.* 280, 30392-30399.

Daugherty B L, DeMartino J A, Law M F, Kawka D W, Singer I I, Mark G E. "Polymerase chain reaction facilitates the cloning, CDR-grafting, and rapid expression of a murine monoclonal antibody directed against the CD18 component of leukocyte integrins." *Nucleic Acids Res.* 1991 19(9):2471-6.

de Larco, J. E. and Todaro, G. J. (1978) *J. Cell. Physiol.* 94, 335-342.

de Larco, J. E., Reynolds, R., Carlberg, K., Engle, C., and Todaro, G. J. (1980) *J. Biol. Chem.* 255, 3685-3690.

den Eynde, B. and Scott, A. M. Tumor Antigens. In: P. J. Delves and I. M. Roitt (eds.), Encyclopedia of Immunology, Second Edition, pp. 2424 31. London: Academic Press, 1998.

DeNardo S J, Kroger L A, DeNardo G L. "A new era for radiolabeled antibodies in cancer?" *Curr. Opin. Immunol.* 1999; 11: 563-9.

Divgi, C. R., Welt, S., Kris, M., Real, F. X., Yeh, S. D., Gralla, R., Merchant, B., Schweighart, S., Unger, M., Larson, S. M., et al. "Phase I and imaging trial of indium 11-labeled anti-epidermal growth factor receptor monoclonal antibody 225 in patients with squamous cell lung carcinoma." *J. Natl. Cancer Inst.,* 83: 97-104, 1991.

Domagala, T., Konstantopoulos, N., Smyth, F., Jorissen, R. N., Fabri, L., Geleick, D., Lax, I., Schlessinger, J., Sawyer, W., Howlett, G. J., Burgess, A. W., and Nice, E. C. "Stoichiometry, kinetic and binding analysis of the interaction between Epidermal Growth Factor (EGF) and the Extracellular Domain of the EGF receptor." *Growth Factors.* 18: 11-29, 2000.

Domagala, T., N. Konstantopoulos, et al. (2000)."Stoichiometry, kinetic and binding analysis of the interaction between epidermal growth factor (EGF) and the extracellular domain of the EGF receptor." *Growth Factors* 18 (1):11-29.

Safa, M. M. and K. A. Foon (2001)."Adjuvant immunotherapy for melanoma and colorectal cancers." *Semin. Oncol.* 28 (1): 68-92.

Ekstrand A J, Sugawa N, James C D, et al. "Amplified and rearranged epidermal growth factor receptor genes in human glioblastomas reveal deletions of sequences encoding portions of the N- or C-terminal tails." *Proc. Natl. Acad. Sci. USA* 1992; 89: 4309-13.

Ekstrand, A. J., James, C. D., Cavenee, W. K., Seliger, B., Pettersson, R. F., and Collins, V. P. (1991) *Cancer Res.* 51, 2164-2172.

Emsley, P. and Cowtan, K. (2004) *Acta crystallographica* 60, 2126-2132.

Faillot, T., Magdelenat, H., Mady, E., Stasiecki, P., Fohanno, D., Gropp, P., Poisson, M., and Delattre, J. Y. "A Phase I study of an anti-epidermal growth factor receptor monoclonal antibody for the treatment of malignant gliomas." *Neurosurgery* (Baltimore), 39: 478-483, 1996.

Fairlie, W. D., Uboldi, A. D., De Souza, D. P., Hemmings, G. 1, Nicola, N. A., and Baca, M. (2002) *Protein expression and purification* 26, 171-178.

Fan, Z., and Mendelsohn, J. "Therapeutic application of antigrowth factor receptor antibodies." *Curr. Opin. Oncol.,* 10: 67-73, 1998.

Fan, Z., Baselga, J., Masui, H., and Mendelsohn, J. "Antitumor effect of antiepidermal growth factor receptor monoclonal antibodies plus cis-diamminedichloroplatinum on well established A431 cell xenografts." *Cancer Res.,* 53: 4637-4642, 1993.

Fan, Z., Masui, H., Altas, I., and Mendelsohn, J. "Blockade of epidermal growth factor receptor function by bivalent and monovalent fragments of 225 anti-epidermal growth factor receptor monoclonal antibodies." *Cancer Res.,* 53: 4322-4328, 1993.

Feldkamp, M. M., Lala, P., Lau, N., Roncari, L., and Guha, A. "Expression of activated-epidermal growth factor receptors, Ras-guanosine triphosphate, and mitogenactivated protein kinase in human glioblastoma multiforme specimens." *Neurosurgery* (Baltimore), 45: 1442-1453, 1999.

Ferguson, K. M., Berger, M. B., Mendrola, J. M., Cho, H. S., Leahy, D. J., and Lemmon, M. A. (2003) *Mol. Cell.* 11, 507-517.

Fernandes H, Cohen S, Bishayee S. "Glycosylation-induced conformational modification positively regulates receptor-receptor association: a study with an aberrant epidermal growth factor receptor (EGFRvIII/deEGFR) expressed in cancer cells." *J. Biol. Chem.* 2001; 276: 5375-83.

Filmus J, Pollak M N, Cailleau R, et al. "MDA-468, a human breast cancer cell line with a high number of epidermal growth factor (EGF) receptors, has an amplified EGF receptor gene and is growth inhibited by EGF." *Biochem. Biophys. Res. Commun.* 1985; 128: 898-905.

Filmus, J., Trent, J. M., Pollak, M. N., and Buick, R. N. "Epidermal growth factor receptor gene-amplified MDA-468 breast cancer cell line and its nonamplified variants." *Mol. Cell. Biol.,* 7: 251-257, 1987.

Gadella, T. W. J. and Jovin, T. M. (1995) *Journal of Cell Biology* 129, 1543-1558.

Gan H. K., Walker F., Burgess A. W., Rigopoulos A., Scott A. M. and Johns T. G. "The Epidermal Growth Factor Receptor (EGFR) Tyrosine Kinase Inhibitor AG1478 Increases the Formation of Inactive Untethered EGFR Dimers: Implications For Combination Therapy With Monoclonal Antibody 806." *J. Biol. Chem.* (2007);282(5):2840-50.

Garcia de Palazzo, I.E., Adams, G. P., Sundareshan, P., Wong, A. J., Testa, J. R., Bigner, D. D., and Weiner, L. M. "Expression of mutated epidermal growth factor receptor by non-smalt cell along carcinomas." *Cancer Res.*, 53: 3217-3220, 1993.

Garrett, T. P., McKern, N. M., Lou, M., Elleman, T. C., Adams, T. E., Lovrecz, G. 0., Zhu, H. J., Walker, F., Frenkel, M. J., Hoyne, P. A., Jorissen, R. N., Nice, E. C., Burgess, A. W., and Ward, C. W. (2002) *Cell*, 110, 763-773.

Garrett, T. P., McKern, N. M., Lou, M., Elleman, T. C., Adams, T. E., Lovrecz, G. 0., Kofler, M., Jorissen, R. N., Nice, E. c., Burgess, A. W., and Ward, C. W. (2003) *Mol. Cell*, 11, 495-505.

Gill, G. N., Kawamoto, T., Cochet, C., Le, A., Sato, J. D., Masui, H., McLeod, C., and Mendelsohn, J. (1984) *J. Biol. Chem.* 259, 7755-7760.

Goldstein N I, Prewett M, Zuklys K, et al. "Biological efficacy of a chimeric antibody to the epidermal growth factor receptor in a human tumor xenograft model." *Clin. Cancer Res.* 1995; 1: 1311-8.

Grandis, J. R., Melhem, M. F., Gooding, W. E., Day, R., Holst, V. A., Wagener, M. M., Drenning, S. D., and Tweardy, D. J. "Levels of TGP-a and BOER protein in head and neck squamous cell carcinoma and patient survival." *J. Natl. Cancer Inst.*, 90: 32CE, 1998.

Green, M. C., Murray, J. L., and Hortobagyi, G. N. "Monoclonal antibody therapy for solid tumors." *Cancer Treat. Rev.*, 26: 269-286, 2000.

Gunther, N., Betzel, C., and Weber, W. "The secreted form of the epidermal growth factor receptor. Characterization and crystallization of the receptor ligand complex." *J. Biol. Chem.* 265:22082-5, 1990.

Halaisch, M. E., Schmidt, U., Botefur, I. C., Holland, J. P., and Ohnuma, T. "Marked inhibition of glioblastoma target cell tumorigenicity in vitro by retrovirus-mediated transfer of a hairpin ribozyme against deletion-mutant epidermal growth factor receptor messenger RNA." *J. Neurosurg.*, 92: 297-305, 2000.

Han, Y., Caday, C. G., Nanda, A., Cavenee, W. K., and Huang, H. J. "Tyrphostin AG1478 preferentially inhibits human glioma cells expressing truncated rather than wild-type epidermal growth factor receptors. *Cancer Res.*" 56:3859-3861, 1996.

Harari, D., and Yarden, Y. "Molecular mechanisms underlying ErbB2/HER2 action in breast cancer." *Oncogene*, 19: 6102-6114, 2000.

Hills D, Rowlinson-Busza G, Gullick W J. "Specific targeting of a mutant, activated EGF receptor found in glioblastoma using a monoclonal antibody." *Int. J. Cancer* 1995; 63: 537-43.

Hogg, P. J. (2003) *Trends in biochemical sciences* 28, 210-214.

Holbro, T. and Hynes, N. E. (2004) *Annu. Rev. Pharmacol. Toxicol.* 44:195-217, 195-217.

Hooft, R. W., Vriend, G., Sander, C., and Abola, E. E. (1996) *Nature* 381, 272.

Huang H S, Nagane M, Klingbeil C K, et al. "The enhanced tumorigenic activity of a mutant epidermal growth factor receptor common in human cancers is mediated by threshold levels of constitutive tyrosine phosphorylation and unattenuated signaling." *J. Biol. Chem.* 1997; 272: 2927-35.

Humphrey, P. A., Wong, A. I., Vogelstein, B., Zalutsky, M. R., Fuller, G. N., Archer, G. E., Friedman, H. S., Kwatra, M. M., Bigner, S. H., and Bigner, D. D. "Anti-synthetic peptide antibody reacting at the fusion junction of deletion mutant epidermal growth factor receptors in human glioblastoma" (1990) *Proc. Natl. Acad. Sci. USA* 87, 4207-4211.

Johns T G, Perera R M, Vernes S C, Vitali A A, Cao D X, Cavenee W K, Scott A M and Furnari F B. "The efficacy of EGFR-specific antibodies against glioma xenografts is influenced by receptor levels, activation status and heterodimerization." *Clin. Cancer Res*. (2007); 13(6): 1911-1925.

Johns T G, Stockert E, Ritter G, Jungbluth A A, H-J. Su Huang, Cavenee W K, Smyth F E, Hall C M, Watson N, Nice E C, Gullick W J, Old U, Burgess A W, Scott A M. "Novel monoclonal antibody specific for the DE2-7 Epidermal Growth Factor Receptor (EGFR) that also recognizes the EGFR expressed in cells containing amplification of the EGFR gene." *Int. J. Cancer* (2002) 98: 398-408

Johns, T. G., Adams, T. E., Cochran, J. R., Hall, N. E., Hoyne, P. A., Olsen, M. J., Kim, Y S., Rothacker, J., Nice, E. C., Walker, F., Ritter, G., Jungbluth, A. A., Old, L. J., Ward, C. W., Burgess, A. W., Wittrup, K. D., and Scott, A. M. "Identification of the Epitope for the EGFR-Specific Monoclonal Antibody 806 Reveals that it Preferentially Recognizes an Untethered Form of the Receptor." *J. Biol. Chem.* (2004) 279: 30375-30384

Johns, T. G., et al., "Novel monoclonal antibody specific for the de2-7 epidermal growth factor receptor (EGFR) that also recognizes the EGFR expressed in cells containing amplification of the EGFR gene." *Int. J. Cancer*, 2002. 98(3): p. 398-408.

Johns, T. G., Luwor, R. B., Murone, C., Walker, F., Weinstock, J., Vitali, A. A., Perera, R. M., Old, L. J., Nice, E. C., Burgess, A. W. and Scott, A. M. "Anti-tumor efficacy of cytotoxic drugs and the monoclonal antibody 806 is enhanced by the epidermal growth factor receptor (EGFR) inhibitor AG1478." *PNAS* (2003) 100: 15871-15876

Johns, T. G., Mellman I., Cartwright G. A., Ritter G., Old L. J., Burgess A. W. and Scott A. M. "The anti-tumor monoclonal antibody 806 recognizes a high-mannose form of the EGF receptor that reaches the cell surface when cells over-express the receptor." *FASEB J.* (2005) 19(7):780-2.

Jorissen, R. N., Walker, F. W., Pouliot, N., Garrett, T. P. J., Ward, C. W., and Burgess, A. W. "Epidermal growth factor receptor: mechanisms of activation and signaling." *Exp. Cell Res.* 284, 31-53.2003.

Jungbluth, A. A., Stockert, E., Huang, H-J. S., Collins, V P, Coplan, K., Iversen, K., Kolb, D., Johns T. G., Scott A. M., Gullick W. J., Ritter, G., Cohen L., Cavanee W. K., Old, L. J. A "Monoclonal Antibody Recognizing Human Cancers with Amplification/Over-Expression of the Human Epidermal Growth Factor Receptor." *PNAS* (2003) 100: 639-644.

Korshunov, A., Golanov, A., Sycheva, R., and Pronin, I. "Prognostic value of tumor associated antigen immunoreactivity and apoptosis in cerebral glioblastomas: an analysis of 163 cases." *J. Clin. Pathol.*, 52, -574-580, 1999.

Kwok T T, Sutherland R M. "Differences in EGF related radiosensitisation of human squamous carcinoma cells with high and low numbers of EGF receptors." *Br. J. Cancer* 1991; 64: 251-4.

Laskowski, R. A., MacArthur, M. W., Moss, D. S., and Thornton, J. M. (1993) J. Appl. Cryst. 26, 283-291.

Lee F. T., Mountain A. J., O'Keefe G. J., Sagona J., Rigopoulos A., Smyth F. E., Govindan S. V., Goldenberg D. M., Old L. J. and Scott A M "ImmunoPET detection of xenografts expressing de2-7 EGFR using Iodine-124 labelled ch806 via residualising ligand IMPR4." *J. Nucl. Med.* (2006) 47 (5) suppl 1: 429P.

Li D., Ji H., Zaghlul S., McNamara K., Liang M. C., Shimamura T., Kubo S., Takahashi M., Chirieac L. R., Padera R. F., Scott A. M., Jungbluth, A. A., Cavenee W. K., Old L. J., Demetri G. D., Wong K K. "Therapeutic anti-EGFR antibody 806 generates responses in murine de novo EGFR mutant-dependent lung carcinomas." *J. Clin. Invest.* (2007); 117(2): 346-352.

Lindmo, T., et al., "Determination of the immunoreactive fraction of radiolabeled monoclonal antibodies by linear extrapolation to binding at infinite antigen excess." *J. Immunol. Methods,* 1984. 72(1): p. 77-89.

Liu, Z., Panousis, C., Smyth, F. E., Murphy, R., Wirth, V., Cartwright, G., Johns, T. G., and Scott, A. M. "Generation of Anti-Idiotype Antibodies for Application in Clinical Immunotherapy Laboratory Analyses." *Hybridoma and Hybridomics,* (2003) 22 (4): 219-228.

Luwor R B, Johns T G, Murone C, H-J. Su Huang, Cavenee W K, Ritter G, Old L J, Burgess A W, Scott A M. "Monoclonal Antibody 806 Inhibits the Growth of Tumor Xenografts Expressing Either the DE2-7 or Amplified Epidermal Growth Factor Receptor (EGFR) but not Wild-Type EGFR." *Cancer Research* (2001) 61: 5355-5361.

Luwor, R. B., Zhu, H-J., Walker, F., Vitali A. A., Perera, R. M., Burgess, A. W., Scott, A. M. and Johns, T. G. "The Tumor Specific de2-7 Epidermal Growth Factor Receptor (EGFR) confers Increased survival in BaF/3 Cells Via a PI-3 Kinase Dependent Mechanism." *Oncogene* (2004) 23: 6095-6104

MacDonald, A., Chisholm, G. D., and Habib, F. K. (1990) *Br. J Cancer.* 62, 579-584.

Masui, H., Kawamoto, T., Sato, J. D., Wolf, B., Sato, G., and Mendelsohn, J. "Growth inhibition of human tumor cells in athymic mice by anti-epidermal growth factor receptor monoclonal antibodies." *Cancer Res.,* 44: 1002-1007, 1984.

Mellinghoff, I. K., Cloughesy, T. F., and Mischel, P. S. (2007) *Clin. Cancer Res.* 13, 378-381.

Mendelsohn, J. "Epidermal growth factor receptor inhibition by a monoclonal antibody as anticancer therapy. *Clin. Cancer Res."* 3:2703-2707, 1997.

Mickey, D. D., Stone, K. R., Wunderli, H., Mickey, G. H., Vollmer, R. T., and Paulson, D. F. (1977) *Cancer Res.* 37, 4049-4058.

Mineo C, Gill G N, Anderson R G. "Regulated migration of epidermal growth factor receptor from caveolae." *J. Biol. Chem.* 1999; 274: 30636-43.

Mishima K, Johns T G, Luwor R B, Scott A M, Stockert E, Jungbluth A A, Ji X, Suvarna P, Voland J R, Old U, H-J. Su Huang, Cavenee W K. "Growth Suppression of Intracranial Xenografted Glioblastomas Overexpressing Mutant Epidermal Growth Factor Receptors by Systemic Administration of Monoclonal Antibody (mAb) 806, a Novel Monoclonal Antibody Directed to the Receptor." *Cancer Research* (2001) 61: 5349-5354.

Mishima, K. Nagane, M., Lin, H., Cavenee, W. K., and Huang, H-J. S. "Expression of a tumor-specific mutant epidermal growth factor receptor mediates glioma cell invasion in vivo." *Proc. Am. Assoc. Cancer Res.,* 40: 519, 1999.

Mishima, K., Mazar, A. P., Gown, A., Skelly, M., Ji, X. D., Wang, X. D., Jones, T. R., Cavenee, W. K., and Huang, H-J. S. "A peptide derived from the non-receptor-binding region of urokinase plasminogen activator inhibits glioblastoma growth and angiogenesis in vivo in combination with cisplatin." *Proc. Natl. Acad. Sci. USA,* 97: 8484-8489, 2000.

Moscatello, D. K., Holgado-Madruga, M., Godwin, A. K., Ramirez, G., Gunn, G., Zoltick, P. W., Biegel, J. A., Hayes, R. L., and Wong, A. J. "Frequent expression of a mutant epidermal growth factor receptor in multiple human tumors." *Cancer Res.,* 55: 5536-5539, 1995.

Murshudov, G. N., Vagin, A. A., and Dodson, E. J. (1997) *Acta crystallographica* 53, 240-255.

Nagane, M., Coufal, F., Lin, H., Bogler, O., Cavenee, W. K., and Huang, H. J. "A common mutant epidermal growth factor receptor confers enhanced tumorigenicity on human glioblastoma cells by increasing proliferation and reducing apoptosis." *Cancer Res.* 56: 5079-86, 1996.

Nagane, M., Levitzki, A., Gazit, A., Cavenee, W. K., and Huang, H-J. S. "Drug resistance of human glioblastoma cells conferred by a tumor-specific mutant epidermal growth factor receptor through modulation of Bcl-XL and caspase-3-like proteases." *Proc. Natl. Acad. Sci. USA,* 95: 5724-5729, 1998.

Nagane, M., Lin, H., Cavenee, W. K., and Huang, H-J. S. "Aberrant receptor signaling in human malignant gliomas: mechanisms and therapeutic implications." *Cancer Lett.,* 162 (Suppl. 1):517-S21, 2001.

Neidhardt, F. C., Bloch, P. L. and Smith, D. F. (1974) *Journal of bacteriology* 119.736-747.

Nishikawa, R., Ji, X. D., Harmon, R. C., Lazar, C. S., Gill, G. N., Cavenee, W. K., and Huang, H. J. A mutant epidermal growth factor receptor common in human glioma confers enhanced tumorigenicity. *Proc. Natl. Acad. Sci. USA,* 91:7727-7731, 1994.

Ogiso, H., Ishitani, R, Nureki, 0., Fukai, S., Yamanaka, M., Kim, l. H., Saito, K., Sakamoto, A., Inoue, M., Shirouzu, M., and Yokoyama, S. (2002) *Cell* 20: 110, 775-787.

Okamoto S, Yoshikawa K, Obata Y, et al. "Monoclonal antibody against the fusion junction of a deletion-mutant epidermal growth factor receptor." *Br. J. Cancer* 1996; 73: 1366-72.

Olapade-Olaopa, E. 0., Moscatello, D. K., MacKay, E. H., Horsburgh, T., Sandhu, D. P., Terry, T. R., Wong, A. J., and Habib, F. K. "Evidence for the differential expression of a variant EGF receptor protein in human prostate cancer." *Br. J. Cancer.* 82: 186-94, 2000.

Old, L. J. "Immunotherapy for cancer." *Sci. Am.,* 275: 102-109, 1996.

Otwinowski, Z. and Minor, W. (1997) "Processing of X-ray diffraction data collected in oscillation mode." *Academic Press* (New York).

Padlan E A. "A possible procedure for reducing the immunogenicity of antibody variable domains while preserving their ligand-binding properties." *Mol. Immunol.* 1991 28(4-5):489-98.

Padlan et al., EP 519596, Merck/NIH

Palacios, R, Henson, G., Steinmetz, M., and McKeam, J. P. (1984) *Nature.* 309, 126-131.

Panousis, C., Rayzman, V. M., Johns, T. G., Renner C., Liu Z., Cartwright, G., Lee F-T., Wang, D., Gan, H., Cao, D., Kypridis, A., Smyth, F. E., Brechbiel, M. W., Burgess, A. W., Old, L. J. and Scott, A. M. "Engineering and characterization of chimeric monoclonal antibody 806 (ch806) for targeted immunotherapy of tumours expressing de2-7 EGFR or amplified EGFR." *Br. J. Cancer* (2005) 92:1069-1077.

PCT Patent WO02092771, 2002.

Perera R. M., Narita Y., Furnari, F. B., Luwor, R. B., Burgess, A. W., Old, L. J., Cavenee, W. K., Scott, A. M. and Johns, T. G. "A novel EGFR antibody that displays synergistic anti-tumor activity when combined with conventional EGFR therapeutics." *Clinical Cancer Research* (2005) 11: 6390-6399.

Perera R. M., Zoncu R., Johns T. G., Pypaert M., Lee F. T., Mellman I., Old L. J., Toomre D. K., and Scott A. M. "Internalization, intracellular trafficking, and biodistribution of monoclonal antibody 806: a novel anti-epidermal growth factor receptor antibody." *Neoplasia.* (2007); 9(12):1099-110

Perez-Soler, R., Donato, N. J., Shin, D. M., Rosenblum, M. G., Zhang, H. Z., Tornos, C., Brewer, H., Chan, J. C., Lee, J. S., Hong, W. K., et al. "Tumor epidermal growth factor receptor studies in patients with non-small-cell lung cancer or head and neck cancer treated with monoclonal antibody RG 83852." *J. Clin. Oncol.,* 12: 730-739, 1994.

Pietras, R. J., Pegam, M. D-, Finn, R-S., Maneval, D. A., and Slmon, D. J. "Remission of human breast cancer xenografts on therapy with humanized monoclonal antibody to HER-2 receptor and DNA-reactive drugs." *Oncogene,* 17: 2235-2249, 1998.

Ponten J, Macintyre E H. "Long term culture of normal and neoplastic human glia." *Acta Pathol. Microbiol. Scand.* 1968; 74: 465-86.

Press, O. W., DeSantes, K., Anderson, S. K., and Geissler, F "Inhibition of catabolism of radiolabeled antibodies by tumor cells using lysosomotropic amines and carboxylic ionophores." *Cancer Res.* 50: 1243-50, 1990.

Reist C J, Batra S K, Pegram C N, et al. "In vitro and in vivo behavior of radiolabeled chimeric anti-EGFRvIII monoclonal antibody: comparison with its murine parent."*Nucl. Med. Biol.* 1997; 24: 639-47.

Reist, C. J., Archer, G. E., Kurpad, S. N., Wikstrand, C. J., Vaidyanathan, G., Willingham, M. C., Moscatello, D. K., Wong, A. J., Bigner, D. D., and Zalutsky, M. R. "Tumor-specific anti-epidermal growth factor receptor variant III monoclonal antibodies: use of the tyramine-cellobiose radioiodination method enhances cellular retention and uptake in tumor xenografts." *Cancer Res.,* 55: 4375-4382, 1995.

Reist, C. J., Archer, G. E., Wikstrand, C. J., Bigner, D. D., and Zalutsky, M. R. "Improved targeting of an anti-epidermal growth factor receptor variant III monoclonal antibody in tumor xenografts after labeling using N-succinimidyl 5-iodo-3-pyridinecarboxylate." *Cancer Res.* 57: 1510-5, 1997.

Reist, C. J., Batra, S. K., Pegram, C. N., Bigner, D. D., and Zalutsky, M. R. "In vitro and in vivo behavior of radiolabeled chimeric anti-EGFRvIII monoclonal antibody: comparison with its murine parent." *Nucl. Med. Biol.* 24: 63947, 1997.

Reist, C. J., Garg, P. K., Alston, K. L., Bigner, D. D., and Zalutsky, M. R. "Radioiodination of internalizing monoclonal antibodies using N-succinimidyl 5-iodo-3-pyridinecarboxylate." *Cancer Res.* 56: 4970-7, 1996.

Rodeck, U., Herlyn, M., Herlyn, D., Molthoff, C., Atkinson, B., Varello, M., Steplewski, Z., and Koprowski, H. "Tumor growth modulation by a monoclonal antibody to the epidermal growth factor receptor: immunologically mediated and effector cell-independent effects." *Cancer Res.,* 47: 3692-3696, 1987.

Salomon, D. S., Brandt, R., Ciardiello, F., and Normanno, N. "Epidermal growth factor-related peptides and their receptors in human malignancies." *Crit. Rev. Oncol. Hematol.,* 19: 183-232, 1995.

Sampson, J. H, Crotty, L. E., Lee, S., Archer, G. E., Ashley, D. M., Wikstrand, C. J., Hale, L. P., Small, C., Dranoff, G., Friedman, A. H., Friedman, H. S., and Bigner, D. D, "Unarmed, tumor-specific monoclonal antibody effectively treats brain tumors." *Proc. Natl. Acad. Sci. USA,* 97: 7503-7508, 2000.

Santon, J. B., Cronin, M. T., MacLeod, C. L., Mendelsohn, J., Masui, H., and Gill, G. N. "Effects of epidermal growth factor receptor concentration on tumorigenicity of A431 cells in nude mice." *Cancer Res.* 46: 4701-5, 1986.

Sato, J. D., Le, A. D., and Kawamoto, T. "Derivation and assay of biological effects of monoclonal antibodies to epidermal growth factor receptors." *Methods Enzymol.* 146: 63-81, 1987.

Schlessinger, J. (2002) *Cell* 20; 110, 669-672.

Scott A. M., Gill S. S., Lee F., Liu Z., Skrinos E., Murone C., Saunder T., Chappell B., Papenfuss A., Old L. J. "A Phase I single dose escalation trial of ch806 in patients with advanced tumors expressing the 806 antigen." *Journal of Clinical Oncology,* 2006 ASCO Annual Meeting Proceedings Part I. Vol. 24, No. 18S (June 20 Supplement), (2006): 13028.

Scott A. M., Lee F T., Tebbutt N., Herbertson R., Gill S. S., Liu Z., Skrinos E., Murone C., Saunder T. H., Chappell B., Papenfuss A. T., Poon A. M. T., Hopkins W., Smyth F. E., MacGregor D., Chem. L. M., Jungbluth A. A., Ritter, G., Brechbiel M. W., Murphy R., Burgess A W, Hoffman E. W., Johns T. J., Old L. J. "A Phase I clinical trial with monoclonal antibody ch806 targeting transitional state and mutant epidermal growth factor receptors." *Proc. Natl. Acad. Sci. USA,* (2007) 104 (10): 4071-6. Epub 2007 Feb. 28.

Scott, A. M., and Welt, S. Antibody-based immunological therapy. *Curr. Opin. Immunol.,* 9: 717-722, 1997.

Seymour L. "Novel anti-cancer agents in development: exciting prospects and new challenges." *Cancer Treat. Rev.* 1999; 25: 301-12.

Sizeland, A. M. and Burgess, A. W. (1991) *Mol. Cell. Bio.* 11, 4005-4014.

Sizeland, A. M. and Burgess, A. W. (1992) *Mol. Biol. Cell* 3, 1235-1243.

Slamon, D. J., Godolphin, W., Jones, L. A., Holt, J. A., Wong, S. G., Keith, D. E., Levin, W. J., Stuart, S. G., Udove, J., Ullrich, A., and Press, M. F. "Studies of the HER-2/neu proto-oncogene in human breast and ovarian cancer." *Science* (Wash. DC). 244: 707-712, 1989.

Sliwkowski, M. X., Lofgren, J. A., Lewis, G. D., Hotaling, T. E., Fendly, B. M., and Fox, J. A. "Nonclinical studies addressing the mechanism of action of trastuzumab (Herceptin)." *Semin. Oncol.,* 26 (Suppl. 12): 60-70, 1999.

Sok, J. c., Coppelli, F. M., Thomas, S. M., Lango, M. N., Xi, S., Hunt, J. l., Freilino, M. l., Graner, M. W., Wikstrand, C. J., Bigner, D. D., Gooding, W. E., Furnari, F. B., and Grandis, J. R. (2006) *Clin. Cancer Res.* 12, 5064-5073.

Stamos, J., Sliwkowski, M. X., and Eigenbrot, C. (2002) *J. Biol. Chem.* 277, 46265-46272.

Sturgis, E. M., Sacks, P. G., Masui, H., Mendelsohn, J., and Schantz, S. P. "Effects of antiepidermal growth factor receptor antibody 528 on the proliferation and differentiation of head and neck cancer." *Otolaryngol. Head Neck Surg.* 111: 633-43, 1994.

Sugawa, N., Ekstrand, A. J., James, C. D., and Collins, V. P. "Identical splicing of aberrant epidermal growth factor receptor transcripts from amplified rearranged genes in human glioblastomas." *Proc. Natl. Acad. Sci. USA,* 87: 8602-8606, 1990.

Tang, C. K., Gong, X. Q., Moscatello, D. K., Wong, A. J., and Lippman, M. E. "Epidermal growth factor receptor in enhances tumorigenicity in human breast cancer." *Cancer Res.,* 60: 3081-3087, 2000.

Teramoto, T., Onda, M., Tokunaga, A., and Asano, G "Inhibitory effect of antiepidermal growth factor receptor antibody on a human gastric cancer." *Cancer* (Phila.), 77: 1639-1645, 1996.

Todaro, G. J., Delarco, J. E., and Cohen, S. (1976) *Nature* 264, 26-31.

Trail, P. A., and Bianchi, A. B. "Monoclonal antibody drug conjugates in the treatment of cancer." *Curr. Opin. Immunol.*, 11: 584-588, 1999.

Uemura, H., E. Okajima, et al. (1994)."Internal image anti-idiotype antibodies related to renal-cell carcinoma-associated antigen G250." *Int. J. Cancer* 56 (4): 609-14.

Ullrich, A., Coussens, L., Hayflick, J. S., Dull, T. J., Gray, A., Tam, A. W., Lee, J., Yarden, Y., Libermann, T. A., Schlessinger, J., and. (1984) *Nature*. 309, 418-425.

Vagin, A. and Teplyakov, A. (1997) *J. Appl. Cryst.* 30, 1022-1025.

van de Loosdrecht, A. A., Beelen, R. H., Ossenkoppele, G. J., Broekhoven, M. G., and Langenhuijsen, M. M. (1994) *J. Immunol. Methods.* 174, 311-320.

Voldborg, B. R., Damstrup, L., Spang-Thomsen, M., and Poulsen, H. S. "Epidermal growth factor receptor (EGFR) and EGFR mutations, function and possible role in clinical trials." *Ann. Oncol.*, 8: 1197-1206, 1997.

Wade, J. D., Hojo, K., Kawasaki, K., Johns, T. G., Catimel, B., Rothacker, J., and Nice, E. C. (2006) *Anal. Biochem.* 348, 315-317.

Waksal, H. W. "Role of an anti-epidermal growth factor receptor in treating cancer." *Cancer Metastasis Rev.*, 18: 427-436, 1999.

Walker, F., Orchard, S. G., Jorissen, R N., Hall, N. E., Zhang, H. H., Hoyne, P. A., Adams, T. E., Johns, T. G., Ward, C., Garrett, T. P., Zhu, H. 1., Nerrie, M., Scott, A. M., Nice, E. C., and Burgess, A. W. (2004) *J. Biol. Chem.* 79, 22387-22398.

Weiner, L. M. "An overview of monoclonal antibody therapy of cancer." *Semin. Oncol.*, 26 (Suppl. 12): 41-50, 1999.

Wersall, P., Ohlsson, I., Biberfeld, P., Collins, V. P., von Krusenstjerna, S., Larsson, S., Mellstedt, H., and Boethius, J. "Intratumoral infusion of the monoclonal antibody, mAb 425, against the epidermal-growth-factor receptor in patients with advanced malignant glioma." *Cancer Immunol. Immunother.*, 44: 157-164, 1997.

Whitson K. B., Red M. L., Whitson S. R., McCoy A., Vitali A. A., Walker F., Johns T. G., Beth A. H. and Staros J. A. "Functional Effects of Selective Glycosylation at Asn-579 of the Epidermal Growth Factor Receptor." *Biochemistry* (2005) 44: 14920-14931

Wikstrand, C. J., Cokgor, I., Sampson, J. H., and Bigner, D. D. "Monoclonal antibody therapy of human gliomas: current status and future approaches." *Cancer Metastasis Rev.*, 18: 451-464, 1999.

Wikstrand, C. J., Hale, L. P., Batra, S. K., Hill, M. L., Humphrey, P. A., Kurpad, S, N., McLendon, R. E., Moscatello, D., Pegram, C. N., Reist, C. J., et al. "Monoclonal antibodies against EGFRvIII are tumor specific and react with breast and lung carcinomas and malignant gliomas." *Cancer Res.* 55: 3140-3148, 1995.

Wikstrand, C. J., McLendon, R. E., Friedman, A. H., and Bigner, D. D. "Cell surface localization and density of the tumor-associated variant of the epidermal growth factor receptor, EGFRvIII." *Cancer Res.* 57: 4130-40, 1997.

Wikstrand, C. J., Reist, C. J., Archer, G. E., Zalutsky, M. R., and Bier, D. D. "The class III variant of the epidermal growth factor receptor (EGFRvIII): characterization and utilization as an immunotherapeutic target." *J Neurovirol.*, 4: 148-158, 1998.

Wong, A. J., Ruppert, J. M., Bigner, S. H., Grzeschik, C. H., Humphrey, P. A., Bigner, D. S., and Vogelstein, B. "Structural alterations of the epidermal growth factor receptor gene in human gliomas." *Proc. Natl. Acad. Sci. USA,* 89: 2965-2969, 1992.

Yamazaki H, Fukui Y, Ueyama Y, et al. "Amplification of the structurally and functionally altered epidermal growth factor receptor gene (c-erbB) in human brain tumors." *Mol. Cell. Biol.* 1988; 8:1816-20.

Yamazaki H, Ohba Y, Tamaoki N, et al. "A deletion mutation within the ligand binding domain is responsible for activation of epidermal growth factor receptor gene in human brain tumors." *Jpn. J. Cancer Res.* 1990; 81: 773-9.

Yarden, Y. and Schlessinger, J. (1987) *Biochemistry.* 26, 1443-1451.

Yarden, Y. and Sliwkowski, M. X. (2001) *Nat. Rev. Mol. Cell. Biol.* 2, 127-137.

Yen, L., Benlimame, N., Nic, Z. R., Xiao, D., Wang, T., Al Moustafa, A. E., Esumi, H., Milanini, J., Hynes, N. E., Pages, G., and Alaoui-Jamali, M. A. (2002) *Mol. Biol. Cell.* 13(10:4029-44.

Ymer, S., Tucker, W. Q., Sanderson, C. 1., Hapel, A. J., Campbell, H. D., and Young, 1. G. (1985) *Nature*. 19-25; 317, 255-258.

Zhang, x., Gureasko, J., Shen, K., Cole, P. A., and Kuriyan, J. (2006) Cell. 125, 1137-1149.

Burgess A W, Cho H S, Eigenbrot C, Ferguson K M, Garrett T P, Leahy D J, Lemmon M A, Sliwkowski M X, Ward C W, & Yokoyama S (2003) *Mol. Cell.* 12:541-552.

Ferguson K M (2008) *Annu. Rev. Biophys.* 37, 353-373.

Mendelsohn J & Baselga J (2006) *Semin. Oncol.* 33, 369-385.

Herbst R S, Kim E S, & Harari P M (2001) *Expert Opin. Biol. Ther.* 1, 719-732.

Lynch D H & Yang X D (2002) *Semin. Oncol.* 29, 47-50.

Baselga J & Arteaga C L (2005) *J. Clin. Oncol.* 23, 2445-2459.

Burgess A W (2008) *Growth Factors* 26, 263-274.

Milano G, Spano J P, & Leyland-Jones B (2008) *Br. J. Cancer* 99, 1-5.

Solomon B M & Jatoi A (2008) *Curr. Oncol. Rep.* 10, 304-308.

Nishikawa R, Ji X D, Harmon R C, Lazar C S, Gill G N, Cavenee W K, & Huang H J (1994) *Proc. Natl. Acad. Sci. USA.* 91, 7727-7731.

Humphrey P A, Wong A J, Vogelstein B, Zalutsky M R, Fuller G N, Archer G E, Friedman H S, Kwatra M M, Bigner S H, & Bigner D D (1990) *Proc. Natl. Acad. Sci. USA* 87, 4207-4211.

Johns T G, Stockert E, Ritter G, Jungbluth A A, Huang H J, Cavenee W K, Smyth F E, Hall C M, Watson N, Nice E C, et al. (2002) *Int. J. Cancer.* 98, 398-408.

Jungbluth A A, Stockert E, Huang H J, Collins V P, Coplan K, Iversen K, Kolb D, Johns T J, Scott A M, Gullick W J, et al. (2003) *Proc. Natl. Acad. Sci. USA* 100, 639-644.

Scott A M, Lee F T, Tebbutt N, Herbertson R, Gill S S, Liu Z, Skrinos E, Murone C, Saunder T H, Chappell B, et al. (2007) *Proc. Natl. Acad. Sci. USA* 104, 4071-4076.

Johns T G, Luwor R B, Murone C, Walker F, Weinstock J, Vitali A A, Perera R M, Jungbluth A A, Stockert E, Old L J, et al. (2003) *Proc. Natl. Acad. Sci. USA* 100, 15871-15876.

Perera R M, Narita Y, Furnari F B, Gan H K, Murone C, Ahlkvist M, Luwor R B, Burgess A W, Stockert E, Jungbluth A A, et al. (2005) *Clin. Cancer. Res.* 11, 6390-6399.

Johns T G, Adams T E, Cochran J R, Hall N E, Hoyne P A, Olsen M J, Kim Y S, Rothacker J, Nice E C, Walker F, et al. (2004) *J. Biol. Chem.* 279, 30375-30384.

Walker F, Orchard S G, Jorissen R N, Hall N E, Zhang H H, Hoyne P A, Adams T E, Johns T G, Ward C, Garrett T P, et al. (2004) *J. Biol. Chem.* 279, 22387-22398.

Sivasubramanian A, Chao G, Pressler H M, Wittrup K D, & Gray J J (2006) *Structure* 14, 401-414.

Luwor R B, Johns T G, Murone C, Huang H J, Cavenee W K, Ritter G, Old U, Burgess A W, & Scott A M (2001) *Cancer Res.* 61, 5355-5361.

Ching K Z, Ramsey E, Pettigrew N, D'Cunha R, Jason M, & Dodd J G (1993) *Mol. Cell. Biochem.* 126, 151-158.

Sizeland A M & Burgess A W (1991) *Mol. Cell. Biol.* 11, 4005-4014.

Chao G, Cochran J R, & Wittrup K D (2004) *J. Mol. Biol.* 342, 539-550.

Garrett T P, McKern N M, Lou M, Elleman T C, Adams T E, Lovrecz G O, Zhu H J, Walker F, Frenkel M J, Hoyne P A, et al. (2002) *Cell* 110, 763-773.

Li S, Schmitz K R, Jeffrey P D, Wiltzius J J, Kussie P, & Ferguson K M (2005) *Cancer Cell.* 7, 301-311.

Hogg P J (2003) *Trends Biochem. Sci.* 28, 210-214.

Li S, Kussie P, & Ferguson K M (2008) *Structure* 16, 216-227.

Schmiedel J, Blaukat A, L1S, Knochel T, & Ferguson K M (2008) *Cancer Cell* 13, 365-373.

Sandler A B (2006) *Oncology* (Williston Park) 20, 35-40.

Sampson J H, Crotty L E, Lee S, Archer G E, Ashley D M, Wikstrand C J, Hale L P, Small C, Dranoff G, Friedman A H, et al. (2000) *Proc. Natl. Acad. Sci. USA* 97, 7503-7508.

Ullrich A, Coussens L, Hayflick J S, Dull T J, Gray A, Tam A W, Lee J, Yarden Y, Libermann T A, & Schlessinger J (1984) *Nature.* 309, 418-425.

Walker F, Hibbs M L, Zhang H H, Gonez U, & Burgess A W (1998) *Growth Factors* 16, 53-67.

Wade J D, Hojo K, Kawasaki K, Johns T G, Catimel B, Rothacker J, & Nice E C (2006) *Anal. Biochem.* 348, 315-317.

Vagin A A & Isupov M N (2001) *Acta Crystallogr. D. Biol. Crystallogr.* 57, 1451-1456.

Murshudov G N, Vagin A A, & Dodson E J (1997) *Acta Crystallogr. D. Biol. Crystallogr.* 53, 240-255.

Ferguson K M, Berger M B, Mendrola J M, Cho H S, Leahy D J, & Lemmon M A (2003) *Mol. Cell.* 11, 507-517.

Rettig W J, Old L J (1989) *Annu. Rev. Immunol.* 7:481-511.

Van den Eynde B J, Scott A M (1998) in *Encyclopedia of Immunology*, eds Roitt D P J, Roitt I M (Academic Press: London), pp 2424-2431.

Maloney D G, Grillo-Lopez A J, White C A, Bodkin D, Schilder R J, Neidhart J A, Janakiraman N, Foon K A, Liles T M, Dallaire B K, et al. (1997) *Blood* 90(6):2188-2195.

Baselga J, Artega C L (2005) *J. Clin. Oncol.* 23:2445-2449.

Voldborg B R, Damstrup L, Spang-Thomsen M, Poulsen H S (1997) *Ann. Oncol.* 8(12): 1197-206.

Baselga J, Tripathy D, Mendelsohn J, Baughman S, Benz C C, Dantis L, Sklarin N T, Seidman A D, Hudis C A, Moore J, et al. (1996) *J. Clin. Oncol.* 14:737-744.

Welt S, Divgi C R, Real F X, Yeh S D, Garin-Chesa P, Finstad C L, Sakamoto J, Cohen A, Sigurdson E R, Kemeny N, et al. (1990) *J. Clin. Oncol.* 8(11):1894-906.

Scott A M, Lee F T, Jones R, Hopkins W, MacGregor D, Cebon J, Hannah A, U P, Rigopolous A, Sturrock S, et al. (2005) *Clin. Cancer Res.* 11(13):4810-4817.

Steffens M G, Boerman O C, Oosterwijk-Wakka J C, Oosterhof G O, Witjes J A, Koenders E B, Oyen W J, Buijs W C, Debruyne F M, Corstens F H, et al. (1997) *J. Clin. Oncol.* 15:1529-1537.

Scott A M, Geleick D, Rubira M, Clarke K, Nice E C, Smyth F E, Stockert E, Richards E C, Carr F J, Harris W J, et al. (2000) *Cancer Res* 60:3254-3261.

Scott A M, Lee F-T, Hopkins W, Cebon J S, Wheatley J M, Liu Z, Smyth F E, Murone C, Sturrock S, MacGregor D, et al. (2001) *J. Clin. Oncol.* 19(19):3976-3987.

Welt S, Divgi C R, Scott A M, Garin-Chesa P, Finn R D, Graham M, Carswell E A, Cohen A, Larson S M, Old L J (1994) *J. Clin. Oncol.* 12:1193-1203.

Scott A M, Wiseman G, Welt S, Adjei A, Lee F T, Hopkins W, Divgi C R, Hanson L H, Mitchell P, Gansen D N, et al. (2003) *Clin. Cancer Res.* 9:1639-47.

Sugawa N, Ekstrand A J, James C D, Collins V P (1990) *Proc. Natl. Acad. Sci. USA.* 87(21):8602-8606.

Wong A J, Bigner S H, Bigner D D, Kinzler K W, Hamilton S R, Vogelstein B (1987) *Proc. Natl. Acad. Sci. USA* 84(19): 6899-6903.

Nishikawa R, Ji X D, Harmon R C, Lazar C S, Gill G N, Cavenee W K, Huang H J (1994) *Proc. Natl. Acad. Sci. USA* 91(16):7727-7731.

Hills D, Rowlinson-Busza D, Gullick W J (1995) *Int. J. Cancer* 63(4):537-543.

Sridhar S S, Seymour L, Shepherd F A (2003) *Lancet Oncol.* 4(7):397-406.

Goldstein N I, Prewett M, Zuklys K, Rockwell P, Mendelsohn J (1995) *Clin. Cancer Res.* 1(11):1311-1318.

Humphrey P A, Wong A J, Vogelstein B, Zalutsky M R, Fuller G N, Archer G E, Friedman H S, Kwatra M M, Bigner S H, Bigner D D (1990) *Proc. Natl. Acad. Sci. USA* 87(11): 4207-4211.

Baselga J, Pfister D, Cooper M R, Cohen R, Burtness B, Bos M, D'Andrea G, Seidman A, Norton L, Gunnett K, et al. (2000) *J. Clin. Oncol.* 18(4):904-914.

Graeven U, Kremer B, Sudhoff T, Kiling B, Rojo F, Weber D, Tillner J, Unal C, Schmiegel W (2006) *Br. J. Cancer* 94(9): 1293-1299.

Ramos T C, Figueredo J, Catala M, Gonzales S, Selva J C, Cruz T M, Toldeo C, Silva S, Pestano Y, Ramos M, et al. (2006) *Cancer Biol. Ther.* 5(4):375-379.

Johns T G, Stockert E, Ritter G, Jungbluth A A, Huang H J, Cavenee W K, Smyth F E, Hall C M, Watson N, Nice E C, et al. (2002) *Int. J. Cancer* 98(3):398-408.

Jungbluth A A, Stockert E, Huang H J, Collins V P, Coplan K, Iversen K, Kolb D, Johns T G, Scott A M, Gullick W J, et al. (2003) *Proc. Natl. Acad. Sci. USA.* 100(2): 639-644.

Johns T G, Adams T E, Wittrup K D, Hall N E, Hoyne P A, Cochrane J R, Olsen M J, Kim Y S, Rothacker J, Nice E C, et al. (2004) *J. Biol. Chem.* 279(29):30375-30384.

Johns T G, Mellman I, Cartwright G A, Ritter G, Old L J, Burgess A W, Scott A M (2005) *FASEB J.* 19(7):780-782.

Luwor R B, Johns T G, Murone C, Huang H J, Cavenee W K, Ritter G, Old L J, Burgess A W, Scott A M (2001) *Cancer Res.* 61(14): p. 5355-5361.

Johns T G, Luwor R B, Murone C, Walker F, Weinstock J, Vitali A A, Perera R M, Jungbluth A A, Stockert E, Old L J, et al. (2003) *Proc. Natl. Acad. Sci. USA.* 100(26):15871-15876.

Mishima K, Johns T G, Luwor R B, Scott A M, Stockert E, Jungbluth A A, Ji X D, Suvarna P, Voland J R, Old L J, et al. (2001) *Cancer Res.* 61(14):5349-5354.

Perera R M, Narita Y, Furnari F B, Tavernasi M L, Luwor R B, Burgess A W, Stockert E, Jungbluth A A, Old L J, Cavenee W K, et al. (2005) *Clin. Cancer Res.* 11(17):6390-6399.

Panousis C, Rayzman V M, Johns T G, Renner C, Liu Z, Cartwright G, Lee F-T, Wang D, Kypridis A, Smyth F E, et al. (2005) *Br. J. Cancer.* 92(6):1069-1077.

Divgi C R, Welt S, Kris M, Real F X, Yeh S D, Gralla R, Merchant B, Schweighart S, Unger M, Larson S M, et al. (1991) *J. Natl. Cancer Inst.* 83(2):97-104.

Baselga J (2001) *Eur. J. Cancer* 37 Suppl 4:S16-22.

Gibson T B, Ranganathan A, Grothey A (2006) *Clin. Colorectal Cancer* 6(1):29-31.

Rowinsky E K, Schwartz G H, Gollob J A, Thompson J A, Vogelzang N J, Figlin R, Bukowski R, Haas N, Lockbaum P, Li Y P, et al. (2004) *J. Clin. Oncol.* 22:3003-3015.

Tan A R, Moore D F, Hidalgo M, Doroshow J H, Polpin E A, Goodin S, Mauro D, Rubin E H (2006) *Clin. Cancer Res.* 12(21): 6517-6522.

Lacouture A E (2006) *Nature Rev. Cancer.* 6:803-812.

Adams G P, Weiner L M (2005) *Nat. Biotechnol.* 23(9): 1147-1157.

Liu Z, Panousis C, Smyth F E, Murphy R, Wirth V, Cartwright G, Johns T G, Scott A M (2003) *Hybrid Hybridomics* 22(4):219-28.

Stabin M G, Sparks R B, Crowe E (2005) *J. Nucl. Med.* 46(6):1023-1027.

Ritter G, Cohen L S, Williams C Jr, Richards E C, Old U, Welt S (2001) *Cancer Res.* 61(18):685-6859.

This invention may be embodied in other forms or carried out in other ways without departing from the spirit or essential characteristics thereof. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout the Specification and provided in a list of references above, each of which is incorporated herein by reference in its entirety.

What is claimed is:

1. An isolated anti-Epidermal Growth Factor Receptor (EGFR) antibody comprising a heavy chain variable region comprising the amino acid sequence set forth in SEQ ID NO: 164, and a light chain variable region comprising the amino acid sequence set forth in SEQ ID NO: 166.

2. The isolated antibody according to claim 1, wherein said isolated antibody is in the form of an antibody F(ab')2, scFv fragment, diabody, triabody or tetrabody.

3. The isolated antibody according to claim 1, further comprising a detectable label.

4. The isolated antibody according to claim 3, wherein said detectable label is a radiolabel.

5. The isolated antibody according to claim 4, wherein said radiolabel is selected from the group consisting of $^{3}$H, $^{14}$C, $^{32}$P, $^{35}$S, $^{36}$Cl, $^{51}$Cr, $^{58}$Co, $^{59}$Fe, $^{90}$Y, $^{121}$I, $^{124}$I, $^{125}$I, $^{131}$I, $^{111}$In, $^{211}$At, $^{198}$Au, $^{67}$Cu, $^{225}$Ac, $^{213}$Bi, $^{99}$Tc and $^{186}$Re.

6. The isolated antibody according to claim 1, wherein said isolated antibody is pegylated.

7. An isolated nucleic acid which comprises a sequence encoding the isolated antibody of claim 1.

8. A method of preparing the isolated antibody according to claim 1, comprising expressing a nucleic acid under conditions to bring about expression of said antibody, and recovering said antibody.

9. A kit for the diagnosis of a tumor in which EGFR is aberrantly expressed or EGFR is expressed in the form of a truncated protein, comprising the isolated antibody of claim 1.

10. The kit according to claim 9, further comprising reagents and/or instructions for use.

11. A unicellular host transformed with a recombinant DNA molecule which encodes the isolated antibody of claim 1.

12. A unicellular host transformed with a recombinant DNA molecule which encodes the isolated antibody of claim 1, wherein the unicellular host is selected from the group consisting of E. coli, Pseudomonas, Bacillus, Streptomyces, yeast, a mammalian cell, a plant cell, an insect cell, and a human cell in tissue culture.

13. The isolated antibody according to claim 1, wherein said heavy chain comprises the constant region set forth in SEQ ID NO: 43.

14. The isolated antibody according to claim 1, wherein said light chain comprises the constant region set forth in SEQ ID NO: 48.

15. The isolated antibody according to claim 14, wherein the said antibody is an IgG isotype.

16. The isolated antibody according to claim 15, wherein the said IgG isotype is an IgG1 isotype.

17. A pharmaceutical composition comprising the isolated antibody according to claim 1.

18. The isolated antibody according to claim 1, conjugated to a cytotoxic agent.

19. An immunoconjugate comprising an isolated anti-Epidermal Growth Factor Receptor (EGFR) antibody conjugated to a cytotoxic agent, wherein said antibody is an IgG isotype, comprises a heavy chain variable region comprising the amino acid sequence set forth in SEQ ID NO: 164, and comprises a light chain variable region comprising the amino acid sequence set forth in SEQ ID NO: 166.

20. The immunoconjugate of claim 19, wherein said antibody comprises a light chain constant region comprising the amino acid sequence set forth in SEQ ID NO: 48.

21. The immunoconjugate of claim 19, wherein said antibody is an IgG1 isotype.

22. A pharmaceutical composition comprising the immunoconjugate according to claim 19.

23. The immunoconjugate of claim 19, wherein said antibody comprises a kappa light chain.

24. The isolated antibody of claim 1, wherein said antibody comprises a kappa light chain.

25. The unicellular host of claim 12, wherein said mammalian cell is selected from the group consisting of a Chinese Hamster Ovary (CHO) cell, a YB/20 cell, a NS0 cell, an SP2/0 cell, an R1.1 cell, a B-W cell, an L-M cell, a COS 1 cell, a COS 7 cell, a BSC1 cell, a BSC40 cell, and a BMT10 cell.

* * * * *

```
SEQUENCE LISTING

<160> NUMBER OF SEQ ID NOS: 195

<210> SEQ ID NO 1
<211> LENGTH: 402
<212> TYPE: DNA
<213> ORGANISM: Mus musculus

<400> SEQUENCE: 1
atgagagtgc tgattctttt gtggctgttc acagcctttc ctggtgtcct gtctgatgtg      60
cagcttcagg agtcgggacc tagcctggtg aaaccttctc agtctctgtc cctcacctgc     120
actgtcactg gctactcaat caccagtgat tttgcctgga ctggatccg gcagtttcca      180 ggaaacaagc tggagtggat gggctacata agttatagtg gtaacactag gtacaaccca     240
tctctcaaaa gtcgaatctc tatcactcga gacacatcca agaaccaatt cttcctgcag     300
ttgaattctg tgactattga ggacacagcc acatattact gtgtaacggc gggacgcggg     360
tttccttatt ggggccaagg gactctggtc actgtctctg ca                        402

<210> SEQ ID NO 2
<211> LENGTH: 134
<212> TYPE: PRT
<213> ORGANISM: Mus musculus

<400> SEQUENCE: 2

Met Arg Val Leu Ile Leu Leu Trp Leu Phe Thr Ala Phe Pro Gly Val
1               5                   10                  15

Leu Ser Asp Val Gln Leu Gln Glu Ser Gly Pro Ser Leu Val Lys Pro
                20                  25                  30

Ser Gln Ser Leu Ser Leu Thr Cys Thr Val Thr Gly Tyr Ser Ile Thr
            35                  40                  45

Ser Asp Phe Ala Trp Asn Trp Ile Arg Gln Phe Pro Gly Asn Lys Leu
        50                  55                  60

Glu Trp Met Gly Tyr Ile Ser Tyr Ser Gly Asn Thr Arg Tyr Asn Pro
65                  70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Ile Glu Asp Thr Ala Thr Tyr
            100                 105                 110

Tyr Cys Val Thr Ala Gly Arg Gly Phe Pro Tyr Trp Gly Gln Gly Thr
        115                 120                 125

Leu Val Thr Val Ser Ala
    130

<210> SEQ ID NO 3
```

-continued

```
<211> LENGTH: 384
<212> TYPE: DNA
<213> ORGANISM: Mus musculus

<400> SEQUENCE: 3
atggtgtcca cagctcagtt ccttgcattc ttgttgcttt ggtttccagg tgcaagatgt      60
gacatcctga tgacccaatc tccatcctcc atgtctgtat ctctgggaga cacagtcagc     120
atcacttgcc attcaagtca ggacattaac agtaatatag ggtggttgca gcagagacca     180
gggaaatcat ttaagggcct gatctatcat ggaaccaact tggacgatga agttccatca     240
aggttcagtg gcagtggatc tggagccgat tattctctca ccatcagcag cctggaatct     300
gaagattttg cagactatta ctgtgtacag tatgctcagt ttccgtggac gttcggtgga     360
ggcaccaagc tggaaatcaa acgt                                            384

<210> SEQ ID NO 4
<211> LENGTH: 128
<212> TYPE: PRT
<213> ORGANISM: Mus musculus

<400> SEQUENCE: 4

Met Val Ser Thr Ala Gln Phe Leu Ala Phe Leu Leu Leu Trp Phe Pro
1               5                   10                  15

Gly Ala Arg Cys Asp Ile Leu Met Thr Gln Ser Pro Ser Ser Met Ser
            20                  25                  30

Val Ser Leu Gly Asp Thr Val Ser Ile Thr Cys His Ser Ser Gln Asp
        35                  40                  45

Ile Asn Ser Asn Ile Gly Trp Leu Gln Gln Arg Pro Gly Lys Ser Phe
    50                  55                  60

Lys Gly Leu Ile Tyr His Gly Thr Asn Leu Asp Asp Glu Val Pro Ser
65                  70                  75                  80

Arg Phe Ser Gly Ser Gly Ser Gly Ala Asp Tyr Ser Leu Thr Ile Ser
                85                  90                  95

Ser Leu Glu Ser Glu Asp Phe Ala Asp Tyr Tyr Cys Val Gln Tyr Ala
            100                 105                 110

Gln Phe Pro Trp Thr Phe Gly Gly Gly Thr Lys Leu Glu Ile Lys Arg
        115                 120                 125

<210> SEQ ID NO 5
<211> LENGTH: 13
<212> TYPE: PRT
<213> ORGANISM: Artificial Sequence
<220> FEATURE:
<223> OTHER INFORMATION: biotinylated at position 1

<400> SEQUENCE: 5

Leu Glu Glu Lys Lys Gly Asn Tyr Val Val Thr Asp His
1               5                   10

<210> SEQ ID NO 6
<211> LENGTH: 13
<212> TYPE: PRT
<213> ORGANISM: Artificial Sequence
<220> FEATURE:
<223> OTHER INFORMATION: biotinylated at position 13

<400> SEQUENCE: 6

Leu Glu Glu Lys Lys Gly Asn Tyr Val Val Thr Asp His
1               5                   10
```

<210> SEQ ID NO 7
<211> LENGTH: 6149
<212> TYPE: DNA
<213> ORGANISM: Artificial Sequence
<220> FEATURE:
<223> OTHER INFORMATION: synthetic vector

<400> SEQUENCE: 7

| | | | | | |
|---|---|---|---|---|---|
| ctcgagagcg | ggcagtgagc | gcaacgcaat | taatgtgagt | tagctcactc | attaggcacc | 60 |
| ccaggcttta | cactttatgc | tcccggctcg | tatgttgtgt | ggagattgtg | agcggataac | 120 |
| aatttcacac | agaattcgtg | aggctccggt | gcccgtcagt | gggcagagcg | cacatcgccc | 180 |
| acagtccccg | agaagttggg | gggaggggtc | ggcaattgaa | ccgtgcccta | gagaaggtgg | 240 |
| cgcggggtaa | actgggaaag | tgatgtcgtg | tactggctcc | gcctttttcc | cgagggtggg | 300 |
| ggagaaccgt | atataagtgc | agtagtcgcc | gtgaacgttc | tttttcgcaa | cgggtttgcc | 360 |
| gccagaacac | aggtaagtgc | cgtgtgtggt | tcccgcgggc | ctggcctctt | tacgggttat | 420 |
| ggcccttgcg | tgccttgaat | tacttccacg | cccctggctg | cagtacgtga | ttcttgatcc | 480 |
| cgagcttcgg | gttggaagtg | ggtgggagag | ttcgaggcct | tgcgcttaag | gagccccttc | 540 |
| gcctcgtgct | tgagttgagg | cctggcctgg | gcgctgggc | cgccgcgtgc | gaatctggtg | 600 |
| gcaccttcgc | gcctgtctcg | ctgctttcga | taagtctcta | gccatttaaa | attttgatg | 660 |
| acctgctgcg | acgcttttttt | tctggcaaga | tagtcttgta | aatgcgggcc | aagatctgca | 720 |
| cactggtatt | tcggtttttg | gggccgcggg | cggcgacggg | gcccgtgcgt | cccagcgcac | 780 |
| atgttcggcg | aggcggggcc | tgcgagcgcg | gccaccgaga | tcggacggg | ggtagtctca | 840 |
| agctggccgg | cctgctctgg | tgcctggcct | cgcgccgccg | tgtatcgccc | cgccctgggc | 900 |
| ggcaaggctg | gcccggtcgg | caccagttgc | gtgagcggaa | agatggccgc | ttccggccc | 960 |
| tgctgcaggg | agctcaaaat | ggaggacgcg | gcgctcggga | gagcgggcgg | gtgagtcacc | 1020 |
| cacacaaagg | aaaagggcct | ttccgtcctc | agccgtcgct | tcatgtgact | ccacggagta | 1080 |
| ccgggcgccg | tccaggcacc | tcgattagtt | ctcgagcttt | tggagtacgt | cgtctttagg | 1140 |
| ttggggggag | gggttttatg | cgatggagtt | tccccacact | gagtgggtgg | agactgaagt | 1200 |
| taggccagct | tggcacttga | tgtaattctc | cttggaattt | gccctttttg | agtttggatc | 1260 |
| ttggttcatt | ctcaagcctc | agacagtggt | tcaaagtttt | tttcttccat | ttcaggtgta | 1320 |
| cgcgtctcgg | gaagctttag | tttaaacgcc | gccaccatgg | tgtccacagc | tcagttcctt | 1380 |
| gcattcttgt | tgctttggtt | tccaggtgca | agatgtgaca | tcctgatgac | ccaatctcca | 1440 |
| tcctccatgt | ctgtatctct | gggagacaca | gtcagcatca | cttgccattc | aagtcaggac | 1500 |
| attaacagta | atataggggtg | gttgcagcag | agaccaggga | atcatttaa | gggcctgatc | 1560 |
| tatcatggaa | ccaacttgga | cgatgaagtt | ccatcaaggt | tcagtggcag | tggatctgga | 1620 |
| gccgattatt | ctctcaccat | cagcagcctg | gaatctgaag | attttgcaga | ctattactgt | 1680 |
| gtacagcatg | ctcagtttcc | gtggacgttc | ggtggaggca | ccaagctgga | aatcaaacgg | 1740 |
| gtgagtggat | ccatctggga | taagcatgct | gtttttctgtc | tgtccctaac | atgccctgtg | 1800 |
| attatgcgca | acaacacac | ccaagggcag | aactttgtta | cttaaacacc | atcctgtttg | 1860 |
| cttcttttcct | caggaactgt | ggctgcacca | tctgtcttca | tcttcccgcc | atctgatgag | 1920 |
| cagttgaaat | ctggaactgc | ctctgttgtg | tgcctgctga | ataacttcta | tcccagagag | 1980 |
| gccaaagtac | agtggaaggt | ggataacgcc | ctccaatcgg | gtaactccca | ggagagtgtc | 2040 |
| acagagcagg | acagcaagga | cagcacctac | agcctcagca | gcaccctgac | gctgagcaaa | 2100 |

```
gcagactacg agaaacacaa agtctacgcc tgcgaagtca cccatcaggg cctgagctcg    2160
cccgtcacaa agagcttcaa caggggagag tgttgagcta gaactaacta actaagctag    2220
caacggtttc cctctagcgg gatcaattcc gcccccccccc cctaacgtta ctggccgaag   2280
ccgcttggaa taaggccggt gtgcgtttgt ctatatgtta ttttccacca tattgccgtc    2340
ttttggcaat gtgagggccc ggaaacctgg ccctgtcttc ttgacgagca ttcctagggg    2400
tctttcccct ctcgccaaag gaatgcaagg tctgttgaat gtcgtgaagg aagcagttcc    2460
tctggaagct tcttgaagac aaacaacgtc tgtagcgacc ctttgcaggc agcggaaccc    2520
cccacctggc gacaggtgcc tctgcggcca aaagccacgt gtataagata cacctgcaaa    2580
ggcggcacaa ccccagtgcc acgttgtgag ttggatagtt gtggaaagag tcaaatggct    2640
ctcctcaagc gtattcaaca aggggctgaa ggatgcccag aaggtacccc attgtatggg    2700
atctgatctg gggcctcggt gcacatgctt tacgtgtgtt tagtcgaggt taaaaaacgt    2760
ctaggccccc cgaaccacgg ggacgtggtt ttcctttgaa aaacacgata ataccatggt    2820
tgaacaagat ggattgcacg caggttctcc ggccgcttgg gtggagaggc tattcggcta    2880
tgactgggca caacagacaa tcggctgctc tgatgccgcc gtgttccggc tgtcagcgca    2940
ggggcgcccg gttcttttg tcaagaccga cctgtccggt gccctgaatg aactgcagga    3000
cgaggcagcg cggctatcgt ggctggccac gacgggcgtt ccttgcgcag ctgtgctcga    3060
cgttgtcact gaagcgggaa gggactggct gctattgggc gaagtgccgg ggcaggatct    3120
cctgtcatct caccttgctc ctgccgagaa agtatccatc atggctgatg caatgcggcg    3180
gctgcatacg cttgatccgg ctacctgccc attcgaccac caagcgaaac atcgcatcga    3240
gcgagcacgt actcggatgg aagccggtct tgtcgatcag gatgatctgg acgaagagca    3300
tcaggggctc gcgccagccg aactgttcgc caggctcaag gcgcgcatgc ccgacggcga    3360
ggatctcgtc gtgacccatg gcgatgcctg cttgccgaat atcatggtgg aaaatggccg    3420
cttttctgga ttcatcgact gtggccggct gggtgtggcg gaccgctatc aggacatagc    3480
gttggctacc cgtgatattg ctgaagagct tggcggcgaa tgggctgacc gcttcctcgt    3540
gctttacggt atcgccgctc ccgattcgca gcgcatcgcc ttctatcgcc ttcttgacga    3600
gttcttctga gtcgatcgac ctggcgtaat agcgaagagg cccgcaccga tcgcccttcc    3660
caacagttgc gcagcctgaa tggcgaatgg gacgcgccct gtagcggcgc attaagcgcg    3720
gcgggtgtgg tggttacgcg cagcgtgacc gctacacttg ccagcgccct agcgcccgct    3780
cctttcgctt tcttcccttc ctttctcgcc acgttcgccg gctttccccg tcaagctcta    3840
aatcgggggc tccctttagg gttccgattt agtgctttac ggcacctcga ccccaaaaaa    3900
cttgattagg gtgatggttc acgtagtggg ccatcgccct gatagacggt ttttcgcctt    3960
tgacgttgga gtccacgttc tttaatagtg gactcttgtt ccaaactgga acaacactca    4020
accctatctc ggtctattta agggatttt gccgatttc ggcctattgg ttaaaaaatg    4080
agctgattta acaaaattta acgcgaattt taacaaaata ttaacgctta caatttaggt    4140 ggcactttc ggggaaatgt gcgcggaacc cctatatttg tttatttttc taaatacatt    4200
caaatatgta tccgctcatg agacaataac cctgataaat gcttcaataa tattgaaaaa    4260
ggaagagtat gagtattcaa catttccgtg tcgcccttat cccttttttt gcggcatttt    4320
gccttactgt ttttgctcac ccagaaacgc tggtgaaagt aaaagatgct gaagatcagt    4380
tgggtgcacg agtgggttac atcgaactgg atctcaacag cggtaagatc cttgagagtt    4440
ttcgccccga agaacgtttt ccaatgatga gcacttttaa agttctgcta tgtggcgcgg    4500
```

```
tattatcccg tattgacgcc gggcaagagc aactcggtcg ccgcatacac tattctcaga    4560
atgacttggt tgagtactca ccagtcacag aaaagcatat tacggatggc atgacagtaa    4620
gagaattatg cagtgctgcc ataaccatga gtgataacac tgcggccaac ttacttctga    4680
caacgatcgg aggaccgaag gagctaaccg cttttttgca caacatgggg gatcatgtaa    4740
ctcgccttga tcgttgggaa ccggagctga tgaagccat accaaacgac gagcgtgaca    4800
ccacgatgcc tgtagcaatg gcaacaacgt tgcgcaaact attaactggc gaactactta    4860
ctctagcttc ccggcaacaa ttaatagact ggatggaggc ggataaagtt gcaggaccac    4920
ttctgcgctc ggcccttccg gctggctggt ttattgctga taaatctgga gccggtgagc    4980
gtgggtctcg cggtatcatt gcagcactgg ggccagatgg taagccctcc cgtatcgtag    5040
ttatctacac gacggggagt caggcaacta tggatgaacg aaatagacag atcgctgaga    5100
taggtgcctc actgattaag cattggtaac tgtcagacca agtttactca tatatacttt    5160
agattgattt aaaacttcat ttttaattta aaaggatcta ggtgaagatc ctttttgata    5220
atctcatgac caaaatccct taacgtgagt tttcgttcca ctgagcgtca gaccccgtag    5280
aaaagatcaa aggatgttct tgagatcctt ttttctgca cgtaatctgc tgcttgcaaa    5340
caaaaaacca ccgctaccag cggtggtttg tttgccggat caagagctac caactctttt    5400
tccgaaggta actggcttca gcagagcgca gataccaaat actgtccttc tagtgtagcc    5460
gtagttaggc caccacttca agaactctgt agcaccgcct acatacctcg ctctgctaat    5520
cctgttacca gtggctgctg ccagtggcga taagtcgtgt cttaccgggt tggactcaag    5580
acgatagtta ccggataagg cgcagcggtc gggctgaacg gggggttcgt gcacacagcc    5640
cagcttggag cgaacgacct acaccgaact gagataccta cagcgtgagc tatgagaaag    5700
cgccacgctt cccgaaggga gaaaggcgga caggtatccg gtaagcggca gggtcggaac    5760
aggagagcgc acgagggagc ttccaggggg aaacgcctgg tatctttata gtcctgtcgg    5820
gtttcgccac ctctgacttg agcgtcgatt tttgtgatgc tcgtcagggg ggcggagcct    5880
atggaaaaac gccagcaacg cggccttttt acggttcctg gccttttgct ggccttttgc    5940
tcacatgttc tttcctgcgt tatcccctga ttctgtggat aaccgtatta ccgcctttga    6000
gtgagctgat accgctcgcc gcagccgaac gaccgagcgc agcgagtcag tgagcgagga    6060
agcggaagag cgcccaatac gcaaaccgcc tctccccgcg cgttggccga ttcattaatg    6120
caggtatcac gaggcccttt cgtcttcac                                      6149
```

<210> SEQ ID NO 8
<211> LENGTH: 6625
<212> TYPE: DNA
<213> ORGANISM: Artificial Sequence
<220> FEATURE:
<223> OTHER INFORMATION: synthetic vector

<400> SEQUENCE: 8

```
ctcgagagcg ggcagtgagc gcaacgcaat taatgtgagt tagctcactc attaggcacc      60
ccaggcttta cactttatgc tcccggctcg tatgttgtgt ggagattgtg agcggataac     120
aatttcacac agaattcgtg aggctccggt gcccgtcagt gggcagagcg cacatcgccc     180
acagtccccg agaagttggg gggaggggtc ggcaattgaa ccggtgccta gagaaggtgg     240
cgcggggtaa actgggaaag tgatgtcgtg tactggctcc gcctttttcc cgagggtggg     300
ggagaaccgt atataagtgc agtagtcgcc gtgaacgttc ttttcgcaa cgggtttgcc     360
```

```
gccagaacac aggtaagtgc cgtgtgtggt tcccgcgggc ctggcctctt tacgggttat      420
ggcccttgcg tgccttgaat tacttccacg cccctggctg cagtacgtga ttcttgatcc      480
cgagcttcgg gttggaagtg ggtgggagag ttcgaggcct tgcgcttaag gagccccttc      540
gcctcgtgct tgagttgagg cctggcctgg gcgctgggc cgccgcgtgc gaatctggtg       600
gcaccttcgc gcctgtctcg ctgctttcga taagtctcta gccatttaaa attttttgatg    660 acctgctgcg acgcttttt tctggcaaga tagtcttgta aatgcgggcc aagatctgca      720
cactggtatt tcggttttg gggccgcggg cggcgacggg gcccgtgcgt cccagcgcac       780
atgttcggcg aggcgggcc tgcgagcgcg gccaccgaga atcggacggg ggtagtctca       840
agctggccgg cctgctctgg tgcctggcct cgcgccgccg tgtatcgccc cgccctgggc     900
ggcaaggctg gcccggtcgg caccagttgc gtgagcggaa agatggccgc ttcccggccc     960
tgctgcaggg agctcaaaat ggaggacgcg cgctcggga gagcgggcgg gtgagtcacc     1020
cacacaaagg aaaagggcct ttccgtcctc agccgtcgct tcatgtgact ccacggagta     1080
ccgggcgccg tccaggcacc tcgattagtt ctcgagcttt tggagtacgt cgtctttagg     1140
ttggggggag gggttttatg cgatggagtt tccccacact gagtgggtgg agactgaagt     1200
taggccagct tggcacttga tgtaattctc cttggaattt gcccttttg agtttggatc      1260 ttggttcatt ctcaagcctc agacagtggt tcaaagtttt tttcttccat ttcaggtgta     1320
cgcgtctcgg gaagctttag tttaaacgcc gccaccatga gagtgctgat tcttttgtgg     1380
ctgttcacag cctttcctgg tgtcctgtct gatgtgcagc ttcaggagtc gggacctagc     1440
ctggtgaaac cttctcagac tctgtccctc acctgcactg tcactggcta ctcaatcacc     1500
agtgattttg cctggaactg gatccggcag tttccaggaa acaagctgga gtggatgggc     1560
tacataagtt atagtggtaa cactaggtac aacccatctc tcaaaagtcg aatctctatc     1620
actcgagaca catccaagaa ccaattcttc ctgcagttga attctgtgac tattgaggac     1680
acagccacat attactgtgt aacggcggga cgcgggtttc cttattgggg ccaagggact    1740
ctggtcactg tctctgcaca gtgagtggat cctctgcgcc tgggcccagc tctgtcccac     1800
accgcggtca catggcacca cctctcttgc agcctccacc aagggcccat cggtcttccc     1860
cctggcaccc tcctccaaga gcacctctgg gggcacagcg gccctgggct gcctggtcaa     1920
ggactacttc cccgaaccgg tgacggtgtc gtggaactca ggcgccctga ccagcggcgt    1980
gcacaccttc ccggctgtcc tacagtcctc aggactctac tccctcagca gcgtggtgac     2040
cgtgccctcc agcagcttgg gcacccagac ctacatctgc aacgtgaatc acaagcccag     2100
caacaccaag gtggacaaga aagttgagcc caaatcttgt gacaaaactc acacatgccc     2160
accgtgccca gcacctgaac tcctgggggg accgtcagtc ttcctcttcc ccccaaaacc     2220
caaggacacc ctcatgatct cccggacccc tgaggtcaca tgcgtggtgg tggacgtgag     2280
ccacgaagac cctgaggtca agttcaactg gtacgtggac ggcgtggagg tgcataacgc     2340
caagacaaag ccgcgggagg agcagtacaa cagcacgtac cgggtggtca gcgtcctcac     2400
cgtcctgcac caggactggc tgaatggcaa ggagtacaag tgcaaggtct ccaacaaagc     2460
cctcccagcc cccatcgaga aaaccatctc caaagccaaa gggcagcccc gagaaccaca     2520
ggtgtacacc ctgcccccat cccgggagga gatgaccaag aaccaggtca gcctgacctg     2580
cctggtcaaa ggcttctatc ccagcgacat cgccgtggag tgggagagca atgggcagcc     2640
ggagaacaac tacaagacca cgcctcccgt gctggactcc gacggctcct tcttcctcta     2700
cagcaagctc accgtggaca agagcaggtg gcagcagggg aacgtcttct catgctccgt     2760
```

```
gatgcatgag gctctgcaca accactacac gcagaagagc ctctccctgt ctccgggtaa    2820
atgagctaga aactaactaa gctagcaacg gtttccctct agcgggatca attccgcccc    2880
ccccccctaa cgttactggc cgaagccgct tggaataagg ccggtgtgcg tttgtctata    2940
tgttattttc caccatattg ccgtcttttg caatgtgag ggcccggaaa cctggccctg    3000
tcttcttgac gagcattcct aggggtcttt ccctctcgc caaaggaatg caaggtctgt    3060
tgaatgtcgt gaaggaagca gttcctctgg aagcttcttg aagacaaaca acgtctgtag    3120
cgaccctttg caggcagcgg aaccccccac ctggcgacag gtgcctctgc ggccaaaagc    3180
cacgtgtata agatacacct gcaaaggcgg cacaacccca gtgccacgtt gtgagttgga    3240
tagttgtgga aagagtcaaa tggctctcct caagcgtatt caacaagggg ctgaaggatg    3300
cccagaaggt accccattgt atgggatctg atctggggcc tcggtgcaca tgctttacgt    3360
gtgtttagtc gaggttaaaa aacgtctagg ccccccgaac cacggggacg tggttttcct    3420
ttgaaaaaca cgataatacc atggttcgac cattgaactg catcgtcgcc gtgtcccaaa    3480
atatggggat tggcaagaac ggagacctac cctggcctcc gctcaggaac gagttcaagt    3540
acttccaaag aatgaccaca acctcttcag tggaaggtaa acagaatctg gtgattatgg    3600
gtaggaaaac ctggttctcc attcctgaga agaatcgacc tttaaaggac agaattaatg    3660
gttcgatata gttctcagta gagaactcaa agaaccacca cgaggagctc attttcttgc    3720
caaaagtttg gatgatgcct taagacttat tgaacaaccg gaattggcaa gtaaagtaga    3780
catggtttgg atagtcggag gcagttctgt ttaccaggaa gccatgaatc aaccaggcca    3840
cctcagactc tttgtgacaa ggatcatgca ggaatttgaa agtgacacgt ttttcccaga    3900
aattgatttg gggaaatata aacttctccc agaatacccca ggcgtcctct ctgaggtcca    3960
ggaggaaaaa ggcatcaagt ataagtttga agtctacgag aagaaagact aacaggaaga    4020
tgctttcaag ttctctgctc ccctcctaaa gctatgcatt tttataagac catgggactt    4080
ttgctggtcg atcgacctgg cgtaatagcg aagaggcccg caccgatcgc ccttcccaac    4140
agttgcgcag cctgaatggc gaatgggacg cgccctgtag cggcgcatta agcgcggcgg    4200
gtgtggtggt tacgcgcagc gtgaccgcta cacttgccag cgccctagcg cccgctcctt    4260
tcgctttctt cccttccttt ctcgccacgt tcgccggctt tccccgtcaa gctctaaatc    4320
gggggctccc tttagggttc cgatttagtg ctttacggca cctcgacccc aaaaaacttg    4380
attagggtga tggttcacgt agtgggccat cgccctgata cggttttt cgcctttgac    4440 gttggagtcc acgttcttta atagtggact cttgttccaa actggaacaa cactcaaccc    4500
tatctcggtc tatttataag ggattttgcc gatttcggcc tattggttaa aaaatgagct    4560
gatttaacaa aatttaacgc gaattttaac aaaatattaa cgcttacaat ttaggtggca    4620
cttttcgggg aaatgtgcgc ggaaccccta tatttgttta ttttcctaaa tacattcaaa    4680
tatgtatccg ctcatgagac aataaccctg ataaatgctt caataatatt gaaaaggaa    4740 gagtatgagt attcaacatt tccgtgtcgc ccttattccc ttttttgcgg cattttgcct    4800
tactgttttt gctcacccag aaacgctggt gaaagtaaaa gatgctgaag atcagttggg    4860
tgcacgagtg ggttacatcg aactggatct caacagcggt aagatccttg agagttttcg    4920
ccccgaagaa cgttttccaa tgatgagcac ttttaaagtt ctgctatgtg gcgcggtatt    4980
atcccgtatt gacgccgggc aagagcaact cggtcgccgc atacactatt ctcagaatga    5040
cttggttgag tactcaccag tcacagaaaa gcatattacg gatggcatga cagtaagaga    5100
```

| | |
|---|---|
| attatgcagt gctgccataa ccatgagtga taacactgcg gccaacttac ttctgacaac | 5160 |
| gatcggagga ccgaaggagc taaccgcttt tttgcacaac atgggggatc atgtaactcg | 5220 |
| ccttgatcgt tgggaaccgg agctgaatga agccatacca aacgacgagc gtgacaccac | 5280 |
| gatgcctgta gcaatggcaa caacgttgcg caaactatta actggcgaac tacttactct | 5340 |
| agcttcccgg caacaattaa tagactggat ggaggcggat aaagttgcag gaccacttct | 5400 |
| gcgctcggcc cttccggctg ctggttttat tgctgataaa tctggagccg gtgagcgtgg | 5460 |
| gtctcgcggt atcattgcag cactggggcc agatggtaag ccctcccgta tcgtagttat | 5520 |
| ctacacgacg gggagtcagg caactatgga tgaacgaaat agacagatcg ctgagatagg | 5580 |
| tgcctcactg attaagcatt ggtaactgtc agaccaagtt tactcatata tactttagat | 5640 |
| tgatttaaaa cttcattttt aatttaaaag gatctaggtg aagatccttt ttgataatct | 5700 |
| catgaccaaa atcccttaac gtgagttttc gttccactga gcgtcagacc ccgtagaaaa | 5760 |
| gatcaaagga tgttcttgag atcctttttt tctgcacgta atctgctgct tgcaaacaaa | 5820 |
| aaaccaccgc taccagcggt ggtttgtttg ccggatcaag agctaccaac tcttttttccg | 5880 |
| aaggtaactg gcttcagcag agcgcagata ccaaatactg tccttctagt gtagccgtag | 5940 |
| ttaggccacc acttcaagaa ctctgtagca ccgcctacat acctcgctct gctaatcctg | 6000 |
| ttaccagtgg ctgctgccag tggcgataag tcgtgtctta ccgggttgga ctcaagacga | 6060 |
| tagttaccgg ataaggcgca gcggtcgggc tgaacggggg gttcgtgcac acagcccagc | 6120 |
| ttggagcgaa cgacctacac cgaactgaga tacctacagc gtgagctatg agaaagcgcc | 6180 |
| acgcttcccg aagggagaaa ggcggacagg tatccggtaa gcggcagggt cggaacagga | 6240 |
| gagcgcacga gggagcttcc agggggaaac gcctggtatc tttatagtcc tgtcgggttt | 6300 |
| cgccacctct gacttgagcg tcgatttttg tgatgctcgt caggggggcg gagcctatgg | 6360 |
| aaaaacgcca gcaacgcggc ctttttacgg ttcctggcct tttgctggcc ttttgctcac | 6420 |
| atgttctttc ctgcgttatc ccctgattct gtggataacc gtattaccgc ctttgagtga | 6480 |
| gctgataccg ctcgccgcag ccgaacgacc gagcgcagcg agtcagtgag cgaggaagcg | 6540 |
| gaagagcgcc caatacgcaa accgcctctc cccgcgcgtt ggccgattca ttaatgcagg | 6600 |
| tatcacgagg ccctttcgtc ttcac | 6625 |

<210> SEQ ID NO 9
<211> LENGTH: 234
<212> TYPE: PRT
<213> ORGANISM: Artificial Sequence
<220> FEATURE:
<223> OTHER INFORMATION: synthetic vector

<400> SEQUENCE: 9

Met Val Ser Thr Ala Gln Phe Leu Ala Phe Leu Leu Leu Trp Phe Pro
1               5                   10                  15

Gly Ala Arg Cys Asp Ile Leu Met Thr Gln Ser Pro Ser Ser Met Ser
            20                  25                  30

Val Ser Leu Gly Asp Thr Val Ser Ile Thr Cys His Ser Ser Gln Asp
        35                  40                  45

Ile Asn Ser Asn Ile Gly Trp Leu Gln Gln Arg Pro Gly Lys Ser Phe
    50                  55                  60

Lys Gly Leu Ile Tyr His Gly Thr Asn Leu Asp Asp Glu Val Pro Ser
65                  70                  75                  80

Arg Phe Ser Gly Ser Gly Ser Gly Ala Asp Tyr Ser Leu Thr Ile Ser
                85                  90                  95

```
Ser Leu Glu Ser Glu Asp Phe Ala Asp Tyr Tyr Cys Val Gln His Ala
            100                 105                 110

Gln Phe Pro Trp Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 10
<211> LENGTH: 463
<212> TYPE: PRT
<213> ORGANISM: Artificial Sequence
<220> FEATURE:
<223> OTHER INFORMATION: synthetic vector

<400> SEQUENCE: 10

Met Arg Val Leu Ile Leu Leu Trp Leu Phe Thr Ala Phe Pro Gly Val
1               5                   10                  15

Leu Ser Asp Val Gln Leu Gln Glu Ser Gly Pro Ser Leu Val Lys Pro
            20                  25                  30

Ser Gln Thr Leu Ser Leu Thr Cys Thr Val Thr Gly Tyr Ser Ile Thr
        35                  40                  45

Ser Asp Phe Ala Trp Asn Trp Ile Arg Gln Phe Pro Gly Asn Lys Leu
    50                  55                  60

Glu Trp Met Gly Tyr Ile Ser Tyr Ser Gly Asn Thr Arg Tyr Asn Pro
65                  70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Ile Glu Asp Thr Ala Thr Tyr
            100                 105                 110

Tyr Cys Val Thr Ala Gly Arg Gly Phe Pro Tyr Trp Gly Gln Gly Thr
        115                 120                 125

Leu Val Thr Val Ser Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
    210                 215                 220
```

```
Thr Lys Val Asp Lys Lys Val Glu Pro Lys Ser Cys Asp Lys Thr His
225                 230                 235                 240

Thr Cys Pro Pro Cys Pro Ala Pro Glu Leu Leu Gly Gly Pro Ser Val
            245                 250                 255

Phe Leu Phe Pro Pro Lys Pro Lys Asp Thr Leu Met Ile Ser Arg Thr
        260                 265                 270

Pro Glu Val Thr Cys Val Val Val Asp Val Ser His Glu Asp Pro Glu
    275                 280                 285

Val Lys Phe Asn Trp Tyr Val Asp Gly Val Glu Val His Asn Ala Lys
290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 11
<211> LENGTH: 116
<212> TYPE: PRT
<213> ORGANISM: Mus musculus

<400> SEQUENCE: 11

Asp Val Gln Leu Gln Glu Ser Gly Pro Ser Leu Val Lys Pro Ser Gln
1               5                   10                  15

Ser Leu Ser Leu Thr Cys Thr Val Thr Gly Tyr Ser Ile Thr Ser Asp
            20                  25                  30

Phe Ala Trp Asn Trp Ile Arg Gln Phe Pro Gly Asn Lys Leu Glu Trp
        35                  40                  45

Met Gly Tyr Ile Ser Tyr Ser Gly Asn Thr Arg Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ile Glu Asp Thr Ala Thr Tyr Tyr Cys
                85                  90                  95

Val Thr Ala Gly Arg Gly Phe Pro Tyr Trp Gly Gln Gly Thr Leu Val
            100                 105                 110

Thr Val Ser Ala
        115
```

```
<210> SEQ ID NO 12
<211> LENGTH: 108
<212> TYPE: PRT
<213> ORGANISM: Mus musculus

<400> SEQUENCE: 12

Asp Ile Leu Met Thr Gln Ser Pro Ser Ser Met Ser Val Ser Leu Gly
1               5                   10                  15

Asp Thr Val Ser Ile Thr Cys His Ser Ser Gln Asp Ile Asn Ser Asn
            20                  25                  30

Ile Gly Trp Leu Gln Gln Arg Pro Gly Lys Ser Phe Lys Gly Leu Ile
        35                  40                  45

Tyr His Gly Thr Asn Leu Asp Asp Glu Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Trp
                85                  90                  95

Thr Phe Gly Gly Gly Thr Lys Leu Glu Ile Lys Arg
            100                 105

<210> SEQ ID NO 13
<211> LENGTH: 13
<212> TYPE: PRT
<213> ORGANISM: Artificial Sequence
<220> FEATURE:
<223> OTHER INFORMATION: synthetic

<400> SEQUENCE: 13

Leu Glu Glu Lys Lys Gly Asn Tyr Val Val Thr Asp His
1               5                   10

<210> SEQ ID NO 14
<211> LENGTH: 16
<212> TYPE: PRT
<213> ORGANISM: Artificial Sequence
<220> FEATURE:
<223> OTHER INFORMATION: synthetic

<400> SEQUENCE: 14

Cys Gly Ala Asp Ser Tyr Glu Met Glu Glu Asp Gly Val Arg Lys Cys
1               5                   10                  15

<210> SEQ ID NO 15
<211> LENGTH: 6
<212> TYPE: PRT
<213> ORGANISM: Mus musculus

<400> SEQUENCE: 15

Ser Asp Phe Ala Trp Asn
1               5

<210> SEQ ID NO 16
<211> LENGTH: 16
<212> TYPE: PRT
<213> ORGANISM: Mus musculus

<400> SEQUENCE: 16

Tyr Ile Ser Tyr Ser Gly Asn Thr Arg Tyr Asn Pro Ser Leu Lys Ser
1               5                   10                  15

<210> SEQ ID NO 17
<211> LENGTH: 9
```

```
<212> TYPE: PRT
<213> ORGANISM: Mus musculus

<400> SEQUENCE: 17

Val Thr Ala Gly Arg Gly Phe Pro Tyr
1               5

<210> SEQ ID NO 18
<211> LENGTH: 11
<212> TYPE: PRT
<213> ORGANISM: Mus musculus

<400> SEQUENCE: 18

His Ser Ser Gln Asp Ile Asn Ser Asn Ile Gly
1               5                   10

<210> SEQ ID NO 19
<211> LENGTH: 7
<212> TYPE: PRT
<213> ORGANISM: Mus musculus

<400> SEQUENCE: 19

His Gly Thr Asn Leu Asp Asp
1               5

<210> SEQ ID NO 20
<211> LENGTH: 9
<212> TYPE: PRT
<213> ORGANISM: Mus musculus

<400> SEQUENCE: 20

Val Gln Tyr Ala Gln Phe Pro Trp Thr
1               5

<210> SEQ ID NO 21
<211> LENGTH: 348
<212> TYPE: DNA
<213> ORGANISM: Mus musculus

<400> SEQUENCE: 21
gatgtgcagc ttcaggagtc gggacctagc ctggtgaaac cttctcagtc tctgtccctc      60
acctgcactg tcactggcta ctcaatcacc agtgactatg cctggaactg gatccggcag     120
tttccaggaa acaaactgga gtggatgggc tacataagtt acagtgctaa cactaggtac     180
aacccatctc tcaaaagtcg aatctctatc actcgagaca catccaagaa ccaattcttc     240
ctgcagttga attctgtgac tactgaggac acagccacat attactgtgc aacggcggga     300
cgcgggtttc cttactgggg ccaagggact ctggtcactg tctctgca                  348

<210> SEQ ID NO 22
<211> LENGTH: 116
<212> TYPE: PRT
<213> ORGANISM: Mus musculus

<400> SEQUENCE: 22

Asp Val Gln Leu Gln Glu Ser Gly Pro Ser Leu Val Lys Pro Ser Gln
1               5                   10                  15

Ser Leu Ser Leu Thr Cys Thr Val Thr Gly Tyr Ser Ile Thr Ser Asp
                20                  25                  30

Tyr Ala Trp Asn Trp Ile Arg Gln Phe Pro Gly Asn Lys Leu Glu Trp
            35                  40                  45

Met Gly Tyr Ile Ser Tyr Ser Ala Asn Thr Arg Tyr Asn Pro Ser Leu
```

```
                50                  55                  60
Lys Ser Arg Ile Ser Ile Thr Arg Asp Thr Ser Lys Asn Gln Phe Phe
 65                  70                  75                  80

Leu Gln Leu Asn Ser Val Thr Glu Asp Thr Ala Thr Tyr Tyr Cys
                 85                  90                  95

Ala Thr Ala Gly Arg Gly Phe Pro Tyr Trp Gly Gln Gly Thr Leu Val
            100                 105                 110

Thr Val Ser Ala
        115

<210> SEQ ID NO 23
<211> LENGTH: 6
<212> TYPE: PRT
<213> ORGANISM: Mus musculus

<400> SEQUENCE: 23

Ser Asp Tyr Ala Trp Asn
1               5

<210> SEQ ID NO 24
<211> LENGTH: 16
<212> TYPE: PRT
<213> ORGANISM: Mus musculus

<400> SEQUENCE: 24

Tyr Ile Ser Tyr Ser Ala Asn Thr Arg Tyr Asn Pro Ser Leu Lys Ser
1               5                   10                  15

<210> SEQ ID NO 25
<211> LENGTH: 7
<212> TYPE: PRT
<213> ORGANISM: Mus musculus

<400> SEQUENCE: 25

Ala Gly Arg Gly Phe Pro Tyr
1               5

<210> SEQ ID NO 26
<211> LENGTH: 324
<212> TYPE: DNA
<213> ORGANISM: Mus musculus

<400> SEQUENCE: 26
gacatcctga tgacccaatc tccatcctcc atgtctctat ctctgggaga cacagtcagt     60
atcacttgcc attcaagtca ggacattaac agtaatatag gtggttgca gcagaaacca    120
gggaaatcat ttaagggcct gatctatcat ggaaccaact tggacgatgg agttccatca    180
aggttcagtg gcagtggatc tggagccgat tattctctca ccatcagcag cctggaatct    240
gaagattttg tagactatta ctgtgtacag tatggtcagt ttccgtggac gttcggtgga    300
ggcaccaagc tggaaatcaa acgg                                          324

<210> SEQ ID NO 27
<211> LENGTH: 108
<212> TYPE: PRT
<213> ORGANISM: Mus musculus

<400> SEQUENCE: 27

Asp Ile Leu Met Thr Gln Ser Pro Ser Ser Met Ser Leu Ser Leu Gly
1               5                   10                  15

Asp Thr Val Ser Ile Thr Cys His Ser Ser Gln Asp Ile Asn Ser Asn
```

```
                20                  25                  30
Ile Gly Trp Leu Gln Gln Lys Pro Gly Lys Ser Phe Lys Gly Leu Ile
            35                  40                  45

Tyr His Gly Thr Asn Leu Asp Asp Gly Val Pro Ser Arg Phe Ser Gly
        50                  55                  60

Ser Gly Ser Gly Ala Asp Tyr Ser Leu Thr Ile Ser Ser Leu Glu Ser
65                  70                  75                  80

Glu Asp Phe Val Asp Tyr Tyr Cys Val Gln Tyr Gly Gln Phe Pro Trp
                85                  90                  95

Thr Phe Gly Gly Gly Thr Lys Leu Glu Ile Lys Arg
            100                 105

<210> SEQ ID NO 28
<211> LENGTH: 11
<212> TYPE: PRT
<213> ORGANISM: Mus musculus

<400> SEQUENCE: 28

His Ser Ser Gln Asp Ile Asn Ser Asn Ile Gly
1               5                   10

<210> SEQ ID NO 29
<211> LENGTH: 7
<212> TYPE: PRT
<213> ORGANISM: Mus musculus

<400> SEQUENCE: 29

His Gly Thr Asn Leu Asp Asp
1               5

<210> SEQ ID NO 30
<211> LENGTH: 9
<212> TYPE: PRT
<213> ORGANISM: Mus musculus

<400> SEQUENCE: 30

Val Gln Tyr Gly Gln Phe Pro Trp Thr
1               5

<210> SEQ ID NO 31
<211> LENGTH: 348
<212> TYPE: DNA
<213> ORGANISM: Mus musculus

<400> SEQUENCE: 31
gatgtgcagc ttcaggggtc gggacctagc ctggtgaaac cttctcagtc tctgtccctc      60
acctgcactg tcactggcta ctcaatcacc agtgattatg cctggaactg gatccggcag     120
tttccaggaa acaaactgga gtggatgggc tacataagct acagtggtaa cactagatac     180
aacccatctc tcagaagtcg aatctctatc actcgagaca catccaagaa ccaattcttc     240
ctgcagttga attctgtgac tactgaggac acagccacat attactgtgc aacggcggga     300
cgcggatttc cttactgggg ccaagggact ctggtcactg tctctgca                  348

<210> SEQ ID NO 32
<211> LENGTH: 116
<212> TYPE: PRT
<213> ORGANISM: Mus musculus

<400> SEQUENCE: 32

Asp Val Gln Leu Gln Gly Ser Gly Pro Ser Leu Val Lys Pro Ser Gln
```

```
                1               5                  10                  15
Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
            35                  40                  45

Met Gly Tyr Ile Ser Tyr Ser Gly Asn Thr Arg Tyr Asn Pro Ser Leu
     50                  55                  60

Arg Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                85                  90                  95

Ala Thr Ala Gly Arg Gly Phe Pro Tyr Trp Gly Gln Gly Thr Leu Val
            100                 105                 110

Thr Val Ser Ala
            115
```

<210> SEQ ID NO 33
<211> LENGTH: 6
<212> TYPE: PRT
<213> ORGANISM: Mus musculus

<400> SEQUENCE: 33

```
Ser Asp Tyr Ala Trp Asn
1               5
```

<210> SEQ ID NO 34
<211> LENGTH: 16
<212> TYPE: PRT
<213> ORGANISM: Mus musculus

<400> SEQUENCE: 34

```
Tyr Ile Ser Tyr Ser Gly Asn Thr Arg Tyr Asn Pro Ser Leu Arg Ser
1               5                   10                  15
```

<210> SEQ ID NO 35
<211> LENGTH: 9
<212> TYPE: PRT
<213> ORGANISM: Mus musculus

<400> SEQUENCE: 35

```
Ala Thr Ala Gly Arg Gly Phe Pro Tyr
1               5
```

<210> SEQ ID NO 36
<211> LENGTH: 322
<212> TYPE: DNA
<213> ORGANISM: Mus musculus

<400> SEQUENCE: 36

```
gacatcctga tgacccaatc tccatcctcc atgtctgtgt ctctgggaga cacagtcaac    60
atcacttgcc attcaagtca ggacattaac agtaatatag gtggttgca gcagaaacca   120 gggaaatcat ttaagggcct gatctatcat ggaaccaact tggacgatgg agttccatca   180
aggttcagtg gcagtggatc tggagccgat tattctctca ccatcagcag cctggaatct   240
gaggattttg cagactatta ctgtgtacag tatggtcagt ttccgtggac gttcggtgga   300
ggcaccaagc tggaaatcaa ac                                            322
```

<210> SEQ ID NO 37
<211> LENGTH: 108

```
<212> TYPE: PRT
<213> ORGANISM: Mus musculus

<400> SEQUENCE: 37

Asp Ile Leu Met Thr Gln Ser Pro Ser Ser Met Ser Val Ser Leu Gly
1               5                   10                  15

Asp Thr Val Asn Ile Thr Cys His Ser Ser Gln Asp Ile Asn Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Asp Asp Gly Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Gly Gln Phe Pro Trp
                85                  90                  95

Thr Phe Gly Gly Gly Thr Lys Leu Glu Ile Lys Arg
            100                 105

<210> SEQ ID NO 38
<211> LENGTH: 11
<212> TYPE: PRT
<213> ORGANISM: Mus musculus

<400> SEQUENCE: 38

His Ser Ser Gln Asp Ile Asn Ser Asn Ile Gly
1               5                   10

<210> SEQ ID NO 39
<211> LENGTH: 7
<212> TYPE: PRT
<213> ORGANISM: Artificial Sequence
<220> FEATURE:
<223> OTHER INFORMATION: synthetic

<400> SEQUENCE: 39

His Gly Thr Asn Leu Asp Asp
1               5

<210> SEQ ID NO 40
<211> LENGTH: 9
<212> TYPE: PRT
<213> ORGANISM: Mus musculus

<400> SEQUENCE: 40

Val Gln Tyr Gly Gln Phe Pro Trp Thr
1               5

<210> SEQ ID NO 41
<211> LENGTH: 11891
<212> TYPE: DNA
<213> ORGANISM: Artificial Sequence
<220> FEATURE:
<223> OTHER INFORMATION: synthetic vector

<400> SEQUENCE: 41
aagcttgccg ccaccatgga ttggacctgg cgcattctct ttctggtagc agccgccaca      60 ggtaagggc tgccaaatcc cagtgaggag gaagggatcg aaggtcacca tcgaagccag     120
tcacccagtg aagggggctt ccatccactc ctgtgtcttc tctacaggtg tccacagcca     180
ggtgcagctc caagagagtg gacctgggct tgtcaagccg agtcaaactt tgtccctaac     240
```

```
atgtactgtg tccggatact ctatctcatc agattttgcg tggaattgga taaggcagcc      300
accagggaaa ggtttagaat ggatgggcta catatcatac tctgggaaca ccagatatca      360
accttctctg aaaagccgga tcacaatctc aagggacacg tcgaagaatc agttcttcct      420
gaaactgaac tccgttacag ccgcagacac agcaacatat tactgcgtaa ccgctggcag      480
aggcttcccc tattggggac agggcaccct agtgacagtg agcagcggta agatggcaca      540
ccgtggccgg cctctgcgcc tgggcccagc tctgtcccac accgcggtca catggcacct      600
tttctcttcc agcctccacc aagggcccca gcgtgttccc cctggccccc agcagcaaga      660
gcaccagcgg cggcacagcc gccctgggct gcctggtgaa ggactacttc cccgagcccg      720
tgaccgtgag ctggaacagc ggagccctga cctccggcgt gcacaccttc cccgccgtgc      780
tgcagacag cggcctgtac agcctgagca gcgtggtgac cgtgcccagc agcagcctgg      840
gcacccagac ctacatctgc aacgtgaacc acaagcccag caacaccaag gtggacaaga      900
aggtggagcc caagagctgc gacaagaccc acacctgccc cccctgccca gccccagagc      960
tgctgggcgg accctccgtg ttcctgttcc cccccaagcc caaggacacc ctgatgatca     1020
gcaggacccc cgaggtgacc tgcgtggtgg tggacgtgag ccacgaggac ccagaggtga     1080
agttcaattg gtatgtggac ggcgtggagg tgcacaacgc caagaccaag cccagagaag     1140
agcagtacaa cagcacctac agggtggtgt ccgtgctgac cgtgctgcac caggactggc     1200
tgaacggcaa ggaatacaaa tgcaaggtct ccaacaaggc cctgccagcc ccatcgaaa      1260
agaccatcag caaggccaag ggccagccac gggagcccca ggtgtacacc ctgccccct      1320
cccgggacga gtgcaccaag aaccaggtgt ccctgacctg tctggtgaag ggcttctacc     1380
ccagcgacat cgccgtggag tgggagagca cggccagcc cgagaacaac tacaagacca     1440
cccccccagt gctggacagc gacggcagct tcttcctgta cagcaagctg accgtggaca     1500
agagcaggtg gcagcagggc aacgtgttca gctgcagcgt gatgcacgag gccctgcaca     1560
accactacac ccagaagagc ctgagcctgt ccccggcaa gtgatgacga cgcggccgtg     1620
cggacgaccg aattcattga tcataatcag ccataccaca tttgtagagg ttttacttgc     1680
tttaaaaaac ctcccacacc tccccctgaa cctgaaacat aaaatgaatg caattgttgt     1740
tgttaacttg tttattgcag cttataatgg ttacaaataa agcaatagca tcacaaattt     1800
cacaaataaa gcattttttt cactgcattc tagttgtggt ttgtccaaac tcatcaatgt     1860
atcttatcat gtctggcggc cgccgatatt tgaaaatatg gcatattgaa aatgtcgccg     1920
atgtgagttt ctgtgtaact gatatcgcca ttttccaaa agtgattttt gggcatacgc      1980
gatatctggc gatagcgctt atatcgttta cgggggatgg cgatagacga ctttggtgac     2040
ttgggcgatt ctgtgtgtcg caaatatcgc agtttcgata taggtgacag acgatatgag     2100
gctatatcgc cgatagaggc gacatcaagc tggcacatgg ccaatgcata tcgatctata     2160
cattgaatca atattggcca ttagccatat tattcattgg ttatatagca taaatcaata     2220
ttggctattg gccattgcat acgttgtatc catatcataa tatgtacatt tatattggct     2280
catgtccaac attaccgcca tgttgacatt gattattgac tagttattaa tagtaatcaa     2340
ttacggggtc attagttcat agcccatata tggagttccg cgttacataa cttacggtaa     2400
atggcccgcc tggctgaccg cccaacgacc cccgcccatt gacgtcaata atgacgtatg     2460
ttcccatagt aacgccaata gggactttcc attgacgtca atgggtggag tatttacggt     2520
aaactgccca cttggcagta catcaagtgt atcatatgcc aagtacgccc cctattgacg     2580
tcaatgacgg taaatggccc gcctggcatt atgcccagta catgacctta tgggactttc     2640
```

```
ctacttggca gtacatctac gtattagtca tcgctattac catggtgatg cggttttggc    2700
agtacatcaa tgggcgtgga tagcggtttg actcacgggg atttccaagt ctccacccca    2760
ttgacgtcaa tgggagtttg ttttggcacc aaaatcaacg ggactttcca aaatgtcgta    2820
acaactccgc cccattgacg caaatgggcg gtaggcgtgt acggtgggag gtctatataa    2880
gcagagctcg tttagtgaac cgtcagatcg cctggagacg ccatccacgc tgttttgacc    2940
tccatagaag acaccgggac cgatccagcc tccgcggccg ggaacggtgc attggaacgc    3000
ggattccccg tgccaagagt gacgtaagta ccgcctatag agtctatagg cccaccccct    3060
tggcttctta tgcatgctat actgtttttg gcttggggtc tatacacccc cgcttcctca    3120
tgttataggt gatggtatag cttagcctat aggtgtgggt tattgaccat tattgaccac    3180

tcccctattg gtgacgatac tttccattac taatccataa catggctctt tgccacaact    3240
ctctttattg gctatatgcc aatacactgt ccttcagaga ctgacacgga ctctgtattt    3300

ttacaggatg gggtctcatt tattatttac aaattcacat atacaacacc accgtcccca    3360 gtgcccgcag ттттттaттaa acataacgtg ggatctccac gcgaatctcg gtacgtgtt    3420 ccggacatgg gctcttctcc ggtagcggcg gagcttctac atccgagccc tgctcccatg    3480
cctccagcga ctcatggtcg ctcggcagct ccttgctcct aacagtggag gccagactta    3540
ggcacagcac gatgcccacc accaccagtg tgccgcacaa ggccgtggcg gtagggtatg    3600

tgtctgaaaa tgagctcggg gagcgggctt gcaccgctga cgcatttgga agacttaagg    3660
cagcggcaga agaagatgca ggcagctgag ttgttgtgtt ctgataagag tcagaggtaa    3720
ctcccgttgc ggtgctgtta acggtggagg gcagtgtagt ctgagcagta ctcgttgctg    3780
ccgcgcgcgc caccagacat aatagctgac agactaacag actgttcctt tccatgggtc    3840

ttttctgcag tcaccgtcct tgacacgaag cttgccgcca ccatggattg gacttggaga    3900

atactgtttc ttgtagcagc cgcaacaggt aaggggctgc caaatcccag tgaggaggaa    3960
gggatcgaag gtgaccatcg aagccagtca aggggggcgga ccgcttccat ccactcctgt    4020
gtcttctcta caggtgttca cagtgatatt cagatgactc agaгтccaтc cagcatgtca    4080 gtctccgtgg gagatagggt gacgataacc tgtcattcaa gccaagacat caactccaat    4140
attggatggc tccaacagaa gcctggtaag tccttcaaag gactaatcta tcacggaaca    4200
aacttggacg acggcgtgcc atcgagattt tcagggtctg gcagcgggac cgactataca    4260
ctgaccatct ctagcttaca accagaggac tttgccacat actactgcgt ccagtacgct    4320
cagttcccct ggacattcgg cggcggcaca aaactgaaaa tcaaacgtga gtagcggtcc    4380
gttaattaaa gatccttcta aactctgagg gggtcggatg acgtggccat tgttacttaa    4440
acaccatcct gtttgcttct ttcctcagga accgtcgcag ctccctccgt gttcatcttc    4500
cccccatccg acgagcaact gaagtcaggc acagcctccg tggtgtgcct ccttaataac    4560

ttttacccaa gagaggccaa agtccagtgg aaagtggaca acgcactaca gagcgggaac    4620

tctcaggaaa gcgtgacaga gcaggactca aaagattcaa catacagcct atcttctacc    4680
ctgacactgt caaaagctga ttatgaaaag cacaaagtat atgcctgtga agtaactcat    4740
cagggactca gcagccctgt cactaaaagt tttaatagag gcgaatgctg ataagcggcc    4800
gtgcggacga ccgaattcat tgatcataat cagccatacc acatttgtag aggтттттacт    4860

tgctttaaaa aacctcccac acctccccct gaacctgaaa cataaaatga atgcaattgt    4920

tgttgttaac ttgtttattg cagcttataa tggttacaaa taaagcaata gcatcacaaa    4980
```

```
tttcacaaat aaagcatttt tttcactgca ttctagttgt ggtttgtcca aactcatcaa    5040
tgtatcttat catgtctgga tcctctacgc cggacgcatc gtggccggca tcaccggcgc    5100
cacaggtgcg gttgctggcg cctatatcgc cgacatcacc gatggggaag atcgggctcg    5160
ccacttcggg ctcatgagcg cttgtttcgg cgtgggtatg gtggcaggcc ccgtggccgg    5220
gggactgttg ggcgccatct ccttgcatgc accattcctt gcggcggcgg tgctcaacgg    5280
cctcaaccta ctactgggct gcttcctaat gcaggagtcg cataagggag agcgtcgacc    5340
tcgggccgcg ttgctggcgt ttttccatag gctccgcccc cctgacgagc atcacaaaaa    5400
tcgacgctca agtcagaggt ggcgaaaccc gacaggacta taaagatacc aggcgtttcc    5460
ccctggaagc tccctcgtgc gctctcctgt tccgaccctg ccgcttaccg gatacctgtc    5520
cgcctttctc ccttcgggaa gcgtggcgct ttctcatagc tcacgctgta ggtatctcag    5580
ttcggtgtag gtcgttcgct ccaagctggg ctgtgtgcac gaaccccccg ttcagcccga    5640
ccgctgcgcc ttatccggta actatcgtct tgagtccaac ccggtaagac acgacttatc    5700
gccactggca gcagccactg gtaacaggat tagcagagcg aggtatgtag gcggtgctac    5760
agagttcttg aagtggtggc ctaactacgg ctacactaga agaacagtat ttggtatctg    5820
cgctctgctg aagccagtta ccttcggaaa aagagttggt agctcttgat ccggcaaaca    5880
aaccaccgct ggtagcgtgg gttttttgt ttgcaagcag cagattacgc gcagaaaaaa    5940
aggatctcaa gaagatcctt tgatcttttc tacgggtct gacgctcagt ggaacgaaaa    6000
ctcacgttaa gggattttgg tcatgagatt atcaaaaagg atcttcacct agatcctttt    6060
aaattaaaaa tgaagtttta atcaatcta agtatatat gagtaaactt ggtctgacag    6120
ttaccaatgc ttaatcagtg aggcacctat ctcagcgatc tgtctatttc gttcatccat    6180
agttgcctga ctccccgtcg tgtagataac tacgatacgg gagggcttac catctggccc    6240
cagtgctgca atgataccgc gagacccacg ctcaccggct ccagatttat cagcaataaa    6300
ccagccagcc ggaagggccg agcgcagaag tggtcctgca actttatccg cctccatcca    6360
gtctattaat tgttgccggg aagctagagt aagtagttcg ccagttaata gtttgcgcaa    6420
cgttgttgcc attgctacag gcatcgtggt gtcacgctcg tcgtttggta tggcttcatt    6480
cagctccggt tcccaacgat caaggcgagt tacatgatcc cccatgttgt gcaaaaaagc    6540
ggttagctcc ttcggtcctc cgatcgttgt cagaagtaag ttggccgcag tgttatcact    6600
catggttatg gcagcactgc ataattctct tactgtcatg ccatccgtaa gatgcttttc    6660
tgtgactggt gagtactcaa ccaagtcatt ctgagaatag tgtatgcggc gaccgagttg    6720
ctcttgcccg gcgtcaatac gggataatac cgcgccacat agcagaactt taaaagtgct    6780
catcattgga aaacgttctt cggggcgaaa actctcaagg atcttaccgc tgttgagatc    6840
cagttcgatg taacccactc gtgcacccaa ctgatcttca gcatctttta ctttcaccag    6900
cgtttctggg tgagcaaaaa caggaaggca aaatgccgca aaaagggaa taagggcgac    6960
acggaaatgt tgaatactca tactcttcct ttttcaatat tattgaagca tttatcaggg    7020
ttattgtctc atgagcggat acatatttga atgtatttag aaaaataaac aaataggggt    7080
tccgcgcaca tttccccgaa aagtgccacc tgacgtctaa gaaaccatta ttatcatgac    7140
attaacctat aaaaataggc gtatcacgag gccctgatgg ctctttgcgg cacccatcgt    7200
tcgtaatgtt ccgtggcacc gaggacaacc ctcaagagaa aatgtaatca cactggctca    7260
ccttcgggtg ggcctttctg cgtttataag agacactttt atgtttaaga aggttggtaa    7320
attccttgcg gctttggcag ccaagctaga tccggctgtg gaatgtgtgt cagttagggt    7380
```

```
gtggaaagtc cccaggctcc ccagcaggca gaagtatgca aagcatgcat ctcaattagt    7440
cagcaaccag gtgtggaaag tccccaggct ccccagcagg cagaagtatg caaagcatgc    7500
atctcaatta gtcagcaacc atagtcccgc ccctaactcc gcccatcccg cccctaactc    7560
cgcccagttc cgcccattct ccgccccatg gctgactaat ttttttatt tatgcagagg     7620 ccgaggccgc ctcggcctct gagctattcc agaagtagtg aggaggcttt tttggaggcc    7680
taggcttttg caaaaagcta gcttggggcc accgctcaga gcaccttcca ccatggccac    7740
ctcagcaagt tcccacttga acaaaaacat caagcaaatg tacttgtgcc tgccccaggg    7800
tgagaaagtc caagccatgt atatctgggt tgatggtact ggagaaggac tgcgctgcaa    7860
aacccgcacc ctggactgtg agcccaagtg tgtagaagag ttacctgagt ggaattttga    7920
tggctctagt cctttcagt ctgagggctc aacagtgac atgtatctca gccctgttgc      7980
catgtttcgg gacccttcc gcagagatcc caacaagctg gtgttctgtg aagttttcaa     8040
gtacaaccgg aagcctgcag agaccaattt aaggcactcg tgtaaacgga taatggacat    8100
ggtgagcaac cagcacccct ggtttggaat ggaacaggag tatactctga tgggaacaga    8160 tgggcacccct tttggttggc cttccaatgg ctttcctggg ccccaaggtc cgtattactg    8220
tggtgtgggc gcagacaaag cctatggcag ggatatcgtg gaggctcact accgcgcctg    8280
cttgtatgct ggggtcaaga ttacaggaac aaatgctgag gtcatgcctg cccagtggga    8340
actccaaata ggaccctgtg aaggaatccg catgggagat catctctggg tggcccgttt    8400
catcttgcat cgagtatgtg aagactttgg ggtaatagca acctttgacc ccaagcccat    8460
tcctgggaac tggaatggtg caggctgcca taccaacttt agcaccaagg ccatgcggga    8520
ggagaatggt ctgaagcaca tcgaggaggc catcgagaaa ctaagcaagc ggcaccggta    8580
ccacattcga gcctacgatc caagggggg cctggacaat gcccgtggtc tgactgggtt     8640
ccacgaaacg tccaacatca acgacttttc tgctggtgtc gccaatcgca gtgccagcat    8700
ccgcattccc cggactgtcg gccaggagaa gaaaggttac tttgaagacc gcggccctc     8760 tgccaattgt gaccccttg cagtgacaga agccatcgtc cgcacatgcc ttctcaatga     8820
gactggcgac gagcccttcc aatacaaaaa ctaattagac tttgagtgat cttgagcctt    8880
tcctagttca tcccaccccg ccccagagag atctttgtga aggaaccta cttctgtggt     8940 gtgacataat tggacaaact acctacagag atttaaagct ctaaggtaaa tataaaattt    9000
ttaagtgtat aatgtgttaa actactgatt ctaattgttt gtgtatttta gattccaacc    9060 tatgaactg atgaatggga gcagtggtgg aatgcctta atgaggaaaa cctgttttgc      9120
tcagaagaaa tgccatctag tgatgatgag gctactgctg actctcaaca ttctactcct    9180
ccaaaaaaga agagaaaggt agaagacccc aaggactttc cttcagaatt gctaagtttt    9240
ttgagtcatg ctgtgtttag taatagaact cttgcttgct ttgctattta caccacaaag    9300 gaaaagctg cactgctata caagaaaatt atggaaaaat attctgtaac ctttataagt     9360
aggcataaca gttataatca taacatactg ttttttctta ctccacacag gcatagagtg    9420
tctgctatta ataactatgc tcaaaaattg tgtaccttta gctttttaat ttgtaaaggg    9480
gttaataagg aatatttgat gtatagtgcc ttgactagag atcataatca gccataccac    9540
atttgtagag gttttacttg cttaaaaaa cctcccacac ctccccctga acctgaaaca     9600
taaaatgaat gcaattgttg ttgttaactt gtttattgca gcttataatg gttacaaata    9660
aagcaatagc atcacaaatt tcacaaataa agcattttttt tcactgcatt ctagttgtgg   9720
```

```
tttgtccaaa ctcatcaatg tatcttatca tgtctggatc tagcttcgtg tcaaggacgg    9780
tgactgcagt gaataataaa atgtgtgttt gtccgaaata cgcgttttga gatttctgtc    9840
gccgactaaa ttcatgtcgc gcgatagtgg tgtttatcgc cgatagagat ggcgatattg    9900
gaaaaatcga tatttgaaaa tatggcatat tgaaaatgtc gccgatgtga gtttctgtgt    9960
aactgatatc gccatttttc caaaagtgat ttttgggcat acgcgatatc tggcgatagc   10020
gcttatatcg tttacggggg atggcgatag acgactttgg tgacttgggc gattctgtgt   10080
gtcgcaaata tcgcagtttc gatataggtg acagacgata tgaggctata tcgccgatag   10140
aggcgacatc aagctggcac atggccaatg catatcgatc tatacattga atcaatattg   10200
gccattagcc atattattca ttggttatat agcataaatc aatattggct attggccatt   10260
gcatacgttg tatccatatc ataatatgta catttatatt ggctcatgtc caacattacc   10320
gccatgttga cattgattat tgactagtta ttaatagtaa tcaattacgg ggtcattagt   10380
tcatagccca tatatggagt tccgcgttac ataacttacg gtaaatggcc cgcctggctg   10440
accgcccaac gacccccgcc cattgacgtc aataatgacg tatgttccca tagtaacgcc   10500
aatagggact ttccattgac gtcaatgggt ggagtattta cggtaaactg cccacttggc   10560
agtacatcaa gtgtatcata tgccaagtac gccccctatt gacgtcaatg acggtaaatg   10620
gcccgcctgg cattatgccc agtacatgac cttatgggac tttcctactt ggcagtacat   10680
ctacgtatta gtcatcgcta ttaccatggt gatgcggttt tggcagtaca tcaatgggcg   10740
tggatagcgg tttgactcac ggggatttcc aagtctccac cccattgacg tcaatgggag   10800
tttgttttgg caccaaaatc aacgggactt tccaaaatgt cgtaacaact ccgccccatt   10860
gacgcaaatg ggcggtaggc gtgtacggtg ggaggtctat ataagcagag ctcgtttagt   10920
gaaccgtcag atcgcctgga gacgccatcc acgctgtttt gacctccata agagacaccg   10980
ggaccgatcc agcctccgcg gccgggaacg gtgcattgga acgcggattc cccgtgccaa   11040
gagtgacgta agtaccgcct atagagtcta taggcccacc cccttggctt cttatgcatg   11100
ctatactgtt tttggcttgg ggtctataca cccccgcttc ctcatgttat aggtgatggt   11160
atagcttagc ctataggtgt gggttattga ccattattga ccactcccct attggtgacg   11220
atactttcca ttactaatcc ataacatggc tctttgccac aactctcttt attggctata   11280
tgccaataca ctgtccttca gagactgaca cggactctgt attttttacag gatgggtct   11340
catttattat ttacaaattc acatatacaa caccaccgtc cccagtgccc gcagttttta   11400
ttaaacataa cgtgggatct ccacgcgaat ctcgggtacg tgttccggac atgggctctt   11460
ctccggtagc ggcggagctt ctacatccga gccctgctcc catgcctcca gcgactcatg   11520
gtcgctcggc agctccttgc tcctaacagt ggaggccaga cttaggcaca gcacgatgcc   11580
caccaccacc agtgtgccgc acaaggccgt ggcggtaggg tatgtgtctg aaaatgagct   11640
cggggagcgg gcttgcaccg ctgacgcatt tggaagactt aaggcagcgg cagaagaaga   11700
tgcaggcagc tgagttgttg tgttctgata agagtcagag gtaactcccg ttgcggtgct   11760
gttaacggtg gagggcagtg tagtctgagc agtactcgtt gctgccgcgc gcgccaccag   11820
acataatagc tgacagacta acagactgtt cctttccatg ggtctttttct gcagtcaccg   11880
tccttgacac g                                                        11891
```

<210> SEQ ID NO 42
<211> LENGTH: 135
<212> TYPE: PRT
<213> ORGANISM: Artificial Sequence

```
<220> FEATURE:
<223> OTHER INFORMATION: synthetic

<400> SEQUENCE: 42

Met Asp Trp Thr Trp Arg Ile Leu Phe Leu Val Ala Ala Thr Gly
1               5                   10                  15

Val His Ser Gln Val Gln Leu Gln Glu Ser Gly Pro Gly Leu Val Lys
            20                  25                  30

Pro Ser Gln Thr Leu Ser Leu Thr Cys Thr Val Ser Gly Tyr Ser Ile
            35                  40                  45

Ser Ser Asp Phe Ala Trp Asn Trp Ile Arg Gln Pro Pro Gly Lys Gly
        50                  55                  60

Leu Glu Trp Met Gly Tyr Ile Ser Tyr Ser Gly Asn Thr Arg Tyr Gln
65                  70                  75                  80

Pro Ser Leu Lys Ser Arg Ile Thr Ile Ser Arg Asp Thr Ser Lys Asn
                85                  90                  95

Gln Phe Phe Leu Lys Leu Asn Ser Val Thr Ala Ala Asp Thr Ala Thr
            100                 105                 110

Tyr Tyr Cys Val Thr Ala Gly Arg Gly Phe Pro Tyr Trp Gly Gln Gly
        115                 120                 125

Thr Leu Val Thr Val Ser Ser
        130                 135

<210> SEQ ID NO 43
<211> LENGTH: 330
<212> TYPE: PRT
<213> ORGANISM: Artificial Sequence
<220> FEATURE:
<223> OTHER INFORMATION: synthetic

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
                195                 200                 205
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Cys Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 44
<211> LENGTH: 6
<212> TYPE: PRT
<213> ORGANISM: Artificial Sequence
<220> FEATURE:
<223> OTHER INFORMATION: synthetic

<400> SEQUENCE: 44

Ser Asp Phe Ala Trp Asn
1               5

<210> SEQ ID NO 45
<211> LENGTH: 16
<212> TYPE: PRT
<213> ORGANISM: Artificial Sequence
<220> FEATURE:
<223> OTHER INFORMATION: synthetic

<400> SEQUENCE: 45

Tyr Ile Ser Tyr Ser Gly Asn Thr Arg Tyr Gln Pro Ser Leu Lys Ser
1               5                   10                  15

<210> SEQ ID NO 46
<211> LENGTH: 9
<212> TYPE: PRT
<213> ORGANISM: Artificial Sequence
<220> FEATURE:
<223> OTHER INFORMATION: synthetic

<400> SEQUENCE: 46

Val Thr Ala Gly Arg Gly Phe Pro Tyr
1               5

<210> SEQ ID NO 47
<211> LENGTH: 127
<212> TYPE: PRT
<213> ORGANISM: Artificial Sequence
<220> FEATURE:
<223> OTHER INFORMATION: synthetic

<400> SEQUENCE: 47

Met Asp Trp Thr Trp Arg Ile Leu Phe Leu Val Ala Ala Ala Thr Gly
1               5                   10                  15

Val His Ser Asp Ile Gln Met Thr Gln Ser Pro Ser Ser Met Ser Val
```

```
            20                  25                  30
Ser Val Gly Asp Arg Val Thr Ile Thr Cys His Ser Ser Gln Asp Ile
            35                  40                  45

Asn Ser Asn Ile Gly Trp Leu Gln Gln Lys Pro Gly Lys Ser Phe Lys
        50                  55                  60

Gly Leu Ile Tyr His Gly Thr Asn Leu Asp Asp Gly Val Pro Ser Arg
65                  70                  75                  80

Phe Ser Gly Ser Gly Ser Gly Thr Asp Tyr Thr Leu Thr Ile Ser Ser
                85                  90                  95

Leu Gln Pro Glu Asp Phe Ala Thr Tyr Tyr Cys Val Gln Tyr Ala Gln
            100                 105                 110

Phe Pro Trp Thr Phe Gly Gly Gly Thr Lys Leu Glu Ile Lys Arg
            115                 120                 125
```

<210> SEQ ID NO 48
<211> LENGTH: 106
<212> TYPE: PRT
<213> ORGANISM: Artificial Sequence
<220> FEATURE:
<223> OTHER INFORMATION: synthetic

<400> SEQUENCE: 48

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 49
<211> LENGTH: 11
<212> TYPE: PRT
<213> ORGANISM: Artificial Sequence
<220> FEATURE:
<223> OTHER INFORMATION: synthetic

<400> SEQUENCE: 49

```
His Ser Ser Gln Asp Ile Asn Ser Asn Ile Gly
1               5                   10
```

<210> SEQ ID NO 50
<211> LENGTH: 7
<212> TYPE: PRT
<213> ORGANISM: Artificial Sequence
<220> FEATURE:
<223> OTHER INFORMATION: synthetic

<400> SEQUENCE: 50

```
His Gly Thr Asn Leu Asp Asp
1               5
```

<210> SEQ ID NO 51

```
<211> LENGTH: 9
<212> TYPE: PRT
<213> ORGANISM: Artificial Sequence
<220> FEATURE:
<223> OTHER INFORMATION: synthetic

<400> SEQUENCE: 51

Val Gln Tyr Ala Gln Phe Pro Trp Thr
1               5

<210> SEQ ID NO 52
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 52
gagaagcttg ccgccaccat ggattggacc tggcgcattc                                40

<210> SEQ ID NO 53
<211> LENGTH: 79
<212> TYPE: DNA
<213> ORGANISM: Artificial Sequence
<220> FEATURE:
<223> OTHER INFORMATION: synthetic oligonucleotide

<400> SEQUENCE: 53
cccttcctcc tcactgggat tggcagccc cttacctgtg gcggctgcta ccagaaagag            60
aatgcgccag gtccaatcc                                                       79

<210> SEQ ID NO 54
<211> LENGTH: 79
<212> TYPE: DNA
<213> ORGANISM: Artificial Sequence
<220> FEATURE:
<223> OTHER INFORMATION: synthetic oligonucleotide

<400> SEQUENCE: 54
cccagtgagg aggaagggat cgaaggtcac catcgaagcc agtcaagggg gcttccatcc           60
actcctgtgt cttctctac                                                       79

<210> SEQ ID NO 55
<211> LENGTH: 80
<212> TYPE: DNA
<213> ORGANISM: Artificial Sequence
<220> FEATURE:
<223> OTHER INFORMATION: synthetic oligonucleotide

<400> SEQUENCE: 55
gactcggctt gacaagccca ggtccactct cttggagctg cacctggctg tggacacctg          60
tagagaagac acaggagtgg                                                      80

<210> SEQ ID NO 56
<211> LENGTH: 84
<212> TYPE: DNA
<213> ORGANISM: Artificial Sequence
<220> FEATURE:
<223> OTHER INFORMATION: synthetic oligonucleotide

<400> SEQUENCE: 56
gggcttgtca agccgagtca aactttgtcc ctaacatgta ctgtgtccgg atactctatc          60
tcatcagatt ttgcgtggaa ttgg                                                 84
```

```
<210> SEQ ID NO 57
<211> LENGTH: 80
<212> TYPE: DNA
<213> ORGANISM: Artificial Sequence
<220> FEATURE:
<223> OTHER INFORMATION: synthetic oligonucleotide

<400> SEQUENCE: 57
cccagagtat gatatgtagc ccatccattc taaacctttc cctggtggct gccttatcca    60
attccacgca aaatctgatg                                                80

<210> SEQ ID NO 58
<211> LENGTH: 79
<212> TYPE: DNA
<213> ORGANISM: Artificial Sequence
<220> FEATURE:
<223> OTHER INFORMATION: synthetic oligonucleotide

<400> SEQUENCE: 58
gggctacata tcatactctg ggaacaccag atatcaaccc tctctgaaaa gccggatcac    60
aatcactagg gacacgtcg                                                 79

<210> SEQ ID NO 59
<211> LENGTH: 83
<212> TYPE: DNA
<213> ORGANISM: Artificial Sequence
<220> FEATURE:
<223> OTHER INFORMATION: synthetic oligonucleotide

<400> SEQUENCE: 59
gcagtaatat gttgctgtgt ctggggctgt aacggagttc agctgcagga agaactggct    60
cttcgacgtg tccctagtga ttg                                            83

<210> SEQ ID NO 60
<211> LENGTH: 81
<212> TYPE: DNA
<213> ORGANISM: Artificial Sequence
<220> FEATURE:
<223> OTHER INFORMATION: synthetic oligonucleotide

<400> SEQUENCE: 60
ccagacacag caacatatta ctgcgtaacc gctggcagag gcttcccta ttggggacag     60 ggcaccctag tgacagtgag c                                              81

<210> SEQ ID NO 61
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 61
cacggatcca tcttaccgct gctcactgtc actagggtg                           39

<210> SEQ ID NO 62
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 62
gagaagcttg ccgccaccat ggattg                                         26
```

<210> SEQ ID NO 63
<211> LENGTH: 80
<212> TYPE: DNA
<213> ORGANISM: Artificial Sequence
<220> FEATURE:
<223> OTHER INFORMATION: synthetic oligonucleotide

<400> SEQUENCE: 63
ctgggatttg gcagcccctt acctgttgcg gctgctacaa gaaacagtat tctccaagtc    60
caatccatgg tggcggcaag                                                80

<210> SEQ ID NO 64
<211> LENGTH: 78
<212> TYPE: DNA
<213> ORGANISM: Artificial Sequence
<220> FEATURE:
<223> OTHER INFORMATION: synthetic oligonucleotide

<400> SEQUENCE: 64
ggggctgcca atcccagtg aggaggaagg gatcgaaggt gaccatcgaa gccagtcaag    60
ggggcttcca tccactcc                                                  78

<210> SEQ ID NO 65
<211> LENGTH: 77
<212> TYPE: DNA
<213> ORGANISM: Artificial Sequence
<220> FEATURE:
<223> OTHER INFORMATION: synthetic oligonucleotide

<400> SEQUENCE: 65
catgctggat ggactctgag tcatctgaat atcactgtga acacctgtag agaagacaca    60
ggagtggatg gaagccc                                                   77

<210> SEQ ID NO 66
<211> LENGTH: 80
<212> TYPE: DNA
<213> ORGANISM: Artificial Sequence
<220> FEATURE:
<223> OTHER INFORMATION: synthetic oligonucleotide

<400> SEQUENCE: 66
ctcagagtcc atccagcatg tcagtctccg tgggagatag ggtgacgata acctgtcatt    60
caagccaaga catcaactcc                                                80

<210> SEQ ID NO 67
<211> LENGTH: 82
<212> TYPE: DNA
<213> ORGANISM: Artificial Sequence
<220> FEATURE:
<223> OTHER INFORMATION: synthetic oligonucleotide

<400> SEQUENCE: 67
gttccgtgat agattagtcc tttgaaggac ttaccaggct tctgttggag ccatccaata    60
ttggagttga tgtcttggct tg                                             82

<210> SEQ ID NO 68
<211> LENGTH: 84
<212> TYPE: DNA
<213> ORGANISM: Artificial Sequence
<220> FEATURE:
<223> OTHER INFORMATION: synthetic oligonucleotide

```
<400> SEQUENCE: 68
caaaggacta atctatcacg aacaaactt ggacgacggc gtgccatcga gattttcagg    60
gtctggcagc gggaccgact atac                                          84

<210> SEQ ID NO 69
<211> LENGTH: 76
<212> TYPE: DNA
<213> ORGANISM: Artificial Sequence
<220> FEATURE:
<223> OTHER INFORMATION: synthetic oligonucleotide

<400> SEQUENCE: 69
gtgctggacg cagtagtatg tggcaaagtc ttctggctct aagctagaga tggtcagtgt    60
atagtcggtc ccgctg                                                   76

<210> SEQ ID NO 70
<211> LENGTH: 79
<212> TYPE: DNA
<213> ORGANISM: Artificial Sequence
<220> FEATURE:
<223> OTHER INFORMATION: synthetic oligonucleotide

<400> SEQUENCE: 70
catactactg cgtccagcac gctcagttcc cctggacatt cggcggcggc acaaaactgg    60
aaatcaaacg tgagtaggg                                                79

<210> SEQ ID NO 71
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 71
ctcggatccc tactcacgtt tgatttcc                                      28

<210> SEQ ID NO 72
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 72
gacggatcct tctaaactct gaggggtcg gatgacg                             37

<210> SEQ ID NO 73
<211> LENGTH: 78
<212> TYPE: DNA
<213> ORGANISM: Artificial Sequence
<220> FEATURE:
<223> OTHER INFORMATION: synthetic oligonucleotide

<400> SEQUENCE: 73
ggagctgcga cggttcctga ggaaagaagc aaacaggatg gtgtttaagt aacaatggcc    60
acgtcatccg accccctc                                                 78

<210> SEQ ID NO 74
<211> LENGTH: 78
<212> TYPE: DNA
<213> ORGANISM: Artificial Sequence
<220> FEATURE:
<223> OTHER INFORMATION: synthetic oligonucleotide
```

<400> SEQUENCE: 74
ggaaccgtcg cagctccctc cgtgttcatc ttccccccat ccgacgagca actgaagtca    60
ggcacagcct ccgtggtg                                                  78

<210> SEQ ID NO 75
<211> LENGTH: 78
<212> TYPE: DNA
<213> ORGANISM: Artificial Sequence
<220> FEATURE:
<223> OTHER INFORMATION: synthetic oligonucleotide

<400> SEQUENCE: 75
gtgcgttgtc cactttccac tggactttgg cctctcttgg gtaaaagtta ttaaggaggc    60
acaccacgga ggctgtgc                                                  78

<210> SEQ ID NO 76
<211> LENGTH: 83
<212> TYPE: DNA
<213> ORGANISM: Artificial Sequence
<220> FEATURE:
<223> OTHER INFORMATION: synthetic oligonucleotide

<400> SEQUENCE: 76
gtggaaagtg gacaacgcac tacagagcgg gaactctcag gaaagcgtga cagagcagga    60
ctcaaaagat tcaacataca gcc                                            83

<210> SEQ ID NO 77
<211> LENGTH: 88
<212> TYPE: DNA
<213> ORGANISM: Artificial Sequence
<220> FEATURE:
<223> OTHER INFORMATION: synthetic oligonucleotide

<400> SEQUENCE: 77
cttcacaggc atataccttg tgcttttcat aatcagcttt tgacagtgtc agggtagaag    60
ataggctgta tgttgaatct tttgagtc                                       88

<210> SEQ ID NO 78
<211> LENGTH: 71
<212> TYPE: DNA
<213> ORGANISM: Artificial Sequence
<220> FEATURE:
<223> OTHER INFORMATION: synthetic oligonucleotide

<400> SEQUENCE: 78
gcacaaggta tatgcctgtg aagtaactca tcagggactc agcagccctg tcactaaaag    60 tttttaataga g                                                        71

<210> SEQ ID NO 79
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 79
cctgcggccg cttatcagca ttcgcctcta ttaaaacttt tggtgagagg g              51

<210> SEQ ID NO 80
<211> LENGTH: 1128
<212> TYPE: DNA

<213> ORGANISM: Artificial Sequence
<220> FEATURE:
<223> OTHER INFORMATION: synthetic

<400> SEQUENCE: 80

```
aagatggcac accgtggccg gcctctgcgc ctgggcccag ctctgtccca caccgcggtc      60
acatggcacc ttttctcttc cagcctccac caagggcccc agcgtgttcc ccctggcccc     120
cagcagcaag agcaccagcg gcggcacagc cgccctgggc tgcctggtga aggactactt     180
ccccgagccc gtgaccgtga gctggaacag cggagccctg acctccggcg tgcacacctt     240
ccccgccgtg ctgcagagca gcggcctgta cagcctgagc agcgtggtga ccgtgcccag     300
cagcagcctg ggcacccaga cctacatctg caacgtgaac cacaagccca gcaacaccaa     360
ggtggacaag aaggtggagc ccaagagctg cgacaagacc cacacctgcc ccccctgccc     420
agccccagag ctgctgggcg gaccctccgt gttcctgttc cccccaagc ccaaggacac      480
cctgatgatc agcaggaccc ccgaggtgac ctgcgtggtg gtggacgtga gccacgagga     540
cccagaggtg aagttcaatt ggtatgtgga cggcgtggag gtgcacaacg ccaagaccaa     600
gcccagagaa gagcagtaca acagcaccta caggtggtg tccgtgctga ccgtgctgca      660
ccaggactgg ctgaacggca aggaatacaa atgcaaggtc tccaacaagg ccctgccagc     720
ccccatcgaa aagaccatca gcaaggccaa gggccagcca cgggagcccc aggtgtacac     780
cctgccccc tcccgggacg agtgcaccaa gaaccaggtg tccctgacct gtctggtgaa      840
gggcttctac cccagcgaca tcgccgtgga gtgggagagc aacggccagc cgagaacaa      900
ctacaagacc ccccccag tgctggacag cgacggcagc ttcttcctgt acagcaagct       960
gaccgtggac aagagcaggt ggcagcaggg caacgtgttc agctgcagcg tgatgcacga    1020
ggccctgcac aaccactaca cccagaagag cctgagcctg tcccccggca agtgatgacg    1080
acgcggccgt gcggacgacc gaattcattg atcataatca gccatacc                 1128
```

<210> SEQ ID NO 81
<211> LENGTH: 465
<212> TYPE: PRT
<213> ORGANISM: Artificial Sequence
<220> FEATURE:
<223> OTHER INFORMATION: synthetic

<400> SEQUENCE: 81

```
Met Asp Trp Thr Trp Arg Ile Leu Phe Leu Val Ala Ala Ala Thr Gly
1               5                   10                  15

Val His Ser Gln Val Gln Leu Gln Glu Ser Gly Pro Gly Leu Val Lys
            20                  25                  30

Pro Ser Gln Thr Leu Ser Leu Thr Cys Thr Val Ser Gly Tyr Ser Ile
        35                  40                  45

Ser Ser Asp Phe Ala Trp Asn Trp Ile Arg Gln Pro Pro Gly Lys Gly
    50                  55                  60

Leu Glu Trp Met Gly Tyr Ile Ser Tyr Ser Gly Asn Thr Arg Tyr Gln
65                  70                  75                  80

Pro Ser Leu Lys Ser Arg Ile Thr Ile Ser Arg Asp Thr Ser Lys Asn
                85                  90                  95

Gln Phe Phe Leu Lys Leu Asn Ser Val Thr Ala Ala Asp Thr Ala Thr
            100                 105                 110

Tyr Tyr Cys Val Thr Ala Gly Arg Gly Phe Pro Tyr Trp Gly Gln Gly
        115                 120                 125

Thr Leu Val Thr Val Ser Ser Ala Ser Thr Lys Gly Pro Ser Val Phe
```

```
                130             135             140
Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Val Asp Val Ser His Glu Asp
            275                 280                 285

Pro Glu Val Lys Phe Asn Trp Tyr Val Asp Gly Val Glu Val His Asn
        290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
                340                 345                 350

Thr Ile Ser Lys Ala Lys Gly Gln Pro Arg Glu Pro Gln Val Tyr Thr
            355                 360                 365

Leu Pro Pro Ser Arg Asp Glu Cys Thr Lys Asn Gln Val Ser Leu Thr
        370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
                420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
        450                 455                 460
Lys
465

<210> SEQ ID NO 82
<211> LENGTH: 209
<212> TYPE: PRT
<213> ORGANISM: Artificial Sequence
<220> FEATURE:
<223> OTHER INFORMATION: synthetic

<400> SEQUENCE: 82

Met Asp Trp Thr Trp Arg Ile Leu Phe Leu Val Ala Ala Ala Thr Gly
1               5                   10                  15

Val His Ser Asp Ile Gln Met Thr Gln Ser Pro Ser Ser Met Ser Val
```

```
            20                  25                  30
Ser Val Gly Asp Arg Val Thr Ile Thr Cys His Ser Ser Gln Asp Ile
        35                  40                  45

Asn Ser Asn Ile Gly Trp Leu Gln Gln Lys Pro Gly Lys Ser Phe Lys
    50                  55                  60

Gly Leu Ile Tyr His Gly Thr Asn Leu Asp Asp Gly Val Pro Ser Arg
65                  70                  75                  80

Phe Ser Gly Ser Gly Ser Gly Thr Asp Tyr Thr Leu Thr Ile Ser Ser
                85                  90                  95

Leu Glu Pro Glu Asp Phe Ala Thr Tyr Tyr Cys Val Gln His Ala Gln
            100                 105                 110

Phe Pro Trp Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys

<210> SEQ ID NO 83
<211> LENGTH: 233
<212> TYPE: PRT
<213> ORGANISM: Artificial Sequence
<220> FEATURE:
<223> OTHER INFORMATION: synthetic

<400> SEQUENCE: 83

Met Asp Trp Thr Trp Arg Ile Leu Phe Leu Val Ala Ala Ala Thr Gly
1               5                   10                  15

Val His Ser Asp Ile Gln Met Thr Gln Ser Pro Ser Ser Met Ser Val
            20                  25                  30

Ser Val Gly Asp Arg Val Thr Ile Thr Cys His Ser Ser Gln Asp Ile
        35                  40                  45

Asn Ser Asn Ile Gly Trp Leu Gln Gln Lys Pro Gly Lys Ser Phe Lys
    50                  55                  60

Gly Leu Ile Tyr His Gly Thr Asn Leu Asp Asp Gly Val Pro Ser Arg
65                  70                  75                  80

Phe Ser Gly Ser Gly Ser Gly Thr Asp Tyr Thr Leu Thr Ile Ser Ser
                85                  90                  95

Leu Gln Pro Glu Asp Phe Ala Thr Tyr Tyr Cys Val Gln Tyr Ala Gln
            100                 105                 110

Phe Pro Trp Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175
```

```
Asn Ser Gln Glu Ser Val Thr Glu Gln Asp Ser Lys Asp Ser Thr Tyr
                180                 185                 190
Ser Leu Ser Ser Thr Leu Thr Leu Ser Lys Ala Asp Tyr Glu Lys His
            195                 200                 205
Lys Val Tyr Ala Cys Glu Val Thr His Gln Gly Leu Ser Ser Pro Val
        210                 215                 220
Thr Lys Ser Phe Asn Arg Gly Glu Cys
225                 230
```

<210> SEQ ID NO 84
<211> LENGTH: 7
<212> TYPE: PRT
<213> ORGANISM: Mus musculus

<400> SEQUENCE: 84

```
Cys Val Gln His Ala Gln Phe
1               5
```

<210> SEQ ID NO 85
<211> LENGTH: 7
<212> TYPE: PRT
<213> ORGANISM: Mus musculus

<400> SEQUENCE: 85

```
Cys Val Gln Tyr Ala Gln Phe
1               5
```

<210> SEQ ID NO 86
<211> LENGTH: 40
<212> TYPE: DNA
<213> ORGANISM: Artificial Sequence
<220> FEATURE:
<223> OTHER INFORMATION: synthetic primer

<400> SEQUENCE: 86
ccacatacta ctgcgtccag tacgctcagt tcccctggac                         40

<210> SEQ ID NO 87
<211> LENGTH: 20
<212> TYPE: DNA
<213> ORGANISM: Artificial Sequence
<220> FEATURE:
<223> OTHER INFORMATION: synthetic primer

<400> SEQUENCE: 87
ctggacgcag tagtatgtgg                                               20

<210> SEQ ID NO 88
<211> LENGTH: 26
<212> TYPE: DNA
<213> ORGANISM: Artificial Sequence
<220> FEATURE:
<223> OTHER INFORMATION: synthetic primer

<400> SEQUENCE: 88
gagaagcttg ccgccaccat ggattg                                        26

<210> SEQ ID NO 89
<211> LENGTH: 28
<212> TYPE: DNA
<213> ORGANISM: Artificial Sequence
<220> FEATURE:
<223> OTHER INFORMATION: synthetic primer

<400> SEQUENCE: 89
cactgggtga ctggcttcga tggtgacc                                        28

<210> SEQ ID NO 90
<211> LENGTH: 49
<212> TYPE: DNA
<213> ORGANISM: Artificial Sequence
<220> FEATURE:
<223> OTHER INFORMATION: synthetic primer

<400> SEQUENCE: 90
ggtcaccatc gaagccagtc acccagtgaa gggggcttcc atccactcc                 49

<210> SEQ ID NO 91
<211> LENGTH: 44
<212> TYPE: DNA
<213> ORGANISM: Artificial Sequence
<220> FEATURE:
<223> OTHER INFORMATION: synthetic primer

<400> SEQUENCE: 91
ccaagatctg gccggccacg gtgtgccatc ttaccgctgc tcac                      44

<210> SEQ ID NO 92
<211> LENGTH: 22
<212> TYPE: DNA
<213> ORGANISM: Artificial Sequence
<220> FEATURE:
<223> OTHER INFORMATION: synthetic primer

<400> SEQUENCE: 92
gagaagcttg ccgccaccat gg                                              22

<210> SEQ ID NO 93
<211> LENGTH: 25
<212> TYPE: DNA
<213> ORGANISM: Artificial Sequence
<220> FEATURE:
<223> OTHER INFORMATION: synthetic primer

<400> SEQUENCE: 93
cggtccgccc ccttgactgg cttcg                                           25

<210> SEQ ID NO 94
<211> LENGTH: 45
<212> TYPE: DNA
<213> ORGANISM: Artificial Sequence
<220> FEATURE:
<223> OTHER INFORMATION: synthetic primer

<400> SEQUENCE: 94
cgaagccagt caaggggggcg gaccgcttcc atccactcct gtgtc                    45

<210> SEQ ID NO 95
<211> LENGTH: 50
<212> TYPE: DNA
<213> ORGANISM: Artificial Sequence
<220> FEATURE:
<223> OTHER INFORMATION: synthetic primer

<400> SEQUENCE: 95
ccaagatctt taattaacgg accgctactc acgtttgatt tccagttttg                50

<210> SEQ ID NO 96
<211> LENGTH: 7

```
<212> TYPE: PRT
<213> ORGANISM: Mus musculus

<400> SEQUENCE: 96

Ser Val Thr Ile Glu Asp Thr
1               5

<210> SEQ ID NO 97
<211> LENGTH: 7
<212> TYPE: PRT
<213> ORGANISM: Artificial Sequence
<220> FEATURE:
<223> OTHER INFORMATION: synthetic

<400> SEQUENCE: 97

Ser Val Thr Ala Pro Asp Thr
1               5

<210> SEQ ID NO 98
<211> LENGTH: 7
<212> TYPE: PRT
<213> ORGANISM: Artificial Sequence
<220> FEATURE:
<223> OTHER INFORMATION: synthetic

<400> SEQUENCE: 98

Ser Val Thr Ala Ala Asp Thr
1               5

<210> SEQ ID NO 99
<211> LENGTH: 49
<212> TYPE: DNA
<213> ORGANISM: Artificial Sequence
<220> FEATURE:
<223> OTHER INFORMATION: synthetic primer

<400> SEQUENCE: 99
ctgcagctga actccgttac agccgcagac acagcaacat attactgcg              49

<210> SEQ ID NO 100
<211> LENGTH: 49
<212> TYPE: DNA
<213> ORGANISM: Artificial Sequence
<220> FEATURE:
<223> OTHER INFORMATION: synthetic primer

<400> SEQUENCE: 100
cgcagtaata tgttgctgtg tctgcggctg taacggagtt cagctgcag              49

<210> SEQ ID NO 101
<211> LENGTH: 12
<212> TYPE: PRT
<213> ORGANISM: Artificial Sequence
<220> FEATURE:
<223> OTHER INFORMATION: synthetic

<400> SEQUENCE: 101

Thr Arg Asp Thr Ser Lys Ser Gln Phe Phe Leu Gln
1               5                   10

<210> SEQ ID NO 102
<211> LENGTH: 12
<212> TYPE: PRT
<213> ORGANISM: Artificial Sequence
<220> FEATURE:
<223> OTHER INFORMATION: synthetic
```

<400> SEQUENCE: 102

Ser Arg Asp Thr Ser Lys Asn Gln Phe Phe Leu Lys
1               5                   10

<210> SEQ ID NO 103
<211> LENGTH: 49
<212> TYPE: DNA
<213> ORGANISM: Artificial Sequence
<220> FEATURE:
<223> OTHER INFORMATION: synthetic primer

<400> SEQUENCE: 103
ggtcaccatc gaagccagtc acccagtgaa gggggcttcc atccactcc         49

<210> SEQ ID NO 104
<211> LENGTH: 45
<212> TYPE: DNA
<213> ORGANISM: Artificial Sequence
<220> FEATURE:
<223> OTHER INFORMATION: synthetic primer

<400> SEQUENCE: 104
gattcttcga cgtgtccctt gagattgtga tccggctttt cagag             45

<210> SEQ ID NO 105
<211> LENGTH: 55
<212> TYPE: DNA
<213> ORGANISM: Artificial Sequence
<220> FEATURE:
<223> OTHER INFORMATION: synthetic primer

<400> SEQUENCE: 105
caagggacac gtcgaagaat cagttcttcc tgaaactgaa ctccgttaca gccgc   55

<210> SEQ ID NO 106
<211> LENGTH: 44
<212> TYPE: DNA
<213> ORGANISM: Artificial Sequence
<220> FEATURE:
<223> OTHER INFORMATION: synthetic primer

<400> SEQUENCE: 106
ccaagatctg gccggccacg gtgtgccatc ttaccgctgc tcac              44

<210> SEQ ID NO 107
<211> LENGTH: 6
<212> TYPE: PRT
<213> ORGANISM: Artificial Sequence
<220> FEATURE:
<223> OTHER INFORMATION: synthetic

<400> SEQUENCE: 107

Ser Ser Leu Glu Pro Glu
1               5

<210> SEQ ID NO 108
<211> LENGTH: 6
<212> TYPE: PRT
<213> ORGANISM: Artificial Sequence
<220> FEATURE:
<223> OTHER INFORMATION: synthetic

<400> SEQUENCE: 108

Ser Ser Leu Gln Pro Glu
1               5

<210> SEQ ID NO 109
<211> LENGTH: 45
<212> TYPE: DNA
<213> ORGANISM: Artificial Sequence
<220> FEATURE:
<223> OTHER INFORMATION: synthetic primer

<400> SEQUENCE: 109
cgaagccagt caaggggggcg daccgcttcc atccactcct gtgtc                45

<210> SEQ ID NO 110
<211> LENGTH: 34
<212> TYPE: DNA
<213> ORGANISM: Artificial Sequence
<220> FEATURE:
<223> OTHER INFORMATION: synthetic primer

<400> SEQUENCE: 110
ctctggttgt aagctagaga tggtcagtgt atag                34

<210> SEQ ID NO 111
<211> LENGTH: 45
<212> TYPE: DNA
<213> ORGANISM: Artificial Sequence
<220> FEATURE:
<223> OTHER INFORMATION: synthetic primer

<400> SEQUENCE: 111
ccatctctag cttacaacca gaggactttg ccacatacta ctgcg                45

<210> SEQ ID NO 112
<211> LENGTH: 50
<212> TYPE: DNA
<213> ORGANISM: Artificial Sequence
<220> FEATURE:
<223> OTHER INFORMATION: synthetic primer

<400> SEQUENCE: 112
ccaagatctt taattaacgg accgctactc acgtttgatt tccagttttg                50

<210> SEQ ID NO 113
<211> LENGTH: 8
<212> TYPE: PRT
<213> ORGANISM: Artificial Sequence
<220> FEATURE:
<223> OTHER INFORMATION: synthetic

<400> SEQUENCE: 113

Val Tyr Ala Cys Glu Val Thr His
1               5

<210> SEQ ID NO 114
<211> LENGTH: 21
<212> TYPE: DNA
<213> ORGANISM: Artificial Sequence
<220> FEATURE:
<223> OTHER INFORMATION: synthetic primer

<400> SEQUENCE: 114
ggcggcacaa aactggaaat c                21

<210> SEQ ID NO 115
<211> LENGTH: 59
<212> TYPE: DNA
<213> ORGANISM: Artificial Sequence
<220> FEATURE:

<223> OTHER INFORMATION: synthetic primer

<400> SEQUENCE: 115
gatgagttac ttcacaggca tatactttgt gcttttcata atcagctttt gacagtgtc    59

<210> SEQ ID NO 116
<211> LENGTH: 26
<212> TYPE: DNA
<213> ORGANISM: Artificial Sequence
<220> FEATURE:
<223> OTHER INFORMATION: synthetic primer

<400> SEQUENCE: 116
agtatatgcc tgtgaagtaa ctcatc    26

<210> SEQ ID NO 117
<211> LENGTH: 17
<212> TYPE: DNA
<213> ORGANISM: Artificial Sequence
<220> FEATURE:
<223> OTHER INFORMATION: synthetic primer

<400> SEQUENCE: 117
gccacgatgc gtccggc    17

<210> SEQ ID NO 118
<211> LENGTH: 23
<212> TYPE: DNA
<213> ORGANISM: Artificial Sequence
<220> FEATURE:
<223> OTHER INFORMATION: synthetic primer

<400> SEQUENCE: 118
gcacttgatg taattctcct tgg    23

<210> SEQ ID NO 119
<211> LENGTH: 19
<212> TYPE: DNA
<213> ORGANISM: Artificial Sequence
<220> FEATURE:
<223> OTHER INFORMATION: synthetic primer

<400> SEQUENCE: 119
gaagtagtcc ttgaccagg    19

<210> SEQ ID NO 120
<211> LENGTH: 23
<212> TYPE: DNA
<213> ORGANISM: Artificial Sequence
<220> FEATURE:
<223> OTHER INFORMATION: synthetic primer

<400> SEQUENCE: 120
gaagatgaag acagatggtg cag    23

<210> SEQ ID NO 121
<211> LENGTH: 20
<212> TYPE: DNA
<213> ORGANISM: Artificial Sequence
<220> FEATURE:
<223> OTHER INFORMATION: synthetic primer

<400> SEQUENCE: 121
cggtggaggg cagtgtagtc    20

```
<210> SEQ ID NO 122
<211> LENGTH: 21
<212> TYPE: DNA
<213> ORGANISM: Artificial Sequence
<220> FEATURE:
<223> OTHER INFORMATION: synthetic primer

<400> SEQUENCE: 122
gtgatgctat tgctttattt g                                              21

<210> SEQ ID NO 123
<211> LENGTH: 21
<212> TYPE: DNA
<213> ORGANISM: Artificial Sequence
<220> FEATURE:
<223> OTHER INFORMATION: synthetic primer

<400> SEQUENCE: 123
catacctacc agttctgcgc c                                              21

<210> SEQ ID NO 124
<211> LENGTH: 21
<212> TYPE: DNA
<213> ORGANISM: Artificial Sequence
<220> FEATURE:
<223> OTHER INFORMATION: synthetic primer

<400> SEQUENCE: 124
ccatcctgtt tgcttctttc c                                              21

<210> SEQ ID NO 125
<211> LENGTH: 17
<212> TYPE: DNA
<213> ORGANISM: Artificial Sequence
<220> FEATURE:
<223> OTHER INFORMATION: synthetic primer

<400> SEQUENCE: 125
gacagggctg ctgagtc                                                   17

<210> SEQ ID NO 126
<211> LENGTH: 22
<212> TYPE: DNA
<213> ORGANISM: Artificial Sequence
<220> FEATURE:
<223> OTHER INFORMATION: synthetic primer

<400> SEQUENCE: 126
gtgcagctcc aagagagtgg ac                                             22

<210> SEQ ID NO 127
<211> LENGTH: 20
<212> TYPE: DNA
<213> ORGANISM: Artificial Sequence
<220> FEATURE:
<223> OTHER INFORMATION: synthetic primer

<400> SEQUENCE: 127
cagagtccat ccagcatgtc                                                20

<210> SEQ ID NO 128
<211> LENGTH: 363
<212> TYPE: DNA
<213> ORGANISM: Mus musculus

<400> SEQUENCE: 128
```

```
ttagtcaagc tgcaggagtc tggacctagc ctggtgaaac cttctcagtc tctgtccctc    60
acctgcactg tcactggcta ctcaatcacc agtgactatg cctggaactg gatccggcag   120
tttccaggaa acaaactgga gtggatgggc tacataagtt acagtgctaa cactaggtac   180
aacccatctc tcaaaagtcg aatctctatc actcgagaca catccaagaa ccaattcttc   240
ctgcagttga attctgtgac tactgaggac acagccacat attactgtgc aacggcggga   300
cgcgggtttc cttactgggg ccaagggact ctggtcactg tctctgcagc caaaacgaca   360
ccc                                                                 363
```

<210> SEQ ID NO 129
<211> LENGTH: 116
<212> TYPE: PRT
<213> ORGANISM: Mus musculus

<400> SEQUENCE: 129

```
Leu Val Lys Leu Gln Glu Ser Gly Pro Ser Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Ala Asn Thr Arg Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Thr Ala Gly Arg Gly Phe Pro Tyr Trp Gly Gln Gly Thr Leu Val
            100                 105                 110

Thr Val Ser Ala
        115
```

<210> SEQ ID NO 130
<211> LENGTH: 6
<212> TYPE: PRT
<213> ORGANISM: Mus musculus

<400> SEQUENCE: 130

```
Ser Asp Tyr Ala Trp Asn
1               5
```

<210> SEQ ID NO 131
<211> LENGTH: 16
<212> TYPE: PRT
<213> ORGANISM: Mus musculus

<400> SEQUENCE: 131

```
Tyr Ile Ser Tyr Ser Ala Asn Thr Arg Tyr Asn Pro Ser Leu Lys Ser
1               5                   10                  15
```

<210> SEQ ID NO 132
<211> LENGTH: 9
<212> TYPE: PRT
<213> ORGANISM: Mus musculus

<400> SEQUENCE: 132

```
Ala Thr Ala Gly Arg Gly Phe Pro Tyr
1               5
```

<210> SEQ ID NO 133
<211> LENGTH: 324
<212> TYPE: DNA
<213> ORGANISM: Mus musculus

<400> SEQUENCE: 133

```
gacattgtgc tgacccagtc tccatcctcc atgtctctat ctctgggaga cacagtcagt    60
atcacttgcc attcaagtca ggacattaac agtaatatag gtggttgca gcagaaacca   120
gggaaatcat ttaagggcct gatctatcat ggaaccaact tggacgatgg agttccatca   180
aggttcagtg gcagtggatc tggagccgat tattctctca ccatcagcag cctggaatct   240
gaagattttg tagactatta ctgtgtacag tatggtcagt ttccgtggac gttcggtgga   300
ggcaccaagc tggaaatcaa acgg                                          324
```

<210> SEQ ID NO 134
<211> LENGTH: 107
<212> TYPE: PRT
<213> ORGANISM: Mus musculus

<400> SEQUENCE: 134

```
Asp Ile Val Leu Thr Gln Ser Pro Ser Ser Met Ser Leu Ser Leu Gly
1               5                   10                  15
Asp Thr Val Ser Ile Thr Cys His Ser Ser Gln Asp Ile Ser Asn Ile
            20                  25                  30
Gly Trp Leu Gln Gln Lys Pro Gly Lys Ser Phe Lys Gly Leu Ile Tyr
        35                  40                  45
His Gly Thr Asn Leu Glu Asp Gly Val Pro Ser Arg Phe Ser Gly Ser
    50                  55                  60
Gly Ser Gly Ala Asp Tyr Ser Leu Thr Ile Ser Ser Leu Glu Ser Glu
65                  70                  75                  80
Asp Phe Val Asp Tyr Tyr Cys Val Gln Tyr Gly Gln Phe Pro Trp Thr
                85                  90                  95
Phe Gly Gly Gly Thr Lys Leu Glu Ile Lys Arg
            100                 105
```

<210> SEQ ID NO 135
<211> LENGTH: 11
<212> TYPE: PRT
<213> ORGANISM: Mus musculus

<400> SEQUENCE: 135

```
His Ser Ser Gln Asp Ile Ser Ser Asn Ile Gly
1               5                   10
```

<210> SEQ ID NO 136
<211> LENGTH: 7
<212> TYPE: PRT
<213> ORGANISM: Mus musculus

<400> SEQUENCE: 136

```
His Gly Thr Asn Leu Glu Asp
1               5
```

<210> SEQ ID NO 137
<211> LENGTH: 10
<212> TYPE: PRT
<213> ORGANISM: Mus musculus

<400> SEQUENCE: 137

```
Cys Val Gln Tyr Gly Gln Phe Pro Trp Thr
1               5                   10
```

<210> SEQ ID NO 138
<211> LENGTH: 16
<212> TYPE: PRT
<213> ORGANISM: Artificial Sequence
<220> FEATURE:
<223> OTHER INFORMATION: synthetic

<400> SEQUENCE: 138

```
Cys Gly Ala Asp Ser Tyr Glu Met Glu Asp Gly Val Arg Lys Cys
1               5                   10                  15
```

<210> SEQ ID NO 139
<211> LENGTH: 7
<212> TYPE: PRT
<213> ORGANISM: Mus musculus

<400> SEQUENCE: 139

```
His Gly Thr Asn Leu Asp Asp
1               5
```

<210> SEQ ID NO 140
<211> LENGTH: 7
<212> TYPE: PRT
<213> ORGANISM: Mus musculus

<400> SEQUENCE: 140

```
His Gly Thr Asn Leu Asp Asp
1               5
```

<210> SEQ ID NO 141
<211> LENGTH: 7
<212> TYPE: PRT
<213> ORGANISM: Mus musculus

<400> SEQUENCE: 141

```
His Gly Thr Asn Leu Glu Asp
1               5
```

<210> SEQ ID NO 142
<211> LENGTH: 7
<212> TYPE: PRT
<213> ORGANISM: Mus musculus

<400> SEQUENCE: 142

```
His Gly Thr Asn Leu Asp Asp
1               5
```

<210> SEQ ID NO 143
<211> LENGTH: 11
<212> TYPE: PRT
<213> ORGANISM: Mus musculus

<400> SEQUENCE: 143

```
Gly Tyr Ser Ile Thr Ser Asp Phe Ala Trp Asn
1               5                   10
```

<210> SEQ ID NO 144
<211> LENGTH: 17
<212> TYPE: PRT
<213> ORGANISM: Mus musculus

<400> SEQUENCE: 144

Gly Tyr Ile Ser Tyr Ser Gly Asn Thr Arg Tyr Asn Pro Ser Leu Lys
1               5                   10                  15

Ser

<210> SEQ ID NO 145
<211> LENGTH: 11
<212> TYPE: PRT
<213> ORGANISM: Mus musculus

<400> SEQUENCE: 145

Gly Tyr Ser Ile Thr Ser Asp Tyr Ala Trp Asn
1               5                   10

<210> SEQ ID NO 146
<211> LENGTH: 17
<212> TYPE: PRT
<213> ORGANISM: Artificial Sequence
<220> FEATURE:
<223> OTHER INFORMATION: synthetic

<400> SEQUENCE: 146

Gly Tyr Ile Ser Tyr Ser Ala Asn Thr Arg Tyr Asn Pro Ser Leu Lys
1               5                   10                  15

Ser

<210> SEQ ID NO 147
<211> LENGTH: 11
<212> TYPE: PRT
<213> ORGANISM: Mus musculus

<400> SEQUENCE: 147

Gly Tyr Ser Ile Thr Ser Asp Tyr Ala Trp Asn
1               5                   10

<210> SEQ ID NO 148
<211> LENGTH: 17
<212> TYPE: PRT
<213> ORGANISM: Mus musculus

<400> SEQUENCE: 148

Gly Tyr Ile Ser Tyr Ser Ala Asn Thr Arg Tyr Asn Pro Ser Leu Lys
1               5                   10                  15

Ser

<210> SEQ ID NO 149
<211> LENGTH: 11
<212> TYPE: PRT
<213> ORGANISM: Mus musculus

<400> SEQUENCE: 149

Gly Tyr Ser Ile Thr Ser Asp Tyr Ala Trp Asn
1               5                   10

<210> SEQ ID NO 150
<211> LENGTH: 17
<212> TYPE: PRT
<213> ORGANISM: Mus musculus

<400> SEQUENCE: 150

Gly Tyr Ile Ser Tyr Ser Gly Asn Thr Arg Tyr Asn Pro Ser Leu Arg
1               5                   10                  15

Ser

```
<210> SEQ ID NO 151
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Xaa is an amino acid residue having an
      uncharged polar R group

<400> SEQUENCE: 151

His Ser Ser Gln Asp Ile Xaa Ser Asn Ile Gly
1               5                   10

<210> SEQ ID NO 152
<211> LENGTH: 7
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (6)..(6)
<223> OTHER INFORMATION: Xaa is an amino acid residue having a
      charged polar R group

<400> SEQUENCE: 152

His Gly Thr Asn Leu Xaa Asp
1               5

<210> SEQ ID NO 153
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: Xaa is selected from the group consisting of
      Ala, Gly, and an amino acid residue which is conservatively
      substituted for Ala or Gly

<400> SEQUENCE: 153

Val Gln Tyr Xaa Gln Phe Pro Trp Thr
1               5

<210> SEQ ID NO 154
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: Xaa is selected from the group consisting of
      Phe, Tyr, and an amino acid residue which is conservatively
      substituted for Phe or Tyr

<400> SEQUENCE: 154

Ser Asp Xaa Ala Trp Asn
1               5

<210> SEQ ID NO 155
<211> LENGTH: 16
<212> TYPE: PRT
<213> ORGANISM: Artificial Sequence
```

```
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: Xaa is an amino acid residue having an
      uncharged polar R group

<400> SEQUENCE: 155

Tyr Ile Ser Tyr Ser Gly Asn Thr Arg Tyr Xaa Pro Ser Leu Lys Ser
1               5                   10                  15

<210> SEQ ID NO 156
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (6)..(6)
<223> OTHER INFORMATION: Xaa is selected from the group consisting of
      Gly, Ala, and an amino acid residue which is conservatively
      substituted for Gly or Ala
<220> FEATURE:
<221> NAME/KEY: MISC_FEATURE
<222> LOCATION: (6)..(6)
<223> OTHER INFORMATIO: Xaa is selected from the group consisting of
      Gly, Ala, and an amino acid residue which is conservatively
      substituted for Gly or Ala

<400> SEQUENCE: 156

Tyr Ile Ser Tyr Ser Xaa Asn Thr Arg Tyr Asn Pro Ser Leu Lys Ser
1               5                   10                  15

<210> SEQ ID NO 157
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (15)..(15)
<223> OTHER INFORMATION: Xaa is a basic amino acid residue

<400> SEQUENCE: 157

Tyr Ile Ser Tyr Ser Gly Asn Thr Arg Tyr Asn Pro Ser Leu Xaa Ser
1               5                   10                  15

<210> SEQ ID NO 158
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is selected from the group consisting of
      Val, Ala, and an amino acid residue which is conservatively
      substituted for Val or Ala

<400> SEQUENCE: 158

Xaa Thr Ala Gly Arg Gly Phe Pro Tyr
1               5

<210> SEQ ID NO 159
<211> LENGTH: 16
<212> TYPE: PRT
<213> ORGANISM: Artificial Sequence
```

```
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: Xaa is an amino acid residue having an
      uncharged polar R group

<400> SEQUENCE: 159

Tyr Ile Ser Tyr Ser Gly Asn Thr Arg Tyr Xaa Pro Ser Leu Lys Ser
1               5                   10                  15

<210> SEQ ID NO 160
<211> LENGTH: 128
<212> TYPE: PRT
<213> ORGANISM: Artificial Sequence
<220> FEATURE:
<223> OTHER INFORMATION: synthetic vector

<400> SEQUENCE: 160

Met Val Ser Thr Ala Gln Phe Leu Ala Phe Leu Leu Leu Trp Phe Pro
1               5                   10                  15

Gly Ala Arg Cys Asp Ile Leu Met Thr Gln Ser Pro Ser Ser Met Ser
                20                  25                  30

Val Ser Leu Gly Asp Thr Val Ser Ile Thr Cys His Ser Ser Gln Asp
            35                  40                  45

Ile Asn Ser Asn Ile Gly Trp Leu Gln Gln Arg Pro Gly Lys Ser Phe
        50                  55                  60

Lys Gly Leu Ile Tyr His Gly Thr Asn Leu Asp Asp Glu Val Pro Ser
65                  70                  75                  80

Arg Phe Ser Gly Ser Gly Ser Gly Ala Asp Tyr Ser Leu Thr Ile Ser
                85                  90                  95

Ser Leu Glu Ser Glu Asp Phe Ala Asp Tyr Tyr Cys Val Gln His Ala
            100                 105                 110

Gln Phe Pro Trp Thr Phe Gly Gly Thr Lys Leu Glu Ile Lys Arg
        115                 120                 125

<210> SEQ ID NO 161
<211> LENGTH: 134
<212> TYPE: PRT
<213> ORGANISM: Artificial Sequence
<220> FEATURE:
<223> OTHER INFORMATION: synthetic vector

<400> SEQUENCE: 161

Met Arg Val Leu Ile Leu Leu Trp Leu Phe Thr Ala Phe Pro Gly Val
1               5                   10                  15

Leu Ser Asp Val Gln Leu Gln Glu Ser Gly Pro Ser Leu Val Lys Pro
                20                  25                  30

Ser Gln Thr Leu Ser Leu Thr Cys Thr Val Thr Gly Tyr Ser Ile Thr
            35                  40                  45

Ser Asp Phe Ala Trp Asn Trp Ile Arg Gln Phe Pro Gly Asn Lys Leu
        50                  55                  60

Glu Trp Met Gly Tyr Ile Ser Tyr Ser Gly Asn Thr Arg Tyr Asn Pro
65                  70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Ile Glu Asp Thr Ala Thr Tyr
            100                 105                 110

Tyr Cys Val Thr Ala Gly Arg Gly Phe Pro Tyr Trp Gly Gln Gly Thr
```

```
            115                 120                 125
Leu Val Thr Val Ser Ala
    130

<210> SEQ ID NO 162
<211> LENGTH: 11891
<212> TYPE: DNA
<213> ORGANISM: Artificial Sequence
<220> FEATURE:
<223> OTHER INFORMATION: plasmid

<400> SEQUENCE: 162
ttcgaacggc ggtggtacct aacctggacc gcgtaagaga aagaccatcg tcggcggtgt      60
ccattccccg acggtttagg gtcactcctc cttccctagc ttccagtggt agcttcggtc     120
agtgggtcac ttcccccgaa ggtaggtgag gacacagaag agatgtccac aggtgtcggt     180
ccacgtcgag gttctctcac ctggacccga acagttcggc tcagtttgaa acagggattg     240
tacatgacac aggcctatga gatagagtag tctaaaacgc accttaacct attccgtcgg     300
tggtcccttt ccaaatctta cctacccgat gtatagtatg agacccttgt ggtctatagt     360
tggaagagac ttttcggcct agtgttagag ttccctgtgc agcttcttag tcaagaagga     420
ctttgacttg aggcaatgtc ggcgtctgtg tcgttgtata atgacgcatt ggcgaccgtc     480
tccgaagggg ataaccnctg tcccgtggga tcactgtcac tcgtcgccat tctaccgtgt     540
ggcaccggcc ggagacgcgg acccgggtcg agacagggtg tggcgccagt gtaccgtgga     600
aaagagaagg tcgaggtgg ttcccggggt cgcacaaggg ggaccggggg tcgtcgttct     660
cgtggtcgcc gccgtgtcgg cgggacccga cggaccactt cctgatgaag gggctcgggc     720
actggcactc gaccttgtcg cctcgggact ggaggccgca cgtgtggaag gggcggcacg     780
acgtctcgtc gccggacatg tcggactcgt cgcaccactg gcacgggtcg tcgtcggacc     840
cgtgggtctg gatgtagacg ttgcacttgg tgttcgggtc gttgtggttc cacctgttct     900
tccacctcgg gttctcgacg ctgttctggg tgtggacggg gggacgggt cggggtctcg     960 acgacccgcc tgggaggcac aaggacaagg gggggttcgg gttcctgtgg gactactagt    1020
cgtcctgggg gctccactgg acgcaccacc acctgcactc ggtgctcctg ggtctccact    1080
tcaagttaac catacacctg ccgcacctcc acgtgttgcg gttctggttc gggtctcttc    1140
tcgtcatgtt gtcgtggatg tcccaccaca ggcacgactg gcacgacgtg gtcctgaccg    1200
acttgccgtt ccttatgttt acgttccaga ggttgttccg ggacggtcgg gggtagcttt    1260
tctggtagtc gttccggttc ccggtcggtg ccctcggggt ccacatgtgg gacgggggga    1320
gggccctgct cacgtggttc ttggtccaca gggactggac agaccacttc ccgaagatgg    1380
ggtcgctgta gcggcacctc accctctcgt tgccggtcgg gctcttgttg atgttctggt    1440 ggggggggtca cgacctgtcg ctgccgtcga agaaggacat gtcgttcgac tggcacctgt    1500
tctcgtccac cgtcgtcccg ttgcacaagt cgacgtcgca ctacgtgctc cgggacgtgt    1560
tggtgatgtg ggtcttctcg gactcggaca ggggccgtt cactactgct gcgccggcac    1620
gcctgctggc ttaagtaact agtattagtc ggtatggtgt aaacatctcc aaaatgaacg    1680
aaattttttg gagggtgtgg aggggggactt ggactttgta ttttacttac gttaacaaca    1740
acaattgaac aaataacgtc gaatattacc aatgtttatt tcgttatcgt agtgtttaaa    1800
gtgtttattt cgtaaaaaaa gtgacgtaag atcaacacca aacaggtttg agtagttaca    1860
tagaatagta cagaccgccg gcggctataa acttttatac cgtataactt ttacagcggc    1920
```

```
tacactcaaa gacacattga ctatagcggt aaaaaggttt tcactaaaaa cccgtatgcg   1980
ctatagaccg ctatcgcgaa tatagcaaat gccccctacc gctatctgct gaaaccactg   2040
aacccgctaa gacacacagc gtttatagcg tcaaagctat atccactgtc tgctatactc   2100
cgatatagcg gctatctccg ctgtagttcg accgtgtacc ggttacgtat agctagatat   2160
gtaacttagt tataaccggt aatcggtata ataagtaacc aatatatcgt atttagttat   2220
aaccgataac cggtaacgta tgcaacatag gtatagtatt atacatgtaa atataaccga   2280
gtacaggttg taatggcggt acaactgtaa ctaataactg atcaataatt atcattagtt   2340
aatgccccag taatcaagta tcgggtatat acctcaaggc gcaatgtatt gaatgccatt   2400
taccgggcgg accgactggc gggttgctgg gggcgggtaa ctgcagttat tactgcatac   2460
aagggtatca ttgcggttat ccctgaaagg taactgcagt tacccacctc ataaatgcca   2520
tttgacgggt gaaccgtcat gtagttcaca tagtatacgg ttcatgcggg ggataactgc   2580
agttactgcc atttaccggg cggaccgtaa tacgggtcat gtactggaat accctgaaag   2640
gatgaaccgt catgtagatg cataatcagt agcgataatg gtaccactac gccaaaaccg   2700
tcatgtagtt acccgcacct atcgccaaac tgagtgcccc taaaggttca gaggtggggt   2760
aactgcagtt accctcaaac aaaaccgtgg ttttagttgc cctgaaaggt ttacagcat   2820
tgttgaggcg gggtaactgc gtttacccgc catccgcaca tgccaccctc cagatatatt   2880
cgtctcgagc aaatcacttg gcagtctagc ggacctctgc ggtaggtgcg acaaaactgg   2940
aggtatcttc tgtggccctg gctaggtcgg aggcgccggc ccttgccacg taaccttgcg   3000
cctaaggggc acggttctca ctgcattcat ggcggatatc tcagatatcc gggtgggga   3060
accgaagaat acgtacgata tgacaaaaac cgaaccccag atatgtgggg gcgaaggagt   3120
acaatatcca ctaccatatc gaatcggata tccacaccca ataactggta ataactggtg   3180
aggggataac cactgctatg aaaggtaatg attaggtatt gtaccgagaa acggtgttga   3240
gagaaataac cgatatacgg ttatgtgaca ggaagtctct gactgtgcct gagacataaa   3300
aatgtcctac cccagagtaa ataataaatg tttaagtgta tatgttgtgg tggcaggggt   3360
cacgggcgtc aaaaataatt tgtattgcac cctagaggtg cgcttagagc ccatgcacaa   3420
ggcctgtacc cgagaagagg ccatcgccgc ctcgaagatg taggctcggg acgagggtac   3480
ggaggtcgct gagtaccagc gagccgtcga ggaacgagga ttgtcacctc cggtctgaat   3540
ccgtgtcgtg ctacgggtgg tggtggtcac acggcgtgtt ccggcaccgc catcccatac   3600
acagactttt actcgagccc ctcgcccgaa cgtggcgact gcgtaaacct tctgaattcc   3660
gtcgccgtct tcttctacgt ccgtcgactc aacaacacaa gactattctc agtctccatt   3720
gagggcaacg ccacgacaat tgccacctcc cgtcacatca gactcgtcat gagcaacgac   3780
ggcgcgcgcg gtggtctgta ttatcgactg tctgattgtc tgacaaggaa aggtacccag   3840
aaaagacgtc agtggcagga actgtgcttc gaacggcggt ggtacctaac ctgaacctct   3900
tatgacaaag aacatcgtcg gcgttgtcca ttccccgacg gtttagggtc actcctcctt   3960
ccctagcttc cactggtagc ttcggtcagt tcccccgcct ggcgaaggta ggtgaggaca   4020
cagaagagat gtccacaagt gtcactataa gtctactgag tctcaggtag gtcgtacagt   4080
cagaggcacc ctctatccca ctgctattgg acagtaagtt cggttctgta gttgaggtta   4140
taacctaccg aggttgtctt cggaccattc aggaagtttc ctgattagat agtgccttgt   4200
ttgaacctgc tgccgcacgg tagctctaaa agtcccagac cgtcgccctg gctgatatgt   4260
gactggtaga gatcgaatgt tggtctcctg aaacggtgta tgatgacgca ggtcatgcga   4320
```

```
gtcaagggga cctgtaagcc gccgccgtgt tttgaccttt agtttgcact catcgccagg    4380
caattaattt ctaggaagat ttgagactcc cccagcctac tgcaccggta acaatgaatt    4440
tgtggtagga caaacgaaga aaggagtcct tggcagcgtc gagggaggca caagtagaag    4500
gggggtaggc tgctcgttga cttcagtccg tgtcggaggc accacacgga ggaattattg    4560
aaaatgggtt ctctccggtt tcaggtcacc tttcacctgt tgcgtgatgt ctcgcccttg    4620
agagtccttt cgcactgtct cgtcctgagt tttctaagtt gtatgtcgga tagaagatgg    4680
gactgtgaca gttttcgact aatactttc gtgtttcata tacggacact tcattgagta    4740
gtccctgagt cgtcgggaca gtgattttca aaattatctc cgcttacgac tattcgccgg    4800
cacgcctgct ggcttaagta actagtatta gtcggtatgg tgtaaacatc tccaaaatga    4860
acgaaatttt ttggagggtg tggagggga cttggacttt gtattttact tacgttaaca    4920
acaacaattg aacaaataac gtcgaatatt accaatgttt atttcgttat cgtagtgttt    4980
aaagtgttta tttcgtaaaa aaagtgacgt aagatcaaca ccaaacaggt ttgagtagtt    5040
acatagaata gtacagacct aggagatgcg gcctgcgtag caccggccgt agtggccgcg    5100
gtgtccacgc caacgaccgc ggatatagcg gctgtagtgg ctaccccttc tagcccgagc    5160
ggtgaagccc gagtactcgc gaacaaagcc gcacccatac caccgtccgg ggcaccggcc    5220
ccctgacaac ccgcggtaga ggaacgtacg tggtaaggaa cgccgccgcc acgagttgcc    5280
ggagttggat gatgacccga cgaaggatta cgtcctcagc gtattccctc tcgcagctgg    5340
agcccggcgc aacgaccgca aaaaggtatc cgaggcgggg ggactgctcg tagtgttttt    5400
agctgcgagt tcagtctcca ccgctttggg ctgtcctgat atttctatgg tccgcaaagg    5460
gggaccttcg agggagcacg cgagaggaca aggctgggac ggcgaatggc ctatggacag    5520
gcggaaagag ggaagcccct tcgcaccgcga aagagtatcg agtgcgacat ccatagagtc    5580 aagcccacatc cagcaagcga ggttcgaccc gacacacgtg cttgggggc aagtcgggct    5640 ggcgacgcgg aataggccat tgatagcaga actcaggttg ggccattctg tgctgaatag    5700
cggtgaccgt cgtcggtgac cattgtccta atcgtctcgc tccatacatc cgccacgatg    5760
tctcaagaac ttcaccaccg gattgatgcc gatgtgatct tcttgtcata aaccatagac    5820
gcgagacgac ttcggtcaat ggaagccttt ttctcaacca tcgagaacta ggccgtttgt    5880
ttggtggcga ccatcgccac caaaaaaaca aacgttcgtc gtctaatgcg cgtctttttt    5940
tcctagagtt cttctaggaa actagaaaag atgccccaga ctgcgagtca ccttgctttt    6000
gagtgcaatt ccctaaaacc agtactctaa tagttttcc tagaagtgga tctaggaaaa    6060 tttaatttt acttcaaaat ttagttagat ttcatatata ctcatttgaa ccagactgtc    6120
aatggttacg aattagtcac tccgtggata gagtcgctag acagataaag caagtaggta    6180
tcaacggact gaggggcagc acatctattg atgctatgcc ctcccgaatg gtagaccggg    6240
gtcacgacgt tactatggcg ctctgggtgc gagtggccga ggtctaaata gtcgttattt    6300
ggtcggtcgg ccttcccggc tcgcgtcttc accaggacgt tgaaataggc ggaggtaggt    6360
cagataatta acaacggccc ttcgatctca ttcatcaagc ggtcaattat caaacgcgtt    6420
gcaacaacgg taacgatgtc cgtagcacca cagtgcgagc agcaaaccat accgaagtaa    6480
gtcgaggcca agggttgcta gttccgctca atgtactagg gggtacaaca cgttttttcg    6540
ccaatcgagg aagccaggag gctagcaaca gtcttcattc aaccggcgtc acaatagtga    6600
gtaccaatac cgtcgtgacg tattaagaga atgacagtac ggtaggcatt ctacgaaaag    6660
```

```
acactgacca ctcatgagtt ggttcagtaa gactcttatc acatacgccg ctggctcaac    6720
gagaacgggc cgcagttatg ccctattatg gcgcggtgta tcgtcttgaa attttcacga    6780
gtagtaacct tttgcaagaa gccccgcttt tgagagttcc tagaatggcg acaactctag    6840
gtcaagctac attgggtgag cacgtgggtt gactagaagt cgtagaaaat gaaagtggtc    6900
gcaaagaccc actcgttttt gtccttccgt tttacggcgt tttttccctt attcccgctg    6960
tgcctttaca acttatgagt atgagaagga aaaagttata ataacttcgt aaatagtccc    7020
aataacagag tactcgccta tgtataaact tacataaatc ttttttatttg tttatcccca    7080 aggcgcgtgt aaagggggctt tcacggtgg actgcagatt ctttggtaat aatagtactg    7140
taattggata ttttttatccg catagtgctc cgggactacc gagaaacgcc gtgggtagca    7200
agcattacaa ggcaccgtgg ctcctgttgg gagttctctt ttacattagt gtgaccgagt    7260
ggaagcccac ccggaaagac gcaaatattc ctctgtgaaa tacaaattct tccaaccatt    7320
taaggaacgc cgaaaccgtc ggttcgatct aggccgacac cttacacaca gtcaatccca    7380
cacctttcag gggtccgagg ggtcgtccgt cttcatacgt ttcgtacgta gagttaatca    7440
gtcgttggtc cacacctttc aggggtccga ggggtcgtcc gtcttcatac gtttcgtacg    7500
tagagttaat cagtcgttgg tatcagggcg gggattgagg cgggtagggc ggggattgag    7560
gcgggtcaag gcgggtaaga ggcggggtac cgactgatta aaaaaaataa atacgtctcc    7620
ggctccggcg gagccggaga ctcgataagg tcttcatcac tcctccgaaa aaacctccgg    7680
atccgaaaac gttttttcgat cgaaccccgg tggcgagtct cgtggaaggt ggtaccggtg    7740
gagtcgttca agggtgaact tgtttttgta gttcgtttac atgaacacgg acggggtccc    7800
actctttcag gttcggtaca tatagaccca actaccatga cctcttcctg acgcgacgtt    7860
ttgggcgtgg gacctgacac tcgggttcac acatcttctc aatggactca ccttaaaact    7920
accgagatca tggaaagtca gactcccgag gttgtcactg tacatagagt cgggacaacg    7980
gtacaaagcc ctggggaagg cgtctctagg gttgttcgac cacaagacac ttcaaaagtt    8040
catgttggcc ttcggacgtc tctggttaaa ttccgtgagc acatttgcct attacctgta    8100
ccactcgttg gtcgtgggga ccaaaacctta ccttgtcctc atatgagact acccttgtct    8160
acccgtggga aaaccaaccg gaaggttacc gaaaggaccc ggggttccag gcataatgac    8220
accacacccg cgtctgtttc ggataccgtc cctatagcac ctccgagtga tggcgcggac    8280
gaacatacga ccccagttct aatgtccttg tttacgactc cagtacggac gggtcaccct    8340
tgaggtttat cctgggacac ttccttaggc gtaccctcta gtagagaccc accgggcaaa    8400
gtagaacgta gctcatacac ttctgaaacc ccattatcgt tggaaactgg ggttcgggta    8460
aggacccttg accttaccac gtccgacggt atggttgaaa tcgtggttcc ggtacgccct    8520
cctcttacca gacttcgtgt agctcctccg gtagctcttt gattcgttcg ccgtggccat    8580
ggtgtaagct cggatgctag ggttccccccc ggacctgtta cggcaccag actgacccaa    8640 ggtgctttgc aggttgtagt tgctgaaaag acgaccacag cggttagcgt cacggtcgta    8700
ggcgtaaggg gcctgacagc cggtcctctt cttttccaatg aaacttctgg cgccggggag    8760
acggttaaca ctggggaaac gtcactgtct tcggtagcag gcgtgtacgg aagagttact    8820
ctgaccgctg ctcgggaagg ttatgttttt gattaatctg aaactcacta gaactcggaa    8880
aggatcaagt agggtggggc ggggtctctc tagaaacact tccttggaat gaagacacca    8940
cactgtatta acctgtttga tggatgtctc taaatttcga gattccattt atattttaaa    9000
aattcacata ttacacaatt tgatgactaa gattaacaaa cacataaaat ctaaggttgg    9060
```

```
ataccttgac tacttaccct cgtcaccacc ttacggaaat tactccttttt ggacaaaacg    9120 agtcttcttt acggtagatc actactactc cgatgacgac tgagagttgt aagatgagga    9180
ggttttttct tctctttcca tcttctgggg ttcctgaaag aagtcttaa cgattcaaaa     9240 aactcagtac gacacaaatc attatcttga gaacgaacga aacgataaat gtggtgtttc    9300 cttttttcgac gtgacgatat gttcttttaa tacctttta taagacattg gaaatattca    9360
tccgtattgt caatattagt attgtatgac aaaaaagaat gaggtgtgtc cgtatctcac    9420
agacgataat tattgatacg agttttaac acatggaaat cgaaaaatta aacatttccc     9480
caattattcc ttataaacta catatcacgg aactgatctc tagtattagt cggtatggtg    9540
taaacatctc caaaatgaac gaaatttttt ggagggtgtg gaggggggact tggactttgt   9600 attttactta cgttaacaac aacaattgaa caaataacgt cgaatattac caatgtttat    9660
ttcgttatcg tagtgtttaa agtgtttatt tcgtaaaaaa agtgacgtaa gatcaacacc    9720
aaacaggttt gagtagttac atagaatagt acagacctag atcgaagcac agttcctgcc    9780
actgacgtca cttattattt tacacacaaa caggctttat gcgcaaaact ctaaagacag    9840
cggctgattt aagtacagcg cgctatcacc acaaatagcg gctatctcta ccgctataac    9900 cttttagct ataaacttt ataccgtata acttttacag cggctacact caaagacaca     9960
ttgactatag cggtaaaaag gttttcacta aaaacccgta tgcgctatag accgctatcg   10020
cgaatatagc aaatgccccc taccgctatc tgctgaaacc actgaacccg ctaagacaca   10080
cagcgtttat agcgtcaaag ctatatccac tgtctgctat actccgatat agcggctatc   10140
tccgctgtag ttcgaccgtg taccggttac gtatagctag atatgtaact tagttataac   10200
cggtaatcgg tataataagt aaccaatata tcgtatttag ttataaccga taaccggtaa   10260
cgtatgcaac ataggtatag tattatacat gtaaatataa ccgagtacag gttgtaatgg   10320
cggtacaact gtaactaata actgatcaat aattatcatt agttaatgcc ccagtaatca   10380
agtatcgggt atatacctca aggcgcaatg tattgaatgc catttaccgg gcggaccgac   10440 tggcggggttg ctgggggcgg gtaactgcag ttattactgc atacaagggt atcattgcgg   10500
ttatccctga aaggtaactg cagttaccca cctcataaat gccatttgac gggtgaaccg   10560
tcatgtagtt cacatagtat acggttcatg cgggggataa ctgcagttac tgccatttac   10620
cgggcggacc gtaatacggg tcatgtactg gaatacctg aaaggatgaa ccgtcatgta    10680
gatgcataat cagtagcgat aatggtacca ctacgccaaa accgtcatgt agttacccgc   10740
acctatcgcc aaactgagtg cccctaaagg ttcagaggtg gggtaactgc agttaccctc   10800
aaacaaaacc gtggttttag ttgccctgaa aggttttaca gcattgttga ggcggggtaa   10860
ctgcgtttac ccgccatccg cacatgccac cctccagata tattcgtctc gagcaaatca   10920
cttggcagtc tagcggacct ctgcggtagg tgcgacaaaa ctggaggtat cttctgtggc   10980
cctggctagg tcggaggcgc cggccccttgc cacgtaacct tgcgcctaag ggcacggtt   11040 ctcactgcat tcatggcgga tatctcagat atccgggtgg gggaaccgaa gaatacgtac   11100
gatatgacaa aaaccgaacc ccagatatgt ggggcgaag gagtacaata tccactacca   11160
tatcgaatcg gatatccaca cccaataact ggtaataact ggtgagggga taaccactgc   11220
tatgaaaggt aatgattagg tattgtaccg agaaacggtg ttgagagaaa taaccgatat   11280
acggttatgt gacaggaagt ctctgactgt gcctgagaca taaaaatgtc ctaccccaga   11340
gtaaataata aatgtttaag tgtatatgtt gtggtggcag gggtcacggg cgtcaaaaat   11400
```

```
aatttgtatt gcaccctaga ggtgcgctta gagcccatgc acaaggcctg tacccgagaa    11460
gaggccatcg ccgcctcgaa gatgtaggct cgggacgagg gtacggaggt cgctgagtac    11520
cagcgagccg tcgaggaacg aggattgtca cctccggtct gaatccgtgt cgtgctacgg    11580
gtggtggtgg tcacacggcg tgttccggca ccgccatccc atacacagac ttttactcga    11640
gcccctcgcc cgaacgtggc gactgcgtaa accttctgaa ttccgtcgcc gtcttcttct    11700
acgtccgtcg actcaacaac acaagactat tctcagtctc cattgagggc aacgccacga    11760
caattgccac ctcccgtcac atcagactcg tcatgagcaa cgacggcgcg cgcggtggtc    11820
tgtattatcg actgtctgat tgtctgacaa ggaaaggtac ccagaaaaga cgtcagtggc    11880
aggaactgtg c                                                         11891
```

<210> SEQ ID NO 163
<211> LENGTH: 19
<212> TYPE: PRT
<213> ORGANISM: Artificial Sequence
<220> FEATURE:
<223> OTHER INFORMATION: synthetic

<400> SEQUENCE: 163

Met Asp Trp Thr Trp Arg Ile Leu Phe Leu Val Ala Ala Ala Thr Gly
1               5                   10                  15

Val His Ser

<210> SEQ ID NO 164
<211> LENGTH: 116
<212> TYPE: PRT
<213> ORGANISM: Artificial Sequence
<220> FEATURE:
<223> OTHER INFORMATION: synthetic

<400> SEQUENCE: 164

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
                20                  25                  30

Phe Ala Trp Asn Trp Ile Arg Gln Pro Pro Gly Lys Gly Leu Glu Trp
            35                  40                  45

Met Gly Tyr Ile Ser Tyr Ser Gly Asn Thr Arg Tyr Gln Pro Ser Leu
        50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Gly Arg Gly Phe Pro Tyr Trp Gly Gln Gly Thr Leu Val
            100                 105                 110

Thr Val Ser Ser
        115

<210> SEQ ID NO 165
<211> LENGTH: 19
<212> TYPE: PRT
<213> ORGANISM: Artificial Sequence
<220> FEATURE:
<223> OTHER INFORMATION: synthetic

<400> SEQUENCE: 165

Met Asp Trp Thr Trp Arg Ile Leu Phe Leu Val Ala Ala Ala Thr Gly
1               5                   10                  15

Val His Ser

<210> SEQ ID NO 166
<211> LENGTH: 108
<212> TYPE: PRT
<213> ORGANISM: Artificial Sequence
<220> FEATURE:
<223> OTHER INFORMATION: synthetic

<400> SEQUENCE: 166

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Asp Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Leu Glu Ile Lys Arg
            100                 105

<210> SEQ ID NO 167
<211> LENGTH: 116
<212> TYPE: PRT
<213> ORGANISM: Mus musculus

<400> SEQUENCE: 167

Asp Val Gln Leu Gln Glu Ser Gly Pro Ser Leu Val Lys Pro Ser Gln
1               5                   10                  15

Thr Leu Ser Leu Thr Cys Thr Val Thr Gly Tyr Ser Ile Thr Ser Asp
            20                  25                  30

Phe Ala Trp Asn Trp Ile Arg Gln Phe Pro Gly Asn Lys Leu Glu Trp
        35                  40                  45

Met Gly Tyr Ile Ser Tyr Ser Gly Asn Thr Arg Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ile Glu Asp Thr Ala Thr Tyr Tyr Cys
                85                  90                  95

Val Thr Ala Gly Arg Gly Phe Pro Tyr Trp Gly Gln Gly Thr Leu Val
            100                 105                 110

Thr Val Ser Ala
        115

<210> SEQ ID NO 168
<211> LENGTH: 116
<212> TYPE: PRT
<213> ORGANISM: Artificial Sequence
<220> FEATURE:
<223> OTHER INFORMATION: synthetic

<400> SEQUENCE: 168

Gln Val Gln Leu Gln Glu Ser Gly Pro Gly Leu Val Lys Pro Ser Gln
1               5                   10                  15

```
Thr Leu Ser Leu Thr Cys Thr Val Ser Gly Tyr Ser Ile Ser Ser Asp
            20                  25                  30

Phe Ala Trp Asn Trp Ile Arg Gln Pro Pro Lys Gly Leu Glu Trp
        35                  40                  45

Met Gly Tyr Ile Ser Tyr Ser Gly Asn Thr Arg Tyr Gln Pro Ser Leu
    50                  55                  60

Lys Ser Arg Ile Thr Ile Thr Arg Asp Thr Ser Lys Ser Gln Phe Phe
65                  70                  75                  80

Leu Gln Leu Asn Ser Val Thr Ala Pro Asp Thr Ala Thr Tyr Tyr Cys
                85                  90                  95

Val Thr Ala Gly Arg Gly Phe Pro Tyr Trp Gly Gln Gly Thr Leu Val
            100                 105                 110

Thr Val Ser Ser
        115

<210> SEQ ID NO 169
<211> LENGTH: 80
<212> TYPE: DNA
<213> ORGANISM: Artificial Sequence
<220> FEATURE:
<223> OTHER INFORMATION: synthetic oligonucleotide

<400> SEQUENCE: 169
acctaacctg gaccgcgtaa gagaaagacc atcgtcggcg gtgtccattc cccgacggtt    60
tagggtcact cctccttccc                                               80

<210> SEQ ID NO 170
<211> LENGTH: 81
<212> TYPE: DNA
<213> ORGANISM: Artificial Sequence
<220> FEATURE:
<223> OTHER INFORMATION: synthetic oligonucleotide

<400> SEQUENCE: 170
atcccagtga ggaggaaggg atcgaaggtc accatcgaag ccagtcaagg gggcttccat    60
ccactcctgt gtcttctcta c                                             81

<210> SEQ ID NO 171
<211> LENGTH: 80
<212> TYPE: DNA
<213> ORGANISM: Artificial Sequence
<220> FEATURE:
<223> OTHER INFORMATION: synthetic oligonucleotide

<400> SEQUENCE: 171
ggtgaggaca cagaagagat gtccacaggt gtcggtccac gtcgaggttc tctcacctgg    60
acccgaacag ttcggctcag                                               80

<210> SEQ ID NO 172
<211> LENGTH: 85
<212> TYPE: DNA
<213> ORGANISM: Artificial Sequence
<220> FEATURE:
<223> OTHER INFORMATION: synthetic oligonucleotide

<400> SEQUENCE: 172
tgggcttgtc aagccgagtc aaactttgtc cctaacatgt actgtgtccg atactctat    60 ctcatcagat tttgcgtgga attgg                                         85

<210> SEQ ID NO 173
```

```
<210> SEQ ID NO 173
<211> LENGTH: 82
<212> TYPE: DNA
<213> ORGANISM: Artificial Sequence
<220> FEATURE:
<223> OTHER INFORMATION: synthetic oligonucleotide

<400> SEQUENCE: 173
gagtagtcta aaacgcacct taacctattc cgtcggtggt ccctttccaa atcttaccta        60
cccgatgtat agtatgagac cc                                                82

<210> SEQ ID NO 174
<211> LENGTH: 80
<212> TYPE: DNA
<213> ORGANISM: Artificial Sequence
<220> FEATURE:
<223> OTHER INFORMATION: synthetic oligonucleotide

<400> SEQUENCE: 174
gggctacata tcatactctg gaacaccag atatcaaccc tctctgaaaa gccggatcac         60
aatcactagg gacacgtcga                                                   80

<210> SEQ ID NO 175
<211> LENGTH: 83
<212> TYPE: DNA
<213> ORGANISM: Artificial Sequence
<220> FEATURE:
<223> OTHER INFORMATION: synthetic oligonucleotide

<400> SEQUENCE: 175
gttagtgatc cctgtgcagc ttctcggtca agaaggacgt cgacttgagg caatgtcggg        60
gtctgtgtcg ttgtataatg acg                                               83

<210> SEQ ID NO 176
<211> LENGTH: 82
<212> TYPE: DNA
<213> ORGANISM: Artificial Sequence
<220> FEATURE:
<223> OTHER INFORMATION: synthetic oligonucleotide

<400> SEQUENCE: 176
ccagacacag caacatatta ctgcgtaacc gctggcagag gcttccccta ttggggacag        60
ggcaccctag tgacagtgag ca                                                82

<210> SEQ ID NO 177
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 177
gtgggatcac tgtcactcgt cgccattcta cctaggcac                              39

<210> SEQ ID NO 178
<211> LENGTH: 1128
<212> TYPE: DNA
<213> ORGANISM: Artificial Sequence
<220> FEATURE:
<223> OTHER INFORMATION: synthetic

<400> SEQUENCE: 178
ttctaccgtg tggcaccggc cggagacgcg gacccgggtc gagacagggt gtggcgccag        60
tgtaccgtgg aaaagagaag gtcggaggtg gttcccgggg tcgcacaagg gggaccgggg      120
```

```
gtcgtcgttc tcgtggtcgc cgccgtgtcg gcgggacccg acggaccact tcctgatgaa    180
ggggctcggg cactggcact cgaccttgtc gcctcgggac tggaggccgc acgtgtggaa    240
ggggcggcac gacgtctcgt cgccggacat gtcggactcg tcgcaccact ggcacgggtc    300
gtcgtcggac ccgtgggtct ggatgtagac gttgcacttg tgttcgggt cgttgtggtt    360 ccacctgttc ttccacctcg ggttctcgac gctgttctgg gtgtggacgg ggggacggg    420 tcggggtctc gacgacccgc ctgggaggca aaggacaag ggggggttcg ggttcctgtg    480
ggactactag tcgtcctggg ggctccactg gacgcaccac cacctgcact cggtgctcct    540
gggtctccac ttcaagttaa ccatacacct gccgcacctc cacgtgttgc ggttctggtt    600
cgggtctctt ctcgtcatgt tgtcgtggat gtcccaccac aggcacgact ggcacgacgt    660
ggtcctgacc gacttgccgt tcctatgtt tacgttccag aggttgttcc gggacggtcg    720
ggggtagctt ttctggtagt cgttccggtt cccggtcggt gccctcgggg tccacatgtg    780
ggacgggggg agggccctgc tcacgtggtt cttggtccac agggactgga cagaccactt    840
cccgaagatg gggtcgctgt agcggcacct caccctctcg ttgccggtcg ggctcttgtt    900
gatgttctgg tgggggggtc acgacctgtc gctgccgtcg aagaaggaca tgtcgttcga    960
ctggcacctg ttctcgtcca ccgtcgtccc gttgcacaag tcgacgtcgc actacgtgct   1020
ccgggacgtg ttggtgatgt gggtcttctc ggactcggac aggggccgt tcactactgc   1080 tgcgccggca cgcctgctgg cttaagtaac tagtattagt cggtatgg              1128
```

<210> SEQ ID NO 179
<211> LENGTH: 107
<212> TYPE: PRT
<213> ORGANISM: Mus musculus

<400> SEQUENCE: 179

Asp Ile Leu Met Thr Gln Ser Pro Ser Met Ser Val Ser Leu Gly
1               5                   10                  15

Asp Thr Val Ser Ile Thr Cys His Ser Ser Gln Asp Ile Asn Ser Asn
            20                  25                  30

Ile Gly Trp Leu Gln Gln Arg Pro Gly Lys Ser Phe Lys Gly Leu Ile
        35                  40                  45

Tyr His Gly Thr Asn Leu Asp Asp Glu Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln His Ala Gln Phe Pro Trp
                85                  90                  95

Thr Phe Gly Gly Gly Thr Lys Leu Glu Ile Lys
            100                 105

<210> SEQ ID NO 180
<211> LENGTH: 107
<212> TYPE: PRT
<213> ORGANISM: Artificial Sequence
<220> FEATURE:
<223> OTHER INFORMATION: synthetic

<400> SEQUENCE: 180

Asp Ile Leu Met Thr Gln Ser Pro Ser Met Ser Val Ser Leu Gly
1               5                   10                  15

Asp Thr Val Ser Ile Thr Cys His Ser Ser Gln Asp Ile Asn Ser Asn
            20                  25                  30

```
Ile Gly Trp Leu Gln Gln Arg Pro Gly Lys Ser Phe Lys Gly Leu Ile
         35                  40                  45
Tyr His Gly Thr Asn Leu Asp Asp Glu Val Pro Ser Arg Phe Ser Gly
     50                  55                  60
Ser Gly Ser Gly Thr Asp Tyr Thr Leu Thr Ile Ser Ser Leu Glu Pro
65                  70                  75                  80
Glu Asp Phe Ala Thr Tyr Tyr Cys Val Gln Tyr Ala Gln Phe Pro Trp
                 85                  90                  95
Thr Phe Gly Gly Gly Thr Lys Leu Glu Ile Lys
            100                 105

<210> SEQ ID NO 181
<211> LENGTH: 80
<212> TYPE: DNA
<213> ORGANISM: Artificial Sequence
<220> FEATURE:
<223> OTHER INFORMATION: synthetic oligonucleotide

<400> SEQUENCE: 181
gaacggcggt ggtacctaac ctgaacctct tatgacaaag aacatcgtcg gcgttgtcca    60
ttccccgacg gtttagggtc                                                80

<210> SEQ ID NO 182
<211> LENGTH: 80
<212> TYPE: DNA
<213> ORGANISM: Artificial Sequence
<220> FEATURE:
<223> OTHER INFORMATION: synthetic oligonucleotide

<400> SEQUENCE: 182
aaggggctgc caaatcccag tgaggaggaa gggatcgaag gtgaccatcg aagccagtca    60 aggggggcttc catccactcc                                               80

<210> SEQ ID NO 183
<211> LENGTH: 80
<212> TYPE: DNA
<213> ORGANISM: Artificial Sequence
<220> FEATURE:
<223> OTHER INFORMATION: synthetic oligonucleotide

<400> SEQUENCE: 183
tcccccgaag gtaggtgagg acacagaaga gatgtccaca agtgtcacta taagtctact    60
gagtctcagg taggtcgtac                                                80

<210> SEQ ID NO 184
<211> LENGTH: 82
<212> TYPE: DNA
<213> ORGANISM: Artificial Sequence
<220> FEATURE:
<223> OTHER INFORMATION: synthetic oligonucleotide

<400> SEQUENCE: 184
gttcggttct gtagttgagg ttataaccta ccgaggttgt cttcggacca ttcaggaagt    60
ttcctgatta gatagtgcct tg                                             82

<210> SEQ ID NO 185
<211> LENGTH: 80
<212> TYPE: DNA
<213> ORGANISM: Artificial Sequence
<220> FEATURE:
<223> OTHER INFORMATION: synthetic oligonucleotide
```

<400> SEQUENCE: 185
gaccgtcgcc ctggctgata tgtgactggt agagatcgaa tctcggtctt ctgaaacggt    60
gtatgatgac gcaggtcgtg                                                 80

<210> SEQ ID NO 186
<211> LENGTH: 80
<212> TYPE: DNA
<213> ORGANISM: Artificial Sequence
<220> FEATURE:
<223> OTHER INFORMATION: synthetic oligonucleotide

<400> SEQUENCE: 186
catactactg cgtccagcac gctcagttcc cctggacatt cggcggcggc acaaaactgg    60
aaatcaaacg tgagtaggga                                                 80

<210> SEQ ID NO 187
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 187
cctttagttt gcactcatcc ctaggctc                                         28

<210> SEQ ID NO 188
<211> LENGTH: 233
<212> TYPE: PRT
<213> ORGANISM: Artificial Sequence
<220> FEATURE:
<223> OTHER INFORMATION: synthetic

<400> SEQUENCE: 188

Met Asp Trp Thr Trp Arg Ile Leu Phe Leu Val Ala Ala Ala Thr Gly
1               5                   10                  15

Val His Ser Asp Ile Gln Met Thr Gln Ser Pro Ser Ser Met Ser Val
            20                  25                  30

Ser Val Gly Asp Arg Val Thr Ile Thr Cys His Ser Ser Gln Asp Ile
        35                  40                  45

Asn Ser Asn Ile Gly Trp Leu Gln Gln Lys Pro Gly Lys Ser Phe Lys
    50                  55                  60

Gly Leu Ile Tyr His Gly Thr Asn Leu Asp Asp Gly Val Pro Ser Arg
65                  70                  75                  80

Phe Ser Gly Ser Gly Ser Gly Thr Asp Tyr Thr Leu Thr Ile Ser Ser
                85                  90                  95

Leu Gln Pro Glu Asp Phe Ala Thr Tyr Tyr Cys Val Gln Tyr Ala Gln
            100                 105                 110

Phe Pro Trp Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Val Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys Gly
        195                 200                 205

Lys Val Tyr Ala Cys Glu Val Thr His Gln His Leu Ser Ser Pro Val
    210                 215                 220

Thr Lys Ser Phe Asn Arg Gly Glu Cys
225                 230

<210> SEQ ID NO 189
<211> LENGTH: 704
<212> TYPE: DNA
<213> ORGANISM: Artificial Sequence
<220> FEATURE:
<223> OTHER INFORMATION: synthetic

<400> SEQUENCE: 189

| | | | | | |
|---|---|---|---|---|---|
| atggtgtcca | cagctcagtt | ccttgcattc | ttgttgcttt | ggtttccagg | tgcaagatgt | 60 |
| gacatcctga | tgacccaatc | tccatcctcc | atgtctgtat | ctctgggaga | cacagtcagc | 120 |
| atcacttgcc | attcaagtca | ggacattaac | agtaatatag | gtggttgca | gcagagacca | 180 |
| gggaaatcat | ttaagggcct | gatctatcat | ggaaccaact | tggacgatga | agttccatca | 240 |
| aggttcagtg | gcagtggatc | tggagccgat | tattctctca | ccatcagcag | cctggaatct | 300 |
| gaagattttg | cagactatta | ctgtgtacag | tatgctcagt | ttccgtggac | gttcggtgga | 360 |
| ggcaccaagc | tggaaatcaa | acgaactgtg | gctgcaccat | ctgtcttcat | cttcccgcca | 420 |
| tctgatgagc | agttgaaatc | tggaactgcc | tctgttgtgt | gcctgctgaa | taacttctat | 480 |
| cccagagagg | ccaaagtaca | gtggaaggtg | gataacgccc | tccaatcggg | taactcccag | 540 |
| gagagtgtca | cagagcagga | cagcaaggac | agcacctaca | gcctcagcag | caccctgacg | 600 |
| ctgagcaaag | cagactacga | gaaacacaaa | gtctacgcct | gcgaagtcac | ccatcagggc | 660 |
| ctgagctcgc | ccgtcacaaa | gagcttcaac | aggggagagt | gttg | | 704 |

<210> SEQ ID NO 190
<211> LENGTH: 702
<212> TYPE: DNA
<213> ORGANISM: Artificial Sequence
<220> FEATURE:
<223> OTHER INFORMATION: synthetic

<400> SEQUENCE: 190

| | | | | | |
|---|---|---|---|---|---|
| atggattgga | cttggagaat | actgtttctt | gtagcagccg | caacaggtgt | tcacagtgat | 60 |
| attcagatga | ctcagagtcc | atccagcatg | tcagtctccg | tgggagatag | ggtgacgata | 120 |
| acctgtcatt | caagccaaga | catcaactcc | aatattggat | ggctccaaca | gaagcctggt | 180 |
| aagtccttca | aggactaat | ctatcacgga | acaaacttgg | acgacggcgt | gccatcgaga | 240 |
| ttttcagggt | ctggcagcgg | gaccgactat | acactgacca | tctctagctt | acaaccagag | 300 |
| gactttgcca | catactactg | cgtccagtac | gctcagttcc | cctggacatt | cggcggcggc | 360 |
| acaaaactgg | aaatcaaacg | aaccgtcgca | gctccctccg | tgttcatctt | cccccccatcc | 420 |
| gacgagcaac | tgaagtcagg | cacagcctcc | gtggtgtgcc | tccttaataa | cttttaccca | 480 |
| agagaggcca | agtccagtg | gaaagtggac | aacgcactac | agagcgggaa | ctctcaggaa | 540 |
| agcgtgacag | agcaggactc | aaaagattca | acatacagcc | tatcttctac | cctgacactg | 600 |
| tcaaaagctg | attatgaaaa | gcacaaagta | tatgcctgtg | aagtaactca | tcagggactc | 660 |
| agcagccctg | tcactaaaag | tttaatagga | ggcgaatgct | ga | | 702 |

<210> SEQ ID NO 191

<210> SEQ ID NO 191 (continued)
<211> LENGTH: 408
<212> TYPE: DNA
<213> ORGANISM: Artificial Sequence
<220> FEATURE:
<223> OTHER INFORMATION: synthetic

<400> SEQUENCE: 191

```
gccaccatga gagtgctgat tcttttgtgg ctgttcacag cctttcctgg tgtcctgtct    60
gatgtgcagc ttcaggagtc gggacctagc ctggtgaaac cttctcagac tctgtccctc   120
acctgcactg tcactggcta ctcaatcacc agtgattttg cctggaactg gatccggcag   180
tttccaggaa acaagctgga gtggatgggc tacataagtt atagtggtaa cactaggtac   240
aacccatctc tcaaaagtcg aatctctatc actcgagaca catccaagaa ccaattcttc   300
ctgcagttga attctgtgac tattgaggac acagccacat attactgtgt aacggcggga   360
cgcgggttc cttattgggg ccaagggact ctggtcactg tctctgca                 408
```

<210> SEQ ID NO 192
<211> LENGTH: 405
<212> TYPE: DNA
<213> ORGANISM: Artificial Sequence
<220> FEATURE:
<223> OTHER INFORMATION: synthetic

<400> SEQUENCE: 192

```
atggattgga cctggcgcat tctctttctg gtagcagccg ccacaggtgt ccacagccag    60
gtgcagctcc aagagagtgg acctgggctt gtcaagccga gtcaaacttt gtccctaaca   120
tgtactgtgt ccggatactc tatctcatca gattttgcgt ggaattggat aaggcagcca   180
ccagggaaag gtttagaatg gatgggctac atatcatact ctgggaacac cagatatcaa   240
ccttctctga aaagccggat cacaatctca agggacacgt cgaagaatca gttcttcctg   300
aaactgaact ccgttacagc cgcagacaca gcaacatatt actgcgtaac cgctggcaga   360
ggcttcccct attggggaca gggcacccta gtgacagtga gcagc                   405
```

<210> SEQ ID NO 193
<211> LENGTH: 8
<212> TYPE: PRT
<213> ORGANISM: Mus musculus

<400> SEQUENCE: 193

Tyr His Gly Thr Asn Leu Asp Asp
1               5

<210> SEQ ID NO 194
<211> LENGTH: 8
<212> TYPE: PRT
<213> ORGANISM: Mus musculus

<400> SEQUENCE: 194

Tyr His Gly Thr Asn Leu Glu Asp
1               5

<210> SEQ ID NO 195
<211> LENGTH: 9
<212> TYPE: PRT
<213> ORGANISM: Mus musculus

<400> SEQUENCE: 195

Val Gln Tyr Ala Gln Phe Pro Trp Thr
1               5